US012291565B2

(12) United States Patent
Liu et al.

(10) Patent No.: US 12,291,565 B2
(45) Date of Patent: May 6, 2025

(54) TAU BINDING COMPOUNDS

(71) Applicant: VOYAGER THERAPEUTICS, INC., Lexington, MA (US)

(72) Inventors: Wencheng Liu, Cambridge, MA (US); Todd Carter, Winchester, MA (US); Ishan Sanjeev Shah, Andover, MA (US); Christopher Joseph Murray, Poleglass (IE); James Bernard McClory, Ballynaskeagh (IE); Dinah Wen-Yee Sah, Hopkinton, MA (US)

(73) Assignee: VOYAGER THERAPEUTICS, INC., Lexington, MA (US)

( * ) Notice: Subject to any disclaimer, the term of this patent is extended or adjusted under 35 U.S.C. 154(b) by 0 days.

(21) Appl. No.: 18/734,892

(22) Filed: Jun. 5, 2024

(65) Prior Publication Data

US 2024/0391988 A1    Nov. 28, 2024

Related U.S. Application Data

(63) Continuation of application No. PCT/US2023/074239, filed on Sep. 14, 2023.

(60) Provisional application No. 63/448,913, filed on Feb. 28, 2023, provisional application No. 63/406,924, filed on Sep. 15, 2022.

(51) Int. Cl.
*C07K 16/18* (2006.01)
*A61K 39/00* (2006.01)
*A61P 25/28* (2006.01)
*C12N 15/86* (2006.01)

(52) U.S. Cl.
CPC ............. *C07K 16/18* (2013.01); *A61P 25/28* (2018.01); *A61K 2039/505* (2013.01); *A61K 2039/545* (2013.01); *C07K 2317/24* (2013.01); *C07K 2317/565* (2013.01); *C12N 2750/14143* (2013.01)

(58) Field of Classification Search
CPC ............... C07K 16/18; C07K 2317/24; C07K 2317/31; C07K 2317/565; A61P 25/28; C12N 15/86; C12N 2750/14143; A61K 2039/505; A61K 2039/545
See application file for complete search history.

(56) References Cited

U.S. PATENT DOCUMENTS

| | | | |
|---|---|---|---|
| 7,176,290 B2 | 2/2007 | Mandelkow et al. | |
| 8,609,097 B2 | 12/2013 | Bohrmann et al. | |
| 8,697,076 B2 * | 4/2014 | Binder | C07K 16/18 514/17.7 |
| 8,703,137 B2 | 4/2014 | Chain | |
| 9,290,567 B2 | 3/2016 | Bohrmann et al. | |
| 9,304,138 B2 | 4/2016 | Pfeifer et al. | |
| 9,540,434 B2 | 1/2017 | Pfeifer et al. | |
| 9,562,091 B2 | 2/2017 | Grueninger et al. | |
| 9,598,485 B2 | 3/2017 | Ayalon et al. | |
| 9,657,091 B2 | 5/2017 | Pfeifer et al. | |
| 9,862,763 B2 | 1/2018 | Dengl et al. | |
| 10,066,010 B2 | 9/2018 | Pfeifer et al. | |
| 10,087,245 B2 | 10/2018 | Lafaye et al. | |
| 10,100,104 B2 | 10/2018 | Pfeifer et al. | |
| 10,196,439 B2 | 2/2019 | Pedersen et al. | |
| 10,251,952 B2 | 4/2019 | Bader et al. | |
| 10,400,018 B2 | 9/2019 | Griswold-Prenner et al. | |
| 10,465,000 B2 | 11/2019 | Grueninger et al. | |
| 10,538,582 B2 | 1/2020 | Lafaye et al. | |
| 10,556,950 B2 | 2/2020 | Eguchi et al. | |
| 10,562,962 B2 | 2/2020 | Pedersen et al. | |
| 10,591,492 B2 | 3/2020 | Kolb et al. | |
| 10,822,402 B2 | 11/2020 | Dengl et al. | |
| 10,889,638 B2 | 1/2021 | Barbour et al. | |
| 10,894,822 B2 | 1/2021 | Chain | |
| 10,894,829 B2 | 1/2021 | Eguchi et al. | |
| 10,934,348 B2 | 3/2021 | Pedersen et al. | |
| 10,976,325 B2 | 4/2021 | Kolb et al. | |
| 10,995,137 B2 | 5/2021 | Pedersen et al. | |
| 11,124,563 B2 | 9/2021 | Lafaye et al. | |
| 11,155,609 B2 | 10/2021 | Chain et al. | |
| 11,326,182 B2 | 5/2022 | Paul et al. | |
| 11,859,200 B2 | 1/2024 | Nonnenmacher et al. | |
| 2007/0280935 A1 | 12/2007 | Bohrmann et al. | |
| 2015/0183854 A1 | 7/2015 | Mori et al. | |
| 2021/0070847 A1 * | 3/2021 | Giasson | A61B 5/0073 |
| 2021/0130449 A1 | 5/2021 | Barbour et al. | |
| 2021/0179699 A1 | 6/2021 | Chain | |
| 2021/0206843 A1 | 7/2021 | Pedersen et al. | |
| 2021/0380677 A1 | 12/2021 | Eguchi et al. | |
| 2021/0403541 A1 | 12/2021 | Baker et al. | |

(Continued)

FOREIGN PATENT DOCUMENTS

EP    2625198 B1    7/2015
EP    2899208 A1    7/2015

(Continued)

OTHER PUBLICATIONS

Lombana et al. (Scientific Reports (2015) 5: 17488) (Year: 2015).*
Voyager Therapeutics, Inc. U.S. Appl. No. 18/711,059 (Unpublished). Compositions and Methods for the Treatment of Tau-Related Disorders. (Year: 2022).*
Voyager Therapeutics, Inc. U.S. Appl. No. 18/046,293 (Published). Tau Binding Compounds. (Year: 2022).*
Hasegawa, M. et al. "Characterization of mAb AP422, a novel phosphorylation-dependent monoclonal antibody against tau protein," FEBS Letters vol. 384, 1 (1996): 25-30.
International Search Report and Written Opinion in International Patent Application No. PCT/US2021/027346 dated Sep. 10, 2021.

(Continued)

*Primary Examiner* — Julie Wu
*Assistant Examiner* — Elizabeth A Shupe
(74) *Attorney, Agent, or Firm* — K&L Gates LLP

(57) ABSTRACT

The present disclosure provides anti-tau antibodies and vectorization thereof (e.g., into AAV particles). Also provided are methods of using anti-tau antibodies and/or AAV particles for prevention, treatment, and/or diagnosis of neurological indications.

28 Claims, 1 Drawing Sheet
Specification includes a Sequence Listing.

(56) References Cited

U.S. PATENT DOCUMENTS

| | | |
|---|---|---|
| 2022/0018857 A1 | 1/2022 | Kolb et al. |
| 2022/0064272 A1 | 3/2022 | Chain et al. |
| 2022/0096657 A1 | 3/2022 | Paul et al. |
| 2022/0146535 A1 | 5/2022 | Chai et al. |
| 2022/0339270 A1 | 10/2022 | Liu et al. |
| 2022/0389449 A1 | 12/2022 | Paul et al. |
| 2023/0075314 A1 | 3/2023 | Hou et al. |
| 2023/0192830 A1 | 6/2023 | Carter et al. |
| 2023/0203102 A1 | 6/2023 | Nonnenmacher et al. |
| 2024/0000971 A1 | 1/2024 | Carter et al. |
| 2024/0059766 A1 | 2/2024 | Kurella et al. |
| 2024/0200097 A1 | 6/2024 | Nonnenmacher et al. |

FOREIGN PATENT DOCUMENTS

| | | |
|---|---|---|
| EP | 2764022 B9 | 2/2017 |
| EP | 2670434 B1 | 12/2018 |
| EP | 3135689 B1 | 12/2018 |
| EP | 2834270 B1 | 10/2019 |
| EP | 2857039 B1 | 11/2019 |
| EP | 3164152 B1 | 2/2020 |
| EP | 3313877 B1 | 6/2020 |
| EP | 3662931 A1 | 6/2020 |
| WO | 2004016655 A1 | 2/2004 |
| WO | 2010142423 A2 | 12/2010 |
| WO | 2012045882 A2 | 4/2012 |
| WO | 2012054588 A2 | 4/2012 |
| WO | 2012106363 A2 | 8/2012 |
| WO | 2012149365 A2 | 11/2012 |
| WO | 2013041962 A1 | 3/2013 |
| WO | 2013050567 A1 | 4/2013 |
| WO | 2013151762 A1 | 10/2013 |
| WO | 2013180238 A1 | 12/2013 |
| WO | 2014011972 A1 | 1/2014 |
| WO | 2014028777 A2 | 2/2014 |
| WO | 2014096321 A1 | 6/2014 |
| WO | 2014100600 A2 | 6/2014 |
| WO | 2014150877 A1 | 9/2014 |
| WO | 2014152157 A2 | 9/2014 |
| WO | 2014165271 A2 | 10/2014 |
| WO | 2015091656 A1 | 6/2015 |
| WO | 2015114538 A1 | 8/2015 |
| WO | 2015120364 A1 | 8/2015 |
| WO | 2015122922 A1 | 8/2015 |
| WO | 2015197735 A1 | 12/2015 |
| WO | 2015197820 A1 | 12/2015 |
| WO | 2015197823 A2 | 12/2015 |
| WO | 2015200806 A2 | 12/2015 |
| WO | 2016079597 A1 | 5/2016 |
| WO | 2016196726 A1 | 12/2016 |
| WO | 2016207245 A1 | 12/2016 |
| WO | 2017005732 A1 | 1/2017 |
| WO | 2017005734 A1 | 1/2017 |
| WO | 2017009308 A2 | 1/2017 |
| WO | 2017189959 A1 | 11/2017 |
| WO | 2017189963 A1 | 11/2017 |
| WO | 2017191559 A1 | 11/2017 |
| WO | 2017191560 A1 | 11/2017 |
| WO | 2017191561 A1 | 11/2017 |
| WO | 2018106776 A2 | 6/2018 |
| WO | 2018106781 A1 | 6/2018 |
| WO | 2018127519 A1 | 7/2018 |
| WO | 2018154390 A1 | 8/2018 |
| WO | 2018170351 A1 | 9/2018 |
| WO | 2018178077 A1 | 10/2018 |
| WO | 2019077500 A1 | 4/2019 |
| WO | 2019094595 A2 | 5/2019 |
| WO | 2019110571 A1 | 6/2019 |
| WO | 2019171258 A1 | 9/2019 |
| WO | 2019171259 A1 | 9/2019 |
| WO | 2020097561 A1 | 5/2020 |
| WO | 2020180819 A1 | 9/2020 |
| WO | 2020201828 A1 | 10/2020 |
| WO | 2020223276 A1 | 11/2020 |
| WO | 2020242963 A1 | 12/2020 |
| WO | 202126279 A1 | 2/2021 |
| WO | 2021024209 A1 | 2/2021 |
| WO | 2021110995 A1 | 6/2021 |
| WO | 2021202777 A1 | 10/2021 |
| WO | 2021205359 A1 | 10/2021 |
| WO | 2021211753 A1 | 10/2021 |
| WO | 2021230987 A1 | 11/2021 |
| WO | 2021262791 A1 | 12/2021 |
| WO | 2022013286 A1 | 1/2022 |
| WO | 2022098699 A1 | 5/2022 |
| WO | 2022132923 A1 | 6/2022 |
| WO | 2022144406 A1 | 7/2022 |
| WO | 2023091948 A1 | 5/2023 |
| WO | 2023092004 A1 | 5/2023 |
| WO | 2023250388 A1 | 12/2023 |
| WO | 2024059739 A1 | 3/2024 |
| WO | 2024229389 A1 | 11/2024 |

OTHER PUBLICATIONS

International Search Report and Written Opinion in International Patent Application No. PCT/US2023/074239 dated Jan. 17, 2024.

Ji, C. & Sigurdsson, E. M. "Current Status of Clinical Trials on Tau Immunotherapies," Drugs vol. 81, 10 (2021): 1135-1152.

Lichtenberg-Kraag, B. et al. "Phosphorylation-dependent epitopes of neurofilament antibodies on tau protein and relationship with Alzheimer tau," Proceedings of the National Academy of Sciences of the United States of America vol. 89, 12 (1992): 5384-8.

Liu, W. et al. "Efficacy evaluation of a novel vectorized anti-tau antibody, targeting a C-terminal phospho-tau epitope, using systemic dosing of a blood brain barrier penetrant AAV capsid in mouse models of tauopathies," Alzheimer's & Dementia: The Journal of the Alzheimer's Association vol. 18 (Suppl. 10) e062924 (2022).

Liu, W. et al. "Efficacy of a Novel Vectorized Antibody Targeting the C-Terminal Domain of Tau, Antibody 1, using Systemic Dosing of a Blood Brain Barrier Penetrant AAV Capsid in Mouse Models of Tauopathies," Molecular Therapies vol. 30, 4S1 (2022): 483, Abstract 1031.

Liu, W. et al. "Efficacy of a Novel Vectorized Antibody Targeting the C-Terminal Domain of Tau, Antibody 1, using Systemic Dosing of a Blood Brain Barrier Penetrant AAV Capsid in Mouse Models of Tauopathies," Poster presented at: American Society of Gene + Cell Therapy; May 16-19, 2022; Washington DC.

Liu, W. et al. "Efficacy of a Novel Vectorized Antibody Targeting the C-terminal Domain of Tau, Using Systemic Dosing of a Blood Brain Barrier Penetrant AAV Capsid in Mouse Models of Tauopathies," Poster presented at: Alzheimer's Association International Conference ; Jul. 31,-Aug. 4, 2022; San Diego, CA.

Liu, W. et al. "Identification and Characterization of Novel Anti-tau Antibodies that Inhibit Tau-seed Mediated Pathology in a P301S Tauopathy Mouse Model of Alzheimer's Disease and Tauopathies," Poster presented at: Alzheimer's Association International Conference; Jul. 31,-Aug. 4, 2022; San Diego, CA.

Liu, W. et al. "Identification and characterization of novel anti-tau antibodies that inhibit tau-seed mediated pathology in a P301S tauopathy mousemodel Alzheimer's Disease and tauopathies," Alzheimer's & Dementia: The Journal of the Alzheimer's Association vol. 18 (Suppl. 10) e062878 (2022).

Troquier, L. et al. "Targeting phospho-Ser422 by active Tau Immunotherapy in the THYTau22 mouse model: a suitable therapeutic approach," Current Alzheimer Research vol. 9, 4 (2012): 397-405.

Sadhu, C. et al. "Pharmacokinetics and Pharmacodynamics of an Antibody Targeting Pathological Tau for the Treatment of Alzheimer's Disease: Nonclinical Studies in P301S Mice and Cynomolgus Macaques" Voyager Therapeutics. Alzheimer's Association International Conference, Jul. 28,-Aug. 1, 2024, Philadelphia, PA, USA.

* cited by examiner

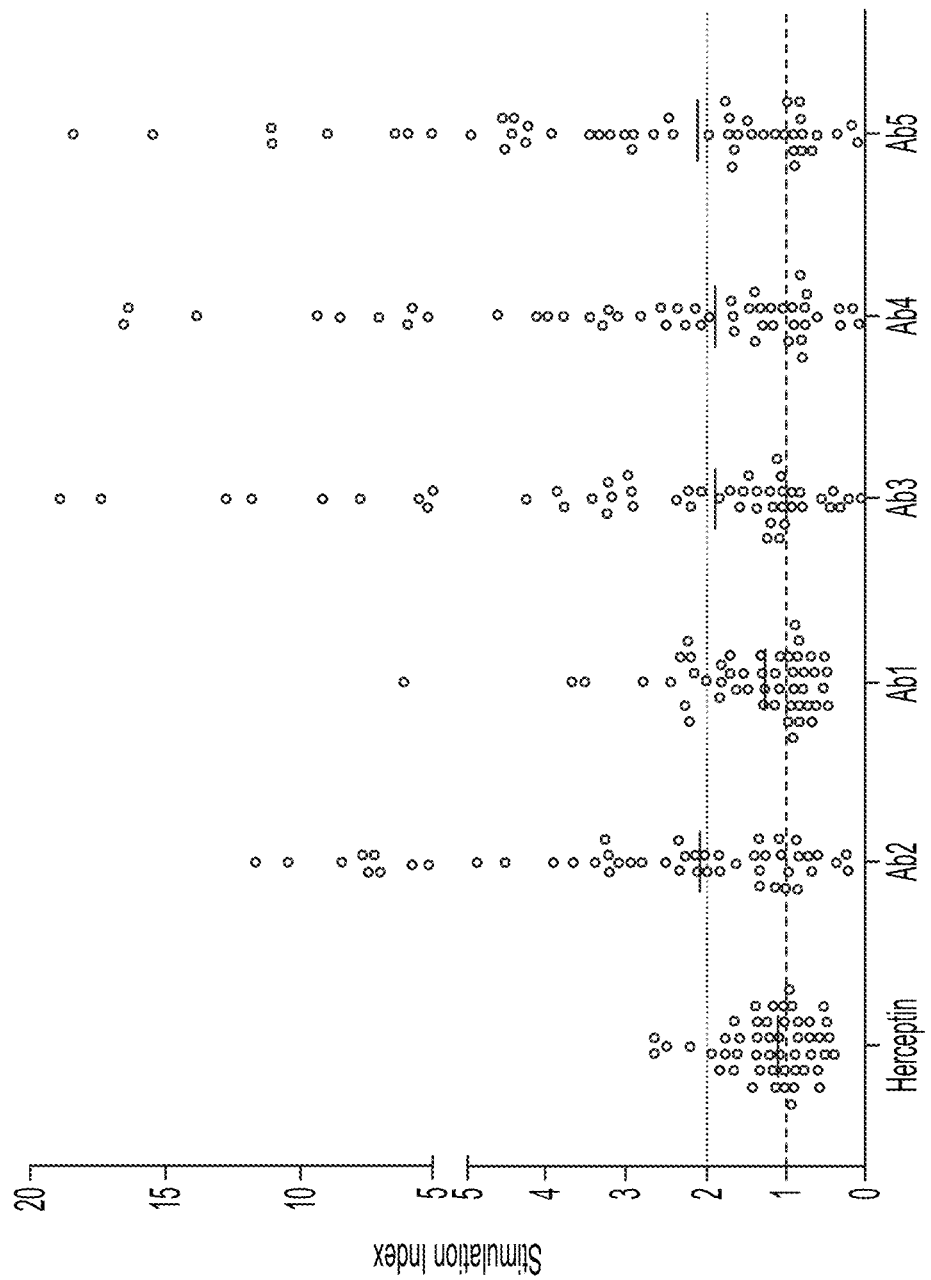

TAU BINDING COMPOUNDS

RELATED APPLICATIONS

This application is a Continuation of International Application No. PCT/US2023/074239, filed on Sep. 14, 2023, which claims priority to U.S. Provisional Application No. 63/406,924 filed on Sep. 15, 2022, and U.S. Provisional Application No. 63/448,913 filed on Feb. 28, 2023; the entire contents of each of which are hereby incorporated by reference in their entirety.

SEQUENCE LISTING

The instant application contains a Sequence Listing which has been submitted electronically in XML format and is hereby incorporated by reference in its entirety. Said XML copy, created on Aug. 23, 2023, is named V2071-3005PCT_SL.xml and is 1,438,459 bytes in size.

FIELD OF THE DISCLOSURE

The present disclosure presents tau binding compounds and adeno-associated virus (AAV) particles comprising the same.

BACKGROUND OF THE INVENTION

Tauopathies are a group of neurodegenerative diseases characterized by the dysfunction and/or aggregation of the microtubule associated protein tau. Tau is normally a soluble protein known to associate with microtubules based on the extent of its phosphorylation. Tau is considered an important component of intracellular trafficking processes, particularly in neuronal cells, given their unique and extended structure. Hyperphosphorylation of tau depresses its binding to microtubules and microtubule assembly activity. Further, hyperphosphorylation of tau renders it prone to misfolding and aggregation. In tauopathies, the tau becomes hyperphosphorylated, misfolds and aggregates as neurofibrillary tangles (NFT) of paired helical filaments (PHF), twisted ribbons or straight filaments. These NFT are largely considered indicative of impending neuronal cell death and thought to contribute to widespread neuronal cell loss, leading to a variety of behavioral and cognitive deficits.

A genetically defined tauopathy was described when mutations in the tau gene were shown to lead to an autosomal dominantly inherited tauopathy known as frontotemporal dementia and parkinsonism linked to chromosome 17 (FTDP-17). This provided evidence that changes in tau could lead to neurodegenerative changes in the brain. These molecules are considered to be more amyloidogenic, meaning they are more likely to become hyperphosphorylated and more likely to aggregate into NFT (Hutton, M. et al., 1998, Nature 393(6686):702-5).

Several approaches have been proposed for therapeutically interfering with progression of tau pathology and preventing the subsequent molecular and cellular consequences. Given that NFT are composed of hyperphosphorylated, misfolded and aggregated forms of tau, interference at each of these stages provides targets that can be pursued. Introducing agents that limit phosphorylation, block misfolding or prevent aggregation are promising strategies. It has also been suggested that introduction of anti-tau antibodies can prevent the trans-neuronal spread of tau pathology.

There remains a need for anti-tau antibodies for use in tauopathy treatment, diagnostics, and other applications. The present disclosure addresses this need with related compounds and methods described herein.

SUMMARY OF THE INVENTION

The present disclosure pertains at least in part to compositions and methods for modulating the level of tau, e.g., aggregation and or distribution of tau, and/or delivery, e.g., vectorized delivery of an antibody that binds to tau, e.g., an anti-tau antibody, e.g., an anti-tau antibody described herein. In some embodiments, the level of tau, e.g., aggregation or distribution, is reduced or inhibited using an anti-tau antibody described herein or an isolated, e.g., recombinant, AAV particle comprising a viral genome encoding an anti-tau antibody, e.g., an anti-tau antibody described herein. In some embodiments, the degradation of tau is increased using an anti-tau antibody described herein or an isolated, e.g., recombinant, AAV particle comprising a viral genome encoding an anti-tau antibody, e.g., an anti-tau antibody described herein. Such inhibition and/or degradation can be useful in treating disorders related to expression of tau and/or neurological disorders, such as tauopathies.

Accordingly, in one aspect, the present disclosure provides an isolated, e.g., recombinant antibody that binds to tau, comprising a heavy chain variable region (VH) comprising one, two, or three of a heavy chain complementary determining region 1 (HC CDR1), a heavy chain complementary determining region 2 (HC CDR2), and/or a heavy chain complementary determining region 3 (HC CDR3) of any of the HC CDR sequences of Table 1 or 4; and/or a light chain variable region (VL) comprising one, two, or three of a light chain complementary determining region 1 (LC CDR1), a light chain complementary determining region 2 (LC CDR2), and/or a light chain complementary determining region 3 (LC CDR3) of any of the LC CDR sequences of Table 1 or 4.

In yet another aspect, the present disclosure provides an antibody that binds to human tau, which comprises a heavy chain variable region (VH) comprising a heavy chain complementary determining region 1 (HC CDR1), a heavy chain complementary determining region 2 (HC CDR2), and a heavy chain complementary determining region 3 (HC CDR3) and/or a light chain variable region (VL) comprising a light chain complementary determining region 1 (LC CDR1), a light chain complementary determining region 2 (LC CDR2), and a light chain complementary determining region 3 (LC CDR3), wherein (a) the HC CDR1, HC CDR2, HC CDR3, LC CDR1, LC CDR2, and LC CDR3 comprise the amino acid sequence of SEQ ID NO: 64, 1145, 1167, 1146, 529, and 571, respectively; (b) the HC CDR1, HC CDR2, HC CDR3, LC CDR1, LC CDR2, and LC CDR3 comprise the amino acid sequence of SEQ ID NO: 1144, 1145, 410, 1146, 529, and 571, respectively; (c) the HC CDR1, HC CDR2, HC CDR3, LC CDR1, LC CDR2, and LC CDR3 comprise the amino acid sequence of SEQ ID NO: 1165, SEQ ID NO: 1166, SEQ ID NO: 1167, SEQ ID NO: 473, RVS, and SEQ ID NO: 571, respectively; or (d) the HC CDR1, HC CDR2, HC CDR3, LC CDR1, LC CDR2, and LC CDR3 comprise the amino acid sequence of SEQ ID NO: 314, 341, 410, 1154, 529, and 571, respectively. In some embodiments, the antibody is a humanized antibody.

In yet another aspect, the present disclosure provides an antibody that binds to human tau, which comprises a heavy chain variable region (VH) comprising a heavy chain complementary determining region 1 (HC CDR1), a heavy chain complementary determining region 2 (HC CDR2), and a heavy chain complementary determining region 3 (HC CDR3) and/or a light chain variable region (VL) comprising a light chain complementary determining region 1 (LC CDR1), a light chain complementary determining region 2 (LC CDR2), and a light chain complementary determining region 3 (LC CDR3), wherein: (a) the HC CDR1, HC CDR2, HC CDR3, LC CDR1, LC CDR2, and LC CDR3 comprise the amino acid sequence of SEQ ID NO: 64, 1145, 1167, 1146, 529, and 571, respectively; (b) the HC CDR1, HC CDR2, HC CDR3, LC CDR1, LC CDR2, and LC CDR3 comprise the amino acid sequence of SEQ ID NO: 1144, 1145, 410, 1146, 529, and 571, respectively; (c) the HC CDR1, HC CDR2, HC CDR3, LC CDR1, LC CDR2, and LC CDR3 comprise the amino acid sequence of SEQ ID NO: 1165, SEQ ID NO: 1166, SEQ ID NO: 1167, SEQ ID NO: 473, RVS, and SEQ ID NO: 571, respectively; or (d) the HC CDR1, HC CDR2, HC CDR3, LC CDR1, LC CDR2, and LC CDR3 comprise the amino acid sequence of SEQ ID NO: 314, 341, 410, 1154, 529, and 571, respectively; and wherein: (i) the VH comprises an amino acid sequence comprising one, two, three, four, five, six, seven, eight, nine, or all of: an amino acid other than Q at position 5, P at position 7, T at position 9, L at position 11, V at position 12, N at position 19, L at position 20, K at position 67, A at position 68, and/or S at position 76, numbered according to SEQ ID NO: 21; and/or (ii) the VL comprises and amino acid sequence comprising one, two, or all of: an amino acid other than D at position 17, Q at position 18, and/or G at position 68, numbered according to SEQ ID NO: 93.

In yet another aspect, the present disclosure provides antibody that binds to human tau, which comprises a heavy chain variable region (VH) comprising a heavy chain complementary determining region 1 (HC CDR1), a heavy chain complementary determining region 2 (HC CDR2), and a heavy chain complementary determining region 3 (HC CDR3) and/or a light chain variable region (VL) comprising a light chain complementary determining region 1 (LC CDR1), a light chain complementary determining region 2 (LC CDR2), and a light chain complementary determining region 3 (LC CDR3), wherein: (a) the HC CDR1, HC CDR2, HC CDR3, LC CDR1, LC CDR2, and LC CDR3 comprise the amino acid sequence of SEQ ID NO: 64, 1145, 1167, 1146, 529, and 571, respectively; (b) the HC CDR1, HC CDR2, HC CDR3, LC CDR1, LC CDR2, and LC CDR3 comprise the amino acid sequence of SEQ ID NO: 1144, 1145, 410, 1146, 529, and 571, respectively; (c) the HC CDR1, HC CDR2, HC CDR3, LC CDR1, LC CDR2, and LC CDR3 comprise the amino acid sequence of SEQ ID NO: 1165, SEQ ID NO: 1166, SEQ ID NO: 1167, SEQ ID NO: 473, RVS, and SEQ ID NO: 571, respectively; or (d) the HC CDR1, HC CDR2, HC CDR3, LC CDR1, LC CDR2, and LC CDR3 comprise the amino acid sequence of SEQ ID NO: 314, 341, 410, 1154, 529, and 571, respectively; and wherein: (i) the VH comprises an amino acid sequence comprising one, two, three, four, five, six, seven, eight, or all of: a V at position 5, an S at position 7, an A at position 9, a V at position 11, a K at position 12, a K at position 19, a V at position 20, an R at position 67, and/or a V at position 68, numbered according to SEQ ID NO: 21; and/or (ii) the VL comprises and amino acid sequence comprising one, two, or all of: Q or E at position 17, P or R at position 18, and/or S at position 68, numbered according to SEQ ID NO: 93.

In yet another aspect, the present disclosure provides antibody that binds to human tau, which comprises a heavy chain variable region (VH) comprising a heavy chain complementary determining region 1 (HC CDR1), a heavy chain complementary determining region 2 (HC CDR2), and a heavy chain complementary determining region 3 (HC CDR3) and/or a light chain variable region (VL) comprising a light chain complementary determining region 1 (LC CDR1), a light chain complementary determining region 2 (LC CDR2), and a light chain complementary determining region 3 (LC CDR3), wherein: (a) the HC CDR1, HC CDR2, HC CDR3, LC CDR1, LC CDR2, and LC CDR3 comprise the amino acid sequence of SEQ ID NO: 64, 1145, 1167, 1146, 529, and 571, respectively; (b) the HC CDR1, HC CDR2, HC CDR3, LC CDR1, LC CDR2, and LC CDR3 comprise the amino acid sequence of SEQ ID NO: 1144, 1145, 410, 1146, 529, and 571, respectively; (c) the HC CDR1, HC CDR2, HC CDR3, LC CDR1, LC CDR2, and LC CDR3 comprise the amino acid sequence of SEQ ID NO: 1165, SEQ ID NO: 1166, SEQ ID NO: 1167, SEQ ID NO: 473, RVS, and SEQ ID NO: 571, respectively; or (d) the HC CDR1, HC CDR2, HC CDR3, LC CDR1, LC CDR2, and LC CDR3 comprise the amino acid sequence of SEQ ID NO: 314, 341, 410, 1154, 529, and 571, respectively; and wherein: (i) the VH comprises an amino acid sequence at least 86% (e.g., at least 90, 92, 95, 96, 97, 98, or 99%) identical to the amino acid sequence of any one of SEQ ID NOs: 67-71; and/or (ii) the VL comprises an amino acid sequence at least 91% (e.g., at least 92, 95, 96, 97, 98, or 99%) identical to the amino acid sequence of any one of SEQ ID NOs: 72-76.

In yet another aspect, the present disclosure provides an antibody that binds to human tau, which comprises a heavy chain variable region (VH) comprising a heavy chain complementary determining region 1 (HC CDR1), a heavy chain complementary determining region 2 (HC CDR2), and a heavy chain complementary determining region 3 (HC CDR3) and a light chain variable region (VL) comprising a light chain complementary determining region 1 (LC CDR1), a light chain complementary determining region 2 (LC CDR2), and a light chain complementary determining region 3 (LC CDR3), wherein: (a) the HC CDR1, HC CDR2, HC CDR3, LC CDR1, LC CDR2, and LC CDR3 comprise the amino acid sequence of SEQ ID NO: 64, 1145, 1167, 1146, 529, and 571, respectively; (b) the HC CDR1, HC CDR2, HC CDR3, LC CDR1, LC CDR2, and LC CDR3 comprise the amino acid sequence of SEQ ID NO: 1144, 1145, 410, 1146, 529, and 571, respectively; (c) the HC CDR1, HC CDR2, HC CDR3, LC CDR1, LC CDR2, and LC CDR3 comprise the amino acid sequence of SEQ ID NO: 1165, SEQ ID NO: 1166, SEQ ID NO: 1167, SEQ ID NO: 473, RVS, and SEQ ID NO: 571, respectively; or (d) the HC CDR1, HC CDR2, HC CDR3, LC CDR1, LC CDR2, and LC CDR3 comprise the amino acid sequence of SEQ ID NO: 314, 341, 410, 1154, 529, and 571, respectively; and wherein: (i) the VH comprises 1, 2, 3, 4, 5, 6, 7, 8, 9, 10, 11, 12, 13, 14, 15, 16, 17, 18, 19, 20, 21, or all of: V at position 5; S at position 7; A at position 9; V at position 11; K at position 12; S at position 14; A at position 16; K at position 19; V at position 20; R at position 38; Q at position 39; A at position 40; Q at position 43; R at position 67; V at position 68; I at position 71; R at position 72; D at position 73; T at position 74; T at position 76; T at position 84; and/or L at position 113, numbered according to SEQ ID NO: 21; and (ii) the VL comprises 1, 2, 3, 4, 5, 6, 7, 8, 9, 10, 11, 12, or all of: I at position 2; S at position 7; S at position 12; T at position 14; P at position 15; Q at position 17; P at position 18; Q at position 50; S at position 68; V at position 88; Y at position 92; Q at position 105; and/or V at position 109, numbered according to SEQ ID NO: 93.

In yet another aspect, the present disclosure provides n antibody that binds to human tau, which comprises a heavy chain variable region (VH) comprising a heavy chain complementary determining region 1 (HC CDR1), a heavy chain complementary determining region 2 (HC CDR2), and a heavy chain complementary determining region 3 (HC CDR3) and/or a light chain variable region (VL) comprising a light chain complementary determining region 1 (LC CDR1), a light chain complementary determining region 2 (LC CDR2), and a light chain complementary determining region 3 (LC CDR3), wherein: (a) the HC CDR1, HC CDR2, HC CDR3, LC CDR1, LC CDR2, and LC CDR3 comprise the amino acid sequence of SEQ ID NO: 64, 1145, 1167, 1146, 529, and 571, respectively; (b) the HC CDR1, HC CDR2, HC CDR3, LC CDR1, LC CDR2, and LC CDR3 comprise the amino acid sequence of SEQ ID NO: 1144, 1145, 410, 1146, 529, and 571, respectively; (c) the HC CDR1, HC CDR2, HC CDR3, LC CDR1, LC CDR2, and LC CDR3 comprise the amino acid sequence of SEQ ID NO: 1165, SEQ ID NO: 1166, SEQ ID NO: 1167, SEQ ID NO: 473, RVS, and SEQ ID NO: 571, respectively; or (d) the HC CDR1, HC CDR2, HC CDR3, LC CDR1, LC CDR2, and LC CDR3 comprise the amino acid sequence of SEQ ID NO: 314, 341, 410, 1154, 529, and 571, respectively; and wherein: (i) the VH comprises the amino acid sequence of SEQ ID NO: 69, or an amino acid sequence at least 86% (e.g., at least 90, 92, 95, 96, 97, 98, or 99%) identical to the amino acid sequence of SEQ ID NO: 69; and/or (ii) the VL comprises the amino acid sequence of SEQ ID NO: 73, or an amino acid sequence at least 91% (e.g., at least 92, 95, 96, 97, 98, or 99%) identical to the amino acid sequence of SEQ ID NO: 73.

In yet another aspect, the present disclosure provides an antibody that binds to human tau, which comprises a heavy chain variable region (VH) comprising the amino acid sequence of SEQ ID NO: 69, and a light chain variable region (VL) comprising the amino acid sequence of SEQ ID NO: 73.

In yet another aspect, the present disclosure provides an antibody that binds to human tau, which comprises a heavy chain (HC) comprising the amino acid sequence of SEQ ID NO: 172, and a light chain (LC) comprising the amino acid sequence of SEQ ID NO: 176.

In yet another aspect, the present disclosure provides a nucleic acid encoding an antibody that binds to tau (e.g., an anti-tau antibody described herein).

In yet another aspect, the present disclosure provides vector encoding an antibody that binds to tau (e.g., an anti-tau antibody described herein).

In another aspect, the present disclosure provides a host cell comprising an antibody that binds to tau (e.g., an anti-tau antibody described herein) or a nucleic acid encoding an antibody that binds to tau (e.g., an anti-tau antibody described herein). In some embodiments, the host cell is a mammalian cell, an insect cell, or a bacterial cell.

In yet another aspect, the present disclosure provides a method of producing an antibody that binds to tau (e.g., an anti-tau antibody described herein). In some embodiments, the method comprising culturing a host cell comprising an anti-tau antibody described herein under conditions suitable for gene expression.

In yet another aspect, the present disclosure provides a viral genome comprising a promoter operably linked to a nucleic acid encoding an antibody that binds to tau (e.g., an anti-tau antibody described herein). In some embodiments, the viral genome further comprises an internal terminal repeat (ITR) sequence (e.g., an ITR region described herein), an enhancer (e.g., an enhancer described herein), an intron region (e.g., an intron region described herein) and/or an exon region (e.g., an exon region described herein), a poly A signal region (e.g., a poly A signal sequence described herein), and/or an encoded miR binding site.

In yet another aspect, the present disclosure provides an isolated, e.g., recombinant, AAV particle comprising a capsid protein and a viral genome comprising nucleic acid encoding an antibody that binds to tau (e.g., an anti-tau antibody described herein). In some embodiments, the capsid protein comprises an AAV capsid protein, e.g., a wild-type AAV capsid protein or a functional variant thereof. In some embodiments, the capsid protein comprises, or is chosen from, an AAV9 capsid protein, an AAV5 capsid protein, a VOY101 capsid protein, a PHP.N capsid protein, or a PHP.B capsid protein, or a functional variant thereof.

In yet another aspect, the present disclosure provides method of delivering an exogenous antibody that binds to tau (e.g., an anti-tau antibody described herein), to a subject. In some embodiments, the subject has or is diagnosed as having a neurological disorder, a tauopathy, and/or a disease associated with expression of tau. In some embodiments, the disease associated with Tau expression, the neurological disorder, or the tauopathy comprises AD, FTDP-17, FTLD, FTD, CTE, PSP, Down's syndrome, Pick's disease, CBD, Corticobasal syndrome, ALS, Prion diseases, CJD, Multiple system atrophy, mild cognitive impairment, Tangle-only dementia, or Progressive subcortical gliosis.

In yet another aspect, the present disclosure provides a method of treating a subject having or being diagnosed as having a neurological disorder, a tauopathy, and/or a disease associated with expression of tau. In some embodiments, the capsid protein comprises an AAV9 capsid protein or variant thereof. In some embodiments, the capsid protein comprises an AAV5 capsid protein or variant thereof. In some embodiments, the disease associated with Tau expression, the neurological disorder, or the tauopathy comprises AD, FTDP-17, FTLD, FTD, CTE, PSP, Down's syndrome, Pick's disease, CBD, Corticobasal syndrome, ALS, Prion diseases, CJD, Multiple system atrophy, mild cognitive impairment, Tangle-only dementia, or Progressive subcortical gliosis.

Those skilled in the art will recognize or be able to ascertain using no more than routine experimentation, many equivalents to the specific embodiments of the invention described herein. Such equivalents are intended to be encompassed by the following enumerated embodiment.

Enumerated Embodiments

1. An antibody that binds to human tau, which comprises:
   (a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;

(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;

(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571;

optionally wherein, the antibody is a humanized antibody.

2. An antibody that binds to human tau, which comprises:

(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;

(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;

(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and wherein:

(i) the VH comprises an amino acid sequence comprising one, two, three, four, five, six, seven, eight, nine, or all of: an amino acid other than Q at position 5, P at position 7, T at position 9, L at position 11, V at position 12, N at position 19, L at position 20, K at position 67, A at position 68, and/or S at position 76, numbered according to SEQ ID NO: 21; and/or (ii) the VL comprises and amino acid sequence comprising one, two, or all of: an amino acid other than D at position 17, Q at position 18, and/or G at position 68, numbered according to SEQ ID NO: 93.

3. An antibody that binds to human tau, which comprises:

(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;

(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;

(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and wherein:
(i) the VH comprises an amino acid sequence comprising one, two, three, four, five, six, seven, eight, or all of: a V at position 5, an S at position 7, an A at position 9, a V at position 11, a K at position 12, a K at position 19, a V at position 20, an R at position 67, and/or a V at position 68, numbered according to SEQ ID NO: 21; and/or
(ii) the VL comprises and amino acid sequence comprising one, two, or all of: Q or E at position 17, P or R at position 18, and/or S at position 68, numbered according to SEQ ID NO: 93.

4. An antibody that binds to human tau, which comprises:
(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;
(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;
(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or
(d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and wherein:
(i) the VH comprises an amino acid sequence at least 86% (e.g., at least 90, 92, 95, 96, 97, 98, or 99%) identical to the amino acid sequence of any one of SEQ ID NOs: 67-71; and/or
(ii) the VL comprises an amino acid sequence at least 91% (e.g., at least 92, 95, 96, 97, 98, or 99%) identical to the amino acid sequence of any one of SEQ ID NOs: 72-76.

5. The antibody of any one of embodiments 1-4, wherein the HC CDR1 comprises the amino acid sequence of SEQ ID NO: 64, the HC CDR2 comprises the amino acid sequence of SEQ ID NO: 1145, the HC CDR3 comprises the amino acid sequence of SEQ ID NO: 1167, the LC CDR1 comprises the amino acid sequence of SEQ ID NO: 1146, the LC CDR2 comprises the amino acid sequence of SEQ ID NO: 529, and the LC CDR3 comprises the amino acid sequence of SEQ ID NO: 571.

6. The antibody of any one of embodiments 1-5, wherein the HC CDR1 comprises the amino acid sequence of SEQ ID NO: 1144, the HC CDR2 comprises the amino acid sequence of SEQ ID NO: 1145, the HC CDR3 comprises the amino acid sequence of SEQ ID NO: 410, the LC CDR1 comprises the amino acid sequence of SEQ ID NO: 1146, the LC CDR2 comprises the amino acid sequence of SEQ ID NO: 529, and the LC CDR3 comprises the amino acid sequence of SEQ ID NO: 571.

7. The antibody of any one of embodiments 1-6, wherein the HC CDR1 comprises the amino acid sequence of SEQ ID NO: 1165, the HC CDR2 comprises the amino acid sequence of SEQ ID NO: 1166, the HC CDR3 comprises the amino acid sequence of SEQ ID NO: 1167, the LC CDR1 comprises the amino acid sequence of SEQ ID NO: 473, the LC CDR2 comprises the amino acid sequence of RVS, and the LC CDR3 comprises the amino acid sequence of SEQ ID NO: 571.

8. The antibody of any one of embodiments 1-7, wherein the HC CDR1 comprises the amino acid sequence of SEQ ID NO: 314, the HC CDR2 comprises the amino acid sequence of SEQ ID NO: 341, the HC CDR3 comprises the amino acid sequence of SEQ ID NO: 410, the LC CDR1 comprises the amino acid sequence of SEQ ID NO: 1154, the LC CDR2 comprises the amino acid sequence of SEQ ID NO: 529, and the LC CDR3 comprises the amino acid sequence of SEQ ID NO: 571.

9. The antibody of any one of embodiments 1-8, wherein the VH comprises an amino acid sequence comprising one, two, three, four, five, six, seven, eight, nine, or all of: an amino acid other than Q at position 5, P at position 7, T at position 9, L at position 11, V at position 12, N at position 19, L at position 20, K at position 67, A at position 68, and/or S at position 76, numbered according to SEQ ID NO: 21.

10. The antibody of any one of embodiments 1-9, wherein the VH comprises:
(a) 1, 2, 3, 4, 5, 6, 7, 8, 9, 10, 11, 12, 13, 14, 15, 16, 17, 18, 19, 20, 21, or all of: an amino acid other than Q at position 5; an amino acid other than Q at position 6; an amino acid other than P at position 7; an amino acid other than T at position 9; an amino acid other than L at position 11; an amino acid other than V at position 12; an amino acid other than S at position 16; an amino acid other than N at position 19; an amino acid other than L at position 20; an amino acid other than I at position 48; an amino acid other than K at position 67; an amino acid other than A at position 68; an amino acid other than L at position 70; an amino acid other than S at position 76; an amino acid other than T at position 77; an amino acid other than V at position 79; an amino acid other than F at position 80; an amino acid other than I at position 81; an amino acid other than Q at position 82; an amino acid other than T at position 87; an amino acid other than S at position 91; and/or an amino acid other than S at position 113, numbered according to SEQ ID NO: 21;

(b) 1, 2, 3, 4, 5, 6, 7, 8, 9, 10, 11, 12, 13, 14, 15, 16, 17, 18, 19, 20, or all of: an amino acid other than Q at position 5; an amino acid other than P at position 7; an amino acid other than T at position 9; an amino acid other than L at position 11; an amino acid other than V at position 12; an amino acid other than S at position 16; an amino acid other than N at position 19; an amino acid other than L at position 20; an amino acid other than K at position 38; an amino acid other than K at position 67; an amino acid other than A at position 68; an amino acid other than L at position 70; an amino acid other than S at position 76; an amino acid other than T at position 77; an amino acid other than V at position 79; an amino acid other than F at position 80; an amino acid other than I at position 81; an amino acid other than Q at position 82; an amino acid other than T at position 87; an amino acid other than E at position 89; and/or an amino acid other than S at position 113, numbered according to SEQ ID NO: 21;

(c) 1, 2, 3, 4, 5, 6, 7, 8, 9, 10, 11, 12, 13, 14, 15, 16, 17, 18, 19, 20, 21, or all of: an amino acid other than Q at position 5; an amino acid other than P at position 7; an amino acid other than T at position 9; an amino acid other than L at position 11; an amino acid other than V at position 12; an amino acid other than P at position 14; an amino acid other than S at position 16; an amino acid other than N at position 19; an amino acid other than L at position 20; an amino acid other than K at position 38; an amino acid other than E at position 39; an amino acid other than R at position 40; an amino acid other than H at position 43; an amino acid other than K at position 67; an amino acid other than A at position 68; an amino acid other than T at position 71; an amino acid other than V at position 72; an amino acid other than H at position 73; an amino acid other than K at position 74; an amino acid other than S at position 76; an amino acid other than S at position 84; and/or an amino acid other than S at position 113, numbered according to SEQ ID NO: 21;

(d) 1, 2, 3, 4, 5, 6, 7, 8, 9, 10, 11, 12, 13, 14, 15, 16, 17, 18, 19, or all of: an amino acid other than Q at position 1; an amino acid other than Q at position 5; an amino acid other than P at position 7; an amino acid other than T at position 9; an amino acid other than L at position 11; an amino acid other than V at position 12; an amino acid other than N at position 19; an amino acid other than L at position 20; an amino acid other than K at position 67; an amino acid other than A at position 68; an amino acid other than L at position 70; an amino acid other than S at position 76; an amino acid other than V at position 79; an amino acid other than F at position 80; an amino acid other than I at position 81; an amino acid other than Q at position 82; an amino acid other than S at position 85; an amino acid other than E at position 89, an amino acid other than S at position 113; and/or an amino acid other than T at position 115, numbered according to SEQ ID NO: 21; or (e) 1, 2, 3, 4, 5, 6, 7, 8, 9, 10, 11, 12, 13, 14, 15, 16 or all of: an amino acid other than Q at position 5; an amino acid other than P at position 7; an amino acid other than T at position 9; an amino acid other than L at position 11; an amino acid other than V at position 12; an amino acid other than S at position 16; an amino acid other than N at position 19; an amino acid other than L at position 20; an amino acid other than H at position 43; an amino acid other than I at position 48; an amino acid other than K at position 67; an amino acid other than A at position 68; an amino acid other than L at position 70; an amino acid other than S at position 76; an amino acid other than T at position 77; an amino acid other than T at position 87; and/or an amino acid other than S at position 91, numbered according to SEQ ID NO: 21.

11. The antibody of any one of embodiments 1-10, wherein the VH comprises 1, 2, 3, 4, 5, 6, 7, 8, 9, 10, 11, 12, 13, 14, 15, 16, 17, 18, 19, 20, 21, or all of: an amino acid other than Q at position 5; an amino acid other than P at position 7; an amino acid other than T at position 9; an amino acid other than L at position 11; an amino acid other than V at position 12; an amino acid other than P at position 14; an amino acid other than S at position 16; an amino acid other than N at position 19; an amino acid other than L at position 20; an amino acid other than K at position 38; an amino acid other than E at position 39; an amino acid other than R at position 40; an amino acid other than H at position 43; an amino acid other than K at position 67; an amino acid other than A at position 68; an amino acid other than T at position 71; an amino acid other than V at position 72; an amino acid other than H at position 73; an amino acid other than K at position 74; an amino acid other than S at position 76; an amino acid other than S at position 84; and/or an amino acid other than S at position 113, numbered according to SEQ ID NO: 21.

12. The antibody of any one of embodiments 1-10, wherein the VH comprises 1, 2, 3, 4, 5, 6, 7, 8, 9, 10, 11, 12, 13, 14, 15, 16, 17, 18, 19, 20, 21, or all of: an amino acid other than Q at position 5; an amino acid other than Q at position 6; an amino acid other than P at position 7; an amino acid other than T at position 9; an amino acid other than L at position 11; an amino acid other than V at position 12; an amino acid other than S at position 16; an amino acid other than N at position 19; an amino acid other than L at position 20; an amino acid other than I at position 48; an amino acid other than K at position 67; an amino acid other than A at position 68; an amino acid other than L at position 70; an amino acid other than S at position 76; an amino acid other than T at position 77; an amino acid other than V at position 79; an amino acid other than F at position 80; an amino acid other than I at position 81; an amino acid other than Q at position 82; an amino acid other than T at position 87; an amino acid other than S at position 91; and/or an amino acid other than S at position 113, numbered according to SEQ ID NO: 21.

13. The antibody of any one of embodiments 1-10, wherein the VH comprises 1, 2, 3, 4, 5, 6, 7, 8, 9, 10, 11, 12, 13, 14, 15, 16, 17, 18, 19, or all of: an amino acid other than Q at position 1; an amino acid other than Q at position 5; an amino acid other than P at position 7; an amino acid other than T at position 9; an amino acid other than L at position 11; an amino acid other than V at position 12; an amino acid other than N at position 19; an amino acid other than L at position 20; an amino acid other than K at position 67; an amino acid other than A at position 68; an amino acid other than L at position 70; an amino acid other than S at position 76; an amino acid other than V at position 79; an amino acid other than F at position 80; an amino acid other than I at position 81; an amino acid other than Q at position 82; an amino acid other than S at position 85; an amino acid other than E at position 89, an amino acid other than S at position 113; and/or an amino acid other than T at position 115, numbered according to SEQ ID NO: 21.

14. The antibody of any one of embodiments 1-10, wherein the VH comprises 1, 2, 3, 4, 5, 6, 7, 8, 9, 10, 11, 12, 13, 14, 15, 16 or all of: an amino acid other than Q at position 5; an amino acid other than P at position 7; an amino acid other than T at position 9; an amino acid other than L at position 11; an amino acid other than V at position 12; an amino acid other than S at position 16; an amino acid other than N at position 19; an amino acid other than L at position 20; an amino acid other than H at position 43; an amino acid other than I at position 48; an amino acid other than K at position 67; an amino acid other than A at position 68; an amino acid other than L at position 70; an amino acid other than S at position 76; an amino acid other than T at position 77; an amino acid other than T at position 87; and/or an amino acid other than S at position 91, numbered according to SEQ ID NO: 21.

15. The antibody of any one of embodiments 1-14, wherein the VH comprises an amino acid sequence comprising one, two, three, four, five, six, seven, eight, or all of: a V at position 5, an S at position 7, an A at position 9, a V at position 11, a K at position 12, a K at position 19, a V at position 20, an R at position 67, and/or a V at position 68, numbered according to SEQ ID NO: 21

16. The antibody of any one of embodiments 1-15, wherein the VH comprises:
  (a) 1, 2, 3, 4, 5, 6, 7, 8, 9, 10, 11, 12, 13, 14, 15, 16, 17, 18, 19, 20, 21, or all of: V at position 5; E at position 6; S at position 7; A at position 9; V at position 11; K at position 12; A at position 16; K at position 19; V at position 20; M at position 48; R at position 67; V at position 68; I at position 70; A at position 76; S at position 77; A at position 79; Y at position 80; M at position 81; E at position 82; R at position 87; T at position 91; and/or T at position 113, numbered according to SEQ ID NO: 21;
  (b) 1, 2, 3, 4, 5, 6, 7, 8, 9, 10, 11, 12, 13, 14, 15, 16, 17, 18, 19, 20, or all of: V at position 5; S at position 7; A at position 9; V at position 11; K at position 12; A at position 16; K at position 19; V at position 20; R at position 38; R at position 67; V at position 68; M at position 70; I at position 76; S at position 77; A at position 79; Y at position 80; M at position 81; E at position 82; R at position 87; D at position 89; and/or L at position 113, numbered according to SEQ ID NO: 21;
  (c) 1, 2, 3, 4, 5, 6, 7, 8, 9, 10, 11, 12, 13, 14, 15, 16, 17, 18, 19, 20, 21, or all of: V at position 5; S at position 7; A at position 9; V at position 11; K at position 12; S at position 14; A at position 16; K at position 19; V at position 20; R at position 38; Q at position 39; A at position 40; Q at position 43; R at position 67; V at position 68; I at position 71; R at position 72; D at position 73; T at position 74; T at position 76; T at position 84; and/or L at position 113, numbered according to SEQ ID NO: 21;
  (d) 1, 2, 3, 4, 5, 6, 7, 8, 9, 10, 11, 12, 13, 14, 15, 16, 17, 18, 19, or all of: E at position 1; V at position 5; S at position 7; A at position 9; V at position 11; K at position 12; K at position 19; V at position 20; R at position 67; V at position 68; M at position 70; I at position 76; A at position 79; Y at position 80; M at position 81; E at position 82; R at position 85; D at position 89, L at position 113; and/or S at position 115, numbered according to SEQ ID NO: 21; or
  (e) 1, 2, 3, 4, 5, 6, 7, 8, 9, 10, 11, 12, 13, 14, 15, 16 or all of: V at position 5; S at position 7; A at position 9; V at position 11; K at position 12; A at position 16; K at position 19; V at position 20; Q at position 43; M at position 48; R at position 67; V at position 68; M at position 70; T at position 76; S at position 77; R at position 87; and/or T at position 91, numbered according to SEQ ID NO: 21.

17. The antibody of any one of embodiments 1-11, 15, or 16, wherein the VH comprises 1, 2, 3, 4, 5, 6, 7, 8, 9, 10, 11, 12, 13, 14, 15, 16, 17, 18, 19, 20, 21, or all of: V at position 5; S at position 7; A at position 9; V at position 11; K at position 12; S at position 14; A at position 16; K at position 19; V at position 20; R at position 38; Q at position 39; A at position 40; Q at position 43; R at position 67; V at position 68; I at position 71; R at position 72; D at position 73; T at position 74; T at position 76; T at position 84; and/or L at position 113, numbered according to SEQ ID NO: 21.

18. The antibody of any one of embodiments 1-10, 12, 15, or 16, wherein the VH comprises 1, 2, 3, 4, 5, 6, 7, 8, 9, 10, 11, 12, 13, 14, 15, 16, 17, 18, 19, 20, 21, or all of: V at position 5; E at position 6; S at position 7; A at position 9; V at position 11; K at position 12; A at position 16; K at position 19; V at position 20; M at position 48; R at position 67; V at position 68; I at position 70; A at position 76; S at position 77; A at position 79; Y at position 80; M at position 81; E at position 82; R at position 87; T at position 91; and/or T at position 113, numbered according to SEQ ID NO: 21.

19. The antibody of any one of embodiments 1-10, 13, 15, or 16, wherein the VH comprises 1, 2, 3, 4, 5, 6, 7, 8, 9, 10, 11, 12, 13, 14, 15, 16, 17, 18, 19, or all of: E at position 1; V at position 5; S at position 7; A at position 9; V at position 11; K at position 12; K at position 19; V at position 20; R at position 67; V at position 68; M at position 70; I at position 76; A at position 79; Y at position 80; M at position 81; E at position 82; R at position 85; D at position 89, L at position 113; and/or S at position 115, numbered according to SEQ ID NO: 21.

20. The antibody of any one of embodiments 1-10 or 14-16, wherein the VH comprises 1, 2, 3, 4, 5, 6, 7, 8, 9, 10, 11, 12, 13, 14, 15, 16 or all of: V at position 5; S at position 7; A at position 9; V at position 11; K at position 12; A at position 16; K at position 19; V at position 20; Q at position 43; M at position 48; R at position 67; V at position 68; M at position 70; T at position 76; S at position 77; R at position 87; and/or T at position 91, numbered according to SEQ ID NO: 21

21. The antibody of any one of embodiments 1-20, wherein the VL comprises and amino acid sequence comprising one, two, or all of: an amino acid other than D at position 17, Q at position 18, and/or G at position 68, numbered according to SEQ ID NO: 93.

22. The antibody of any one of embodiments 1-21, wherein the VL comprises:
   (a) 1, 2, 3, 4, 5, 6, 7, 8, 9, 10, or all of: an amino acid other than T at position 7; an amino acid other than S at position 14; an amino acid other than D at position 17; an amino acid other than Q at position 18; an amino acid other than L at position 42; an amino acid other than K at position 44; an amino acid other than K at position 50; an amino acid other than G at position 68; an amino acid other than L at position 88; an amino acid other than F at position 92; and/or an amino acid other than G at position 105, numbered according to SEQ ID NO: 93;
   (b) 1, 2, 3, 4, 5, 6, 7, 8, 9, 10, 11, 12, or all of: an amino acid other than V at position 2; an amino acid other than T at position 7; an amino acid other than P at position 12; an amino acid other than S at position 14; an amino acid other than L at position 15; an amino acid other than D at position 17; an amino acid other than Q at position 18; an amino acid other than K at position 50; an amino acid other than G at position 68; an amino acid other than L at position 88; an amino acid other than F at position 92; an amino acid other than G at position 105; and/or an amino acid other than L at position 109, numbered according to SEQ ID NO: 93;
   (c) 1, 2, 3, 4, 5, 6, 7, 8, 9, 10, 11, 12, 13, or all of: an amino acid other than V at position 2; an amino acid other than L at position 11; an amino acid other than T at position 14; an amino acid other than D at position 17; an amino acid other than Q at position 18; an amino acid other than L at position 42; an amino acid other than K at position 44; an amino acid other than S at position 48; an amino acid other than K at position 50; an amino acid other than G at position 68; an amino acid other than S at position 72; an amino acid other than S at position 81; an amino acid other than L at position 88; and/or an amino acid other than G at position 105, numbered according to SEQ ID NO: 93;
   (d) 1, 2, 3, 4, 5, 6, 7, 8, 9, 10, 11, or all of: an amino acid other than V at position 2; an amino acid other than V at position 3; an amino acid other than T at position 7; an amino acid other than S at position 14; an amino acid other than D at position 17; an amino acid other than Q at position 18; an amino acid other than L at position 42; an amino acid other than K at position 44; an amino acid other than K at position 50; an amino acid other than L at position 51; an amino acid other than G at position 68; and/or an amino acid other than L at position 88, numbered according to SEQ ID NO: 93;
   (e) 1, 2, 3, 4, 5, 6, 7, 8, 9, 10, 11, 12, 13, 14, 15, 16, 17, 18, 19, 20, 21, or all of: an amino acid other than D at position 1; an amino acid other than V at position 2; an amino acid other than M at position 4; an amino acid other than T at position 7; an amino acid other than L at position 9; an amino acid other than S at position 10; an amino acid other than P at position 12; an amino acid other than V at position 13; an amino acid other than L at position 15; an amino acid other than D at position 17; an amino acid other than Q at position 18; an amino acid other than S at position 20; an amino acid other than I at position 21; an amino acid other than S at position 48; an amino acid other than V at position 63; an amino acid other than G at position 68; an amino acid other than S at position 72; an amino acid other than K at position 79; an amino acid other than R at position 82; an amino acid other than V at position 83; an amino acid other than A at position 85; and/or an amino acid other than G at position 89, numbered according to SEQ ID NO: 93.

23. The antibody of any one of embodiments 1-22, wherein the VL comprises 1, 2, 3, 4, 5, 6, 7, 8, 9, 10, 11, 12, or all of: an amino acid other than V at position 2; an amino acid other than T at position 7; an amino acid other than P at position 12; an amino acid other than S at position 14; an amino acid other than L at position 15; an amino acid other than D at position 17; an amino acid other than Q at position 18; an amino acid other than K at position 50; an amino acid other than G at position 68; an amino acid other than L at position 88; an amino acid other than F at position 92; an amino acid other than G at position 105; and/or an amino acid other than L at position 109, numbered according to SEQ ID NO: 93.

24. The antibody of any one of embodiments 1-22, wherein the VL comprises 1, 2, 3, 4, 5, 6, 7, 8, 9, 10, or all of: an amino acid other than T at position 7; an amino acid other than S at position 14; an amino acid other than D at position 17; an amino acid other than Q at position 18; an amino acid other than L at position 42; an amino acid other than K at position 44; an amino acid other than K at position 50; an amino acid other than G at position 68; an amino acid other than L at position 88; an amino acid other than F at position 92; and/or an amino acid other than G at position 105, numbered according to SEQ ID NO: 93.

25. The antibody of any one of embodiments 1-22, wherein the VL comprises 1, 2, 3, 4, 5, 6, 7, 8, 9, 10, 11, 12, 13, or all of: an amino acid other than V at position 2; an amino acid other than L at position 11; an amino acid other than T at position 14; an amino acid other than D at position 17; an amino acid other than Q at position 18; an amino acid other than L at position 42; an amino acid other than K at position 44; an amino acid other than S at position 48; an amino acid other than K at position 50; an amino acid other than G at position 68; an amino acid other than S at position 72; an amino acid other than S at position 81; an amino acid other than L at position 88; and/or an amino acid other than G at position 105, numbered according to SEQ ID NO: 93.

26. The antibody of any one of embodiments 1-25, wherein the VL comprises and amino acid sequence comprising one, two, or all of: Q or E at position 17, P or R at position 18, and/or S at position 68, numbered according to SEQ ID NO: 93

27. The antibody of any one of embodiments 1-26, wherein the VL comprises:
   (a) 1, 2, 3, 4, 5, 6, 7, 8, 9, 10, or all of: S at position 7; T at position 14; Q at position 17; P at position 18; Q at position 42; R at position 44; R at position 50;

S at position 68; V at position 88; Y at position 92; and/or Q at position 105, numbered according to SEQ ID NO: 93;
(b) 1, 2, 3, 4, 5, 6, 7, 8, 9, 10, 11, 12, or all of: I at position 2; S at position 7; S at position 12; T at position 14; P at position 15; Q at position 17; P at position 18; Q at position 50; S at position 68; V at position 88; Y at position 92; Q at position 105; and/or V at position 109, numbered according to SEQ ID NO: 93;
(c) 1, 2, 3, 4, 5, 6, 7, 8, 9, 10, 11, 12, 13, or all of: I at position 2; S at position 11; T at position 14; Q at position 17; P at position 18; Q at position 42; R at position 44; P at position 48; R at position 50; S at position 68; A at position 72; N at position 81; V at position 88; and/or Q at position 105, numbered according to SEQ ID NO: 93;
(d) 1, 2, 3, 4, 5, 6, 7, 8, 9, 10, 11, or all of: I at position 2; E at position 3; S at position 7; T at position 14; Q at position 17; P at position 18; Q at position 42; R at position 44; R at position 50; R at position 51; S at position 68; and/or V at position 88, numbered according to SEQ ID NO: 93; or
(e) 1, 2, 3, 4, 5, 6, 7, 8, 9, 10, 11, 12, 13, 14, 15, 16, 17, 18, 19, 20, 21, or all of: E at position 1; I at position 2; L at position 4; S at position 7; A at position 9; T at position 10; S at position 12; L at position 13; P at position 15; E at position 17; R at position 18; T at position 20; L at position 21; A at position 48; I at position 63; S at position 68; P at position 72; T at position 79; S at position 82; L at position 83; P at position 85; and/or A at position 89, numbered according to SEQ ID NO: 93.

28. The antibody of any one of embodiments 1-23, 26, or 27, wherein the VL comprises 1, 2, 3, 4, 5, 6, 7, 8, 9, 10, 11, 12, or all of: I at position 2; S at position 7; S at position 12; T at position 14; P at position 15; Q at position 17; P at position 18; Q at position 50; S at position 68; V at position 88; Y at position 92; Q at position 105; and/or V at position 109, numbered according to SEQ ID NO: 93.

29. The antibody of any one of embodiments 1-22, 24, 26, or 27, wherein the VL comprises 1, 2, 3, 4, 5, 6, 7, 8, 9, 10, or all of: S at position 7; T at position 14; Q at position 17; P at position 18; Q at position 42; R at position 44; R at position 50; S at position 68; V at position 88; Y at position 92; and/or Q at position 105, numbered according to SEQ ID NO: 93.

30. The antibody of any one of embodiments 1-22 or 24-27, wherein the VL comprises 1, 2, 3, 4, 5, 6, 7, 8, 9, 10, 11, 12, 13, or all of: I at position 2; S at position 11; T at position 14; Q at position 17; P at position 18; Q at position 42; R at position 44; P at position 48; R at position 50; S at position 68; A at position 72; N at position 81; V at position 88; and/or Q at position 105, numbered according to SEQ ID NO: 93.

31. The antibody of any one of embodiments 1-30, wherein:
(i) the VH comprises one, two, three, or four framework regions, e.g., one, two, three, or all of a FRH1, FRH2, FRH3, and/or FRH4; optionally wherein the VH comprises from N-terminus to C-terminus, FRH1-CDRH1-FRH2-CDRH2-FRH3-CDRH3-FRH4; and/or
(ii) the VL comprises one, two, three, or four framework regions, e.g., one, two, three, or all of a FRL1, FRL2, FRL3, and/or FRL4; optionally wherein the VL comprises from N terminus to C-terminus, FRL1-CDRL1-FRL2-CDRL2-FRL3-CDRL3-FRL4.

32. The antibody of embodiment 31, wherein:
(a) (i) the FRH1 corresponds to positions 1-25 of a heavy chain variable region, numbered according to any one of SEQ ID NOs: 21 or 67-71; the FRH2 corresponds to positions 36-49, numbered according to any one of SEQ ID NOs: 21 or 67-71; the FRH3 corresponds to positions 67-96, numbered according to any one of SEQ ID NOs: 21 or 67-71; and/or the FRH4 corresponds to positions 108-118, numbered according to any one of SEQ ID NOs: 21 or 67-71; or
(ii) the FRH1 corresponds to positions 1-30 of a heavy chain variable region, numbered according to any one of SEQ ID NOs: 21 or 67-71; the FRH2 corresponds to positions 36-49, numbered according to any one of SEQ ID NOs: 21 or 67-71; the FRH3 corresponds to positions 67-98, numbered according to any one of SEQ ID NOs: 21 or 67-71; and/or the FRH4 corresponds to positions 108-118, numbered according to any one of SEQ ID NOs: 21 or 67-71; and/or
(b) the FRL1 corresponds to positions 1-23 of a light chain variable region, numbered according to any one of SEQ ID NOs: 72-76 or 93; the FRL2 corresponds to positions 40-54 of a light chain variable region, numbered according to any one of SEQ ID NOs: 72-76 or 93; the FRL3 corresponds to positions 62-93 of a light chain variable region, numbered according to any one of SEQ ID NOs: 72-76 or 93; and/or the FRL4 corresponds to positions 103-112, numbered according to any one of SEQ ID NOs: 72-76 or 93.

33. The antibody of any one of the preceding embodiments, wherein
(a) the VH comprises one, two, three, or all of:
(i) a FRH1 comprising amino acids 1-25 or 1-30 of any one of SEQ ID NOs: 67-71 (optionally any one of SEQ ID NOs: 67 or 69-72); an amino acid sequence comprising one, two, three but no more than four modifications (e.g., substitutions, e.g., conservative substitutions) relative to amino acids 1-25 or 1-30 of any one of SEQ ID NOs: 67-71 (optionally any one of SEQ ID NOs: 67 or 69-72); or an amino acid sequence comprising one, two, three, but no more than four different amino acids relative to amino acids 1-25 or 1-30 of any one of SEQ ID NOs: 67-71 (optionally any one of SEQ ID NOs: 67 or 69-72);
(ii) a FRH2 comprising amino acids 36-49 of any one of SEQ ID NOs: 67-71 (optionally any one of SEQ ID NOs: 67 or 69-72); an amino acid sequence comprising one, two, three but no more than four modifications (e.g., substitutions, e.g., conservative substitutions) relative to amino acids 36-49 of any one of SEQ ID NOs: 67-71 (optionally any one of SEQ ID NOs: 67 or 69-72); or an amino acid sequence comprising one, two, three, but no more than four different amino acids relative to amino acids 36-49 of any one of SEQ ID NOs: 67-71 (optionally any one of SEQ ID NOs: 67 or 69-72);
(iii) a FRH3 comprising amino acids 67-96 or 67-98 of any one of SEQ ID NOs: 67-71 (optionally any one of SEQ ID NOs: 67 or 69-72); an amino acid sequence comprising one, two, three but no more than four modifications (e.g., substitutions, e.g., conservative substitutions) relative to amino acids 67-96 or 67-98 of any one of SEQ ID NOs: 67-71 (optionally any one of SEQ ID NOs: 67 or 69-72); or an amino acid sequence comprising one, two, three, but no more than four different amino acids relative to amino acids 67-96 or 67-98 of any one of SEQ ID NOs: 67-71 (optionally any one of SEQ ID NOs: 67 or 69-72); and/or (iv) a FRH4 comprising amino acids 108-118 of any one of SEQ ID NOs: 67-71 (optionally any one of SEQ ID NOs: 67 or 69-72); an amino acid sequence comprising one, two, three but no more than four modifications (e.g., substitutions, e.g., conservative substitutions) relative to amino acids 108-118 of any one of SEQ ID NOs: 67-71 (optionally any one of SEQ ID NOs: 67 or 69-72); or an amino acid sequence comprising one, two, three, but no more than four different amino acids relative to amino acids 108-118 of any one of SEQ ID NOs: 67-71 (optionally any one of SEQ ID NOs: 67 or 69-72); and/or (b) the VL comprises one, two, three or all of:

(i) a FRL1 comprising amino acids 1-23 of any one of SEQ ID NOs: 72-76 (optionally any one of SEQ ID NOs: 72-74); an amino acid sequence comprising one, two, three but no more than four modifications (e.g., substitutions, e.g., conservative substitutions) relative to amino acids 1-23 of any one of SEQ ID NOs: 72-76 (optionally any one of SEQ ID NOs: 72-74); or an amino acid sequence comprising one, two, three but no more than four different amino acids relative to amino acids 1-23 of any one of SEQ ID NOs: 72-76 (optionally any one of SEQ ID NOs: 72-74);

(ii) a FRL2 comprising amino acids 40-54 of any one of SEQ ID NOs: 72-76 (optionally any one of SEQ ID NOs: 72-74); an amino acid sequence comprising one, two, three but no more than four modifications (e.g., substitutions, e.g., conservative substitutions) relative to amino acids 40-54 of any one of SEQ ID NOs: 72-76 (optionally any one of SEQ ID NOs: 72-74); or an amino acid sequence comprising one, two, three but no more than four different amino acids relative to amino acids 40-54 of any one of SEQ ID NOs: 72-76 (optionally any one of SEQ ID NOs: 72-74);

(iii) a FRL3 comprising amino acids 62-93 of any one of SEQ ID NOs: 72-76 (optionally any one of SEQ ID NOs: 72-74); an amino acid sequence comprising one, two, three but no more than four modifications (e.g., substitutions, e.g., conservative substitutions) relative to amino acids 62-93 of any one of SEQ ID NOs: 72-76 (optionally any one of SEQ ID NOs: 72-74); or an amino acid sequence comprising one, two, three but no more than four different amino acids relative to amino acids 62-93 of any one of SEQ ID NOs: 72-76 (optionally any one of SEQ ID NOs: 72-74); and/or (iv) a FRL4 comprising amino acids 103-112 of any one of SEQ ID NOs: 72-76 (optionally any one of SEQ ID NOs: 72-74); an amino acid sequence comprising one, two, three but no more than four modifications (e.g., substitutions, e.g., conservative substitutions) relative to amino acids 103-112 of any one of SEQ ID NOs: 72-76 (optionally any one of SEQ ID NOs: 72-74); or an amino acid sequence comprising one, two, three but no more than four different amino acids relative to amino acids 103-112 of any one of SEQ ID NOs: 72-76 (optionally any one of SEQ ID NOs: 72-74).

34. The antibody of any one of embodiments 1-33, wherein the:
(i) the VH does not comprise one, two, three, or all of a FRH1 comprising amino acids 1-25 or 1-30 of SEQ ID NO: 21; a FRH2 comprising amino acids 36-49 of SEQ ID NO: 21; an FRH3 comprising amino acids 67-96 or 67-98 of SEQ ID NO: 21; and/or a FRH4 comprising amino acids 108-118 of SEQ ID NO: 21; and/or
(ii) the VL does not comprise one, two, three, or all of a FRL1 comprising amino acids 1-23 of SEQ ID NO: 93; a FRL2 comprising amino acids 40-54 of SEQ ID NO: 93; an FRL3 comprising amino acids 62-93 of SEQ ID NO: 93; and/or a FRL4 comprising amino acids 103-112 of SEQ ID NO: 93.

35. The antibody of any one of embodiments 1-34, wherein VH comprises the amino acid sequence of any one of SEQ ID NOs: 67-71; or an amino acid sequence at least 86% (e.g., at least 90, 92, 95, 96, 97, 98, or 99%) identical to the amino acid sequence of any one of SEQ ID NOs: 67-71.

36. The antibody of any one of embodiments 1-35, wherein the VH comprises an amino acid sequence comprising at least one, two, three, four, or five but no more than 16 modifications, e.g., substitutions (e.g., conservative substitutions) relative to the amino acid sequence of any one of SEQ ID NOs: 67-71.

37. The antibody of any one of embodiments 1-36, wherein the VH comprises an amino acid sequence comprising at least one, two, three, four, or five but no more than 16 different amino acids relative to the amino acid sequence of any one of SEQ ID NOs: 67-71.

38. The antibody of any one of embodiments 1-11, 15-17, or 21-37, wherein VH comprises the amino acid sequence of SEQ ID NO: 69; or an amino acid sequence at least 86% (e.g., at least 90, 92, 95, 96, 97, 98, or 99%) identical to the amino acid sequence of SEQ ID NO: 69.

39. The antibody of any one of embodiments 1-11, 15-17, or 21-38, wherein the VH comprises an amino acid sequence comprising at least one, two, three, four, or five but no more than 16 modifications, e.g., substitutions (e.g., conservative substitutions) relative to the amino acid sequence of SEQ ID NO: 69.

40. The antibody of any one of embodiments 1-11, 15-17, or 21-39, wherein the VH comprises an amino acid sequence comprising at least one, two, three, four, or five but no more than 16 different amino acids relative to the amino acid sequence of SEQ ID NO: 69.

41. The antibody of any one of embodiments 1-10, 12, 15, 16, 18 or 21-37, wherein VH comprises:
(i) the amino acid sequence of SEQ ID NO: 67; or an amino acid sequence at least 86% (e.g., at least 90, 92, 95, 96, 97, 98, or 99%) identical to the amino acid sequence of SEQ ID NO: 67;
(ii) an amino acid sequence comprising at least one, two, three, four, or five but no more than 16 modifications, e.g., substitutions (e.g., conservative substitutions) relative to the amino acid sequence of SEQ ID NO: 67; or (iii) an amino acid sequence comprising at least one, two, three, four, or five but no more than 16 different amino acids relative to the amino acid sequence of SEQ ID NO: 67.

42. The antibody of any one of embodiments 1-10, 13, 15, 16, 19, or 21-37, wherein VH comprises:
    (i) the amino acid sequence of SEQ ID NO: 70; or an amino acid sequence at least 86% (e.g., at least 90, 92, 95, 96, 97, 98, or 99%) identical to the amino acid sequence of SEQ ID NO: 70;
    (ii) an amino acid sequence comprising at least one, two, three, four, or five but no more than 16 modifications, e.g., substitutions (e.g., conservative substitutions) relative to the amino acid sequence of SEQ ID NO: 70; or
    (iii) an amino acid sequence comprising at least one, two, three, four, or five but no more than 16 different amino acids relative to the amino acid sequence of SEQ ID NO: 70.

43. The antibody of any one of embodiments 1-10, 15, 16, or 20-37, wherein VH comprises:
    (i) the amino acid sequence of SEQ ID NO: 71; or an amino acid sequence at least 86% (e.g., at least 90, 92, 95, 96, 97, 98, or 99%) identical to the amino acid sequence of SEQ ID NO: 71;
    (ii) an amino acid sequence comprising at least one, two, three, four, or five but no more than 16 modifications, e.g., substitutions (e.g., conservative substitutions) relative to the amino acid sequence of SEQ ID NO: 71; or
    (iii) an amino acid sequence comprising at least one, two, three, four, or five but no more than 16 different amino acids relative to the amino acid sequence of SEQ ID NO: 71.

44. The antibody of any one of embodiments 1-43, wherein VL comprises the amino acid sequence of any one of SEQ ID NOs: 72-76; or an amino acid sequence at least 91% (e.g., at least 92, 95, 96, 97, 98, or 99%) identical to the amino acid sequence of any one of SEQ ID NOs: 72-76.

45. The antibody of any one of embodiments 1-44, wherein the VL comprises an amino acid sequence comprising at least one, two, three, four, or five but no more than 10 modifications, e.g., substitutions (e.g., conservative substitutions) relative to the amino acid sequence of any one of SEQ ID NOs: 72-76.

46. The antibody of any one of embodiments 1-45, wherein the VL comprises an amino acid sequence comprising at least one, two, three, four, or five but no more than 10 different amino acids relative to the amino acid sequence of any one of SEQ ID NOs: 72-76.

47. The antibody of any one of embodiments 1-23, 26-28, or 31-46, wherein VL comprises the amino acid sequence of SEQ ID NO: 73; or an amino acid sequence at least 91% (e.g., at least 92, 95, 96, 97, 98, or 99%) identical to the amino acid sequence of SEQ ID NO: 73.

48. The antibody of any one of embodiments 1-23, 26-28, or 31-47, wherein the VL comprises an amino acid sequence comprising at least one, two, three, four, or five but no more than 10 modifications, e.g., substitutions (e.g., conservative substitutions) relative to the amino acid sequence of SEQ ID NO: 73.

49. The antibody of any one of embodiments 1-23, 26-28, or 31-48, wherein the VL comprises an amino acid sequence comprising at least one, two, three, four, or five but no more than 10 different amino acids relative to the amino acid sequence of SEQ ID NO: 73.

50. The antibody of any one of embodiments 1-22, 24, 26, 27, 29 or 31-46, wherein VL comprises:
    (i) the amino acid sequence of SEQ ID NO: 72; or an amino acid sequence at least 91% (e.g., at least 92, 95, 96, 97, 98, or 99%) identical to the amino acid sequence of SEQ ID NO: 72;
    (ii) an amino acid sequence comprising at least one, two, three, four, or five but no more than 10 modifications, e.g., substitutions (e.g., conservative substitutions) relative to the amino acid sequence of SEQ ID NO: 72;
    (iii) an amino acid sequence comprising at least one, two, three, four, or five but no more than 10 different amino acids relative to the amino acid sequence of SEQ ID NO: 72.

51. The antibody of any one of embodiments 1-22 or 24-27, or 30-46, wherein VL comprises:
    (i) the amino acid sequence of SEQ ID NO: 74; or an amino acid sequence at least 91% (e.g., at least 92, 95, 96, 97, 98, or 99%) identical to the amino acid sequence of SEQ ID NO: 74;
    (ii) an amino acid sequence comprising at least one, two, three, four, or five but no more than 10 modifications, e.g., substitutions (e.g., conservative substitutions) relative to the amino acid sequence of SEQ ID NO: 74;
    (iii) an amino acid sequence comprising at least one, two, three, four, or five but no more than 10 different amino acids relative to the amino acid sequence of SEQ ID NO: 74.

52. The antibody of any one of embodiments 1-51, wherein:
    (a) the VH comprises the amino acid sequence of any one of SEQ ID NOs: 67-71, or an amino acid sequence at least 86% (e.g., at least 90, 92, 95, 96, 97, 98, or 99%) identical to the amino acid sequence of any one of SEQ ID NOs: 67-71; an amino acid sequence comprising at least one, two, three, four, or five but no more than 10 modifications, e.g., substitutions (e.g., conservative substitutions) relative to the amino acid sequence of any one of SEQ ID NOs: 67-71; or an amino acid sequence comprising at least one, two, three, four, or five but no more than 16 different amino acids relative to the amino acid sequence of any one of SEQ ID NOs: 67-71; and
    (b) the VL comprises the amino acid sequence of any one of SEQ ID NOs: 72-76; or an amino acid sequence at least 91% (e.g., at least 92, 95, 96, 97, 98, or 99%) identical to the amino acid sequence of any one of SEQ ID NOs: 72-76; an amino acid sequence comprising at least one, two, three, four, or five but no more than 10 modifications, e.g., substitutions (e.g., conservative substitutions) relative to the amino acid sequence of any one of SEQ ID NOs: 72-76; or an amino acid sequence comprising at least one, two, three, four, or five but no more than 10 different amino acids relative to the amino acid sequence of any one of SEQ ID NOs: 72-76.

53. The antibody of any one of embodiments 1-52, wherein:
    (a) the VH comprises the amino acid sequence of any one of SEQ ID NOs: 67 or 69-71, or an amino acid sequence at least 86% (e.g., at least 90, 92, 95, 96, 97, 98, or 99%) identical to the amino acid sequence of any one of SEQ ID NOs: 67 or 69-71; an amino acid sequence comprising at least one, two, three, four, or five but no more than 10 modifications, e.g., substitutions (e.g., conservative substitutions) relative to the amino acid sequence of any one of SEQ ID NOs: 67 or 69-71; or an amino acid sequence comprising at least one, two, three, four, or five but no more than 16 different amino acids relative to the amino acid sequence of any one of SEQ ID NOs: 67 or 69-71; and (b) the VL comprises the amino acid sequence of any one of SEQ ID NOs: 72-74; or an amino acid sequence at least 91% (e.g., at least 92, 95, 96, 97, 98, or 99%) identical to the amino acid sequence of any one of SEQ ID NOs: 72-74; an amino acid sequence comprising at least one, two, three, four, or five but no more than 10 modifications, e.g., substitutions (e.g., conservative substitutions) relative to the amino acid sequence of any one of SEQ ID NOs: 72-74; or an amino acid sequence comprising at least one, two, three, four, or five but no more than 10 different amino acids relative to the amino acid sequence of any one of SEQ ID NOs: 72-74.

54. The antibody of any one of embodiments 1-53, wherein:
  (a) the VH comprises the amino acid sequence of any one of SEQ ID NOs: 67-71, or an amino acid sequence at least 95%, 96%, 97%, 98%, or 99% identical to the amino acid sequence of any one of SEQ ID NOs: 67-71; and
  (b) the VL comprises the amino acid sequence of any one of SEQ ID NOs: 72-76; or an amino acid sequence at least 95%, 96%, 97%, 98%, or 99% identical to the amino acid sequence of any one of SEQ ID NOs: 72-76.

55. The antibody of any one of embodiments 1-54, wherein:
  (a) the VH comprises the amino acid sequence of any one of SEQ ID NOs: 67 or 69-71, or an amino acid sequence at least 95%, 96%, 97%, 98%, or 99% identical to the amino acid sequence of any one of SEQ ID NOs: 67 or 69-71; and
  (b) the VL comprises the amino acid sequence of any one of SEQ ID NOs: 72-74; or an amino acid sequence at least 95%, 96%, 97%, 98%, or 99% identical to the amino acid sequence of any one of SEQ ID NOs: 72-74.

56. The antibody of any one of embodiments 1-58, wherein:
  (i) the VH comprises the amino acid sequence of SEQ ID NO: 67, or an amino acid sequence at least 86%, 87%, 88%, 90%, 95%, 96%, 97%, 98%, or 99% identical to the amino acid sequence of SEQ ID NO: 67; and the VL comprises the amino acid sequence of SEQ ID NO: 72, or an amino acid sequence at least 91%, 93%, 95%, 96%, 97%, 98%, or 99% identical to the amino acid sequence of SEQ ID NO: 72;
  (ii) the VH comprises the amino acid sequence of SEQ ID NO: 67, or an amino acid sequence at least 86%, 87%, 88%, 90%, 95%, 96%, 97%, 98%, or 99% identical to the amino acid sequence of SEQ ID NO: 67; and the VL comprises the amino acid sequence of SEQ ID NO: 73, or an amino acid sequence at least 91%, 93%, 95%, 96%, 97%, 98%, or 99% identical to the amino acid sequence of SEQ ID NO: 73;
  (iii) the VH comprises the amino acid sequence of SEQ ID NO: 67, or an amino acid sequence at least 86%, 87%, 88%, 90%, 95%, 96%, 97%, 98%, or 99% identical to the amino acid sequence of SEQ ID NO: 67; and the VL comprises the amino acid sequence of SEQ ID NO: 74, or an amino acid sequence at least 91%, 93%, 95%, 96%, 97%, 98%, or 99% identical to the amino acid sequence of SEQ ID NO: 74;
  (iv) the VH comprises the amino acid sequence of SEQ ID NO: 67, or an amino acid sequence at least 86%, 87%, 88%, 90%, 95%, 96%, 97%, 98%, or 99% identical to the amino acid sequence of SEQ ID NO: 67; and the VL comprises the amino acid sequence of SEQ ID NO: 75, or an amino acid sequence at least 91%, 93%, 95%, 96%, 97%, 98%, or 99% identical to the amino acid sequence of SEQ ID NO: 75;
  (v) the VH comprises the amino acid sequence of SEQ ID NO: 67, or an amino acid sequence at least 86%, 87%, 88%, 90%, 95%, 96%, 97%, 98%, or 99% identical to the amino acid sequence of SEQ ID NO: 67; and the VL comprises the amino acid sequence of SEQ ID NO: 76, or an amino acid sequence at least 91%, 93%, 95%, 96%, 97%, 98%, or 99% identical to the amino acid sequence of SEQ ID NO: 76;
  (vi) the VH comprises the amino acid sequence of SEQ ID NO: 68, or an amino acid sequence at least 86%, 87%, 88%, 90%, 95%, 96%, 97%, 98%, or 99% identical to the amino acid sequence of SEQ ID NO: 68; and the VL comprises the amino acid sequence of SEQ ID NO: 72, or an amino acid sequence at least 91%, 93%, 95%, 96%, 97%, 98%, or 99% identical to the amino acid sequence of SEQ ID NO: 72;
  (vii) the VH comprises the amino acid sequence of SEQ ID NO: 68, or an amino acid sequence at least 86%, 87%, 88%, 90%, 95%, 96%, 97%, 98%, or 99% identical to the amino acid sequence of SEQ ID NO: 68; and the VL comprises the amino acid sequence of SEQ ID NO: 73, or an amino acid sequence at least 91%, 93%, 95%, 96%, 97%, 98%, or 99% identical to the amino acid sequence of SEQ ID NO: 73;
  (viii) the VH comprises the amino acid sequence of SEQ ID NO: 68, or an amino acid sequence at least 86%, 87%, 88%, 90%, 95%, 96%, 97%, 98%, or 99% identical to the amino acid sequence of SEQ ID NO: 68; and the VL comprises the amino acid sequence of SEQ ID NO: 74, or an amino acid sequence at least 91%, 93%, 95%, 96%, 97%, 98%, or 99% identical to the amino acid sequence of SEQ ID NO: 74;
  (ix) the VH comprises the amino acid sequence of SEQ ID NO: 68, or an amino acid sequence at least 86%, 87%, 88%, 90%, 95%, 96%, 97%, 98%, or 99% identical to the amino acid sequence of SEQ ID NO: 68; and the VL comprises the amino acid sequence of SEQ ID NO: 75, or an amino acid sequence at least 91%, 93%, 95%, 96%, 97%, 98%, or 99% identical to the amino acid sequence of SEQ ID NO: 75;
  (x) the VH comprises the amino acid sequence of SEQ ID NO: 68, or an amino acid sequence at least 86%, 87%, 88%, 90%, 95%, 96%, 97%, 98%, or 99% identical to the amino acid sequence of SEQ ID NO: 68; and the VL comprises the amino acid sequence of SEQ ID NO: 76, or an amino acid sequence at least 91%, 93%, 95%, 96%, 97%, 98%, or 99% identical to the amino acid sequence of SEQ ID NO: 76;
  (xi) the VH comprises the amino acid sequence of SEQ ID NO: 69, or an amino acid sequence at least 86%, 87%, 88%, 90%, 95%, 96%, 97%, 98%, or 99% identical to the amino acid sequence of SEQ ID NO: 69; and the VL comprises the amino acid sequence of SEQ ID NO: 72, or an amino acid sequence at least 91%, 93%, 95%, 96%, 97%, 98%, or 99% identical to the amino acid sequence of SEQ ID NO: 72;

(xii) the VH comprises the amino acid sequence of SEQ ID NO: 69, or an amino acid sequence at least 86%, 87%, 88%, 90%, 95%, 96%, 97%, 98%, or 99% identical to the amino acid sequence of SEQ ID NO: 69; and the VL comprises the amino acid sequence of SEQ ID NO: 73, or an amino acid sequence at least 91%, 93%, 95%, 96%, 97%, 98%, or 99% identical to the amino acid sequence of SEQ ID NO: 73;

(xiii) the VH comprises the amino acid sequence of SEQ ID NO: 69, or an amino acid sequence at least 86%, 87%, 88%, 90%, 95%, 96%, 97%, 98%, or 99% identical to the amino acid sequence of SEQ ID NO: 69; and the VL comprises the amino acid sequence of SEQ ID NO: 74, or an amino acid sequence at least 91%, 93%, 95%, 96%, 97%, 98%, or 99% identical to the amino acid sequence of SEQ ID NO: 74;

(xiv) the VH comprises the amino acid sequence of SEQ ID NO: 69, or an amino acid sequence at least 86%, 87%, 88%, 90%, 95%, 96%, 97%, 98%, or 99% identical to the amino acid sequence of SEQ ID NO: 69; and the VL comprises the amino acid sequence of SEQ ID NO: 75, or an amino acid sequence at least 91%, 93%, 95%, 96%, 97%, 98%, or 99% identical to the amino acid sequence of SEQ ID NO: 75;

(xv) the VH comprises the amino acid sequence of SEQ ID NO: 69, or an amino acid sequence at least 86%, 87%, 88%, 90%, 95%, 96%, 97%, 98%, or 99% identical to the amino acid sequence of SEQ ID NO: 69; and the VL comprises the amino acid sequence of SEQ ID NO: 76, or an amino acid sequence at least 91%, 93%, 95%, 96%, 97%, 98%, or 99% identical to the amino acid sequence of SEQ ID NO: 76;

(xvi) the VH comprises the amino acid sequence of SEQ ID NO: 70, or an amino acid sequence at least 86%, 87%, 88%, 90%, 95%, 96%, 97%, 98%, or 99% identical to the amino acid sequence of SEQ ID NO: 70; and the VL comprises the amino acid sequence of SEQ ID NO: 72, or an amino acid sequence at least 91%, 93%, 95%, 96%, 97%, 98%, or 99% identical to the amino acid sequence of SEQ ID NO: 72;

(xvii) the VH comprises the amino acid sequence of SEQ ID NO: 70, or an amino acid sequence at least 86%, 87%, 88%, 90%, 95%, 96%, 97%, 98%, or 99% identical to the amino acid sequence of SEQ ID NO: 70; and the VL comprises the amino acid sequence of SEQ ID NO: 73, or an amino acid sequence at least 91%, 93%, 95%, 96%, 97%, 98%, or 99% identical to the amino acid sequence of SEQ ID NO: 73;

(xviii) the VH comprises the amino acid sequence of SEQ ID NO: 70, or an amino acid sequence at least 86%, 87%, 88%, 90%, 95%, 96%, 97%, 98%, or 99% identical to the amino acid sequence of SEQ ID NO: 70; and the VL comprises the amino acid sequence of SEQ ID NO: 74, or an amino acid sequence at least 91%, 93%, 95%, 96%, 97%, 98%, or 99% identical to the amino acid sequence of SEQ ID NO: 74;

(xix) the VH comprises the amino acid sequence of SEQ ID NO: 70, or an amino acid sequence at least 86%, 87%, 88%, 90%, 95%, 96%, 97%, 98%, or 99% identical to the amino acid sequence of SEQ ID NO: 70; and the VL comprises the amino acid sequence of SEQ ID NO: 75, or an amino acid sequence at least 91%, 93%, 95%, 96%, 97%, 98%, or 99% identical to the amino acid sequence of SEQ ID NO: 75;

(xx) the VH comprises the amino acid sequence of SEQ ID NO: 70, or an amino acid sequence at least 86%, 87%, 88%, 90%, 95%, 96%, 97%, 98%, or 99% identical to the amino acid sequence of SEQ ID NO: 70; and the VL comprises the amino acid sequence of SEQ ID NO: 76, or an amino acid sequence at least 91%, 93%, 95%, 96%, 97%, 98%, or 99% identical to the amino acid sequence of SEQ ID NO: 76;

(xxi) the VH comprises the amino acid sequence of SEQ ID NO: 71, or an amino acid sequence at least 86%, 87%, 88%, 90%, 95%, 96%, 97%, 98%, or 99% identical to the amino acid sequence of SEQ ID NO: 71; and the VL comprises the amino acid sequence of SEQ ID NO: 72, or an amino acid sequence at least 91%, 93%, 95%, 96%, 97%, 98%, or 99% identical to the amino acid sequence of SEQ ID NO: 72;

(xxii) the VH comprises the amino acid sequence of SEQ ID NO: 71, or an amino acid sequence at least 86%, 87%, 88%, 90%, 95%, 96%, 97%, 98%, or 99% identical to the amino acid sequence of SEQ ID NO: 71; and the VL comprises the amino acid sequence of SEQ ID NO: 73, or an amino acid sequence at least 91%, 93%, 95%, 96%, 97%, 98%, or 99% identical to the amino acid sequence of SEQ ID NO: 73;

(xxiii) the VH comprises the amino acid sequence of SEQ ID NO: 71, or an amino acid sequence at least 86%, 87%, 88%, 90%, 95%, 96%, 97%, 98%, or 99% identical to the amino acid sequence of SEQ ID NO: 71; and the VL comprises the amino acid sequence of SEQ ID NO: 74, or an amino acid sequence at least 91%, 93%, 95%, 96%, 97%, 98%, or 99% identical to the amino acid sequence of SEQ ID NO: 74;

(xxiv) the VH comprises the amino acid sequence of SEQ ID NO: 71, or an amino acid sequence at least 86%, 87%, 88%, 90%, 95%, 96%, 97%, 98%, or 99% identical to the amino acid sequence of SEQ ID NO: 71; and the VL comprises the amino acid sequence of SEQ ID NO: 75, or an amino acid sequence at least 91%, 93%, 95%, 96%, 97%, 98%, or 99% identical to the amino acid sequence of SEQ ID NO: 75; or (xv) the VH comprises the amino acid sequence of SEQ ID NO: 71, or an amino acid sequence at least 86%, 87%, 88%, 90%, 95%, 96%, 97%, 98%, or 99% identical to the amino acid sequence of SEQ ID NO: 71; and the VL comprises the amino acid sequence of SEQ ID NO: 76, or an amino acid sequence at least 91%, 93%, 95%, 96%, 97%, 98%, or 99% identical to the amino acid sequence of SEQ ID NO: 76.

57. The antibody of any one of embodiments 1-11, 15-17, 21-23, 26-28, 31-38, 44-49, or 52-56, wherein:

(i) the VH comprises the amino acid sequence of SEQ ID NO: 69, or an amino acid sequence at least 86%, 87%, 88%, 90%, 95%, 96%, 97%, 98%, or 99% identical to the amino acid sequence of SEQ ID NO: 69; an amino acid sequence comprising at least one, two, three, four, or five but no more than 10 modifications, e.g., substitutions (e.g., conservative substitutions) relative to the amino acid sequence of SEQ ID NO: 69; or an amino acid sequence comprising at least one, two, three, four, or five but no more than 16 different amino acids relative to the amino acid sequence of any one of SEQ ID NO: 69; and (ii) the VL comprises the amino acid sequence of SEQ ID NO: 73, or an amino acid sequence at least 91%, 93%, 95%, 96%, 97%, 98%, or 99% identical to the amino acid sequence of SEQ ID NO: 73; an amino acid sequence comprising at least one, two, three, four, or five but no more than 10 modifications, e.g., substitutions (e.g., conservative substitutions) relative to the amino acid sequence of SEQ ID NO: 73; or an amino acid sequence comprising at least one, two, three, four, or five but no more than 16 different amino acids relative to the amino acid sequence of any one of SEQ ID NO: 73.

58. The antibody of any one of embodiments 1-11, 15-17, 21-23, 26-28, 31-38, 44-49, or 52-57, wherein the VH comprises the amino acid sequence of SEQ ID NO: 69 and the VL comprises the amino acid sequence of SEQ ID NO: 73.

59. The antibody of any one of embodiments 1-10, 12, 15, 16, 18, 21, 22, 24, 26, 27, 29, 31-37, 41, 44-46, 50, or 52-56, wherein:
    (i) the VH comprises the amino acid sequence of SEQ ID NO: 67, or an amino acid sequence at least 86%, 87%, 88%, 90%, 95%, 96%, 97%, 98%, or 99% identical to the amino acid sequence of SEQ ID NO: 67; an amino acid sequence comprising at least one, two, three, four, or five but no more than 10 modifications, e.g., substitutions (e.g., conservative substitutions) relative to the amino acid sequence of SEQ ID NO: 67; or an amino acid sequence comprising at least one, two, three, four, or five but no more than 16 different amino acids relative to the amino acid sequence of any one of SEQ ID NO: 67; and
    (ii) the VL comprises the amino acid sequence of SEQ ID NO: 72, or an amino acid sequence at least 91%, 93%, 95%, 96%, 97%, 98%, or 99% identical to the amino acid sequence of SEQ ID NO: 72; an amino acid sequence comprising at least one, two, three, four, or five but no more than 10 modifications, e.g., substitutions (e.g., conservative substitutions) relative to the amino acid sequence of SEQ ID NO: 72; or an amino acid sequence comprising at least one, two, three, four, or five but no more than 16 different amino acids relative to the amino acid sequence of any one of SEQ ID NO: 72.

60. The antibody of any one of embodiments 1-10, 13, 15, 16, 19, 21, 22, 24, 26, 27, 29, 31-37, 42, 44-46, 50, or 52-56, wherein:
    (i) the VH comprises the amino acid sequence of SEQ ID NO: 70, or an amino acid sequence at least 86%, 87%, 88%, 90%, 95%, 96%, 97%, 98%, or 99% identical to the amino acid sequence of SEQ ID NO: 70; an amino acid sequence comprising at least one, two, three, four, or five but no more than 10 modifications, e.g., substitutions (e.g., conservative substitutions) relative to the amino acid sequence of SEQ ID NO: 70; or an amino acid sequence comprising at least one, two, three, four, or five but no more than 16 different amino acids relative to the amino acid sequence of any one of SEQ ID NO: 70; and
    (ii) the VL comprises the amino acid sequence of SEQ ID NO: 72, or an amino acid sequence at least 91%, 93%, 95%, 96%, 97%, 98%, or 99% identical to the amino acid sequence of SEQ ID NO: 72; an amino acid sequence comprising at least one, two, three, four, or five but no more than 10 modifications, e.g., substitutions (e.g., conservative substitutions) relative to the amino acid sequence of SEQ ID NO: 72; or an amino acid sequence comprising at least one, two, three, four, or five but no more than 16 different amino acids relative to the amino acid sequence of any one of SEQ ID NO: 72.

61. The antibody of any one of embodiments 1-10, 14-16, 20-23, 31-37, 43-49, or 52-56, wherein:
    (i) the VH comprises the amino acid sequence of SEQ ID NO: 71, or an amino acid sequence at least 86%, 87%, 88%, 90%, 95%, 96%, 97%, 98%, or 99% identical to the amino acid sequence of SEQ ID NO: 71; an amino acid sequence comprising at least one, two, three, four, or five but no more than 10 modifications, e.g., substitutions (e.g., conservative substitutions) relative to the amino acid sequence of SEQ ID NO: 71; or an amino acid sequence comprising at least one, two, three, four, or five but no more than 16 different amino acids relative to the amino acid sequence of any one of SEQ ID NO: 71; and
    (ii) the VL comprises the amino acid sequence of SEQ ID NO: 73, or an amino acid sequence at least 91%, 93%, 95%, 96%, 97%, 98%, or 99% identical to the amino acid sequence of SEQ ID NO: 73; an amino acid sequence comprising at least one, two, three, four, or five but no more than 10 modifications, e.g., substitutions (e.g., conservative substitutions) relative to the amino acid sequence of SEQ ID NO: 73; or an amino acid sequence comprising at least one, two, three, four, or five but no more than 16 different amino acids relative to the amino acid sequence of any one of SEQ ID NO: 73.

62. The antibody of any one of embodiments 1-10, 14-16, 20-22, 25-27, 30-37, 43-46, or 51-56, wherein:
    (i) the VH comprises the amino acid sequence of SEQ ID NO: 71, or an amino acid sequence at least 86%, 87%, 88%, 90%, 95%, 96%, 97%, 98%, or 99% identical to the amino acid sequence of SEQ ID NO: 71; an amino acid sequence comprising at least one, two, three, four, or five but no more than 10 modifications, e.g., substitutions (e.g., conservative substitutions) relative to the amino acid sequence of SEQ ID NO: 71; or an amino acid sequence comprising at least one, two, three, four, or five but no more than 16 different amino acids relative to the amino acid sequence of any one of SEQ ID NO: 71; and
    (ii) the VL comprises the amino acid sequence of SEQ ID NO: 74, or an amino acid sequence at least 91%, 93%, 95%, 96%, 97%, 98%, or 99% identical to the amino acid sequence of SEQ ID NO: 74; an amino acid sequence comprising at least one, two, three, four, or five but no more than 10 modifications, e.g., substitutions (e.g., conservative substitutions) relative to the amino acid sequence of SEQ ID NO: 74; or an amino acid sequence comprising at least one, two, three, four, or five but no more than 16 different amino acids relative to the amino acid sequence of any one of SEQ ID NO: 74.

63. The antibody of any one of embodiments 1-62, wherein:
  (i) the nucleotide sequence encoding the VH comprises the nucleotide sequence of any one of SEQ ID NOs: 156-160, or a nucleotide sequence at least 80% (e.g., at least 85%, 87%, 90%, 91%, 95%, 96%, 97%, 98%, or 99%) identical thereto; and/or
  (ii) the nucleotide sequence encoding the VL comprises the nucleotide sequence of any one of SEQ ID NOs: 161-165; or a nucleotide sequence at least 80% (e.g., at least 85%, 87%, 90%, 91%, 95%, 96%, 97%, 98%, or 99%) identical thereto.

64. The antibody of any one of embodiments 1-63, wherein:
  (i) the nucleotide sequence encoding the VH comprises the nucleotide sequence of any one of SEQ ID NOs: 156 or 158-160, or a nucleotide sequence at least 80% (e.g., at least 85%, 87%, 90%, 91%, 95%, 96%, 97%, 98%, or 99%) identical thereto; and/or
  (ii) the nucleotide sequence encoding the VL comprises the nucleotide sequence of any one of SEQ ID NOs: 161-163; or a nucleotide sequence at least 80% (e.g., at least 85%, 87%, 90%, 91%, 95%, 96%, 97%, 98%, or 99%) identical thereto.

65. The antibody of any one of embodiments 1-11, 15-17, 21-23, 26-28, 31-38, 44-49, 52-58, 63, or 64, wherein:
  (i) the nucleotide sequence encoding the VH comprises the nucleotide sequence of SEQ ID NO: 158, or a nucleotide sequence at least 80% (e.g., at least 85%, 87%, 90%, 91%, 95%, 96%, 97%, 98%, or 99%) identical thereto; and/or
  (ii) the nucleotide sequence encoding the VL comprises the nucleotide sequence of any one of SEQ ID NO: 162; or a nucleotide sequence at least 80% (e.g., at least 85%, 87%, 90%, 91%, 95%, 96%, 97%, 98%, or 99%) identical thereto.

66. The antibody of any one of embodiments 1-10, 12, 15, 16, 18, 21, 22, 24, 26, 27, 29, 31-37, 41, 44-46, 50, 52-56, 59, 63, or 64, wherein:
  (i) the nucleotide sequence encoding the VH comprises the nucleotide sequence of SEQ ID NO: 156, or a nucleotide sequence at least 80% (e.g., at least 85%, 87%, 90%, 91%, 95%, 96%, 97%, 98%, or 99%) identical thereto; and/or
  (ii) the nucleotide sequence encoding the VL comprises the nucleotide sequence of any one of SEQ ID NO: 161; or a nucleotide sequence at least 80% (e.g., at least 85%, 87%, 90%, 91%, 95%, 96%, 97%, 98%, or 99%) identical thereto.

67. The antibody of any one of embodiments 1-10, 13, 15, 16, 19, 21, 22, 24, 26, 27, 29, 31-37, 42, 44-46, 50, 52-56, 60, 63, or 64, wherein:
  (i) the nucleotide sequence encoding the VH comprises the nucleotide sequence of SEQ ID NO: 159, or a nucleotide sequence at least 80% (e.g., at least 85%, 87%, 90%, 91%, 95%, 96%, 97%, 98%, or 99%) identical thereto; and/or
  (ii) the nucleotide sequence encoding the VL comprises the nucleotide sequence of any one of SEQ ID NO: 161; or a nucleotide sequence at least 80% (e.g., at least 85%, 87%, 90%, 91%, 95%, 96%, 97%, 98%, or 99%) identical thereto.

68. The antibody of any one of embodiments 1-10, 14-16, 20-23, 25-27, 30-37, 43-49, 51-56, 61-64, wherein:
  (i) the nucleotide sequence encoding the VH comprises the nucleotide sequence of SEQ ID NO: 160, or a nucleotide sequence at least 80% (e.g., at least 85%, 87%, 90%, 91%, 95%, 96%, 97%, 98%, or 99%) identical thereto; and/or
  (ii) the nucleotide sequence encoding the VL comprises the nucleotide sequence of any one of SEQ ID NO: 162 or 163; or a nucleotide sequence at least 80% (e.g., at least 85%, 87%, 90%, 91%, 95%, 96%, 97%, 98%, or 99%) identical thereto.

69. The antibody of any one of the preceding embodiments, which does not comprise the amino acid sequence of SEQ ID NO: 21 and/or the amino acid sequence of SEQ ID NO: 93.

70. An antibody that binds to human tau, which comprises:
  (a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;
  (b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;
  (c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or
  (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and
  wherein:
  (i) the VH comprises 1, 2, 3, 4, 5, 6, 7, 8, 9, 10, 11, 12, 13, 14, 15, 16, 17, 18, 19, 20, 21, or all of: V at position 5; S at position 7; A at position 9; V at position 11; K at position 12; S at position 14; A at position 16; K at position 19; V at position 20; R at position 38; Q at position 39; A at position 40; Q at position 43; R at position 67; V at position 68; I at position 71; R at position 72; D at position 73; T at position 74; T at position 76; T at position 84; and/or L at position 113, numbered according to SEQ ID NO: 21; and
(ii) the VL comprises 1, 2, 3, 4, 5, 6, 7, 8, 9, 10, 11, 12, or all of: I at position 2; S at position 7; S at position 12; T at position 14; P at position 15; Q at position 17; P at position 18; Q at position 50; S at position 68; V at position 88; Y at position 92; Q at position 105; and/or V at position 109, numbered according to SEQ ID NO: 93.

71. An antibody that binds to human tau, which comprises:
(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;
(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;
(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or
(d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and
wherein:
(i) the VH comprises the amino acid sequence of SEQ ID NO: 69, or an amino acid sequence at least 86% (e.g., at least 90, 92, 95, 96, 97, 98, or 99%) identical to the amino acid sequence of SEQ ID NO: 69; and/or
(ii) the VL comprises the amino acid sequence of SEQ ID NO: 73, or an amino acid sequence at least 91% (e.g., at least 92, 95, 96, 97, 98, or 99%) identical to the amino acid sequence of SEQ ID NO: 73.

72. An antibody that binds to human tau, which comprises a heavy chain variable region (VH) comprising the amino acid sequence of SEQ ID NO: 69, and a light chain variable region (VL) comprising the amino acid sequence of SEQ ID NO: 73.

73. An antibody that binds to human tau, which comprises:
(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;
(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;
(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or
(d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and
wherein:
(i) the VH comprises 1, 2, 3, 4, 5, 6, 7, 8, 9, 10, 11, 12, 13, 14, 15, 16, 17, 18, 19, 20, 21, or all of: V at position 5; E at position 6; S at position 7; A at position 9; V at position 11; K at position 12; A at position 16; K at position 19; V at position 20; M at position 48; R at position 67; V at position 68; I at position 70; A at position 76; S at position 77; A at position 79; Y at position 80; M at position 81; E at position 82; R at position 87; T at position 91; and/or T at position 113, numbered according to SEQ ID NO: 21; and
(ii) the VL comprises 1, 2, 3, 4, 5, 6, 7, 8, 9, 10, or all of: S at position 7; T at position 14; Q at position 17; P at position 18; Q at position 42; R at position 44; R at position 50; S at position 68; V at position 88; Y at position 92; and/or Q at position 105, numbered according to SEQ ID NO: 93.

74. An antibody that binds to human tau, which comprises:
(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;
(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;
(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or
(d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and
wherein:
(i) the VH comprises the amino acid sequence of SEQ ID NO: 67, or an amino acid sequence at least 86% (e.g., at least 90, 92, 95, 96, 97, 98, or 99%) identical to the amino acid sequence of SEQ ID NO: 67; and/or
(ii) the VL comprises the amino acid sequence of SEQ ID NO: 72, or an amino acid sequence at least 91% (e.g., at least 92, 95, 96, 97, 98, or 99%) identical to the amino acid sequence of SEQ ID NO: 72.

75. An antibody that binds to human tau, which comprises a heavy chain variable region (VH) comprising the amino acid sequence of SEQ ID NO: 67, and a light chain variable region (VL) comprising the amino acid sequence of SEQ ID NO: 72.

76. An antibody that binds to human tau, which comprises:
(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;
(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;
(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or
(d) a VH comprising a HC CDR1 the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and
wherein:
(i) the VH comprises 1, 2, 3, 4, 5, 6, 7, 8, 9, 10, 11, 12, 13, 14, 15, 16, 17, 18, 19, or all of: E at position 1; V at position 5; S at position 7; A at position 9; V at position 11; K at position 12; K at position 19; V at position 20; R at position 67; V at position 68; M at position 70; I at position 76; A at position 79; Y at position 80; M at position 81; E at position 82; R at position 85; D at position 89; L at position 113; and/or S at position 115, numbered according to SEQ ID NO: 21; and
(ii) the VL comprises 1, 2, 3, 4, 5, 6, 7, 8, 9, 10, or all of: S at position 7; T at position 14; Q at position 17; P at position 18; Q at position 42; R at position 44;

R at position 50; S at position 68; V at position 88; Y at position 92; and/or Q at position 105, numbered according to SEQ ID NO: 93.

77. An antibody that binds to human tau, which comprises:
    (a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;
    (b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;
    (c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or
    (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and
    wherein:
    (i) the VH comprises the amino acid sequence of SEQ ID NO: 70, or an amino acid sequence at least 86% (e.g., at least 90, 92, 95, 96, 97, 98, or 99%) identical to the amino acid sequence of SEQ ID NO: 70; and/or
    (ii) the VL comprises the amino acid sequence of SEQ ID NO: 72, or an amino acid sequence at least 91% (e.g., at least 92, 95, 96, 97, 98, or 99%) identical to the amino acid sequence of SEQ ID NO: 72.

78. An antibody that binds to human tau, which comprises a heavy chain variable region (VH) comprising the amino acid sequence of SEQ ID NO: 70, and a light chain variable region (VL) comprising the amino acid sequence of SEQ ID NO: 72.

79. An antibody that binds to human tau, which comprises:
    (a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;
    (b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;
    (c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or
    (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and
    wherein:
    (i) the VH comprises 1, 2, 3, 4, 5, 6, 7, 8, 9, 10, 11, 12, 13, 14, 15, 16 or all of: V at position 5; S at position 7; A at position 9; V at position 11; K at position 12; A at position 16; K at position 19; V at position 20; Q at position 43; M at position 48; R at position 67; V at position 68; M at position 70; T at position 76; S at position 77; R at position 87; and/or T at position 91, numbered according to SEQ ID NO: 21; and
    (ii) the VL comprises 1, 2, 3, 4, 5, 6, 7, 8, 9, 10, 11, 12, or all of: I at position 2; S at position 7; S at position 12; T at position 14; P at position 15; Q at position 17; P at position 18; Q at position 50; S at position 68; V at position 88; Y at position 92; Q at position 105; and/or V at position 109, numbered according to SEQ ID NO: 93.

80. An antibody that binds to human tau, which comprises:

(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;

(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;

(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and wherein:

(i) the VH comprises the amino acid sequence of SEQ ID NO: 71, or an amino acid sequence at least 86% (e.g., at least 90, 92, 95, 96, 97, 98, or 99%) identical to the amino acid sequence of SEQ ID NO: 71; and/or (ii) the VL comprises the amino acid sequence of SEQ ID NO: 73, or an amino acid sequence at least 91% (e.g., at least 92, 95, 96, 97, 98, or 99%) identical to the amino acid sequence of SEQ ID NO: 73.

81. An antibody that binds to human tau, which comprises a heavy chain variable region (VH) comprising the amino acid sequence of SEQ ID NO: 71, and a light chain variable region (VL) comprising the amino acid sequence of SEQ ID NO: 73.

82. An antibody that binds to human tau, which comprises:

(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3 (HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;

(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;

(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and wherein:

(i) the VH comprises 1, 2, 3, 4, 5, 6, 7, 8, 9, 10, 11, 12, 13, 14, 15, 16 or all of: V at position 5; S at position 7; A at position 9; V at position 11; K at position 12; A at position 16; K at position 19; V at position 20; Q at position 43; M at position 48; R at position 67; V at position 68; M at position 70; T at position 76; S at position 77; R at position 87; and/or T at position 91, numbered according to SEQ ID NO: 21; and (ii) the VL comprises 1, 2, 3, 4, 5, 6, 7, 8, 9, 10, 11, 12, 13, or all of: I at position 2; S at position 11; T at position 14; Q at position 17; P at position 18; Q at position 42; R at position 44; P at position 48; R at position 50; S at position 68; A at position 72; N at position 81; V at position 88; and/or Q at position 105, numbered according to SEQ ID NO: 93.

83. An antibody that binds to human tau, which comprises:

(a) a heavy chain variable region (VH) comprising a heavy chain complementarity determining region 1 (HC CDR1) comprising the amino acid sequence of SEQ ID NO: 64, a heavy chain complementarity determining region 2 (HC CDR2) comprising the amino acid sequence of SEQ ID NO: 1145, and a heavy chain complementarity determining region 3

(HC CDR3) comprising the amino acid sequence of SEQ ID NO: 1167; and a light chain variable region (VL) comprising a light chain complementarity determining region 1 (LC CDR1) comprising the amino acid sequence of SEQ ID NO: 1146, a light chain complementarity determining region 2 (LC CDR2) comprising the amino acid sequence of SEQ ID NO: 529, and a light chain complementarity determining region 3 (LC CDR3) comprising the amino acid sequence of SEQ ID NO: 571;

(b) a VH comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a VL comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571;

(c) a VH comprising a HC CDR1 comprising the amino acid sequence of SEQ ID NO: 1165, a HC CDR2 comprising the amino acid sequence of SEQ ID NO: 1166, and a HC CDR3 comprising the amino acid sequence of SEQ ID NO: 1167; and a VL comprising a LC CDR1 comprising the amino acid sequence of SEQ ID NO: 473, a LC CDR2 comprising the amino acid sequence of RVS, and a LC CDR3 comprising the amino acid sequence of SEQ ID NO: 571; or (d) a VH comprising a HC CDR1 comprising the amino acid sequence of SEQ ID NO: 314, a HC CDR2 comprising the amino acid sequence of SEQ ID NO: 341, and a HC CDR3 comprising the amino acid sequence of SEQ ID NO: 410; and a VL comprising a LC CDR1 comprising the amino acid sequence of SEQ ID NO: 1154, a LC CDR2 comprising the amino acid sequence of SEQ ID NO: 529, and a LC CDR3 comprising the amino acid sequence of SEQ ID NO: 571; and wherein:
  (i) the VH comprises the amino acid sequence of SEQ ID NO: 71, or an amino acid sequence at least 86% (e.g., at least 90, 92, 95, 96, 97, 98, or 99%) identical to the amino acid sequence of SEQ ID NO: 71; and/or
  (ii) the VL comprises the amino acid sequence of SEQ ID NO: 74, or an amino acid sequence at least 91% (e.g., at least 92, 95, 96, 97, 98, or 99%) identical to the amino acid sequence of SEQ ID NO: 74.

84. An antibody that binds to human tau, which comprises a heavy chain variable region (VH) comprising the amino acid sequence of SEQ ID NO: 71, and a light chain variable region (VL) comprising the amino acid sequence of SEQ ID NO: 74.

85. The antibody of any one of the preceding embodiments, wherein the antibody is a humanized antibody.

86. The antibody of any one of the preceding embodiments, which is a full length antibody, a bispecific antibody, an Fab, an F(ab')$_2$, an Fv, or a single chain Fv fragment (scFv).

87. The antibody of any one of the preceding embodiments, which comprises a heavy chain constant region selected from IgG1, IgG2, IgG3, IgG4; and/or a light chain constant region of kappa or lambda.

88. The antibody of any one of the preceding embodiments, which comprises a heavy chain constant region of IgG4 and a light chain constant region of kappa.

89. The antibody of any one of the preceding embodiments, wherein:
  (i) the antibody comprises a human IgG4 constant region, comprising an amino acid other than serine at position 228 according to EU numbering;
  (ii) the antibody comprises a human IgG4 constant region, comprising a serine to proline substitution (e.g., mutation) at position 228 according to EU numbering;
  (iii) the antibody comprises a heavy chain constant region (e.g., a human IgG4 constant region) comprising the amino acid sequence of SEQ ID NO: 194, or an amino acid sequence at least 85%, 90%, 95%, 96%, 97%, 98%, or 99% identical to SEQ ID NO: 194; and/or
  (iv) the antibody comprises a heavy chain constant region (e.g., a human IgG4 constant region), wherein the nucleotide sequence encoding the heavy chain constant region comprises the nucleotide sequence of any one of SEQ ID NOs: 195, 196, 198, or 199, or a nucleotide sequence at least 85%, 90%, 95%, 96%, 97%, 98%, or 99% identical any one of SEQ ID NOs: 195, 196, 198, or 199.

90. The antibody of any one of embodiments 1-35, wherein the antibody comprises a light chain constant region (e.g., a light chain constant region of kappa), wherein:
  (i) the light chain constant region comprises the amino acid sequence of SEQ ID NO: 200, or an amino acid sequence at least 85%, 90%, 95%, 96%, 97%, 98%, or 99% identical to SEQ ID NO: 200; and/or
  (ii) the nucleotide sequence encoding the light chain constant region comprises the nucleotide sequence of SEQ ID NO: 201 or 202, or a nucleotide sequence at least 85%, 90%, 95%, 96%, 97%, 98%, or 99% identical to SEQ ID NO: 201 or 202.

91. The antibody of any one of embodiments 1-90, wherein the antibody comprises a heavy chain comprising the amino acid sequence of any one of SEQ ID NOs: 170-174, or an amino acid sequence at least 85%, 90%, 95%, 96%, 97%, 98%, or 99% identical to any one of SEQ ID NOs: 170-174.

92. The antibody of any one of embodiments 1-91, wherein the antibody comprises a light chain comprising the amino acid sequence of any one of SEQ ID NOs: 175-179, or an amino acid sequence at least 85%, 90%, 95%, 96%, 97%, 98%, or 99% identical to any one of SEQ ID NOs: 175-179.

93. The antibody of any one of embodiments 1-92, wherein the antibody comprises:
  (i) a heavy chain comprising the amino acid sequence of any one of SEQ ID NOs: 170-174, or an amino acid sequence at least 85%, 90%, 95%, 96%, 97%, 98%, or 99% identical to any one of SEQ ID NOs: 170-174; and
  (ii) a light chain comprising the amino acid sequence of any one of SEQ ID NOs: 175-179, or an amino acid sequence at least 85%, 90%, 95%, 96%, 97%, 98%, or 99% identical to any one of SEQ ID NOs: 175-179.

94. The antibody of any one of embodiments 1-93, wherein the antibody comprises:
  (i) a heavy chain comprising the amino acid sequence of any one of SEQ ID NOs: 170 or 172-174, or an amino acid sequence at least 85%, 90%, 95%, 96%, 97%, 98%, or 99% identical to any one of SEQ ID NOs: 170 or 172-174; and (ii) a light chain comprising the amino acid sequence of any one of SEQ ID NOs: 175-177, or an amino acid sequence at least 85%, 90%, 95%, 96%, 97%, 98%, or 99% identical to any one of SEQ ID NOs: 175-177.

95. The antibody of any one of the preceding embodiments, which comprises:
(i) a heavy chain comprising the amino acid sequence of SEQ ID NO: 170, or an amino acid sequence at least 85%, 90%, 95%, 96%, 97%, 98%, or 99% identical to SEQ ID NO: 170; and a light chain comprising the amino acid sequence of SEQ ID NO: 175, or an amino acid sequence at least 85%, 90%, 95%, 96%, 97%, 98%, or 99% identical to SEQ ID NO: 175;
(ii) a heavy chain comprising the amino acid sequence of SEQ ID NO: 170, or an amino acid sequence at least 85%, 90%, 95%, 96%, 97%, 98%, or 99% identical to SEQ ID NO: 170; and a light chain comprising the amino acid sequence of SEQ ID NO: 176, or an amino acid sequence at least 85%, 90%, 95%, 96%, 97%, 98%, or 99% identical to SEQ ID NO: 176;
(iii) a heavy chain comprising the amino acid sequence of SEQ ID NO: 170, or an amino acid sequence at least 85%, 90%, 95%, 96%, 97%, 98%, or 99% identical to SEQ ID NO: 170; and a light chain comprising the amino acid sequence of SEQ ID NO: 177, or an amino acid sequence at least 85%, 90%, 95%, 96%, 97%, 98%, or 99% identical to SEQ ID NO: 177;
(iv) a heavy chain comprising the amino acid sequence of SEQ ID NO: 170, or an amino acid sequence at least 85%, 90%, 95%, 96%, 97%, 98%, or 99% identical to SEQ ID NO: 170; and a light chain comprising the amino acid sequence of SEQ ID NO: 178, or an amino acid sequence at least 85%, 90%, 95%, 96%, 97%, 98%, or 99% identical to SEQ ID NO: 178;
(v) a heavy chain comprising the amino acid sequence of SEQ ID NO: 170, or an amino acid sequence at least 85%, 90%, 95%, 96%, 97%, 98%, or 99% identical to SEQ ID NO: 170; and a light chain comprising the amino acid sequence of SEQ ID NO: 179, or an amino acid sequence at least 85%, 90%, 95%, 96%, 97%, 98%, or 99% identical to SEQ ID NO: 179;
(vi) a heavy chain comprising the amino acid sequence of SEQ ID NO: 171, or an amino acid sequence at least 85%, 90%, 95%, 96%, 97%, 98%, or 99% identical to SEQ ID NO: 171; and a light chain comprising the amino acid sequence of SEQ ID NO: 175, or an amino acid sequence at least 85%, 90%, 95%, 96%, 97%, 98%, or 99% identical to SEQ ID NO: 175;
(vii) a heavy chain comprising the amino acid sequence of SEQ ID NO: 171, or an amino acid sequence at least 85%, 90%, 95%, 96%, 97%, 98%, or 99% identical to SEQ ID NO: 171; and a light chain comprising the amino acid sequence of SEQ ID NO: 176, or an amino acid sequence at least 85%, 90%, 95%, 96%, 97%, 98%, or 99% identical to SEQ ID NO: 176;
(viii) a heavy chain comprising the amino acid sequence of SEQ ID NO: 171, or an amino acid sequence at least 85%, 90%, 95%, 96%, 97%, 98%, or 99% identical to SEQ ID NO: 171; and a light chain comprising the amino acid sequence of SEQ ID NO: 177, or an amino acid sequence at least 85%, 90%, 95%, 96%, 97%, 98%, or 99% identical to SEQ ID NO: 177;
(ix) a heavy chain comprising the amino acid sequence of SEQ ID NO: 171, or an amino acid sequence at least 85%, 90%, 95%, 96%, 97%, 98%, or 99% identical to SEQ ID NO: 171; and a light chain comprising the amino acid sequence of SEQ ID NO: 178, or an amino acid sequence at least 85%, 90%, 95%, 96%, 97%, 98%, or 99% identical to SEQ ID NO: 178;
(x) a heavy chain comprising the amino acid sequence of SEQ ID NO: 171, or an amino acid sequence at least 85%, 90%, 95%, 96%, 97%, 98%, or 99% identical to SEQ ID NO: 171; and a light chain comprising the amino acid sequence of SEQ ID NO: 179, or an amino acid sequence at least 85%, 90%, 95%, 96%, 97%, 98%, or 99% identical to SEQ ID NO: 179;
(xi) a heavy chain comprising the amino acid sequence of SEQ ID NO: 172, or an amino acid sequence at least 85%, 90%, 95%, 96%, 97%, 98%, or 99% identical to SEQ ID NO: 172; and a light chain comprising the amino acid sequence of SEQ ID NO: 175, or an amino acid sequence at least 85%, 90%, 95%, 96%, 97%, 98%, or 99% identical to SEQ ID NO: 175;
(xii) a heavy chain comprising the amino acid sequence of SEQ ID NO: 172, or an amino acid sequence at least 85%, 90%, 95%, 96%, 97%, 98%, or 99% identical to SEQ ID NO: 172; and a light chain comprising the amino acid sequence of SEQ ID NO: 176, or an amino acid sequence at least 85%, 90%, 95%, 96%, 97%, 98%, or 99% identical to SEQ ID NO: 176;
(xiii) a heavy chain comprising the amino acid sequence of SEQ ID NO: 172, or an amino acid sequence at least 85%, 90%, 95%, 96%, 97%, 98%, or 99% identical to SEQ ID NO: 172; and a light chain comprising the amino acid sequence of SEQ ID NO: 177, or an amino acid sequence at least 85%, 90%, 95%, 96%, 97%, 98%, or 99% identical to SEQ ID NO: 177;
(xiv) a heavy chain comprising the amino acid sequence of SEQ ID NO: 172, or an amino acid sequence at least 85%, 90%, 95%, 96%, 97%, 98%, or 99% identical to SEQ ID NO: 172; and a light chain comprising the amino acid sequence of SEQ ID NO: 178, or an amino acid sequence at least 85%, 90%, 95%, 96%, 97%, 98%, or 99% identical to SEQ ID NO: 178;
(xv) a heavy chain comprising the amino acid sequence of SEQ ID NO: 172, or an amino acid sequence at least 85%, 90%, 95%, 96%, 97%, 98%, or 99% identical to SEQ ID NO: 172; and a light chain comprising the amino acid sequence of SEQ ID NO: 179, or an amino acid sequence at least 85%, 90%, 95%, 96%, 97%, 98%, or 99% identical to SEQ ID NO: 179;
(xvi) a heavy chain comprising the amino acid sequence of SEQ ID NO: 173, or an amino acid sequence at least 85%, 90%, 95%, 96%, 97%, 98%, or 99% identical to SEQ ID NO: 173; and a light chain comprising the amino acid sequence of SEQ ID NO: 175, or an amino acid sequence at least 85%, 90%, 95%, 96%, 97%, 98%, or 99% identical to SEQ ID NO: 175;

(xvii) a heavy chain comprising the amino acid sequence of SEQ ID NO: 173, or an amino acid sequence at least 85%, 90%, 95%, 96%, 97%, 98%, or 99% identical to SEQ ID NO: 173; and a light chain comprising the amino acid sequence of SEQ ID NO: 176, or an amino acid sequence at least 85%, 90%, 95%, 96%, 97%, 98%, or 99% identical to SEQ ID NO: 176;

(xviii) a heavy chain comprising the amino acid sequence of SEQ ID NO: 173, or an amino acid sequence at least 85%, 90%, 95%, 96%, 97%, 98%, or 99% identical to SEQ ID NO: 173; and a light chain comprising the amino acid sequence of SEQ ID NO: 177, or an amino acid sequence at least 85%, 90%, 95%, 96%, 97%, 98%, or 99% identical to SEQ ID NO: 177;

(xix) a heavy chain comprising the amino acid sequence of SEQ ID NO: 173, or an amino acid sequence at least 85%, 90%, 95%, 96%, 97%, 98%, or 99% identical to SEQ ID NO: 173; and a light chain comprising the amino acid sequence of SEQ ID NO: 178, or an amino acid sequence at least 85%, 90%, 95%, 96%, 97%, 98%, or 99% identical to SEQ ID NO: 178;

(xx) a heavy chain comprising the amino acid sequence of SEQ ID NO: 173, or an amino acid sequence at least 85%, 90%, 95%, 96%, 97%, 98%, or 99% identical to SEQ ID NO: 173; and a light chain comprising the amino acid sequence of SEQ ID NO: 179, or an amino acid sequence at least 85%, 90%, 95%, 96%, 97%, 98%, or 99% identical to SEQ ID NO: 179;

(xxi) a heavy chain comprising the amino acid sequence of SEQ ID NO: 174, or an amino acid sequence at least 85%, 90%, 95%, 96%, 97%, 98%, or 99% identical to SEQ ID NO: 174; and a light chain comprising the amino acid sequence of SEQ ID NO: 175, or an amino acid sequence at least 85%, 90%, 95%, 96%, 97%, 98%, or 99% identical to SEQ ID NO: 175;

(xxii) a heavy chain comprising the amino acid sequence of SEQ ID NO: 174, or an amino acid sequence at least 85%, 90%, 95%, 96%, 97%, 98%, or 99% identical to SEQ ID NO: 174; and a light chain comprising the amino acid sequence of SEQ ID NO: 176, or an amino acid sequence at least 85%, 90%, 95%, 96%, 97%, 98%, or 99% identical to SEQ ID NO: 176;

(xxiii) a heavy chain comprising the amino acid sequence of SEQ ID NO: 174, or an amino acid sequence at least 85%, 90%, 95%, 96%, 97%, 98%, or 99% identical to SEQ ID NO: 174; and a light chain comprising the amino acid sequence of SEQ ID NO: 177, or an amino acid sequence at least 85%, 90%, 95%, 96%, 97%, 98%, or 99% identical to SEQ ID NO: 177;

(xxiv) a heavy chain comprising the amino acid sequence of SEQ ID NO: 174, or an amino acid sequence at least 85%, 90%, 95%, 96%, 97%, 98%, or 99% identical to SEQ ID NO: 174; and a light chain comprising the amino acid sequence of SEQ ID NO: 178, or an amino acid sequence at least 85%, 90%, 95%, 96%, 97%, 98%, or 99% identical to SEQ ID NO: 178; or (xxv) a heavy chain comprising the amino acid sequence of SEQ ID NO: 174, or an amino acid sequence at least 85%, 90%, 95%, 96%, 97%, 98%, or 99% identical to SEQ ID NO: 174; and a light chain comprising the amino acid sequence of SEQ ID NO: 179, or an amino acid sequence at least 85%, 90%, 95%, 96%, 97%, 98%, or 99% identical to SEQ ID NO: 179.

96. The antibody of any one of embodiments 1-11, 15-17, 21-23, 26-28, 31-38, 44-49, 52-58, 63-65, 70-72, or 85-95, which comprises a heavy chain comprising the amino acid sequence of SEQ ID NO: 172, or an amino acid sequence at least 85%, 90%, 95%, 96%, 97%, 98%, or 99% identical to SEQ ID NO: 172; and a light chain comprising the amino acid sequence of SEQ ID NO: 176, or an amino acid sequence at least 85%, 90%, 95%, 96%, 97%, 98%, or 99% identical to SEQ ID NO: 176.

97. The antibody of any one of embodiments 1-11, 15-17, 21-23, 26-28, 31-38, 44-49, 52-58, 63-65, 69-72, or 85-96, which comprises a heavy chain comprising the amino acid sequence of SEQ ID NO: 172 and a light chain comprising the amino acid sequence of SEQ ID NO: 176.

98. The antibody of any one of embodiments 1-10, 12, 15, 16, 18, 21, 22, 24, 26, 27, 29, 31-37, 41, 44-46, 50, 52-56, 59, 63, 64, 69, 73-75, or 85-95, which comprises a heavy chain comprising the amino acid sequence of SEQ ID NO: 170, or an amino acid sequence at least 85%, 90%, 95%, 96%, 97%, 98%, or 99% identical to SEQ ID NO: 170; and a light chain comprising the amino acid sequence of SEQ ID NO: 175, or an amino acid sequence at least 85%, 90%, 95%, 96%, 97%, 98%, or 99% identical to SEQ ID NO: 175.

99. The antibody of any one of embodiments 1-10, 13, 15, 16, 19, 21, 22, 24, 26, 27, 29, 31-37, 42, 44-46, 50, 52-56, 60, 63, 64, 67, 69, 76-78, or 85-95, which comprises a heavy chain comprising the amino acid sequence of SEQ ID NO: 173, or an amino acid sequence at least 85%, 90%, 95%, 96%, 97%, 98%, or 99% identical to SEQ ID NO: 173; and a light chain comprising the amino acid sequence of SEQ ID NO: 175, or an amino acid sequence at least 85%, 90%, 95%, 96%, 97%, 98%, or 99% identical to SEQ ID NO: 175.

100. The antibody of any one of embodiments 1-10, 14-16, 20-23, 31-37, 43-49, 52-56, 51, 63, 64, 68, 69, 79-81, 85-95, which comprises a heavy chain comprising the amino acid sequence of SEQ ID NO: 174, or an amino acid sequence at least 85%, 90%, 95%, 96%, 97%, 98%, or 99% identical to SEQ ID NO: 174; and a light chain comprising the amino acid sequence of SEQ ID NO: 176, or an amino acid sequence at least 85%, 90%, 95%, 96%, 97%, 98%, or 99% identical to SEQ ID NO: 176.

101. The antibody of any one of embodiments 1-10, 14-16, 20-22, 25-27, 30-37, 43-46, 51-56, 62-64, 68, 69, 82-95, which comprises a heavy chain comprising the amino acid sequence of SEQ ID NO: 174, or an amino acid sequence at least 85%, 90%, 95%, 96%, 97%, 98%, or 99% identical to SEQ ID NO: 174; and a light chain comprising the amino acid sequence of SEQ ID NO: 177, or an amino acid sequence at least 85%, 90%, 95%, 96%, 97%, 98%, or 99% identical to SEQ ID NO: 177.

102. The antibody of any one of the preceding embodiments, which comprises:

(i) a heavy chain, wherein the nucleotide sequence encoding the heavy chain comprises the nucleotide sequence of any one of SEQ ID NOs: 180-184, or an nucleotide acid sequence at least 85%, 90%, 95%, 96%, 97%, 98%, or 99% identical to any one of SEQ ID NOs: 180-184; and/or (ii) a light chain, where the nucleotide sequence encoding the light chain comprises the nucleotide sequence of any one of SEQ ID NOs: 185-189, or an nucleotide acid sequence at least 85%, 90%, 95%, 96%, 97%, 98%, or 99% identical to any one of SEQ ID NOs: 185-189.

103. The antibody of any one of the preceding embodiments, which comprises:
(i) a heavy chain, wherein the nucleotide sequence encoding the heavy chain comprises the nucleotide sequence of any one of SEQ ID NOs: 180 or 182-184, or an nucleotide acid sequence at least 85%, 90%, 95%, 96%, 97%, 98%, or 99% identical to any one of SEQ ID NOs: 180 or 182-184; and/or
(ii) a light chain, where the nucleotide sequence encoding the light chain comprises the nucleotide sequence of any one of SEQ ID NOs: 185-187, or an nucleotide acid sequence at least 85%, 90%, 95%, 96%, 97%, 98%, or 99% identical to any one of SEQ ID NOs: 185-187.

104. The antibody of any one of embodiments 1-11, 15-17, 21-23, 26-28, 31-38, 44-49, 52-58, 63-65, 70-72, 85-98, 102, or 103, which comprises:
(i) a heavy chain, wherein the nucleotide sequence encoding the heavy chain comprises the nucleotide sequence of SEQ ID NO: 182, or an nucleotide acid sequence at least 85%, 90%, 95%, 96%, 97%, 98%, or 99% identical to SEQ ID NO: 182; and/or
(ii) a light chain, where the nucleotide sequence encoding the light chain comprises the nucleotide sequence of SEQ ID NO: 186, or an nucleotide acid sequence at least 85%, 90%, 95%, 96%, 97%, 98%, or 99% identical to SEQ ID NO: 186.

105. The antibody of any one of embodiments 1-10, 12, 15, 16, 18, 21, 22, 24, 26, 27, 29, 31-37, 41, 44-46, 50, 52-56, 59, 63, 64, 69, 73-75, 85-95, 98, 102, or 103, which comprises:
(i) a heavy chain, wherein the nucleotide sequence encoding the heavy chain comprises the nucleotide sequence of SEQ ID NO: 180, or an nucleotide acid sequence at least 85%, 90%, 95%, 96%, 97%, 98%, or 99% identical to SEQ ID NO: 180; and/or
(ii) a light chain, where the nucleotide sequence encoding the light chain comprises the nucleotide sequence of SEQ ID NO: 185, or an nucleotide acid sequence at least 85%, 90%, 95%, 96%, 97%, 98%, or 99% identical to SEQ ID NO: 185.

106. The antibody of any one of embodiments 1-10, 13, 15, 16, 19, 21, 22, 24, 26, 27, 29, 31-37, 42, 44-46, 50, 52-56, 60, 63, 64, 67, 69, 76-78, 85-95, 99, 102, or 103, which comprises:
(i) a heavy chain, wherein the nucleotide sequence encoding the heavy chain comprises the nucleotide sequence of SEQ ID NO: 183, or an nucleotide acid sequence at least 85%, 90%, 95%, 96%, 97%, 98%, or 99% identical to SEQ ID NO: 183; and/or
(ii) a light chain, where the nucleotide sequence encoding the light chain comprises the nucleotide sequence of SEQ ID NO: 185, or an nucleotide acid sequence at least 85%, 90%, 95%, 96%, 97%, 98%, or 99% identical to SEQ ID NO: 185.

107. The antibody of any one of embodiments 1-10, 14-16, 20-23, 25-27, 30-37, 43-49, 51-56, 51, 62-65, 68, 69, 79-95, or 100-103, which comprises:
(i) a heavy chain, wherein the nucleotide sequence encoding the heavy chain comprises the nucleotide sequence of SEQ ID NO: 184, or an nucleotide acid sequence at least 85%, 90%, 95%, 96%, 97%, 98%, or 99% identical to SEQ ID NO: 184; and/or
(ii) a light chain, where the nucleotide sequence encoding the light chain comprises the nucleotide sequence of SEQ ID NO: 186 or 187, or an nucleotide acid sequence at least 85%, 90%, 95%, 96%, 97%, 98%, or 99% identical to SEQ ID NO: 186 or 187.

108. The antibody of any one of the preceding embodiments, wherein the antibody binds the C-terminus of a tau protein, e.g., residues 409-436 numbered according to SEQ ID NO: 920.

109. The antibody of any one of the preceding embodiments, wherein the antibody binds a phosphorylated residue of a tau protein.

110. The antibody of any one of the preceding embodiments, wherein the antibody binds phosphorylated serine at position 422 (e.g., pS422), numbered according to SEQ ID NO: 920.

111. The antibody of any one of the preceding embodiments, wherein the antibody preferentially binds pathological tau (e.g., PHF-tau or ePHF), compared to wild-type tau, e.g., as measured by an assay, e.g., an ELISA assay, an SPR assay or a Biacore assay, e.g., an assay as described in Example 1 or Example 8.

112. The antibody of any one of the preceding embodiments, which reduces, e.g., inhibits, aggregation of tau.

113. The antibody of any one of the preceding embodiments, which binds an epitope comprising a region formed by a complex of at least two tau proteins, e.g., a tau dimer.

114. The antibody of any one of the preceding embodiments which has one, two, three, four, five, or all of the following properties:
(i) is capable of binding to iPHF with an affinity of at least about 24-50 pM (e.g., an affinity of at least about 24, 29, 30, 32, 33, 35, 37, 39, 41, 43, 45, 47, or 48 pM), e.g., when measured by an assay (e.g., an SPR or Biacore assay), e.g., an assay as described in Example 8;
(ii) is capable of binding to phosphorylated serine at position 422 (e.g., pS422) of human tau, numbered according to SEQ ID NO: 920 (e.g., a peptide comprising the amino acid sequence of SEQ ID NO: 33), with an affinity of at least about 29-77 pM (e.g., an affinity of at least about 29, 33, 35, 38, 39, 40, 41, 43, 44, 45, 47, 50, 53, 54, 55, 60, 65, 70, 75, 76, or 77 pM), e.g., when measured by an assay (e.g., an SPR or Biacore assay), e.g., an assay as described in Example 8;
(iii) is capable of binding to ePHF with an affinity of at least about 0.08-0.2 nM (e.g., at least about 0.08, 0.085, 0.09, 0.095, 0.1, 0.11, 0.12, 0.13, 0.14, 0.15, 0.16, 0.17, 0.18, 0.19 or 0.2 nM), e.g., when measured by an assay (e.g., an ELISA assay), e.g., an assay as described in Example 8;
(iv) demonstrates low polyspecificity, e.g., a BVP score of at least about 1.6-6 (e.g., a BVP score of at least about 1.6, 1.7, 1.8, 2, 2.2, 2.5, 2.7, 3, 3.2, 3.5, 3.7, 3.9, 4, 4.5, 5, 5.5, or 6), e.g., when measured by an assay (e.g., a BVP ELISA assay), e.g., an assay as described in Example 8;

(v) is capable of binding pathological tau, e.g., as measured by an assay, e.g., an IHC assay, e.g., an assay as described in Example 8; and/or (vi) preferentially binds pathological tau (e.g., PHF-tau or ePHF), compared to wild-type tau, e.g., as measured by an assay, e.g., an ELISA assay, an SPR assay or a Biacore assay, e.g., an assay as described in Example 8.

115. The antibody of any one of the preceding embodiments wherein the antibody demonstrates a low immunogenicity risk (e.g., having a response rate of no more than about 55% (e.g., no more than about 50, 46, 48, 30, 24, or 20%) of donors (e.g., in PBMC cells isolated from the donor), e.g., as measured by an assay, e.g., a T-cell proliferation assay, e.g., an assay as described in Example 8.

116. An antibody that competes for binding to tau with the antibody of any one of the preceding embodiments.

117. An antibody that binds to the same epitope as, substantially the same epitope as, or an epitope that overlaps with, the epitope of the antibody of any one of the preceding embodiments.

118. A nucleic acid encoding the antibody of any one of the preceding claims.

119. The nucleic acid of embodiment 118, which encodes:
(i) a VH, wherein the nucleotide sequence encoding the VH comprises the nucleotide sequence of any one of SEQ ID NOs: 156-160, or a nucleotide sequence at least 86% (e.g., at least 87%, 90%, 95%, 96%, 97%, 98%, or 99%) identical thereto; and/or
(ii) a VL, wherein the nucleotide sequence encoding the VL comprises the nucleotide sequence of any one of SEQ ID NOs: 161-165; or a nucleotide sequence at least 86% (e.g., at least 91%, 95%, 96%, 97%, 98%, or 99%) identical thereto.

120. The nucleic acid of embodiment 118 or 119, which encodes:
(i) a VH, wherein the nucleotide sequence encoding the VH comprises the nucleotide sequence of any one of SEQ ID NOs: 156 or 158-160, or a nucleotide sequence at least 86% (e.g., at least 87%, 90%, 95%, 96%, 97%, 98%, or 99%) identical thereto; and/or
(ii) a VL, wherein the nucleotide sequence encoding the VL comprises the nucleotide sequence of any one of SEQ ID NOs: 161-163; or a nucleotide sequence at least 86% (e.g., at least 91%, 95%, 96%, 97%, 98%, or 99%) identical thereto.

121. The nucleic acid of any one of embodiments 118-120, which encodes:
(i) a heavy chain, wherein the nucleotide sequence encoding the heavy chain comprises the nucleotide sequence of any one of SEQ ID NOs: 180-184, or a nucleotide sequence at least 86% (e.g., at least 87%, 90%, 95%, 96%, 97%, 98%, or 99%) identical thereto; and/or
(ii) a light chain, wherein the nucleotide sequence encoding the light chain comprises the nucleotide sequence of any one of SEQ ID NOs: 185-189; or a nucleotide sequence at least 86% (e.g., at least 91%, 95%, 96%, 97%, 98%, or 99%) identical thereto.

122. The nucleic acid of any one of embodiments 118-121, which encodes:
(i) a heavy chain, wherein the nucleotide sequence encoding the heavy chain comprises the nucleotide sequence of any one of SEQ ID NOs: 180 or 182-184, or a nucleotide sequence at least 86% (e.g., at least 87%, 90%, 95%, 96%, 97%, 98%, or 99%) identical thereto; and/or
(ii) a light chain, wherein the nucleotide sequence encoding the light chain comprises the nucleotide sequence of any one of SEQ ID NOs: 185-187; or a nucleotide sequence at least 86% (e.g., at least 91%, 95%, 96%, 97%, 98%, or 99%) identical thereto.

123. The nucleic acid of any one of embodiments 118-122, which encodes:
(i) a VH, wherein the nucleotide sequence encoding the VH comprises the nucleotide sequence of SEQ ID NO: 158, or a nucleotide sequence at least 86% (e.g., at least 87%, 90%, 95%, 96%, 97%, 98%, or 99%) identical thereto; and a VL wherein the nucleotide sequence encoding the VL comprises the nucleotide sequence of SEQ ID NO: 162; or a nucleotide sequence at least 86% (e.g., at least 91%, 95%, 96%, 97%, 98%, or 99%) identical thereto; and/or
(ii) a heavy chain, wherein the nucleotide sequence encoding the heavy chain comprises the nucleotide sequence of SEQ ID NO: 182, or a nucleotide sequence at least 86% (e.g., at least 87%, 90%, 95%, 96%, 97%, 98%, or 99%) identical thereto; and a light chain, wherein the nucleotide sequence encoding the light chain comprises the nucleotide sequence of SEQ ID NO: 186; or a nucleotide sequence at least 86% (e.g., at least 91%, 95%, 96%, 97%, 98%, or 99%) identical thereto.

124. The nucleic acid of any one of embodiments 118-123, which is codon optimized.

125. An antibody encoded by the nucleic acid of any one of embodiments 118-124.

126. The antibody of any one of embodiments 1-117 or 125 or the nucleic acid of any one of embodiments 118-124, which is isolated, e.g., recombinant.

127. A vector comprising the nucleic acid of any one of embodiments 118-124 or 126, or a nucleic acid encoding the antibody of any one of embodiments 1-117, 125 or 126.

128. A host cell comprising the nucleic acid of any one of embodiments 118-124 or 126, a nucleic acid encoding the antibody of any one of embodiments 1-117, 125, or 126, the antibody of any one of embodiments 1-117, 125, or 126, or the vector of embodiment 127.

129. The host cell of embodiment 128, wherein the host cell is an insect cell, a bacterial cell, or a mammalian cell.

130. A method of producing an antibody, the method comprising culturing the host cell of embodiment 128 or 129, under conditions suitable for gene expression.

131. An isolated nucleic acid encoding a payload, wherein the encoded payload comprises the antibody of any one of embodiments 1-117, 125 or 126.

132. The nucleic acid of embodiment 131, further encoding a signal sequence, optionally wherein the nucleotide sequence encoding the signal sequence comprises the nucleotide sequence of any of the signal sequences listed in Table 14, or a nucleotide sequence with at least 95% sequence identity thereto.

133. The nucleic acid of embodiment 131 or 132, further encoding a second signal sequence, optionally wherein the nucleotide sequence encoding the signal sequence comprises the nucleotide sequence of any of the signal sequences listed in Table 14, or a nucleotide sequence with at least 95% sequence identity thereto.

134. The nucleic acid of any one of embodiments 131-133, wherein the:
   (i) the nucleotide sequence encoding the signal sequence is located 5' relative to the nucleotide sequence encoding the VH; and/or
   (ii) the nucleotide sequence encoding the signal sequence is located 5' relative to the nucleotide sequence encoding the VL.
135. The nucleic acid of any one of embodiments 131-134, wherein the sequences of the encoded VH and VL are connected directly, e.g., without a linker.
136. The nucleic acid of any one of embodiments 131-135, wherein the sequences of the encoded VH and VL are connected via a linker.
137. The nucleic acid of embodiment 136, wherein the linker comprises the nucleotide sequence of any of the linker sequences provided in Table 15, or a nucleotide sequence with at least 95% sequence identity thereto.
138. The nucleic acid of any one of embodiments 131-137, wherein the encoded payload is a full length antibody, a bispecific antibody, an Fab, an F(ab')₂, an Fv, or a single chain Fv fragment (scFv).
139. A viral genome comprising a promoter operably linked to the nucleic acid encoding a payload comprising the antibody of any one of embodiments 1-117, 125, or 126; or the nucleic acid of any one of embodiments 131-138.
140. The viral genome of embodiment 139, wherein the promoter:
   (i) is chosen from human elongation factor 1α-subunit (EF1α), cytomegalovirus (CMV) immediate-early enhancer and/or promoter, chicken β-actin (CBA) and its derivative CAG, β glucuronidase (GUSB), or ubiquitin C (UBC), neuron-specific enolase (NSE), platelet-derived growth factor (PDGF), platelet-derived growth factor B-chain (PDGF-β), intercellular adhesion molecule 2 (ICAM-2), synapsin (Syn), methyl-CpG binding protein 2 (MeCP2), Ca2+/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2), glial fibrillary acidic protein (GFAP), myelin basic protein (MBP), or a fragment, e.g., a truncation, or a functional variant thereof; and/or
   (ii) comprises the nucleotide sequence of any of the promoter sequences provided in Table 11, or a nucleotide sequence at least 95% identical thereto.
141. The viral genome of embodiment 139 or 140, which further comprises an enhancer, optionally wherein the enhancer is a CMV immediate-early (CMVie) enhancer.
142. The viral genome of any one of embodiments 139-141, which further comprises a polyadenylation (polyA) signal region.
143. The viral genome of embodiment 142, wherein the polyA signal region comprises the nucleotide sequence of any of SEQ ID NO: 1134-1136, or a nucleotide sequence with at least 95% identity thereto.
144. The viral genome of any one of embodiments 139-143, further comprising an inverted terminal repeat (ITR) sequence.
145. The viral genome of embodiment 144, wherein:
   (i) the ITR sequence is positioned 5' relative to the encoded payload; and/or
   (ii) the ITR sequence is positioned 3' relative to the encoded payload.
146. The viral genome of any one of embodiments 139-145, which comprises an ITR sequence positioned 5' relative to the encoded payload and an ITR sequence positioned 3' relative to the encoded payload.
147. The viral genome of any one of embodiments 139-146, wherein the ITR sequence comprises a nucleotide sequence of any one of SEQ ID NOs: 1035-1038, or a nucleotide sequence with at least 80%, 85%, 90%, or 95% sequence identity thereto.
148. The viral genome of any one of embodiments 139-147, further comprising an intron region.
149. The viral genome of embodiment 148, wherein the intron region comprises a nucleotide sequence of any of the intron regions listed in Table 13, or a nucleotide sequence with at least 95% identity thereto.
150. The viral genome of any one of embodiments 139-149, comprising at least one, two, or three intron regions.
151. The viral genome of any one of embodiments 139-150, further comprising an exon region.
152. The viral genome of embodiment 151, wherein the exon region comprises the nucleotide sequence of any of the exon sequences in Table 12, or a nucleotide sequence with at least 95% identity thereto.
153. The viral genome of any one of embodiments 139-152, comprising at least one, two, or three exon regions.
154. The viral genome of any one of embodiments 139-153, which further comprises a Kozak sequence, optionally wherein the Kozak sequence comprises the nucleotide sequence of GCCGCCACCATG (SEQ ID NO: 1079) or GAGGAGCCACC (SEQ ID NO: 1089).
155. The viral genome of any one of embodiments 139-154, which further comprises a nucleotide sequence encoding a miR binding site, e.g., a miR binding site that modulates, e.g., reduces, expression of the payload encoded by the viral genome in a cell or tissue where the corresponding miRNA is expressed.
156. The viral genome of embodiment 155, which comprises at least 1-5 copies of an encoded miR binding site, e.g., at least 1, 2, 3, 4, or 5 copies.
157. The viral genome of any one of embodiments 139-156, which comprises at least 3 copies of an encoded miR binding sites, optionally wherein all three copies comprise the same miR binding site, or at least one, two, or all of the copies comprise a different miR binding site.
158. The viral genome of any one of embodiments 139-157, which comprises at least 4 copies of an encoded miR binding site, optionally wherein all four copies comprise the same miR binding site, or at least one, two, three, or all of the copies comprise a different miR binding site.
159. The viral genome of any one of embodiments 155-158, wherein the encoded miR binding site comprises a miR122 binding site, a miR183 binding site, a miR-142-3p, or a combination thereof, optionally wherein:
   (i) the encoded miR122 binding site comprises the nucleotide sequence of SEQ ID NO: 1029, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifications of SEQ ID NO: 1029;
(ii) the encoded miR183 binding site comprises the nucleotide sequence of SEQ ID NO: 1032, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifications of SEQ ID NO: 1032; and/or
(iii) the encoded miR-142-3p binding site comprises the nucleotide sequence of SEQ ID NO: 1031, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifications of SEQ ID NO: 1031.

160. The viral genome of any one of embodiments 139-159, which is single stranded or self complementary.

161. The viral genome of any one of embodiments 139-160, which further comprises:
(i) a nucleotide sequence encoding a Rep protein, e.g., a non-structural protein, wherein the Rep protein comprises a Rep78 protein, a Rep68, Rep52 protein, and/or a Rep40 protein; or
(ii) a second nucleic acid comprising a nucleotide sequence encoding a Rep protein, e.g., a non-structural protein, wherein the Rep protein comprises a Rep78 protein, a Rep68, Rep52 protein, and/or a Rep40 protein.

162. The viral genome of embodiment 161, wherein the Rep78 protein, the Rep68 protein, the Rep52 protein, and/or the Rep40 protein are encoded by at least one Rep gene.

163. The viral genome of any one of embodiments 139-162, which further comprises:
(i) a nucleotide sequence encodes a capsid protein, e.g., a structural protein, wherein the capsid protein comprises a VP1 polypeptide, a VP2 polypeptide, and/or a VP3 polypeptide; or
(ii) a second nucleic acid comprising a nucleotide sequence encodes a capsid protein, e.g., a structural protein, wherein the capsid protein comprises a VP1 polypeptide, a VP2 polypeptide, and/or a VP3 polypeptide.

164. The viral genome of embodiment 163, wherein the VP1 polypeptide, the VP2 polypeptide, and/or the VP3 polypeptide are encoded by at least one Cap gene.

165. A vector comprising the viral genome of any one embodiments 139-164.

166. An isolated, e.g., recombinant AAV particle comprising:
(i) a capsid protein, and,
(ii) the nucleic acid of any one of embodiments 131-138, or the viral genome of any one of embodiments 139-164.

167. The isolated AAV particle of embodiment 166, wherein:
(i) the capsid protein comprises the amino acid sequence of SEQ ID NO: 1003, or an amino acid sequence with at least 80% (e.g., at least about 85, 90, 95, 96, 97, 98, or 99%) sequence identity thereto;
(ii) the capsid protein comprises an amino acid sequence having at least one, two or three modifications but not more than 30, 20 or 10 modifications of the amino acid sequence of SEQ ID NO: 1003;
(iii) the capsid protein comprises the amino acid sequence of SEQ ID NO: 1011, or an amino acid sequence with at least 80% (e.g., at least about 85, 90, 95, 96, 97, 98, or 99%) sequence identity thereto;
(iv) the capsid protein comprises an amino acid sequence having at least one, two or three modifications but not more than 30, 20 or 10 modifications of the amino acid sequence of SEQ ID NO: 1011;
(v) the capsid protein comprises an amino acid sequence encoded by the nucleotide sequence of SEQ ID NO: 1002, or a sequence with at least 80% (e.g., at least about 85, 90, 95, 96, 97, 98, or 99%) sequence identity thereto; and/or
(vi) the nucleotide sequence encoding the capsid protein comprises the nucleotide sequence of SEQ ID NO: 1002, or a sequence with at least 80% (e.g., at least about 85, 90, 95, 96, 97, 98, or 99%) sequence identity thereto.

168. The isolated AAV particle of embodiment 166 or 167, wherein the capsid protein comprises:
(i) an amino acid substitution at position K449, e.g., a K449R substitution, numbered according to SEQ ID NO:1003;
(ii) an insert comprising the amino acid sequence of TLAVPFK (SEQ ID NO: 1151), optionally wherein the insert is present immediately subsequent to position 588, relative to a reference sequence numbered according to SEQ ID NO:1003;
(iii) an amino acid other than "A" at position 587 and/or an amino acid other than "Q" at position 588, numbered according to SEQ ID NO: 1003; and/or
(iv) the amino acid substitution of A587D and/or Q588G, numbered according to SEQ ID NO: 1003.

169. The AAV particle of any one of embodiments 166-168, wherein the capsid protein comprises (i) the amino acid substitution of K449R numbered according to SEQ ID NO: 1003; and (ii) an insert comprising the amino acid sequence of TLAVPFK (SEQ ID NO: 1151), optionally wherein the insert is present immediately subsequent to position 588 of SEQ ID NO: 1003.

170. The AAV particle of any one of embodiments 166-169, wherein the capsid protein comprises (i) the amino acid substitution of K449R numbered according to SEQ ID NO: 1003; (ii) an insert comprising the amino acid sequence of TLAVPFK (SEQ ID NO: 1151), optionally wherein the insert is present immediately subsequent to position 588, relative to a reference sequence numbered according to SEQ ID NO: 1003; and (iii) the amino acid substitutions of A587D and Q588G, numbered according to SEQ ID NO: 1003.

171. The AAV particle of any one of embodiments 166-169, wherein the capsid protein comprises (i) an insert comprising the amino acid sequence of TLAVPFK (SEQ ID NO: 1151), optionally wherein the insert is present immediately subsequent to position 588, relative to a reference sequence numbered according to SEQ ID NO: 1003; and (ii) the amino acid substitutions of A587D and Q588G, numbered according to SEQ ID NO: 1003.

172. The AAV particle of any one of embodiments 166-171, wherein the capsid protein comprises a VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3

(PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP (3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), AAVPHP.N (PHP.N), PHP.S, AAV1, AAV2, AAV2 variant, AAV2/3 variant, AAV4, AAV5, AAV6, AAV7, AAV8, AAV9.47, AAV9 (hu14), AAV9, AAV9 K449R, AAV10, AAV11, AAV12, AAVrh8, AAVrh10, AAVDJ, AAVDJ8, or AAV2G9 capsid protein, or a functional variant thereof.

173. The AAV particle of any one of embodiments 166-172, wherein the capsid protein comprises an AAV5 capsid protein or variant thereof or an AAV9 capsid protein or variant thereof.

174. The AAV particle of any one of embodiments 166-173, wherein the capsid protein comprises:
    (i) the amino acid sequence of SEQ ID NO: 1023, or an amino acid sequence substantially identical (e.g., having at least 70%, 75%, 80%, 85%, 90%, 92%, 95%, 97%, 98%, or 99% sequence identity) thereto;
    (ii) an amino acid sequence comprising at least one, two, or three modifications but no more than 30, 20, or 10 modifications, e.g., substitutions, relative to the amino acid sequence of SEQ ID NO: 1023; or,
    (iii) an amino acid sequence encoded by the nucleotide sequence of SEQ ID NO: 1022 or a nucleotide sequence substantially identical (e.g., having at least 70%, 75%, 80%, 85%, 90%, 92%, 95%, 97%, 98%, or 99% sequence identity) thereto.

175. The AAV particle of embodiment 174, wherein the nucleotide sequence encoding the capsid protein comprises the nucleotide sequence of SEQ ID NO: 1022, or a nucleotide sequence substantially identical (e.g., having at least 70%, 75%, 80%, 85%, 90%, 92%, 95%, 97%, 98%, or 99% sequence identity) thereto.

176. A host cell comprising the nucleic acid of any one of embodiments 131-138, the viral genome of any one of embodiments 139-164, or the AAV particle of any one of embodiments 166-175, optionally wherein the host cell is an insect cell, a bacterial cell or a mammalian cell.

177. A nucleic acid encoding the viral genome of any one of embodiments 139-164, and a backbone region suitable for replication of the viral genome in a cell, e.g., a bacterial cell (e.g., wherein the backbone region comprises one or both of a bacterial origin of replication and a selectable marker).

178. A method of making a viral genome, the method comprising:
    (i) providing the nucleic acid molecule comprising the viral genome of any one of embodiments 139-164; and
    (ii) excising the viral genome from the backbone region, e.g., by cleaving the nucleic acid molecule at upstream and downstream of the viral genome.

179. A method of making an isolated, e.g., recombinant, AAV particle, the method comprising
    (i) providing a host cell comprising the viral genome of embodiment 176; and
    (ii) incubating the host cell under conditions suitable to enclose the viral genome in a capsid protein; thereby making the isolated AAV particle.

180. The method of embodiment 179, further comprising, prior to step (i), introducing a first nucleic acid molecule comprising the viral genome into the host cell.

181. The method of any one of embodiments 178-180, wherein the host cell comprises a second nucleic acid encoding a capsid protein.

182. The method of embodiment 181, wherein the second nucleic acid molecule is introduced into the host cell prior to, concurrently with, or after the first nucleic acid molecule.

183. A pharmaceutical composition comprising the antibody of any one of embodiments 1-117, 125, or 126, an AAV particle of any one of embodiments 166-175, or an AAV particle comprising the viral genome of any one of embodiments 139-164, or the isolated nucleic acid of any one of embodiments 131-138, and a pharmaceutically acceptable excipient.

184. A method of delivering an exogenous antibody that binds to tau, to a subject, comprising administering an effective amount of the pharmaceutical composition of embodiment 183, the antibody of any one of embodiments 1-117, 125, or 126, an AAV particle of any one of embodiments 166-175, or an AAV particle comprising the viral genome of any one of embodiments 139-164, or the isolated nucleic acid of any one of embodiments 131-138.

185. The method of embodiment 184, wherein the subject has, has been diagnosed with having, or is at risk of having a disease associated with expression of tau, e.g., aberrant tau expression.

186. The method of embodiment 184 or 185, wherein the subject has, has been diagnosed with having, or is at risk of having a neurological, e.g., neurodegenerative disorder, mild cognitive impairment, or a traumatic brain injury (TBI).

187. The method of any one of embodiments 184-186, wherein the subject has, has been diagnosed with having, or is at risk of having a tauopathy.

188. A method of treating a subject having or diagnosed with having a disease associated with expression of tau comprising administering to the subject an effective amount of the pharmaceutical composition of embodiment 183, the antibody of any one of embodiments 1-117, 125, or 126, an AAV particle of any one of embodiments 166-175, or an AAV particle comprising the viral genome of any one of embodiments 139-164, or the isolated nucleic acid of any one of embodiments 131-138.

189. A method of treating a subject having or diagnosed with having a neurological, e.g., neurodegenerative disorder, or a traumatic brain injury (TBI), comprising administering to the subject an effective amount of the pharmaceutical composition of embodiment 183, the antibody of any one of embodiments 1-117, 125, or 126, an AAV particle of any one of embodiments 166-175, or an AAV particle comprising the viral genome of any one of embodiments 139-164, or the isolated nucleic acid of any one of embodiments 131-138.

190. A method of treating a subject having or diagnosed with having a tauopathy comprising administering to the subject an effective amount of the pharmaceutical composition of embodiment 183, the antibody of any one of embodiments 1-117, 125, or 126, an AAV particle of any one of embodiments 166-175, or an AAV particle comprising the viral genome of any one of embodiments 139-164, or the isolated nucleic acid of any one of embodiments 131-138.

191. The method of any one of embodiments 185-190, wherein the disease associated with Tau expression, the neurological disorder, or the tauopathy comprises AD, FTDP-17, FTLD, FTD, CTE, PSP, Down's syndrome, Pick's disease, CBD, Corticobasal syndrome, ALS, Prion diseases, CJD, Multiple system atrophy, mild cognitive impairment, Tangle-only dementia, or Progressive subcortical gliosis.

192. The method of any one of embodiments 188-191, where treating comprises prevention of progression of the disease in the subject.

193. The method of any one of embodiments 184-192, wherein the subject is a human.

194. The method of any one of embodiments 184-193, wherein the antibody or the AAV particle is administered to the subject intravenously, intramuscularly, via intraparenchymal administration, intracerebroventricularly, via intra-cisterna magna (ICM) injection, intrathecally, via focused ultrasound (FUS), e.g., coupled with the intravenous administration of microbubbles (FUS-MB), or MRI-guided FUS coupled with intravenous administration.

195. The method of any one of embodiments 184-194, wherein the antibody or the AAV particle is administered to the subject intravenously.

196. The method of any one of embodiments 184-194, wherein the antibody or the AAV particle is administered to the subject via intra-cisterna magna injection (ICM).

197. The method of any one of embodiments 184-196, further comprising evaluating, e.g., measuring, the level of antibodies generated in a subject, e.g., in a cell or tissue of the subject.

198. The method of any one of embodiments 184-197, wherein the administration results in the generation of antibodies, e.g., 0.001 µg/mL to 100 mg/mL of antibodies, in the subject, e.g., in a cell or tissue of the subject.

199. The method of embodiment 198, wherein the cell is a neuronal cell.

200. The method of embodiment 198, wherein the tissue is a central nervous system tissue, e.g., a brain tissue.

201. The method of any one of embodiments 184-200, further comprising performing a blood test, an imaging test (e.g., a PET scan or a PET scan in combination with biomarker, e.g., serum biomarker staining), a CNS biopsy sample, or an aqueous cerebral spinal fluid biopsy.

202. The method of any one of embodiments 197-201, wherein measuring the level of antibodies is performed prior to, during, or subsequent to treatment with the antibody or AAV particle.

203. The method of any one of embodiments 184-202, wherein the subject has a level of antibodies that is a greater than a reference level, e.g., a subject that has not received treatment with the antibody or the AAV particle, e.g., has not been administered the antibody or the AAV particle.

204. The method of any one of embodiments 184-203, further comprising administration of an additional therapeutic agent and/or therapy suitable for treatment or prevention of a disorder associated with tau expression, a neurological, e.g., neurodegenerative disorder.

205. The method of embodiment 204, wherein the additional therapeutic agent and/or therapy comprises a cholinesterase inhibitor (e.g., donepezil, rivastigmine, and/or galantamine), an N-methyl D-aspartate (NMDA) antagonist (e.g., memantine), an antipsychotic drug, an anti-anxiety drug, an anticonvulsant, a dopamine agonist (e.g., pramipexole, ropinirole, rotigotine, and/or apomorphine), an MAO B inhibitor (e.g., selegiline, rasagiline, and/or safinamide), catechol O-methyltransferase (COMT) inhibitors (entacapone, opicapone, and/or tolcapone), anticholinergics (e.g., benztropine and/or trihexyphenidyl), amantadine, carbidopa-levodopa, deep brain simulation (DBS), or a combination thereof.

206. The antibody of any one of embodiments 1-117, 125, or 126, the pharmaceutical composition of embodiment 183, or the AAV particle of any one of embodiments 166-175, for use in the manufacture of a medicament.

207. The antibody of any one of embodiments 1-117, 125, or 126, the pharmaceutical composition of embodiment 183, or the AAV particle of any one of embodiments 166-175, for use in the treatment of a disease associated with tau expression.

208. The antibody of any one of embodiments 1-117, 125, or 126, the pharmaceutical composition of embodiment 183, or the AAV particle of any one of embodiments 166-175, for use in the treatment of a neurological, e.g., neurodegenerative, disorder, or a traumatic brain injury (TBI).

209. The antibody of any one of embodiments 1-117, 125, or 126, the pharmaceutical composition of embodiment 183, or the AAV particle of any one of embodiments 166-175, for use in the treatment of a tauopathy.

210. Use of an effective amount of the antibody of any one of embodiments 1-117, 125, or 126, the pharmaceutical composition of embodiment 183, or the AAV particle of any one of embodiments 166-175, in the manufacture of a medicament.

211. Use of the antibody of any one of embodiments 1-117, 125, or 126, the pharmaceutical composition of embodiment 183, or the AAV particle of any one of embodiments 166-175, in the manufacture of a medicament for the treatment of a disease associated with tau expression, a neurological e.g., neurodegenerative, disorder, a tauopathy, mild cognitive impairment, or a traumatic brain injury (TBI).

212. An AAV viral genome comprising a nucleotide sequence encoding an antibody that binds to tau, fragment or variant thereof, wherein the AAV viral genome comprises in 5' to 3' order:
(i) a 5' adeno-associated (AAV) ITR, optionally wherein the 5' AAV ITR comprises the nucleotide sequence of SEQ ID NO: 1035, or a nucleotide sequence at least 70%, 75%, 80%, 85%, 90%, 95% or 99% identical thereto;
(ii) an enhancer, optionally wherein the enhancer comprises the nucleotide sequence of 1050, or a nucleotide sequence at least 70%, 75%, 80%, 85%, 90%, 95% or 99% identical thereto;
(iii) a promoter (e.g., a CBA promoter or a variant thereof), optionally wherein the promoter comprises the nucleotide sequence of SEQ ID NO: 1042, or a nucleotide sequence at least 70%, 75%, 80%, 85%, 90%, 95% or 99% identical thereto;
(iv) an intron, optionally wherein the intron comprises the nucleotide sequence of SEQ ID NO: 1067, or a nucleotide sequence at least 70%, 75%, 80%, 85%, 90%, 95% or 99% identical thereto;
(v) a nucleotide sequence encoding a first signal sequence, optionally wherein:
  (a) the first encoded signal sequence comprises the amino acid sequence of SEQ ID NO: 1; an amino acid sequence comprising one, two, three, but no more than four different amino acids relative to SEQ ID NO: 1; or an amino acid sequence comprising one, two, three, but no more than four modifications, e.g., substitutions, e.g., conservative substitutions, relative to SEQ ID NO: 1; and/or
  (b) the nucleotide sequence encoding the first signal sequence comprises the sequence of SEQ ID NO: 1083, or a nucleotide sequence at least 70%, 75%, 80%, 85%, 90%, 95% or 99% identical thereto;
(vi) a nucleotide sequence encoding a heavy chain variable region, wherein:
  (a) the encoded heavy chain variable region comprises the amino acid sequence of SEQ ID NO: 21, or an amino acid sequence at least 70%, 75%, 80%, 85%, 90%, 95% or 99% identical thereto; and/or
  (b) the nucleotide sequence encoding the heavy chain variable region comprises the nucleotide sequence of SEQ ID NO: 7, or a nucleotide sequence at least 70%, 75%, 80%, 85%, 90%, 95% or 99% identical thereto;
(v) a nucleotide sequence encoding a heavy chain constant region, optionally wherein:
  (a) the encoded heavy chain constant region comprises the amino acid sequence of SEQ ID NO: 16 or an amino acid sequence at least 70%, 75%, 80%, 85%, 90%, 95% or 99% identical thereto; and/or
  (b) the nucleotide sequence encoding the heavy chain constant region comprises the nucleotide sequence of SEQ ID NO: 805, or a nucleotide sequence at least 70%, 75%, 80%, 85%, 90%, 95% or 99% identical thereto;
(vi) a first linker, optionally wherein the first linker comprises the nucleotide sequence of SEQ ID NO: 1724; a nucleotide sequence comprising one, two, three but no more than four different nucleotides relative to the nucleotide sequence of SEQ ID NO: 1724; a nucleotide sequence comprising one, two, three but no more than four modifications, e.g., substitutions, relative to SEQ ID NO: 1724;
(vii) a second linker, optionally wherein the second linker comprises the nucleotide sequence of SEQ ID NO: 1726; a nucleotide sequence comprising one, two, three but no more than four different nucleotides relative to the nucleotide sequence of SEQ ID NO: 1726; a nucleotide sequence comprising one, two, three but no more than four modifications, e.g., substitutions, relative to SEQ ID NO: 1726;
(viii) a nucleotide sequence encoding a second signal sequence, optionally wherein:
  (a) the first encoded signal sequence comprises the amino acid sequence of SEQ ID NO: 2; an amino acid sequence comprising one, two, three, but no more than four different amino acids relative to SEQ ID NO: 2; or an amino acid sequence comprising one, two, three, but no more than four modifications, e.g., substitutions, e.g., conservative substitutions, relative to SEQ ID NO: 2; and/or
  (b) the nucleotide sequence encoding the second signal sequence comprises the sequence of SEQ ID NO: 1085, or a nucleotide sequence at least 70%, 75%, 80%, 85%, 90%, 95% or 99% identical thereto;
(ix) a nucleotide sequence encoding a light chain variable region, wherein:
  (a) the encoded light chain variable region comprises the amino acid sequence of SEQ ID NO: 93, or an amino acid sequence at least 70%, 75%, 80%, 85%, 90%, 95% or 99% identical thereto; and/or
  (b) the nucleotide sequence encoding the light chain variable region comprises the nucleotide sequence of SEQ ID NO: 11, or a nucleotide sequence at least 70%, 75%, 80%, 85%, 90%, 95% or 99% identical thereto;
(x) a nucleotide sequence encoding a light chain constant region, optionally wherein:
  (a) the encoded light chain constant region comprises the amino acid sequence of SEQ ID NO: 18, or an amino acid sequence at least 70%, 75%, 80%, 85%, 90%, 95% or 99% identical thereto; and/or
  (b) the nucleotide sequence encoding the light chain constant region comprises the nucleotide sequence of SEQ ID NO: 17, or a nucleotide sequence at least 70%, 75%, 80%, 85%, 90%, 95% or 99% identical thereto;
(xi) a polyA signal sequence, optionally wherein the polyA signal sequence comprises the nucleotide sequence of SEQ ID NO: 1134, or a nucleotide sequence at least 70%, 75%, 80%, 85%, 90%, 95% or 99% identical thereto; and
(xii) a 3' AAV ITR, optionally wherein the 3' AAV ITR comprises the nucleotide sequence of SEQ ID NO: 1037, or a nucleotide sequence at least 70%, 75%, 80%, 85%, 90%, 95% or 99% identical thereto.

213. An AAV viral genome comprising the nucleotide sequence of SEQ ID NO: 15, or a nucleotide sequence at least 70%, 75%, 80%, 85%, 90%, 95% or 99% identical thereto.

214. The viral genome of any one of embodiments 139-164 or 212, which comprises the nucleotide sequence of SEQ ID NO: 15, or a nucleotide sequence at least 70%, 75%, 80%, 85%, 90%, 95% or 99% identical thereto.

BRIEF DESCRIPTION OF THE DRAWINGS

FIG. 1 is a graph depicting the stimulation index (ratio of the number of proliferating T cells of sample over blank) for each antibody following incubation with PBMC cells from 50 healthy donors representative for the global population based on HLA-DRB1 expression, as a measure of relative immunogenicity risk. The antibodies tested include, from left to right on the X axis, the Herceptin control, Ab2, Ab1, Ab3, Ab4, and Ab5. A simulation index greater than or equal to 2.0 is considered a positive response.

DETAILED DESCRIPTION

I. Compositions

In some embodiments, the present disclosure provides compositions that interact with human microtubule associated protein tau. Such compositions may be antibodies that bind tau protein epitopes, referred to herein as anti-tau antibodies. Dysfunction and/or aggregation of tau is found in a class of neurodegenerative diseases referred to as tauopathies. Tau hyperphosphorylation leads to aggregation and depressed tau-dependent microtubule assembly. In tauopathies, the tau aggregates form paired helical filaments (PHF) found in neurofibrillary tangles (NFTs). These aggregates lead to neuronal loss and cognitive decline. Anti-tau antibodies of the present disclosure may be useful for treating and/or diagnosing tauopathies, as well as other applications described herein.

Antibodies

In some embodiments, compounds (e.g., anti-tau antibodies) and compositions of the present disclosure include antibodies or fragments thereof. In some embodiments, the antibody described herein bind tau. For example, the antibody binds to an epitope, e.g., a confirmation epitope, phosphorylated epitope, or a linear epitope, on tau, e.g., as described herein.

As used herein, the term "antibody" is referred to in the broadest sense and specifically covers various embodiments including, but not limited to monoclonal antibodies, polyclonal antibodies, multispecific antibodies (e.g. bispecific antibodies formed from at least two intact antibodies), single chain Fv (scFv) formats, and antibody fragments (such as Fab, F(ab'), F(ab')$_2$, Fv, etc.), so long as they exhibit a desired functional or biological activity. Antibodies are primarily amino acid-based molecules but may also include one or more modifications (including, but not limited to the addition of sugar moieties, fluorescent moieties, chemical tags, etc.).

Antibodies (including antigen-binding fragments thereof) of the present disclosure may include, but are not limited to, polyclonal, monoclonal antibodies, multispecific antibodies, bispecific antibodies, trispecific antibodies, human antibodies, humanized antibodies, chimeric antibodies, single chain antibodies, diabodies, linear antibodies, Fab fragments, F(ab') fragments, F(ab')$_2$ fragments, Fv fragments, fragments produced by a Fab expression library, variable domains, anti-idiotypic (anti-Id) antibodies (including, e.g., anti-Id antibodies to antibodies of the invention), intracellularly made antibodies (i.e., intrabodies), codon-optimized antibodies, scFv fragments, tandem scFv antibodies, bispecific T-cell engagers, mAb2 antibodies, chimeric antigen receptors (CAR), tetravalent bispecific antibodies, biosynthetic antibodies, native antibodies, miniaturized antibodies, unibodies, maxibodies, and epitope-binding fragments of any of the above.

In some embodiments, the antibody comprises at least one immunoglobulin variable domain sequence. An antibody may include, for example, full-length, mature antibodies and antigen-binding fragments of an antibody. For example, an antibody can include a heavy (H) chain variable domain sequence (abbreviated herein as VH), and a light (L) chain variable domain sequence (abbreviated herein as VL). In another example, an antibody includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., human IgG1, IgG2, IgG3, and IgG4, and murine IgG1, IgG2a, IgG2b, IgG2c, and IgG3) of antibodies. The antibodies of the present disclosure can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

In some embodiments, an antibody of the present disclosure comprises a functional fragment or variant thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

As used herein, the term "antibody fragment" refers to a portion of an intact antibody or fusion-protein thereof, in some cases including at least one antigen binding region. Examples of antigen-binding fragments include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci. USA 85:5879-5883); and (viii) a single domain antibody. These antibody fragments are obtained using conventional techniques known to those with skill in the art, and the fragments are screened for utility in the same manner as are intact antibodies. An antibody fragment can also be incorporated into single domain antibodies, maxibodies, minibodies, nanobodies, intrabodies, diabodies, triabodies, tetrabodies, v-NAR and bis-scFv (see, for example, Hollinger and Hudson, Nature Biotechnology 23:1126-1136, 2005). "In some embodiments, papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. Antibodies of the present disclosure may include one or more of these fragments and may, for example, be generated through enzymatic digestion of whole antibodies or through recombinant expression.

In some embodiments, the antibody can be single domain antibody. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

"Native antibodies" are usually heterotetrameric glycoproteins of about 150,000 Daltons, composed of two identical light (L) chains and two identical heavy (H) chains. Genes encoding antibody heavy and light chains are known and segments making up each have been well characterized and described (Matsuda, F. et al., 1998. The Journal of Experimental Medicine. 188(11); 2151-62 and Li, A. et al., 2004. Blood. 103 (12:4602-9, the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. In some embodiments, the VH and VL regions of the antibody described herein can be subdivided into regions of hypervariability, termed complementarity determining regions (CDR), interspersed with regions that are more conserved, termed framework regions (FR).

As used herein, the term "hypervariable region" refers to a region within a variable domain that includes amino acid residues responsible for antigen binding. The amino acids present within the hypervariable regions determine the structure of the complementarity determining regions (CDRs) that become part of the antigen-binding site of the antibody.

As used herein, the term "CDR" refers to a region of an antibody that includes a structure that is complimentary to its target antigen or epitope. CDR regions generally confer antigen specificity and binding affinity. Other portions of the variable domain, not interacting with the antigen, are each referred to as a "framework region" (FR). The antigen-binding site (also known as the antigen combining site or paratope) includes the amino acid residues necessary to interact with a particular antigen. The exact residues making up the antigen-binding site may be determined by CDR analysis.

As used herein, the term "CDR analysis" refers to any process used to determine which antibody variable domain residues make up the CDRs. The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196: 901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). CDR analysis may be conducted by co-crystallography with bound antigen. In some embodiments, CDR analysis may include computational assessments based on comparisons with other antibodies (Strohl, W. R. Therapeutic Antibody Engineering. Woodhead Publishing, Philadelphia PA. 2012. Ch. 3, p 47-54, the contents of which are herein incorporated by reference in their entirety). CDR analysis and/or the precise amino acid sequence boundaries may include the use of numbering schemes including, but not limited to, those taught by Kabat [Wu, T. T. et al., 1970, JEM, 132(2): 211-50 and Johnson, G. et al., 2000, Nucleic Acids Res. 28(1): 214-8, the contents of each of which are herein incorporated by reference in their entirety], Chothia [Chothia and Lesk, J. Mol. Biol. 196, 901 (1987), Chothia et al., Nature 342, 877 (1989), and Al-Lazikani, B. et al., 1997, J. Mol. Biol. 273(4): 927-48, the contents of each of which are herein incorporated by reference in their entirety], Lefranc (Lefranc, M. P. et al., 2005, Immunome Res. 1:3), and Honegger (Honegger, A. and Pluckthun, A. 2001. J. Mol. Biol. 309(3):657-70, the contents of which are herein incorporated by reference in their entirety). In some embodiments, the CDRs defined according the Chothia number scheme are also sometimes referred to as hypervariable loops.

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3).

For example, under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

For example by combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

In general, the VH and VL domains have three CDRs each. VL CDRs are referred to herein as LC CDR1, LC CDR2 and LC CDR3, in order of occurrence when moving from N- to C-terminus along the variable domain polypeptide. VH CDRs are referred to herein as HC CDR1, HC CDR2, and HC CDR3, in order of occurrence when moving from N- to C-terminus along the variable domain polypeptide. Each of the CDRs have favored canonical structures with the exception of the HC CDR3, which includes amino acid sequences that may be highly variable in sequence and length between antibodies resulting in a variety of three-dimensional structures in antigen-binding domains (Nikoloudis, D. et al., 2014. PeerJ. 2:e456). In some cases, CDRH3s may be analyzed among a panel of related antibodies to assess antibody diversity. Various methods of determining CDR sequences are known in the art and may be applied to known antibody sequences (Strohl, W. R. Therapeutic Antibody Engineering. Woodhead Publishing, Philadelphia PA. 2012. Ch. 3, p 47-54, the contents of which are herein incorporated by reference in their entirety).

In some embodiments, the antigen binding domain of the antibodies of the present disclosure is the part of the antibody that comprises determinants that form an interface that binds to the tau polypeptide or an epitope thereof. With respect to proteins (or protein mimetics), the antigen-binding site typically includes one or more loops (of at least four amino acids or amino acid mimics) that form an interface that binds to the tau polypeptide. Typically, the antigen-binding site of an antibody includes at least one or two CDRs and/or hypervariable loops, or more typically at least three, four, five or six CDRs and/or hypervariable loops.

In yet other embodiments, the antibody has a heavy chain constant region chosen from, e.g., the heavy chain constant regions of IgG1, IgG2, IgG3, IgG4, IgM, IgA1, IgA2, IgD, and IgE; particularly, chosen from, e.g., the human heavy chain constant regions of IgG1, IgG2, IgG3, and IgG4, or the murine heavy chain constant regions of IgG1, IgG2a, IgG2b, IgG2c, and IgG3. In another embodiment, the antibody has a light chain constant region chosen from, e.g., the (e.g., murine or human) light chain constant regions of kappa or lambda.

The constant region can be altered, e.g., mutated, to modify the properties of the antibody (e.g., to increase or decrease one or more of: Fc receptor binding, antibody glycosylation, the number of cysteine residues, effector cell function, and/or complement function). In some embodiments the antibody has: effector function; and can fix complement. In other embodiments the antibody does not recruit effector cells; or fix complement. In other embodiments, the antibody has reduced or no ability to bind an Fc receptor. For example, it is an isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

As used herein, the term "Fv" refers to an antibody fragment that includes the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain (to form a single chain Fv (scFv)] or through the introduction of a disulfide bridge between heavy and light chain variable domains (Strohl, W. R. Therapeutic Antibody Engineering. Woodhead Publishing, Philadelphia PA. 2012. Ch. 3, p 46-47, the contents of which are herein incorporated by reference in their entirety).

Antibody "light chains" from any vertebrate species can be assigned to one of two clearly distinct types, called kappa and lambda based on amino acid sequences of their constant domains. Depending on the amino acid sequence of the constant domain of their heavy chains, antibodies can be assigned to different classes.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen. In some embodiments, antibodies of the present disclosure are prepared as scFvFc antibodies. The term "scFvFc" refers to an antibody format which includes the fusion of one or more scFv with an antibody Fc domain.

The term "chimeric antibody" refers to an antibody with portions derived from two or more sources. Chimeric antibodies may include portions derived from different species. For example, chimeric antibodies may include antibodies with mouse variable domains and human constant domains. Further examples of chimeric antibodies and methods for producing them include any of those described in Morrison, S. L., *Transfectomas provide novel chimeric antibodies*. Science. 1985 Sep. 20; 229(4719):1202-7; Gillies, S. D. et al., *High-level expression of chimeric antibodies using adapted cDNA variable region cassettes*. J Immunol Methods. 1989 Dec. 20; 125(1-2):191-202.; and U.S. Pat. Nos. 5,807,715; 4,816,567; and 4,816,397, the contents of each of which are incorporated herein by reference in their entirety.

The term "diabodies" refers to small antibody fragments with two antigen-binding sites, which fragments include a heavy chain variable domain VH connected to a light chain variable domain VL in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), the contents of each of which are incorporated herein by reference in their entirety.

The term "intrabody" refers to a form of antibody that is not secreted from a cell in which it is produced, but instead targets one or more intracellular protein(s). Intrabodies may be used to affect a multitude of cellular processes including, but not limited to intracellular trafficking, transcription, translation, metabolic processes, proliferative signaling and cell division. In some embodiments, methods of the present invention may include intrabody-based therapies. In some such embodiments, variable domain sequences and/or CDR sequences disclosed herein may be incorporated into one or more constructs for intrabody-based therapy. In some cases, intrabodies of the invention may target one or more glycated intracellular proteins or may modulate the interaction between one or more glycated intracellular protein and an alternative protein.

The term "chimeric antigen receptor" or "CAR" as used herein, refers to artificial receptors that are engineered to be expressed on the surface of immune effector cells resulting in specific targeting of such immune effector cells to cells expressing entities that bind with high affinity to the artificial receptors. CARs may be designed to include one or more segments of an antibody, antibody variable domain and/or antibody CDR, such that when such CARs are expressed on immune effector cells, the immune effector cells bind and clear any cells that are recognized by the antibody portions of the CARs. In some cases, CARs are designed to specifically bind cancer cells, leading to immune-regulated clearance of the cancer cells.

The antibody of the invention can be a monoclonal antibody or a polyclonal antibody. The term "monoclonal antibody" as used herein refers to an antibody obtained from a population of substantially homogeneous cells (or clones), e.g., the individual antibodies making up the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen.

The modifier "monoclonal" indicates the character of the antibody as being obtained from a substantially homogeneous population of antibodies, and is not to be construed as requiring production of the antibody by any particular method.

In some embodiments, the antibody comprises an amino acid sequence of an antibody in which the variable region, or a portion thereof, e.g., the CDRs, are generated in a non-human organism, e.g., a rat or mouse. Antibodies comprising chimeric, CDR-grafted, and humanized antibodies are within the invention. Antibodies comprising the sequences of antibodies generated in a non-human organism, e.g., a rat or mouse, and then modified, e.g., in the variable framework or constant region, to decrease antigenicity in a human are within the invention.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

Antibodies of the present disclosure may be from any animal origin including mammals, birds, reptiles, and insects. Mammalian antibodies may be, for example, of human, murine (e.g., mouse or rat), donkey, sheep, rabbit, goat, guinea pig, camel, bovine, or horse origin.

In some embodiments, antibodies of the present disclosure may be antibody mimetics. The term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; 6,348,584). In some embodiments, antibody mimetics may be those known in the art including, but are not limited to affibody molecules, affilins, affitins, anticalins, avimers, DARPins, Fynomers and Kunitz and domain peptides. In other embodiments, antibody mimetics may include one or more non-peptide region.

As used herein, the term "antibody variant" refers to a biomolecule resembling an antibody in structure, sequence and/or function, but including some differences in their amino acid sequence, composition or structure as compared to another antibody or a native antibody.

Multispecific Antibodies

In some embodiments, the antibody is a multispecific antibody, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In some embodiments, the first and second epitopes are on the same antigen, e.g., the same protein (or subunit of a multimeric protein). In some embodiments, the first and second epitopes overlap. In some embodiments, the first and second epitopes do not overlap. In some embodiments, the first and second epitopes are on different antigens, e.g., the different proteins (or different subunits of a multimeric protein). In some embodiments, a multispecific antibody comprises a third, fourth or fifth immunoglobulin variable domain. In some embodiments, a multispecific antibody is a bispecific antibody, a trispecific antibody, or tetraspecific antibody. In some embodiments, the anti-tau antibody is a multispecific antibody.

In some embodiments, a multispecific antibody is a bispecific antibody. A bispecific antibody has specificity for no more than two antigens. A bispecific antibody is characterized by a first immunoglobulin variable domain sequence which has binding specificity for a first epitope and a second immunoglobulin variable domain sequence that has binding specificity for a second epitope. In some embodiments, the first and second epitopes are on the same antigen, e.g., the same protein (or subunit of a multimeric protein). In some embodiments, the first and second epitopes overlap. In some embodiments, the first and second epitopes do not overlap. In some embodiments, the first and second epitopes are on different antigens, e.g., the different proteins (or different subunits of a multimeric protein). In some embodiments, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In some embodiments, a bispecific antibody comprises a half antibody having binding specificity for a first epitope and a half antibody having binding specificity for a second epitope. In some embodiments, a bispecific antibody comprises a half antibody, or fragment thereof, having binding specificity for a first epitope and a half antibody, or fragment thereof, having binding specificity for a second epitope. In some embodiments, a bispecific antibody comprises a scFv, or fragment thereof, have binding specificity for a first epitope and a scFv, or fragment thereof, have binding specificity for a second epitope. In some embodiment, the anti-tau antibody is a bispecific antibody.

In some embodiments, the sequences of the antibody of the present disclosure can be generated from bispecific or heterodimeric antibody produced using protocols known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also disclosed creating bispecific, trispecific, or tetraspecific molecules, as described, in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620.

Intrabody

In some embodiments, payloads may encode intrabodies. Intrabodies are a form of antibody that is not secreted from a cell in which it is produced, but instead targets one or more intracellular proteins. Intrabodies are expressed and function intracellularly, and may be used to affect a multitude of cellular processes including, but not limited to intracellular trafficking, transcription, translation, metabolic processes, proliferative signaling and cell division. In some embodiments, methods described herein include intrabody-based therapies. In some such embodiments, variable domain sequences and/or CDR sequences disclosed herein are incorporated into one or more constructs for intrabody-based therapy. For example, intrabodies may target one or more glycated intracellular proteins or may modulate the interaction between one or more glycated intracellular proteins and an alternative protein.

More than two decades ago, intracellular antibodies against intracellular targets were first described (Biocca, Neuberger and Cattaneo EMBO J. 9:101-108, 1990). The intracellular expression of intrabodies in different compartments of mammalian cells allows blocking or modulation of the function of endogenous molecules (Biocca, et al., EMBO J. 9:101-108, 1990; Colby et al., Proc. Natl. Acad. Sci. U.S.A. 101:17616-21, 2004). Intrabodies can alter protein folding, protein-protein, protein-DNA, protein-RNA interactions and protein modification. They can induce a phenotypic knockout and work as neutralizing agents by direct binding to the target antigen, by diverting its intracellular trafficking or by inhibiting its association with binding partners. They have been largely employed as research tools and are emerging as therapeutic molecules for the treatment of human diseases such as viral pathologies, cancer and misfolding diseases. The fast-growing bio-market of recombinant antibodies provides intrabodies with enhanced binding specificity, stability, and solubility, together with lower immunogenicity, for their use in therapy (Biocca, abstract in Antibody Expression and Production Cell Engineering Volume 7, 2011, pp. 179-195).

In some embodiments, intrabodies have advantages over interfering RNA (iRNA); for example, iRNA has been shown to exert multiple non-specific effects, whereas intrabodies have been shown to have high specificity and affinity to target antigens. Furthermore, as proteins, intrabodies possess a much longer active half-life than iRNA. Thus, when the active half-life of the intracellular target molecule is long, gene silencing through iRNA may be slow to yield an effect, whereas the effects of intrabody expression can be almost instantaneous. Lastly, it is possible to design intrabodies to block certain binding interactions of a particular target molecule, while sparing others.

Intrabodies are often single chain variable fragments (scFvs) expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies may be produced for use in the viral genomes using methods known in the art, such as those disclosed and reviewed in: (Marasco et al., 1993 Proc. Natl. Acad. Sci. USA, 90:7889-7893; Chen et al., 1994, Hum. Gene Ther. 5:595-601; Chen et al., 1994, Proc. Natl. Acad. Sci. USA, 91:5932-5936; Maciejewski et al., 1995, Nature Med., 1:667-673; Marasco, 1995, Immunotech, 1: 1-19; Mhashilkar, et al., 1995, EMBO J. 14:1542-51; Chen et al., 1996, Hum. Gene Therap., 7:1515-1525; Marasco, Gene Ther. 4:11-15, 1997; Rondon and Marasco, 1997, Annu. Rev. Microbiol. 51:257-283; Cohen, et al., 1998, Oncogene 17:2445-56; Proba et al., 1998, J. Mol. Biol. 275:245-253; Cohen et al., 1998, Oncogene 17:2445-2456; Hassanzadeh, et al., 1998, FEBS Lett. 437:81-6; Richardson et al., 1998, Gene Ther. 5:635-44; Ohage and Steipe, 1999, J. Mol. Biol. 291:1119-1128; Ohage et al., 1999, J. Mol. Biol. 291:1129-1134; Wirtz and Steipe, 1999, Protein Sci. 8:2245-2250; Zhu et al., 1999, J. Immunol. Methods 231: 207-222; Arafat et al., 2000, Cancer Gene Ther. 7:1250-6; der Maur et al., 2002, J. Biol. Chem. 277:45075-85; Mhashilkar et al., 2002, Gene Ther. 9:307-19; and Wheeler et al., 2003, FASEB J. 17:1733-5; and references cited therein). In particular, a CCR5 intrabody has been produced by Steinberger et al., 2000, Proc. Natl. Acad. Sci. USA 97:805-810). See generally Marasco, WA, 1998, "Intrabodies: Basic Research and Clinical Gene Therapy Applications" Springer: New York; and for a review of scFvs, see Pluckthun in "The Pharmacology of Monoclonal Antibodies," 1994, vol. 113, Rosenburg and Moore eds. Springer-Verlag, New York, pp. 269-315.

Sequences from donor antibodies may be used to develop intrabodies. Intrabodies are often recombinantly expressed as single domain fragments such as isolated VH and VL domains or as a single chain variable fragment (scFv) antibody within the cell. For example, intrabodies are often expressed as a single polypeptide to form a single chain antibody comprising the variable domains of the heavy and light chains joined by a flexible linker polypeptide. Intrabodies typically lack disulfide bonds and are capable of modulating the expression or activity of target genes through their specific binding activity. Single chain antibodies can also be expressed as a single chain variable region fragment joined to the light chain constant region.

As is known in the art, an intrabody can be engineered into recombinant polynucleotide vectors to encode sub-cellular trafficking signals at its N or C terminus to allow expression at high concentrations in the sub-cellular compartments where a target protein is located. For example, intrabodies targeted to the endoplasmic reticulum (ER) are engineered to incorporate a leader peptide and, optionally, a C-terminal ER retention signal, such as the KDEL amino acid motif (SEQ ID NO: 4545). Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

There are certain technical challenges with intrabody expression. In particular, protein conformational folding and structural stability of the newly synthesized intrabody within the cell is affected by reducing conditions of the intracellular environment.

Intrabodies may be promising therapeutic agents for the treatment of misfolding diseases, including tauopathies, prion diseases, Alzheimer's, Parkinson's, and Huntington's, because of their virtually infinite ability to specifically recognize the different conformations of a protein, including pathological isoforms, and because they can be targeted to the potential sites of aggregation (both intra- and extracellular sites). These molecules can work as neutralizing agents against amyloidogenic proteins by preventing their aggregation, and/or as molecular shunters of intracellular traffic by rerouting the protein from its potential aggregation site (Cardinale, and Biocca, Curr. Mol. Med. 2008, 8:2-11).

Antibody Development

Antibodies according to the present disclosure may be developed using methods standard in the art. Two primary antibody preparation technologies are immunization and antibody display technology. In either case, desired antibodies are identified from a larger pool of candidates based on affinity for a specific target or epitope. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen.

Antigens

Antibodies may be developed (e.g., through immunization) or selected (e.g., from pool of candidates), for example, using any naturally occurring or synthetic antigen. As used herein, an "antigen" is an entity which induces or evokes an immune response in an organism and may also refer to an antibody binding partner. An immune response is characterized by the reaction of the cells, tissues and/or organs of an organism to the presence of a foreign entity. Such an immune response typically leads to the production by the organism of one or more antibodies against the foreign entity. In some embodiments, antigens include tau proteins.

As used herein, the term "tau protein" refers to proteins or protein complexes that include microtubule-associated protein tau or peptide fragments thereof. Tau proteins may include enriched paired helical filament tau protein (ePHF), also referred to as "sarkosyl insoluble tau," or fragments thereof. Tau proteins may include one or more phosphorylated residues. Such phosphorylated residues may correspond to tau proteins associated with disease (also referred to herein as "pathological tau").

Immunization

In some embodiments, antibodies may be prepared by immunizing a host with an antigen of interest. Host animals (e.g., mice, rabbits, goats, or llamas) may be immunized with an antigenic protein to elicit lymphocytes that specifically bind to the antigen. Lymphocytes may be collected and fused with immortalized cell lines to generate hybridomas which can be cultured in a suitable culture medium to promote growth (e.g., see Kohler, G. et al., Continuous cultures of fused cells secreting antibody of predefined specificity. Nature. 1975 Aug. 7; 256(5517):495-7, the contents of which are herein incorporated by reference in their entirety). Alternatively, lymphocytes may be immunized in vitro.

Lymphocytes may be fused with immortalized cell lines using suitable fusing agents (e.g., polyethylene glycol) to form a hybridoma cell (e.g., see Goding, J. W., Monoclonal Antibodies: Principles and Practice. Academic Press. 1986; 59-1031, the contents of which are herein incorporated by reference in their entirety). Immortalized cell lines may be transformed mammalian cells, particularly myeloma cells of rodent, rabbit, bovine, or human origin. In some embodiments, rat or mouse myeloma cell lines are employed. Hybridoma cells may be cultured in suitable culture media, typically including one or more substances that inhibit the growth or survival of unfused cells. For example, parental cells lacking the enzyme hypoxanthine guanine phosphoribosyl transferase (HGPRT or HPRT) may be used and culture media for resulting hybridoma cells may be supplemented with hypoxanthine, aminopterin, and thymidine ("HAT medium") to prevent growth of HGPRT-deficient (unfused) cells.

Desirable properties for immortalized cell lines may include, but are not limited to, efficient fusing, supportive of high level antibody expression by selected antibody-producing cells, and sensitivity to unfused cell-inhibitory media (e.g., HAT media). In some embodiments, immortalized cell lines are murine myeloma lines. Such cell lines may be obtained, for example, from the Salk Institute Cell Distribution Center (San Diego, CA) or the American Type Culture Collection, (Manassas, VA). Human myeloma and mouse-human heteromyeloma cell lines may also be used for the production of human monoclonal antibodies (e.g., see Kozbor, D. et al., A human hybrid myeloma for production of human monoclonal antibodies. J Immunol. 1984 December; 133(6):3001-5 and Brodeur, B. et al., Monoclonal Antibody Production Techniques and Applications. Marcel Dekker, Inc., New York. 1987; 33:51-63, the contents of each of which are herein incorporated by reference in their entireties).

Hybridoma cell culture media may be assayed for the presence of monoclonal antibodies with desired binding specificity. Assays may include, but are not limited to, immunoprecipitation assay, in vitro binding assay, radioimmunoassay (RIA), surface plasmon resonance (SPR) assay, and/or enzyme-linked immunosorbent assay (ELISA). In some embodiments, binding specificity of monoclonal antibodies may be determined by Scatchard analysis (Munson, P. J. et al., Ligand: a versatile computerized approach for characterization of ligand-binding systems. Anal Biochem. 1980 Sep. 1; 107(1):220-39, the contents of which are herein incorporated by reference in their entirety).

Antibodies produced by cultured hybridomas may be analyzed to determine binding specificity for target antigens. Once antibodies with desirable characteristics are identified, corresponding hybridomas may be subcloned through limiting dilution procedures and grown by standard methods. Antibodies produced by hybridomas may be isolated and purified using standard immunoglobulin purification procedures such as, for example, protein A-Sepharose, hydroxyapatite chromatography, gel electrophoresis, dialysis, or affinity chromatography. Alternatively, hybridoma cells may be grown in vivo as ascites in a mammal. In some embodiments, antibodies may be isolated directly from serum of immunized hosts.

In some embodiments, recombinant versions of antibodies generated through immunization may be prepared. Such antibodies may be prepared using genomic antibody sequences from selected hybridomas. Hybridoma genomic antibody sequences may be obtained by extracting RNA molecules from antibody-producing hybridoma cells and producing cDNA by reverse transcriptase polymerase chain reaction (PCR). PCR may be used to amplify cDNA using primers specific for antibody heavy and light chains. PCR products may then be subcloned into plasmids for sequence analysis. Antibodies may be produced by insertion of resulting antibody sequences into expression vectors. Some recombinant antibodies may be prepared using synthetic nucleic acid constructs that encode amino acid sequences corresponding to amino acid sequences obtained from isolated hybridoma antibodies.

Antibody Display

In some embodiments, antibodies may be developed using antibody display technologies. "Display technology" refers to systems and methods for expressing amino acid-based candidate compounds in a format where they are linked with nucleic acids encoding them and are accessible to a target or ligand. Candidate compounds are expressed at the surface of a host capsid or cell in most systems, however, some host-free systems (e.g., ribosomal display) exist. Display technologies may be used to generate display "libraries," which include sets of candidate compound library members. Display libraries with antibodies (or variants or fragments thereof) as library members are referred to herein as "antibody display libraries." Antibodies may be designed, selected, or optimized by screening target antigens using antibody display libraries. Antibody display libraries may include millions to billions of members, each expressing unique antibody domains. Antibody fragments displayed may be scFv antibody fragments, which are fusion proteins of VH and VL antibody domains joined by a flexible linker. Display libraries may include antibody fragments with differing levels of diversity between variable domain framework regions and CDRs. Display library antibody fragment CDRs may include unique variable loop lengths and/or sequences. Antibody variable domains or CDRs obtained from display library selection may be directly incorporated into antibody sequences for recombinant antibody production or mutated and utilized for further optimization through in vitro affinity maturation.

Antibody display libraries may include antibody phage display libraries. Antibody phage display libraries utilize phage virus particles as hosts with millions to billions of members, each expressing unique antibody domains. Such libraries may provide richly diverse sources that may be used to select potentially hundreds of antibody fragments with diverse levels of affinity for one or more antigens of interest (McCafferty, et al., 1990. Nature. 348:552-4; Edwards, B. M. et al., 2003. JMB. 334:103-18; Schofield, D. et al., 2007. Genome Biol. 8, R254 and Pershad, K. et al., 2010. Protein Engineering Design and Selection. 23:279-88; the contents of each of which are herein incorporated by reference in their entirety). Antibody fragments displayed may be scFv antibody fragments. Phage display library members may be expressed as fusion proteins, linked to viral coat proteins (e.g. the N-terminus of the viral pIII coat protein). VL chains may be expressed separately for assembly with VH chains in the periplasm prior to complex incorporation into viral coats. Precipitated library members may be sequenced from the bound phage to obtain cDNA encoding desired antibody domains.

In some embodiments, antibody display libraries may be generated using yeast surface display technology. Antibody yeast display libraries are made up of yeast cells with surface displayed antibodies or antibody fragments. Antibody yeast display libraries may include antibody variable domains expressed on the surface of *Saccharomyces cerevisiae* cells. Yeast display libraries may be developed by displaying antibody fragments of interest as fusion proteins with yeast surface proteins (e.g. Aga2p protein). Yeast cells displaying antibodies or antibody fragments with affinity for a specific target may be isolated according to standard methods. Such methods may include, but are not limited to, magnetic separation and flow cytometry.

Recombinant Synthesis

Antibodies of the present disclosure may be prepared using recombinant DNA technology and related processes. Constructs (e.g., DNA expression plasmids) encoding antibodies may be prepared and used to synthesize full antibodies or portions thereof. In some embodiments, DNA sequences encoding antibody variable domains of the present disclosure may be inserted into expression vectors (e.g., mammalian expression vectors) encoding other antibody domains and used to prepare antibodies with the inserted variable domains. DNA sequences encoding antibody variable domains may be inserted downstream of upstream expression vector regions with promoter/enhancer elements and/or encoding immunoglobulin signal sequences. DNA sequences encoding antibody variable domains may be inserted upstream of downstream expression vector regions encoding immunoglobulin constant domains. Encoded constant domains may be from any class (e.g., IgG, IgA, IgD, IgE, and IgM) or species (e.g., human, mouse, rabbit, rat, and non-human primate). In some embodiments, encoded constant domains encode human IgG (e.g., IgG1, IgG2, IgG3, or IgG4) constant domains. In some embodiments, encoded constant domains encode mouse IgG (e.g., IgG1, IgG2a, IgG2b, IgG2c, or IgG3) constant domains.

Expression vectors encoding antibodies of the present disclosure may be used to transfect cells for antibody production. Such cells may be mammalian cells. Cell lines with stable transfection of antibody expression vectors may be prepared and used to establish stable cell lines. Cell lines producing antibodies may be expanded for expression of antibodies which may be isolated or purified from cell culture media.

Antibody Characterization

In some embodiments, antibodies of the present disclosure may be identified, selected, or excluded based on different characteristics. Such characteristics may include, but are not limited to, physical and functional characteristics. Physical characteristics may include features of antibody structures [e.g., amino acid sequence or residues; secondary, tertiary, or quaternary protein structure; post-translational modifications (e.g., glycosylations); chemical bonds, and stability]. Functional characteristics may include, but are not limited to, antibody affinity (i.e., for specific epitopes and/or antigens) and antibody activity (e.g., antibody ability to activate or inhibit a target, process, or pathway).

Antibody Binding and Affinity

In some embodiments, antibodies of the present disclosure may be identified, selected, or excluded based on binding and/or level of affinity for specific epitopes and/or antigens. Antibody binding and/or affinity level may be assessed with different antigen formats. In some embodiments, antibody affinity for different antigen formats may be tested in vitro (e.g., by ELISA). Anti-tau antibody in vitro testing may be carried out using brain samples or fractions. Such samples or fractions may be obtained from subjects with AD (e.g., human AD patients). In some embodiments, brain samples or fractions may be obtained from non-human subjects. Such non-human subjects may include non-human animals used in AD disease model studies (e.g., mice, rats, and primates). In some embodiments, brain samples or fractions used for antibody affinity testing may be derived from TG4510/P301S mouse strains. Antibody affinity may be compared against control samples lacking the particular antigen for which affinity is being analyzed. In some embodiments, control samples used for anti-tau antibody testing may include brain samples or fractions from non-diseased human subjects. In some embodiments, brain samples or fractions from wild type and/or Tau knockout mouse strains may be used as control samples.

In vitro affinity testing may be carried out (e.g., by ELISA) using recombinant or isolated protein antigens. For example, recombinant or isolated ePHF may be used for anti-tau antibody affinity testing. In some embodiments, anti-tau antibodies of the present disclosure may exhibit a half maximal effective concentration (EC50) of from about 0.01 nM to about 100 nM for binding to ePHF when assessed by ELISA. In some embodiments, the exhibited EC50 may be less than about 50 nM, less than about 20 nM, less than about 10 nM, or less than about 1 nM. In some embodiments, anti-tau antibodies of the present disclosure may exhibit an EC50 of from about 0.01 nM to about 100 nM for binding to any of the antigens listed in Table 8, or an epitope that includes or is included within any of the antigens (including, but not limited to conformational epitopes), when assessed by ELISA. In some embodiments, the exhibited EC50 may be less than about 50 nM, less than about 20 nM, less than about 10 nM, or less than about 1 nM.

In some embodiments, anti-tau antibodies of the present disclosure bind to pathological tau, but do not bind to non-pathological tau. Such antibodies may be referred to herein as being "selective" for pathological forms of tau. In some embodiments, anti-tau antibodies of the present disclosure bind to tau tangles.

In some embodiments, antibody affinity analysis may be used to identify, select, or exclude polyspecific antibodies. As used herein, the term "polyspecific antibody" refers to an antibody with affinity for more than one epitope or antigen. In some embodiments, polyspecific antibodies may be identified, selected, or excluded based on relative affinity for each epitope or antigen recognized. For example, a polyspecific antibody may be selected for use or further development based on higher affinity for one epitope or antigen over a second epitope or antigen for which the polyspecific antibody demonstrates affinity.

In some embodiments, anti-tau antibodies may be tested for competition with other anti-tau antibodies. Such testing may be carried out to provide information on the specific epitope recognized by an antibody and may yield information related to level of epitope affinity in comparison to the competing antibody. In some embodiments, anti-tau antibodies used in antibody binding and/or affinity analysis may include anti-tau antibody PT3, as described in U.S. Pat. No. 9,371,376; anti-tau antibody C10.2, as described in U.S. Pat. No. 10,196,439 (referred to as antibody "C10-2," therein); anti-tau antibody IPN002, as described in U.S. Pat. No. 10,040,847; anti-tau antibody AT8 (ThermoFisher, Waltham, MA); anti-tau antibody AT100 (ThermoFisher, Waltham, MA); anti-tau antibody AT120 as described in U.S. Pat. No. 5,843,779; or anti-tau antibody PT76, as described in Vandermeeren, M. et al., J Alzheimers Dis. 2018; 65(1):265-281.

Antibody Activity

In some embodiments, antibodies of the present disclosure may be identified, selected, or excluded based on their ability to promote or reduce a certain activity. Antibody activity may be assessed using analytical assays. Such assays may be selected or designed to detect, screen, measure, and/or rank antibodies based on such antibody activity.

Anti-tau antibodies may be characterized by ability to inhibit tau aggregation. Inhibition may be based on physical disruption of tau aggregation or may be based on anti-tau antibody-dependent depletion (immunodepletion) of tau protein. Characterization based on tau aggregation inhibition may be assessed using one or more assays of tau aggregation. In some embodiments, anti-tau antibodies may be characterized by tau seeding assay. Tau seeding assays typically involve in vitro initiation of tau aggregation and assessment of aggregation inhibition by candidate compounds being tested. Tau seeding assays may be carried out using tau aggregation biosensor cells. Tau aggregation biosensor cells yield a detectable signal (e.g., a fluorescent signal) in response to tau aggregation. Tau aggregation biosensor cells may be cultured with recombinant or isolated tau or with samples from high tau brain tissues or fluids (to promote tau aggregation) and treated with or without candidate compounds to assess tau aggregation inhibition. In some embodiments, anti-tau antibodies may be used to deplete tau from media prior to incubation with biosensor cells. Aggregation levels with depleted media may be compared to aggregation levels with non-depleted media to assess anti-tau antibody inhibitory function. Tau aggregation biosensor cells may include, but are not limited to, tau RD Biosensor cells. In some embodiments, neurons expressing human tau may be used.

In some embodiments, anti-tau antibodies of the present disclosure may inhibit tau aggregation with a half maximal inhibitory concentration (IC50) of from about 1 nM to about 30 nM as determined by immunodepletion assay (e.g., using tau RD Biosensor cells).

Antibody Modification

Antibodies may be modified to obtain variants with one or more altered properties. Such properties may include or relate to antibody structure, function, affinity, specificity, protein folding, stability, manufacturing, expression, and/or immunogenicity (i.e., immune reactions in subjects being treated with such antibodies). In some embodiments, antibody fragments or variants may be used to modify another antibody or may be incorporated into a synthetic antibody.

Antibody modification may include amino acid sequence modifications. Such modifications may include, but are not limited to, amino acid deletions, additions, and/or substitutions. Modifications may be informed by amino acid sequence analysis. Such analysis may include alignment of amino acid sequences between different antibodies or antibody variants. Two or more antibodies may be compared to identify residues or regions suitable for modification. Compared antibodies may include those binding to the same epitope. Compared antibodies may bind to different epitopes (separate or overlapping) of the same protein or target (e.g., to identify residues or regions conferring specificity to specific epitopes). Comparisons may include light and/or heavy chain sequence variation analysis, CDR sequence variation analysis, germline sequence analysis, and/or framework sequence analysis. Information obtained from such analysis may be used to identify amino acid residues, segments of amino acids, amino acid side chains, CDR lengths, and/or other features or properties that are conserved or variable among antibodies binding to the same or different epitopes.

In some embodiments, modified versions of anti-tau antibodies described above may be prepared by adding, deleting, or substituting one or more CDR amino acid residues.

In some embodiments, anti-tau antibodies may be modified by amino acid sequence alignment of antibodies binding to similar targets and preparing modified antibodies with one or more amino acid deletions, substitutions, or insertions based on analysis of the aligned sequences.

The present disclosure includes amino acid consensus sequences for CDR region sequences, showing specific amino acids that may be modified or amino acid residue positions that may be more generally substituted (shown using variable "X") in antibody amino acid sequences, e.g. as described in Table 1.

TABLE 1

Consensus CDRs for exemplary anti-tau antibodies V0022, V0023 and V0024

| SEQ ID NO | Description | Sequence |
|---|---|---|
| SEQ ID NO: 1180 (Chothia) | HCDR1 | $GX_1TFTX_2X_3$, wherein $X_1$ is F or Y; $X_2$ is R or I; and $X_3$ is Y or F |
| SEQ ID NO: 341 (Chothia) | HCDR2 | NPNNGG |
| SEQ ID NO: 410 (Chothia) | HCDR3 | GTGTGAMDY |
| SEQ ID NO: 1181 (Chothia) | LCDR1 | $RSSQSLVHX_1NGX_2TX_3LY$, wherein $X_1$ is N or S; $X_2$ is I or N; and $X_3$ is Y or H |
| SEQ ID NO: 1182 (Chothia) | LCDR2 | $RVSX_1RFS$, wherein $X_1$ is N or S |
| SEQ ID NO: 571 (Chothia) | LCDR3 | FQGTHVPRT |
| (Kabat) | HCDR1 | $X_1X_2WMH$, wherein $X_1$ is R or I; and $X_2$ is Y or F |
| SEQ ID NO: 1184 (Kabat) | HCDR2 | $X_1INPNNGGX_2DX_3NEX_4FKX_5$, wherein $X_1$ is N or K; $X_2$ is T or G; $X_3$ is F, Y, or N; $X_4$ is K or R; and $X_5$ is N or S; |
| SEQ ID NO: 410 (Kabat) | HCDR3 | GTGTGAMDY |
| SEQ ID NO: 1185 (Kabat) | LCDR1 | $RSSQSLVHX_1NGX_2TX_3LY$, wherein $X_1$ is N or S; $X_2$ is I or N; and $X_3$ is Y or H |
| SEQ ID NO: 1182 (Kabat) | LCDR2 | $RVSX_1RFS$, wherein $X_1$ is N or S |
| SEQ ID NO: 571 (Kabat) | LCDR3 | FQGTHVPRT |
| SEQ ID NO: 1186 (IMGT) | HCDR1 | $GX_1TFTX_2X_3W$, wherein $X_1$ is F or Y; $X_2$ is R or I; and $X_3$ is Y or F |

TABLE 1-continued

Consensus CDRs for exemplary anti-tau antibodies V0022, V0023 and V0024

| SEQ ID NO | Description | Sequence |
|---|---|---|
| SEQ ID NO: 1187 (IMGT) | HCDR2 | INPNNGGX$_1$, wherein X$_1$ is T or G |
| SEQ ID NO: 1167 (IMGT) | HCDR3 | ARGTGTGAMDY |
| SEQ ID NO: 1188 (IMGT) | LCDR1 | QSLVHX$_1$NGX$_2$TX$_3$, wherein X$_1$ is N or S; X$_2$ is I or N; and X$_3$ is Y or H |
| (IMGT) | LCDR2 | RVS |
| SEQ ID NO: 571 (IMGT) | LCDR3 | FQGTHVPRT |

Functional Modifications

In some embodiments, antibodies of the present disclosure may be modified to optimize one or more functional properties (e.g., antibody affinity or activity). Non-limiting examples of antibody functional properties include epitope or antigen affinity, ability to mobilize or immobilize targets, and ability to activate or inhibit a target, process, or pathway. In some embodiments, functional properties include or relate to ability to modulate protein-protein interactions, protein aggregation, enzyme activity, receptor-ligand interactions, cellular signaling pathways, proteolytic cascades, and/or biological or physiological responses.

Antibody modifications may optimize antibodies by modulating epitope affinity. Such modifications may be carried out by affinity maturation. Affinity maturation technology is used to identify sequences encoding CDRs with highest affinity for target antigens. In some embodiments, antibody display technologies (e.g., phage or yeast) may be used. Such methods may include mutating nucleotide sequences encoding parental antibodies being optimized. Nucleotide sequences may be mutated randomly as a whole or to vary expression at specific amino acid residues to create millions to billions of variants. Sites or residues may be selected for mutation based on sequences or amino acid frequencies observed in natural human antibody repertoires. Variants may be subjected to repeated rounds of affinity screening (e.g., using display library screening technologies, surface plasmon resonance technologies, fluorescence-associated cell sorting (FACS) analysis, enzyme-linked immunosorbent assay (ELISA), etc.) for target antigen binding. Repeated rounds of selection, mutation, and expression may be carried out to identify antibody fragment sequences with highest affinity for target antigens. Such sequences may be directly incorporated into antibody sequences for production. In some cases, the goal of affinity maturation is to increase antibody affinity by at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100 fold, at least 500-fold, at least 1,000-fold, or more than 1,000-fold as compared to the affinity of an original or starting antibody. In cases where affinity is less than desired, the process may be repeated.

In some embodiments, antibody affinity may be assessed with different antigen formats. In some embodiments, antibody affinity for different antigen formats may be tested in vitro (e.g., by ELISA). In vitro testing may be carried out using brain samples or fractions. Such samples or fractions may be obtained from subjects with AD (e.g., human AD patients). In some embodiments, brain samples or fractions may be obtained from non-human subjects. Such non-human subjects may include non-human animals used in AD disease model studies (e.g., mice, rats, and primates). In some embodiments, brain samples or fractions used for antibody affinity testing may be derived from TG4510/P301S mouse strains. Antibody affinity may be compared against control samples lacking the particular antigen for which affinity is being analyzed. In some embodiments, control samples may include brain samples or fraction from non-diseased human subjects. In some embodiments, brain samples or fractions from wild type and/or Tau knockout mouse strains may be used as control samples. In vitro affinity testing may be carried out (e.g., by ELISA) using recombinant or isolated protein antigens. In some embodiments, recombinant or isolated ePHF is used for antibody affinity testing. In some embodiments, antigens listed in Table 8 may be used.

In some embodiments, antibody affinity analysis may be used to modulate antibody polyspecificity (e.g., to reduce or enhance antibody polyspecificity). Such modulation may include modulating relative affinity for two or more epitopes or antigens. For example, antibodies may be optimized for higher affinity for one epitope or antigen over a second epitope or antigen.

Antibodies may be modified to optimize antibody functional properties. Such functional properties may be assessed or engineered based on analytical assay results relating to one or more antibody functional properties. Assays may be used to screen multiple antibodies to identify or rank antibodies based on functional criteria. Anti-tau antibodies may be modified to optimize tau aggregation inhibition. Such inhibition may be based on physical disruption of tau aggregation or may be based on the ability of anti-tau antibodies to deplete tau protein from assay samples. Optimization based on tau aggregation inhibition may be assessed using one or more assays of tau aggregation (e.g., by tau seeding assay).

Production Modifications

In some embodiments, modifications may be made to optimize antibody production. Such modifications may include or relate to one or more of protein folding, stability, expression, and/or immunogenicity. Modifications may be carried out to address one or more antibody features negatively impacting production. Such features may include, but are not limited to, unpaired cysteines or irregular disulfides; glycosylation sites (e.g., N-linked NXS/T sites); acid cleavage sites, amino acid oxidation sites, conformity with mouse germline sequences; asparagine deamidation sites; aspartate isomerization sites; N-terminal pyroglutamate formation sites; and aggregation-prone amino acid sequence regions (e.g., within CDR sequences).

In some embodiments, antibodies of the present disclosure may be prepared using recombinant DNA technology (e.g., see U.S. Pat. No. 4,816,567, which is hereby incorporated by reference in its entirety). Antibody-encoding DNA may be isolated and sequenced using conventional procedures (e.g., by using oligonucleotide probes that are capable of binding specifically to genes encoding the heavy and light chains of murine antibodies). In some embodiments, hybridoma cells may be used as a preferred source of DNA. Once isolated, the DNA can be placed into expression vectors, which are then transfected into host cells. Host cells may include, but are not limited to HEK293 cells, HEK293T cells, simian COS cells, Chinese hamster ovary (CHO) cells, and myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide.

Antibody Humanization

In some embodiments, anti-tau antibodies of the present disclosure may be prepared as humanized antibodies. "Humanized" antibodies are chimeric antibodies that contain minimal sequences (e.g., variable domains or CDRs) derived from non-human immunoglobulins (e.g., murine immunoglobulins). Humanized antibodies may be prepared from human (recipient) immunoglobulins in which residues from the hypervariable regions are replaced by hypervariable region residues from one or more non-human "donor" antibodies (e.g., mouse, rat, rabbit, or nonhuman primate). Donor antibodies may be selected based on desired specificity, affinity, and/or capacity. Humanized antibodies may include one or more back-mutation that includes the reversion of one or more amino acids back to amino acids found in a donor antibody. Conversely, residues from donor antibodies included in humanized antibodies may be mutated to match residues present in human recipient antibodies. Back-mutations may be introduced to reduce human immune response to the humanized antibodies. In some embodiments, back-mutations are introduced to avoid issues with antibody manufacturing (e.g., protein aggregation or post-translational modification).

For construction of expression plasmids encoding fully humanized antibodies with human constant regions, DNA sequences encoding antibody variable regions may be inserted into expression vectors (e.g., mammalian expression vectors) between an upstream promoter/enhancer and immunoglobulin signal sequence and a downstream immunoglobulin constant region gene. DNA samples may then be transfected into mammalian cells for antibody production. Constant domains from any class of human antibody may be used. There are five major classes of intact human antibodies: IgA, IgD, IgE, IgG, and IgM, and several of these may be further divided into subclasses (isotypes), e.g., IgG1 (human and murine), IgG2 (human), IgG2a (murine), IgG2b (murine), IgG2c (murine), IgG3 (human and murine), IgG4 (human), IgA (murine), IgA1 (human), and IgA2 (human).

Cell lines with stable transfection of DNA encoding humanized antibodies may be prepared and used to establish stable cell lines. Cell lines producing humanized antibodies may be expanded for expression of humanized antibodies that may be harvested and purified from cell culture media.

In some embodiments, humanized antibodies of the present disclosure may have cross-reactivity with non-human species. Species cross-reactivity may allow antibodies to be used in different animals for various purposes. For example, cross-reactive antibodies may be used in pre-clinical animal studies to provide information about antibody efficacy and/or toxicity. Non-human species may include, but are not limited to, mouse, rat, rabbit, dog, pig, goat, sheep, and nonhuman primates (e.g., Cynomolgus monkeys).

Antibody Conjugates

In some embodiments, antibodies of the present disclosure may be or be prepared as antibody conjugates. As used herein, the term "conjugate" refers to any agent, cargo, or chemical moiety that is attached to a recipient entity or the process of attaching such an agent, cargo, or chemical moiety. As used herein, the term "antibody conjugate" refers to any antibody with an attached agent, cargo, or chemical moiety. Conjugates utilized to prepare antibody conjugates may include therapeutic agents. Such therapeutic agents may include drugs. Antibody conjugates that include a conjugated drug are referred to herein as "antibody drug conjugates." Antibody drug conjugates may be used to direct conjugated drugs to specific targets based on the affinity of associated antibodies for proteins or epitopes associated with such targets. Such antibody drug conjugates may be used to localize biological activity associated with such conjugated drugs to targeted cells, tissues, organs, or other targeted entities. In some embodiments, conjugates utilized to prepare antibody conjugates include detectable labels. Antibodies may be conjugated with detectable labels for purposes of detection. Such detectable labels may include, but are not limited to, radioisotopes, fluorophores, chromophores, chemiluminescent compounds, enzymes, enzyme co-factors, dyes, metal ions, ligands, biotin, avidin, streptavidin, haptens, quantum dots, or any other detectable labels known in the art or described herein.

Conjugates may be attached to antibodies directly or via a linker. Direct attachment may be by covalent bonding or by non-covalent association (e.g., ionic bonds, hydrostatic bonds, hydrophobic bonds, hydrogen bonds, hybridization, etc.). Linkers used for conjugate attachment may include any chemical structure capable of connecting an antibody to a conjugate. In some embodiments, linkers include polymeric molecules (e.g., nucleic acids, polypeptides, polyethylene glycols, carbohydrates, lipids, or combinations thereof). Antibody conjugate linkers may be cleavable (e.g., through contact with an enzyme, change in pH, or change in temperature).

Exemplary Anti-Tau Antibodies

In some embodiments, the anti-tau antibody comprises at least one antigen-binding domain, e.g., a variable region or antigen binding fragment thereof, from an antibody described herein, e.g., from V0004, V0009, V0022, V0023, V0024, or V0052, e.g., as described in Table 1 or 4, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises at least one antigen-binding domain, e.g., a variable region or antigen binding fragment thereof, from an antibody described in WO 2021/211753, the contents of which are hereby incorporated by reference in its entirety, or a sequence substantially identical (e.g., having at least about 70%, 75%, 80%, 85%, 90%, 92%, 95%, 97%, 98%, or 99% sequence identity) to any of the antibody sequences disclosed in WO 2021/211753.

In some embodiments, the anti-tau antibody comprises a heavy chain variable region from an antibody described herein, e.g., chosen from V0004, V0009, V0022, V0023, V0024, or V0052, e.g., as described in Table 4, or a sequence substantially identical (e.g., having at least about 70%, 75%, 80%, 85%, 90%, 92%, 95%, 97%, 98%, or 99% sequence identity) to any of the aforesaid sequences. In some embodiments, the heavy chain variable region comprises an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a heavy chain variable region provided in Table 4.

In some embodiments, the nucleotide sequence encoding the anti-tau antibody comprises the nucleotide sequence of a heavy chain variable region from an antibody described herein, e.g., chosen from V0004, V0009, V0022, V0023, V0024, or V0052, e.g., as described in Table 4, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a light chain variable region from an antibody described herein, e.g., chosen from V0004, V0009, V0022, V0023, V0024, or V0052, e.g., as described in Table 4, or a sequence substantially identical (e.g., having at least about 70%, 75%, 80%, 85%, 90%, 92%, 95%, 97%, 98%, or 99% sequence identity) to any of the aforesaid sequences. In some embodiments, the light chain variable region comprises an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a light chain variable region provided in Table 4.

In some embodiments, the nucleotide sequence encoding the anti-tau antibody comprises the nucleotide sequence of a light chain variable region from an antibody described herein, e.g., chosen from V0004, V0009, V0022, V0023, V0024, or V0052, e.g., as described in Table 4, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a heavy chain variable region and a light chain variable region from an antibody described herein, e.g., chosen from V0004, V0009, V0022, V0023, V0024, or V0052, e.g., as described in Table 4, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region comprising an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a heavy chain variable region provided in Table 4; and a light chain variable region comprising an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a light chain variable region provided in Table 4.

In some embodiments, the anti-tau antibody comprises a heavy chain constant region, e.g., a human IgG1, IgG2, IgG3, or IgG4 constant regions, or a murine IgG1, IgG2A, IgG2B, IgG2C, or IgG3 constant regions. In some embodiments, the heavy chain constant comprises an amino acid sequence set forth in Table 5, or a sequence substantially identical (e.g., having at least about 70%, 75%, 80%, 85%, 90%, 92%, 95%, 97%, 98%, or 99% sequence identity) to any of the aforesaid sequences. In some embodiments, a nucleic acid encoding the heavy chain constant region comprises a nucleotide sequence set forth in Table 5, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a light chain constant region, e.g., a kappa light chain constant region, e.g., a human kappa or lambda light chain constant region or a murine kappa or lambda light chain constant region. In some embodiments, the light chain constant comprises an amino acid sequence set forth in Table 5, or a sequence substantially identical (e.g., having at least about 70%, 75%, 80%, 85%, 90%, 92%, 95%, 97%, 98%, or 99% sequence identity) to any of the aforesaid sequences. In some embodiments, nucleic acid encoding the light chain constant region comprises a nucleotide sequence set forth in Table 5, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a heavy chain constant region and a light chain constant region. In some embodiments, the heavy chain constant region and the light chain constant region comprise an amino acid sequence set forth in Table 5, or a sequence substantially identical (e.g., having at least about 80%, 85%, 90%, 92%, 95%, 97%, 98%, or 99% sequence identity) thereto. In some embodiments, the nucleotide sequence encoding the anti-tau antibody comprises the nucleotide sequence of a heavy chain constant region and the nucleotide sequence of a kappa or lambda light chain constant region. In some embodiments, the nucleotide sequence encoding the heavy chain constant region and light chain constant region comprise a nucleotide sequence set forth in Table 5, or a nucleotide sequence substantially identical (e.g., having at least about 80%, 85%, 90%, 92%, 95%, 97%, 98%, or 99% sequence identity) thereto.

In some embodiments, the anti-tau antibody comprises a heavy chain variable region and a constant region, a light chain variable region and a constant region, or both, comprising an amino acid sequence of Table 4 for variable region, and an amino acid sequence of Table 5 for constant region; or is encoded by a nucleic acid sequence of Table 4, and 5; or a sequence substantially identical (e.g., having at least about 80%, 85%, 90%, 92%, 95%, 97%, 98%, or 99% sequence identity) to any of the aforesaid sequences.

In some embodiments, the anti-tau antibody comprises at least one, two, or three complementarity determining regions (CDRs) from a heavy chain variable region comprising an amino acid sequence in Table 4, or is encoded by a nucleic acid sequence in Table 4; or a sequence substantially identical (e.g., having at least about 70%, 75%, 80%, 85%, 90%, 92%, 95%, 97%, 98%, or 99% sequence identity) to any of the aforesaid sequences. In some embodiments, one, two, three, four, five, or all of the CDRs have one, two, three, four, five or more changes, e.g., amino acid substitutions, insertions, or deletions, relative to the amino acid sequence shown in Table 4, or encoded by a nucleotide sequence shown in Table 4. In some embodiments, the encoded anti-tau antibody includes a substitution in a heavy chain CDR, e.g., one or more substitutions in a CDR1, CDR2 and/or CDR3 of the heavy chain.

In some embodiments, the anti-tau antibody comprises at least one, two, or three complementarity determining regions (CDRs) from a light chain variable region comprising an amino acid sequence in Table 4, or is encoded by a nucleic acid sequence in Table 4; or a sequence substantially identical (e.g., having at least about 80%, 85%, 90%, 92%, 95%, 97%, 98%, or 99% sequence identity) to any of the aforesaid sequences. In some embodiments, one, two, three, four, five, or all of the CDRs have one, two, three, four, five or more changes, e.g., amino acid substitutions, insertions, or deletions, relative to the amino acid sequence shown in Table 4, or encoded by a nucleotide sequence shown in Table 4. In some embodiments, the anti-tau antibody includes a substitution in a light chain CDR, e.g., one or more substitutions in a CDR1, CDR2 and/or CDR3 of the light chain.

In some embodiments, the anti-tau antibody comprises at least one, two, three, four, five or six CDRs (or collectively all of the CDRs) from a heavy and light chain variable region comprising an amino acid sequence shown in Table 4, or is encoded by a nucleotide sequence shown in Table 4. In some embodiments, one or more of the CDRs (or collectively all of the CDRs) have one, two, three, four, five, six or more changes, e.g., amino acid substitutions, insertions, or deletions, relative to the CDRs shown in Table 4, or encoded by a nucleotide sequence shown in Table 4.

In some embodiments, the anti-tau antibody comprises all three CDRs from a heavy chain variable region, all three CDRs from light chain variable region, or both (e.g., all six CDRs from a heavy chain variable region and a light chain variable region) comprising an amino acid sequence shown in Table 4, or is encoded by a nucleotide sequence shown in Table 4.

In some embodiments, an anti-tau antibody of the present disclosure may include CDRs identified through CDR analysis of variable domain sequences presented herein via co-crystallography with bound antigen; by computational assessments based on comparisons with other antibodies (e.g., see Strohl, W. R. Therapeutic Antibody Engineering. Woodhead Publishing, Philadelphia PA. 2012. Ch. 3, p 47-54); or Kabat, Chothia, Al-Lazikani, Lefranc, or Honegger numbering schemes, as described previously.

TABLE 4

Exemplary anti-tau antibodies

| Ab ID | SEQ ID NO | Description | Sequence |
|---|---|---|---|
| V0004 | 299 | HC CDR1 (Chothia) | DYTFTNY |
| | 343 | HC CDR2 (Chothia) | DPNSGG |
| | 395 | HC CDR3 (Chothia) | DFDV |
| | 1140 | HC CDR1 (Kabat) | NYWMH |
| | 1141 | HC CDR2 (Kabat) | RIDPNSGGTRYNEKFKN |
| | 395 | HC CDR3 (Kabat) | DFDV |
| | 1155 | HC CDR1 (IMGT) | DYTFTNYW |
| | 1156 | HC CDR2 (IMGT) | IDPNSGGT |
| | 1157 | HC CDR3 (IMGT) | AGDFDV |
| | 4 | VH | QVQLQQPGAELVKPGASVKLSCKASDYTFTNYWMHWVKQRPGR GLEWIGRIDPNSGGTRYNEKFKNKATLTVDKPSSTAYMHLSSL TSEDSAVYYCAGDFDVWGTGTTVTVSS |
| | 150 | DNA VH | CAGGTCCAACTGCAGCAGCCTGGGGCTGAGCTTGTGAAGCCTG GGGCTTCAGTGAAGCTGTCCTGCAAGGCTTCTGACTACACCTT CACCAACTACTGGATGCACTGGGTGAAGCAGAGGCCTGGACGA GGCCTTGAGTGGATAGGAAGGATTGATCCTAATAGTGGTGGTA CTAGGTACAATGAGAAGTTCAAGAACAAGGCCACACTGACTGT TGACAAACCCTCCAGCACAGCCTACATGCATCTCAGCAGCCTG ACATCTGAGGACTCTGCGGTCTATTATTGTGCAGGGGACTTCG ATGTCTGGGGCACAGGGACCACGGTCACCGTCTCCTCA |
| | 460 | LC CDR1 (Chothia) | RASGNIHNYLA |
| | 518 | LC CDR2 (Chothia) | NAKTLPD |
| | 557 | LC CDR3 (Chothia) | QHFWSTPLT |
| | 460 | LC CDR1 (Kabat) | RASGNIHNYLA |
| | 518 | LC CDR2 (Kabat) | NAKTLPD |
| | 557 | LC CDR3 (Kabat) | QHFWSTPLT |
| | 1158 | LC CDR1 (IMGT) | GNIHNY |
| | | LC CDR2 (IMGT) | NAK |

TABLE 4-continued

Exemplary anti-tau antibodies

| Ab ID | SEQ ID NO | Description | Sequence |
|---|---|---|---|
| | 557 | LC CDR3 (IMGT) | QHFWSTPLT |
| | 78 | VL | DIQMTQSPASLSASVGETVTITCRASGNIHNYLAWYQQRQGKS PQLLVYNAKTLPDGVPSRFSGSGSGTQYSLKINSLQPEDFGSY CCQHFWSTPLTFGAGTKLELK |
| | 224 | DNA VL | GACATCCAGATGACTCAGTCTCCAGCCTCCCTATCTGCATCTG TGGGAGAAACTGTCACCATCACATGTCGAGCAAGTGGGAATAT TCACAATTATTTAGCATGGTATCAGCAGAGACAGGGAAAATCT CCTCAGCTCCTGGTCTATAATGCAAAAACCTTACCAGATGGTG TGCCATCAAGGTTCAGTGGCAGTGGATCAGGAACACAATATTC TCTCAAGATCAACAGCCTGCAGCCTGAAGATTTTGGGAGTTAT TGCTGTCAACATTTTTGGAGTACTCCGCTCACGTTCGGTGCTG GGACCAAGTTGGAGCTGAAA |
| V0009 | 304 | HC CDR1 (Chothia) | GFTFTDY |
| | 347 | HC CDR2 (Chothia) | RNKAKGFT |
| | 400 | HC CDR3 (Chothia) | DINY |
| | 1142 | HC CDR1 (Kabat) | DYYMS |
| | 1143 | HC CDR2 (Kabat) | LIRNKAKGFTTEYSASVKG |
| | 400 | HC CDR3 (Kabat) | DINY |
| | 1160 | HC CDR1 (IMGT) | GFTFTDYY |
| | 1161 | HC CDR2 (IMGT) | IRNKAKGFTT |
| | 1162 | HC CDR3 (IMGT) | VRDINY |
| | 9 | VH | EVQLVESGGALVQPGGSLSLSCAASGFTFTDYYMSWVRQPPGK ALEWLALIRNKAKGFTTEYSASVKGRFTISRDNSQSILLFQMN DLRADDSATYYCVRDINYWGQGTTLTVSS |
| | 155 | DNA VH | GAGGTGCAGCTGGTGGAGTCTGGAGGAGCCTTGGTACAGCCTG GGGGTTCTCTGAGTCTCTCCTGTGCAGCTTCTGGATTCACCTT CACTGATTACTACATGAGCTGGGTCCGCCAGCCTCCAGGGAAG GCACTTGAGTGGCTGGCTTTGATTAGAAACAAAGCTAAAGGTT TCACAACAGAATACAGTGCATCTGTGAAGGGTCGGTTCACCAT CTCCAGAGATAATTCCCAAAGCATCCTCCTTTTTCAAATGAAT GACCTGAGAGCTGACGACAGTGCCACTTATTACTGTGTAAGAG ATATAAACTACTGGGGCCAAGGCACCACTCTCACAGTCTCCTC A |
| | 464 | LC CDR1 (Chothia) | KSSQSLLYSTNQENYLA |
| | 523 | LC CDR2 Chothia) | WASSRES |
| | 562 | LC CDR3 (Chothia) | QQYYSYPRT |
| | 464 | LC CDR1 (Kabat) | KSSQSLLYSTNQENYLA |
| | 523 | LC CDR2 (Kabat) | WASSRES |
| | 562 | LC CDR3 (Kabat) | QQYYSYPRT |
| | 1163 | LC CDR1 (IMGT) | QSLLYSTNQENY |
| | | LC CDR2 (IMGT) | WAS |
| | 562 | LC CDR3 (IMGT) | QQYYSYPRT |
| | 83 | VL | DIVMSQSPSSLAVSVGEKVTMSCKSSQSLLYSTNQENYLAWYQ QKPGQSPKLLIYWASSRESGVPDRFTGSGSGTDFTLTISSVKA EDLAVYYCQQYYSYPRTFGGGTKLEIK |
| | 229 | DNA VL | GACATTGTGATGTCACAGTCTCCATCCTCCCTAGCTGTGTCAG TTGGAGAGAAGGTTACTATGAGCTGCAAGTCCAGTCAGAGCCT TTTATATAGTACCAATCAAGAGAACTACTTGGCCTGGTACCAG CAGAAACCAGGGCAGTCTCCTAAACTGCTGATTTACTGGGCAT CCTCTAGGGAATCTGGGGTCCCTGATCGCTTTACAGGCAGTGG ATCTGGGACAGATTTCACTCTCACCATCAGCAGTGTGAAGGCT GAAGACCTGGCAGTTTATTACTGTCAGCAATATTATAGCTATC CTCGGACGTTCGGTGGAGGCACCAAGCTGGAAATCAAA |

TABLE 4-continued

Exemplary anti-tau antibodies

| Ab ID | SEQ ID NO | Description | Sequence |
|---|---|---|---|
| V0022 | 314 | HC CDR1 (Chothia) | GFTFTRY |
| | 341 | HC CDR2 (Chothia) | NPNNGG |
| | 410 | HC CDR3 (Chothia) | GTGTGAMDY |
| | 1144 | HC CDR1 (Kabat) | RYWMH |
| | 1145 | HC CDR2 (Kabat) | NINPNNGGTDFNEKFKN |
| | 410 | HC CDR3 (Kabat) | GTGTGAMDY |
| | 1165 | HC CDR1 (IMGT) | GFTFTRYW |
| | 1166 | HC CDR2 (IMGT) | INPNNGGT |
| | 1167 | HC CDR3 (IMGT) | ARGTGTGAMDY |
| | 64 | HC CDR1 (Alternative) | GFTFTRYWMH |
| | 1145 | HC CDR2 (Alternative) | NINPNNGGTDFNEKFKN |
| | 1167 | HC CDR3 (Alternative) | ARGTGTGAMDY |
| | 21 | VH | QVQLQQPGTELVKPGSSVNLSCKASGFTFTRYWMHWVKERPGH GLEWIGNINPNNGGTDFNEKFKNKATLTVHKSSTTVFIQLSSL TSEDSAVYYCARGTGTGAMDYWGQGTSVTVSS |
| | 167 | DNA VH | CAGGTCCAACTGCAGCAGCCTGGGACTGAACTGGTGAAGCCTG GGTCTTCAGTGAACCTGTCCTGCAAGGCTTCTGGCTTCACCTT CACCAGGTACTGGATGCACTGGGTGAAGGAGAGGCCTGGACAT GGCCTTGAGTGGATTGGAAATATTAATCCTAACAATGGTGGTA CTGACTTCAATGAGAAGTTCAAGAACAAGGCCACACTGACTGT ACACAAGTCCTCCACCACAGTCTTCATCCAACTCAGCAGCCTG ACATCTGAGGACTCTGCGGTCTATTATTGTGCAAGAGGAACTG GGACGGGAGCTATGGACTACTGGGGTCAAGGAACCTCAGTCAC CGTCTCCTCA |
| | 7 | DNA VH | caagtgcagctgcagcagcctggcaccgagctggtgaaacctg gatctagcgtgaatctgagctgcaaggccagcggctttacctt caccagatactggatgcactgggtcaaggaacgccaggccac ggcctggaatggatcggcaatatcaaccccaacaacggcggaa cagatttcaacgagaagttcaagaacaaggctacactgaccgt gcacaaaagctccaccaccgtgttcatccagctgagctctctg acaagcgaggacagcgccgtgtactattgtgccagaggcaccg gcaccggcgccatggactactggggccagggaacatctgtgac agtgtccagc |
| | 190 | DNA VH | CAAGTGCAGCTGCAGCAACCGGGCACAGAGCTGGTGAAGCCTG GCAGCAGCGTGAACCTGAGCTGCAAGGCTAGCGGCTTCACCTT CACAAGATACTGGATGCACTGGGTGAAGGAGAGACCTGGCCAC GGCCTGGAGTGGATCGGCAACATCAACCCTAACAACGGCGGCA CCGACTTCAACGAGAAGTTCAAGAACAAGGCCACCCTGACCGT GCACAAGAGCAGCACCACCGTGTTCATTCAGCTGAGCAGCCTG ACAAGCGAGGACAGCGCCGTGTACTACTGCGCTAGAGGCACCG GCACCGGCGCCATGGACTACTGGGGCCAAGGCACAAGCGTGAC CGTGTCGTCGGC |
| | 8 | Heavy Chain | QVQLQQPGTELVKPGSSVNLSCKASGFTFTRYWMHWVKERPGH GLEWIGNINPNNGGTDFNEKFKNKATLTVHKSSTTVFIQLSSL TSEDSAVYYCARGTGTGAMDYWGQGTSVTVSSAKTTPPSVYPL APGSAAQTNSMVTLGCLVKGYFPEPVTVTWNSGSLSSGVHTFP AVLQSDLYTLSSSVTVPSSTWPSETVTCNVAHPASSTKVDKKI VPRDCGCKPCICTVPEVSSVFIFPPKPKDVLTITLTPKVTCVV VDISKDDPEVQFSWFVDDVEVHTAQTQPREEQFNSTFRSVSEL PIMHQDWLNGKEFKCRVNSAAFPAPIEKTISKTKGRPKAPQVY TIPPPKEQMAKDKVSLTCMITDFFPEDITVEWQWNGQPAENYK NTQPIMDTDGSYFVYSKLNVQKSNWEAGNTFTCSVLHEGLHNH HTEKSLSHSPG |
| | 65 | Heavy Chain | QVQLQQPGTELVKPGSSVNLSCKASGFTFTRYWMHWVKERPGH GLEWIGNINPNNGGTDFNEKFKNKATLTVHKSSTTVFIQLSSL TSEDSAVYYCARGTGTGAMDYWGQGTSVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEFLGGPSVFLFPPKPKDTLMISRTPEVT CVVVDVSQEDPEVQFNWYVDGVEVHNAKTKPREEQFNSTYRVV |

TABLE 4-continued

Exemplary anti-tau antibodies

| Ab ID | SEQ ID NO | Description | Sequence |
|---|---|---|---|
| | | | SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| | 10 | DNA Heavy Chain | caagtgcagctgcagcagcctggcaccgagctggtgaaacctg gatctagcgtgaatctgagctgcaaggccagcggctttacctt caccagatactggatgcactgggtcaaggaacggccaggccac ggcctggaatggatcggcaatatcaaccccaacaacggcggaa cagatttcaacgagaagttcaagaacaaggctacactgaccgt gcacaaaagctccaccaccgtgttcatccagctgagctctctg acaagcgaggacagcgccgtgtactattgtgccagaggcaccg gcaccggcgccatggactactggggccagggaacatctgtgac agtgtccagcgccaaaacgacacccccatctgtctatccactg gcccctggatctgctgcccaaactaactccatggtgaccctgg gatgcctggtcaagggctatttccctgagccagtgacagtgac ctggaactctggatccctgtccagcggtgtgcacaccttccca gctgtcctgcagtctgacctctacactctgagcagctcagtga ctgtcccctccagcacctggcccagcgagaccgtcacctgcaa cgttgcccaccggccagcagcaccaaggtggacaagaaaatt gtgcccagggattgtggttgtaagccttgcatatgtacagtcc cagaagtatcatctgtcttcatcttcccccaaagcccaagga tgtgctcaccattactctgactcctaaggtcacgtgtgttgtg gtagacatcagcaaggatgatcccgaggtccagttcagctggt ttgtagatgatgtggaggtgcacacagctcagacgcaacccg ggaggagcagttcaacagcactttccgctcagtcagtgaactt cccatcatgcaccaggactggctcaatggcaaggagttcaaat gcagggtcaacagtgcagctttccctgccccatcgagaaaac catctccaaaaccaaaggcagaccgaaggctccacaggtgtac accattccacctcccaaggagcagatggccaaggataaagtca gtctgacctgcatgataacagacttcttccctgaagacattac tgtggagtggcagtggaatgggcagccagcggagaactacaag aacactcagcccatcatggacacagatggctcttacttcgtct acagcaagctcaatgtgcagaagagcaactgggaggcaggaaa tactttcacctgctctgtgttacatgagggcctgcacaaccac catactgagaagagcctctcccactctcctggt |
| | 191 | DNA Heavy Chain | CAAGTGCAGCTGCAGCAACCGGGCACAGAGCTGGTGAAGCCTG GCAGCAGCGTGAACCTGAGCTGCAAGGCTAGCGGCTTCACCTT CACAAGATACTGGATGCACTGGGTGAAGGAGAGACCTGGCCAC GGCCTGGAGTGGATCGGCAACATCAACCCTAACAACGGCGGCA CCGACTTCAACGAGAAGTTCAAGAACAAGGCCACCCTGACCGT GCACAAGAGCAGCACCACCGTGTTCATTCAGCTGAGCAGCCTG ACAAGCGAGGACAGCGCCGTGTACTACTGCGCTAGAGGCACCG GCACCGGCGCCATGGACTACTGGGGCCAAGGCACAAGCGTGAC CGTGTCGTCGGCTAGCACCAAGGGTCCTTCCGTGTTTCCTCTA GCCCCTTGCAGCAGAAGCACAAGCGAGAGCACCGCCGCCCTGG GCTGCCTGGTTAAAGATTATTTCCCTGAGCCTGTGACCGTGAG CTGGAATAGCGGCGCCCTGACAAGCGGCGTGCACACCTTCCCT GCCGTGCTGCAGAGCAGCGGCCTGTACAGCCTGAGCAGCGTGG TGACCGTGCCTTCTAGCAGCCTGGGTACTAAGACCTACACCTG CAACGTGGACCACAAGCCTAGCAACACCAAGGTGGACAAGAGA GTGGAGAGCAAGTACGGTCCTCCGTGTCCCCGTGCCCTGCCC CTGAGTTCCTGGGCGGCCCTAGCGTTTTCTTGTTTCCACCTAA GCCTAAGGACACCCTGATGATCAGCAGAACCCCTGAGGTGACC TGCGTGGTGGTGGACGTGAGCCAAGAGGACCCTGAGGTGCAGT TCAACTGGTACGTGGACGGCGTGGAGGTGCACAACGCCAAGAC CAAGCCTAGAGAGGAGCAGTTCAACAGCACCTACAGAGTGGTG AGCGTGCTGACCGTGCTGCACCAAGACTGGCTGAACGGCAAGG AGTACAAGTGCAAGGTGAGCAACAAGGGCCTGCCTAGCAGTAT TGAAAAGACCATCAGCAAGGCCAAGGGACAGCCTAGAGAGCCT CAAGTGTACACCCTGCCTCCTAGCCAAGAGGAGATGACCAAGA ACCAAGTGAGCCTGACCTGCCTGGTGAAGGGGTTTTACCCTAG CGACATCGCCGTGGAGTGGGAGAGCAACGGACAGCCTGAGAAC AACTACAAGACCACCCCTCCTGTGCTGGACAGCGACGGCAGCT TCTTCCTGTACAGCAGACTGACCGTGGACAAGAGCAGATGGCA AGAGGGCAACGTGTTCAGCTGCAGCGTGATGCACGAGGCCCTG CACAACCACTACACACAGAAGAGCCTGAGCCTGAGCCTGGGCA AG |
| | 1154 | LC CDR1 (Chothia) | RSSQSLVHNNGITYLY |
| | 529 | LC CDR2 (Chothia) | RVSNRFS |
| | 571 | LC CDR3 (Chothia) | FQGTHVPRT |

TABLE 4-continued

Exemplary anti-tau antibodies

| Ab ID | SEQ ID NO | Description | Sequence |
|---|---|---|---|
| | 1146 | LC CDR1 (Kabat) | RSSQSLVHNNGITYLY |
| | 529 | LC CDR2 (Kabat) | RVSNRFS |
| | 571 | LC CDR3 (Kabat) | FQGTHVPRT |
| | 473 | LC CDR1 (IMGT) | QSLVHNNGITY |
| | | LC CDR2 (IMGT) | RVS |
| | 571 | LC CDR3 (IMGT) | FQGTHVPRT |
| | 1146 | LC CDR1 (Alternative) | RSSQSLVHNNGITYLY |
| | 529 | LC CDR2 (Alternative) | RVSNRFS |
| | 571 | LC CDR3 (Alternative) | FQGTHVPRT |
| | 93 | VL | DVVMTQTPLSLPVSLGDQASISCRSSQSLVHNNGITYLYWYLQ KPGQSPKLLIYRVSNRFSGVPDRFGGSGSGTDFTLKISRVEAE DLGVYFCFQGTHVPRTFGGGTKLEIK |
| | 11 | DNA VL | gatgtggtgatgacacagacccctctgagcctgcctgtgtccc tcggcgaccaggccagcatcagctgtagaagcagccaatctct ggtgcacaacaatggcatcacctacctgtactggtatctgcag aaacctggccagagccccaagctgctgatctaccgggtgtcca atcggttcagcggagtgccagatagatttggcggatctggcag cggcaccgacttcaccctgaagatctctagagtcgaggccgag gacctgggcgtgtacttctgcttccagggcacacacgtgccca gaaccttcggcggcggaacaaagctggaaatcaag |
| | 241 | DNA VL | GATGTTGTGATGACCCAAACTCCACTCTCCCTGCCTGTCAGTC TTGGAGATCAAGCTTCCATCTCTTGCAGATCTAGTCAGAGCCT TGTACACAACAATGGAATCACCTATTTATATTGGTACCTGCAG AAGCCAGGCCAGTCTCCAAAGCTCCTGATCTACAGGGTTTCCA ACCGATTTTCTGGGGTCCCAGACAGGTTCGGTGGCAGTGGATC AGGGACAGATTTCACACTCAAGATCAGCAGAGTGGAGGCTGAG GATCTGGGAGTTTATTTCTGCTTTCAAGGTACACATGTTCCTC GGACGTTCGGTGGAGGCACCAAGCTGGAAATCAAA |
| | 192 | DNA VL | GACGTGGTGATGACACAGACCCCTCTGAGCCTGCCTGTGAGCC TGGGCGACCAAGCTAGCATCAGCTGCAGAAGCTCTCAGAGCCT GGTGCACAACAACGGCATCACCTACCTGTACTGGTACCTGCAG AAGCCTGGACAGAGCCCTAAGCTGCTGATCTACAGAGTGAGCA ACAGATTCAGCGGCGTGCCTGACAGATTCGGCGGCAGCGGCAG CGGCACCGACTTCACCCTGAAGATCAGCAGAGTGGAGGCCGAG GACCTGGGCGTGTACTTCTGCTTCCAAGGCACGCATGTACCTA GAACCTTCGGCGGCGGCACCAAGCTGGAGATCAAG |
| | 12 | Light Chain | DVVMTQTPLSLPVSLGDQASISCRSSQSLVHNNGITYLYWYLQ KPGQSPKLLIYRVSNRFSGVPDRFGGSGSGTDFTLKISRVEAE DLGVYFCFQGTHVPRTFGGGTKLEIKRADAAPTVSIFPPSSEQ LTSGGASVVCFLNNFYPKDINVKWKIDGSERQNGVLNSWTDQD SKDSTYSMSSTLTLTKDEYERHNSYTCEATHKTSTSPIVKSFN RNEC |
| | 66 | Light Chain | DVVMTQTPLSLPVSLGDQASISCRSSQSLVHNNGITYLYWYLQ KPGQSPKLLIYRVSNRFSGVPDRFGGSGSGTDFTLKISRVEAE DLGVYFCFQGTHVPRTFGGGTKLEIKRTVAAPSVFIFPPSDEQ LKSGTASVVCLLNNFYPREAKVQWKVDNALQSGNSQESVTEQD SKDSTYSLSSTLTLSKADYEKHKVYACEVTHQGLSSPVTKSFN RGEC |
| | 13 | DNA Light Chain | gatgtggtgatgacacagacccctctgagcctgcctgtgtccc tcggcgaccaggccagcatcagctgtagaagcagccaatctct ggtgcacaacaatggcatcacctacctgtactggtatctgcag aaacctggccagagccccaagctgctgatctaccgggtgtcca atcggttcagcggagtgccagatagatttggcggatctggcag cggcaccgacttcaccctgaagatctctagagtcgaggccgag gacctgggcgtgtacttctgcttccagggcacacacgtgccca gaaccttcggcggcggaacaaagctggaaatcaagcgggctga tgctgcaccaactgtatccatcttcccaccatccagtgagcag ttaacatctggaggtgcctcagtcgtgtgcttcttgaacaact ctaccccaaagacatcaatgtcaagtggaagattgatggcag tgaacgacaaaatggcgtcctgaacagttggactgatcaggac agcaaagacagcacctacagcatgagcagcaccctcacgttga ccaaggacgagtatgaacgacataacagctatacctgtgaggc cactcacaagacatcaacttcacccattgtcaagagcttcaac aggaatgagtgt |

TABLE 4-continued

Exemplary anti-tau antibodies

| Ab ID | SEQ ID NO | Description | Sequence |
|---|---|---|---|
| | 193 | DNA Light Chain | GACGTGGTGATGACACAGACCCCTCTGAGCCTGCCTGTGAGCC TGGGCGACCAAGCTAGCATCAGCTGCAGAAGCTCTCAGAGCCT GGTGCACAACAACGGCATCACCTACCTGTACTGGTACCTGCAG AAGCCTGGACAGAGCCCTAAGCTGCTGATCTACAGAGTGAGCA ACAGATTCAGCGGCGTGCCTGACAGATTCGGCGGCAGCGGCAG CGGCACCGACTTCACCCTGAAGATCAGCAGAGTGGAGGCCGAG GACCTGGGCGTGTACTTCTGCTTCCAAGGCACGCATGTACCTA GAACCTTCGGCGGCGGCACCAAGCTGGAGATCAAGAGAACCGT GGCCGCCCCTAGCGTGTTCATCTTCCCTCCTAGCGACGAGCAG CTGAAGAGCGGCACCGCTAGCGTGGTGTGCCTGCTGAACAACT TCTACCCTAGAGAGGCCAAGGTGCAGTGGAAGGTGGACAACGC CCTGCAGAGCGGCAACAGCCAAGAGAGCGTGACCGAGCAAGAC AGCAAGGACAGCACCTACAGCCTGAGCAGCACCCTGACCCTGA GCAAGGCCGACTACGAGAAGCACAAGGTGTACGCCTGCGAGGT GACCCACCAAGGCCTGAGCAGCCCTGTGACCAAGAGCTTCAAC AGAGGCGAGTGC |
| V0023 | 315 | HC CDR1 (Chothia) | GYTFTIF |
| | 341 | HC CDR2 (Chothia) | NPNNGG |
| | 410 | HC CDR3 (Chothia) | GTGTGAMDY |
| | 1147 | HC CDR1 (Kabat) | IFWMH |
| | 1148 | HC CDR2 (Kabat) | KINPNNGGGDYNEKFKS |
| | 410 | HC CDR3 (Kabat) | GTGTGAMDY |
| | 1168 | HC CDR1 (IMGT) | GYTFTIFW |
| | 1169 | HC CDR2 (IMGT) | INPNNGGG |
| | 1167 | HC CDR3 (IMGT) | ARGTGTGAMDY |
| | 22 | VH | QVQLQQPGTELVKPGASVKLSCKASGYTFTIFWMHWVKQRPGH GLEWIGKINPNNGGGDYNEKFKSKATLTVDKSSTTAYLQLSSL TSEDSAVYYCARGTGTGAMDYWGQGTSVTVSS |
| | 168 | DNA VH | CAGGTCCAACTGCAGCAGCCTGGGACTGAACTGGTGAAGCCTG GGGCTTCAGTGAAGCTGTCCTGCAAGGCTTCTGGCTACACCTT CACCATCTTCTGGATGCACTGGGTGAAGCAGAGGCCTGGACAT GGCCTTGAGTGGATTGGAAAGATTAATCCTAACAATGGAGGTG GTGACTACAATGAGAAATTCAAGAGTAAGGCCACATTGACTGT AGACAAATCCTCCACCACAGCCTACTTGCAGCTCAGCAGCCTG ACATCTGAGGACTCTGCGGTCTATTATTGTGCAAGAGGAACTG GGACGGGAGCTATGGACTACTGGGGTCAAGGAACCTCAGTCAC CGTCTCCTCA |
| | 474 | LC CDR 1 (Chothia) | RSSQSLVHSNGITHLY |
| | 529 | LC CDR2 (Chothia) | RVSNRFS |
| | 571 | LC CDR3 (Chothia) | FQGTHVPRT |
| | 474 | LC CDR1 (Kabat) | RSSQSLVHSNGITHLY |
| | 529 | LC CDR2 (Kabat) | RVSNRFS |
| | 571 | LC CDR3 (Kabat) | FQGTHVPRT |
| | 1170 | LC CDR1 (IMGT) | QSLVHSNGITH |
| | | LC CDR2 (IMGT) | RVS |
| | 571 | LC CDR3 (IMGT) | FQGTHVPRT |
| | 94 | VL | DVVMTQTPLSLPVSLGDHASISCRSSQSLVHSNGITHLYWYLQ RPGQTPKLLIYRVSNRFSGVPDRFSGSGSGTDFTLKISSVEAE DLGVYFCFQGTHVPRTFGGGTKLEIE |
| | 242 | DNA VL | GATGTTGTGATGACCCAAACTCCACTCTCCCTGCCTGTCAGTC TTGGAGATCACGCTTCCATCTCTTGCAGATCTAGTCAGAGCCT TGTACACAGCAATGGAATCACCCATTTATATTGGTACCTGCAG AGGCCAGGCCAGACTCCAAAGCTCCTGATCTACAGGGTTTCCA ACCGATTTTCTGGGGTCCCAGACAGGTTCAGTGGCAGTGGATC |

TABLE 4-continued

Exemplary anti-tau antibodies

| Ab ID | SEQ ID NO | Description | Sequence |
|---|---|---|---|
| | | | AGGGACAGATTTCACACTCAAGATCAGCAGCGTGGAGGCTGAG GATCTGGGAGTTTATTTCTGCTTTCAAGGTACACATGTTCCTC GGACGTTCGGTGGAGGCACCAAGCTGGAAATCGAA |
| V0024 | 316 | HC CDR1 (Chothia) | GYTFTRF |
| | 341 | HC CDR2 (Chothia) | NPNNGG |
| | 410 | HC CDR3 (Chothia) | GTGTGAMDY |
| | 1149 | HC CDR1 (Kabat) | RFWMH |
| | 1150 | HC CDR2 (Kabat) | NINPNNGGTDNNERFKS |
| | 410 | HC CDR3 (Kabat) | GTGTGAMDY |
| | 1171 | HC CDR1 (IMGT) | GYTFTRFW |
| | 1166 | HC CDR2 (IMGT) | INPNNGGT |
| | 1167 | HC CDR3 (IMGT) | ARGTGTGAMDY |
| | 23 | VH | QVQLQQPGTELVKPGASVKLSCKASGYTFTRFWMHWVKQRPGQ GLEWIGNINPNNGGTDNNERFKSKATLTVDRSSSTAYMQLSSL TSEDSAVYYCARGTGTGAMDYWGQGTSVTVSS |
| | 169 | DNA VH | CAGGTCCAACTGCAGCAGCCTGGGACTGAACTGGTGAAGCCTG GGGCTTCAGTGAAGCTGTCCTGCAAGGCTTCTGGCTACACCTT CACCAGGTTCTGGATGCACTGGGTGAAGCAGAGGCCTGGACAA GGCCTTGAGTGGATTGGAAATATTAATCCTAACAATGGTGGTA CTGACAATAATGAGAGGTTCAAGAGCAAGGCCACACTGACTGT AGACAGATCCTCCAGCACAGCCTACATGCAGCTCAGCAGCCTG ACATCTGAGGACTCTGCGGTCTATTATTGTGCAAGAGGAACTG GGACGGGAGCTATGGACTACTGGGGTCAAGGAACCTCAGTCAC CGTCTCCTCA |
| | 475 | LC CDR 1 (Chothia) | RSSQSLVHSNGNTHLY |
| | 530 | LC CDR2 (Chothia) | RVSSRFS |
| | 571 | LC CDR3 (Chothia) | FQGTHVPRT |
| | 475 | LC CDR1 (Kabat) | RSSQSLVHSNGNTHLY |
| | 530 | LC CDR2 (Kabat) | RVSSRFS |
| | 571 | LC CDR3 (Kabat) | FQGTHVPRT |
| | 1172 | LC CDR1 (IMGT) | QSLVHSNGNTH |
| | | LC CDR2 (IMGT) | RVS |
| | 571 | LC CDR3 (IMGT) | FQGTHVPRT |
| | 95 | VL | DVVMTQTPLSLPVSLGDQASISCRSSQSLVHSNGNTHLYWYLQ KPGQSPKLLIYRVSSRFSGVPDRFSGSGSGTDFTLKISRVEAE DLGVYFCFQGTHVPRTFGGGTKLEIK |
| | 243 | DNA VL | GATGTGGTGATGACCCAAACTCCACTCTCCCTGCCTGTCAGTC TTGGAGATCAGGCTTCCATCTCTTGCAGATCTAGTCAGAGCCT TGTACACAGCAATGGAAACACCCATTTATATTGGTACCTGCAG AAGCCAGGCCAGTCTCCAAAGCTCCTGATCTACAGGGTTTCCA GCCGATTTTCTGGGGTCCCAGACAGGTTCAGTGGCAGTGGATC AGGGACAGATTTCACACTCAAGATCAGCAGAGTGGAGGCTGAG GATCTGGGAGTTTATTTCTGCTTTCAGGGTACACATGTTCCTC GGACGTTCGGTGGAGGCACCAAGCTGGAAATCAAA |
| V0052 | 325 | HC CDR1 (Chothia) | GFSLSTSAM |
| | 362 | HC CDR2 (Chothia) | YWDDD |
| | 435 | HC CDR3 (Chothia) | RRRGYGMDY |
| | 1152 | HC CDR1 (Kabat) | TSAMGVS |
| | 1153 | HC CDR2 (Kabat) | HIYWDDDKRYNPSLKS |

TABLE 4-continued

Exemplary anti-tau antibodies

| Ab ID | SEQ ID NO | Description | Sequence |
|---|---|---|---|
| | 435 | HC CDR3 (Kabat) | RRRGYGMDY |
| | 1173 | HC CDR1 (IMGT) | GFSLSTSAMG |
| | 1174 | HC CDR2 (IMGT) | IYWDDDK |
| | 1175 | HC CDR3 (IMGT) | ARRRGYGMDY |
| | 51 | VH | QITLKESGPGILQSSQTLSLTCSFSGFSLSTSAMGVSWIRQPS GEGLEWLAHIYWDDDKRYNPSLKSRLTISKDTSRNQVFLKITS VDTADTATYYCARRRGYGMDYWGQGTSVTVSS |
| | 197 | DNA VH | CAGATTACTCTGAAAGAGTCTGGCCCTGGGATATTGCAGTCCT CCCAGACCCTCAGTCTGACTTGTTCTTTCTCTGGGTTTTCACT GAGCACTTCTGCTATGGGTGTGAGTTGGATTCGTCAGCCTTCA GGAGAGGGTCTGGAGTGGCTGGCACACATTTACTGGGATGATG ACAAGCGCTATAACCCATCCCTGAAGAGCCGGCTCACAATCTC CAAGGATACCTCCAGAAACCAGGTATTCCTCAAGATCACCAGT GTGGACACTGCAGATACTGCCACATACTACTGTGCTCGAAGAA GGAGGGGGTATGGTATGGACTACTGGGGTCAAGGAACCTCAGT CACCGTCTCCTCA |
| | 495 | LC CDR 1 (Chothia) | KASQSVSNDVA |
| | 540 | LC CDR2 (Chothia) | YASNRCT |
| | 587 | LC CDR3 (Chothia) | QQDYRSPLT |
| | 495 | LC CDR1 (Kabat) | KASQSVSNDVA |
| | 540 | LC CDR2 (Kabat) | YASNRCT |
| | 587 | LC CDR3 (Kabat) | QQDYRSPLT |
| | 1176 | LC CDR1 (IMGT) | QSVSND |
| | | LC CDR2 (IMGT) | YAS |
| | 587 | LC CDR3 (IMGT) | QQDYRSPLT |
| | 122 | VL | SIVMTQTPKFLLVSAGDRVTITCKASQSVSNDVAWYQQKPGQS PKLLIYYASNRCTGVPDRFTGSGYGTDFTFTISTVQAEDLAVY FCQQDYRSPLTFGAGTKLELK |
| | 270 | DNA VL | AGTATTGTGATGACCCAGACTCCCAAATTCCTGCTTGTATCAG CAGGAGACAGGGTTACCATAACCTGCAAGGCCAGTCAGAGTGT GAGTAATGATGTAGCTTGGTACCAACAGAAGCCAGGGCAGTCT CCTAAACTGCTAATATACTATGCATCCAATCGCTGCACTGGAG TCCCTGATCGCTTCACTGGCAGTGGATATGGGACGGATTTCAC TTTCACCATCAGCACTGTACAGGCTGAAGACCTGGCAGTTTAT TTCTGTCAGCAGGATTATAGGTCTCCGCTCACGTTCGGTGCTG GGACCAAGCTGGAGCTGAAA |

TABLE 4A

Exemplary Humanized Heavy Chain Variable Regions and Heavy Chains of V0022

| Description | SEQ ID NO | Sequence |
|---|---|---|
| VH1 | 67 | QVQLVESGAEVKKPGASVKVSCKASGFTFTRYWMHWVKERPGHGLEWMGNINP NNGGTDFNEKFKNRVTITVHKSASTAYMELSSLRSEDTAVYYCARGTGTGAMD YWGQGTTVTVSS |
| DNA VH1 | 156 | CAAGTGCAGCTGGTGGAGAGCGGCGCCGAGGTGAAGAAGCCTGGCGCTAGCGT GAAGGTGAGCTGCAAGGCTAGCGGCTTCACCTTCACCAAGATACTGGATGCACT GGGTGAAGGAGAGACCTGGCCACGGCCTGGAGTGGATGGGCAACATCAACCCT AACAACGGCGGCACCGACTTCAACGAGAAGTTCAAGAACAGAGTGACCATCAC CGTGCACAAGAGCGCGTCGACCGCTTACATGGAGCTGAGCAGCCTGAGAAGCG AGGACACCGCCGTGTACTACTGCGCTAGAGGCACCGGCACCGGCGCCATGGAC TACTGGGGCCAAGGCACCACCGTGACCGTCTCGTCC |
| Heavy Chain 1 | 170 | QVQLVESGAEVKKPGASVKVSCKASGFTFTRYWMHWVKERPGHGLEWMGNINP NNGGTDFNEKFKNRVTITVHKSASTAYMELSSLRSEDTAVYYCARGTGTGAMD YWGQGTTVTVSSASTKGPSVFPLAPCSRSTSESTAALGCLVKDYFPEPVTVSW |

TABLE 4A-continued

Exemplary Humanized Heavy Chain Variable Regions and Heavy Chains of V0022

| Description | SEQ ID NO | Sequence |
|---|---|---|
| | | NSGALTSGVHTFPAVLQSSGLYSLSSVVTVPSSSLGTKTYTCNVDHKPSNTKV<br>DKRVESKYGPPCPPCPAPEFLGGPSVFLFPPKPKDTLMISRTPEVTCVVVDVS<br>QEDPEVQFNWYVDGVEVHNAKTKPREEQFNSTYRVVSVLTVLHQDWLNGKEYK<br>CKVSNKGLPSSIEKTISKAKGQPREPQVYTLPPSQEEMTKNQVSLTCLVKGFY<br>PSDIAVEWESNGQPENNYKTTPPVLDSDGSFFLYSRLTVDKSRWQEGNVFSCS<br>VMHEALHNHYTQKSLSLSLGK |
| DNA Heavy Chain 1 | 180 | CAAGTGCAGCTGGTGGAGAGCGGCGCCGAGGTGAAGAAGCCTGGCGCTAGCGT<br>GAAGGTGAGCTGCAAGGCTAGCGGCTTCACCTTCACAAGATACTGGATGCACT<br>GGGTGAAGGAGAGACCTGGCCACGGCCTGGAGTGGATGGGCAACATCAACCCT<br>AACAACGGCGGCACCGACTTCAACGAGAAGTTCAAGAACAGAGTGACCATCAC<br>CGTGCACAAGAGCGCGTCGACCGCTTACATGGAGCTGAGCAGCCTGAGAAGCG<br>AGGACACCGCCGTGTACTACTGCGCTAGAGGCACCGGCACCGGCGCCATGGAC<br>TACTGGGGCCAAGGCACCACCGTGACCGTCTCGTCCGCTAGCACGAAAGGTCC<br>AAGCGTTTTCCCTCTAGCCCCTTGCAGCAGAAGCACAAGCGAGAGCACCGCCG<br>CCCTGGGCTGCCTTGTAAAAGATTACTTCCCTGAGCCTGTGACCGTGAGTTGG<br>AACAGCGGCGCCCTGACAAGCGGCGTGCACACCTTCCCTGCCGTGCTGCAGAG<br>CAGCGGCCTGTACAGCCTGAGCAGCGTGGTGACCGTGCCAAGCAGCAGCCTGG<br>GCACCAAGACCTACACCTGCAACGTGGACCACAAGCCTAGCAACACCAAGGTG<br>GACAAGAGAGTGGAGAGCAAGTACGGTCCTCCGTGTCCCCCGTGCCCTGCCCC<br>TGAGTTCCTGGGCGGCCCTTCGGTGTTTCTGTTTCCACCTAAGCCTAAGGACA<br>CCCTGATGATCAGCAGAACCCCTGAGGTGACCTGCGTGGTGGTGGACGTGAGC<br>CAAGAGGACCCTGAGGTGCAGTTCAACTGGTACGTGGACGGCGTGGAGGTGCA<br>CAACGCCAAGACCAAGCCTAGAGAGGAGCAGTTCAACAGCACCTACAGAGTGG<br>TGAGCGTGCTGACCGTGCTGCACCAAGACTGGCTGAACGGCAAGGAGTACAAG<br>TGCAAGGTGAGCAACAAGGGCCTGCCTAGTTCCATTGAGAAGACCATCAGCAA<br>GGCCAAGGGACAGCCTAGAGAGCCTCAAGTGTACACCCTGCCTCCTAGCCAAG<br>AGGAGATGACCAAGAACCAAGTGAGCCTGACCTGCCTGGTGAAGGGATTCTAC<br>CCTAGCGACATCGCCGTGGAGTGGGAGAGCAACGGACAGCCTGAGAACAACTA<br>CAAGACCACCCCTCCTGTGCTGGACAGCGACGGCAGCTTCTTCCTGTACAGCA<br>GACTGACCGTGGACAAGAGCAGATGGCAAGAGGGCAACGTGTTCAGCTGCAGC<br>GTGATGCACGAGGCCCTGCACAACCACTACACACAGAAGAGCCTGAGCCTGAG<br>CCTGGGCAAG |
| VH2 | 68 | QVQLVQSGAEVKKPGASVKVSCKASGFTFTRYWMHWVRERPGHGLEWIGNINP<br>NNGGTDFNEKFKNRVTMTVHKSISTAYMELSSLRSDDSAVYYCARGTGTGAMD<br>YWGQGTLVTVSS |
| DNA VH2 | 157 | CAAGTGCAGCTGGTGCAGAGCGGCGCCGAGGTGAAGAAGCCTGGCGCTAGCGT<br>GAAGGTGAGCTGCAAGGCTAGCGGCTTCACCTTCACAAGATACTGGATGCACT<br>GGGTGAGAGAGAGACCTGGCCACGGCCTGGAGTGGATCGGCAACATCAACCCT<br>AACAACGGCGGCACCGACTTCAACGAGAAGTTCAAGAACAGAGTGACCATGAC<br>CGTGCACAAGAGCATCAGCACCGCCTACATGGAGCTGAGCAGCCTGAGAAGCG<br>ACGACAGCGCCGTGTACTACTGCGCTAGAGGCACCGGCACCGGCGCCATGGAC<br>TACTGGGGCCAAGGCACCCTGGTGACGGTAAGCTCC |
| Heavy Chain 2 | 171 | QVQLVQSGAEVKKPGASVKVSCKASGFTFTRYWMHWVRERPGHGLEWIGNINP<br>NNGGTDFNEKFKNRVTMTVHKSISTAYMELSSLRSDDSAVYYCARGTGTGAMD<br>YWGQGTLVTVSSASTKGPSVFPLAPCSRSTSESTAALGCLVKDYFPEPVTVSW<br>NSGALTSGVHTFPAVLQSSGLYSLSSVVTVPSSSLGTKTYTCNVDHKPSNTKV<br>DKRVESKYGPPCPPCPAPEFLGGPSVFLFPPKPKDTLMISRTPEVTCVVVDVS<br>QEDPEVQFNWYVDGVEVHNAKTKPREEQFNSTYRVVSVLTVLHQDWLNGKEYK<br>CKVSNKGLPSSIEKTISKAKGQPREPQVYTLPPSQEEMTKNQVSLTCLVKGFY<br>PSDIAVEWESNGQPENNYKTTPPVLDSDGSFFLYSRLTVDKSRWQEGNVFSCS<br>VMHEALHNHYTQKSLSLSLGK |
| DNA Heavy Chain 2 | 181 | CAAGTGCAGCTGGTGCAGAGCGGCGCCGAGGTGAAGAAGCCTGGCGCTAGCGT<br>GAAGGTGAGCTGCAAGGCTAGCGGCTTCACCTTCACAAGATACTGGATGCACT<br>GGGTGAGAGAGAGACCTGGCCACGGCCTGGAGTGGATCGGCAACATCAACCCT<br>AACAACGGCGGCACCGACTTCAACGAGAAGTTCAAGAACAGAGTGACCATGAC<br>CGTGCACAAGAGCATCAGCACCGCCTACATGGAGCTGAGCAGCCTGAGAAGCG<br>ACGACAGCGCCGTGTACTACTGCGCTAGAGGCACCGGCACCGGCGCCATGGAC<br>TACTGGGGCCAAGGCACCCTGGTGACGGTAAGCTCCGCTAGCACCAAGGGTCC<br>TAGTGTATTTCCCTAGCCCCTTGCAGCAGAAGCACAAGCGAGAGCACCGCCG<br>CCCTGGGCTGCCTTGTGAAGGACTACTTCCCTGAGCCTGTCACAGTGTCCTGG<br>AATAGCGGCGCCCTGACAAGCGGCGTGCACACCTTCCCTGCCGTGCTGCAGAG<br>CAGCGGCCTGTACAGCCTGAGCAGCGTGGTGACCGTGCCTTCGTCGAGCCTGG<br>GCACCAAGACCTACACCTGCAACGTGGACCACAAGCCTAGCAACACCAAGGTG<br>GACAAGAGAGTGGAGAGCAAGTACGGTCCTCCGTGTCCCCCGTGCCCTGCCCC<br>TGAGTTCCTGGGCGGCCCTAGCGTGTTCCTATTTCCACCTAAGCCTAAGGACA<br>CCCTGATGATCAGCAGAACCCCTGAGGTGACCTGCGTGGTGGTGGACGTGAGC<br>CAAGAGGACCCTGAGGTGCAGTTCAACTGGTACGTGGACGGCGTGGAGGTGCA<br>CAACGCCAAGACCAAGCCTAGAGAGGAGCAGTTCAACAGCACCTACAGAGTGG<br>TGAGCGTGCTGACCGTGCTGCACCAAGACTGGCTGAACGGCAAGGAGTACAAG<br>TGCAAGGTGAGCAACAAGGGCCTGCCTAGCAGTATCGAGAAGACCATCAGCAA |

TABLE 4A-continued

Exemplary Humanized Heavy Chain Variable Regions and Heavy Chains of V0022

| Description | SEQ ID NO | Sequence |
|---|---|---|
| | | GGCCAAGGGACAGCCTAGAGAGCCTCAAGTGTACACCCTGCCTCCTAGCCAAG<br>AGGAGATGACCAAGAACCAAGTGAGCCTGACCTGCCTGGTAAAAGGTTTCTAC<br>CCTAGCGACATCGCCGTGGAGTGGGAGAGCAACGGACAGCCTGAGAACAACTA<br>CAAGACCACCCCTCCTGTGCTGGACAGCGACGGCAGCTTCTTCCTGTACAGCA<br>GACTGACCGTGGACAAGAGCAGATGGCAAGAGGGCAACGTGTTCAGCTGCAGC<br>GTGATGCACGAGGCCCTGCACAACCACTACACACAGAAGAGCCTGAGCCTGAG<br>CCTGGGCAAG |
| VH3 | 69 | QVQLVQSGAEVKKSGASVKVSCKASGFTFTRYWMHWVRQAPGQGLEWIGNINP<br>NNGGTDFNEKFKNRVTLIRDTSTTTVFIQLTSLTSEDSAVYYCARGTGTGAMD<br>YWGQGTLVTVSS |
| DNA VH3 | 158 | CAAGTGCAGCTGGTGCAGAGCGGCGCCGAGGTGAAGAAGAGCGGCGCTAGCGT<br>GAAGGTGAGCTGCAAGGCTAGCGGCTTCACCTTCACAAGATACTGGATGCACT<br>GGGTGAGACAAGCCCCTGGCCAAGGCCTGGAGTGGATCGGCAACATCAACCCT<br>AACAACGGCGGCACCGACTTCAACGAGAAGTTCAAGAACAGAGTGACCCTGAT<br>CAGAGACACAAGCACCACCACCGTGTTCATTCAGCTGACAAGCCTGACAAGCG<br>AGGACAGCGCCGTGTACTACTGCGCTAGAGGCACCGGCACCGGCGCCATGGAC<br>TACTGGGGCCAAGGCACCCTGGTGACGGTAAGCTCC |
| Heavy Chain 3 | 172 | QVQLVQSGAEVKKSGASVKVSCKASGFTFTRYWMHWVRQAPGQGLEWIGNINP<br>NNGGTDFNEKFKNRVTLIRDTSTTTVFIQLTSLTSEDSAVYYCARGTGTGAMD<br>YWGQGTLVTVSSASTKGPSVFPLAPCSRSTSESTAALGCLVKDYFPEPVTVSW<br>NSGALTSGVHTFPAVLQSSGLYSLSSVVTVPSSSLGTKTYTCNVDHKPSNTKV<br>DKRVESKYGPPCPPCPAPEFLGGPSVFLFPPKPKDTLMISRTPEVTCVVVDVS<br>QEDPEVQFNWYVDGVEVHNAKTKPREEQFNSTYRVVSVLTVLHQDWLNGKEYK<br>CKVSNKGLPSSIEKTISKAKGQPREPQVYTLPPSQEEMTKNQVSLTCLVKGFY<br>PSDIAVEWESNGQPENNYKTTPPVLDSDGSFFLYSRLTVDKSRWQEGNVFSCS<br>VMHEALHNHYTQKSLSLSLGK |
| DNA Heavy Chain 3 | 182 | CAAGTGCAGCTGGTGCAGAGCGGCGCCGAGGTGAAGAAGAGCGGCGCTAGCGT<br>GAAGGTGAGCTGCAAGGCTAGCGGCTTCACCTTCACAAGATACTGGATGCACT<br>GGGTGAGACAAGCCCCTGGCCAAGGCCTGGAGTGGATCGGCAACATCAACCCT<br>AACAACGGCGGCACCGACTTCAACGAGAAGTTCAAGAACAGAGTGACCCTGAT<br>CAGAGACACAAGCACCACCACCGTGTTCATTCAGCTGACAAGCCTGACAAGCG<br>AGGACAGCGCCGTGTACTACTGCGCTAGAGGCACCGGCACCGGCGCCATGGAC<br>TACTGGGGCCAAGGCACCCTGGTGACGGTAAGCTCCTAGCACCAAGGGTCC<br>TAGTGTATTTCCCCTAGCCCCTTGCAGCAGAAGCACAAGCGAGAGCACCGCCG<br>CCCTGGGCTGCTTGGTGAAGGACTACTTCCCTGAGCCTGTCACAGTGTCCTGG<br>AATAGCGGCGCCCTGACAAGCGGCGTGCACACCTTCCCTGCCGTGCTGCAGAG<br>CAGCGGCCTGTACAGCCTGAGCAGCGTGGTGACCGTGCCTTCGTCGAGCCTGG<br>GCACCAAGACCTACACCTGCAACGTGGACCACAAGCCTAGCAACACCAAGGTG<br>GACAAGAGAGTGGAGAGCAAGTACGGTCCTCCGTGTCCCCCGTGCCCTGCCCC<br>TGAGTTCCTGGGCGGCCCTAGCGTGTTCCTATTTCCACCTAAGCCTAAGGACA<br>CCCTGATGATCAGCAGAACCCCTGAGGTGACCTGCGTGGTGGTGGACGTGAGC<br>CAAGAGGACCCTGAGGTGCAGTTCAACTGGTACGTGGACGGCGTGGAGGTGCA<br>CAACGCCAAGACCAAGCCTAGAGAGGAGCAGTTCAACAGCACCTACAGAGTGG<br>TGAGCGTGCTGACCGTGCTGCACCAAGACTGGCTGAACGGCAAGGAGTACAAG<br>TGCAAGGTGAGCAACAAGGGCCTGCCTAGCAGTATCGAGAAGACCATCAGCAA<br>GGCCAAGGGACAGCCTAGAGAGCCTCAAGTGTACACCCTGCCTCCTAGCCAAG<br>AGGAGATGACCAAGAACCAAGTGAGCCTGACCTGCCTGGTAAAAGGTTTCTAC<br>CCTAGCGACATCGCCGTGGAGTGGGAGAGCAACGGACAGCCTGAGAACAACTA<br>CAAGACCACCCCTCCTGTGCTGGACAGCGACGGCAGCTTCTTCCTGTACAGCA<br>GACTGACCGTGGACAAGAGCAGATGGCAAGAGGGCAACGTGTTCAGCTGCAGC<br>GTGATGCACGAGGCCCTGCACAACCACTACACACAGAAGAGCCTGAGCCTGAG<br>CCTGGGCAAG |
| VH4 | 70 | EVQLVQSGAEVKKPGSSVKVSCKASGFTFTRYWMHWVKERPGHGLEWIGNINP<br>NNGGTDFNEKFKNRVTMTVHKSITTAYMELSRLTSDDSAVYYCARGTGTGAMD<br>YWGQGTLVSVSS |
| DNA VH4 | 159 | GAGGTGCAGCTGGTGCAGAGCGGCGCCGAGGTGAAGAAGCCTGGCAGCAGCGT<br>GAAGGTGAGCTGCAAGGCTAGCGGCTTCACCTTCACAAGATACTGGATGCACT<br>GGGTGAAGGAGAGACCTGGCCACGGCCTGGAGTGGATCGGCAACATCAACCCT<br>AACAACGGCGGCACCGACTTCAACGAGAAGTTCAAGAACAGAGTGACCATGAC<br>CGTGCACAAGAGCATCACCACCGCCTACATGGAGCTGAGCCGGTTAACCTCCG<br>ACGACAGCGCCGTGTACTACTGCGCTAGAGGCACCGGCACCGGCGCCATGGAC<br>TACTGGGGCCAAGGCACCCTGGTGAGCGTGAGCAGC |
| Heavy Chain 4 | 173 | EVQLVQSGAEVKKPGSSVKVSCKASGFTFTRYWMHWVKERPGHGLEWIGNINP<br>NNGGTDFNEKFKNRVTMTVHKSITTAYMELSRLTSDDSAVYYCARGTGTGAMD<br>YWGQGTLVSVSSASTKGPSVFPLAPCSRSTSESTAALGCLVKDYFPEPVTVSW<br>NSGALTSGVHTFPAVLQSSGLYSLSSVVTVPSSSLGTKTYTCNVDHKPSNTKV<br>DKRVESKYGPPCPPCPAPEFLGGPSVFLFPPKPKDTLMISRTPEVTCVVVDVS<br>QEDPEVQFNWYVDGVEVHNAKTKPREEQFNSTYRVVSVLTVLHQDWLNGKEYK |

TABLE 4A-continued

Exemplary Humanized Heavy Chain Variable Regions and Heavy Chains of V0022

| Description | SEQ ID NO | Sequence |
|---|---|---|
| | | CKVSNKGLPSSIEKTISKAKGQPREPQVYTLPPSQEEMTKNQVSLTCLVKGFY PSDIAVEWESNGQPENNYKTTPPVLDSDGSFFLYSRLTVDKSRWQEGNVFSCS VMHEALHNHYTQKSLSLSLGK |
| DNA Heavy Chain 4 | 183 | GAGGTGCAGCTGGTGCAGAGCGGCGCCGAGGTGAAGAAGCCTGGCAGCAGCGT GAAGGTGAGCTGCAAGGCTAGCGGCTTCACCTTCACAAGATACTGGATGCACT GGGTGAAGGAGAGACCTGGCCACGGCCTGGAGTGGATCGGCAACATCAACCCT AACAACGGCGGCACCGACTTCAACGAGAAGTTCAAGAACAGAGTGACCATGAC CGTGCACAAGAGCATCACCACCGCCTACATGGAGCTGAGCCGGTTAACCTCCG ACGACAGCGCCGTGTACTACTGCGCTAGAGGCACCGGCACCGGCGCCATGGAC TACTGGGGCCAAGGCACCCTGGTGAGCGTGAGCAGCGCTAGCACCAAGGGTCC TAGTGTATTTCCCCTAGCCCCTTGCAGCAGAAGCACAAGCGAGAGCACCGCCG CCCTGGGCTGCTTGGTGAAGGACTACTTCCCTGAGCCTGTGACCGTGAGCTGG AACAGCGGCGCCCTGACAAGCGGCGTGCACACCTTCCCTGCCGTGCTGCAGAG CAGCGGCCTGTACAGCCTGAGCAGCGTGGTGACCGTGCCTTCGTCGAGCCTGG GCACCAAGACCTACACCTGCAACGTGGACCACAAGCCTAGCAACACCAAGGTG GACAAGAGAGTGGAGAGCAAGTACGGTCCTCCGTGTCCCCCGTGCCCTGCCCC TGAGTTCCTGGGCGGCCCTAGCGTGTTCCTATTTCCACCTAAGCCTAAGGACA CCCTGATGATCAGCAGAACCCCTGAGGTGACCTGCGTGGTGGTGGACGTGAGC CAAGAGGACCCTGAGGTGCAGTTCAACTGGTACGTGGACGGCGTGGAGGTGCA CAACGCCAAGACCAAGCCTAGAGAGGAGCAGTTCAACAGCACCTACAGAGTGG TGAGCGTGCTGACCGTGCTGCACCAAGACTGGCTGAACGGCAAGGAGTACAAG TGCAAGGTGAGCAACAAGGGCCTGCCTAGCAGTATCGAGAAGACCATCAGCAA GGCCAAGGGACAGCCTAGAGAGCCTCAAGTGTACACCCTGCCTCCTAGCCAAG AGGAGATGACCAAGAACCAAGTGAGCCTGACCTGCCTGGTAAAAGGTTTCTAC CCTAGCGACATCGCCGTGGAGTGGGAGAGCAACGGACAGCCTGAGAACAACTA CAAGACCACCCCTCCTGTGCTGGACAGCGACGGCAGCTTCTTCCTGTACTCCC GCCTGACGGTTGACAAGAGCAGATGGCAAGAGGGCAACGTGTTCAGCTGCAGC GTGATGCACGAGGCCCTGCACAACCACTACACACAGAAGAGCCTGAGCCTGAG CCTGGGCAAG |
| VH5 | 71 | QVQLVQSGAEVKKPGASVKVSCKASGFTFTRYWMHWVKERPGQGLEWMGNINP NNGGTDFNEKFKNRVTMTVHKSTSTVFIQLSSLRSEDTAVYYCARGTGTGAMD YWGQGTSVTVSS |
| DNA VH5 | 160 | CAAGTGCAGCTGGTGCAGAGCGGCGCCGAGGTGAAGAAGCCTGGCGCTAGCGT GAAGGTGAGCTGCAAGGCTAGCGGCTTCACCTTCACAAGATACTGGATGCACT GGGTGAAGGAGAGACCTGGCCAAGGCCTGGAGTGGATGGGCAACATCAACCCT AACAACGGCGGCACCGACTTCAACGAGAAGTTCAAGAACAGAGTGACCATGAC CGTGCACAAGAGCACAAGCACCGTGTTCATTCAGCTGAGCAGCCTGAGAAGCG AGGACACCGCCGTGTACTACTGCGCTAGAGGCACCGGCACCGGCGCCATGGAC TACTGGGGCCAAGGCACAAGCGTGACGGTAAGCTCC |
| Heavy Chain 5 | 174 | QVQLVQSGAEVKKPGASVKVSCKASGFTFTRYWMHWVKERPGQGLEWMGNINP NNGGTDFNEKFKNRVTMTVHKSTSTVFIQLSSLRSEDTAVYYCARGTGTGAMD YWGQGTSVTVSSASTKGPSVFPLAPCSRSTSESTAALGCLVKDYFPEPVTVSW NSGALTSGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVKGFY PSDIAVEWESNGQPENNYKTTPPVLDSDGSFFLYSRLTVDKSRWQEGNVFSCS VMHEALHNHYTQKSLSLSLGK |
| DNA Heavy Chain 5 | 184 | CAAGTGCAGCTGGTGCAGAGCGGCGCCGAGGTGAAGAAGCCTGGCGCTAGCGT GAAGGTGAGCTGCAAGGCTAGCGGCTTCACCTTCACAAGATACTGGATGCACT GGGTGAAGGAGAGACCTGGCCAAGGCCTGGAGTGGATGGGCAACATCAACCCT AACAACGGCGGCACCGACTTCAACGAGAAGTTCAAGAACAGAGTGACCATGAC CGTGCACAAGAGCACAAGCACCGTGTTCATTCAGCTGAGCAGCCTGAGAAGCG AGGACACCGCCGTGTACTACTGCGCTAGAGGCACCGGCACCGGCGCCATGGAC TACTGGGGCCAAGGCACAAGCGTGACGGTAAGCTCCGCTAGCACCAAGGGTCC TAGTGTATTTCCCCTAGCCCCTTGCAGCAGAAGCACAAGCGAGAGCACCGCCG CCCTGGGCTGCTTGGTGAAGGACTACTTCCCTGAGCCTGTCACAGTGTCCTGG AATAGCGGCGCCCTGACAAGCGGCGTGCACACCTTCCCTGCCGTGCTGCAGAG CAGCGGCCTGTACAGCCTGAGCAGCGTGGTGACCGTGCCTTCGTCGAGCCTGG GCACCAAGACCTACACCTGCAACGTGGACCACAAGCCTAGCAACACCAAGGTG GACAAGAGAGTGGAGAGCAAGTACGGTCCTCCGTGTCCCCCGTGCCCTGCCCC TGAGTTCCTGGGCGGCCCTAGCGTGTTCCTATTTCCACCTAAGCCTAAGGACA CCCTGATGATCAGCAGAACCCCTGAGGTGACCTGCGTGGTGGTGGACGTGAGC CAAGAGGACCCTGAGGTGCAGTTCAACTGGTACGTGGACGGCGTGGAGGTGCA CAACGCCAAGACCAAGCCTAGAGAGGAGCAGTTCAACAGCACCTACAGAGTGG TGAGCGTGCTGACCGTGCTGCACCAAGACTGGCTGAACGGCAAGGAGTACAAG TGCAAGGTGAGCAACAAGGGCCTGCCTAGCAGTATCGAGAAGACCATCAGCAA GGCCAAGGGACAGCCTAGAGAGCCTCAAGTGTACACCCTGCCTCCTAGCCAAG AGGAGATGACCAAGAACCAAGTGAGCCTGACCTGCCTGGTAAAAGGTTTCTAC CCTAGCGACATCGCCGTGGAGTGGGAGAGCAACGGACAGCCTGAGAACAACTA |

TABLE 4A-continued

Exemplary Humanized Heavy Chain Variable Regions and Heavy Chains of V0022

| Description | SEQ ID NO | Sequence |
|---|---|---|
| | | CAAGACCACCCCTCCTGTGCTGGACAGCGACGGCAGCTTCTTCCTGTACAGCA<br>GACTGACCGTGGACAAGAGCAGATGGCAAGAGGGCAACGTGTTCAGCTGCAGC<br>GTGATGCACGAGGCCCTGCACAACCACTACACACAGAAGAGCCTGAGCCTGAG<br>CCTGGGCAAG |

TABLE 4B

Exemplary Humanized Light Chain Variable Regions and Light Chains of V0022

| Description | SEQ ID NO | Sequence |
|---|---|---|
| VL1 | 72 | DVVMTQSPLSLPVTLGQPASISCRSSQSLVHNNGITYLYWYQQRPGQSPRLLI<br>YRVSNRFSGVPDRFSGSGSGTDFTLKISRVEAEDVGVYYCFQGTHVPRTFGQG<br>TKLEIK |
| DNA VL1 | 161 | GACGTGGTGATGACACAGAGCCCTCTGAGCCTGCCTGTGACCCTGGGACAGCC<br>TGCTAGCATCAGCTGCAGAAGCTCTCAGAGCCTGGTGCACAACAACGGCATCA<br>CCTACCTGTACTGGTATCAGCAGAGACCTGGACAGAGCCCTAGACTGCTGATC<br>TACAGAGTGAGCAACAGATTCAGCGGCGTGCCTGACAGATTCTCCGGCTCCGG<br>CAGCGGCACCGACTTCACCCTGAAGATCAGCAGAGTGGAGGCCGAGGACGTGG<br>GCGTGTACTACTGCTTTCAAGGCACCCATGTCCCTAGAACCTTCGGCCAAGGC<br>ACCAAGCTGGAGATCAAG |
| Light Chain 1 | 175 | DVVMTQSPLSLPVTLGQPASISCRSSQSLVHNNGITYLYWYQQRPGQSPRLLI<br>YRVSNRFSGVPDRFSGSGSGTDFTLKISRVEAEDVGVYYCFQGTHVPRTFGQG<br>TKLEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTK<br>SFNRGEC |
| DNA Light Chain 1 | 185 | GACGTGGTGATGACACAGAGCCCTCTGAGCCTGCCTGTGACCCTGGGACAGCC<br>TGCTAGCATCAGCTGCAGAAGCTCTCAGAGCCTGGTGCACAACAACGGCATCA<br>CCTACCTGTACTGGTATCAGCAGAGACCTGGACAGAGCCCTAGACTGCTGATC<br>TACAGAGTGAGCAACAGATTCAGCGGCGTGCCTGACAGATTCTCCGGCTCCGG<br>CAGCGGCACCGACTTCACCCTGAAGATCAGCAGAGTGGAGGCCGAGGACGTGG<br>GCGTGTACTACTGCTTTCAAGGCACCCATGTCCCTAGAACCTTCGGCCAAGGC<br>ACCAAGCTGGAGATCAAGAGAACCGTGGCCGCCCCTAGCGTGTTCATCTTCCC<br>TCCTAGCGACGAGCAGCTGAAGAGCGGCACCGCTAGCGTGGTGTGCCTGCTGA<br>ACAACTTCTACCCTAGAGAGGCCAAGGTGCAGTGGAAGGTGGACAACGCCCTG<br>CAGAGCGGCAACAGCCAAGAGAGCGTGACCGAGCAAGACAGCAAGGACAGCAC<br>CTACAGCCTGAGCAGCACCCTGACCCTGAGCAAGGCCGACTACGAGAAGCACA<br>AGGTGTACGCCTGCGAGGTGACCCACCAAGGGCCTGAGCAGCCCTGTGACCAAG<br>AGCTTCAACAGAGGCGAGTGC |
| VL2 | 73 | DIVMTQSPLSLSVTPGQPASISCRSSQSLVHNNGITYLYWYLQKPGQSPQLLI<br>YRVSNRFSGVPDRFSGSGSGTDFTLKISRVEAEDVGVYYCFQGTHVPRTFGQG<br>TKVEIK |
| DNA VL2 | 162 | GACATCGTGATGACACAGAGCCCTCTGAGCCTGAGCGTGACCCCTGGACAGCC<br>TGCTAGCATCAGCTGCAGAAGCTCTCAGAGCCTGGTGCACAACAACGGCATCA<br>CCTACCTGTACTGGTACCTGCAGAAGCCTGGACAGAGCCCTCAGCTGCTGATC<br>TACAGAGTGAGCAACAGATTCAGCGGCGTGCCTGACAGATTCTCCGGCTCCGG<br>CAGCGGCACCGACTTCACCCTGAAGATCAGCAGAGTGGAGGCCGAGGACGTGG<br>GCGTGTACTACTGCTTTCAAGGCACCCATGTCCCTAGAACCTTCGGCCAAGGC<br>ACCAAGGTGGAGATCAAG |
| Light Chain 2 | 176 | DIVMTQSPLSLSVTPGQPASISCRSSQSLVHNNGITYLYWYLQKPGQSPQLLI<br>YRVSNRFSGVPDRFSGSGSGTDFTLKISRVEAEDVGVYYCFQGTHVPRTFGQG<br>TKVEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTK<br>SFNRGEC |
| DNA Light Chain 2 | 186 | GACATCGTGATGACACAGAGCCCTCTGAGCCTGAGCGTGACCCCTGGACAGCC<br>TGCTAGCATCAGCTGCAGAAGCTCTCAGAGCCTGGTGCACAACAACGGCATCA<br>CCTACCTGTACTGGTACCTGCAGAAGCCTGGACAGAGCCCTCAGCTGCTGATC<br>TACAGAGTGAGCAACAGATTCAGCGGCGTGCCTGACAGATTCTCCGGCTCCGG<br>CAGCGGCACCGACTTCACCCTGAAGATCAGCAGAGTGGAGGCCGAGGACGTGG<br>GCGTGTACTACTGCTTTCAAGGCACCCATGTCCCTAGAACCTTCGGCCAAGGC<br>ACCAAGGTGGAGATCAAGAGAACCGTGGCCGCCCCTAGCGTGTTCATCTTCCC<br>TCCTAGCGACGAGCAGCTGAAGAGCGGCACCGCTAGCGTGGTGTGCCTGCTGA<br>ACAACTTCTACCCTAGAGAGGCCAAGGTGCAGTGGAAGGTGGACAACGCCCTG |

TABLE 4B-continued

Exemplary Humanized Light Chain Variable Regions and Light Chains of V0022

| Description | SEQ ID NO | Sequence |
|---|---|---|
| | | CAGAGCGGCAACAGCCAAGAGAGCGTGACCGAGCAAGACAGCAAGGACAGCAC<br>CTACAGCCTGAGCAGCACCCTGACCCTGAGCAAGGCCGACTACGAGAAGCACA<br>AGGTGTACGCCTGCGAGGTGACCCACCAAGGCCTGAGCAGCCCTGTGACCAAG<br>AGCTTCAACAGAGGCGAGTGC |
| VL3 | 74 | DIVMTQTPLSSPVTLGQPASISCRSSQSLVHNNGITYLYWYQQRPGQPPRLLI<br>YRVSNRFSGVPDRFSGSGAGTDFTLKINRVEAEDVGVYFCFQGTHVPRTFGQG<br>TKLEIK |
| DNA VL3 | 163 | GACATCGTGATGACACAGACCCCTCTCAGCAGCCCTGTGACCCTAGGACAGCC<br>TGCTAGCATCAGCTGCAGAAGCTCTCAGAGCCTGGTGCACAACAACGGCATCA<br>CCTACCTGTACTGGTATCAGCAGAGACCTGGACAGCCTCCTAGACTGCTGATC<br>TACAGAGTGAGCAACAGATTCAGCGGAGTACCTGACAGATTTAGCGGTTCCGG<br>CGCCGGCACCGACTTCACCCTGAAGATCAACAGAGTGGAGGCCGAGGACGTGG<br>GCGTGTACTTCTGCTTTCAAGGCACCCATGTCCCTAGAACCTTCGGCCAAGGC<br>ACCAAGCTGGAGATCAAG |
| Light Chain 3 | 177 | DIVMTQTPLSSPVTLGQPASISCRSSQSLVHNNGITYLYWYQQRPGQPPRLLI<br>YRVSNRFSGVPDRFSGSGAGTDFTLKINRVEAEDVGVYFCFQGTHVPRTFGQG<br>TKLEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTK<br>SFNRGEC |
| DNA Light Chain 3 | 187 | GACATCGTGATGACACAGACCCCTCTCAGCAGCCCTGTGACCCTAGGACAGCC<br>TGCTAGCATCAGCTGCAGAAGCTCTCAGAGCCTGGTGCACAACAACGGCATCA<br>CCTACCTGTACTGGTATCAGCAGAGACCTGGACAGCCTCCTAGACTGCTGATC<br>TACAGAGTGAGCAACAGATTCAGCGGAGTACCTGACAGATTTAGCGGTTCCGG<br>CGCCGGCACCGACTTCACCCTGAAGATCAACAGAGTGGAGGCCGAGGACGTGG<br>GCGTGTACTTCTGCTTTCAAGGCACCCATGTCCCTAGAACCTTCGGCCAAGGC<br>ACCAAGCTGGAGATCAAGAGAACCGTGGCCGCCCCTAGCGTGTTCATCTTCCC<br>TCCTAGCGACGAGCAGCTGAAGAGCGGCACCGCTAGCGTGGTGTGCCTGCTGA<br>ACAACTTCTACCCTAGAGAGGCCAAGGTGCAGTGGAAGGTGGACAACGCCCTG<br>CAGAGCGGCAACAGCCAAGAGAGCGTGACCGAGCAAGACAGCAAGGACAGCAC<br>CTACAGCCTGAGCAGCACCCTGACCCTGAGCAAGGCCGACTACGAGAAGCACA<br>AGGTGTACGCCTGCGAGGTGACCCACCAAGGCCTGTCAAGCCCTGTAACTAAG<br>AGCTTCAACAGAGGCGAGTGC |
| VL4 | 75 | DIEMTQSPLSLPVTLGQPASISCRSSQSLVHNNGITYLYWYQQRPGQSPRRLI<br>YRVSNRFSGVPDRFSGSGSGTDFTLKISRVEAEDVGVYFCFQGTHVPRTFGGG<br>TKLEIK |
| DNA VL4 | 164 | GACATCGAGATGACACAGAGCCCTCTGAGCCTGCCTGTGACCCTGGGACAGCC<br>TGCTAGCATCAGCTGCAGAAGCTCTCAGAGCCTGGTGCACAACAACGGCATCA<br>CCTACCTGTACTGGTATCAGCAGAGACCTGGACAGAGCCCTAGAAGACTGATC<br>TACAGAGTGAGCAACAGATTCAGCGGCGTGCCTGACAGATTCTCCGGCTCCGG<br>CAGCGGCACCGACTTCACCCTGAAGATCAGCAGAGTGGAGGCCGAGGACGTGG<br>GCGTGTACTTCTGCTTTCAAGGCACCCATGTCCCTAGAACCTTCGGCGGCGGC<br>ACCAAGCTGGAGATCAAG |
| Light Chain 4 | 178 | DIEMTQSPLSLPVTLGQPASISCRSSQSLVHNNGITYLYWYQQRPGQSPRRLI<br>YRVSNRFSGVPDRFSGSGSGTDFTLKISRVEAEDVGVYFCFQGTHVPRTFGGG<br>TKLEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTK<br>SFNRGEC |
| DNA Light Chain 4 | 188 | GACATCGAGATGACACAGAGCCCTCTGAGCCTGCCTGTGACCCTGGGACAGCC<br>TGCTAGCATCAGCTGCAGAAGCTCTCAGAGCCTGGTGCACAACAACGGCATCA<br>CCTACCTGTACTGGTATCAGCAGAGACCTGGACAGAGCCCTAGAAGACTGATC<br>TACAGAGTGAGCAACAGATTCAGCGGCGTGCCTGACAGATTCTCCGGCTCCGG<br>CAGCGGCACCGACTTCACCCTGAAGATCAGCAGAGTGGAGGCCGAGGACGTGG<br>GCGTGTACTTCTGCTTTCAAGGCACCCATGTCCCTAGAACCTTCGGCGGCGGC<br>ACCAAGCTGGAGATCAAGAGAACCGTGGCCGCCCCTAGCGTGTTCATCTTCCC<br>TCCTAGCGACGAGCAGCTGAAGAGCGGCACCGCTAGCGTGGTGTGCCTGCTGA<br>ACAACTTCTACCCTAGAGAGGCCAAGGTGCAGTGGAAGGTGGACAACGCCCTG<br>CAGAGCGGCAACAGCCAAGAGAGCGTGACCGAGCAAGACAGCAAGGACAGCAC<br>CTACAGCCTGAGCAGCACCCTGACCCTGAGCAAGGCCGACTACGAGAAGCACA<br>AGGTGTACGCCTGCGAGGTGACCCACCAAGGCCTGAGCAGCCCTGTGACCAAG<br>AGCTTCAACAGAGGCGAGTGC |
| VL5 | 76 | EIVLTQSPATLSLSPGERATLSCRSSQSLVHNNGITYLYWYLQKPGQAPKLLI<br>YRVSNRFSGIPDRFSGSGPGTDFTLTISSLEPEDLAVYFCFQGTHVPRTFGGG<br>TKLEIK |

TABLE 4B-continued

Exemplary Humanized Light Chain Variable Regions and Light Chains of V0022

| Description | SEQ ID NO | Sequence |
|---|---|---|
| DNA VL5 | 165 | GAGATCGTGCTGACACAGAGCCCTGCGACACTGAGCCTGAGCCCTGGCGAGAG<br>AGCTACGCTGAGCTGCCGCAGCTCTCAGAGCCTGGTGCACAACAACGGCATCA<br>CCTACCTGTACTGGTACCTGCAGAAGCCTGGCCAAGCTCCTAAGCTGCTGATC<br>TACAGAGTGAGCAACAGATTCAGCGGCATCCCTGACAGATTCTCCGGCTCCGG<br>CCCTGGCACCGACTTCACCCTGACCATCAGCAGCCTGGAGCCTGAGGACCTGG<br>CCGTGTACTTCTGCTTCCAAGGCACCCATGTACCTAGAACCTTCGGCGGCGGC<br>ACCAAGCTGGAGATCAAG |
| Light Chain 5 | 179 | EIVLTQSPATLSLSPGERATLSCRSSQSLVHNNGITYLYWYLQKPGQAPKLLI<br>YRVSNRFSGIPDRFSGSGPGTDFTLTISSLEPEDLAVYFCFQGTHVPRTFGGG<br>TKLEIKRTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGLSSPVTK<br>SFNRGEC |
| DNA Light Chain 5 | 189 | GAGATCGTGCTGACACAGAGCCCTGCGACACTGAGCCTGAGCCCTGGCGAGAG<br>AGCTACGCTGAGCTGCCGCAGCTCTCAGAGCCTGGTGCACAACAACGGCATCA<br>CCTACCTGTACTGGTACCTGCAGAAGCCTGGCCAAGCCCCTAAGCTGCTGATC<br>TACAGAGTGAGCAACAGATTCAGCGGCATCCCTGACAGATTCTCCGGCTCCGG<br>CCCTGGCACCGACTTCACCCTGACCATCAGCAGCCTGGAGCCTGAGGACCTGG<br>CCGTGTACTTCTGCTTCCAAGGCACCCATGTACCTAGAACCTTCGGCGGCGGC<br>ACCAAGCTGGAGATCAAGAGAACCGTGGCCGCCCCTAGCGTGTTCATCTTCCC<br>TCCTAGCGACGAGCAGCTGAAGAGCGGCACCGCTAGCGTGGTGTGCCTGCTGA<br>ACAACTTCTACCCTAGAGAGGCCAAGGTGCAGTGGAAGGTGGACAACGCCCTG<br>CAGAGCGGCAACAGCCAAGGAGCGTGACCGAGCAAGACAGCAAGGACAGCAC<br>CTACAGCCTGAGCAGCACCCTGACCCTGAGCAAGGCCGACTACGAGAAGCACA<br>AGGTGTACGCCTGCGAGGTGACCCACCAAGGCCTGAGCAGCCCTGTGACCAAG<br>AGCTTCAACAGAGGCGAGTGC |

TABLE 4C

Exemplary anti-tau humanized V0022 antibodies

| Ab ID | SEQ ID NO or Sequence | Description |
|---|---|---|
| Ab1 | 314 | HC CDR1 (Chothia) |
| | 341 | HC CDR2 (Chothia) |
| | 410 | HC CDR3 (Chothia) |
| | 1144 | HC CDR1 (Kabat) |
| | 1145 | HC CDR2 (Kabat) |
| | 410 | HC CDR3 (Kabat) |
| | 1165 | HC CDR1 (IMGT) |
| | 1166 | HC CDR2 (IMGT) |
| | 1167 | HC CDR3 (IMGT) |
| | 64 | HC CDR1 (Alternative) |
| | 1145 | HC CDR2 (Alternative) |
| | 1167 | HC CDR3 (Alternative) |
| | 69 | VH3 |
| | 158 | DNA VH3 |
| | 172 | Heavy Chain 3 |
| | 182 | DNA Heavy Chain 3 |
| | 1154 | LC CDR1 (Chothia) |
| | 529 | LC CDR2 (Chothia) |
| | 571 | LC CDR3 (Chothia) |
| | 1146 | LC CDR1 (Kabat) |
| | 529 | LC CDR2 (Kabat) |
| | 571 | LC CDR3 (Kabat) |
| | 473 | LC CDR1 (IMGT) |
| | RVS | LC CDR2 (IMGT) |
| | 571 | LC CDR3 (IMGT) |
| | 1146 | LC CDR1 (Alternative) |
| | 529 | LC CDR2 (Alternative) |
| | 571 | LC CDR3 (Alternative) |
| | 73 | VL2 |
| | 162 | DNA VL2 |
| | 176 | Light Chain 2 |
| | 186 | DNA Light Chain 2 |
| Ab2 | 314 | HC CDR1 (Chothia) |
| | 341 | HC CDR2 (Chothia) |
| | 410 | HC CDR3 (Chothia) |
| | 1144 | HC CDR1 (Kabat) |
| | 1145 | HC CDR2 (Kabat) |
| | 410 | HC CDR3 (Kabat) |
| | 1165 | HC CDR1 (IMGT) |
| | 1166 | HC CDR2 (IMGT) |
| | 1167 | HC CDR3 (IMGT) |
| | 64 | HC CDR1 (Alternative) |
| | 1145 | HC CDR2 (Alternative) |
| | 1167 | HC CDR3 (Alternative) |
| | 67 | VH1 |
| | 156 | DNA VH1 |
| | 170 | Heavy Chain 1 |
| | 180 | DNA Heavy Chain 1 |
| | 1154 | LC CDR1 (Chothia) |
| | 529 | LC CDR2 (Chothia) |
| | 571 | LC CDR3 (Chothia) |
| | 1146 | LC CDR1 (Kabat) |
| | 529 | LC CDR2 (Kabat) |
| | 571 | LC CDR3 (Kabat) |
| | 473 | LC CDR1 (IMGT) |
| | RVS | LC CDR2 (IMGT) |
| | 571 | LC CDR3 (IMGT) |
| | 1146 | LC CDR1 (Alternative) |
| | 529 | LC CDR2 (Alternative) |
| | 571 | LC CDR3 (Alternative) |
| | 72 | VL1 |
| | 161 | DNA VL1 |
| | 175 | Light Chain 1 |
| | 185 | DNA Light Chain 1 |
| Ab3 | 314 | HC CDR1 (Chothia) |
| | 341 | HC CDR2 (Chothia) |
| | 410 | HC CDR3 (Chothia) |
| | 1144 | HC CDR1 (Kabat) |
| | 1145 | HC CDR2 (Kabat) |
| | 410 | HC CDR3 (Kabat) |
| | 1165 | HC CDR1 (IMGT) |
| | 1166 | HC CDR2 (IMGT) |
| | 1167 | HC CDR3 (IMGT) |
| | 64 | HC CDR1 (Alternative) |

TABLE 4C-continued

Exemplary anti-tau humanized V0022 antibodies

| Ab ID | SEQ ID NO or Sequence | Description |
|---|---|---|
| | 1145 | HC CDR2 (Alternative) |
| | 1167 | HC CDR3 (Alternative) |
| | 70 | VH4 |
| | 159 | DNA VH4 |
| | 173 | Heavy Chain 4 |
| | 183 | DNA Heavy Chain 4 |
| | 1154 | LC CDR1 (Chothia) |
| | 529 | LC CDR2 (Chothia) |
| | 571 | LC CDR3 (Chothia) |
| | 1146 | LC CDR1 (Kabat) |
| | 529 | LC CDR2 (Kabat) |
| | 571 | LC CDR3 (Kabat) |
| | 473 | LC CDR1 (IMGT) |
| | RVS | LC CDR2 (IMGT) |
| | 571 | LC CDR3 (IMGT) |
| | 1146 | LC CDR1 (Alternative) |
| | 529 | LC CDR2 (Alternative) |
| | 571 | LC CDR3 (Alternative) |
| | 72 | VL1 |
| | 161 | DNA VL1 |
| | 175 | Light Chain 1 |
| | 185 | DNA Light Chain 1 |
| Ab4 | 314 | HC CDR1 (Chothia) |
| | 341 | HC CDR2 (Chothia) |
| | 410 | HC CDR3 (Chothia) |
| | 1144 | HC CDR1 (Kabat) |
| | 1145 | HC CDR2 (Kabat) |
| | 410 | HC CDR3 (Kabat) |
| | 1165 | HC CDR1 (IMGT) |
| | 1166 | HC CDR2 (IMGT) |
| | 1167 | HC CDR3 (IMGT) |
| | 64 | HC CDR1 (Alternative) |
| | 1145 | HC CDR2 (Alternative) |
| | 1167 | HC CDR3 (Alternative) |
| | 71 | VH5 |
| | 160 | DNA VH5 |
| | 174 | Heavy Chain 5 |
| | 184 | DNA Heavy Chain 5 |
| | 1154 | LC CDR1 (Chothia) |
| | 529 | LC CDR2 (Chothia) |
| | 571 | LC CDR3 (Chothia) |
| | 1146 | LC CDR1 (Kabat) |
| | 529 | LC CDR2 (Kabat) |
| | 571 | LC CDR3 (Kabat) |
| | 473 | LC CDR1 (IMGT) |
| | RVS | LC CDR2 (IMGT) |
| | 571 | LC CDR3 (IMGT) |
| | 1146 | LC CDR1 (Alternative) |
| | 529 | LC CDR2 (Alternative) |
| | 571 | LC CDR3 (Alternative) |
| | 73 | VL2 |
| | 162 | DNA VL2 |
| | 176 | Light Chain 2 |
| | 186 | DNA Light Chain 2 |
| Ab5 | 314 | HC CDR1 (Chothia) |
| | 341 | HC CDR2 (Chothia) |
| | 410 | HC CDR3 (Chothia) |
| | 1144 | HC CDR1 (Kabat) |
| | 1145 | HC CDR2 (Kabat) |
| | 410 | HC CDR3 (Kabat) |
| | 1165 | HC CDR1 (IMGT) |
| | 1166 | HC CDR2 (IMGT) |
| | 1167 | HC CDR3 (IMGT) |
| | 64 | HC CDR1 (Alternative) |
| | 1145 | HC CDR2 (Alternative) |
| | 1167 | HC CDR3 (Alternative) |
| | 71 | VH5 |
| | 160 | DNA VH5 |
| | 174 | Heavy Chain 5 |
| | 184 | DNA Heavy Chain 5 |
| | 1154 | LC CDR1 (Chothia) |
| | 529 | LC CDR2 (Chothia) |
| | 571 | LC CDR3 (Chothia) |
| | 1146 | LC CDR1 (Kabat) |
| | 529 | LC CDR2 (Kabat) |
| | 571 | LC CDR3 (Kabat) |
| | 473 | LC CDR1 (IMGT) |
| | RVS | LC CDR2 (IMGT) |
| | 571 | LC CDR3 (IMGT) |
| | 1146 | LC CDR1 (Alternative) |
| | 529 | LC CDR2 (Alternative) |
| | 571 | LC CDR3 (Alternative) |
| | 74 | VL3 |
| | 163 | DNA VL3 |
| | 177 | Light Chain 3 |
| | 187 | DNA Light Chain 3 |

TABLE 5

Constant Regions of Heavy Chains and Light Chains

| Description | SEQ ID NO | Sequence |
|---|---|---|
| Constant Region of Heavy Chain, secreted form & membrane-bound form (mIgG1) | 1189 | AKTTPPSVYPLAPGSAAQTNSMVTLGCLVKGYFPEPVTVTWNSGSLSSGVHTF PAVLQSDLYTLSSSVTVPSSPRPSETVTCNVAHPASSTKVDKKIVPRDCGCKP CICTVPEVSSVFIFPPKPKDVLTITLTPKVTCVVVDISKDDPEVQFSWFVDDV EVHTAQTQPREEQFNSTFRSVSELPIMHQDWLNGKEFKCRVNSAAFPAPIEKT ISKTKGRPKAPQVYTIPPPKEQMAKDKVSLTCMITDFFPEDITVEWQWNGQPA ENYKNTQPIMNINGSYFVYSKLNVQKSNWEAGNTFTCSVLHEGLHNHHTEKSL SHSPGK |
| | 1190 | AKTTPPSVYPLAPGSAAQTNSMVTLGCLVKGYFPEPVTVTWNSGSLSSGVHTF PAVLQSDLYTLSSSVTVPSSPRPSETVTCNVAHPASSTKVDKKIVPRDCGCKP CICTVPEVSSVFIFPPKPKDVLTITLTPKVTCVVVDISKDDPEVQFSWFVDDV EVHTAQTQPREEQFNSTFRSVSELPIMHQDWLNGKEFKCRVNSAAFPAPIEKT ISKTKGRPKAPQVYTIPPPKEQMAKDKVSLTCMITDFFPEDITVEWQWNGQPA ENYKNTQPIMNINGSYFVYSKLNVQKSNWEAGNTFTCSVLHEGLHNHHTEKSL SHSPGLQLDETCAEAQDGELDGLWTTITIFISLFLLSVCYSAAVTLFKVKWIF SSVVELKQTLVPEYKNMIGQAP |
| Constant Region of murine Heavy | 1191 | AKTTAPSVYPLAPVCGDTTGSSVTLGCLVKGYFPEPVTLTWNSGSLSSGVHTF PAVLQSDLYTLSSSVTVTSSTWPSQSITCNVAHPASSTKVDKKIEPRGPTIKP CPPCKCPAPNLLGGPSVFIFPPKIKDVLMISLSPIVTCVVVDVSEDDPDVQIS |

TABLE 5-continued

Constant Regions of Heavy Chains and Light Chains

| Description | SEQ ID NO | Sequence |
|---|---|---|
| Chain, (mIgG2A) | | WFVNNVEVHTAQTQTHREDYNSTLRVVSALPIQHQDWMSGKEFKCKVNNKDLP<br>APIERTISKPKGSVRAPQVYVLPPPEEEMTKKQVTLTCMVTDEMPEDIYVEWT<br>NNGKTELNYKNTEPVLDSDGSYFMYSKLRVEKKNWVERNSYSCSVVHEGLHNH<br>HTTKSFSRTPGK |
| DNA Constant Region of Heavy Chain (mIgG2A) | 1192 | GCTAAAACAACAGCCCCATCGGTCTATCCACTGGCCCCTGTGTGTGGAGATAC<br>AACTGGCTCCTCGGTGACTCTAGGATGCCTGGTCAAGGGTTATTTCCCTGAGC<br>CAGTGACCTTGACCTGGAACTCTGGATCCCTGTCCAGTGGTGTGCACACCTTC<br>CCAGCTGTCCTGCAGTCTGACCTCTACACCCTCAGCAGCTCAGTGACTGTAAC<br>CTCGAGCACCTGGCCCAGCCAGTCCATCACCTGCAATGTGGCCCACCCGGCAA<br>GCAGCACCAAGGTGGACAAGAAAATTGAGCCCAGAGGGCCCACAATCAAGCCC<br>TGTCCTCCATGCAAATGCCCAGCACCTAACCTCTTGGGTGGACCATCCGTCTT<br>CATCTTCCCTCCAAAGATCAAGGATGTACTCATGATCTCCCTGAGCCCCATAG<br>TCACATGTGTGGTGGTGGATGTGAGCGAGGATGACCCAGATGTCCAGATCAGC<br>TGGTTTGTGAACAACGTGGAAGTACACACAGCTCAGACACAAACCCATAGAGA<br>GGATTACAACAGTACTCTCCGGGTGGTCAGTGCCCTCCCCATCCAGCACCAGG<br>ACTGGATGAGTGGCAAGGAGTTCAAATGCAAGGTCAACAACAAAGACCTCCCA<br>GCGCCCATCGAGAGAACCATCTCAAAACCCAAAGGGTCAGTAAGAGCTCCACA<br>GGTATATGTCTTGCCTCCACCAGAAGAAGAGATGACTAAGAAACAGGTCACTC<br>TGACCTGCATGGTCACAGACTTCATGCCTGAAGACATTTACGTGGAGTGGACC<br>AACAACGGGAAAACAGAGCTAAACTACAAGAACACTGAACCAGTCCTGGACTC<br>TGATGGTTCTTACTTCATGTACAGCAAGCTGAGAGTGGAAAAGAAGAACTGGG<br>TGGAAAGAAATAGCTACTCCTGTTCAGTGGTCCACGAGGGTCTGCACAATCAC<br>CACACGACTAAGAGCTTCTCCCGGACTCCGGGTAAA |
| Constant Region of Heavy Chain, secreted form (mIgG2A) | 1193 | AKTTAPSVYPLVPVCGGTTGSSVTLGCLVKGYFPEPVTLTWNSGSLSSGVHTF<br>PALLQSGLYTLSSSVTVTSNTWPSQTITCNVAHPASSTKVDKKIEPRVPITQN<br>PCPPHQRVPPCAAPDLLGGPSVFIFPPKIKDVLMISLSPMVTCVVVDVSEDDP<br>DVQISWFVNNVEVHTAQTQTHREDYNSTLRVVSALPIQHQDWMSGKEFKCKVN<br>NRALPSPIEKTISKPRGPVRAPQVYVLPPPAEEMTKKEFSLTCMITGFLPAEI<br>AVDWTSNGRTEQNYKNTATVLDSDGSYFMYSKLRVQKSTWERGSLFACSVVHE<br>VLHNHLTTKTISRSLGK |
| Constant Region of murine Heavy Chain, secreted form (mIgG2B) | 1194 | KTTPPSVYPLAPGCGDTTGSSVTLGCLVKGYFPESVTVTWNSGSLSSSVHTFP<br>ALLQSGLYTMSSSVTVPSSTWPSQTVTCSVAHPASSTTVDKKLEPSGPISTIN<br>PCPPCKECHKCPAPNLEGGPSVFIFPPNIKDVLMISLTPKVTCVVVDVSEDDP<br>DVQISWFVNNVEVHTAQTQTHREDYNSTIRVVSTLPIQHQDWMSGKEFKCKVN<br>NKDLPSPIERTISKIKGLVRAPQVYILPPPAEQLSRKDVSLTCLVVGENPGDI<br>SVEWTSNGHTEENYKDTAPVLDSDGSYFIYSKLNMKTSKWEKTDSFSCNVRHE<br>GLKNYYLKKTISRSPGLDLDDICAEAKDGELDGLWTTITIFISLFLLSVCYSA<br>SVTLFKVKWIFSSVVELKQKISPDYRNMIGQGA |
| Constant Region of murine Heavy Chain, (mIgG2B) | 1195 | KTTAPSVYPLAPVCGGTTGSSVTLGCLVKGYFPEPVTLTWNSGSLSSGVHTFP<br>ALLQSGLYTLSSSVTVTSNTWPSQTITCNVAHPASSTKVDKKIEPRVPITQNP<br>CPPLKECPPCAAPDLLGGPSVFIFPPKIKDVLMISLSPMVTCVVVDVSEDDPD<br>VQISWFVNNVEVHTAQTQTHREDYNSTLRVVSALPIQHQDWMSGKEFKCKVNN<br>RALPSPIEKTISKPRGPVRAPQVYVLPPPAEEMTKKEFSLTCMITGFLPAEIA<br>VDWTSNGRTEQNYKNTATVLDSDGSYFMYSKLRVQKSTWERGSLFACSVVHEG<br>LHNHLTTKTISRSLGLDLDDVCTEAQDGELDGLWTTITIFISLFLLSVCYSAS<br>VTLFKVKWIFSSVVELKQKISPDYRNMIGQGA |
| Constant Region of murine Heavy Chain, secreted form (mIgG3) | 1196 | TTTAPSVYPLVPGCSDTSGSSVTLGCLVKGYFPEPVTVKWNYGALSSGVRTVS<br>SVLQSGFYSLSSLVTVPSSTWPSQTVICNVAHPASKTELIKRIEPRIPKPSTP<br>PGSSCPPGNILGGPSVFIFPPKPKDALMISLTPKVTCVVVDVSEDDPDVHVSW<br>FVDNKEVHTAWTQPREAQYNSTFRVVSALPIQHQDWMRGKEFKCKVNNKALPA<br>PIERTISKPKGRAQTPQVYTIPPPREQMSKKKVSLTCLVTNFFSEAISVEWER<br>NGELEQDYKNTPPILDSDGTYFLYSKLTVDTDSWLQGEIFTCSVVHEALHNHH<br>TQKNLSRSPELELNETCAEAQDGELDGLWTTITIFISLFLLSVCYSASVTLFK<br>VKWIFSSVVQVKQTAIPDYRNMIGQGA |
| Constant Region of Murine Kappa Light Chain | 1197 | ADAAPTVSIFPPSSEQLTSGGASVVCFLNNFYPKDINVKWKIDGSERQNGVLN<br>SWTDQDSKDSTYSMSSTLTLTKDEYERHNSYTCEATHKTSTSPIVKSENRNEC |
| DNA Constant Region of Murine Kappa Light Chain | 1198 | GCAGATGCTGCACCAACTGTATCCATCTTCCCACCATCCAGTGAGCAGTTAAC<br>ATCTGGAGGTGCCTCAGTCGTGTGCTTCTTGAACAACTTCTACCCCAAAGACA<br>TCAATGTCAAGTGGAAGATTGATGGCAGTGAACGACAAAATGGCGTCCTGAAC<br>AGTTGGACTGATCAGGACAGCAAAGACAGCACCTACAGCATGAGCAGCACCCT<br>CACGTTGACCAAGGACGAGTATGAACGACATAACAGCTATACCTGTGAGGCCA<br>CTCACAAGACATCAACTTCACCCATTGTCAAGAGCTTCAACAGGAATGAGTGT |
| Constant Region of | 1199 | QPKSSPSVTLFPPSSEELETNKATLVCTITDFYPGVVTVDWKVDGTPVTQGME<br>TTQPSKQSNNKYMASSYLTLTARAWERHSSYSCQVTHEGHTVEKSLSRADCS |

TABLE 5-continued

Constant Regions of Heavy Chains and Light Chains

| Description | SEQ ID NO | Sequence |
|---|---|---|
| murine Lambda Light Chain (subclasses 1, 2, and 3) | 1200 | QPKSTPTLTVFPPSSEELKENKATLVCLISNFSPSGVTVAWKANGTPITQGVDTSNPTKEGNKFMASSFLHLTSDQWRSHNSFTCQVTHEGDTVEKSLSPAECL |
| | 1201 | QPKSTPTLTMFPPSPEELQENKATLVCLISNFSPSGVTVAWKANGTPITQGVDTSNPTKEDNKYMASSFLHLTSDQWRSHNSFTCQVTHEGDTVEKSLSPAECL |
| Constant Region of human Heavy Chain (hIgG1) | 1202 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| DNA Constant Region of human Heavy Chain (hIgG1) | 1203 | GCCAGCACAAAAGGGCCCAGTGTGTTCCCGCTCGCACCAAGCAGCAAATCAACGTCAGGCGGCACAGCCGCGTTGGGTTGCCTTGTAAAAGACTACTTCCCAGAACCAGTTACGGTGTCATGGAACAGTGGTGCACTCACGAGCGGCGTTCATACCTTCCCCGCCGTACTTCAGAGTTCAGGTCTTTACTCACTTTCCAGCGTGGTCACAGTACCGTCAAGCTCTCTTGGAACACAGACATATATCTGTAACGTAAATCATAAGCCTAGCAATACCAAAGTCGATAAACGAGTGGAACCCAAGAGTTGTGATAAAACCCACACCTGTCCCCCTTGCCCGGCACCGGAACTGCTGGGTGGTCCATCAGTATTCTTGTTTCCGCCTAAGCCAAAGGACACACTGATGATATCCAGAACTCCAGAGGTTACGTGCGTAGTCGTGGACGTCAGTCATGAAGACCCCGAAGTTAAGTTCAACTGGTACGTGGATGGTGTGGAAGTACATAATGCGAAGACGAAACCCAGGGAAGAACAATATAACTCAACTTATAGGGTAGTCAGCGTCTTGACTGTACTTCACCAAGATTGGTTGAATGGCAAAGAGTACAAATGCAAGGTAAGCAACAAAGCATTGCCTGCGCCAATCGAAAAGACTATCTCAAAAGCAAAGGGCCAGCCACGCGAACCACAAGTGTATACATTGCCGCCCAGTCGGGAAGAAATGACGAAAATCAAGTCAGTCTCACATGCCTCGTGAAAGGATTTTATCCCTCTGACATAGCTGTGGAGTGGGAAAGTAATGGCCAACCCGAAAATAATTACAAAACGACGCCTCCCGTTTTGGACTCAGATGGGAGTTTTTTCCTTTACAGTAAGCTGACGGTTGACAAAAGCAGGTGGCAACAAGGGAACGTCTTTTCTTGTAGTGTGATGCATGAGGCGCTCCACAATCATTACACTCAAAAATCCTTGAGCCTGTCTCCAGGC |
| Constant Region of Heavy Chain (hIgG2) | 1204 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPGK |
| Constant Region of Heavy Chain (hIgG3) | 1205 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRVELKTPLGDTTHTCPRCPEPKSCDTPPPCPRCPEPKSCDTPPPCPRCPEPKSCDTPPPCPRCPAPELLGGPSVFLFPPKPKDTLMISRTPEVTCVVVDVSHEDPEVQFKWYVDGVEVHNAKTKPREEQYNSTFRVVSVLTVLHQDWLNGKEYKCKVSNKALPAPIEKTISKTKGQPREPQVYTLPPSREEMTKNQVSLTCLVKGFYPSDIAVEWESSGQPENNYNTTPPMLDSDGSFFLYSKLTVDKSRWQQGNIFSCSVMHEALHNRFTQKSLSLSPGK |
| Constant Region of human Heavy Chain (hIgG4) | 1206 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| Constant Region of human Light Chain (hIgG Lambda, subclasses 1, 2, 3, 6, and 7) | 1207 | GQPKANPTVTLFPPPSSEELQANKATLVCLISDFYPGAVTVAWKADGSPVKAGVETTKPSKQSNNKYAASSYLSLTPEQWKSHRSYSCQVTHEGSTVEKTVAPTECS |
| | 1208 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| | 1209 | GQPKAAPSVTLFPPSSEELQANKATLVCLISDFYPGAVTVAWKADSSPVKAGVETTTPSKQSNNKYAASSYLSLTPEQWKSHKSYSCQVTHEGSTVEKTVAPTECS |
| | 1210 | GQPKAAPSVTLFPPSSEELQANKATLVCLISDFYPGAVKVAWKADSSPVNTGVETTTPSKQSNNKYAASSYLSLTPEQWKSHRSYSCQVTHEGSTVEKTVAPAECS |
| | 1211 | GQPKAAPSVTLFPPSSEELQANKATLVCLVSDFNPGAVTVAWKADGSPVKVGVETTKPSKQSNNKYAASSYLSLTPEQWKSHRSYSCRVTHEGSTVEKTVAPAECS |
| Constant Region of human Light Chain (hIgG Kappa) | 1212 | TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 5-continued

Constant Regions of Heavy Chains and Light Chains

| Description | SEQ ID NO | Sequence |
|---|---|---|
| DNA Constant Region of human Light Chain (hIgG kappa) | 1213 | ACTGTCGCAGCACCTTCTGTCTTCATCTTTCCGCCAAGCGATGAACAGTTGAA<br>ATCTGGAACAGCGTCCGTGGTGTGCCTGCTCAACAACTTCTATCCTCGGGAAG<br>CGAAGGTGCAATGGAAGGTAGATAATGCTCTTCAGAGTGGCAATTCCCAAGAG<br>TCAGTTACGGAGCAAGATAGCAAGGACAGCACGTATTCCCTGTCTAGTACGTT<br>GACTCTTTCCAAGGCTGACTATGAAAAGCACAAGGTGTATGCCTGTGAAGTAA<br>CCCACCAAGGTCTCTCAAGTCCTGTAACTAAGAGCTTTAATCGAGGAGAATGC |
| Murine IgG1 Heavy Chain constant region (DNA) | 805 | GCCAAAACGACACCCCCATCTGTCTATCCACTGGCCCCTGGATCTGCTGCCCA<br>AACTAACTCCATGGTGACCCTGGGATGCCTGGTCAAGGGCTATTTCCCTGAGC<br>CAGTGACAGTGACCTGGAACTCTGGATCCCTGTCCAGCGGTGTGCACACCTTC<br>CCAGCTGTCCTGCAGTCTGACCTCTACACTCTGAGCAGCTCAGTGACTGTCCC<br>CTCCAGCACCTGGCCCAGCGAGACCGTCACCTGCAACGTTGCCCACCCGGCCA<br>GCAGCACCAAGGTGGACAAGAAAATTGTGCCCAGGGATTGTGGTTGTAAGCCT<br>TGCATATGTACAGTCCCAGAAGTATATCTGTCTTCATCTTCCCCCCAAAGCC<br>CAAGGATGTGCTCACCATTACTCTGACTCCTAAGGTCACGTGTGTTGTGGTAG<br>ACATCAGCAAGGATGATCCCGAGGTCCAGITCAGCTGGTTTGTAGATGATGTG<br>GAGGTGCACACAGCTCAGACGCAACCCCGGGAGGAGCAGTTCAACAGCACTTT<br>CCGCTCAGTCAGTGAACTTCCCATCATGCACCAGGACTGGCTCAATGGCAAGG<br>AGTTCAAATGCAGGGTCAACAGTGCAGCTTTCCCTGCCCCCATCGAGAAAACC<br>ATCTCCAAAACCAAAGGCAGACCGAAGGCTCCACAGGTGTACACCATTCCACC<br>TCCCAAGGAGCAGATGGCCAAGGATAAAGTCAGTCTGACCTGCATGATAACAG<br>ACTTCTTCCCTGAAGACATTACTGTGGAGTGGCAGTGGAATGGGCAGCCAGCG<br>GAGAACTACAAGAACACTCAGCCCATCATGGACACAGATGGCTCTTACTTCGT<br>CTACAGCAAGCTCAATGTGCAGAAGAGCAACTGGGAGGCAGGAAATACTTTCA<br>CCTGCTCTGTGTTACATGAGGGCCTGCACAACCACCATACTGAGAAGAGCCTC<br>TCCCACTCTCCTGGT |
| Murine IgG1 Heavy Chain constant region (amino acid) | 16 | AKTTPPSVYPLAPGSAAQTNSMVTLGCLVKGYFPEPVTVTWNSGSLSSGVHTF<br>PAVLQSDLYTLSSSVTVPSSTWPSETVTCNVAHPASSTKVDKKIVPRDCGCKP<br>CICTVPEVSSVFIFPPKPKDVLTITLTPKVTCVVVDISKDDPEVQFSWFVDDV<br>EVHTAQTQPREEQFNSTFRSVSELPIMHQDWLNGKEFKCRVNSAAFPAPIEKT<br>ISKTKGRPKAPQVYTIPPPKEQMAKDKVSLTCMITDFFPEDITVEWQWNGQPA<br>ENYKNTQPIMDTDGSYFVYSKLNVQKSNWEAGNTFTCSVLHEGLHNHHTEKSL<br>SHSPG |
| Murine IgG1 kappa light chain constant region (DNA) | 17 | CGGGCTGATGCTGCACCAACTGTATCCATCTTCCCACCATCCAGTGAGCAGTT<br>AACATCTGGAGGTGCCTCAGTCGTGTGCTTCTTGAACAACTTCTACCCCAAAG<br>ACATCAATGTCAAGTGGAAGATTGATGGCAGTGAACGACAAAATGGCGTCCTG<br>AACAGTTGGACTGATCAGGACAGCAAAGACAGCACCTACAGCATGAGCAGCAC<br>CCTCACGTTGACCAAGGACGAGTATGAACGACATAACAGCTATACCTGTGAGG<br>CCACTCACAAGACATCAACTTCACCCATTGTCAAGAGCTTCAACAGGAATGAG<br>TGT |
| Murine IgG1 kappa light chain constant region (amino acid) | 18 | RADAAPTVSIFPPSSEQLTSGGASVVCFLNNFYPKDINVKWKIDGSERQNGVL<br>NSWTDQDSKDSTYSMSSTLTLTKDEYERHNSYTCEATHKTSTSPIVKSENRNE<br>C |
| Human heavy Chain Constant Region (Human IgG4) | 194 | ASTKGPSVFPLAPCSRSTSESTAALGCLVKDYFPEPVTVSWNSGALTSGVHTF<br>PAVLQSSGLYSLSSVVTVPSSSLGTKTYTCNVDHKPSNTKVDKRVESKYGPPC<br>PPCPAPEFLGGPSVFLFPPKPKDTLMISRTPEVTCVVVDVSQEDPEVQFNWYV<br>DGVEVHNAKTKPREEQFNSTYRVVSVLTVLHQDWLNGKEYKCKVSNKGLPSSI<br>EKTISKAKGQPREPQVYTLPPSQEEMTKNQVSLTCLVKGFYPSDIAVEWESNG<br>QPENNYKTTPPVLDSDGSFFLYSRLTVDKSRWQEGNVFSCSVMHEALHNHYTQ<br>KSLSLSLGK |
| DNA Human heavy Chain Constant Region (Human IgG4) | 195 | GCTAGCACCAAGGGTCCTTCCGTGTTTCCTCTAGCCCCTTGCAGCAGAAGCAC<br>AAGCGAGAGCACCGCCGCCCTGGGCTGCCTGGTTAAAGATTATTTCCCTGAGC<br>CTGTGACCGTGAGCTGGAATAGCGGCGCCCTGACAAGCGGCGTGCACACCTTC<br>CCTGCCGTGCTGCAGAGCAGCGGCCTGTACAGCCTGAGCAGCGTGGTGACCGT<br>GCCTTCTAGCAGCCTGGGTACTAAGACCTACACCTGCAACGTGGACCACAAGC<br>CTAGCAACACCAAGGTGGACAAGAGAGTGGAGAGCAAGTACGGTCCTCCGTGT<br>CCCCCGTGCCCTGCCCCTGAGTTCCTGGGCGGCCCTAGCGTTTTCTTGTTTCC<br>ACCTAAGCCTAAGGACACCCTGATGATCAGCAGAACCCCTGAGGTGACCTGCG<br>TGGTGGTGGACGTGAGCCAAGAGGACCCTGAGGTGCAGTTCAACTGGTACGTG<br>GACGGCGTGGAGGTGCACAACGCCAAGACCAAGCCTAGAGAGGAGCAGTTCAA<br>CAGCACCTACAGAGTGGTGAGCGTGCTGACCGTGCTGCACCAAGACTGGCTGA<br>ACGGCAAGGAGTACAAGTGCAAGGTGAGCAACAAGGGCCTGCCTAGCAGTATT<br>GAAAAGACCATCAGCAAGGCCAAGGGACAGCCTAGAGAGCCTCAAGTGTACAC<br>CCTGCCTCCTAGCCAAGAGGAGATGACCAAGAACCAAGTGAGCCTGACCTGCC<br>TGGTCAAGGGGTTTTACCCTAGCGACATCGCCGTGGAGTGGGAGAGCAACGGA |

TABLE 5-continued

Constant Regions of Heavy Chains and Light Chains

| Description | SEQ ID NO | Sequence |
|---|---|---|
| | | CAGCCTGAGAACAACTACAAGACCACCCCTCCTGTGCTGGACAGCGACGGCAG<br>CTTCTTCCTGTACAGCAGACTGACCGTGGACAAGAGCAGATGGCAAGAGGGCA<br>ACGTGTTCAGCTGCAGCGTGATGCACGAGGCCCTGCACAACCACTACACACAG<br>AAGAGCCTGAGCCTGAGCCTGGGCAAG |
| DNA Human heavy Chain Constant Region (Human IgG4) | 196 | GCTAGCACGAAAGGTCCAAGCGTTTTCCCTCTAGCCCCTTGCAGCAGAAGCAC<br>AAGCGAGAGCACCGCCGCCCTGGGCTGCCTTGTAAAAGATTACTTCCCTGAGC<br>CTGTGACCGTGAGTTGGAACAGCGGCGCCCTGACAAGCGGCGTGCACACCTTC<br>CCTGCCGTGCTGCAGAGCAGCGGCCTGTACAGCCTGAGCAGCGTGGTGACCGT<br>GCCAAGCAGCAGCCTGGGCACCAAGACCTACACCTGCAACGTGGACCACAAGC<br>CTAGCAACACCAAGGTGGACAAGAGAGTGGAGAGCAAGTACGGTCCTCCGTGT<br>CCCCCGTGCCCTGCCCCTGAGTTCCTGGGCGGCCCTTCGGTGTTTCTGTTTCC<br>ACCTAAGCCTAAGGACACCCTGATGATCAGCAGAACCCCTGAGGTGACCTGCG<br>TGGTGGTGGACGTGAGCCAAGAGGACCCTGAGGTGCAGTTCAACTGGTACGTG<br>GACGGCGTGGAGGTGCACAACGCCAAGACCAAGCCTAGAGAGGAGCAGTTCAA<br>CAGCACCTACAGAGTGGTGAGCGTGCTGACCGTGCTGCACCAAGACTGGCTGA<br>ACGGCAAGGAGTACAAGTGCAAGGTGAGCAACAAGGGCCTGCCTAGTTCCATT<br>GAGAAGACCATCAGCAAGGCCAAGGGACAGCCTAGAGAGCCTCAAGTGTACAC<br>CCTGCCTCCTAGCCAAGAGGAGATGACCAAGAACCAAGTGAGCCTGACCTGCC<br>TGGTGAAGGGATTCTACCCTAGCGACATCGCCGTGGAGTGGGAGAGCAACGGA<br>CAGCCTGAGAACAACTACAAGACCACCCCTCCTGTGCTGGACAGCGACGGCAG<br>CTTCTTCCTGTACAGCAGACTGACCGTGGACAAGAGCAGATGGCAAGAGGGCA<br>ACGTGTTCAGCTGCAGCGTGATGCACGAGGCCCTGCACAACCACTACACACAG<br>AAGAGCCTGAGCCTGAGCCTGGGCAAG |
| DNA Human heavy Chain Constant Region (Human IgG4) | 198 | GCTAGCACCAAGGGTCCTAGTGTATTTCCCCTAGCCCCTTGCAGCAGAAGCAC<br>AAGCGAGAGCACCGCCGCCCTGGGCTGCTTGGTGAAGGACTACTTCCCTGAGC<br>CTGTCACAGTGTCCTGGAATAGCGGCGCCCTGACAAGCGGCGTGCACACCTTC<br>CCTGCCGTGCTGCAGAGCAGCGGCCTGTACAGCCTGAGCAGCGTGGTGACCGT<br>GCCTTCGTCGAGCCTGGGCACCAAGACCTACACCTGCAACGTGGACCACAAGC<br>CTAGCAACACCAAGGTGGACAAGAGAGTGGAGAGCAAGTACGGTCCTCCGTGT<br>CCCCCGTGCCCTGCCCCTGAGTTCCTGGGCGGCCCTAGCGTGTTCCTATTTCC<br>ACCTAAGCCTAAGGACACCCTGATGATCAGCAGAACCCCTGAGGTGACCTGCG<br>TGGTGGTGGACGTGAGCCAAGAGGACCCTGAGGTGCAGTTCAACTGGTACGTG<br>GACGGCGTGGAGGTGCACAACGCCAAGACCAAGCCTAGAGAGGAGCAGTTCAA<br>CAGCACCTACAGAGTGGTGAGCGTGCTGACCGTGCTGCACCAAGACTGGCTGA<br>ACGGCAAGGAGTACAAGTGCAAGGTGAGCAACAAGGGCCTGCCTAGCAGTATC<br>GAGAAGACCATCAGCAAGGCCAAGGGACAGCCTAGAGAGCCTCAAGTGTACAC<br>CCTGCCTCCTAGCCAAGAGGAGATGACCAAGAACCAAGTGAGCCTGACCTGCC<br>TGGTAAAAGGTTTCTACCCTAGCGACATCGCCGTGGAGTGGGAGAGCAACGGA<br>CAGCCTGAGAACAACTACAAGACCACCCCTCCTGTGCTGGACAGCGACGGCAG<br>CTTCTTCCTGTACAGCAGACTGACCGTGGACAAGAGCAGATGGCAAGAGGGCA<br>ACGTGTTCAGCTGCAGCGTGATGCACGAGGCCCTGCACAACCACTACACACAG<br>AAGAGCCTGAGCCTGAGCCTGGGCAAG |
| DNA Human heavy Chain Constant Region (Human IgG4) | 199 | GCTAGCACCAAGGGTCCTAGTGTATTTCCCCTAGCCCCTTGCAGCAGAAGCAC<br>AAGCGAGAGCACCGCCGCCCTGGGCTGCTTGGTGAAGGACTACTTCCCTGAGC<br>CTGTGACCGTGAGCTGGAACAGCGGCGCCCTGACAAGCGGCGTGCACACCTTC<br>CCTGCCGTGCTGCAGAGCAGCGGCCTGTACAGCCTGAGCAGCGTGGTGACCGT<br>GCCTTCGTCGAGCCTGGGCACCAAGACCTACACCTGCAACGTGGACCACAAGC<br>CTAGCAACACCAAGGTGGACAAGAGAGTGGAGAGCAAGTACGGTCCTCCGTGT<br>CCCCCGTGCCCTGCCCCTGAGTTCCTGGGCGGCCCTAGCGTGTTCCTATTTCC<br>ACCTAAGCCTAAGGACACCCTGATGATCAGCAGAACCCCTGAGGTGACCTGCG<br>TGGTGGTGGACGTGAGCCAAGAGGACCCTGAGGTGCAGTTCAACTGGTACGTG<br>GACGGCGTGGAGGTGCACAACGCCAAGACCAAGCCTAGAGAGGAGCAGTTCAA<br>CAGCACCTACAGAGTGGTGAGCGTGCTGACCGTGCTGCACCAAGACTGGCTGA<br>ACGGCAAGGAGTACAAGTGCAAGGTGAGCAACAAGGGCCTGCCTAGCAGTATC<br>GAGAAGACCATCAGCAAGGCCAAGGGACAGCCTAGAGAGCCTCAAGTGTACAC<br>CCTGCCTCCTAGCCAAGAGGAGATGACCAAGAACCAAGTGAGCCTGACCTGCC<br>TGGTAAAAGGTTTCTACCCTAGCGACATCGCCGTGGAGTGGGAGAGCAACGGA<br>CAGCCTGAGAACAACTACAAGACCACCCCTCCTGTGCTGGACAGCGACGGCAG<br>CTTCTTCCTGTACTCCCGCCTGACGGTTGACAAGAGCAGATGGCAAGAGGGCA<br>ACGTGTTCAGCTGCAGCGTGATGCACGAGGCCCTGCACAACCACTACACACAG<br>AAGAGCCTGAGCCTGAGCCTGGGCAAG |
| Human light Chain Constant region (Human IgG kappa) | 200 | RTVAAPSVFIFPPSDEQLKSGTASVVCLLNNFYPREAKVQWKVDNALQSGNSQ<br>ESVTEQDSKDSTYSLSSTLTLSKADYEKHKVYACEVTHQGLSSPVTKSENRGE<br>C |

TABLE 5-continued

Constant Regions of Heavy Chains and Light Chains

| Description | SEQ ID NO | Sequence |
|---|---|---|
| DNA Human light chain Constant region (Human IgG kappa) | 201 | AGAACCGTGGCCGCCCCTAGCGTGTTCATCTTCCCTCCTAGCGACGAGCAGCT<br>GAAGAGCGGCACCGCTAGCGTGGTGTGCCTGCTGAACAACTTCTACCCTAGAG<br>AGGCCAAGGTGCAGTGGAAGGTGGACAACGCCCTGCAGAGCGGCAACAGCCAA<br>GAGAGCGTGACCGAGCAAGACAGCAAGGACAGCACCTACAGCCTGAGCAGCAC<br>CCTGACCCTGAGCAAGGCCGACTACGAGAAGCACAAGGTGTACGCCTGCGAGG<br>TGACCCACCAAGGCCTGAGCAGCCCTGTGACCAAGAGCTTCAACAGAGGCGAG<br>TGC |
| DNA Human light Chain Constant region (Human IgG kappa) | 202 | AGAACCGTGGCCGCCCCTAGCGTGTTCATCTTCCCTCCTAGCGACGAGCAGCT<br>GAAGAGCGGCACCGCTAGCGTGGTGTGCCTGCTGAACAACTTCTACCCTAGAG<br>AGGCCAAGGTGCAGTGGAAGGTGGACAACGCCCTGCAGAGCGGCAACAGCCAA<br>GAGAGCGTGACCGAGCAAGACAGCAAGGACAGCACCTACAGCCTGAGCAGCAC<br>CCTGACCCTGAGCAAGGCCGACTACGAGAAGCACAAGGTGTACGCCTGCGAGG<br>TGACCCACCAAGGCCTGTCAAGCCCTGTAACTAAGAGCTTCAACAGAGGCGAG<br>TGC |

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 299, 343, and 395, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 460, 518, and 557, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 299, 343, 395, 460, 518, and 557, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 299, 343, 395, 460, 518, or 557.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1140, 1141, and 395, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 460, 518, and 557, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1140, 1141, 395, 460, 518, and 557, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1140, 1141, 395, 460, 518, and 557.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1155, 1156, and 1157, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1158, NAK, and SEQ ID NO: 557, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1155, SEQ ID NO: 1156, SEQ ID NO: 1157, SEQ ID NO: 1158, NAK, and SEQ ID NO: 557, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1155, SEQ ID NO: 1156, SEQ ID NO: 1157, SEQ ID NO: 1158, NAK, and SEQ ID NO: 557.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 304, 347, and 400, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 464, 523, and 562, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 304, 347, 400, 464, 523, and 562, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 304, 347, 400, 464, 523, and 562.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1142, 1143, and 400, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 464, 523, and 562, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1142, 1143, 400, 464, 523, and 562, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1142, 1143, 400, 464, 523, and 562.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1160, 1161, and 1162, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1163, WAS, and SEQ ID NO: 562, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1160, SEQ ID NO: 1161, SEQ ID NO: 1162, SEQ ID NO: 1163, WAS, and SEQ ID NO: 562, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1160, SEQ ID NO: 1161, SEQ ID NO: 1162, SEQ ID NO: 1163, WAS, and SEQ ID NO: 562.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 314, 341, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1154, 529, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 314, 341, 410, 1154, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 314, 341, 410, 1154, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1144, 1145, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1146, 529, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1144, 1145, 410, 1146, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1144, 1145, 410, 1146, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1165, 1166, and 1167, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 473, RVS, and SEQ ID NO: 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1165, SEQ ID NO: 1166, SEQ ID NO: 1167, SEQ ID NO: 473, RVS, and SEQ ID NO: 571, respectively. In some embodiments, one or more of the CDRs (or collectively all of the CDRs) have one, two, three, four, five or more changes, e.g., amino acid substitutions, insertions, or deletions, relative to the amino acid sequence of any one of SEQ ID NO: 1165, SEQ ID NO: 1166, SEQ ID NO: 1167, SEQ ID NO: 473, RVS, and SEQ ID NO: 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 64, 1145, and 1167, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1146, 529, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 64, 1145, 1167, 1146, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 64, 1145, 1167, 1146, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 315, 341, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 474, 529, and 571, respectively.

In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 315, 341, 410, 474, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 315, 341, 410, 474, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1147, 1148, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 474, 529, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1147, 1148, 410, 474, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1147, 1148, 410, 474, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1168, 1169, and 1167, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1170, RVS, and SEQ ID NO: 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1168, SEQ ID NO: 1169, SEQ ID NO: 1167, SEQ ID NO: 1170, RVS, and SEQ ID NO: 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1168, SEQ ID NO: 1169, SEQ ID NO: 1167, SEQ ID NO: 1170, RVS, and SEQ ID NO: 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 316, 341, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 475, 530, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 316, 341, 410, 475, 530, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 316, 341, 410, 475, 530, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1149, 1150, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 475, 530, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1149, 1150, 410, 475, 530, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1149, 1150, 410, 475, 530, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1171, 1166, and 1167, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1172, RVS, and SEQ ID NO: 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1171, SEQ ID NO: 1166, SEQ ID NO: 1167, SEQ ID NO: 1172, RVS, and SEQ ID NO: 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1171, SEQ ID NO: 1166, SEQ ID NO: 1167, SEQ ID NO: 1172, RVS, and SEQ ID NO: 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 325, 362, and 435, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 495, 540, and 587, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 325, 362, 435, 495, 540, and 587, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 325, 362, 435, 495, 540, and 587.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1152, 1153, and 435, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 495, 540, and 587, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1152, 1153, 435, 495, 540, and 587, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1152, 1153, 435, 495, 540, and 587.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1173, 1174, and 1175, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1176, YAS, and SEQ ID NO: 587, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1173, SEQ ID NO: 1174, SEQ ID NO: 1175, SEQ ID NO: 1176, YAS, and SEQ ID NO: 587, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1173, SEQ ID NO: 1174, SEQ ID NO: 1175, SEQ ID NO: 1176, YAS, and SEQ ID NO: 587.

In some embodiments, the anti-tau antibody comprises a heavy chain variable region comprising the amino acid sequence of SEQ ID NO: 4; or encoded by the nucleotide sequence of SEQ ID NO: 150; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 78; or encoded by the nucleotide sequence of SEQ ID NO: 224; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 4 and 78, respectively; or encoded by the nucleotide sequences of SEQ ID NO: 150 and 224, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 150, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 224, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 9; or encoded by the nucleotide sequence of SEQ ID NO: 155; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 83; or encoded by the nucleotide sequence of SEQ ID NO: 229; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 9 and 83, respectively; or encoded by the nucleotide sequences of SEQ ID NO: 155 and 229, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 155, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 229, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 21; or encoded by the nucleotide sequence of SEQ ID NO: 167; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 93; or encoded by the nucleotide sequence of SEQ ID NO: 241; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 21 and 93, respectively; or encoded by the nucleotide sequences of SEQ ID NO: 167 and 241, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 21 and 93, respectively; or encoded by the nucleotide sequences of SEQ ID NO: 7 and 11, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 167, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 241, or a sequence substantially identical (e.g., having at least about 80%, 85%, 90%, 92%, 95%, 97%, 98%, or 99% sequence identity). In some embodiments, the nucleotide sequence encoding the heavy chain variable region of the anti-tau antibody comprises the nucleotide sequence of SEQ ID NO: 7, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 11, or a sequence substantially identical (e.g., having at least about 80%, 85%, 90%, 92%, 95%, 97%, 98%, or 99% sequence identity) thereto.

In some embodiments, the antibody that binds to tau comprises a heavy chain variable region comprising the amino acid sequence of any one of SEQ ID NOs: 67-71, or a sequence substantially identical (e.g., having at least about 80%, 85%, 90%, 92%, 95%, 97%, 98%, or 99% sequence identity) to any of the aforesaid sequences. In some embodiments, the antibody comprises a light chain variable region comprising the amino acid sequence of any one of SEQ ID NOs: 72-76, or a sequence substantially identical (e.g., having at least about 80%, 85%, 90%, 92%, 95%, 97%, 98%, or 99% sequence identity) to any of the aforesaid sequences. In some embodiments, the antibody comprises a heavy chain variable region comprising the amino acid sequence of any one of SEQ ID NOs: 67-71, or a sequence substantially identical (e.g., having at least about 80%, 85%, 90%, 92%, 95%, 97%, 98%, or 99% sequence identity) to any of the aforesaid sequences; and a light chain variable region comprising the amino acid sequence of any one of SEQ ID NOs: 72-76, or a sequence substantially identical (e.g., having at least about 80%, 85%, 90%, 92%, 95%, 97%, 98%, or 99% sequence identity) to any of the aforesaid sequences. In some embodiments, the nucleotide sequence encoding a heavy chain variable region of the antibody comprises the nucleotide sequence of any one of SEQ ID NOs: 156-160, or a sequence substantially identical (e.g., having at least about 80%, 85%, 90%, 92%, 95%, 97%, 98%, or 99% sequence identity) to any of the aforesaid sequences. In some embodiments, the nucleotide sequence encoding a light chain variable region of the antibody comprises the nucleotide sequence of any one of SEQ ID NOs: 161-165, or a sequence substantially identical (e.g., having at least about 80%, 85%, 90%, 92%, 95%, 97%, 98%, or 99% sequence identity) to any of the aforesaid sequences. In some embodiments, the nucleotide sequence encoding the heavy chain variable region comprises the nucleotide sequence of any one of SEQ ID NOs: 156-160, or a sequence substantially identical (e.g., having at least about 80%, 85%, 90%, 92%, 95%, 97%, 98%, or 99% sequence identity) to any of the aforesaid sequences; and the nucleotide sequence encoding the light chain variable region comprises the nucleotide sequence of any one of SEQ ID NOs: 161-165, or a sequence substantially identical (e.g., having at least about 80%, 85%, 90%, 92%, 95%, 97%, 98%, or 99% sequence identity) to any of the aforesaid sequences.

In some embodiments, the antibody that binds to tau comprises a heavy chain variable region comprising the amino acid sequence of any one of SEQ ID NOs: 67 or 69-71, or a sequence substantially identical (e.g., having at least about 80%, 85%, 90%, 92%, 95%, 97%, 98%, or 99% sequence identity) to any of the aforesaid sequences. In some embodiments, the antibody comprises a light chain variable region comprising the amino acid sequence of any one of SEQ ID NOs: 72-74, or a sequence substantially identical (e.g., having at least about 80%, 85%, 90%, 92%, 95%, 97%, 98%, or 99% sequence identity) to any of the aforesaid sequences. In some embodiments, the antibody comprises a heavy chain variable region comprising the amino acid sequence of any one of SEQ ID NOs: 67 or 69-71, or a sequence substantially identical (e.g., having at least about 80%, 85%, 90%, 92%, 95%, 97%, 98%, or 99% sequence identity) to any of the aforesaid sequences; and a light chain variable region comprising the amino acid sequence of any one of SEQ ID NOs: 72-74, or a sequence substantially identical (e.g., having at least about 80%, 85%, 90%, 92%, 95%, 97%, 98%, or 99% sequence identity) to any of the aforesaid sequences. In some embodiments, the nucleotide sequence encoding a heavy chain variable region of the antibody comprises the nucleotide sequence of any one of SEQ ID NOs: 156 or 158-160, or a sequence substantially identical (e.g., having at least about 80%, 85%, 90%, 92%, 95%, 97%, 98%, or 99% sequence identity) to any of the aforesaid sequences. In some embodiments, the nucleotide sequence encoding a light chain variable region of the antibody comprises the nucleotide sequence of any one of SEQ ID NOs: 161-163, or a sequence substantially identical (e.g., having at least about 80%, 85%, 90%, 92%, 95%, 97%, 98%, or 99% sequence identity) to any of the aforesaid sequences. In some embodiments, the nucleotide sequence encoding the heavy chain variable region comprises the nucleotide sequence of any one of SEQ ID NOs: 156 or 158-160, or a sequence substantially identical (e.g., having at least about 80%, 85%, 90%, 92%, 95%, 97%, 98%, or 99% sequence identity) to any of the aforesaid sequences; and the nucleotide sequence encoding the light chain variable region comprises the nucleotide sequence of any one of SEQ ID NOs: 161-163, or a sequence substantially identical (e.g., having at least about 80%, 85%, 90%, 92%, 95%, 97%, 98%, or 99% sequence identity) to any of the aforesaid sequences.

In some embodiments, the antibody that binds to tau comprises a heavy chain variable region comprising the amino acid sequence of SEQ ID NO: 69, or a sequence substantially identical (e.g., having at least about 80%, 85%, 90%, 92%, 95%, 97%, 98%, or 99% sequence identity) thereto. In some embodiments, the antibody comprises a light chain variable region comprising the amino acid sequence of any one of SEQ ID NOs: 73, or a sequence substantially identical (e.g., having at least about 80%, 85%, 90%, 92%, 95%, 97%, 98%, or 99% sequence identity) thereto. In some embodiments, the antibody comprises a heavy chain variable region comprising the amino acid sequence of SEQ ID NO: 69, or a sequence substantially identical (e.g., having at least about 80%, 85%, 90%, 92%, 95%, 97%, 98%, or 99% sequence identity) thereto; and a light chain variable region comprising the amino acid sequence of SEQ ID NO: 73, or a sequence substantially identical (e.g., having at least about 80%, 85%, 90%, 92%, 95%, 97%, 98%, or 99% sequence identity) thereto. In some embodiments, the nucleotide sequence encoding a heavy chain variable region of the antibody comprises the nucleotide sequence of SEQ ID NO: 158, or a sequence substantially identical (e.g., having at least about 80%, 85%, 90%, 92%, 95%, 97%, 98%, or 99% sequence identity) thereto. In some embodiments, the nucleotide sequence encoding a light chain variable region of the antibody comprises the nucleotide sequence of SEQ ID NO: 162, or a sequence substantially identical (e.g., having at least about 80%, 85%, 90%, 92%, 95%, 97%, 98%, or 99% sequence identity) thereto. In some embodiments, the nucleotide sequence encoding the heavy chain variable region comprises the nucleotide sequence of SEQ ID NOs: 158, or a sequence substantially identical (e.g., having at least about 80%, 85%, 90%, 92%, 95%, 97%, 98%, or 99% sequence identity) thereto; and the nucleotide sequence encoding the light chain variable region comprises the nucleotide sequence of SEQ ID NO: 162, or a sequence substantially identical (e.g., having at least about 80%, 85%, 90%, 92%, 95%, 97%, 98%, or 99% sequence identity) thereto.

In some embodiments, the anti-tau antibody comprises a heavy chain comprising the amino acid sequence of any one of SEQ ID NOs: 170-174; or encoded by the nucleotide sequence of any one of SEQ ID NOs: 180-184, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain comprising the amino acid sequence of any one of SEQ ID NOs: 175-179; or encoded by the nucleotide sequence of any one of SEQ ID NOs: 185-189, or a sequence substantially identical (e.g., having at least about 70%, 75%, 80%, 85%, 90%, 92%, 95%, 97%, 98%, or 99% sequence identity) to any of the aforesaid sequences. In some embodiments, the antibody comprises a heavy chain comprising the amino acid sequence of any one of SEQ ID NOs: 170-174, or an amino acid sequence substantially identical (e.g., having at least about 70%, 75%, 80%, 85%, 90%, 92%, 95%, 97%, 98%, or 99% sequence identity) to any of the aforesaid sequences; and a light chain comprising the amino acid sequence of any one of SEQ ID NOs: 175-179, or an amino acid sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain of the antibody comprises the nucleotide sequence of any one of SEQ ID NOs: 180-184, or a nucleotide sequence substantially identical (e.g., having at least about 70%, 75%, 80%, 85%, 90%, 92%, 95%, 97%, 98%, or 99% sequence identity) to any of the aforesaid sequences; and the nucleotide sequence encoding the light chain comprises the nucleotide sequence of any one of SEQ ID NOs: 185-189, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a heavy chain comprising the amino acid sequence of any one of SEQ ID NOs: 170 or 172-174; or encoded by the nucleotide sequence of any one of SEQ ID NOs: 180-182, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain comprising the amino acid sequence of any one of SEQ ID NOs: 175-177; or encoded by the nucleotide sequence of any one of SEQ ID NOs: 185-187, or a sequence substantially identical (e.g., having at least about 70%, 75%, 80%, 85%, 90%, 92%, 95%, 97%, 98%, or 99% sequence identity) to any of the aforesaid sequences. In some embodiments, the antibody comprises a heavy chain comprising the amino acid sequence of any one of SEQ ID NOs: 170 or 172-174, or an amino acid sequence substantially identical (e.g., having at least about 70%, 75%, 80%, 85%, 90%, 92%, 95%, 97%, 98%, or 99% sequence identity) to any of the aforesaid sequences; and a light chain comprising the amino acid sequence of any one of SEQ ID NOs: 175-177, or an amino acid sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain of the antibody comprises the nucleotide sequence of any one of SEQ ID NOs: 180 or 182-184, or a nucleotide sequence substantially identical (e.g., having at least about 70%, 75%, 80%, 85%, 90%, 92%, 95%, 97%, 98%, or 99% sequence identity) to any of the aforesaid sequences; and the nucleotide sequence encoding the light chain comprises the nucleotide sequence of any one of SEQ ID NOs: 185-187, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a heavy chain comprising the amino acid sequence of SEQ ID NO: 172; or encoded by the nucleotide sequence of SEQ ID NO: 182, or a sequence substantially identical (e.g., having at least about 70%, 75%, 80%, 85%, 90%, 92%, 95%, 97%, 98%, or 99% sequence identity) thereto. In some embodiments, the anti-tau antibody comprises a light chain comprising the amino acid sequence of SEQ ID NO: 176; or encoded by the nucleotide sequence of SEQ ID NOs: 186, or a sequence substantially identical (e.g., having at least about 70%, 75%, 80%, 85%, 90%, 92%, 95%, 97%, 98%, or 99% sequence identity) thereto. In some embodiments, the antibody comprises a heavy chain comprising the amino acid sequence of SEQ ID NO: 172, or an amino acid sequence substantially identical (e.g., having at least about 70%, 75%, 80%, 85%, 90%, 92%, 95%, 97%, 98%, or 99% sequence identity) thereto; and a light chain comprising the amino acid sequence of any one of SEQ ID NO: 176, or an amino acid sequence substantially identical (e.g., having at least about 70%, 75%, 80%, 85%, 90%, 92%, 95%, 97%, 98%, or 99% sequence identity) thereto. In some embodiments, the nucleotide sequence encoding the heavy chain of the antibody comprises the nucleotide sequence of SEQ ID NO: 182, or a nucleotide sequence substantially identical (e.g., having at least about 70%, 75%, 80%, 85%, 90%, 92%, 95%, 97%, 98%, or 99% sequence identity) thereto; and the nucleotide sequence encoding the light chain comprises the nucleotide sequence of SEQ ID NO: 186, or a nucleotide sequence substantially identical (e.g., having at least about 70%, 75%, 80%, 85%, 90%, 92%, 95%, 97%, 98%, or 99% sequence identity) thereto.

In some embodiments, the anti-tau antibody comprises a heavy chain comprising the amino acid sequence of SEQ ID NO: 8 or 65; or encoded by the nucleotide sequence of SEQ ID NO: 10 or 191, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain comprising the amino acid sequence of SEQ ID NO: 12 or 66; or encoded by the nucleotide sequence of SEQ ID NO: 13 or 193, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain and a light chain comprising the amino acid sequences of SEQ ID NO: 8 and 12, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain comprises the nucleotide sequence of SEQ ID NO: 10 or a sequence substantially identical (e.g., having at least about 70%, 75%, 80%, 85%, 90%, 92%, 95%, 97%, 98%, or 99% sequence identity) thereto; and/or the nucleotide sequence encoding the light chain comprises the nucleotide sequence of SEQ ID NO: 13, or a sequence substantially identical (e.g., having at least about 70%, 75%, 80%, 85%, 90%, 92%, 95%, 97%, 98%, or 99% sequence identity) thereto. In some embodiments, the anti-tau antibody comprises a heavy chain and a light chain comprising the amino acid sequences of SEQ ID NO: 65 and 66, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain comprises the nucleotide sequence of SEQ ID NO: 191 or a sequence substantially identical (e.g., having at least about 70%, 75%, 80%, 85%, 90%, 92%, 95%, 97%, 98%, or 99% sequence identity) thereto; and/or the nucleotide sequence encoding the light chain comprises the nucleotide sequence of SEQ ID NO: 193, or a sequence substantially identical (e.g., having at least about 70%, 75%, 80%, 85%, 90%, 92%, 95%, 97%, 98%, or 99% sequence identity) thereto.

In some embodiments, the anti-tau antibody comprises a heavy chain variable region comprising the amino acid sequence of SEQ ID NO: 22; or encoded by the nucleotide sequence of SEQ ID NO: 168; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 94; or encoded by the nucleotide sequence of SEQ ID NO: 242; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 22 and 94, respectively; or encoded by the nucleotide sequences of SEQ ID NO: 168 and 242, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 168, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 242, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 23; or encoded by the nucleotide sequence of SEQ ID NO: 169; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 95; or encoded by the nucleotide sequence of SEQ ID NO: 243; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 23 and 95, respectively; or encoded by the nucleotide sequences of SEQ ID NO: 169 and 243, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 169, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 243, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 51; or encoded by the nucleotide sequence of SEQ ID NO: 197; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 122; or encoded by the nucleotide sequence of SEQ ID NO: 270; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 51 and 122, respectively; or encoded by the nucleotide sequences of SEQ ID NO: 197 and 270, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 197, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 270, or a sequence substantially identical (e.g., having at least about 80%, 85%, 90%, 92%, 95%, 97%, 98%, or 99% sequence identity).

In some embodiments, the anti-tau antibody comprises a VH and/or VL encoded by a codon-optimized nucleic acid sequence. Codon-optimization may be achieved by any method known to one with skill in the art such as, but not limited to, by a method according to Genescript, EMBOSS, Bioinformatics, NUS, NUS2, Geneinfinity, IDT, NUS3, GregThatcher, Insilico, Molbio, N2P, Snapgene, and/or VectorNTI.

In some embodiments, an anti-tau antibody comprises a heavy chain variable region comprising one, two, three, or four framework regions, e.g., one, two, three, or all of a FRH1, FRH2, FRH3, and/or FRH4. In some embodiments, an anti-tau antibody comprises a light chain variable region comprising one, two, three, or four framework regions, e.g., one, two, three, or all of a FRL1, FRL2, FRL3, and/or FRL4. In some embodiments, the heavy chain variable region comprises from N-terminus to C-terminus, FRH1-CDRH1-FRH2-CDRH2-FRH3-CDRH3-FRH4. In some embodiments, the light chain variable region comprises from N terminus to C-terminus, FRL1-CDRL1-FRL2-CDRL2-FRL3-CDRL3-FRL4. In some embodiments, a framework regions is present before a CDR (e.g., a HC or LC CDR1), between two CDRs (e.g., between a CDR1 and CDR2; between a CDR2 and CDR3), and/or after a CDR (e.g., after a CDR3).

In some embodiments, the FRH1 corresponds to positions 1-25 of a heavy chain variable region, numbered according to any one of SEQ ID NOs: 21 or 67-71; the FRH2 corresponds to positions 36-49, numbered according to any one of SEQ ID NOs: 21 or 67-71; the FRH3 corresponds to positions 67-96, numbered according to any one of SEQ ID NOs: 21 or 67-71; and/or the FRH4 corresponds to positions 108-118, numbered according to any one of SEQ ID NOs: 21 or 67-71. In some embodiments, the FRH1 corresponds to positions 1-30 of a heavy chain variable region, numbered according to any one of SEQ ID NOs: 21 or 67-71; the FRH2 corresponds to positions 36-49, numbered according to any one of SEQ ID NOs: 21 or 67-71; the FRH3 corresponds to positions 67-98, numbered according to any one of SEQ ID NOs: 21 or 67-71; and/or the FRH4 corresponds to positions 108-118, numbered according to any one of SEQ ID NOs: 21 or 67-71.

In some embodiments, the FRL1 corresponds to positions 1-23 of a light chain variable region, numbered according to any one of SEQ ID NOs: 72-76 or 93; the FRL2 corresponds to positions 40-54 of a light chain variable region, numbered according to any one of SEQ ID NOs: 72-76 or 93; the FRL3 corresponds to positions 62-93 of a light chain variable region, numbered according to any one of SEQ ID NOs: 72-76 or 93; and/or the FRL4 corresponds to positions 103-112, numbered according to any one of SEQ ID NOs: 72-76 or 93.

In some embodiments, the antibody does not comprise one, two, three, or all of a FRH1 comprising amino acids 1-25 or 1-30 of SEQ ID NO: 21; a FRH2 comprising amino acids 36-49 of SEQ ID NO: 21; an FRH3 comprising amino acids 67-96 or 67-98 of SEQ ID NO: 21; and/or a FRH4 comprising amino acids 108-118 of SEQ ID NO: 21. In some embodiments, the antibody does not comprise one, two, three, or all of a FRL1 comprising amino acids 1-23 of SEQ ID NO: 93; a FRL2 comprising amino acids 40-54 of SEQ ID NO: 93; an FRL3 comprising amino acids 62-93 of SEQ ID NO: 93; and/or a FRL4 comprising amino acids 103-112 of SEQ ID NO: 93.

In some embodiments, the antibody comprises a FRH1 comprising amino acids 1-25 or 1-30 of any one of SEQ ID NOs: 67-71; an amino acid sequence comprising one, two, three but no more than four modifications (e.g., substitutions, e.g., conservative substitutions) relative to amino acids 1-25 or 1-30 of any one of SEQ ID NOs: 67-71; or an amino acid sequence comprising one, two, three, but no more than four different amino acids relative to amino acids 1-25 or 1-30 of any one of SEQ ID NOs: 67-71. In some embodiments, the antibody comprises a FRH2 comprising amino acids 36-49 of any one of SEQ ID NOs: 67-71; an amino acid sequence comprising one, two, three but no more than four modifications (e.g., substitutions, e.g., conservative substitutions) relative to amino acids 36-49 of any one of SEQ ID NOs: 67-71; or an amino acid sequence comprising one, two, three, but no more than four different amino acids relative to amino acids 36-49 of any one of SEQ ID NOs: 67-71. In some embodiments, the antibody comprises a FRH3 comprising amino acids 67-96 or 67-98 of any one of SEQ ID NOs: 67-71; an amino acid sequence comprising one, two, three but no more than four modifications (e.g., substitutions, e.g., conservative substitutions) relative to amino acids 67-96 or 67-98 of any one of SEQ ID NOs: 67-71; or an amino acid sequence comprising one, two, three, but no more than four different amino acids relative to amino acids 67-96 or 67-98 of any one of SEQ ID NOs: 67-71. In some embodiments, the antibody comprises a FRH4 comprising amino acids 108-118 of any one of SEQ ID NOs: 67-71; an amino acid sequence comprising one, two, three but no more than four modifications (e.g., substitutions, e.g., conservative substitutions) relative to amino acids 108-118 of any one of SEQ ID NOs: 67-71; or an amino acid sequence comprising one, two, three, but no more than four different amino acids relative to amino acids 108-118 of any one of SEQ ID NOs: 67-71.

In some embodiments, the antibody comprises a FRL1 comprising amino acids 1-23 of any one of SEQ ID NOs: 72-76; an amino acid sequence comprising one, two, three but no more than four modifications (e.g., substitutions, e.g., conservative substitutions) relative to amino acids 1-23 of any one of SEQ ID NOs: 72-76; or an amino acid sequence comprising one, two, three but no more than four different amino acids relative to amino acids 1-23 of any one of SEQ ID NOs: 72-76. In some embodiments, the antibody comprises a FRL2 comprising amino acids 40-54 of any one of SEQ ID NOs: 72-76; an amino acid sequence comprising one, two, three but no more than four modifications (e.g., substitutions, e.g., conservative substitutions) relative to amino acids 40-54 of any one of SEQ ID NOs: 72-76; or an amino acid sequence comprising one, two, three but no more than four different amino acids relative to amino acids 40-54 of any one of SEQ ID NOs: 72-76. In some embodiments, the antibody comprises a FRL3 comprising amino acids 62-93 of any one of SEQ ID NOs: 72-76; an amino acid sequence comprising one, two, three but no more than four modifications (e.g., substitutions, e.g., conservative substitutions) relative to amino acids 62-93 of any one of SEQ ID NOs: 72-76; or an amino acid sequence comprising one, two, three but no more than four different amino acids relative to amino acids 62-93 of any one of SEQ ID NOs: 72-76. In some embodiments, the antibody comprises a FRL4 comprising amino acids 103-112 of any one of SEQ ID NOs: 72-76; an amino acid sequence comprising one, two, three but no more than four modifications (e.g., substitutions, e.g., conservative substitutions) relative to amino acids 103-112 of any one of SEQ ID NOs: 72-76; or an amino acid sequence comprising one, two, three but no more than four different amino acids relative to amino acids 103-112 of any one of SEQ ID NOs: 72-76.

In some embodiments, an antibody that binds tau does not comprise the amino acid sequence of SEQ ID NO: 21 and/or the amino acid sequence of SEQ ID NO: 93.

Anti-tau antibodies according to the present disclosure may be prepared using any of the antibody sequences (e.g., variable domain amino acid sequences, variable domain amino acid sequence pairs, CDR amino acid sequences, variable domain CDR amino acid sequence sets, variable domain CDR amino acid sequence set pairs, and/or framework region amino acid sequences) presented herein, any may be prepared, for example, as monoclonal antibodies, multispecific antibodies, chimeric antibodies, antibody mimetics, scFvs, or antibody fragments.

binds to tau described herein binds a phosphorylated residue of a tau protein, e.g., phosphorylated serine at position 422 (e.g., pS422), numbered according to SEQ ID NO: 920. In some embodiments, the antibody preferentially binds, e.g., primarily binds, pathological tau, e.g. PHF-tau, compared to wild-type tau. In some embodiments, the antibody demonstrates superior efficacy in a murine seeding model.

TABLE 8

Tau protein antigen sequences

| Antigen | Sequence | SEQ ID NO |
|---|---|---|
| human microtubule-associated protein tau, isoform 2 | MAEPRQEFEVMEDHAGTYGLGDRKDQGGYTMHQDQEGDTDAGLKESPLQTPTEDG SEEPGSETSDAKSTPTAEDVTAPLVDEGAPGKQAAAQPHTEIPEGTTAEEAGIGD TPSLEDEAAGHVTQARMVSKSKDGTGSDDKKAKGADGKTKIATPRGAAPPGQKGQ ANATRIPAKTPPAPKTPPSSGEPPKSGDRSGYSSPGSPGTPGSRSRTPSLPTPPT REPKKVAVVRTPPKSPSSAKSRLQTAPVPMPDLKNVKSKIGSTENLKHQPGGGKV QIINKKLDLSNVQSKCGSKDNIKHVPGGGSVQIVYKPVDLSKVTSKCGSLGNIHH KPGGGQVEVKSEKLDFKDRVQSKIGSLDNITHVPGGGNKKIETHKLTFRENAKAK TDHGAEIVYKSPVVSGDTSPRHLSNVSSTGSIDMVDSPQLATLADEVSASLAKQG L | 920 |
| PT3 epitope peptide (pT212/pT217) | TPGSRSRTPSLPTPPTREPK | 921 |
| Peptide 5 (pT212/pS214/pT217) | GTPGSRSRTPSLPTPPTRE | 922 |
| Peptide 12 (pS396/pS404/pS409) | RENAKAKTDHGAEIVYKSPVVSGDTSPRHLSNVSSTG | 923 |
| Peptide 1 (AT120 epitope) | PTREPKKV | 924 |
| 6C5 epitope peptide | ARMVSKS | 925 |
| UCB D & PT76 epitope peptide | SPSSAKSRLQTAPVPMPDLKNVKS | 926 |

In some embodiments, anti-tau antibodies using any of the antibody sequences presented herein may be prepared as IgA, IgD, IgE, IgG, or IgM antibodies. When prepared as mouse IgG antibodies, anti-tau antibodies may be prepared as IgG1, IgG2a, IgG2b, IgG2c, or IgG3 isotypes. When prepared as human IgG antibodies, anti-tau antibodies may be prepared as IgG1, IgG2, IgG3, or IgG4 isotypes. Anti-tau antibodies prepared as human or humanized antibodies may include one or more human constant domains.

This present disclosure provides in some embodiments, a nucleic acid (e.g., an isolated nucleic acid) encoding any of the above described antibodies, and viral genomes, vectors, AAV particles, and cells comprising the same.

Tau Protein Antigens

In some embodiments, anti-tau antibodies bind to tau protein antigens, e.g., an epitope on a tau protein. Tau protein antigens may include human microtubule-associated protein tau, isoform 2 (SEQ ID NO: 920) or fragments thereof. Tau protein antigens may include ePHF or fragments thereof. Tau protein antigens may include one or more phosphorylated residues. Such phosphorylated residues may correspond to those found with pathological tau. In some embodiments tau protein antigens include any of those listed in Table 8. In the Table, phosphorylated residues associated with each antigen are double-underlined. In some embodiments, tau proteins may include variants (e.g., phosphorylated or unphosphorylated variants) or fragments of the sequences listed. In some embodiments, an antibody that In some embodiments, anti-tau antibodies of the present disclosure bind to tau protein epitopes on tau protein antigens described herein. Such tau protein epitopes may include or be included within a tau protein antigen amino acid sequence listed in Table 8. In some embodiments, anti-tau antibodies of the present disclosure bind to tau protein epitopes that include a region formed by a complex of at least two tau proteins.

In some embodiments, disclosed herein is an encoded an antibody that competes for binding to tau with the aforesaid antibodies. In some embodiments, disclosed herein is an antibody that binds to the same epitope as, substantially the same epitope as, an epitope that overlaps with, or an epitope that substantially overlaps with, the epitope of the aforesaid anti-tau antibody.

In some embodiment, compete or cross-compete refers to the ability of an antibody to interfere with binding of an anti-tau antibody, e.g., an anti-tau antibody provided herein, to a target, e.g., tau protein. The interference with binding can be direct or indirect (e.g., through an allosteric modulation of the antibody or the target). The extent to which an antibody is able to interfere with the binding of another antibody to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-tau antibody is said to compete for binding to the target with a second anti-tau antibody when the binding of the first antibody to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

In some embodiments, an epitope comprises the moieties of an antigen (e.g., a tau protein antigen) that specifically interact with an antibody. Such moieties, referred to herein as epitopic determinants, typically comprise, or are part of, elements such as amino acid side chains or sugar side chains. An epitopic determinate can be defined by methods known in the art or disclosed herein, e.g., by crystallography or by hydrogen-deuterium exchange. At least one or some of the moieties on the antibody, that specifically interact with an epitopic determinant, are typically located in a CDR(s). Typically, an epitope has a specific three dimensional structural characteristics. Typically, an epitope has specific charge characteristics. Some epitopes are linear epitopes while others are conformational epitopes.

In an embodiment, an epitopic determinant is a moiety on the antigen, e.g., such as amino acid side chain or sugar side chain, or part thereof, which, when the antigen and antibody are co-crystallized, is within a predetermined distance, e.g., within 5 Angstroms, of a moiety on the antibody, referred to herein as a crystallographic epitopic determinant. In some embodiments, the crystallographic epitopic determinants of an epitope are collectively referred to as a crystallographic epitope.

A first antibody binds the same epitope as a second antibody (e.g., a reference antibody, e.g., an antibody disclosed herein) if the first antibody specifically interacts with the same epitopic determinants on the antigen as does the second or reference antibody, e.g., when interaction is measured in the same way for both the antibody and the second or reference antibody. Epitopes that overlap share at least one epitopic determinant. A first antibody binds an overlapping epitope with a second antibody (e.g., a reference antibody, e.g., an antibody disclosed herein) when both antibodies specifically interact with a common epitopic determinant. A first and a second antibody (e.g., a reference antibody, e.g., an antibody disclosed herein) bind substantially overlapping epitopes if at least half of the epitopic determinants of the second or reference antibody are found as epitopic determinants in the epitope of the first antibody. A first and a second antibody (e.g., a reference antibody, e.g., an antibody disclosed herein) bind substantially the same epitope if the first antibody binds at least half of the core epitopic determinants of the epitope of the second or reference antibody, wherein the core epitopic determinants are defined by crystallography.

Epitope Specificity

Antibodies of the present disclosure may bind to tau protein epitopes, which may include or be included within the residues of SEQ ID NOs: 920-926. Antibodies may compete for binding to tau protein epitopes with other anti-tau antibodies, including, but not limited to, AT100, AT120, PT3, C10.2, PT76, IPN002, 6C5, and UCB D. Tau protein epitopes may include C-terminal residues 409-436 of human tau (SEQ ID NO: 920). Such epitopes may include residues 413-430 of human tau (SEQ ID NO: 920). Antibody binding to such residues may exhibit a $K_D$ of from about 0.1 nM to about 0.5 nM. In some embodiments, tau protein epitopes may include residues 55-76, 159-194, 219-247, and/or 381-426 of human tau (SEQ ID NO: 920). Such epitopes may include residues 57-72, 175-191, 223-238, and/or 383-400 of human tau (SEQ ID NO: 920). Antibodies binding to such residues may exhibit a $K_D$ of from about 0.5 nM to about 5 nM.

In some embodiments, the present disclosure provides antibodies that compete for binding with second antibodies to tau protein epitopes. Such epitopes may include one or more of residues 32-49, 55-76, 57-72, 159-194, 175-191, 185-200, 219-247, 223-238, 381-426, 383-400, 409-436, and 413-430 of human tau (SEQ ID NO: 920).

Tau protein epitopes may include one or more of residues 409-436 and 413-430 of human tau (SEQ ID NO: 920). Second antibodies competing for binding to such epitopes may include variable domain pairs selected from the group consisting of: a VH with the amino acid sequence of SEQ ID NO: 21 and a VL with the amino acid sequence of SEQ ID NO: 93; a VH with the amino acid sequence of SEQ ID NO: 22 and a VL with the amino acid sequence of SEQ ID NO: 94; and a VH with the amino acid sequence of SEQ ID NO: 23 and a VL with the amino acid sequence of SEQ ID NO: 95.

II. Vectorization

According to the present disclosure, compositions for delivering anti-tau antibodies or functional variants thereof by adeno-associated virus particles (AAVs) are provided. In some embodiments, an AAV particle, e.g., an AAV particle as described herein, or plurality of particles, may be provided, e.g., delivered, via any of several routes of administration, to a cell, tissue, organ, or organism, in vivo, ex vivo, or in vitro.

As used herein, an "AAV particle" is a virus which comprises a capsid and a viral genome with at least one payload region and at least one inverted terminal repeat (ITR) region.

As used herein, "viral genome" or "vector genome" refers to the nucleic acid sequence(s) encapsulated in an AAV particle. Viral genomes comprise at least one payload region encoding polypeptides, e.g., antibodies, antibody-based compositions or fragments thereof.

As used herein, a "payload" or "payload region" is any nucleic acid molecule which encodes one or more polypeptides. At a minimum, a payload region comprises nucleic acid sequences that encode an antibody, an antibody-based composition, or a fragment thereof, but may also optionally comprise one or more functional or regulatory elements to facilitate transcriptional expression and/or polypeptide translation.

In some embodiments, AAV particles, viral genomes and/or payloads, and the methods of their use may be as described in WO2017189963 or WO2020223276, the contents of each of which are herein incorporated by reference in their entirety.

The nucleic acid sequences, viral genomes, and polypeptides disclosed herein may be engineered to contain modular elements and/or sequence motifs assembled to enable expression of an antibody or functional variant thereof, e.g., an antibody described herein. In some embodiments, the nucleic acid sequence encodes an antibody comprising one or more of the CDRs (e.g., heavy chain and/or light chain CDRs) of an antibody, a variable heavy (VH) chain region and/or variable light (VL) chain region, a heavy and/or light chain constant region, or a combination thereof. In some embodiments, the nucleic acid sequence encoding the antibody may also encode a linker, e.g., such that the VH/heavy chain and the VL/light chain of the antibody are connected via a linker. In some embodiments, the viral genome may further comprise a promoter region, an intron, a Kozak sequence, an enhancer, or a polyadenylation sequence. The order of expression, structural position, or concatemer count (e.g., the VH, VL, heavy chain, light chain, and/or linker) may be different within or among different payload regions. The identity, position and number of linkers expressed by payload regions may also vary. In some embodiments, the payload is a region comprising one or more humanized antibody sequences, such as but not limited to, a humanized antibody VL, light chain domain and/or a humanized antibody VH, heavy chain domain, or fragments thereof.

In some embodiments, the present disclosure provides methods for delivering an antibody (e.g., an anti-tau antibody described herein) and/or a nucleic acid sequence encoding an antibody (e.g., an anti-tau antibody described herein) comprised within the viral genome comprised within a recombinant, AAV particle (e.g., an AAV particle described herein) to a cell, tissue, organ, or subject.

Adeno-Associated Viruses (AAVs) and AAV Particles

In some embodiments, AAV are used as a biological tool due to a relatively simple structure, their ability to infect a wide range of cells (including quiescent and dividing cells) without integration into the host genome and without replicating, and their relatively benign immunogenic profile. In some embodiments, the genome, e.g., viral genome, of the virus may be manipulated to contain a minimum of components for the assembly of a functional recombinant virus, or viral particle, which is loaded with or engineered to target a particular tissue and express or deliver a desired payload, e.g., an antibody (e.g., an anti-tau antibody).

In some embodiments, the AAV, e.g., naturally occurring (e.g., wild-type) AAV or a recombinant AAV, comprises a viral genome which is a linear, single-stranded nucleic acid molecule, e.g., DNA (ssDNA). In some embodiments, the viral genome, e.g., of a naturally occurring (e.g., wild-type) AAV, is approximately 5,000 nucleotides (nt) in length. In some embodiments, inverted terminal repeats (ITRs) traditionally cap the viral genome at both the 5' and the 3' end, providing origins of replication for the viral genome. In some embodiments, an AAV viral genome comprises two ITR sequences. In some embodiments, the ITRs have a characteristic T-shaped hairpin structure defined by a self-complementary region (145 nt in wild-type AAV) at the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

In some embodiments, the AAV particle, e.g., an AAV particle (e.g., ssAAVs) described herein comprises a viral genome, e.g., viral genome and/or AAV vector, that is self-complementary (scAAV). In some embodiments, the ssAAV comprises nucleic acid molecules, e.g., DNA strands, that anneal together to form double stranded DNA. In some embodiments, a scAAV allows for rapid expression in a transduced cell as it bypasses second strand synthesis.

In some embodiments, the AAV viral genome further comprises nucleotide sequences for two open reading frames, one for the four non-structural Rep proteins (Rep78, Rep68, Rep52, Rep40, encoded by Rep genes) and one for the three capsid, or structural, proteins (VP1, VP2, VP3, encoded by capsid genes or Cap genes). The Rep proteins are used for replication and packaging, while the capsid proteins are assembled to create the protein shell of the AAV particle, or AAV capsid. In some embodiments, alternative splicing and alternate initiation codons and promoters result in the generation of four different Rep proteins from a single open reading frame and the generation of three capsid proteins from a single open reading frame. For example, in some embodiments, for the AAV9/hu.14 serotype (SEQ ID NO: 138 and SEQ ID NO: 137), VP1 refers to amino acids 1-736, VP2 refers to amino acids 138-736, and VP3 refers to amino acids 203-736. In some embodiments, for the amino acid sequence of SEQ ID NO: 3636, VP1 comprises amino acids 1-743, VP2 comprises amino acids 138-742, and VP3 comprises amino acids 203-742. In some embodiments, VP1 is the full-length capsid sequence, while VP2 and VP3 are shorter components of the whole. As a result, changes in the sequence in the VP3 region, are also changes to VP1 and VP2, however, the percent difference as compared to the parent sequence will be greatest for VP3 since it is the shortest sequence of the three. Though described here in relation to the amino acid sequence, the nucleotide sequence encoding these proteins can be similarly described. In some embodiments, the three capsid proteins assemble to create the AAV capsid protein. In some embodiments, the AAV capsid protein typically comprises a molar ratio of 1:1:10 of VP1:VP2:VP3. In some embodiments, the AAV serotype is defined by the AAV capsid. In some instances, the ITRs are also specifically described by the AAV serotype (e.g., AAV2/9).

In some embodiments, a viral genome of a wild-type, e.g., naturally occurring, AAV can be modified to replace the rep/cap sequences with a nucleic acid comprising a transgene encoding a payload, e.g., an antibody or fragment thereof, wherein the viral genome comprises at least one ITR region. In some embodiments, the viral genome of a recombinant AAV comprises two ITR regions, e.g., a 5'ITR or a 3'ITR. In some embodiments, the rep/cap sequences can be provided in trans during production to generate AAV particles. In some embodiments, the viral genome of an AAV is comprised in an AAV vector, which further encodes a capsid protein e.g., a structural protein, wherein the capsid protein comprises a VP1 polypeptide, a VP2 polypeptide, and/or a VP3 polypeptide; and/or a Rep protein, e.g., a non-structural protein, wherein the Rep protein comprises a Rep78 protein, a Rep68, Rep52 protein, and/or a Rep40 protein (e.g., a Rep25 protein and/or a Rep78 protein).

In some embodiments, in addition to the viral genome comprising a nucleic acid encoding a transgene encoding a payload (e.g., an antibody, e.g., an anti-tau antibody), an AAV particle, e.g., an AAV particle described herein, may comprise the viral genome, in whole or in part, of any naturally occurring and/or recombinant AAV serotype nucleotide sequence or variant. In some embodiments, AAV variants may have sequences of significant homology at the nucleic acid (viral genome or capsid) and amino acid levels (capsids), to produce constructs which are generally physical and functional equivalents, replicate by similar mechanisms, and assemble by similar mechanisms. Chiorini et al., J. Vir. 71:6823-33 (1997); Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74:8635-47 (2000), the contents of each of which are incorporated herein by reference in their entirety.

In some embodiments, AAV particles of the present disclosure are recombinant AAV particles which are replication defective and lacking the nucleotide sequences encoding functional Rep and Cap proteins. In some embodiments, these defective AAV particles may lack most or all parental coding sequences and carry only one or two AAV ITR sequences and the nucleic acid of interest for delivery to a cell, a tissue, an organ, or an organism.

In some embodiments, the viral genome or the AAV vector of the AAV particles described herein comprise at least one control element which provides for the replication, transcription, and translation of a coding sequence encoded therein. In some embodiments, a sufficient number of control elements are present such that the coding sequence of the transgene encoded by the viral genome is capable of being replicated, transcribed, and/or translated in a host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

In some embodiments, the recombinant AAV particles of the present disclosure are capable of providing, e.g., delivering, a transgene to a mammalian cell. In some embodiments, the recombinant AAV particles of the present disclosure are capable of vectorized delivery of an antibody (e.g., an anti-tau antibody) or fragment thereof.

In some embodiments, the AAV particles, vectors, viral genomes, and/or nucleic acids of the present disclosure may be produced recombinantly and may be based on adeno-associated virus (AAV) parent or reference sequences. Methods for producing and/or modifying AAV particles are disclosed in the art such as pseudotyped AAV vectors (PCT Patent Publication Nos. WO200028004; WO200123001; WO2004112727; WO2005005610; and WO2005072364, the content of each of which is incorporated herein by reference in its entirety). In some embodiments, the AAV particles described herein may be modified to enhance the efficiency of delivery, e.g., delivery of a transgene encoding a payload, e.g., an antibody. Without wishing to be bound by theory, it is believed in some embodiments, that a modified, e.g., recombinant, AAV particle can be packaged efficiently and successfully infect target cells at high frequency and with minimal toxicity. In some embodiments, the capsid protein of the AAV particles are engineered according to the methods described in US Publication Number US20130195801, the contents of which are incorporated herein by reference in their entirety.

AAV Capsids and Variants Thereof

In some embodiments, an AAV particle, e.g., an AAV particle for the vectorized delivery of an antibody or fragment thereof described herein (e.g., an anti-tau antibody), may comprise an AAV capsid variant. In some embodiments, the AAV capsid variant comprises a VOY101 capsid polypeptide or a functional variant thereof, a VOY9P39 capsid polypeptide or a functional variant thereof, a VOY9P33 capsid polypeptide or a functional variant thereof, a AAVPHP.B (PHP.B) capsid polypeptide or a functional variant thereof, a AAVPHP.N (PHP.N) capsid polypeptide or a functional variant thereof, an AAV1 capsid polypeptide or a functional variant thereof, an AAV2 capsid polypeptide or a functional variant thereof, an AAV5 capsid polypeptide or a functional variant thereof, an AAV9 capsid polypeptide or a functional variant thereof, an AAV9 K449R capsid polypeptide or a functional variant thereof, an AAVrh10 capsid polypeptide or a functional variant thereof. In some embodiments, the AAV capsid polypeptide, e.g., AAV capsid variant, comprises an amino acid sequence of any of the AAV capsid polypeptides in Table 2, or an amino acid sequence substantially identical (e.g., having at least 70%, 75%, 80%, 85%, 90%, 92%, 95%, 97%, 98%, or 99% sequence identity) thereto. In some embodiments, the nucleotide sequence encoding the AAV capsid polypeptide or functional variant thereof comprises any one of the nucleotide sequence in Table 2, or a nucleotide sequence substantially identical (e.g., having at least 70%, 75%, 80%, 85%, 90%, 92%, 95%, 97%, 98%, or 99% sequence identity) thereto.

TABLE 2

Exemplary full length capsid sequences

| Description | SEQ ID NO: | Sequence Information |
|---|---|---|
| VOY101 | 803 | MAADGYLPDWLEDNLSEGIREWWALKPGAPQPKANQQHQDNARGLVLPGYKYLGPGNGL DKGEPVNAADAAALEHDKAYDQQLKAGDNPYLKYNHADAEFQERLKEDTSFGGNLGRAV FQAKKRLLEPLGLVEEAAKTAPGKKRPVEQSPQEPDSSAGIGKSGAQPAKKRLNFGQTG DTESVPDPQPIGEPPAAPSGVGSLTMASGGGAPVADNNEGADGVGSSSGNWHCDSQWLG DRVITTSTRTWALPTYNNHLYKQISNSTSGGSSNDNAYFGYSTPWGYFDFNRFHCHFSP RDWQRLINNNWGFRPKRLNFKLFNIQVKEVTDNNGVKTIANNLTSTVQVFTDSDYQLPY VLGSAHEGCLPPFPADVFMIPQYGYLTLNDGSQAVGRSSFYCLEYFPSQMLRTGNNFQF SYEFENVPFHSSYAHSQSLDRLMNPLIDQYLYYLSKTINGSGQNQQTLKFSVAGPSNMA VQGRNYIPGPSYRQQRVSTTVTQNNNSEFAWPGASSWALNGRNSLMNPGPAMASHKEGE DRFFPLSGSLIFGKQGTGRDNVDADKVMITNEEEIKTTNPVATESYGQVATNHQSDGTL AVPFKAQAQTGWVQNQGILPGMVWQDRDVYLQGPIWAKIPHTDGNFHPSPLMGGFGMKH PPPQILIKNTPVPADPPTAFNKDKLNSFITQYSTGQVSVEIEWELQKENSKRWNPEIQY TSNYYKSNNVEFAVNTEGVYSEPRPIGTRYLTRNL |
| AAV9/hu.14 K449R | 804 | MAADGYLPDWLEDNLSEGIREWWALKPGAPQPKANQQHQDNARGLVLPGYKYLGPGNGL DKGEPVNAADAAALEHDKAYDQQLKAGDNPYLKYNHADAEFQERLKEDTSFGGNLGRAV FQAKKRLLEPLGLVEEAAKTAPGKKRPVEQSPQEPDSSAGIGKSGAQPAKKRLNFGQTG DTESVPDPQPIGEPPAAPSGVGSLTMASGGGAPVADNNEGADGVGSSSGNWHCDSQWLG DRVITTSTRTWALPTYNNHLYKQISNSTSGGSSNDNAYFGYSTPWGYFDFNRFHCHFSP RDWQRLINNNWGFRPKRLNFKLFNIQVKEVTDNNGVKTIANNLTSTVQVFTDSDYQLPY VLGSAHEGCLPPFPADVEMIPQYGYLTLNDGSQAVGRSSFYCLEYFPSQMLRTGNNFQF SYEFENVPFHSSYAHSQSLDRLMNPLIDQYLYYLSRTINGSGQNQQTLKFSVAGPSNMA VQGRNYIPGPSYRQQRVSTTVTQNNNSEFAWPGASSWALNGRNSLMNPGPAMASHKEGE DRFFPLSGSLIFGKQGTGRDNVDADKVMITNEEEIKTTNPVATESYGQVATNHQSAQAQ AQTGWVQNQGILPGMVWQDRDVYLQGPIWAKIPHTDGNFHPSPLMGGFGMKHPPPQILI KNTPVPADPPTAFNKDKLNSFITQYSTGQVSVEIEWELQKENSKRWNPEIQYTSNYYKS NNVEFAVNTEGVYSEPRPIGTRYLTRNL |

TABLE 2-continued

Exemplary full length capsid sequences

| Description | SEQ ID NO: | Sequence Information |
|---|---|---|
| AAV9/hu.14 WT (amino acid) | 138 | MAADGYLPDWLEDNLSEGIREWWALKPGAPQPKANQQHQDNARGLVLPGYKYLGPGNGL DKGEPVNAADAAALEHDKAYDQQLKAGDNPYLKYNHADAEFQERLKEDTSFGGNLGRAV FQAKKRLLEPLGLVEEAAKTAPGKKRPVEQSPQEPDSSAGIGKSGAQPAKKRLNFGQTG DTESVPDPQPIGEPPAAPSGVGSLTMASGGGAPVADNNEGADGVGSSSGNWHCDSQWLG DRVITTSTRTWALPTYNNHLYKQISNSTSGGSSNDNAYFGYSTPWGYFDFNRFHCHFSP RDWQRLINNNWGFRPKRLNFKLFNIQVKEVTDNNGVKTIANNLTSTVQVFTDSDYQLPY VLGSAHEGCLPPFPADVEMIPQYGYLTLNDGSQAVGRSSFYCLEYFPSQMLRTGNNFQF SYEFENVPFHSSYAHSQSLDRLMNPLIDQYLYYLSKTINGSGQNQQTLKFSVAGPSNMA VQGRNYIPGPSYRQQRVSTTVTQNNNSEFAWPGASSWALNGRNSLMNPGPAMASHKEGE DRFFPLSGSLIFGKQGTGRDNVDADKVMITNEEEIKTTNPVATESYGQVATNHQSAQAQ AQTGWVQNQGILPGMVWQDRDVYLQGPIWAKIPHTDGNFHPSPLMGGFGMKHPPPQILI KNTPVPADPPTAFNKDKLNSFITQYSTGQVSVEIEWELQKENSKRWNPEIQYTSNYYKS NNVEFAVNTEGVYSEPRPIGTRYLTRNL |
| AAV9/hu.14 WT (DNA) | 137 | ATGGCTGCCGATGGTTATCTTCCAGATTGGCTCGAGGACAACCTTAGTGAAGGAATTCG CGAGTGGTGGGCTTTGAAACCTGGAGCCCCTCAACCCAAGGCAAATCAACAACATCAAG ACAACGCTCGAGGTCTTGTGCTTCCGGGTTACAAATACCTTGGACCCGGCAACGGACTC GACAAGGGGGAGCCGGTCAACGCAGCAGACGCGGCGGCCCTCGAGCACGACAAGGCCTA CGACCAGCAGCTCAAGGCCGGAGACAACCCGTACCTCAAGTACAACCACGCCGACGCCG AGTTCCAGGAGCGGCTCAAAGAAGATACGTCTTTTGGGGGCAACCTCGGGCGAGCAGTC TTCCAGGCCAAAAAGAGGCTTCTTGAACCTCTTGGTCTGGTTGAGGAAGCGGCTAAGAC GGCTCCTGGAAAGAAGAGGCCTGTAGAGCAGTCTCCTCAGGAACCGGACTCCTCCGCGG GTATTGGCAAATCGGGTGCACAGCCCGCTAAAAAGAGACTCAATTTCGGTCAGACTGGC GACACAGAGTCAGTCCCAGACCCTCAACCAATCGGAGAACCTCCCGCAGCCCCCTCAGG TGTGGGATCTCTTACAATGGCTTCAGGTGGTGGCGCACCAGTGGCAGACAATAACGAAG GTGCCGATGGAGTGGGTAGTTCCTCGGGAAATTGGCATTGCGATTCCCAATGGCTGGGG GACAGAGTCATCACCACCAGCACCCGAACCTGGGCCCTGCCCACCTACAACAATCACCT CTACAAGCAAATCTCCAACAGCACATCTGGAGGATCTTCAAATGACAACGCCTACTTCG GCTACAGCACCCCCTGGGGGTATTTTGACTTCAACAGATTCCACTGCCACTTCTCACCA CGTGACTGGCAGCGACTCATCAACAACAACTGGGGATTCCGGCCTAAGCGACTCAACTT CAAGCTCTTCAACATTCAGGTCAAGAGGTTACGGACAACAATGGAGTCAAGACCATCG CCAATAACCTTACCAGCACGGTCCAGGTCTTCACGGACTCAGACTATCAGCTCCCGTAC GTGCTCGGGTCGGCTCACGAGGGCTGCCTCCCGCCGTTCCCAGCGGACGTTTTCATGAT TCCTCAGTACGGGTATCTGACGCTTAATGATGGAAGCCAGGCCGTGGGTCGTTCGTCCT TTTACTGCCTGGAATATTTCCCGTCGCAAATGCTAAGAACGGGTAACAACTTCCAGTTC AGCTACGAGTTTGAGAACGTACCTTTCCATAGCAGCTACGCTCACAGCCAAAGCCTGGA CCGACTAATGAATCCACTCATCGACCAATACTTGTACTATCTCTCAAAGACTATTAACG GTTCTGGACAGAATCAACAAACGCTAAAATTCAGTGTGGCCGGACCCAGCAACATGGCT GTCCAGGGAAGAAACTACATACCTGGACCCAGCTACCGACAACAACGTGTCTCAACCAC TGTGACTCAAAACAACAACAGCGAATTTGCTTGGCCTGGAGCTTCTTCTTGGGCTCTCA ATGGACGTAATAGCTTGATGAATCCTGGACCTGCTATGGCCAGCCACAAGAAGGAGAG GACCGTTTCTTTCCTTTGTCTGGATCTTTAATTTTTGGCAAACAAGGAACTGGAAGAGA CAACGTGGATGCGGACAAAGTCATGATAACCAACGAAGAAGAAATTAAAACTACTAACC CGGTAGCAACGGAGTCCTATGGACAAGTGGCCACAAACCACCAGAGTGCCCAAGCACAG GCGCAGACCGGCTGGGTTCAAAACCAAGGAATACTTCCGGGTATGGTTTGGCAGGACAG AGATGTGTACCTGCAAGGACCCATTTGGGCCAAAATTCCTCACACGGACGGCAACTTTC ACCCTTCTCCGCTGATGGGAGGGTTTGGAATGAAGCACCCGCCTCCTCAGATCCTCATC AAAAACACACCTGTACCTGCCGGATCCTCCAACGGCCTTCAACAAGGACAAGCTGAACTC TTTCATCACCCAGTATTCTACTGGCCAAGTCAGCGTGGAGATCGAGTGGGAGCTGCAGA AGGAAAACAGCAAGCGCTGGAACCCGGAGATCCAGTACACTTCCAACTATTACAAGTCT AATAATGTTGAATTTGCTGTTAATACTGAAGGTGTATATAGTGAACCCCGCCCCATTGG CACCAGATACCTGACTCGTAATCTGTAA |

In some embodiments, the AAV capsid variant comprises the amino acid sequence of SEQ ID NO: 138 or an amino acid sequence substantially identical (e.g., having at least 70%, 75%, 80%, 85%, 90%, 92%, 95%, 97%, 98%, or 99% sequence identity) thereto. In some embodiments the AAV capsid variant comprises an amino acid sequence comprising at least one, two, or three modifications but no more than 30, 20, or 10 modifications, e.g., substitutions, relative to the amino acid sequence of SEQ ID NO: 138. In some embodiments, the AAV capsid variant comprises an amino acid sequence encoded by the nucleotide sequence of SEQ ID NO: 137 or a nucleotide sequence substantially identical (e.g., having at least 70%, 75%, 80%, 85%, 90%, 92%, 95%, 97%, 98%, or 99% sequence identity) thereto. In some embodiments, the nucleotide sequence encoding the AAV capsid variant comprises the nucleotide sequence of SEQ ID NO: 137 or a nucleotide sequence substantially identical (e.g., having at least 70%, 75%, 80%, 85%, 90%, 92%, 95%, 97%, 98%, or 99% sequence identity) thereto. In some embodiments, the AAV capsid variant comprises substitution at position K449, e.g., a K449R substitution, numbered according to SEQ ID NO: 138.

In some embodiments, the AAV capsid variant comprises a peptide comprising the amino acid sequence of TLAVPFK (SEQ ID NO: 1262). In some embodiments, the peptide is present immediately subsequent to position 588, relative to a reference sequence numbered according to SEQ ID NO: 138. In some embodiments, the capsid polypeptide comprises the amino acid substitutions of A587D and Q588G, numbered according to SEQ ID NO: 138.

In some embodiments, the AAV capsid variant comprises the amino acid substitution of K449R, numbered according to SEQ ID NO: 138; and a peptide comprising the amino acid sequence of TLAVPFK (SEQ ID NO: 1262), wherein the peptide is present immediately subsequent to position 588, relative to a reference sequence numbered according to SEQ ID NO: 138.

In some embodiments, the AAV capsid variant comprises the amino acid substitution of K449R, numbered according to SEQ ID NO: 138; an peptide comprising the amino acid sequence of TLAVPFK (SEQ ID NO: 1262), wherein the insert is present immediately subsequent to position 588, relative to a reference sequence numbered according to SEQ ID NO: 138; and the amino acid substitutions of A587D and Q588G, numbered according to SEQ ID NO: 138.

In some embodiments, the AAV capsid variant comprises a peptide comprising the amino acid sequence of TLAVPFK (SEQ ID NO: 1262), wherein the insert is present immediately subsequent to position 588, relative to a reference sequence numbered according to SEQ ID NO: 138; and the amino acid substitutions of A587D and Q588G, numbered according to SEQ ID NO: 138.

In some embodiments, the AAV capsid variant comprises the amino acid sequence of SEQ ID NO: 804 or an amino acid sequence substantially identical (e.g., having at least 70%, 75%, 80%, 85%, 90%, 92%, 95%, 97%, 98%, or 99% sequence identity) thereto. In some embodiments the AAV capsid variant comprises an amino acid sequence comprising at least one, two, or three modifications but no more than 30, 20, or 10 modifications, e.g., substitutions, relative to the amino acid sequence of SEQ ID NO: 804, optionally wherein position 449 is not R.

In some embodiments, the AAV capsid variant comprises the amino acid sequence of SEQ ID NO: 804 or an amino acid sequence substantially identical (e.g., having at least 70%, 75%, 80%, 85%, 90%, 92%, 95%, 97%, 98%, or 99% sequence identity) thereto. In some embodiments the AAV capsid variant comprises an amino acid sequence comprising at least one, two, or three modifications but no more than 30, 20, or 10 modifications, e.g., substitutions, relative to the amino acid sequence of SEQ ID NO: 138. In some embodiments, the AAV capsid variant comprises an amino acid sequence encoded by the nucleotide sequence of SEQ ID NO: 137 or a nucleotide sequence substantially identical (e.g., having at least 70%, 75%, 80%, 85%, 90%, 92%, 95%, 97%, 98%, or 99% sequence identity) thereto.

In some embodiments, the AAV capsid variant comprises the amino acid sequence of SEQ ID NO: 804 or an amino acid sequence substantially identical (e.g., having at least 70%, 75%, 80%, 85%, 90%, 92%, 95%, 97%, 98%, or 99% sequence identity) thereto. In some embodiments the AAV capsid variant comprises an amino acid sequence comprising at least one, two, or three modifications but no more than 30, 20, or 10 modifications, e.g., substitutions, relative to the amino acid sequence of SEQ ID NO: 804.

In some embodiments, an AAV particle described herein comprises an AAV capsid variant. In some embodiments, the AAV capsid variant comprises a peptide sequence as described in Table 3. In some embodiments, the AAV capsid variant comprises a peptide sequence as described in WO2021/230987, the contents of which are hereby incorporated by reference in its entirety.

TABLE 3

Exemplary Peptide Sequences

| Peptide | SEQ ID NO: | Amino Acid Sequence | SEQ ID NO: | Nucleotide Sequence |
| --- | --- | --- | --- | --- |
| 1 | 3648 | PLNGAVHLY | 3660 | ccgcttaatggtgccgtccatctttat |
| 2 | 3649 | RDSPKGW | 3661 | cgtgattctccgaagggttggca |
| 3 | 3650 | YSTDVRM | 3662 | tattctacggatgtgaggatgca |
| 4 | 3651 | IVMNSLK | 3663 | attgttatgaattcgttgaaggc |
| 5 | 3652 | RESPRGL | 3664 | cgggagagtcctcgtgggctgca |
| 6 | 3653 | SFNDTRA | 3665 | agttttaatgatactagggctca |
| 7 | 3654 | GGTLAVVSL | 3666 | ggtggtacgttggccgtcgtgtcgctt |
| 8 | 3655 | YGLPKGP | 3667 | tatgggttgccgaagggtcct |
| 9 | 3656 | STGTLRL | 3668 | tcgactgggacgcttcggctt |
| 10 | 3657 | YSTDERM | 3669 | tattcgacggatgagaggatg |
| 11 | 3658 | YSTDERK | 3670 | tattcgacggatgagaggaag |
| 12 | 3659 | YVSSVKM | 3671 | tatgtttcgtctgttaagatg |

In some embodiments, the capsid polypeptide, comprises the amino acid sequence of SEQ ID NO: 803 or an amino acid sequence substantially identical (e.g., having at least 70%, 75%, 80%, 85%, 90%, 92%, 95%, 97%, 98%, or 99% sequence identity) thereto. In some embodiments the AAV capsid variant comprises an amino acid sequence comprising at least one, two, or three modifications but no more than 30, 20, or 10 modifications, e.g., substitutions, relative to the amino acid sequence of SEQ ID NO: 803.

In some embodiments, the AAV capsid variant comprises the amino acid sequence of SEQ ID NO: 138 or an amino acid sequence substantially identical (e.g., having at least In some embodiments, the AAV capsid variant comprises at least 3, 4, 5, 6, 7, 8, or 9 consecutive amino acids from the amino acid sequence of any of SEQ ID NO: 3648-3659. In some embodiments, the AAV capsid variant comprises at least 3, 4, 5, 6, 7, 8, or 9 consecutive amino acids from the amino acid sequence of any of SEQ ID NO: 1725-1775, 1785, 1798, or 1819. In some embodiments, the amino acid sequence is present in loop VIII. In some embodiments, the amino acid sequence is present immediately subsequent to position 586, 588, or 589, relative to a reference sequence numbered according to the amino acid sequence of SEQ ID NO: 138.

In some embodiments, the AAV capsid variant comprises an amino acid sequence comprising at least one, two, or three but no more than four modifications, e.g., substitutions, relative to the amino acid sequence of any of SEQ ID NO: 3648-3659. In some embodiments, the AAV capsid variant comprises an amino acid sequence comprising at least one, two, or three but no more than four modifications, e.g., substitutions, relative to the amino acid sequence of any of SEQ ID NO: 1725-1775, 1785, 1798, or 1819. In some embodiments, the amino acid sequence is present in loop VIII. In some embodiments, the amino acid sequence is present immediately subsequent to position 586, 588, or 589, relative to a reference sequence numbered according to the amino acid sequence of SEQ ID NO: 138. In some embodiments, the amino acid sequence replaces positions 587 and 588, numbered according to SEQ ID NO: 138. In some embodiments, the amino acid sequence is present immediately subsequent to position 586 and replaces positions 587 and 588, numbered according to SEQ ID NO: 138.

In some embodiments, the AAV capsid variant comprises the amino acid sequence of PLNGAVHLY (SEQ ID NO: 3648), or an amino acid sequence having at least one, two, or three but no more than four modifications, e.g., substitutions, relative to the amino acid sequence of PLNGAVHLY (SEQ ID NO: 3648), optionally wherein position 7 is H.

In some embodiments, the AAV capsid variant comprises the amino acid sequence of IVMNSLK (SEQ ID NO: 3651), or an amino acid sequence having at least one, two, or three modifications but no more than four modifications, e.g., substitutions, relative to the amino acid sequence of IVMNSLK (SEQ ID NO: 3651).

In some embodiments, the AAV capsid variant comprises the amino acid sequence of any of SEQ ID NO: 1725-3622. In some embodiments, the AAV capsid variant comprises the amino acid sequence of any of SEQ ID NO: 3648-3659. In some embodiments, the amino acid sequence is present in loop VIII of an AAV capsid variant described herein. In some embodiments, the amino acid sequence is present immediately subsequent to position 586, relative to a reference sequence numbered according to the amino acid sequence of SEQ ID NO: 138. In some embodiments, the amino acid sequence is present immediately subsequent to position 588, relative to a reference sequence numbered according to the amino acid sequence of SEQ ID NO: 138. In some embodiments, the amino acid sequence is present immediately subsequent to position 589, relative to a reference sequence numbered according to the amino acid sequence of SEQ ID NO: 138.

In some embodiments, the AAV capsid variant (e.g., an AAV capsid variant described herein), comprises an amino acid sequence encoded by the nucleotide sequence of any one of SEQ ID NOs: 3660-3671, or a nucleotide sequence substantially identical (e.g., having at least 70%, 75%, 80%, 85%, 90%, 92%, 95%, 97%, 98%, or 99% sequence identity) thereto. In some embodiments, the AAV capsid, e.g., an AAV capsid variant described herein, comprises an amino acid sequence encoded by a nucleotide sequence comprising at least one, two, three, four, five, six, or seven modifications but no more than ten modifications of the nucleotide sequences of any of SEQ ID NOS: 3660-3671.

In some embodiments, the nucleotide sequence encoding the AAV capsid variant (e.g., an AAV capsid variant described herein), comprises the nucleotide sequence of any one of SEQ ID NOs: 3660-3671, or a nucleotide sequence substantially identical (e.g., having at least 70%, 75%, 80%, 85%, 90%, 92%, 95%, 97%, 98%, or 99% sequence identity) thereto. In some embodiments, nucleic acid sequence encoding the AAV capsid variant, e.g., an AAV capsid variant described herein, comprises a nucleotide sequence comprising at least one, two, three, four, five, six, or seven modifications but no more than ten modifications of the nucleotide sequences of any of SEQ ID NOs: 3660-3671.

In some embodiments, the nucleotide sequence encoding the AAV capsid variant (e.g., an AAV capsid variant described herein), comprises the nucleotide sequence of SEQ ID NO: 3660, or a nucleotide sequence substantially identical (e.g., having at least 70%, 75%, 80%, 85%, 90%, 92%, 95%, 97%, 98%, or 99% sequence identity) thereto. In some embodiments, the nucleic acid sequence encoding the AAV capsid variant comprises a nucleotide sequence comprising at least one, two, three, four, five, six, or seven modifications but no more than ten modifications of the nucleotide sequences of SEQ ID NO: 3660.

In some embodiments, the nucleotide sequence encoding the AAV capsid variant (e.g., an AAV capsid variant described herein), comprises the nucleotide sequence of SEQ ID NO: 3663, or a nucleotide sequence substantially identical (e.g., having at least 70%, 75%, 80%, 85%, 90%, 92%, 95%, 97%, 98%, or 99% sequence identity) thereto. In some embodiments, the nucleic acid sequence encoding the AAV capsid variant comprises a nucleotide sequence comprising at least one, two, three, four, five, six, or seven modifications but no more than ten modifications of the nucleotide sequences of SEQ ID NO: 3663.

In some embodiments, the AAV capsid variant comprises an amino acid residue other than "A" at position 587 and/or an amino acid residue other than "Q" at position 588, numbered according to SEQ ID NO: 138. In some embodiments, the AAV capsid variant comprises the amino acid P at position 587 and the amino acid L at position 588, numbered according to SEQ ID NO: 138. In some embodiments, the AAV capsid variant comprises the amino acid G at position 587 and the amino acid G at position 588, numbered according to SEQ ID NO: 138. In some embodiments, the AAV capsid variant comprises the substitutions A587P and Q588L, numbered according to SEQ ID NO: 138. In some embodiments, the AAV capsid variant comprises the substitutions A587G and Q588G, numbered according to SEQ ID NO: 138.

In some embodiments, the AAV capsid variant comprises the amino acid sequence of PLNGAVHLY (SEQ ID NO: 3648), wherein the amino acid sequence of PLNGAVHLY (SEQ ID NO: 3648) is present immediately subsequent to position 586, numbered according to the amino acid sequence of SEQ ID NO: 138. In some embodiments, the AAV capsid variant comprises the amino acid sequence of PLNGAVHLY (SEQ ID NO: 3648) wherein the amino acid sequence of PLNGAVHLY (SEQ ID NO: 3648) replaces positions 587 and 588, numbered according to the amino acid sequence of SEQ ID NO: 138. In some embodiments, the AAV capsid variant comprises the amino acid sequence of PLNGAVHLY (SEQ ID NO: 3648) wherein the amino acid sequence of PLNGAVHLY (SEQ ID NO: 3648) is present immediately subsequent to position 586 and replaces positions 587 and 588, numbered according to SEQ ID NO: 138. In some embodiments, the AAV capsid variant comprises the amino acid sequence of PLNGAVHLY (SEQ ID NO: 3648), wherein the amino acid sequence of PLNGAVHLY (SEQ ID NO: 3648) is present immediately subsequent to position 586, numbered according to the amino acid sequence of SEQ ID NO: 138, and further comprises a deletion of the amino acids AQ at positions 587-588, numbered according to SEQ ID NO: 138.

In some embodiments, the AAV capsid variant comprises the amino acid P at position 587, the amino acid L at position 588, and further comprises the amino acid sequence NGAVHLY (SEQ ID NO: 800), which is present immediately subsequent to position 588, numbered according to SEQ ID NO: 138.

In some embodiments, the AAV capsid variant comprises the amino acid sequence of GGTLAVVSL (SEQ ID NO: 3654), wherein the amino acid sequence of GGTLAVVSL (SEQ ID NO: 3654) is present immediately subsequent to position 586, numbered according to the amino acid sequence of SEQ ID NO: 138. In some embodiments, the AAV capsid variant comprises the amino acid sequence of GGTLAVVSL (SEQ ID NO: 3654), wherein the amino acid sequence of GGTLAVVSL (SEQ ID NO: 3654) replaces positions 587 and 588, numbered according to the amino acid sequence of SEQ ID NO: 138. In some embodiments, the AAV capsid variant comprises the amino acid sequence of GGTLAVVSL (SEQ ID NO: 3654), wherein the amino acid sequence of GGTLAVVSL (SEQ ID NO: 3654) is present immediately subsequent to position 586 and replaces positions 587 and 588, numbered according to SEQ ID NO: 138. In some embodiments, the AAV capsid variant comprises the amino acid sequence of GGTLAVVSL (SEQ ID NO: 3654), wherein the amino acid sequence of GGTLAVVSL (SEQ ID NO: 3654) is present immediately subsequent to position 586, numbered according to the amino acid sequence of SEQ ID NO: 138, and further comprises a deletion of the amino acids AQ at positions 587-588, numbered according to SEQ ID NO: 138.

In some embodiments, the AAV capsid variant comprises the amino acid G at position 587, the amino acid G at position 588, and further comprises the amino acid sequence TLAVVSL (SEQ ID NO: 801), which is present immediately subsequent to position 588, numbered according to SEQ ID NO: 138.

In some embodiments, the AAV capsid variant comprises the amino acid sequence of IVMNSLK (SEQ ID NO: 3651), wherein the amino acid sequence of IVMNSLK (SEQ ID NO: 3651) is present immediately subsequent to position 588, relative to a reference sequence numbered according to the amino acid sequence of SEQ ID NO: 138.

In some embodiments, the AAV capsid variant comprises the amino acid sequence of any of SEQ ID NOs: 3649, 3650, 3652, 3653, or 3655-3659, wherein the amino acid sequence of any of the aforesaid sequences is present immediately subsequent to position 589, relative to a reference sequence numbered according to the amino acid sequence of SEQ ID NO: 138.

In some embodiments, the AAV capsid variant further comprises a substitution at position K449, e.g., a K449R substitution, numbered according to SEQ ID NO: 138. In some embodiments, the AAV capsid variant further comprises a modification, e.g., an insertion, substitution, and/or deletion in loop I, II, IV, and/or VI.

In some embodiments, the AAV capsid variant further comprises an amino acid sequence having at least one, two or three modifications but not more than 30, 20 or 10 modifications of the amino acid sequence of SEQ ID NO: 138. In some embodiments, the AAV capsid variant further comprises the amino acid sequence of SEQ ID NO: 138, or an amino acid sequence with at least 80% (e.g., at least about 85, 90, 95, 96, 97, 98, or 99%) sequence identity thereto. In some embodiments, the AAV capsid variant further comprises an amino acid sequence encoded by the nucleotide sequence of SEQ ID NO: 137, or a sequence with at least 80% (e.g., at least about 85, 90, 95, 96, 97, 98, or 99%) sequence identity thereto.

In some embodiments, an AAV capsid variant of the present disclosure comprises an amino acid sequence as described herein, e.g. an amino acid sequence of an AAV capsid variant chosen from TTD-001, TTD-002, TTD-003, TTD-004, TTD-005, TTD-006, TTD-007, TTD-008, TTD-009, TTD-010, TTD-011, or TTD-012, e.g., as described in Tables 6 and 7. In some embodiments, the AAV capsid variant comprises a sequence as described in WO2021/230987, the contents of which are hereby incorporated by reference in its entirety.

In some embodiments, an AAV capsid variant comprises a VP1, VP2, and/or VP3 protein comprising an amino acid sequence described herein, e.g., an amino acid sequence of an AAV capsid variant chosen from TTD-001, TTD-002, TTD-003, TTD-004, TTD-005, TTD-006, TTD-007, TTD-008, TTD-009, TTD-010, TTD-011, or TTD-012, e.g., as described in Tables 6 and 7.

In some embodiments, an AAV capsid variant described herein comprises an amino acid sequence encoded by a nucleotide sequence as described herein, e.g., a nucleotide sequence of an AAV capsid variant chosen from TTD-001, TTD-002, TTD-003, TTD-004, TTD-005, TTD-006, TTD-007, TTD-008, TTD-009, TTD-010, TTD-011, or TTD-012, e.g., as described in Tables 6 and 9.

In some embodiments, a polynucleotide encoding an AAV capsid variant of the present disclosure comprises a nucleotide sequence described herein, e.g., a nucleotide sequence of an AAV capsid variant chosen from TTD-001, TTD-002, TTD-003, TTD-004, TTD-005, TTD-006, TTD-007, TTD-008, TTD-009, TTD-010, TTD-011, or TTD-012, e.g., as described in Tables 6 and 9.

In some embodiments, insertion of a nucleic acid sequence, targeting nucleic acid sequence, or a peptide into a parent AAV sequence generates the non-limiting exemplary full length capsid sequences, e.g., an AAV capsid variant, as described in Tables 6, 7, and 9.

TABLE 6

Exemplary full length capsid sequences

| Name | VP1 DNA SEQ ID NO: | VP1 Amino Acid SEQ ID NO: | Peptide SEQ ID NO: | DNA sequence encoding Peptide SEQ ID NO: |
|---|---|---|---|---|
| TTD-001 | 3623 | 3636 | 3648 | 3660 |
| TTD-002 | 3624 or 3625 | 3637 | 3649 | 3661 |
| TTD-003 | 3626 | 3638 | 3650 | 3662 |
| TTD-004 | 3627 | 3639 | 3651 | 3663 |
| TTD-005 | 3628 | 3640 | 3652 | 3664 |
| TTD-006 | 3629 | 3641 | 3653 | 3665 |
| TTD-007 | 3630 | 3642 | 3654 | 3666 |
| TTD-008 | 3631 | 3643 | 3655 | 3667 |

TABLE 6-continued

Exemplary full length capsid sequences

| Name | VP1 DNA SEQ ID NO: | VP1 Amino Acid SEQ ID NO: | Peptide SEQ ID NO: | DNA sequence encoding Peptide SEQ ID NO: |
|---|---|---|---|---|
| TTD-009 | 3632 | 3644 | 3656 | 3668 |
| TTD-010 | 3633 | 3645 | 3657 | 3669 |
| TTD-011 | 3634 | 3646 | 3658 | 3670 |
| TTD-012 | 3635 | 3647 | 3659 | 3671 |

TABLE 7

Exemplary full length capsid amino acid sequences

| Name and Annotation | SEQ ID NO: | Amino Acid Sequence |
|---|---|---|
| TTD-001 9 mer peptide underlined, starts at position 587 (immediately subsequent to position 586); 743 aa | 3636 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVFMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSPLNGAVHL YAQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-002 7 mer peptide underlined, starts at position 590 (immediately subsequent to position 589); 743 aa | 3637 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVFMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQARDSPK GWQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-003 7 mer peptide underlined, starts at position 590 (immediately subsequent to position 589); 743 aa | 3638 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVFMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQAYSTDV RMQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-004 7 mer peptide underlined, starts at position 589 (immediately subsequent to position 588); 743 aa | 3639 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVFMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQIVMNSL KAQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |

TABLE 7-continued

Exemplary full length capsid amino acid sequences

| Name and Annotation | SEQ ID NO: | Amino Acid Sequence |
|---|---|---|
| TTD-005 7 mer peptide underlined, starts at position 590 (immediately subsequent to position 589); 743 aa | 3640 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVFMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQARESPR GLQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-006 7 mer peptide underlined, starts at position 590 (immediately subsequent to 589); 743 aa | 3641 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVEMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQASFNDT RAQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-007 9 mer peptide underlined, starts at position 587 (immediately subsequent to position 586); 743 aa | 3642 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVEMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSGGTLAVVS LAQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-008 7 mer peptide underlined, starts at position 590 (immediately subsequent to 589); 743 aa | 3643 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVFMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQAYGLPK GPQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-009 7 mer peptide underlined, starts at position 590 (immediately subsequent to 589); 743 aa | 3644 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVEMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQASTGTL RLQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |

TABLE 7-continued

Exemplary full length capsid amino acid sequences

| Name and Annotation | SEQ ID NO: | Amino Acid Sequence |
| --- | --- | --- |
| TTD-010 7 mer peptide underlined, starts at position 590 (immediately subsequent to 589); 743 aa | 3645 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVEMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQAYSTDE RMQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-011 7 mer peptide underlined, starts at position 590 (immediately subsequent to 589); 743 aa | 3646 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVEMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQAYSTDE RKQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |
| TTD-012 7 mer peptide underlined, starts at position 590 (immediately subsequent to 589); 743 aa | 3647 | MAADGYLPDWLEDNLSEGIREWWALKPGAPQPKANQQHQDNARGLVLPGYKYLG PGNGLDKGEPVNAADAAALEHDKAYDQQLKAGDNPYLKYNHADAEFQERLKEDT SFGGNLGRAVFQAKKRLLEPLGLVEEAAKTAPGKKRPVEQSPQEPDSSAGIGKS GAQPAKKRLNFGQTGDTESVPDPQPIGEPPAAPSGVGSLTMASGGGAPVADNNE GADGVGSSSGNWHCDSQWLGDRVITTSTRTWALPTYNNHLYKQISNSTSGGSSN DNAYFGYSTPWGYFDFNRFHCHFSPRDWQRLINNNWGFRPKRLNFKLFNIQVKE VTDNNGVKTIANNLTSTVQVFTDSDYQLPYVLGSAHEGCLPPFPADVEMIPQYG YLTLNDGSQAVGRSSFYCLEYFPSQMLRTGNNFQFSYEFENVPFHSSYAHSQSL DRLMNPLIDQYLYYLSKTINGSGQNQQTLKFSVAGPSNMAVQGRNYIPGPSYRQ QRVSTTVTQNNNSEFAWPGASSWALNGRNSLMNPGPAMASHKEGEDRFFPLSGS LIFGKQGTGRDNVDADKVMITNEEEIKTTNPVATESYGQVATNHQSAQAYVSSV KMQAQTGWVQNQGILPGMVWQDRDVYLQGPIWAKIPHTDGNFHPSPLMGGFGMK HPPPQILIKNTPVPADPPTAFNKDKLNSFITQYSTGQVSVEIEWELQKENSKRW NPEIQYTSNYYKSNNVEFAVNTEGVYSEPRPIGTRYLTRNL |

TABLE 9

Exemplary full length capsid nucleic acid sequences

| Name and Annotation | SEQ ID NO: | NT Sequence |
| --- | --- | --- |
| TTD-001 9 mer peptide underlined | 3623 | atggctgccgatggttatcttccagattggctcgaggacaaccttagtgaaggaattcgcg agtggtgggctttgaaacctggagcccctcaacccaaggcaaatcaacaacatcaagacaa cgctcgaggtcttgtgcttccggggttacaaatacctggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttggggcaacctcgggcgagcagtcttccaggccaaa aagaggcttcttgaacctcttggtctggttggtgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccctcaggtgtgggatctcttacaatgg cttcaggtggtggcgcaccagtggcagacaataacgaaggtgccgatggagtgggtagttc ctcgggaaattggcattgcgattcccaatggctgggggacagagtcatcaccaccagcact cgaacctgggccctgcccacctacaacaatcacctctacaagcaaatctccaacagcacat ctggaggatcttcaaatgacaacgcctacttcggctacagcacccctgggggtattttga cttcaacagattccactgccacttctcaccacgtgactggcagcgactcatcaacaacaac tggggattccggcctaagcgactcaacttcaagctcttcaacattcaggtcaaagaggtta cggacaacaatggagtcaagaccatcgccaataaccttaccagcacggtccaggtcttcac ggactcagactatcagctcccgtacgtgctcgggtcggctcacgagggctgcctccccgcg ttcccagcggacgttttcatgattcctcagtacgggtatctgacgcttaatgatggaagcc aggccgtgggtcgttcgtccttttactgcctggaatatttcccgtcgcaaatgctaagaac |

TABLE 9-continued

Exemplary full length capsid nucleic acid sequences

| Name and Annotation | SEQ ID NO: | NT Sequence |
|---|---|---|
| | | gggtaacaacttccagttcagctacgagtttgagaacgtacctttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccagggaagaaactacatacctggacccagctaccgacaacaacgt gtctcaaccactgtgactcaaaacaacaacagcgaatttgcttggcctggagcttcttctt gggctctcaatggacgtaatagcttgatgaatcctggacctgctatggccagccacaaaga aggagaggaccgtttctttcctttgtctggatctttaattttggcaaacaaggaactgga agagacaacgtggatgcggacaaagtcatgataaccaacgaagaagaaattaaaactacta acccggtagcaacggagtcctatggacaagtggccacaaaccaccagagtccgcttaatgg tgccgtccatctttatgctcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtggaacccggagatccagtacacttccaacta ttacaagtctaataatgttgaatttgctgttaatactgaaggtgtatatagtgaaccccgc cccattggcaccagatacctgactcgtaatctgtaa |
| TTD-002 7 mer peptide underlined | 3624 | atggctgccgatggttatcttccagattggctcgaggacaaccttagtgaaggaattcgcg agtggtgggctttgaaacttggagcccctcaacccaaggcaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtctttggggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccctcaggtgtgggatctcttacaatgg cttcaggtggtggcgcaccagtggcagacaataacgaaggtgccgatggagtgggtagttc ctcgggaaattggcattgcgattcccaatggctggggacagagtcatcaccaccagcacc cgaacctgggccctgcccacctacaacaatcacctctacaagcaaatctccaacagcacat ctggaggatcttcaaatgacaacgcctacttcggctacagcacccctgggggtatttga cttcaacagattccactgccacttctcaccacgtgactggcagcgactcatcaacaacaac tgggattccggcctaagcgactcaacttcaagctcttcaacattcaggtcaaagaggtta cggacaacaatggagtcaagaccatcgccaataaccttaccagcacggtccaggtcttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtccttttactgcctggaatatttcccgtcgcaaatgctaagaac gggtaacaacttccagttcagctacgagtttgagaacgtacctttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccagggaagaaactacatacctggacccagctaccgacaacaacgt gtctcaaccactgtgactcaaaacaacaacagcgaatttgcttggcctggagcttcttctt gggctctcaatggacgtaatagcttgatgaatcctggacctgctatggccagccacaaaga aggagaggaccgtttctttcctttgtctggatctttaattttggcaaacaaggaactgga agagacaacgtggatgcggacaaagtcatgataaccaacgaagaagaaattaaaactacta acccggtagcaacggagtcctatggacaagtggccacaaaccaccagagtgcacaggctcg tgattctccgaagggttggcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtggaacccggagatccagtacacttccaacta ttacaagtctaataatgttgaatttgctgttaatactgaaggtgtatatagtgaaccccgc cccattggcaccagatacctgactcgtaatctgtaa |
| | 3625 | atggctgccgatggttatcttccagattggctcgaggacaaccttagtgaaggaattcgcg agtggtgggctttgaaacttggagcccctcaacccaaggcaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtctttggggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccctcaggtgtgggatctcttacaatgg cttcaggtggtggcgcaccagtggcagacaataacgaaggtgccgatggagtgggtagttc ctcgggaaattggcattgcgattcccaatggctggggacagagtcatcaccaccagcacc cgaacctgggccctgcccacctacaacaatcacctctacaagcaaatctccaacagcacat ctggaggatcttcaaatgacaacgcctacttcggctacagcacccctgggggtatttga cttcaacagattccactgccacttctcaccacgtgactggcagcgactcatcaacaacaac tgggattccggcctaagcgactcaacttcaagctcttcaacattcaggtcaaagaggtta cggacaacaatggagtcaagaccatcgccaataaccttaccagcacggtccaggtcttcac ggactcagactatcagctcccgtacgtgctcgggtcggctcacgagggctgcctcccgccg ttcccagcggacgttttcatgattcctcagtacgggtatctgacgcttaatgatggaagcc |

TABLE 9-continued

Exemplary full length capsid nucleic acid sequences

| Name and Annotation | SEQ ID NO: | NT Sequence |
|---|---|---|
| | | aggccgtgggtcgttcgtccttttactgcctggaatatttcccgtcgcaaatgctaagaac<br>gggtaacaacttccagttcagctacgagtttgagaacgtacctttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccagggaagaaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatctttaattttttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcacaggctcg<br>tgattctccgaagggttggcaggcgcagaccggctgggttcaaaaccaaggaatacttccg<br>ggtatggtttggcaggacagagatgtgtacctgcaaggaccccatttgggccaaaattcctc<br>acacggacggcaactttcacccttctccgctgatgggagggtttggaatgaagcacccgcc<br>tcctcagatcctcatcaaaaacacacctgtacctgcggatcctccaacgccttcaacaag<br>gacaagctgaactctttcatcacccagtattctactggccaagtcagcgtggagatcgagt<br>gggagctgcagaaggaaaacagcaagcgctggaacccggagatccagtacacttccaacta<br>ttacaagtctaataatgttgaatttgctgttaatactgaaggtgtatatagtgaaccccgc<br>cccattggcaccagatacctgactcgtaatctgtaa |
| TTD-003<br>7 mer peptide underlined | 3626 | atggctgccgatggttatcttccagattggctcgaggacaaccttagtgaaggaattcgcg<br>agtggtgggctttgaaacctggagcccctcaacccaaggcaaatcaacaacatcaagacaa<br>cgctcgaggtcttgtgcttccgggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtcttttgggggcaacctcgggcgagcagtcttccaggccaaa<br>agaggcttcttgaacctcttggtctggttgaggaagcggctaagacggctcctggaaaga<br>gaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctggggacagagtcatcaccaccagcacc<br>cgaacctgggccctgcccacctacaacaatcacctctacaagcaaatctccaacagcacat<br>ctggaggatcttcaaatgacaacgcctacttcggctacagcacccccctgggggtattttga<br>cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgttttcatgattcctcagtacgggtatctgacgcttaatgatgaagcc<br>aggccgtgggtcgttcgtccttttactgcctggaatatttcccgtcgcaaatgctaagaac<br>gggtaacaacttccagttcagctacgagtttgagaacgtacctttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccagggaagaaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatctttaattttttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcacaggctta<br>ttctacggatgtgaggatgcaggcgcagaccggctgggttcaaaaccaaggaatacttccg<br>ggtatggtttggcaggacagagatgtgtacctgcaaggaccccatttgggccaaaattcctc<br>acacggacggcaactttcacccttctccgctgatgggagggtttggaatgaagcacccgcc<br>tcctcagatcctcatcaaaaacacacctgtacctgcCgatcctccaacgccttcaacaag<br>gacaagctgaactctttcatcacccagtattctactggccaagtcagcgtggagatcgagt<br>gggagctgcagaaggaaaacagcaagcgGtggaacccggagatccagtacacttccaacta<br>ttacaagtctaataatgttgaatttgctgttaatactgaaggtgtatatagtgaaccccgc<br>cccattggcaccagatacctgactcgtaatctgtaa |
| TTD-004<br>7 mer peptide underlined | 3627 | atggctgccgatggttatcttccagattggctcgaggacaaccttagtgaaggaattcgcg<br>agtggtgggctttgaaacctggagcccctcaacccaaggcaaatcaacaacatcaagacaa<br>cgctcgaggtcttgtgcttccgggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtcttttgggggcaacctcgggcgagcagtcttccaggccaaa<br>agaggcttcttgaacctcttggtctggttgaggaagcggctaagacggctcctggaaaga<br>gaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctggggacagagtcatcaccaccagcacc<br>cgaacctgggccctgcccacctacaacaatcacctctacaagcaaatctccaacagcacat<br>ctggaggatcttcaaatgacaacgcctacttcggctacagcacccccctgggggtattttga<br>cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg |

TABLE 9-continued

Exemplary full length capsid nucleic acid sequences

| Name and Annotation | SEQ ID NO: | NT Sequence |
|---|---|---|
| | | ttcccagcggacgttttcatgattcctcagtacgggtatctgacgcttaatgatggaagcc<br>aggccgtgggtcgttcgtccttttactgcctggaatatttcccgtcgcaaatgctaagaac<br>gggtaacaacttccagttcagctacgagtttgagaacgtacctttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccagggaagaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatctttaattttttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcacagattgt<br>tatgaattcgttgaaggctcaggcgcagaccggctgggttcaaaaccaaggaatacttccg<br>ggtatggtttggcaggacagagatgtgtacctgcaaggacccatttgggccaaaattcctc<br>acacggacggcaactttcacccttctccgctgatgggagggtttggaatgaagcacccgcc<br>tcctcagatcctcatcaaaaacacacctgtacctgcCgatcctccaacggccttcaacaag<br>gacaagctgaactctttcatcacccagtattctactggccaagtcagcgtggagatcgagt<br>gggagctgcagaaggaaaacagcaagcgGtggaacccggagatccagtacacttccaacta<br>ttacaagtctaataatgttgaatttgctgttaatactgaaggtgtatatagtgaaccccgc<br>cccattggcaccagatacctgactcgtaatctgtaa |
| TTD-005<br>7 mer peptide underlined | 3628 | atggctgccgatggttatcttccagattggctcgaggacaaccttagtgaaggaattcgcg<br>agtggtgggctttgaaacctggagcccctcaacccaaggcaaatcaacaacatcaagacaa<br>cgctcgaggtcttgtgcttccgggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtctttggggggcaacctcggcgagcagtcttccaggccaaa<br>aagaggcttcttgaacctcttggtctggttgaggaagcggctaagacggctcctggaaaga<br>agaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctggggacagagtcatcaccaccagcacc<br>cgaacctgggccctgcccacctacaacaatcacctctacaagcaaatctccaacagcacat<br>ctggaggatcttcaaatgacaacgcctacttcggctacagcaccccctgggggtattttga<br>cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgttttcatgattcctcagtacgggtatctgacgcttaatgatggaagcc<br>aggccgtgggtcgttcgtccttttactgcctggaatatttcccgtcgcaaatgctaagaac<br>gggtaacaacttccagttcagctacgagtttgagaacgtacctttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccagggaagaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatctttaattttttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcacaggctcg<br>ggagagtcctcgtgggctgcaggcgcagaccggctgggttcaaaaccaaggaatacttccg<br>ggtatggtttggcaggacagagatgtgtacctgcaaggacccatttgggccaaaattcctc<br>acacggacggcaactttcacccttctccgctgatgggagggtttggaatgaagcacccgcc<br>tcctcagatcctcatcaaaaacacacctgtacctgcCgatcctccaacgccttcaacaag<br>gacaagctgaactctttcatcacccagtattctactggccaagtcagcgtggagatcgagt<br>gggagctgcagaaggaaaacagcaagcgGtggaacccggagatccagtacacttccaacta<br>ttacaagtctaataatgttgaatttgctgttaatactgaaggtgtatatagtgaaccccgc<br>cccattggcaccagatacctgactcgtaatctgtaa |
| TTD-006<br>7 mer peptide underlined | 3629 | atggctgccgatggttatcttccagattggctcgaggacaaccttagtgaaggaattcgcg<br>agtggtgggctttgaaacctggagcccctcaacccaaggcaaatcaacaacatcaagacaa<br>cgctcgaggtcttgtgcttccgggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtctttggggggcaacctcggcgagcagtcttccaggccaaa<br>aagaggcttcttgaacctcttggtctggttgaggaagcggctaagacggctcctggaaaga<br>agaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctggggacagagtcatcaccaccagcacc<br>cgaacctgggccctgcccacctacaacaatcacctctacaagcaaatctccaacagcacat<br>ctggaggatcttcaaatgacaacgcctacttcggctacagcaccccctgggggtattttga<br>cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac |

TABLE 9-continued

Exemplary full length capsid nucleic acid sequences

| Name and Annotation | SEQ ID NO: | NT Sequence |
|---|---|---|
| | | ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtccttttactgcctggaatatttcccgtcgcaaatgctaagaac gggtaacaacttccagttcagctacgagtttgagaacgtacctttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccagggaagaaactacatacctggacccagctaccgacaacaacgt gtctcaaccactgtgactcaaaacaacaacagcgaatttgcttggcctggagcttcttctt gggctctcaatggacgtaatagcttgatgaatcctggacctgctatggccagccacaaaga aggagaggaccgtttctttcctttgtctggatctttaattttggcaaacaaggaactgga agagacaacgtggatgcggacaaagtcatgataaccaacgaagaagaaattaaaactacta acccggtagcaacggagtcctatgacaagtggccacaaaccaccagagtgcacaggctag ttttaatgatactagggctcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtggaacccggagatccagtacacttccaacta ttacaagtctaataatgttgaatttgctgttaatactgaaggtgtatatagtgaaccccgc cccattggcaccagatacctgactcgtaatctgtaa |
| TTD-007<br>9 mer peptide underlined | 3630 | atggctgccgatggttatcttccagattggctcgaggacaaccttagtgaaggaattcgcg agtggtgggctttgaaacctggagcccctcaacccaaggcaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtctttggggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccctcaggtgtgggatctcttacaatgg cttcaggtggtggcgcaccagtggcagacaataacgaaggtgccgatggagtgggtagttc ctcgggaaattggcattgcgattcccaatggctggggacagagtcatcaccaccagcacc cgaacctgggccctgcccacctacaacaatcacctctacaagcaaatctccaacagcacat ctggaggatcttcaaatgacaacgcctacttcggctacagcacccctgggggtattttga cttcaacagattccactgccacttctcaccacgtgactggcagcgactcatcaacaacaac tggggattccggcctaagcgactcaacttcaagctcttcaacattcaggtcaaagaggtta cggacaacaatggagtcaagaccatcgccaataaccttaccagcacgtccaggtcttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtccttttactgcctggaatatttcccgtcgcaaatgctaagaac gggtaacaacttccagttcagctacgagtttgagaacgtacctttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccagggaagaaactacatacctggacccagctaccgacaacaacgt gtctcaaccactgtgactcaaaacaacaacagcgaatttgcttggcctggagcttcttctt gggctctcaatggacgtaatagcttgatgaatcctggacctgctatggccagccacaaaga aggagaggaccgtttctttcctttgtctggatctttaattttggcaaacaaggaactgga agagacaacgtggatgcggacaaagtcatgataaccaacgaagaagaaattaaaactacta acccggtagcaacggagtcctatgacaagtggccacaaaccaccagagtggtggtacgtt ggccgtcgtgtcgcttgctcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtggaacccggagatccagtacacttccaacta ttacaagtctaataatgttgaatttgctgttaatactgaaggtgtatatagtgaaccccgc cccattggcaccagatacctgactcgtaatctgtaa |
| TTD-008<br>7 mer peptide underlined | 3631 | atggctgccgatggttatcttccagattggctcgaggacaaccttagtgaaggaattcgcg agtggtgggctttgaaacctggagcccctcaacccaaggcaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtctttggggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagcccctcaggtgtgggatctcttacaatgg cttcaggtggtggcgcaccagtggcagacaataacgaaggtgccgatggagtgggtagttc ctcgggaaattggcattgcgattcccaatggctggggacagagtcatcaccaccagcacc cgaacctgggccctgcccacctacaacaatcacctctacaagcaaatctccaacagcacat ctggaggatcttcaaatgacaacgcctacttcggctacagcacccctgggggtattttga cttcaacagattccactgccacttctcaccacgtgactggcagcgactcatcaacaacaac tggggattccggcctaagcgactcaacttcaagctcttcaacattcaggtcaaagaggtta |

TABLE 9-continued

Exemplary full length capsid nucleic acid sequences

| Name and Annotation | SEQ ID NO: | NT Sequence |
|---|---|---|
| | | cggacaacaatggagtcaagaccatcgccaataaccttaccagcacggtccaggtcttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtccttttactgcctggaatatttcccgtcgcaaatgctaagaac gggtaacaacttccagttcagctacgagtttgagaacgtaccttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccagggaagaaactacatacctggacccagctaccgacaacaacgt gtctcaaccactgtgactcaaaacaacaacagcgaatttgcttggcctggagcttcttctt gggctctcaatggacgtaatagcttgatgaatcctggacctgctatggccagccacaaaga aggagaggaccgtttctttcctttgtctggatctttaatttttggcaaacaaggaactgga agagacaacgtggatgcggacaaagtcatgataaccaacgaagaagaaatttaaaactacta acccggtagcaacggagtcctatggacaagtggccacaaaccaccagagtgcacaggctta tgggttgccgaagggtcctcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtgaacccggagatccagtacacttccaacta ttacaagtctaataatgttgaatttgctgttaatactgaaggtgtatatagtgaaccccgc cccattggcaccagatacctgactcgtaatctgtaa |
| TTD-009 7 mer peptide underlined | 3632 | atggctgccgatggttatcttccagattggctcgaggacaaccttagtgaaggaattcgcg agtggtgggctttgaaacctggagcccctcaacccaaggcaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttgggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagccccctcaggtgtgggatctcttacaatgg cttcaggtggtggcgcaccagtggcagacaataacgaaggtgccgatggagtgggtagttc ctcgggaaattggcattgcgattcccaatggctggggacagagtcatcaccaccagcacc cgaacctgggccctgcccacctacaacaatcacctctacaagcaaatctccaacagcacat ctggaggatcttcaaatgacaacgcctacttcggctacagcaccccctgggggtatttga cttcaacagattccactgccacttctcaccacgtgactggcagcgactcatcaacaacaac tggggattccgcctaagcgactcaacttcaagctcttcaacattcaggtcaaagaggtta cggacaacaatggagtcaagaccatcgccaataaccttaccagcacggtccaggtcttcac ggactcagactatcagctcccgtacgtgctcgggtcggctcacgagggctgcctcccgccg ttcccagcggacgttttcatgattcctcagtacgggtatctgacgcttaatgatggaagcc aggccgtgggtcgttcgtccttttactgcctggaatatttcccgtcgcaaatgctaagaac gggtaacaacttccagttcagctacgagtttgagaacgtaccttccatagcagctacgct cacagccaaagcctggaccgactaatgaatccactcatcgaccaatacttgtactatctct caaagactattaacggttctggacagaatcaacaaacgctaaaattcagtgtggccggacc cagcaacatggctgtccagggaagaaactacatacctggacccagctaccgacaacaacgt gtctcaaccactgtgactcaaaacaacaacagcgaatttgcttggcctggagcttcttctt gggctctcaatggacgtaatagcttgatgaatcctggacctgctatggccagccacaaaga aggagaggaccgtttctttcctttgtctggatctttaatttttggcaaacaaggaactgga agagacaacgtggatgcggacaaagtcatgataaccaacgaagaagaaatttaaaactacta acccggtagcaacggagtcctatggacaagtggccacaaaccaccagagtgcacaggcttc gactgggacgcttcggcttcaggcgcagaccggctgggttcaaaaccaaggaatacttccg ggtatggtttggcaggacagagatgtgtacctgcaaggacccatttgggccaaaattcctc acacggacggcaactttcacccttctccgctgatgggagggtttggaatgaagcacccgcc tcctcagatcctcatcaaaaacacacctgtacctgcCgatcctccaacggccttcaacaag gacaagctgaactctttcatcacccagtattctactggccaagtcagcgtggagatcgagt gggagctgcagaaggaaaacagcaagcgGtgaacccggagatccagtacacttccaacta ttacaagtctaataatgttgaatttgctgttaatactgaaggtgtatatagtgaaccccgc cccattggcaccagatacctgactcgtaatctgtaa |
| TTD-010 7 mer peptide underlined | 3633 | atggctgccgatggttatcttccagattggctcgaggacaaccttagtgaaggaattcgcg agtggtgggctttgaaacctggagcccctcaacccaaggcaaatcaacaacatcaagacaa cgctcgaggtcttgtgcttccgggttacaaataccttggacccggcaacggactcgacaag ggggagccggtcaacgcagcagacgcggcggccctcgagcacgacaaggcctacgaccagc agctcaaggccggagacaacccgtacctcaagtacaaccacgccgacgccgagttccagga gcggctcaaagaagatacgtcttttgggggcaacctcgggcgagcagtcttccaggccaaa aagaggcttcttgaacctcttggtctggttgaggaagcggctaagacggctcctggaaaga agaggcctgtagagcagtctcctcaggaaccggactcctccgcgggtattggcaaatcggg tgcacagcccgctaaaaagagactcaatttcggtcagactggcgacacagagtcagtccca gaccctcaaccaatcggagaacctcccgcagccccctcaggtgtgggatctcttacaatgg cttcaggtggtggcgcaccagtggcagacaataacgaaggtgccgatggagtgggtagttc ctcgggaaattggcattgcgattcccaatggctggggacagagtcatcaccaccagcacc cgaacctgggccctgcccacctacaacaatcacctctacaagcaaatctccaacagcacat ctggaggatcttcaaatgacaacgcctacttcggctacagcaccccctgggggtatttga cttcaacagattccactgccacttctcaccacgtgactggcagcgactcatcaacaacaac |

TABLE 9-continued

Exemplary full length capsid nucleic acid sequences

| Name and Annotation | SEQ ID NO: | NT Sequence |
|---|---|---|
| | | tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgttttcatgattcctcagtacgggtatctgacgcttaatgatggaagcc<br>aggccgtgggtcgttcgtccttttactgcctggaatatttcccgtcgcaaatgctaagaac<br>gggtaacaacttccagttcagctacgagtttgagaacgtaccttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccagggaagaaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatcttttaattttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcgcaggcgta<br>ttcgacggatgagaggatgcaggcgcagaccggctgggttcaaaaccaaggaatacttccg<br>ggtatggtttggcaggacagagatgtgtacctgcaaggacccattgggccaaaattcctc<br>acacggacggcaactttcacccttctccgctgatgggagggtttggaatgaagcacccgcc<br>tcctcagatcctcatcaaaaacacacctgtacctgcCgatcctccaacgccttcaacaag<br>gacaagctgaactctttcatcacccagtattctactggccaagtcagcgtggagatcgagt<br>gggagctgcagaaggaaaacagcaagcgGtggaacccggagatccagtcacttccaacta<br>ttacaagtctaataatgttgaatttgctgttaatactgaaggtgtatatagtgaaccccgc<br>cccattggcaccagatacctgactcgtaatctgtaa |
| TTD-011<br>7 mer peptide underlined | 3634 | atggctgccgatggttatcttccagattggctcgaggacaaccttagtgaaggaattcgcg<br>agtggtgggctttgaaacctggagcccctcaacccaaggcaaatcaacaacatcaagacaa<br>cgctcgaggtcttgtgcttccgggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtctttgggggcaacctcgggcgagcagtcttccaggccaaa<br>agaggcttcttgaacctcttggtctggttgaggaagcggctaagacggctcctggaaaga<br>agaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctggggacagagtcatcaccaccagcacc<br>cgaacctgggccctgcccacctacaacaatcacctctacaagcaaatctccaacagcacat<br>ctggaggatcttcaaatgacaacgcctacttcggctacagcacccctggggtattttga<br>cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgttttcatgattcctcagtacgggtatctgacgcttaatgatgaagcc<br>aggccgtgggtcgttcgtccttttactgcctggaatatttcccgtcgcaaatgctaagaac<br>gggtaacaacttccagttcagctacgagtttgagaacgtaccttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccagggaagaaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatcttttaattttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcgcaggcgta<br>ttcgacggatgagaggaagcaggcgcagaccggctgggttcaaaaccaaggaatacttccg<br>ggtatggtttggcaggacagagatgtgtacctgcaaggacccattgggccaaaattcctc<br>acacggacggcaactttcacccttctccgctgatgggagggtttggaatgaagcacccgcc<br>tcctcagatcctcatcaaaaacacacctgtacctgcCgatcctccaacgccttcaacaag<br>gacaagctgaactctttcatcacccagtattctactggccaagtcagcgtggagatcgagt<br>gggagctgcagaaggaaaacagcaagcgGtggaacccggagatccagtcacttccaacta<br>ttacaagtctaataatgttgaatttgctgttaatactgaaggtgtatatagtgaaccccgc<br>cccattggcaccagatacctgactcgtaatctgtaa |
| TTD-012<br>7 mer peptide underlined | 3635 | atggctgccgatggttatcttccagattggctcgaggacaaccttagtgaaggaattcgcg<br>agtggtgggctttgaaacctggagcccctcaacccaaggcaaatcaacaacatcaagacaa<br>cgctcgaggtcttgtgcttccgggttacaaataccttggacccggcaacggactcgacaag<br>ggggagccggtcaacgcagcagacgcggcggccctcgagcacgacaaggcctacgaccagc<br>agctcaaggccggagacaacccgtacctcaagtacaaccacgccgacgccgagttccagga<br>gcggctcaaagaagatacgtctttgggggcaacctcgggcgagcagtcttccaggccaaa<br>agaggcttcttgaacctcttggtctggttgaggaagcggctaagacggctcctggaaaga<br>agaggcctgtagagcagtctcctcaggaaccggactcctccgcgggtattggcaaatcggg<br>tgcacagcccgctaaaaagagactcaatttcggtcagactggcgacacagagtcagtccca<br>gaccctcaaccaatcggagaacctcccgcagcccctcaggtgtgggatctcttacaatgg<br>cttcaggtggtggcgcaccagtggcagacaataacgaaggtgccgatggagtgggtagttc<br>ctcgggaaattggcattgcgattcccaatggctggggacagagtcatcaccaccagcacc<br>cgaacctgggccctgcccacctacaacaatcacctctacaagcaaatctccaacagcacat<br>ctggaggatcttcaaatgacaacgcctacttcggctacagcacccctggggtattttga |

TABLE 9-continued

Exemplary full length capsid nucleic acid sequences

| Name and Annotation | SEQ ID NO: | NT Sequence |
|---|---|---|
| | | cttcaacagattccactgccacttctcaccacgtgactggcagcgactcatcaacaacaac<br>tggggattccggcctaagcgactcaacttcaagctcttcaacattcaggtcaaagaggtta<br>cggacaacaatggagtcaagaccatcgccaataaccttaccagcacggtccaggtcttcac<br>ggactcagactatcagctcccgtacgtgctcgggtcggctcacgagggctgcctcccgccg<br>ttcccagcggacgttttcatgattcctcagtacgggtatctgacgcttaatgatggaagcc<br>aggccgtgggtcgttcgtccttttactgcctggaatatttcccgtcgcaaatgctaagaac<br>gggtaacaacttccagttcagctacgagtttgagaacgtaccttccatagcagctacgct<br>cacagccaaagcctggaccgactaatgaatccactcatcgaccaatacttgtactatctct<br>caaagactattaacggttctggacagaatcaacaaacgctaaaattcagtgtggccggacc<br>cagcaacatggctgtccagggaagaaactacatacctggacccagctaccgacaacaacgt<br>gtctcaaccactgtgactcaaaacaacaacagcgaatttgcttggcctggagcttcttctt<br>gggctctcaatggacgtaatagcttgatgaatcctggacctgctatggccagccacaaaga<br>aggagaggaccgtttctttcctttgtctggatctttaattttggcaaacaaggaactgga<br>agagacaacgtggatgcggacaaagtcatgataaccaacgaagaagaaattaaaactacta<br>acccggtagcaacggagtcctatggacaagtggccacaaaccaccagagtgcacaggctta<br>tgtttcgtctgttaagatgcaggcgcagaccggctgggttcaaaaccaaggaatacttccg<br>ggtatggtttggcaggacagagatgtgtacctgcaaggacccatttgggccaaaattcctc<br>acacggacggcaactttcacccttctccgctgatgggagggtttggaatgaagcacccgcc<br>tcctcagatcctcatcaaaaacacacctgtacctgcCgatcctccaacggccttcaacaag<br>gacaagctgaactctttcatcacccagtattctactggccaagtcagcgtggagatcgagt<br>gggagctgcagaaggaaaacagcaagcgGtggaacccggagatccagtacacttccaacta<br>ttacaagtctaataatgttgaatttgctgttaatactgaaggtgtatatagtgaacccgc<br>cccattggcaccagatacctgactcgtaatctgtaa |

In some embodiments, an AAV capsid variant described herein comprises the amino acid sequence of any one of SEQ ID NOs: 3636-3647, or an amino acid sequence with at least 80% (e.g., at least about 85, 90, 95, 96, 97, 98, or 99%) sequence identity thereto. In some embodiments, an AAV capsid variant described herein comprises the amino acid sequence of SEQ ID NO: 3636, or an amino acid sequence with at least 80% (e.g., at least about 85, 90, 95, 96, 97, 98, or 99%) sequence identity thereto. In some embodiments, an AAV capsid variant described herein comprises the amino acid sequence of SEQ ID NO: 3639, or an amino acid sequence with at least 80% (e.g., at least about 85, 90, 95, 96, 97, 98, or 99%) sequence identity thereto.

In some embodiments, the polynucleotide encoding an AAV capsid variant described herein comprises the nucleotide sequence of any one of SEQ ID NOs: 3623-3635, or a nucleotide sequence with at least 80% (e.g., at least about 85, 90, 95, 96, 97, 98, or 99%) sequence identity thereto. In some embodiments, the polynucleotide encoding an AAV capsid variant described herein comprises the nucleotide sequence of SEQ ID NO: 3623, or a nucleotide sequence with at least 80% (e.g., at least about 85, 90, 95, 96, 97, 98, or 99%) sequence identity thereto. In some embodiments, the polynucleotide encoding an AAV capsid variant described herein comprises the nucleotide sequence of SEQ ID NO: 3627, or a nucleotide sequence with at least 80% (e.g., at least about 85, 90, 95, 96, 97, 98, or 99%) sequence identity thereto. In some embodiments, the nucleic acid sequence encoding an AAV capsid variant described herein is codon optimized.

In some embodiments, the AAV capsid variant comprises a VP2 protein comprising the amino acid sequence corresponding to positions 138-743, of any one of SEQ ID NOs: 3636-3647, or a sequence with at least 80% (e.g., at least about 85, 90, 95, 96, 97, 98, or 99%) sequence identity thereto. In some embodiments, the AAV capsid comprises a VP3 protein comprising the amino acid sequence corresponding to positions 203-743, of any one of SEQ ID NOs: 3636-3647, or a sequence with at least 80% (e.g., at least about 85, 90, 95, 96, 97, 98, or 99%) sequence identity thereto.

In some embodiments, an AAV capsid variant, described herein has an increased tropism for a CNS cell or tissue, e.g., a brain cell, brain tissue, spinal cord cell, or spinal cord tissue, relative to the tropism of a reference sequence comprising the amino acid sequence of SEQ ID NO: 138.

In some embodiments, an AAV capsid variant, described herein transduces a brain region, e.g., selected from dentate nucleus, cerebellar cortex, cerebral cortex, brain stem, hippocampus, thalamus and putamen. In some embodiments, the level of transduction of said brain region is at least 5, 10, 50, 100, 200, 500, 1,000, 2,000, 5,000, or 10,000-fold greater as compared to a reference sequence of SEQ ID NO: 138.

In some embodiments, an AAV capsid variant described herein is enriched at least about 5, 6, 7, 8, 9, or 10-fold, in the brain compared to a reference sequence of SEQ ID NO: 138. In some embodiments, an AAV capsid variant described herein is enriched at least about 20, 30, 40, or 50-fold in the brain compared to a reference sequence of SEQ ID NO: 138. In some embodiments, an AAV capsid variant described herein is enriched at least about 100, 200, 300, or 400-fold in the brain compared to a reference sequence of SEQ ID NO: 138.

In some embodiments, an AAV capsid variant described herein delivers an increased level of viral genomes to a brain region. In some embodiments, the level of viral genomes is increased by at least 5, 10, 20, 30, 40 or 50-fold, as compared to a reference sequence of SEQ ID NO: 138. In some embodiments, the brain region comprises a frontal cortex, sensory cortex, motor cortex, putamen, thalamus, cerebellar cortex, dentate nucleus, caudate, and/or hippocampus.

In some embodiments, an AAV capsid variant described herein delivers an increased level of a payload to a brain region. In some embodiments, the level of the payload is increased by at least 5, 10, 50, 100, 200, 500, 1,000, 2,000, 5,000, or 10,000-fold, as compared to a reference sequence of SEQ ID NO: 138. In some embodiments, the brain region comprises a frontal cortex, sensory cortex, motor cortex, putamen, thalamus, cerebellar cortex, dentate nucleus, caudate, and/or hippocampus.

In some embodiments, an AAV capsid variant described herein delivers an increased level of a payload to a spinal cord region. In some embodiments, the level of the payload is increased by at least 10, 20, 50, 100, 200, 300, 400, 500, 600, 700, 800 or 900-fold, as compared to a reference sequence of SEQ ID NO: 138. In some embodiments, the spinal cord region comprises a cervical, thoracic, and/or lumbar region.

In some embodiments, an AAV capsid variant described herein shows preferential transduction in a brain region relative to the transduction in the dorsal root ganglia (DRG).

In some embodiments, an AAV capsid variant described herein has an increased tropism for a muscle cell or tissue, e.g., a heart cell or tissue, relative to the tropism of a reference sequence comprising the amino acid sequence of SEQ ID NO: 138. In some embodiments, the AAV capsid variant delivers an increased level of a payload to a muscle region. In some embodiments, the payload is increased by at least 10, 15, 20, 30, or 40-fold, as compared to a reference sequence of SEQ ID NO: 138. In some embodiments, the muscle region comprises a heart muscle, quadriceps muscle, and/or a diaphragm muscle region. In some embodiments, the muscle region comprises a heart muscle region, e.g., a heart atrium muscle region or a heart ventricle muscle region.

In some embodiments, an AAV capsid variant of the present disclosure is isolated, e.g., recombinant. In some embodiments, a polynucleotide encoding an AAV capsid variant of the present disclosure is isolated, e.g., recombinant.

Also provided herein are polynucleotide sequences encoding any of the AAV capsid variants described above and AAV particles, vectors, and cells comprising the same.

symmetrically arranged. In some embodiments, the ITR incorporated into viral genome may be comprised of naturally occurring nucleic acid sequences or recombinantly derived nucleic acid sequences.

In some embodiments, the ITR may be of the same AAV serotype as the capsid, e.g., a capsid protein selected from any of the AAV serotypes listed in Table 2, or a functional variant thereof. In some embodiments, the ITR may be of a different AAV serotype than the capsid protein. In some embodiments, the AAV particle comprises a viral genome comprising two ITRs wherein the two ITRs of viral genome are of the same AAV serotype. In other embodiments, the two ITRs of a viral genome are of different AAV serotypes. In some embodiments both ITRs of the viral genome of the AAV particle are AAV2 ITRs or a functional variant thereof.

In some embodiments, the ITR comprises about 120-140 nucleotides in length, e.g., about 130 nucleotides in length. In some embodiments, the ITR comprises about 140-150 nucleotides in length, about 141 nucleotides in length. In some embodiments, the viral genome comprises an ITR region comprising the nucleotide sequence of any of the sequences provided in Table 10 or a nucleotide sequence with at least 70%, 75%, 80%, 85%, 90%, 95% or 99% sequence identity thereto. In some embodiments, the viral genome comprises two ITR regions comprising the nucleotide sequence of any of the sequences provided in Table 10 or a nucleotide sequence with at least 70%, 75%, 80%, 85%, 90%, 95% or 99% sequence identity thereto, wherein the first and second ITR comprise the same sequence or wherein the first and second ITR comprise different sequences.

In some embodiments, the AAV particle viral genome comprises a 5' inverted terminal repeat (5' ITR) sequence region. In some embodiments, the viral genome comprises a 3' inverted terminal repeat (3' ITR) sequence region. Non-limiting examples of 5' ITR and 3' ITR sequence regions are described in Table 10

TABLE 10

Inverted Terminal Repeat (ITR) Sequence Regions

| SEQ ID NO | Sequence |
| --- | --- |
| 1035 | ctgcgcgctcgctcgctcactgaggccgcccgggcaaagcccgggcgtcgggcgacctttggtcg cccggcctcagtgagcgagcgagcgcgcagagagggagtggccaactccatcactagggttcct |
| 1036 | cctgcaggcagctgcgcgctcgctcgctcactgaggccgcccgggcaaagcccgggcgtcgggcg acctttggtcgcccggcctcagtgagcgagcgagcgcgcagagagggagtggccaactccatcac tagggttcct |
| 1037 | aggaaccctagtgatggagttggccactccctctctgcgcgctcgctcgctcactgaggccggg cgaccaaaggtcgcccgacgcccgggctttgcccgggcggcctcagtgagcgagcgagcgcgcag |
| 1038 | aggaaccctagtgatggagttggccactccctctctgcgcgctcgctcgctcactgaggccggg cgaccaaaggtcgcccgacgcccgggctttgcccgggcggcctcagtgagcgagcgagcgcgcag ctgcctgcagg |

Viral Genome Component: Inverted Terminal Repeats (ITRs)

In some embodiments, the viral genome may comprise at least one inverted terminal repeat (ITR) region. In some embodiments, the viral genome comprises at least one ITR region and a nucleic acid encoding a payload, e.g., an antibody (e.g., an anti-tau antibody). In some embodiments, viral genome comprises two ITRs. In some embodiments, the two ITRs flank the nucleic acid encoding the transgene at the 5' and 3' ends. In some embodiments, the ITR functions as an origin of replication comprising recognition sites for replication. In some embodiments, the ITRs comprise sequence regions which can be complementary and In some embodiments, the ITR comprises the nucleotide sequence of any one of SEQ ID NOs: 1035-1038, or a sequence with at least 70%, 75%, 80%, 85%, 90%, 95% or 99% sequence identity thereto. In some embodiments, the ITR comprises the nucleotide sequence of SEQ ID NO: 1035 or a nucleotide sequence with at least 70%, 75%, 80%, 85%, 90%, 95% or 99% sequence identity thereto. In some embodiments, the ITR comprises the nucleotide sequence of SEQ ID NO: 1036 or a nucleotide sequence with at least 70%, 75%, 80%, 85%, 90%, 95% or 99% sequence identity thereto. In some embodiments, the ITR comprises the nucleotide sequence of SEQ ID NO: 1037 or a nucleotide sequence with at least 70%, 75%, 80%, 85%, 90%, 95% or 99% sequence identity thereto. In some embodiments, the ITR comprises the nucleotide sequence of SEQ ID NO: 1038 or a nucleotide sequence with at least 70%, 75%, 80%, 85%, 90%, 95% or 99% sequence identity thereto.

In some embodiments, the viral genome comprises an ITR, e.g., a 5' ITR, comprising the nucleotide sequence of SEQ ID NO: 1035 or a sequence with at least with at least 70%, 75%, 80%, 85%, 90%, 95% or 99% sequence identity thereto; and/or an ITR, e.g., a 3' ITR, comprising the nucleotide sequence of SEQ ID NO: 1037 or a nucleotide sequence at least 70%, 75%, 80%, 85%, 90%, 95% or 99% sequence identity thereto.

Viral Genome Component: Promoters

In some embodiments, the viral genome may comprise an element to enhance the transgene target specificity and/or expression (See e.g., Powell et al. Viral Expression Cassette Elements to Enhance Transgene Target Specificity and Expression in Gene Therapy, 2015; the contents of which are herein incorporated by reference in its entirety). In some embodiments, the AAV particle viral genome may comprise an element to enhance the transgene target specificity and/or expression comprise a promoter, an enhancer, e.g., a CMV enhancer, or both. In some embodiments, the AAV particle viral genome comprises a promoter operably linked to a transgene encoded by a nucleic acid molecule encoding a payload, e.g., antibody (e.g., an anti-tau antibody). In some embodiments, the AAV particle viral genome comprises an enhancer, e.g., a CMV enhancer. In some embodiment, the AAV particle viral genome comprises at least two promoters.

In some embodiments, the viral genome comprises a ubiquitous promoter. In some embodiments, the viral genome comprises a tissue specific promoter.

In some embodiments, the viral genome comprises a promoter that is species specific, inducible, tissue-specific, and/or cell cycle-specific (e.g., as described in Parr et al., Nat. Med. 3:1145-9 (1997); the contents of which are herein incorporated by reference in their entirety). In some embodiments, the viral genome comprises a promoter that is sufficient for expression, e.g., in a target cell, of a payload (e.g., an antibody, e.g., an anti-tau antibody) encoded by a transgene.

In some embodiments, the promoter may be a naturally occurring promoter, or a non-naturally occurring promoter. In some embodiments, the promoter is from a naturally expressed protein. In some embodiments, the promoter is an engineered promoter. In some embodiments, the promoter comprises a viral promoter, plant promoter, and/or a mammalian promoter. In some embodiments, the promoter may be a human promoter. In some embodiments, the promoter may be truncated. In some embodiments, the promoter is not a cell specific promoter.

In some embodiments, the promoter results in expression in one or more, e.g., multiple, cells and/or tissues, e.g., a ubiquitous promoter. In some embodiments, a promoter that results in expression in one or more tissues includes but is not limited to a human elongation factor 1α-subunit (EF1α) promoter, a cytomegalovirus (CMV) immediate-early enhancer and/or promoter, a chicken β-actin (CBA) promoter and its derivative CAG, a β glucuronidase (GUSB) promoter, or ubiquitin C (UBC) promoter. In some embodiments, a tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes. In some embodiments, the promoter is a ubiquitous promoter as described in Yu et al. (Molecular Pain 2011, 7:63), Soderblom et al. (E. Neuro 2015), Gill et al., (Gene Therapy 2001, Vol. 8, 1539-1546), and Husain et al. (Gene Therapy 2009), each of which are incorporated by reference in their entirety. In some embodiments, the promoter is a ubiquitous promoter chosen from CMV, CBA (including derivatives CAG, CB6, CBh, etc.), EF-1α, PGK, UBC, GUSB (hGBp), or UCOE (promoter of HNRPA2B1-CBX3).

In some embodiments, the promoter is a muscle-specific promoter, e.g., a promoter that results in expression in a muscle cell. In some embodiments, a muscle-specific promoter includes but is not limited to a mammalian muscle creatine kinase (MCK) promoter, a mammalian desmin (DES) promoter, a mammalian troponin I (TNNI2) promoter, a synthetic C5-12 promoter, and a mammalian skeletal alpha-actin (ASKA) promoter (see, e.g. U.S. Patent Publication US20110212529, the contents of which are herein incorporated by reference in their entirety).

In some embodiments, the promoter is a nervous system specific promoter, e.g., a promoter that results in expression of a payload in a neuron, an astrocyte, and/or an oligodendrocyte. In some embodiments, a nervous system specific promoter that results in expression in neurons includes but is not limited to a neuron-specific enolase (NSE) promoter, a platelet-derived growth factor (PDGF) promoter, a platelet-derived growth factor B-chain (PDGF-β) promoter, a synapsin (Syn) promoter, a methyl-CpG binding protein 2 (MeCP2) promoter, a $Ca^{2+}$/calmodulin-dependent protein kinase II (CaMKII) promoter, a metabotropic glutamate receptor 2 (mGluR2) promoter, a neurofilament light (NFL) or heavy (NFH) promoter, a β-globin minigene nβ2 promoter, a preproenkephalin (PPE) promoter, a enkephalin (Enk) promoter, and an excitatory amino acid transporter 2 (EAAT2) promoter. In some embodiments, a nervous system specific promoter that results in expression in astrocytes includes but is not limited to a glial fibrillary acidic protein (GFAP) promoter and a EAAT2 promoter. In some embodiments, a nervous system specific promoter that results in expression in oligodendrocytes includes but is not limited to a myelin basic protein (MBP) promoter. In some embodiments, the viral genome comprises a nervous system specific promoter as described in Husain et al. (Gene Therapy 2009), Passini and Wolfe (J. Virol. 2001, 12382-12392), Xu et al. (Gene Therapy 2001, 8, 1323-1332), Drews et al. (Mamm Genome (2007) 18:723-731), and Raymond et al. (Journal of Biological Chemistry (2004) 279(44) 46234-46241), each of which are incorporated by reference in their entirety.

In some embodiments, the promoter is a liver promoter, e.g. a promoter that results in expression a liver cell. In some embodiments, the liver promoter is chosen from human α-1-antitrypsin (hAAT) or thyroxine binding globulin (TBG). In some embodiments, the viral genome comprises an RNA pol III promoter. In some embodiments, the RNA pol III promoter is chosen from U6 or H1.

In some embodiments, the viral genome comprises two promoters. As a non-limiting example, the promoters are an EF1α promoter and a CMV promoter.

In some embodiments, the promoter is a ubiquitin c (UBC) promoter. The UBC promoter may have a size of 300-350 nucleotides. As a non-limiting example, the UBC promoter is 332 nucleotides. In some embodiments, the promoter is a β-glucuronidase (GUSB) promoter. The GUSB promoter may have a size of 350-400 nucleotides. As a non-limiting example, the GUSB promoter is 378 nucleotides. In some embodiments, the promoter is a neurofilament light (NFL) promoter. The NFL promoter may have a size of 600-700 nucleotides. As a non-limiting example, the NFL promoter is 650 nucleotides. In some embodiments, the promoter is a neurofilament heavy (NFH) promoter. The NFH promoter may have a size of 900-950 nucleotides. As a non-limiting example, the NFH promoter is 920 nucleotides. In some embodiments, the promoter is a scn8a promoter. The scn8a promoter may have a size of 450-500 nucleotides. As a non-limiting example, the scn8a promoter is 470 nucleotides. In some embodiments, the promoter is a phosphoglycerate kinase 1 (PGK) promoter.

In some embodiments, the viral genome comprises a promoter chosen from a CAG promoter, a CBA promoter (e.g., a minimal CBA promoter), a CB promoter, a CMV(IE) promoter and/or enhancer, a GFAP promoter, a synapsin promoter, an ICAM2 promoter, or a functional variant thereof. In some embodiments, the viral genome comprises a CAG promoter, a CMVie enhancer, and a minimal CBA promoter. In some embodiments, the viral genome comprises a CMV(IE) promoter and a CB promoter.

In some embodiments, the viral genome comprises an enhancer element, a promoter and/or a 5'UTR intron. The enhancer element, also referred to herein as an "enhancer," may be, but is not limited to, a CMV enhancer, the promoter may be, but is not limited to, a CMV, CBA, UBC, GUSB, NSE, Synapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter; and (9) GFAP promoter.

In some embodiments, a viral genome encoding an antibody that binds to tau described herein comprises a CBA promoter or a functional variant thereof. In some embodiments, the promoter comprises the nucleotide sequence of SEQ ID NO: 1042, or a nucleotide sequence at least 70%, 75%, 80%, 85%, 90%, 95%, 96%, 97%, 98%, or 99% identical thereto. In some embodiments, the promoter comprises the nucleotide sequence of SEQ ID NO: 1042, or a nucleotide sequence at least 95% identical thereto.

In some embodiments, a viral genome encoding an antibody that binds to tau described herein comprises a CMVie enhancer or a functional variant thereof. In some embodiments, the enhancer comprises the nucleotide sequence of SEQ ID NO: 1050, or a nucleotide sequence at least 70%, 75%, 80%, 85%, 90%, 95%, 96%, 97%, 98%, or 99% identical thereto. In some embodiments, the promoter comprises the nucleotide sequence of SEQ ID NO: 1050, or a nucleotide sequence at least 95% identical thereto.

In some embodiments, a viral genome encoding an antibody that binds to tau described herein comprises a CMVie enhancer or a functional variant thereof and a CBA promoter or a functional variant thereof. In some embodiments, the viral genome comprises (i) an enhancer which comprises the nucleotide sequence of SEQ ID NO: 1050, or a nucleotide sequence at least 70%, 75%, 80%, 85%, 90%, 95%, 96%, 97%, 98%, or 99% identical thereto; and (ii) a promoter which comprises the nucleotide sequence of SEQ ID NO: 1042, or a nucleotide sequence at least 70%, 75%, 80%, 85%, 90%, 95%, 96%, 97%, 98%, or 99% identical thereto.

TABLE 11

Exemplary Promoter Sequences

| Name | SEQ ID NO | Sequence |
|---|---|---|
| CAG Promoter Variant 1 | 1039 | CTAGTTATTAATAGTAATCAATTACGGGGTCATTAGTTCATAGCCCATATATGGAGTTCCGCG TTACATAACTTACGGTAAATGGCCCGCCTGGCTGACCGCCCAACGACCCCCGCCCATTGACGT CAATAATGACGTATGTTCCCATAGTAACGCCAATAGGGACTTTCCATTGACGTCAATGGGTGG AGTATTTACGGTAAACTGCCCACTTGGCAGTACATCAAGTGTATCATATGCCAAGTACGCCCC CTATTGACGTCAATGACGGTAAATGGCCCGCCTGGCATTATGCCCAGTACATGACCTTATGGG ACTTTCCTACTTGGCAGTACATCTACGTATTAGTCATCGCTATTACCATGGTCGAGGTGAGCC CCACGTTCTGCTTCACTCTCCCCATCTCCCCCCCCTCCCCACCCCCAATTTTGTATTTATTTA TTTTTTAATTATTTTGTGCAGCGATGGGGGCGGGGGGGGGGGGGGGGCGCGCGCCAGGCGGGG CGGGGCGGGGCGAGGGGCGGGGCGGGGCGAGGCGGAGAGGTGCGGCGGCAGCCAATCAGAGCG GCGCGCTCCGAAAGTTTCCTTTTATGGCGAGGCGGCGGCGGCGGCGGCCCTATAAAAAGCGAA GCGCGCGGCGGGCGGGAGTCGCTGCGCGCTGCCTTCGCCCCGTGCCCCGCTCCGCCGCCGCCT CGCGCCGCCCGCCCCGGCTCTGACTGACCGCGTTACTCCCACAGGTGAGCGGGCGGGACGGCC CTTCTCCTCCGGGCTGTAATTAGCGCTTGGTTTAATGACGGCTTGTTTCTTTTCTGTGGCTGC GTGAAAGCCTTGAGGGGCTCCGGGAGGGCCCTTTGTGCGGGGGGAGCGGCTCGGGGGGTGCGT GCGTGTGTGTGTGCGTGGGGAGCGCGCGCGTGCGGCTCCGCGCTGCCCGGCGGCTGTGAGCGCT GCGGGCGCGGCGCGGGGCTTTGTGCGCTCCGCAGTGTGCGCGAGGGGAGCGCGGCCGGGGGCG GTGCCCCGCGGTGCGGGGGGGCTGCGAGGGGAACAAAGGCTGCGTGCGGGGTGTGTGCGTGG GGGGGTGAGCAGGGGGTGTGGGCGCGTCGGTCGGGCTGCAACCCCCCCTGCACCCCCCTCCCC GAGTTGCTGAGCACGGCCCGGCTTCGGGTGCGGGGCTCCGTACGGGGCGTGGCGCGGGGCTCG CCGTGCCGGGCGGGGGTGGCGGCAGGTGGGGGTGCCGGGCGGGGCGGGGCCGCCTCGGGCCG GGGAGGGCTCGGGGGAGGGGCGCGGCGGCCCCCGGAGCGCCGGCGGCTGTCGAGGCGCGGCGA GCCGCAGCCATTGCCTTTTATGGTAATCGTGCGAGAGGGCGCAGGGACTTCCTTTGTCCCAAA TCTGTGCGGAGCCGAAATCTGGGAGGCGCCGCCGCACCCCCTCTAGCGGGCGCGGGGCGAAGC GGTGCGGCGCCGGCAGGAAGGAAATGGGCGGGAGGGCCTTCGTGCGTCGCCGCGCCGCCGTC CCCTTCTCCCTCTCCAGCCTCGGGGCTGTCCGCGGGGGACGGCTGCCTTCGGGGGGGACGGG GCAGGGCGGGGTTCGGCTTCTGGCGTGTGACCGGCGGCTCTAGAGCCTCTGCTAACCATGTTC ATGCCTTCTTCTTTTTCCTACAGCTCCTGGGCAACGTGCTGGTTATTGTGCTGTCTCATCATT TTGGCAAAGAATTC |

TABLE 11-continued

Exemplary Promoter Sequences

| Name | SEQ ID NO | Sequence |
|---|---|---|
| CMVie Promoter Variant | 1040 | TAGCCCATATATGGAGTTCCGCGTTACATAACTTACGGTAAATGGCCCGCCTGGCTGACCGCC<br>CAACGACCCCCGCCCATTGACGTCAATAATGACGTATGTTCCCATAGTAACGCCAATAGGGAC<br>TTTCCATTGACGTCAATGGGTGGAGTATTTACGGTAAACTGCCCACTTGGCAGTACATCAAGT<br>GTATCATATGCCAAGTACGCCCCCTATTGACGTCAATGACGGTAAATGGCCCGCCTGGCATTA<br>TGCCCAGTACATGACCTTATGGGACTTTCCTACTTGGCAGTACATCT |
| CBA Promoter Variant | 1041 | CATGGTCGAGGTGAGCCCCACGTTCTGCTTCACTCTCCCCATCTCCCCCCCCTCCCCACCCCC<br>AATTTTGTATTTATTTATTTTTAATTATTTTGTGCAGCGATGGGGCGGGGGGGGGGGGGGG<br>GCGCGCGCCAGGCGGGCGGGGCGGGGGGCGAGGGGCGGGGGGGCGAGGCGGAGAGGTGCGGC<br>GGCAGCCAATCAGAGCGGCGCGCTCCGAAAGTTTCCTTTTATGGCGAGGCGGCGGCGGCGGCG<br>GCCCTATAAAAAGCGAAGCGCGCGGCGGGCG |
| CBA Promoter Variant 2 | 1042 | CCACGTTCTGCTTCACTCTCCCCATCTCCCCCCCCTCCCCACCCCCAATTTTGTATTTATTTA<br>TTTTTTAATTATTTTGTGCAGCGATGGGGCGGGGGGGGGGGCGCGCGCCAGGCGGGGCGGG<br>GCGGGGCGAGGGGCGGGGCGGGGCGAGGCGGAGAGGTGCGGCGGCAGCCAATCAGAGCGGCGC<br>GCTCCGAAAGTTTCCTTTTATGGCGAGGCGGCGGCGGCGGCGGCCCTATAAAAAGCGAAGCGC<br>GCGGCGGG |
| CBA Promoter | 1043 | CGACATTGATTATTGACTAGTTATTAATAGTAATCAATTACGGGGTCATTAGTTCATAGCCCA<br>TATATGGAGTTCCGCGTTACATAACTTACGGTAAATGGCCCGCCTGGCTGACCGCCCAACGAC<br>CCCCGCCCATTGACGTCAATAATGACGTATGTTCCCATAGTAACGCCAATAGGGACTTTCCAT<br>TGACGTCAATGGGTGGAGTATTTACGGTAAACTGCCCACTTGGCAGTACATCAAGTGTATCAT<br>ATGCCAAGTACGCCCCCTATTGACGTCAATGACGGTAAATGGCCCGCCTGGCATTATGCCCAG<br>TACATGACCTTATGGGACTTTCCTACTTGGCAGTACATCTACGTATTAGTCATCGCTATTACC<br>ATGTCGAGGCCACGTTCTGCTTCACTCTCCCCATCTCCCCCCCCTCCCCACCCCCAATTTTGT<br>ATTTATTTATTTTTTAATTATTTTGTGCAGCGATGGGGCGGGGGGGGGGGCGCGCGCCAGG<br>CGGGGCGGGGCGGGGCGAGGGGCGGGGCGGGGCGAGGCGGAGAGGTGCGGCGGCAGCCAATCA<br>GAGCGGCGCGCTCCGAAAGTTTCCTTTTATGGCGAGGCGGCGGCGGCGGCGGCCCTATAAAAA<br>GCGAAGCGCGCGGCGGGCGGGAGC |
| GFAP Promoter | 1044 | GATCTAACATATCCTGGTGTGGAGTAGCGGACGCTGCTATGACAGAGGCTCGGGGGCCTGAGC<br>TGGCTCTGTGAGCTGGGGAGGAGGCAGACAGCCAGGCCTTGTCTGCAAGCAGACCTGGCAGCA<br>TTGGGCTGGCCGCCCCCAGGGCCTCCTCTTCATGCCCAGTGAATGACTCACCTTGGCACAGA<br>CACAATGTTCGGGGTGGGCACAGTGCCTGCTTCCCGCCGCACCCCAGCCCCCCTCAAATGCCT<br>TCCGAGAAGCCCATTGAGCAGGGGGCTTGCATTGCACCCCAGCCTGACAGCCTGGCATCTTGG<br>GATAAAAGCAGCACAGCCCCCTAGGGGCTGCCCTTGCTGTGTGGCGCCACCGGCGGTGGAGAA<br>CAAGGCTCTATTCAGCCTGTGCCCAGGAAAGGGGATCAGGGGATGCCCAGGCATGGACAGTGG<br>GTGGCAGGGGGGAGAGGAGGGCTGTCTGCTTCCCAGAAGTCCAAGGACACAAATGGGTGAGG<br>GGAGAGCTCTCCCCATAGCTGGGCTGCGGCCCAACCCCACCCCCTCAGGCTATGCCAGGGGGT<br>GTTGCCAGGGGCACCCGGGCATCGCCAGTCTAGCCCACTCCTTCATAAAGCCCTCGCATCCCA<br>GGAGCGAGCAGAGCCAGAGCAGGTTGGAGAGGAGACGCATCACCTCCGCTGCTCGCGGGGATC<br>CTCTAG |
| Synuclein Promoter | 1045 | TAGTATCTGCAGAGGGCCCTGCGTATGAGTGCAAGTGGGTTTTAGGACCAGGATGAGGCGGGG<br>TGGGGGTGCCTACCTGACGACCGACCCCGACCCACTGGACAAGCACCCAACCCCCATTCCCCA<br>AATTGCGCATCCCCTATCAGAGAGGGGGAGGGGAAACAGGATGCGGCGAGGCGCGTGCGCACT<br>GCCAGCTTCAGCACCGCGGACAGTGCCTTCGCCCCCGCCTGGCGGCGCGCGCCACCGCCGCCT<br>CAGCACTGAAGGCGCGCTGACGTCACTCGCCGGTCCCCCGCAAACTCCCCTTCCCGGCCACCT<br>TGGTCGCGTCCGCGCCGCCGCCGGCCCAGCCGGACCGCACCACGCGAGGCGCGAGATAGGCGG<br>GCACGGGCGCGACCATCTGCGCTGCGGCGCCGGCGACTCAGCGCTGCCTCAGTCTGCGGTGGG<br>CAGCGGAGGAGTCGTGTCGTGCCTGAGAGCGCAGCTGTGCTCCTGGGCACCGCGCAGTCCGCC<br>CCCGCGGCTCCTGGCCAGACCACCCCTAGGACCCCCTGCCCCAAGTCGCAGCC |
| CMVie Promoter Variant 2 | 1046 | CTAGTCGACATTGATTATTGACTAGTTATTAATAGTAATCAATTACGGGGTCATTAGTTCATA<br>GCCCATATATGGAGTTCCGCGTTACATAACTTACGGTAAATGGCCCGCCTGGCTGACCGCCCA<br>ACGACCCCCGCCCATTGACGTCAATAATGACGTATGTTCCCATAGTAACGCCAATAGGGACTT<br>TCCATTGACGTCAATGGGTGGAGTATTTACGGTAAACTGCCCACTTGGCAGTACATCAAGTGT<br>ATCATATGCCAAGTACGCCCCCTATTGACGTCAATGACGGTAAATGGCCCGCCTGGCATTATG<br>CCCAGTACATGACCTTATGGGACTTTCCTACTTGGCAGTACATCTACGTATTAGTCATCGCTA<br>TTAC |
| CAG Promoter Variant 2 | 1047 | CTAGTCGACATTGATTATTGACTAGTTATTAATAGTAATCAATTACGGGGTCATTAGTTCATA<br>GCCCATATATGGAGTTCCGCGTTACATAACTTACGGTAAATGGCCCGCCTGGCTGACCGCCCA<br>ACGACCCCCGCCCATTGACGTCAATAATGACGTATGTTCCCATAGTAACGCCAATAGGGACTT<br>TCCATTGACGTCAATGGGTGGAGTATTTACGGTAAACTGCCCACTTGGCAGTACATCAAGTGT<br>ATCATATGCCAAGTACGCCCCCTATTGACGTCAATGACGGTAAATGGCCCGCCTGGCATTATG<br>CCCAGTACATGACCTTATGGGACTTTCCTACTTGGCAGTACATCTACGTATTAGTCATCGCTA<br>TTACCATGGTCGAGGTGAGCCCCACGTTCTGCTTCACTCTCCCCATCTCCCCCCCCTCCCCAC<br>CCCCAATTTTGTATTTATTTATTTTTTAATTATTTTGTGCAGCGATGGGGCGGGGGGGGGGG<br>GGGGGCGCGCGCCAGGCGGGGCGGGGCGGGGCGAGGGGCGGGGCGGGGCGAGGCGGAGAGGT<br>GCGGCGGCAGCCAATCAGAGCGGCGCGCTCCGAAAGTTTCCTTTTATGGCGAGGCGGCGGCGG<br>CGGCGGCCCTATAAAAAGCGAAGCGCGCGGCGGGCGGGAGTCGCTGCGCGCTGCCTTCGCCCCG<br>TGCCCCGCTCCGCCGCCGCCTCGCGCCGCCCGCCCCGGCTCTGACTGACCGCGTTACTCCCAC<br>AGGTGAGCGGGCGGGACGGCCCTTCCTCCGGGCTGTAATTAGCGCTTGGTTTAATGACGGC |

TABLE 11-continued

Exemplary Promoter Sequences

| Name | SEQ ID NO | Sequence |
|---|---|---|
| | | TTGTTTCTTTTCTGTGGCTGCGTGAAAGCCTTGAGGGGCTCCGGGAGGGCCCTTTGTGCGGGG<br>GGAGCGGCTCGGGGGGTGCGTGCGTGTGTGTGCGTGGGGAGCGCCGCGTGCGGCTCCGCGC<br>TGCCCGGCGGCTGTGAGCGCTGCGGGCGCGGCGCGGGGCTTTGTGCGCTCCGCAGTGTGCGCG<br>AGGGGAGCGCGGCCGGGGGCGGTGCCCCGCGGTGCGGGGGGGGCTGCGAGGGGAACAAAGGCT<br>GCGTGCGGGGTGTGTGCGTGGGGGGGTGAGCAGGGGGTGTGGGCGCGTCGGTCGGGCTGCAAC<br>CCCCCCTGCACCCCCCTCCCCGAGTTGCTGAGCACGGCCCGGCTTCGGGTGCGGGGCTCCGTA<br>CGGGGCGTGGCGCGGGGCTCGCCGTGCCGGGCGGGGGGTGGCGGCAGGTGGGGGTGCCGGGCG<br>GGGCGGGGCCGCCTCGGGCCGGGGAGGGCTCGGGGGAGGGGCGCGGCGGCCCCCGGAGCGCCG<br>GCGGCTGTCGAGGCGCGGCGAGCCGCAGCCATTGCCTTTTATGGTAATCGTGCGAGAGGGCGC<br>AGGGACTTCCTTTGTCCCAAATCTGTGCGGAGCCGAAATCTGGGAGGCGCCGCCGCACCCCCT<br>CTAGCGGGCGCGGGGCGAAGCGGTGCGGCGCCGGCAGGAAGGAAATGGGCGGGGAGGGCCTTC<br>GTGCGTCGCCGCGCCGCCGTCCCCTTCTCCCTCTCCAGCCTCGGGGCTGTCCGCGGGGGGACG<br>GCTGCCTTCGGGGGGGACGGGGCAGGGCGGGGTTCGGCTTCTGGCGTGTGACCGGCGGCTCTA<br>GAGCCTCTGCTAACCATGTTCATGCCTTCTTCTTTTTCCTACAGCTCCTGGGCAACGTGCTGG<br>TTATTGTGCTGTCTCATCATTTTGGCAAAGAATTC |
| CB6 Promoter | 1048 | CTAGTCGACATTGATTATTGACTAGTTATTAATAGTAATCAATTACGGGGTCATTAGTTCATA<br>GCCCATATATGGAGTTCCGCGTTACATAACTTACGGTAAATGGCCCGCCTGGCTGACCGCCCA<br>ACGACCCCCGCCCATTGACGTCAATAATGACGTATGTTCCCATAGTAACGCCAATAGGGACTT<br>TCCATTGACGTCAATGGGTGGAGTATTTACGGTAAACTGCCCACTTGGCAGTACATCAAGTGT<br>ATCATATGCCAAGTACGCCCCCTATTGACGTCAATGACGGTAAATGGCCCGCCTGGCATTATG<br>CCCAGTACATGACCTTATGGGACTTTCCTACTTGGCAGTACATCTACGTA |
| CAG Promoter Variant 3 | 1049 | CTAGTTATTAATAGTAATCAATTACGGGGTCATTAGTTCATAGCCCATATATGGAGTTCCGCG<br>TTACATAACTTACGGTAAATGGCCCGCCTGGCTGACCGCCCAACGACCCCCGCCCATTGACGT<br>CAATAATGACGTATGTTCCCATAGTAACGCCAATAGGGACTTTCCATTGACGTCAATGGGTGG<br>AGTATTTACGGTAAACTGCCCACTTGGCAGTACATCAAGTGTATCATATGCCAAGTACGCCCC<br>CTATTGACGTCAATGACGGTAAATGGCCCGCCTGGCATTATGCCCAGTACATGACCTTATGGG<br>ACTTTCCTACTTGGCAGTACATCTACGTATTAGTCATCGCTATTACCATGGTCGAGGTGAGCC<br>CCACGTTCTGCTTCACTCTCCCCATCTCCCCCCCCTCCCCACCCCCAATTTTGTATTTATTTA<br>TTTTTTAATTATTTTGTGCAGCGATGGGGGCGGGGGGGGGGGGGGCGCGCGCCAGGCGGGG<br>CGGGGCGGGCGAGGGGCGGGGCGGGCGAGGCGGAGAGGTGCGGCGGCAGCCAATCAGAGCG<br>GCGCGCTCCGAAAGTTTCCTTTTATGGCGAGGCGGCGGCGGCGGCGGCCCTATAAAAAGCGAA<br>GCGCGCGGCGGGCGGGAGTCGCTGCGCGCTGCCTTCGCCCCGTGCCCCGCTCCGCCGCCGCCT<br>CGCGCCGCCCGCCCCGGCTCTGACTGACCGCGTTACTCCCACAGGTGAGCGGGCGGGACGGCC<br>CTTCTCCTCCGGGCTGTAATTAGCGCTTGGTTTAATGACGGCTTGTTTCTTTTCTGTGGCTGC<br>GTGAAAGCCTTGAGGGGCTCCGGGAGGGCCCTTTGTGCGGGGGGAGCGGCTCGGGGGGTGCGT<br>GCGTGTGTGTGCGTGGGGAGCGCCGCGTGCGGCTCCGCGCTGCCCGGCGGCTGTGAGCGCT<br>GCGGGCGCGGCGCGGGGCTTTGTGCGCTCCGCAGTGTGCGCGAGGGGAGCGCGGCCGGGGGCG<br>GTGCCCCGCGGTGCGGGGGGGGCTGCGAGGGGAACAAAGGCTGCGTGCGGGGTGTGTGCGTGG<br>GGGGGTGAGCAGGGGGTGTGGGCGCGTCGGTCGGGCTGCAACCCCCCCTGCACCCCCCTCCCC<br>GAGTTGCTGAGCACGGCCCGGCTTCGGGTGCGGGGCTCCGTACGGGGCGTGGCGCGGGGCTCG<br>CCGTGCCGGGCGGGGGGTGGCGGCAGGTGGGGGTGCCGGGCGGGGCGGGGCCGCCTCGGGCCG<br>GGGAGGGCTCGGGGGAGGGGCGCGGCGGCCCCCGGAGCGCCGGCGGCTGTCGAGGCGCGGCGA<br>GCCGCAGCCATTGCCTTTTATGGTAATCGTGCGAGAGGGCGCAGGGACTTCCTTTGTCCCAAA<br>TCTGTGCGGAGCCGAAATCTGGGAGGCGCCGCCGCACCCCCTCTAGCGGGCGCGGGGCGAAGC<br>GGTGCGGCGCCGGCAGGAAGGAAATGGGCGGGAGGGCCTTCGTGCGTCGCCGCGCCGCCGTC<br>CCCTTCTCCCTCTCCAGCCTCGGGGCTGTCCGCGGGGGGACGGCTGCCTTCGGGGGGGACGGG<br>GCAGGGCGGGGTTCGGCTTCTGGCGTGTGACCGGCGGCTCTAGAGCCTCTGCTAACCATGTTC<br>ATGCCTTCTTCTTTTTCCTACAGCTCCTGGGCAACGTGCTGGTTATTGTGCTGTCTCATCATT<br>TTGGCAAAGAATT |
| CMVie Promoter Variant 3 | 1050 | GACATTGATTATTGACTAGTTATTAATAGTAATCAATTACGGGGTCATTAGTTCATAGCCCAT<br>ATATGGAGTTCCGCGTTACATAACTTACGGTAAATGGCCCGCCTGGCTGACCGCCCAACGACC<br>CCCGCCCATTGACGTCAATAATGACGTATGTTCCCATAGTAACGCCAATAGGGACTTTCCATT<br>GACGTCAATGGGTGGAGTATTTACGGTAAACTGCCCACTTGGCAGTACATCAAGTGTATCATA<br>TGCCAAGTACGCCCCCTATTGACGTCAATGACGGTAAATGGCCCGCCTGGCATTATGCCCAGT<br>ACATGACCTTATGGGACTTTCCTACTTGGCAGTACATCTACGTATTAGTCATCGCTATTACCA<br>TG |

In some embodiments, the promoter comprises the nucleotide sequence of any one of SEQ ID NOs: 1039-1050, or a sequence with at least 70%, 75%, 80%, 85%, 90%, 95% or 99% sequence identity thereto. In some embodiments, the promoter comprises the nucleotide sequence of SEQ ID NO: 1039 or a sequence with at least 70%, 75%, 80%, 85%, 90%, 95% or 99% sequence identity thereto. In some embodiments, the promoter comprises the nucleotide sequence of SEQ ID NO: 1040, or a sequence with at least 70%, 75%, 80%, 85%, 90%, 95% or 99% sequence identity thereto. In some embodiments, the promoter comprises the nucleotide sequence of SEQ ID NO: 1041, or a sequence with at least 70%, 75%, 80%, 85%, 90%, 95% or 99% sequence identity thereto. In some embodiments, the promoter comprises the nucleotide sequence of SEQ ID NO: 1042, or a sequence with at least 70%, 75%, 80%, 85%, 90%, 95% or 99% sequence identity thereto. In some embodiments, the promoter comprises the nucleotide sequence of SEQ ID NO: 1043, or a sequence with at least 70%, 75%, 80%, 85%, 90%, 95% or 99% sequence identity thereto. In some embodiments, the promoter comprises the nucleotide sequence of SEQ ID NO: 1044, or a sequence with at least 70%, 75%, 80%, 85%, 90%, 95% or 99% sequence identity thereto. In some embodiments, the promoter comprises the nucleotide sequence of SEQ ID NO: 1050, or a sequence with at least 70%, 75%, 80%, 85%, 90%, 95% or 99% sequence identity thereto.

In some embodiments, the CAG promoter comprises the nucleotide sequence of SEQ ID NO: 1039 or nucleotide sequence with at least 70%, 75%, 80%, 85%, 90%, 95%, or 99% sequence identity thereto. In some embodiments, the CBA promoter (e.g., a minimal CBA promoter) comprises the nucleotide sequence of SEQ ID NO: 1041 or nucleotide sequence with at least 70%, 75%, 80%, 85%, 90%, 95%, or 99% sequence identity thereto. In some embodiments, the CB promoter comprises the nucleotide sequence of SEQ ID NO: 1042 or nucleotide sequence with at least 70%, 75%, 80%, 85%, 90%, 95%, or 99% sequence identity thereto. In some embodiments, the GFAP promoter comprises the nucleotide sequence of SEQ ID NO: 1044 or nucleotide sequence with at least 70%, 75%, 80%, 85%, 90%, 95%, or 99% sequence identity thereto. In some embodiments, the snyapsin promoter comprises the nucleotide sequence of SEQ ID NO: 1045 or nucleotide sequence with at least 70%, 75%, 80%, 85%, 90%, 95%, or 99% sequence identity thereto. In some embodiments, the CMV(IE) promoter comprises the nucleotide sequence of SEQ ID NO: 1050 or nucleotide sequence with at least 70%, 75%, 80%, 85%, 90%, 95%, or 99% sequence identity thereto. In some embodiments, the CMV(ie) enhancer comprises e nucleotide sequence of SEQ ID NO: 1040 or nucleotide sequence with at least 70%, 75%, 80%, 85%, 90%, 95%, or 99% sequence identity thereto.

In some embodiments, the viral genome comprises more than one promoter sequence region. In some embodiments, the viral genome comprises two promoter sequence regions. In some embodiments, the viral genome comprises three promoter sequence regions.

Viral Genome Component: Untranslated Regions (UTRs)

In some embodiments, the viral genome comprises an untranslated region (UTR). In some embodiments, a wild type UTR of a gene are transcribed but not translated. In some embodiments, the 5' UTR starts at the transcription start site and ends at the start codon and the 3' UTR starts immediately following the stop codon and continues until the termination signal for transcription.

In some embodiments, a UTR comprises a feature found in abundantly expressed genes of specific target organs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genome of an AAV particle described herein to enhance expression in hepatic cell lines or liver.

In some embodiments, the viral genome comprises a 5'UTR, e.g., a wild-type (e.g., naturally occurring) 5'UTR or a recombinant (e.g., non-naturally occurring) 5'UTR. In some embodiments, a 5' UTR comprises a feature which plays a role in translation initiation. In some embodiments, a UTR, e.g., a 5' UTR, comprises a Kozak sequence. In some embodiments, a Kozak sequence is involved in the process by which the ribosome initiates translation of many genes. In some embodiments, a Kozak sequence has the consensus sequence of CCR(A/G)CCAUGG, where R is a purine (adenine or guanine) three bases upstream of the start codon (ATG), which is followed by another 'G'. In some embodiments, a Kozak sequence comprises the nucleotide sequence of GAGGAGCCACC (SEQ ID NO: 1089) or a nucleotide sequence with at least 95-99% sequence identity thereto. In some embodiments, a Kozak sequence comprises the nucleotide sequence of GCCGCCACCATG (SEQ ID NO: 1079), or a nucleotide sequence with at least 95-99% sequence identity thereto. In some embodiments, a viral genome comprises a 5'UTR comprising a Kozak sequence. In some embodiments, a viral genome comprises a 5'UTR that does not comprise a Kozak sequence.

In some embodiments, the viral genome comprises a 3'UTR, e.g., a wild-type (e.g., naturally occurring) 3'UTR or a recombinant (e.g., non-naturally occurring) 3'UTR. In some embodiments, a 3' UTR comprises an element that modulates, e.g., increases or decreases, stability of a nucleic acid. In some embodiments, a 3' UTR comprises stretches of Adenosines and Uridines embedded therein, e.g., an AU rich signature. These AU rich signatures are generally prevalent in genes with high rates of turnover and are described, e.g., in Chen et al, 1995, the contents of which are herein incorporated by reference in its entirety. In some embodiments, an AR rich signature comprises an AU rich element (ARE). In some embodiments, a 3'UTR comprises an ARE chosen from a class I ARE (e.g., c-Myc and MyoD), a class II ARE (e.g., GM-CSF and TNF-α), a class III ARE (e.g., c-Jun and Myogenin), or combination thereto. In some embodiments, a class I ARE comprises several dispersed copies of an AUUUA motif within U-rich regions. In some embodiments, a class II ARE comprises two or more overlapping UUAUUUA(U/A)(U/A) nonamers. In some embodiments, a class III ARE comprises U rich regions and/or do not contain an AUUUA motif. In some embodiments, an ARE destabilizes the messenger.

In some embodiments, a 3'UTR comprises a binding site for a protein member of the ELAV family. In some embodiments, a 3' UTR comprises a binding site for an HuR protein. In some embodiments, an HuR protein binds to an ARE of any one of classes I-III and/or increases the stability of mRNA. Without wishing to be bound by theory, it is believed in some embodiments, that a 3'UTR comprising an HuR specific binding sites will lead to HuR binding and, stabilization of a message in vivo.

In some embodiments, the 3' UTR of the viral genome comprises an oligo(dT) sequence for templated addition of a poly-A tail.

In some embodiments, the viral genome comprises a miRNA seed, binding site and/or full sequence. Generally, microRNAs (or miRNA or miR) are 19-25 nucleotide non-coding RNAs that bind to the sites of nucleic acid targets and down-regulate gene expression either by reducing nucleic acid molecule stability or by inhibiting translation. In some embodiments, the microRNA sequence comprises a seed region, e.g., a sequence in the region of positions 2-8 of the mature microRNA, which sequence has perfect Watson-Crick complementarity to the miRNA target sequence of the nucleic acid. In some embodiments, the viral genome may be engineered to include, alter or remove at least one miRNA binding site, sequence, or seed region.

In some embodiments, a UTR from any gene known in the art may be incorporated into the AAV particle viral genome described herein. These UTRs, or portions thereof, may be placed in the same orientation as in the gene from which they were selected, or they may be altered in orientation or location. In some embodiments, the UTR used in the viral genome may be inverted, shortened, lengthened, made with one or more other 5' UTRs or 3' UTRs known in the art. In some embodiments, an altered UTR, comprises a UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides. In some embodiments, the viral genome comprises an artificial UTR, e.g., a UTR that is not a variant of a wild-type, e.g., a naturally occurring, UTR. In some embodiments, the viral genome comprises a UTR selected from a family of transcripts whose proteins share a common function, structure, feature or property.

Viral Genome Component: miR Binding Site

Tissue- or cell-specific expression of the AAV viral particles of the invention can be enhanced by introducing tissue- or cell-specific regulatory sequences, e.g., promoters, enhancers, microRNA binding sites, e.g., a detargeting site. Without wishing to be bound by theory, it is believed that an encoded miR binding site can modulate, e.g., prevent, suppress, or otherwise inhibit, the expression of a gene of interest on the viral genome of the invention, based on the expression of the corresponding endogenous microRNA (miRNA) or a corresponding controlled exogenous miRNA in a tissue or cell, e.g., a non-targeting cell or tissue. In some embodiments, a miR binding site modulates, e.g., reduces, expression of the payload encoded by a viral genome of an AAV particle described herein in a cell or tissue where the corresponding mRNA is expressed.

In some embodiments, the viral genome of an AAV particle described herein comprises a nucleotide sequence encoding a microRNA binding site, e.g., a detargeting site. In some embodiments, the viral genome of an AAV particle described herein comprises a nucleotide sequence encoding a miR binding site, a microRNA binding site series (miR BSs), or a reverse complement thereof.

In some embodiments, the nucleotide sequence encoding the miR binding site series or the miR binding site is located in the 3'-UTR region of the viral genome (e.g., 3' relative to the nucleotide sequence encoding a payload), e.g., before the polyA sequence, 5'-UTR region of the viral genome (e.g., 5' relative to the nucleotide sequence encoding a payload), or both.

In some embodiments, the encoded miR binding site series comprise at least 1-5 copies, e.g., at least 1-3, 2-4, 3-5, 1, 2, 3, 4, 5 or more copies of a miR binding site (miR BS). In some embodiments, all copies are identical, e.g., comprise the same miR binding site. In some embodiments, the miR binding sites within the encoded miR binding site series are continuous and not separated by a spacer. In some embodiments, the miR binding sites within an encoded miR binding site series are separated by a spacer, e.g., a non-coding sequence. In some embodiments, the spacer is about 1 to 6 nucleotides or about 5 to 10 nucleotides, e.g., about 7-8 nucleotides, nucleotides in length. In some embodiments, the spacer coding sequence or reverse complement thereof comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, but no more than four modifications of GATAGTTA.

In some embodiments, the encoded miR binding site series comprise at least 1-5 copies, e.g., at least 1-3, 2-4, 3-5, 1, 2, 3, 4, 5 or more copies of a miR binding site (miR BS). In some embodiments, at least 1, 2, 3, 4, 5, or all of the copies are different, e.g., comprise a different miR binding site. In some embodiments, the miR binding sites within the encoded miR binding site series are continuous and not separated by a spacer. In some embodiments, the miR binding sites within an encoded miR binding site series are separated by a spacer, e.g., a non-coding sequence. In some embodiments, the spacer is about 1 to 6 nucleotides or about 5 to 10 nucleotides, e.g., about 7-8 nucleotides, in length. In some embodiments, the spacer comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, but no more than four modifications of GATAGTTA.

In some embodiments, the encoded miR binding site is substantially identical (e.g., at least 70%, 75%, 80%, 85%, 90%, 95%, 99% or 100% identical), to the miR in the host cell. In some embodiments, the encoded miR binding site comprises at least 1, 2, 3, 4, or 5 mismatches or no more than 6, 7, 8, 9, or 10 mismatches to a miR in the host cell. In some embodiments, the mismatched nucleotides are contiguous. In some embodiments, the mismatched nucleotides are non-contiguous. In some embodiments, the mismatched nucleotides occur outside the seed region-binding sequence of the miR binding site, such as at one or both ends of the miR binding site. In some embodiments, the miR binding site is 100% identical to the miR in the host cell.

In some embodiments, the nucleotide sequence encoding the miR binding site is substantially complimentary (e.g., at least 70%, 75%, 80%, 85%, 90%, 95%, 99% or 100% complimentary), to the miR in the host cell. In some embodiments, to complementary sequence of the nucleotide sequence encoding the miR binding site comprises at least 1, 2, 3, 4, or 5 mismatches or no more than 6, 7, 8, 9, or 10 mismatches to a miR in the host cell. In some embodiments, the mismatched nucleotides are contiguous. In some embodiments, the mismatched nucleotides are non-contiguous. In some embodiments, the mismatched nucleotides occur outside the seed region-binding sequence of the miR binding site, such as at one or both ends of the miR binding site. In some embodiments, the encoded miR binding site is 100% complimentary to the miR in the host cell.

In some embodiments, an encoded miR binding site or sequence region is at least about 10 to about 125 nucleotides in length, e.g., at least about 10 to 50 nucleotides, 10 to 100 nucleotides, 50 to 100 nucleotides, 50 to 125 nucleotides, or 100 to 125 nucleotides in length. In some embodiments, an encoded miR binding site or sequence region is at least about 7 to about 28 nucleotides in length, e.g., at least about 8-28 nucleotides, 7-28 nucleotides, 8-18 nucleotides, 12-28 nucleotides, 20-26 nucleotides, 22 nucleotides, 24 nucleotides, or 26 nucleotides in length, and optionally comprises at least one consecutive region (e.g., 7 or 8 nucleotides) complementary (e.g., fully or partially complementary) to the seed sequence of a miRNA (e.g., a miR122, a miR142, a miR183).

In some embodiments, the encoded miR binding site is complementary (e.g., fully or partially complementary) to a miR expressed in liver or hepatocytes, such as miR122. In some embodiments, the encoded miR binding site or encoded miR binding site series comprises a miR122 binding site sequence. In some embodiments, the encoded miR122 binding site comprises the nucleotide sequence of ACAAACACCATTGTCACACTCCA (SEQ ID NO: 1029), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1029, e.g., wherein the modification can result in a mismatch between the encoded miR binding site and the corresponding miRNA. In some embodiments, the viral genome comprises at least 2, 3, 4, or 5 copies of the encoded miR122 binding site, e.g., an encoded miR122 binding site series, optionally wherein the encoded miR122 binding site series comprises the nucleotide sequence of: ACAAACACCATTGTCACACTCCA-CACAAACACCATTGTCACACTCCACACAAACACC-ATTGTCACACT CCA (SEQ ID NO: 1030), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1030, e.g., wherein the modification can result in a mismatch between the encoded miR binding site and the corresponding miRNA. In some embodiments, at least two of the encoded miR122 binding sites are connected directly, e.g., without a spacer. In other embodiments, at least two of the encoded miR122 binding sites are separated by a spacer, e.g., 1, 2, 3, 4, 5, 6, 7, 8, 9, or 10 nucleotides in length, which is located between two or more consecutive encoded miR122 binding site sequences. In embodiments, the spacer is about 1 to 6 nucleotides or about 5 to 10 nucleotides, e.g., about 7-8, in length. In some embodiments, the spacer coding sequence or reverse complement thereof comprises one or more of (i) GGAT; (ii) CACGTG; (iii) GCATGC, or a repeat of one or more of (i)-(iii). In some embodiments, an encoded miR binding site series comprises at least 3-5 copies (e.g., 4 copies) of a miR122 binding site, with or without a spacer, wherein the spacer is about 1 to 6 nucleotides or about 5 to 10 nucleotides, e.g., about 7-8 nucleotides or about 8 nucleotides, in length. In some embodiments, the spacer comprises the nucleotide sequence of GATAGTTA, or a nucleotide sequence having at least one, two, or three modifications, but no more than four modifications of GATAGTTA.

In some embodiments, the encoded miR binding site is complementary (e.g., fully or partially complementary) to a miR expressed in the heart. In embodiments, the encoded miR binding site or encoded miR binding site series comprises a miR-1 binding site. In some embodiments, the encoded miR-1 binding site comprises the nucleotide sequence of ATACATACTTCTTTACATTCCA (SEQ ID NO: 4679), a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications e.g., substitutions (e.g., conservative substitutions), insertions, or deletions, but no more than ten modifications, e.g., substitutions (e.g., conservative substitutions), insertions, or deletions, to SEQ ID NO: 4679, e.g., wherein the modification can result in a mismatch between the encoded miR binding site and the corresponding miRNA. In some embodiments, the viral genome comprises at least 2, 3, 4, or 5 copies of the encoded miR-1 binding site, e.g., an encoded miR-1 binding site series. In some embodiments, the at least 2, 3, 4, or 5 copies (e.g., 2 or 3 copies) of the encoded miR-1 binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer sequence comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, e.g., substitutions (e.g., conservative substitutions), insertions, or deletions, but no more than four modifications, e.g., substitutions (e.g., conservative substitutions), insertions, or deletions, of GATAGTTA.

In some embodiments, the encoded miR binding site is complementary (e.g., fully or partially complementary) to a miR expressed in hematopoietic lineage, including immune cells (e.g., antigen presenting cells or APC, including dendritic cells (DCs), macrophages, and B-lymphocytes). In some embodiments, the encoded miR binding site complementary to a miR expressed in hematopoietic lineage comprises a nucleotide sequence disclosed, e.g., in US 2018/0066279, the contents of which are incorporated by reference herein in its entirety.

In embodiments, the encoded miR binding site or encoded miR binding site series comprises a miR-142-3p binding site sequence. In some embodiments, the encoded miR-142-3p binding site comprises the nucleotide sequence of TCCAT-AAAGTAGGAAACACTACA (SEQ ID NO: 1031), a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1031, e.g., wherein the modification can result in a mismatch between the encoded miR binding site and the corresponding miRNA. In some embodiments, the viral genome comprises at least 2, 3, 4, or 5 copies of the encoded miR-142-3p binding site, e.g., an encoded miR-142-3p binding site series. In some embodiments, the at least 2, 3, 4, or 5 copies (e.g., 2 or 3 copies) of the encoded miR-142-3p binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer sequence comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, but no more than four modifications of GATAGTTA.

In some embodiments, the encoded miR binding site is complementary (e.g., fully complementary or partially complementary) to a miR expressed in a DRG (dorsal root ganglion) neuron, e.g., a miR183, a miR182, and/or miR96 binding site. In some embodiments, the encoded miR binding site is complementary to a miR expressed in expressed in a DRG neuron comprises a nucleotide sequence disclosed, e.g., in WO2020/132455, the contents of which are incorporated by reference herein in its entirety.

In some embodiments, the encoded miR binding site or encoded miR binding site series comprises a miR183 binding site sequence. In some embodiments, the encoded miR183 binding site comprises the nucleotide sequence of AGTGAATTCTACCA<u><u>GTGCCA</u></u>TA (SEQ ID NO: 1032), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1032, e.g., wherein the modification can result in a mismatch between the encoded miR binding site and the corresponding miRNA. In some embodiments, the sequence complementary to the seed sequence corresponds to the double underlined of the encoded miR-183 binding site sequence. In some embodiments, the viral genome comprises at least comprises at least 2, 3, 4, or 5 copies (e.g., at least 2 or 3 copies) of the encoded miR183 binding site, e.g. an encoded miR183 binding site. In some embodiments, the at least 2, 3, 4, or 5 copies (e.g., 2 or 3 copies) of the encoded miR183 binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer comprises the nucleotide sequence of GATAGTTA, or a nucleotide sequence having at least one, two, or three modifications, but no more than four modifications of GATAGTTA. In some embodiments, the spacer sequence comprises one or more of (i) GGAT; (ii) CACGTG; (iii) GCATGC, or a repeat of one or more of (i)-(iii).

In some embodiments, the encoded miR binding site or the encoded miR binding site series comprises a miR182 binding site sequence. In some embodiments, the encoded miR182 binding site comprises, the nucleotide sequence of AGTGTGAGTTCTACCATTGCCAAA (SEQ ID NO: 1033), a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1033, e.g., wherein the modification can result in a mismatch between the encoded miR binding site and the corresponding miRNA. In some embodiments, the viral genome comprises at least 2, 3, 4, or 5 copies of the encoded miR182 binding site, e.g., an encoded miR182 binding site series. In some embodiments, the at least 2, 3, 4, or 5 copies (e.g., 2 or 3 copies) of the encoded miR182 binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer comprises the nucleotide sequence of GATAGTTA, or a nucleotide sequence having at least one, two, or three modifications, but no more than four modifications of GATAGTTA. In some embodiments, the spacer sequence comprises one or more of (i) GGAT; (ii) CACGTG; (iii) GCATGC, or a repeat of one or more of (i)-(iii).

In certain embodiments, the encoded miR binding site or the encoded miR binding site series comprises a miR96 binding site sequence. In some embodiments, the encoded miR96 binding site comprises the nucleotide sequence of of AGCAAAAATGTGCTAGTGCCAAA (SEQ ID NO: 1034), a sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1034, e.g., wherein the modification can result in a mismatch between the encoded miR binding site and the corresponding miRNA. In some embodiments, the viral genome comprises at least 3, 4, or 5 copies of the encoded miR96 binding site, e.g., an encoded miR96 binding site series. In some embodiments, an encoded miR binding site series comprises at least 3-5 copies (e.g., 4 copies) of a miR96 binding site, with or without a spacer, wherein the spacer is at least about 5 to 10 nucleotides, e.g., about 7-8, in length.

In some embodiments, the viral genome comprises at least 2, 3, 4, or 5 copies of the encoded miR96 binding site, e.g., an encoded miR96 binding site series. In some embodiments, the at least 2, 3, 4, or 5 copies (e.g., 2 or 3 copies) of the encoded miR96 binding site are continuous (e.g., not separated by a spacer) or separated by a spacer. In some embodiments, the spacer is about 1 to 6 nucleotides or about 5 to 10 nucleotides, e.g., about 7-8 nucleotides or about 8 nucleotides, in length. In some embodiments, the spacer comprises the nucleotide sequence of GATAGTTA, or a nucleotide sequence having at least one, two, or three modifications, but no more than four modifications of GATAGTTA. In some embodiments, the spacer sequence comprises one or more of (i) GGAT; (ii) CACGTG; (iii) GCATGC, or a repeat of one or more of (i)-(iii).

In some embodiments, the encoded miR binding site series comprises a miR122 binding site, a miR142 binding site, a miR183 binding site, a miR182 binding site, a miR 96 binding site, or a combination thereof. In some embodiments, the encoded miR binding site series comprises at least 2, 3, 4, or 5 copies of a miR122 binding site, a miR1 binding site, a miR142 binding site, a miR183 binding site, a miR182 binding site, a miR 96 binding site, or a combination thereof. In some embodiments, at least two of the encoded miR binding sites are connected directly, e.g., without a spacer. In other embodiments, at least two of the encoded miR binding sites are separated by a spacer, e.g., 1, 2, 3, 4, 5, 6, 7, 8, 9, or 10 nucleotides in length, which is located between two or more consecutive encoded miR binding site sequences. In embodiments, the spacer is at least about 5 to 10 nucleotides, e.g., about 7-8 nucleotides or about 8 nucleotides, in length. In some embodiments, the spacer coding sequence or reverse complement thereof comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, but no more than four modifications of GATAGTTA.

In some embodiments, an encoded miR binding site series comprises at least 2-5 copies (e.g., 2 or 3 copies) of a combination of at least two, three, four, five, six, or all of a miR122 binding site, a mir1 binding site, a miR142 binding site, a miR183 binding site, a miR182 binding site, a miR96 binding site, wherein each of the miR binding sites within the series are continuous (e.g., not separated by a spacer) or are separated by a spacer. In some embodiments, the spacer is about 1 to 6 nucleotides or about 5 to 10 nucleotides, e.g., about 7-8 nucleotides or about 8 nucleotides, in length. In some embodiments, the spacer sequence comprises one or more of (i) GGAT; (ii) CACGTG; (iii) GCATGC, or a repeat of one or more of (i)-(iii). In some embodiments, the spacer comprises the nucleotide sequence of GATAGTTA, or a nucleotide sequence having at least one, two, or three modifications, but no more than four modifications of GATAGTTA.

Viral Genome Component: Exon Sequence Region

In some embodiments, the viral genome may comprise at least one exon sequence region. In some embodiments, the viral genome comprises at least 2, at least 3, at least 4, or at least 5 exon regions. In some embodiments, the viral genome comprises two Exon sequence regions. In some embodiments, the viral genome comprises three Exon sequence regions. In some embodiments, the viral genome comprises four Exon sequence regions. In some embodiments, the viral genome comprises more than four Exon sequence regions.

In some embodiments, the exon region is provided in Table 12. In some embodiments, the exon region comprises the nucleotide sequence of any one of SEQ ID NOs: 1051-1055, or a nucleotide sequence with at least 70%, 75%, 80%, 85%, 90%, 95%, or 99% sequence identity thereto.

TABLE 12

Exon Sequence Regions

| Description | SEQ ID NO | Sequence |
|---|---|---|
| ie1 exon 1-variant 1 | 1051 | TCAGATCGCCTGGAGACGCCATCCACGCTGTTTTGACCTCCATAGAAGA CACCGGGACCGATCCAGCCTCCGCGGATTCGAATCCCGGCCGGGAACGG TGCATTGGAACGCGGATTCCCCGTGCCAAGAGTGAC |
| ie1 exon 1-variant 2 | 1052 | TTGACCTCCATAGAAGACACCGGGACCGATCCAGCCTCCGCGGATTCGA ATCCCGGCCGGGAACGGTGCATTGGAACGCGGATTCCCCGTGCCAAGAG TGAC |
| ie1 exon 1-variant 3 | 1053 | ATTCGAATCCCGGCCGGGAACGGTGCATTGGAACGCGGATTCCCCGTGC CAAGAGTGAC |
| Human beta globin (HBG) exon3 | 1054 | CTCCTGGGCAACGTGCTGGTCTGTGTGCTGGCCCATCACTTTGGCAAAG AATT |
| rabbit beta globin (RBG) exon 3 | 1055 | CTCCTGGGCAACGTGCTGGTTATTGTGCTGTCTCATCATTTTGGCAAAG AATTC |

Viral Genome Component: Intron Sequence Region

In some embodiments, the viral genome comprises at least one element to enhance the expression of a transgene encoding a payload. In some embodiments, an element that enhances expression of a transgene comprises an introns or functional variant thereof. In some embodiments, the viral genome comprises an intron or functional variant thereof. In some embodiments, the viral genome comprises at least two intron regions, e.g., at least 2 intron regions, at least 3 intron regions, at least 4 intron regions, or 5 or more intron regions.

In some embodiments, the viral genome comprises an intron chosen from a MVM intron (67-97 bps), an F.IX truncated intron 1 (300 bps), an β-globin SD/immunoglobulin heavy chain splice acceptor intron (250 bps), an adenovirus splice donor/immunoglobin splice acceptor intron (500 bps), SV40 late splice donor/splice acceptor intron (19S/16S) (180 bps), or a hybrid adenovirus splice donor/IgG splice acceptor intron (230 bps). In some embodiments, the viral genome comprises a human beta-globin intron region.

In some embodiments, the viral genome comprises an intron region provided in Table 13.

TABLE 13

Intron Sequence Regions

| Sequence Region Name | SEQ ID NO | Sequence |
|---|---|---|
| ie1 intron 1-Variant 1 | 1056 | GTAAGTACCGCCTATAGAGTCTATAGGCCCAC |
| ie1 intron 1-Variant 2 | 1057 | GTAAGTACCGCCTAT |
| HBG intron 2-Variant 1 | 1058 | AAAAAATGCTTTCTTCTTTTAATATACTTTTTGTTTATCTTATTTCTAATA CTTTCCCTAATCTCTTTCTTTCAGGGCAATAATGATACAATGTATCATGCCT CTTTGCACCATTCTAAAGAATAACAGTGATAATTTCTGGGTTAAGGCAATAG CAATATTTCTGCATATAAATATTTCTGCATATAAATTGTAACTGATGTAAGA GGTTTCATATTGCTAATAGCAGCTACAATCCAGCTACCATTCTGCTTTTATT TTATGGTTGGGATAAGGCTGGATTATTCTGAGTCCAAGCTAGGCCCTTTTGC TAATCATGTTCATACCTCTTATCTTCCTCCCACAG |
| HBG intron 2-Variant 2 | 1059 | TCTGCATATAAATTGTAACTGATGTAAGAGGTTTCATATTGCTAATAGCAGC TACAATCCAGCTACCATTCTGCTTTTATTTTATGGTTGGGATAAGGCTGGAT TATTCTGAGTCCAAGCTAGGCCCTTTTGCTAATCATGTTCATACCTCTTATC TTCCTCCCACAG |
| HBG intron 2-Variant 3 | 1060 | AAAAAATGCTTTCTTCTTTTAATATACTTTTCTTTTGCTAATCATGTTCATA CCTCTTATCTTCCTCCCACAG |
| HBG intron 2-Variant 4 | 1061 | AGGCTGGATTATTCTGAGTCCAAGCTAGGCCCTTTTGCTAATCATGTTCATA CCTCTTATCTTCCTCCCACAG |
| HBG intron 2-Variant 5 | 1062 | AAAAAATGCTTTCTTCTTTTCAAGCTAGGCCCTTTTGCTAATCATGTTCATA CCTCTTATCTTCCTCCCACAG |
| HBG intron 2-Variant 6 | 1063 | CAAGCTAGGCCCTTTTGCTAATCATGTTCATACCTCTTATCTTCCTCCCACA G |

TABLE 13-continued

Intron Sequence Regions

| Sequence Region Name | SEQ ID NO | Sequence |
| --- | --- | --- |
| SV40 intron | 1064 | GAACTGAAAAACCAGAAAGTTAACTGGTAAGTTTAGTCTTTTTGTCTTTTAT<br>TTCAGGTCCCGGATCCGGTGGTGGTGCAAATCAAAGAACTGCTCCTCAGTGG<br>ATGTTGCCTTTACTTCTAGGCCTGTACGGAAGTGTTACTTCTGCTCTAAAAG<br>CTGCGGAATTGTACCC |
| Chimeric intron | 1065 | GGAGTCGCTGCGCGCTGCCTTCGCCCCGTGCCCCGCTCCGCCGCCGCCTCGC<br>GCCGCCCGCCCCGGCTCTGACTGACCGCGTTACTCCCACAGGTGAGCGGGCG<br>GGACGGCCCTTCTCCTCCGGGCTGTAATTAGCGCTTGGTTTAATGACGGCTT<br>GTTTCTTTTCTGTGGCTGCGTGAAAGCCTTGAGGGGCTCCGGGAGGGCCCTT<br>TGTGCGGGGGGAGCGGCTCGGGGGGTGCGTGCGTGTGTGTGCGTGGGGAG<br>CGCCGCGTGCGGCTCCGCGCTGCCCGGCGGCTGTGAGCGCTGCGGGCGCGGC<br>GCGGGGCTTTGTGCGCTCCGCAGTGTGCGCGAGGGGAGCGCGGCCGGGGGCG<br>GTGCCCCGCGGTGCGGGGGGGGCTGCGAGGGGAACAAAGGCTGCGTGCGGGG<br>TGTGTGCGTGGGGGGGTGAGCAGGGGGTGTGGGCGCGTCGGTCGGGCTGCAA<br>CCCCCCCTGCACCCCCCTCCCCGAGTTGCTGAGCACGGCCCGGCTTCGGGTG<br>CGGGGCTCCGTACGGGGCGTGGCGCGGGGCTCGCCGTGCCGGGCGGGGGGTG<br>GCGGCAGGTGGGGGTGCCGGGCGGGGCGGGGCCGCCTCGGGCCGGGAGGGC<br>TCGGGGGAGGGCGCGGCGGCCCCCGGAGCGCCGGCGGCTGTCGAGGCGCGG<br>CGAGCCGCAGCCATTGCCTTTTATGGTAATCGTGCGAGAGGGCGCAGGGACT<br>TCCTTTGTCCCAAATCTGTGCGGAGCCGAAATCTGGGAGGCGCCGCCGCACC<br>CCCTCTAGCGGGCGCGGGGCGAAGCGGTGCGGCGCCGGCAGGAAGGAAATGG<br>GCGGGGAGGGCCTTCGTGCGTCGCCGCGCCGCCGTCCCCTTCTCCCTCTCCA<br>GCCTCGGGGCTGTCCGCGGGGGGACGGCTGCCTTCGGGGGGACGGGGCAGG<br>GCGGGGTTCGGCTTCTGGCGTGTGACCGGCGGCTCTAGAGCCTCTGCTAACC<br>ATGTTCATGCCTTCTTCTTTTTCCTACAGCTCCTGGGCAACGTGCTGGTTAT<br>TGTGCTGTCTCATCATTTTGGCAAAGAATTCGAG |
| Rbt betaglobin intron 2 | 1066 | CCTCTGCTAACCATGTTCATGCCTTCTTCTTTTTCCTACAG |
| HGB intron variant 1 | 1067 | TCAGATCGCCTGGAGAGCGCCATCCACGCTGTTTTGACCTCCATAGAAGACAC<br>CGGGACCGATCCAGCCTCCGCGGATTCGAATCCCGGCCGGGAACGGTGCATT<br>GGAACGCGGATTCCCCGTGCCAAGAGTGACGTAAGTACCGCCTATAGAGTCT<br>ATAGGCCCACAAAAAATGCTTTCTTCTTTTAATATACTTTTTTGTTTATCTT<br>ATTTCTAATACTTTCCCTAATCTCTTTCTTCAGGGCAATAATGATACAATG<br>TATCATGCCTCTTTGCACCATTCTAAAGAATAACAGTGATAATTTCTGGGTT<br>AAGGCAATAGCAATATTTCTGCATATAAATATTTCTGCATATAAATTGTAAC<br>TGATGTAAGAGGTTTCATATTGCTAATAGCAGCTACAATCCAGCTACCATTC<br>TGCTTTTATTTTATGGTTGGGATAAGGCTGGATTATTCTGAGTCCAAGCTAG<br>GCCCTTTTGCTAATCATGTTCATACCTCTTATCTTCCTCCCACAGCTCCTGG<br>GCAACGTGCTGGTCTGTGTGCTGGCCCATCACTTTGGCAAAGAATT |
| HGB intron variant 2 | 1068 | ATTCGAATCCCGGCCGGGAACGGTGCATTGGAACGCGGATTCCCCGTGCCAA<br>GAGTGACGTAAGTACCGCCTATAGAGTCTATAGGCCCACAAAAAATGCTTTC<br>TTCTTTTAATATACTTTTTTGTTTATCTTATTTCTAATACTTTCCCTAATCT<br>CTTTCTTTCAGGGCAATAATGATACAATGTATCATGCCTCTTTGCACCATTC<br>TAAAGAATAACAGTGATAATTTCTGGGTTAAGGCAATAGCAATATTTCTGCA<br>TATAAATATTTCTGCATATAAATTGTAACTGATGTAAGAGGTTTCATATTGC<br>TAATAGCAGCTACAATCCAGCTACCATTCTGCTTTTATTTTATGGTTGGGAT<br>AAGGCTGGATTATTCTGAGTCCAAGCTAGGCCCTTTTGCTAATCATGTTCAT<br>ACCTCTTATCTTCCTCCCACAGCTCCTGGGCAACGTGCTGGTCTGTGTGCTG<br>GCCCATCACTTTGGCAAAGAATT |
| HGB intron variant 3 | 1069 | TCAGATCGCCTGGAGACGCCATCCACGCTGTTTTGACCTCCATAGAAGACAC<br>CGGGACCGATCCAGCCTCCGCGGATTCGAATCCCGGCCGGGAACGGTGCATT<br>GGAACGCGGATTCCCCGTGCCAAGAGTGACGTAAGTACCGCCTATAGAGTCT<br>ATAGGCCCACTCTGCATATAAATTGTAACTGATGTAAGAGGTTTCATATTGC<br>TAATAGCAGCTACAATCCAGCTACCATTCTGCTTTTATTTTATGGTTGGGAT<br>AAGGCTGGATTATTCTGAGTCCAAGCTAGGCCCTTTTGCTAATCATGTTCAT<br>ACCTCTTATCTTCCTCCCACAGCTCCTGGGCAACGTGCTGGTCTGTGTGCTG<br>GCCCATCACTTTGGCAAAGAATT |
| HGB intron variant 4 | 1070 | TCAGATCGCCTGGAGACGCCATCCACGCTGTTTTGACCTCCATAGAAGACAC<br>CGGGACCGATCCAGGTAAGTACCGCCTATAGAGTCTATAGGCCCACAAAAAA<br>TGCTTTCTTCTTTTAATATACTTTTTTGTTTATCTTATTTCTAATACTTTCC<br>CTAATCTCTTTCGCTGGATTATTCTGAGTCCAAGCTAGGCCCTTTTGCTAAT<br>CATGTTCATACCTCTTATCTTCCTCCCACAGCTCCTGGGCAACGTGCTGGTC<br>TGTGTGCTGGCCCATCACTTTGGCAAAGAATT |

In some embodiments, the viral genome comprises an intron region of any one of SEQ ID NOs: 1056-1070, or a sequence with at least 70%, 75%, 80%, 85%, 90%, 95%, or 99% sequence identity thereto. In some embodiments, the viral genome comprises an intron comprising the nucleotide sequence of SEQ ID NO: 1067, or a nucleotide sequence with at least 70%, 75%, 80%, 85%, 90%, 95%, or 99% sequence identity thereto.

In some embodiments, the viral genome comprises two intron sequence regions. In some embodiments, the viral genome comprises three intron sequence regions. In some embodiments, the viral genome comprises more than three intron sequence regions.

Viral Genome Component: Polyadenylation Sequence Region

In some embodiments, the viral genome may comprise at least one polyadenylation sequence region. In some embodiments, the viral genome comprises a polyadenylation (referred to herein as poly A, polyA, or poly-A) sequence between the 3' end of the transgene encoding the payload and the 5' end of the 3'ITR. In some embodiments, the viral genome comprises two or more polyA sequences. In some embodiments, the viral genome does not comprise a polyA sequence.

antibody or fragment thereof described herein (e.g., an anti-tau antibody), comprises a nucleic acid comprising a transgene encoding a payload. In some embodiments, the payload comprises an antibody, e.g., an anti-tau antibody. In some embodiments, the payload comprises a secreted protein, an intracellular protein, an extracellular protein, a membrane protein, a structural protein, a functional protein, or a protein, e.g., a mammalian protein, involved in immune system regulation. In some embodiments, a nucleic acid comprises a transgene encoding an antibody that binds to tau.

In some embodiments, the nucleic acid molecule comprising the transgene encoding a payload further comprises a nucleotide sequence encoding a linker (e.g., a linker connecting a heavy chain variable region (VH) and a light chain variable region (VL) of an antibody) and/or a cleavage site. In some embodiments, the nucleic acid molecule comprising the transgene encoding a payload further comprises a nucleotide sequence encoding a signal sequence.

In some embodiments, the nucleic acid encoding the payload may be constructed, e.g., organized, similar to, e.g., mirroring, the natural organization of an mRNA. In some embodiments, the nucleic acid encoding the payload may comprise coding and/or non-coding nucleotide sequences. In

TABLE 17

Exemplary Poly-A Signal Sequence Regions

| SEQ ID NO | Sequence |
| --- | --- |
| 1134 | GATCTTTTTCCCTCTGCCAAAAATTATGGGGACATCATGAAGCCCCTTGAGCATCTGAC<br>TTCTGGCTAATAAAGGAAATTTATTTTCATTGCAATAGTGTGTTGGAATTTTTTGTGTC<br>TCTCACTCG |
| 1135 | GGGTGGCATCCCTGTGACCCCTCCCCAGTGCCTCTCCTGGCCCTGGAAGTTGCCACTCC<br>AGTGCCCACCAGCCTTGTCCTAATAAAATTAAGTTGCATCATTTTGTCTGACTAGGTGT<br>CCTTCTATAATATTATGGGGTGGAGGGGGGTGGTATGGAGCAAGGGGCAAGTTGGGAAG<br>ACAACCTGTAGGGCCTGCGGGGTCTATTGGGAACCAAGCTGGAGTGCAGTGGCACAATC<br>TTGGCTCACTGCAATCTCCGCCTCCTGGGTTCAAGCGATTCTCCTGCCTCAGCCTCCCG<br>AGTTGTTGGGATTCCAGGCATGCATGACCAGGCTCAGCTAATTTTTGTTTTTTGGTAG<br>AGACGGGGTTTCACCATATTGGCCAGGCTGGTCTCCAACTCCTAATCTCAGGTGATCTA<br>CCCACCTTGGCCTCCCAAATTGCTGGGATTACAGGCGTGAACCACTGCTCCCTTCCCTG<br>TCCTT |
| 1136 | GAATTCACTCCTCAGGTGCAGGCTGCCTATCAGAAGGTGGTGGCTGGTGTGGCCAATGC<br>CCTGGCTCACAAATACCACTGAGATCTTTTTCCCTCTGCCAAAAATTATGGGGACATCA<br>TGAAGCCCCTTGAGCATCTGACTTCTGGCTAATAAAGGAAATTTATTTTCATTGCAATA<br>GTGTGTTGGAATTTTTTGTGTCTCTCACTCGGAAGGACATATGGAGGGCAAATCATTT<br>AAAACATCAGAATGAGTATTTGGTTTAGAGTTTGGCAACATATGCCCATATGCTGGCTG<br>CCATGAACAAAGGTTGGCTATAAAGAGGTCATCAGTATATGAAACAGCCCCTGCTGTC<br>CATTCCTTATTCCATAGAAAAGCCTTGACTTGAGGTTAGATTTTTTTATATTTTGTTT<br>TGTGTTATTTTTTCTTTAACATCCCTAAAATTTTCCTTACATGTTTTACTAGCCAGAT<br>TTTTCCTCCTCTCCTGACTACTCCCAGTCATAGCTGTCCCTCTTCTCTTATGGAGATCC<br>CTCGACCTGCAGCCCAAGCTT |

In some embodiments, the polyA signal region comprises the nucleotide sequence of any one of SEQ ID NOs: 1134-1136, or a sequence with at least 70%, 75%, 80%, 85%, 90%, 95%, or 99% sequence identity thereto. In some embodiments, the polyA signal sequence comprises the nucleotide sequence of SEQ ID NO: 1134, or a sequence with at least 70%, 75%, 80%, 85%, 90%, 95%, or 99% sequence identity thereto.

Viral Genome Component: Payload

In some embodiments, an AAV particle, e.g., an AAV particle for the vectorized delivery of an antibody or fragment thereof described herein (e.g., an anti-tau antibody), comprises a payload. In some embodiments, an AAV particle described herein comprises at least two, at least three, or at least 4 payloads. In some embodiments, an AAV particle, e.g., an AAV particle for the vectorized delivery of an some embodiments, the nucleic acid encoding the payload may encode a coding and/or a non-coding RNA.

In such an embodiment, the nucleic acid comprising a transgene encoding a payload (e.g., an antibody or fragment thereof) is replicated and packaged into an AAV particle. In some embodiments, following transduction of a cell with an AAV particle comprising a payload (e.g., an antibody or fragment thereof), the cell expresses the payload. In some embodiments, the payload, e.g., antibody or fragment thereof, produced by a cell transduced by an AAV particle comprising the payload, is secreted from the cell.

In some embodiments, the encoded payload of a viral genome described herein comprises an anti-tau antibody or functional variant, e.g., fragment, thereof. In some embodiments, the functional variant is a humanized variant, such as a humanized variant comprising any one or more (e.g., all 6)

CDR regions of any one of the antibodies in Table 4. In some embodiments, the encoded payload of a viral genome described herein comprises an anti-tau antibody or functional variant thereof described in WO 2021/211753, the contents of which are hereby incorporated by reference in its entirety.

In some embodiments, the nucleotide the encoded antibody comprises a heavy chain variable region (VH) and/or a light chain variable region (VL) sequences, e.g., as provided in Table 4, or variants or fragments thereof; optionally the polypeptide(s) further comprises a heavy chain constant region and/or a light chain constant region, such as those listed in Table 5. The encoded antibody may constitute a full-length antibody (e.g., comprising a VH and a heavy chain constant region, such as those listed in Table 5; and a VL and a light chain constant region, such as those listed in Table 5), or an antibody fragment thereof, such as Fab, F(ab')₂, scFv, etc. The encoded antibody may also comprise a linker between the heavy and light chain sequences or the VH and VL sequences. In some embodiments, the encoded heavy chain or VH is located N-terminal relative to the encoded light chain or VL. In some embodiments, the encoded light chain or VL is located N-terminal relative to the encoded heavy chain or VH.

In some embodiments, the nucleotide sequence encoding the anti-tau antibody comprises, in the 5' to 3' direction, a nucleotide sequence encoding an light chain or a nucleotide sequence encoding a VL, a linker, and a nucleotide sequence encoding a heavy chain or a nucleotide sequence encoding a VH (e.g., light-linker-heavy or L.Linker.H or LH). In another embodiment, the nucleotide sequence encoding the payload does not comprise a linker.

In some embodiments, the nucleotide sequence encoding the anti-tau antibody comprises, in the 5' to 3' direction, a nucleotide sequence encoding an heavy chain or a nucleotide sequence encoding a VH, a linker, and a nucleotide sequence encoding a light chain or a nucleotide sequence encoding a VL (e.g., heavy-linker-light or H.Linker.L or HL). In another embodiment, the nucleotide sequence encoding the payload does not comprise a linker.

In some embodiments, the viral genome comprises a nucleotide sequence encoding a heavy chain. In some embodiments, the encoded heavy chain comprises an amino acid sequence or fragment thereof as provided in Table 4, and/or 5.

In some embodiments, the viral genome comprises a nucleotide sequence encoding a light chain. In some embodiments, the encoded light chain comprises an amino acid sequence or fragments thereof as provided in Table 4, and/or 5.

In some embodiments, the viral genome comprises a nucleotide sequence encoding an anti-tau antibody, wherein the encoded anti-tau antibody comprises at least one antigen-binding domain, e.g., a variable region or antigen binding fragment thereof, from an antibody described herein, e.g., from V0004, V0009, V0022, V0023, V0024, or V0052, e.g., as described in Tables 1 or 4, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises at least one antigen-binding domain, e.g., a variable region or antigen binding fragment thereof, from an antibody described in WO 2021/211753, the contents of which are hereby incorporated by reference in its entirety, or a sequence substantially identical (e.g., having at least about 70%, 75%, 80%, 85%, 90%, 92%, 95%, 97%, 98%, or 99% sequence identity) to any of the antibody sequences disclosed in WO 2021/211753.

In some embodiments, the encoded anti-tau antibody comprises a heavy chain variable region from an antibody described herein, e.g., chosen from V0004, V0009, V0022, V0023, V0024, or V0052, e.g., as described in Table 4, or a sequence substantially identical (e.g., having at least about 70%, 75%, 80%, 85%, 90%, 92%, 95%, 97%, 98%, or 99% sequence identity) to any of the aforesaid sequences. In some embodiments, the heavy chain variable region comprises an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a heavy chain variable region provided in Table 4.

In some embodiments, the nucleotide sequence encoding the anti-tau antibody comprises the nucleotide sequence of a heavy chain variable region from an antibody described herein, e.g., chosen from V0004, V0009, V0022, V0023, V0024, or V0052, e.g., as described in Table 3 or 4, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the encoded anti-tau antibody comprises a light chain variable region from an antibody described herein, e.g., chosen from V0004, V0009, V0022, V0023, V0024, or V0052, e.g., as described in Table 4, or a sequence substantially identical (e.g., having at least about 70%, 75%, 80%, 85%, 90%, 92%, 95%, 97%, 98%, or 99% sequence identity) to any of the aforesaid sequences. In some embodiments, the light chain variable region comprises an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a light chain variable region provided in Table 4.

In some embodiments, the nucleotide sequence encoding the anti-tau antibody comprises the nucleotide sequence of a light chain variable region from an antibody described herein, e.g., chosen from V0004, V0009, V0022, V0023, V0024, or V0052, e.g., as described in Table 4, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the encoded anti-tau antibody comprises a heavy chain variable region and a light chain variable region from an antibody described herein, e.g., chosen from V0004, V0009, V0022, V0023, V0024, or V0052, e.g., as described in Table 4, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region comprising an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a heavy chain variable region provided in Table 4; and a light chain variable region comprising an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a light chain variable region provided in Table 4.

In some embodiments, the anti-tau antibody comprises a heavy chain constant region, e.g., a human IgG1, IgG2, IgG3, or IgG4 constant regions, or a murine IgG1, IgG2A, IgG2B, IgG2C, or IgG3 constant regions. In some embodiments, the heavy chain constant comprises an amino acid sequence set forth in Table 5, or a sequence substantially identical (e.g., having at least about 70%, 75%, 80%, 85%, 90%, 92%, 95%, 97%, 98%, or 99% sequence identity) to any of the aforesaid sequences. In some embodiments, a nucleic acid encoding the heavy chain constant region comprises a nucleotide sequence set forth in Table 5, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the encoded anti-tau antibody comprises a light chain constant region, e.g., a kappa light chain constant region, e.g., a human kappa or lambda light chain constant region or a murine kappa or lambda light chain constant region. In some embodiments, the light chain constant comprises an amino acid sequence set forth in Table 5, or a sequence substantially identical (e.g., having at least about 70%, 75%, 80%, 85%, 90%, 92%, 95%, 97%, 98%, or 99% sequence identity) to any of the aforesaid sequences. In some embodiments, nucleic acid encoding the light chain constant region comprises a nucleotide sequence set forth in Table 5, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the encoded anti-tau antibody comprises a heavy chain constant region and a light chain constant region. In some embodiments, the heavy chain constant region and the light chain constant region comprise an amino acid sequence set forth in Table 5, or a sequence substantially identical (e.g., having at least about 80%, 85%, 90%, 92%, 95%, 97%, 98%, or 99% sequence identity) thereto. In some embodiments, the nucleotide sequence encoding the anti-tau antibody comprises the nucleotide sequence of a heavy chain constant region and the nucleotide sequence of a kappa or lambda light chain constant region. In some embodiments, the nucleotide sequence encoding the heavy chain constant region and light chain constant region comprise a nucleotide sequence set forth in Table 5, or a nucleotide sequence substantially identical (e.g., having at least about 80%, 85%, 90%, 92%, 95%, 97%, 98%, or 99% sequence identity) thereto.

In some embodiments, the encoded anti-tau antibody comprises a heavy chain variable region and a constant region, a light chain variable region and a constant region, or both, comprising an amino acid sequence of Table 4 for variable region, and an amino acid sequence of Table 5 for constant region; or is encoded by a nucleic acid sequence of Table 4, and 5; or a sequence substantially identical (e.g., having at least about 80%, 85%, 90%, 92%, 95%, 97%, 98%, or 99% sequence identity) to any of the aforesaid sequences.

In some embodiments, the encoded anti-tau antibody comprises at least one, two, or three complementarity determining regions (CDRs) from a heavy chain variable region comprising an amino acid sequence in Table 4, or is encoded by a nucleic acid sequence in Table 4; or a sequence substantially identical (e.g., having at least about 70%, 75%, 80%, 85%, 90%, 92%, 95%, 97%, 98%, or 99% sequence identity) to any of the aforesaid sequences. In some embodiments, one, two, three, four, five, or all of the CDRs have one, two, three, four, five or more changes, e.g., amino acid substitutions, insertions, or deletions, relative to the amino acid sequence shown in Table 4, or encoded by a nucleotide sequence shown in Table 4. In some embodiments, the encoded anti-tau antibody includes a substitution in a heavy chain CDR, e.g., one or more substitutions in a CDR1, CDR2 and/or CDR3 of the heavy chain.

In some embodiments, the encoded anti-tau antibody comprises at least one, two, or three complementarity determining regions (CDRs) from a light chain variable region comprising an amino acid sequence in Table 4, or is encoded by a nucleic acid sequence in Table 4; or a sequence substantially identical (e.g., having at least about 80%, 85%, 90%, 92%, 95%, 97%, 98%, or 99% sequence identity) to any of the aforesaid sequences. In some embodiments, one, two, three, four, five, or all of the CDRs have one, two, three, four, five or more changes, e.g., amino acid substitutions, insertions, or deletions, relative to the amino acid sequence shown in Table 4, or encoded by a nucleotide sequence shown in Table 4. In some embodiments, the anti-tau antibody includes a substitution in a light chain CDR, e.g., one or more substitutions in a CDR1, CDR2 and/or CDR3 of the light chain.

In some embodiments, the encoded anti-tau antibody comprises at least one, two, three, four, five or six CDRs (or collectively all of the CDRs) from a heavy and light chain variable region comprising an amino acid sequence shown in Table 4, or is encoded by a nucleotide sequence shown in Table 4. In some embodiments, one or more of the CDRs (or collectively all of the CDRs) have one, two, three, four, five, six or more changes, e.g., amino acid substitutions, insertions, or deletions, relative to the CDRs shown in Table 4, or encoded by a nucleotide sequence shown in Table 4.

In some embodiments, the encoded anti-tau antibody comprises all three CDRs from a heavy chain variable region, all three CDRs from light chain variable region, or both (e.g., all six CDRs from a heavy chain variable region and a light chain variable region) comprising an amino acid sequence shown in Table 4, or is encoded by a nucleotide sequence shown in Table 4.

In some embodiments, an encoded anti-tau antibody of the present disclosure may include CDRs identified through CDR analysis of variable domain sequences presented herein via co-crystallography with bound antigen; by computational assessments based on comparisons with other antibodies (e.g., see Strohl, W. R. Therapeutic Antibody Engineering. Woodhead Publishing, Philadelphia PA. 2012. Ch. 3, p 47-54); or Kabat, Chothia, Al-Lazikani, Lefranc, or Honegger numbering schemes, as described previously.

In some embodiments, the viral genome may comprise one or more components which have been codon-optimized. Codon-optimization may be achieved by any method known to one with skill in the art such as, but not limited to, by a method according to Genscript, EMBOSS, Bioinformatics, NUS, NUS2, Geneinfinity, IDT, NUS3, GregThatcher, Insilico, Molbio, N2P, Snapgene, and/or VectorNTI. Antibody heavy and/or light chain sequences within the same viral genome may be codon-optimized according to the same or according to different methods.

The viral genome may encode an antibody fragment, such as, but not limited to Fab, $F(ab')^2$ or scFv fragments. In some embodiments, the viral genome encodes a Fab antibody fragment. In another embodiment, the viral genome encodes an $F(ab')_2$ antibody fragment. In some embodiments, the viral genome encodes an scFv.

This disclosure also provides in some embodiments, nucleic acids, cells, AAV vectors, and AAV particles comprising the above viral genome.

Payload Component: Signal Sequence Region

In some embodiments, the nucleotide sequence comprising the transgene encoding the payload, e.g., an antibody or fragment thereof, comprises a nucleotide sequence encoding a signal sequence (e.g., a signal sequence region herein). In some embodiments, the nucleotide sequence comprising the transgene encoding the payload comprises two signal sequence regions. In some embodiments, the nucleotide sequence comprising the transgene encoding the payload comprises three or more signal sequence regions.

In some embodiments, the nucleotide sequence encoding the signal sequence is located 5' relative to the nucleotide sequence encoding the VH and/or the heavy chain. In some embodiments, the nucleotide sequence encoding the signal sequence is located 5' relative to the nucleotide sequence encoding the VL and/or the light chain. In some embodiments, the encoded VH, VL, heavy chain, and/or light chain of the encoded antibody comprises a signal sequence at the N-terminus, wherein the signal sequence is optionally cleaved during cellular processing and/or localization of the antibody.

In some embodiments, the signal sequence comprises any one of the signal sequences provided in Table 14 or a functional variant thereof. In some embodiments, the encoded signal sequence comprises an amino acid sequence encoded by any one of the nucleotide sequences provided in Table 14, or an amino acid sequence with at least 70%, 75%, 80%, 85%, 90%, 95%, or 99% sequence identity thereto. In some embodiments, the nucleotide sequence encoding the signal sequence comprises any one of the nucleotide sequences provided in Table 14, or a nucleotide sequence with at least 70%, 75%, 80%, 85%, 90%, 95%, or 99% sequence identity thereto.

In some embodiments, the nucleotide sequence encoding the signal sequence comprises the nucleotide sequence of SEQ ID NO: 1083, or a nucleotide sequence with at least 70%, 75%, 80%, 85%, 90%, 95%, or 99% sequence identity thereto. In some embodiments, the nucleotide sequence is located 5' relative to the nucleotide sequence encoding the VH and/or heavy chain of the antibody. In some embodiments, the nucleotide sequence encoding the signal sequence comprises the nucleotide sequence of SEQ ID NO: 1083 and is located 5' relative to the nucleotide sequence encoding the VH and/or heavy chain of the antibody.

In some embodiments, the nucleotide sequence encoding the signal sequence comprises the nucleotide sequence of SEQ ID NO: 1085, or a nucleotide sequence with at least 70%, 75%, 80%, 85%, 90%, 95%, or 99% sequence identity thereto. In some embodiments, the nucleotide sequence is located 5' relative to the nucleotide sequence encoding the VL and/or light chain of the antibody. In some embodiments, the nucleotide sequence encoding the signal sequence comprises the nucleotide sequence of SEQ ID NO: 1085 and is located 5' relative to the nucleotide sequence encoding the VL and/or light chain of the antibody.

In some embodiments, the encoded signal sequence comprises the amino acid sequence of SEQ ID NO: 1; an amino acid sequence comprising one, two, three, but no more than four different amino acids relative to SEQ ID NO: 1; an amino acid sequence comprising one, two, three, but no more than four modifications, e.g., substitutions (e.g., conservative substitutions), relative to SEQ ID NO: 1; or an amino acid sequence with at least 70%, 75%, 80%, 85%, 90%, 95%, or 99% sequence identity thereto. In some embodiments, the encoded signal sequence is located N-terminal relative to the encoded VH and/or heavy chain of the encoded antibody. In some embodiments, the encoded signal sequence comprises the amino acid sequence of SEQ ID NO: 1 and is located N-terminal to the encoded VH and/or heavy chain of the encoded antibody.

In some embodiments, the encoded signal sequence comprises the amino acid sequence of SEQ ID NO: 2; an amino acid sequence comprising one, two, three, but no more than four different amino acids relative to SEQ ID NO: 2; an amino acid sequence comprising one, two, three, but no more than four modifications, e.g., substitutions (e.g., conservative substitutions), relative to SEQ ID NO: 2; or an amino acid sequence with at least 70%, 75%, 80%, 85%, 90%, 95%, or 99% sequence identity thereto. In some embodiments, the encoded signal sequence is located N-terminal relative to the encoded VL and/or light chain of the encoded antibody. In some embodiments, the encoded signal sequence comprises the amino acid sequence of SEQ ID NO: 2 and is located N-terminal to the encoded VL and/or light chain of the encoded antibody.

TABLE 14

Signal Sequence Regions

| Sequence Region Name | SEQ ID NO | Sequence |
|---|---|---|
| Signal 1 (hGH-2 (84)) | 1071 | ATGGCGACGGGTTCAAGAACTTCCCTACTTCTTGCATTTGGCCTGCTTTGTTTGCCG TGGTTACAGGAGGGCTCGGCAGCTGCC |
| Signal 2 (hGH-2 (93)) | 1072 | GCCGCCACCATGGCGACGGGTTCAAGAACTTCCCTACTTCTTGCATTTGGCCTGCTT TGTTTGCCGTGGTTACAGGAGGGCTCGGCAGCTGCC |
| Signal 3 (EPOh) | 1073 | GCCGCCACCATGGGGGTGCACGAATGTCCTGCCTGGCTGTGGCTTCTCCTGTCCCTG CTGTCGCTCCCTCTGGGCCTCCCAGTCCTGGGCGCTGCC |
| Signal 4 (Gaussia Luc 100) | 1074 | GCCGCCACCATGGGAGTCAAAGTTCTGTTTGCCCTGATCTGCATCGCTGTGGCCGAG GCCGCTGCC |
| Signal 5 (H3) | 1075 | GCCGCCACCATGAAACACCTGTGGTTCTTCCTCCTGCTGGTGGCAGCTCCCAGATGG GTCCTGTCCGCTGCC |
| Signal 6 (H8) | 1076 | GCCGCCACCATGGACCTCCTGCACAAGAACATGAAACACCTGTGGTTCTTCCTCCTC CTGGTGGCAGCTCCCAGATGGGTGCTGTCCGCTGCC |

TABLE 14-continued

Signal Sequence Regions

| Sequence Region Name | SEQ ID NO | Sequence |
|---|---|---|
| Signal 7 (hCtry59) | 1077 | GCCGCCACCATGGCTTTCCTCTGGCTCCTCTCCTGCTGGGCCCTCCTGGGTACCACCTTCGGCGCTGCC |
| Signal 8 (HMM24) | 1078 | GCCGCCACCATGCCCCCCAAGAAGTGCCTGCTGCTGCTGCTGACCCTGCTGCTGCTGATCTCCACCACCTTCGGCGCTGCC |
| Signal 9 (Kozak) | 1079 | GCCGCCACCATG |
| Signal 10 (L1) | 1080 | GCCGCCACCATGGACATGAGGGTCCCTGCTCAGCTCCTGGGGCTCCTGCTGCTCTGGCTCTCAGGTGCCAGATGTGCTGCC |
| Signal 11 (Lucia) | 1081 | GCCGCCACCATGGAAATCAAGGTGCTGTTTGCCCTCATCTGTATTGCTGTTGCTGAGGCAGCTGCC |
| Signal 12 (pSEc) | 1082 | GCCGCCACCATGGAGACAGACACACTCCTGCTATGGGTACTGCTGCTCTGGGTTCCAGGTTCCACTGGTGACGCTGCC |
| Signal 13 DNA (HC signal) | 1083 | ATGAACTTCGGGCTCAGCTTGATTTTCCTTGTCCTTGTTTTAAAAGGTGTCCAGTGT |
| Signal 13 Amino acid (HC signal) | 1 | MNFGLSLIFLVLVLKGVQC |
| Signal 14 (HC signal) | 1084 | ATGGGATGGAGCTGGATCTTTCTCTTTCTCCTGTCAGGAACTACAGGTGTCCTCTCT |
| Signal 15 DNA (LC signal) | 1085 | ATGAAGTTGCCTGTTAGGCTGTTGGTGCTGATGTTCTGGATTCCTGCTTCCAGCAGT |
| Signal 15 Amino Acid (LC signal) | 2 | MKLPVRLLVLMFWIPASSS |
| Signal 16 (HC signal) | 1086 | ATGAACTTCGGGCTCAGCTTGATTTTCCTTGTCCTTGTTTTAAAAGGTGTCCAGTGTGAGGTGAAGCTGGTGGAGAGCGGCGGCGACCTGGTGAAGCCTGGCGGCAGCCTGAAGCTGAGCTGCGCCGCCAGCGGCTTCACCTTCAGCAGCTACGCCATGAGCTGGGTGAGACAGAACCCTGAGAAGAGACTGGAGTGGGTGGCCAGCATCAGCAAGGGCGGCAACACCTACTACCCTAACAGCGTGAAGGGCAGATTCACCATCAGCAGAGACAACGCCAGAAACATCCTGTACCTGCAGATGAGCAGCCTGAGAAGCGAGGACACCGCCCTGTACTACTGCGCCAGAGGCTGGGGCGACTACGGCTGGTTCGCCTACTGGGGCCAGGTGACCCTGGTGACCGTGAGCGCC |
| Signal 17 (HC signal) | 203 | MGWTLVFLFLLSVTAGVHS |
| Signal 17 DNA (HC signal) | 204 | ATGGGCTGGACCCTGGTGTTTCTCTTCCTGCTGAGCGTGACCGCCGGCGTGCACAGC |
| Signal 18 (LC signal) | 205 | MVSSAQFLGLLLLCFQGTRC |
| Signal 18 DNA (LC signal) | 206 | ATGGTGAGCAGCGCTCAGTTCCTGGGCCTGCTGCTGCTGTGTTTTCAAGGCACAAGATGT |
| Signal 18 DNA (LC signal) | 207 | ATGGTGAGCAGCGCTCAGTTCCTGGGCCTGCTGCTGCTGTGCTTCCAAGGCACAAGATGC |
| Signal 18 DNA (LC signal) | 208 | ATGGTGAGCAGCGCTCAGTTCCTGGGCCTGCTGCTGCTGTGTTTCCAAGGGACAAGATGT |

Payload Component: Linkers

In some embodiments, the nucleic acid encoding the payload, e.g., an antibody (e.g., an anti-tau antibody described herein), comprises a nucleotide sequence encoding a linker. In some embodiments, the nucleic acid encoding the payload encodes two or more linkers. In some embodiments, the encoded linker comprises a linker provided in Table 15. In some embodiments, the encoded linker comprises an amino acid sequence encoded by any one of the nucleotide sequences provided in Table 15, or an amino acid sequence with at least 70%, 75%, 80%, 85%, 90%, 95%, or 99% sequence identity thereto. In some embodiments, the nucleotide sequence encoding the linker comprises any one of the nucleotide sequences provided in Table 15, or a nucleotide sequence with at least 70%, 75%, 80%, 85%, 90%, 95%, or 99% sequence identity thereto.

In some embodiments, the nucleotide sequence encoding the linker sequence(s) comprises the nucleotide sequence of any one of SEQ ID NOs: 1724-1739, 2244-2259, 5161, 5162, 5243, 5347, or 5348, or a sequence having at least 70%, 75%, 80%, 85%, 90%, 95%, or 99% sequence identity thereto. In some embodiments, the encoded linker comprises the amino acid sequence of any one of SEQ ID NOs: 601-609; an amino acid sequence comprising one, two, three, but no more than four different amino acids relative to any one of SEQ ID NOs: 601-609; an amino acid sequence comprising one, two, three, but no more than four modifications, e.g., substitutions (e.g., conservative substitutions) relative to any one of SEQ ID NOs: 601-609; or an amino acid sequence having at least 70%, 75%, 80%, 85%, 90%, 95%, or 99% sequence identity to any one of SEQ ID NOs: 601-609.

TABLE 15

Linkers

| Description | SEQ ID NO | Sequence |
| --- | --- | --- |
| Furin | 1724 | AGAAAGAGGCGA |
| Furin | 1725 | CGGGCCAAGCGG |
| T2A | 1726 | GAGGGCAGAGGAAGTCTTCTAACATGCGGTGACGTGGAGGAGAATCCCGGCCCT |
| F2A | 1727 | GGAAGCGGAGTGAAACAGACTTTGAATTTTGACCTTCTCAAGTTGGCGGGAGACGTGGAGTCCAACCCTGGACCT |
| P2A | 1728 | GGAAGCGGAGCTACTAACTTCAGCCTGCTGAAGCAGGCTGGAGACGTGGAGGAGAACCCTGGACCT |
| SG4S (SEQ ID NO: 3) | 1729 | TCCGGAGGCGGCGGCAGC |
| (G4S)3 (SEQ ID NO: 5348) DNA | 1730 | GGTGGTGGTGGTAGCGGCGGCGGCGGCTCTGGTGGTGGTGGATCC |
| (G4S)5 (SEQ ID NO: 604) DNA | 1731 | GGCGGAGGTGGCTCCGGAGGCGGAGGCAGCGGCGGAGGTGGGTCTGGCGGAGGCGGGTGCGGCGGAGGTGGCTCC |
| IRES | 1732 | AATTCCGCCCCTCTCCCCCCCCCCCTCTCCCTCCCCCCCCCCTAACGTTACTGGCCGAAGCCGCTTGGAATAAGGCCGGTGTGCGTTTGTCTATATGTTATTTTCCACCATATTGCCGTCTTTTGGCAATGTGAGGGCCCGGAAACCTGGCCCTGTCTTCTTGACGAGCATTCCTAGGGGTCTTTCCCCTCTCGCCAAAGGAATGCAAGGTCTGTTGAATGTCGTGAAGGAAGCAGTTCCTCTGGAAGCTTCTTGAAGACAAACAACGTCTGTAGCGACCCTTTGCAGGCAGCGGAACCCCCCACCTGGCGACAGGTGCCTCTGCGGCCAAAAGCCACGTGTATAAGATACACCTGCAAAGGCGGCACAACCCCAGTGCCACGTTGTGAGTTGGATAGTTGTGGAAAGAGTCAAATGGCTCTCCTCAAGCGTATTCAACAAGGGGCTGAAGGATGCCCAGAAGGTACCCCATTGTATGGGATCTGATCTGGGGCCTCGGTGCACATGCTTTACATGTGTTTAGTCGAGGTTAAAAAAACGTCTAGGCCCCCCGAACCACGGGGACGTGGTTTTCCTTTGAAAAACACGATGATAATATGGCCACAACC |
| IRES-2 | 1733 | TAACGAATTCCGCCCCTCTCCCCCCCCCCCTCTCCCTCCCCCCCCCCTAACGTTACTGGCCGAAGCCGCTTGGAATAAGGCCGGTGTGCGTTTGTCTATATGTTATTTTCCACCATATTGCCGTCTTTTGGCAATGTGAGGGCCCGGAAACCTGGCCCTGTCTTCTTGACGAGCATTCCTAGGGGTCTTTCCCCTCTCGCCAAAGGAATGCAAGGTCTGTTGAATGTCGTGAAGGAAGCAGTTCCTCTGGAAGCTTCTTGAAGACAAACAACGTCTGTAGCGACCCTTTGCAGGCAGCGGAACCCCCCACCTGGCGACAGGTGCCTCTGCGGCCAAAAGCCACGTGTATAAGATACACCTGCAAAGGCGGCACAACCCCAGTGCCACGTTGTGAGTTGGATAGTTGTGGAAAGAGTCAAATGGCTCTCCTCAAGCGTATTCAACAAGGGGCTGAAGGATGCCCAGAAGGTACCCCATTGTATGGGATCTGATCTGGGGCCTCGGTGCACATGCTTTACATGTGTTTAGTCGAGGTTAAAAAAACGTCTAGGCCCCCCGAACCACGGGGACGTGGTTTTCCTTTGAAAAACACGATGATAATATGGCCACAACCGCCGCCACC |
| hIgG2 hinge | 1734 | GTGGAGAGGAAGTGCTGCGTGGAGTGCCCACCATGCCCTGCCCCTCCTGTGGCC |
| hIgG3 hinge | 1735 | GAGCTCAAAACCCCACTTGGTGACACAACTCACACATGCCCACGGTGCCCAGAGCCCAAATCTTGTGACACACCTCCCCCGTGCCCACGGTGCCCAGCACCTGAACTC |
| hIgG3-2 hinge | 1736 | GAGCTCAAAACCCCACTTGGTGACACAACTCACACATGCCCACGGTGCCCAGAGCCCAAATCTTGTGACACACCTCCCCCGTGCCCACGGTGCCCAGAGCCCAAATCTTGTGACACACCTCCCCATGCCCACGGTGCCCAGCACCTGAACTC |
| hIgG3-3 hinge | 1737 | GAGCTCAAAACCCCACTTGGTGACACAACTCACACATGCCCACGGTGCCCAGAGCCCAAATCTTGTGACACACCTCCCCCGTGCCCACGGTGCCCAGAGCCCAAATCTTGTGACACACCTCCCCCGTGCCCAAGGTGCCCAGCACCTGAACTC |

TABLE 15-continued

Linkers

| Description | SEQ ID NO | Sequence |
| --- | --- | --- |
| msiGG-1 hinge | 1738 | GTGCCCAGGGATTGTGGTTGTAAGCCTTGCATATGTACAGTCCCA |
| msiGG1 hinge | 1739 | GTGCCCAGGGATTGTGGT |
| HigG3 hinge | 2244 | GAGCTCAAAACCCCACTTGGTGACACAACTCACACATGCCCACGGTGCCCAGAGCCC<br>AAATCTTGTGACACACCTCCCCCGTGCCCACGGTGCCCAGAGCCCAAATCTTGTGAC<br>ACAACTCACACATGCCCACGGTGCCCAGAGCCCAAATCTTGTGACACACCTCCCCCG<br>TGCCCAAGGTGCCCAGCACCTGAACTC |
| G4S (SEQ ID NO: 601) DNA | 2245 | GGTGGTGGTGGATCC |
| G4S Amino Acid | 601 | GGGGS |
| (G4S)2 (SEQ ID NO: 602) DNA | 2246 | GGTGGTGGTGGATCCGGTGGTGGTGGATCC |
| (G4S)2 Amino Acid | 602 | GGGGSGGGGS |
| (G4S)3 (SEQ ID NO: 5348) DNA | 2247 | GGTGGTGGTGGATCCGGTGGTGGTGGATCCGGTGGTGGTGGATCC |
| (G4S)4 (SEQ ID NO: 603) DNA | 2248 | GGTGGTGGTGGATCCGGTGGTGGTGGATCCGGTGGTGGTGGATCCGGTGGTGGTGGA<br>TCC |
| (G4S)4 Amino Acid | 603 | GGGGSGGGGSGGGGSGGGGS |
| (G4S)5 (SEQ ID NO: 604) DNA | 2249 | GGTGGTGGTGGTAGCGGCGGCGGCGGCTCTGGTGGTGGTGGATCCGGTGGTGGTGGA<br>TCCGGTGGTGGTGGATCC |
| (G4S)5 Amino Acid | 604 | GGGGSGGGGSGGGGSGGGGSGGGGS |
| (G4S)5 (SEQ ID NO: 604) DNA | 2250 | GGTGGTGGTGGATCCGGTGGTGGTGGATCCGGTGGTGGTGGATCCGGTGGTGGTGGA<br>TCCGGTGGTGGTGGATCC |
| (G4S)6 (SEQ ID NO: 605) DNA | 2251 | GGTGGTGGTGGTAGCGGCGGCGGCGGCTCTGGTGGTGGTGGATCCGGTGGTGGTGGA<br>TCCGGTGGTGGTGGATCCGGTGGTGGTGGATCC |
| (G4S)6 Amino Acid | 605 | GGGGSGGGGSGGGGSGGGGSGGGGSGGGGS |
| (G4S)8 (SEQ ID NO: 607) DNA | 2252 | GGTGGTGGTGGTAGCGGCGGCGGCGGCTCTGGTGGTGGTGGATCCGGTGGTGGTGGA<br>TCCGGTGGTGGTGGATCCGGTGGTGGTGGATCCGGTGGTGGTGGATCCGGTGGTGGT<br>GGATCC |
| (G4S)8 (SEQ ID NO: 607) DNA | 2253 | GGTGGTGGTGGATCCGGTGGTGGTGGATCCGGTGGTGGTGGATCCGGTGGTGGTGGA<br>TCCGGTGGTGGTGGATCCGGTGGTGGTGGATCCGGTGGTGGTGGATCCGGTGGTGGT<br>GGATCC |
| (G4S)8 Amino Acid | 607 | GGGGSGGGGSGGGGSGGGGSGGGGSGGGGSGGGGSGGGGS |
| (G4S)4 (SEQ ID NO: 603) DNA | 2254 | GGTGGTGGTGGTAGCGGCGGCGGCGGCTCTGGTGGTGGTGGATCCGGTGGTGGTGGA<br>TCC |
| (G4S)6 (SEQ ID NO: 605) DNA | 2259 | GGTGGTGGTGGATCCGGTGGTGGTGGATCCGGTGGTGGTGGATCCGGTGGTGGTGGA<br>TCCGGTGGTGGTGGATCCGGTGGTGGTGGATCC |
| G4S (SEQ ID NO: 601) DNA | 5161 | GGAGGAGGAGGAAGT |

TABLE 15-continued

Linkers

| Description | SEQ ID NO | Sequence |
|---|---|---|
| G4S (SEQ ID NO: 601) DNA | 5162 | GGAGGTGGAGGTTCT |
| G4S Amino Acid | 608 | GGGGS |
| GS DNA | 5243 | GGCTCT |
| GS Amino Acid | 609 | GS |
| (G4S)3 (SEQ ID NO: 5348) DNA | 5347 | GGTGGTGGTGGATCCGGAGGAGGAGGAAGTGGAGGTGGAGGTTCT |
| (G4S)3 Amino acid | 5348 | GGGGSGGGGSGGGGS |

In some embodiments, any of the antibodies described herein can have a linker, e.g., a flexible polypeptide linker, of varying lengths, connecting the variable domains (e.g., the VH and the VL) of the antigen binding domain of the antibody. For example, a (Gly4-Ser) n linker, wherein n is 0, 1, 2, 3, 4, 5, 6, 7, or 8 (SEQ ID NO: 802) can be used (e.g., any one of SEQ ID NOs: 1730-1731, 2245-2254, 2259, 5161-5162, 5347, or 5348). In some embodiments, the antibody binds to tau.

In some embodiments, the encoded linker comprises an enzymatic cleavage site, e.g., for intracellular and/or extracellular cleavage. In some embodiments, the linker is cleaved to separate the VH and the VL of the antigen binding domain and/or the heavy chain and light chain of the antibody (e.g., an anti-tau antibody described herein). In some embodiments, the encoded linker comprises a furin linker or a functional variant. In some embodiments, the nucleotide sequence encoding the furin linker comprises the nucleotide sequence of SEQ ID NO: 1724, or a nucleotide sequence with at least 70%, 75%, 80%, 85%, 90%, 95%, or 99% sequence identity thereto. In some embodiments, furin cleaves proteins downstream of a basic amino acid target sequence (e.g., Arg-X-(Arg/Lys)-Arg) (e.g., as described in Thomas, G., 2002. Nature Reviews Molecular Cell Biology 3 (10): 753-66; the contents of which are herein incorporated by reference in its entirety). In some embodiments, the encoded linker comprises a 2A self-cleaving peptide (e.g., a 2A peptide derived from foot-and-mouth disease virus (F2A), porcine teschovirus-1 (P2A), Thoseaasigna virus (T2A), or equine rhinitis A virus (E2A)).

In some embodiments, the encoded linker comprises a T2A self-cleaving peptide linker. In some embodiments, the nucleotide sequence encoding the T2A linker comprises the nucleotide sequence of SEQ ID NO: 1726, or a nucleotide sequence with at least 70%, 75%, 80%, 85%, 90%, 95%, or 99% sequence identity thereto. In some embodiments, the nucleic acid encoding the payload encodes a furin linker and a T2A linker.

Exemplary Viral Genome Encoding an Anti-Tau Antibody

In some embodiments, a viral genome, e.g., an AAV viral genome, described herein, comprises a promoter operably linked to a transgene encoding an anti-tau antibody. In some embodiments, the viral genome further comprises an inverted terminal repeat region, an enhancer, an intron, a polyA region, or a combination thereof. In some embodiments, the AAV viral genome further comprises a miR binding site.

In some embodiments, the viral genome comprises an inverted terminal repeat sequence region (ITR) provided in Table 10, or a nucleotide sequence with at least 70%, 75%, 80%, 85%, 90%, 95% or 99% sequence identity to any of the ITR sequences in Table 10.

This disclosure also provides in some embodiments, an antibody encoded by any of the nucleotide sequences provided in Table 4 and 5 or a nucleotide sequence having at least about 70%, 75%, 80%, 85%, 90%, 92%, 95%, 97%, 98%, or 99% sequence identity) to any of the aforesaid sequences. In some embodiments, the encoded antibody comprises an amino acid sequence provided in Table 4 and 5 or a nucleotide sequence having at least about 70%, 75%, 80%, 85%, 90%, 92%, 95%, 97%, 98%, or 99% sequence identity) to any of the aforesaid sequences.

In some embodiments, the viral genome of an AAV particle described herein comprises the nucleotide sequence, e.g., the nucleic acid sequence from the 5' ITR to the 3' ITR, of any of the nucleotide sequences in Tables 18 and 19, or a nucleotide sequence substantially identical (e.g., having at least about 70%, 75%, 80%, 85%, 90%, 92%, 95%, 97%, 98%, or 99% sequence identity) to any of the aforesaid sequences.

TABLE 18

Exemplary ITR-ITR sequences

| SEQ ID NO: | Sequence |
|---|---|
| 15 | ctgcgcgctcgctcgctcactgaggccgcccgggcaaagcccgggcgtcgggcgacctttggtcgcccg<br>gcctcagtgagcgagcgagcgcgcagagagggagtggccaactccatcactaggggttccttgtagtta<br>atgattaacccgccatgctacttatctaccagggtaatggggatcctctagaactatagctagtcGACA<br>TTGATTATTGACTAGTTATTAATAGTAATCAATTACGGGGTCATTAGTTCATAGCCCATATATGGAGTT<br>CCGCGTTACATAACTTACGGTAAATGGCCCGCCTGGCTGACCGCCCAACGACCCCCGCCCATTGACGTC<br>AATAATGACGTATGTTCCCATAGTAACGCCAATAGGGACTTTCCATTGACGTCAATGGGTGGAGTATTT<br>ACGGTAAACTGCCCACTTGGCAGTACATCAAGTGTATCATATGCCAAGTACGCCCCCTATTGACGTCAA<br>TGACGGTAAATGGCCCGCCTGGCATTATGCCCAGTACATGACCTTATGGGACTTTCCTACTTGGCAGTA<br>CATCTACGTATTAGTCATCGCTATTACCATGtcgaggccacgttctgcttcactctcccatctccccc<br>cctccccaccccaatttgtatttatttattttttaattattttgtgcagcgatggggcgggggg<br>ggggcgcgccaggcggggcggggcggggcgagggcggggcgaggcggagaggtgcggcgg<br>cagccaatcagagcggcgcgctccgaaagtttccttttatggcgaggcggcggcggcggcggccctata<br>aaaagcgaagcgcgcggcgggcgggagcaagcttcgtttagtgaaccgtcagatcgcctggagacgcca<br>tccacgctgttttgacctccatagaagacaccgggaccgatccagcctccgcggattcgaatcccggcc<br>gggaacggtgcattggaacgcggattcccgtgccaagagtgacgtaagtaccgcctatagagtctata<br>ggcccacaaaaaatgctttcttcttttaatatacttttttgtttatcttatttctaatactttccctaa<br>tctctttctttcagggcaataatgatacaatgtatcatgcctctttgcaccattctaaagaataacagt<br>gataaatttctgggttaaggcaatagcaatatttctgcatataaatatttctgcatataaattgtaactg<br>atgtaagaggtttcatattgctaatagcagctacaatccagctaccattctgcttttatttttatggttg<br>ggataaggctggattattctgagtccaagctaggcccttttgctaatcatgttcatacctcttatcttc<br>ctcccacagctcctgggcaacgtgctggtctgtgtgctggcccatcactttggcaaagaattgggattc<br>gaaccggtgccgccaccatgaacttcgggctcagcttgattttccttgtccttgttttaaaaggtgtcc<br>agtgtcaagtgcagctgcagcagcctggcaccgagctggtgaaacctggatctagcgtgaatctgagct<br>gcaaggccagcggctttaccttcaccagatactggatgcactgggtcaaggaacggccaggccacggcc<br>tggaatggatcggcaatatcaaccccaacaacggcggaacagatttcaacgagaagttcaagaacaagg<br>ctacactgaccgtgcacaaaagctccaccaccgtgttcatccagctgagctctctgacaagcgaggaca<br>gcgccgtgtactattgtgccagaggcaccggcaccggcgccatggactactggggccagggaacatctg<br>tgacagtgtccagcgccaaaacgacacccccatctgtctatccactggccctggatctgctgcccaaa<br>ctaactccatggtgaccctgggatgcctggtcaagggctatttccctgagccagtgacagtgacctgga<br>actctggatccctgtccagcggtgtgcacaccttccagctgtcctgcagtctgacctctacactctga<br>gcagctcagtgactgtccctccagcacctggcccagcgagaccgtcacctgcaacgttgcccacccgg<br>ccagcagcaccaaggtggacaagaaaattgtgcccagggattgtggttgtaagccttgcatatgtacag<br>tcccagaagtatcatctgtcttcatcttcccccaaagcccaaggatgtgctcaccattactctgactc<br>ctaaggtcacgtgtgttgtggtagacatcagcaaggatgatcccgaggtccagttcagctggtttgtag<br>atgatgtggaggtgcacacagctcagacgcaaccccgggaggagcagttcaacagcactttccgctcag<br>tcagtgaacttcccatcatgcaccaggactggctcaatggcaaggagttcaaatgcagggtcaacagtg<br>cagctttccctgcccccatcgagaaaaccatctccaaaaccaaaggcagaccgaaggctccacaggtgt<br>acaccattccacctcccaaggagcagatggccaaggataaagtcagtctgacctgcatgataacagact<br>tcttccctgaagacattactgtggagtggcagtggaatgggcagccagcggagaactacaagaacactc<br>agcccatcatggacacagatggctcttacttcgtctacagcaagctcaatgtgcagaagagcaactggg<br>aggcaggaaatactttcacctgctctgtgttacatgagggcctgcacaaccaccatactgagaagagcc<br>tctcccactctcctggtAgaaagaggcgagagggcagaggaagtcttctaacatgcggtgacgtggagg<br>agaatcccggccctatgaagttgcctgttaggctgttggtgctgatgttctggattcctgcttccagca<br>gtgatgtggtgatgacacagaccctctgagcctgcctgtgtcctcggcgaccaggccagcatcagct<br>gtagaagcagccaatctctggtgcacaacaatggcatcacctacctgtactggtatctgcagaaacctg<br>gccagagcccaagctgctgatctaccgggtgtccaatcggttcagcggagtgccagatagatttggcg<br>gatctggcagcggcaccgacttcaccctgaagatctctagagtcgaggccgaggacctgggcgtgtact<br>tctgcttccagggcacacagtgcccagaaccttcggcggcggaacaaagctggaaatcaagcgggctg<br>atgctgcaccaactgtatccatcttcccaccatccagtgagcagttaacatctggaggtgcctcagtcg<br>tgtgcttcttgaacaacttctaccccaaagacatcaatgtcaagtggaagattgatggcagtgaacgac<br>aaaatggcgtcctgaacagttggactgatcaggacagcaaagacagcacctacagcatgagcagcaccc<br>tcacgttgaccaaggacgagtatgaacgacataacagctataccgtgaggccactcacaagacatcaa<br>cttcacccattgtcaagagcttcaacaggaatgagtgttaactcgagagacggggtgaactacgcctgag<br>gatccgatcttttcctctgccaaaaattatggggacatcatgaagcccttgagcatctgacttctg<br>gctaataaaggaaatttattttcattgcaatagtgtgttggaattttttgtgtctctcactcggcctag<br>gtagataagtagcatggcgggttaatcattaactacaaggaaccctagtgatggagttggccactccc<br>tctctgcgcgctcgctcgctcactgaggccgggcgaccaaaggtcgcccgacgcccggctttgcccgg<br>gcggcctcagtgagcgagcgagcgcgcag |

TABLE 19

Exemplary Viral Genome (ITR to ITR) sequences

| SEQ ID NO: | Description (5' to 3') |
|---|---|
| 15 | ITR (SEQ ID NO: 1035); CMVie enhance (SEQ ID NO: 1050); CBA promoter (SEQ ID NO: 1042); intron (SEQ ID NO: 1067); nucleotide sequence encoding a signal sequence (SEQ ID NO: 1083); nucleotide sequence encoding VH (SEQ ID NO: 7); a nucleotide sequence encoding an IgG1 heavy chain constant region (SEQ ID NO: 805); a furin |

TABLE 19-continued

Exemplary Viral Genome (ITR to ITR) sequences

SEQ ID
NO: Description (5' to 3')

cleavage site (SEQ ID NO: 1724); a T2A linker (SEQ ID NO: 1726); a nucleotide sequence
encoding a signal sequence (SEQ ID NO: 1085); a nucleotide sequence encoding a VL
(SEQ ID NO: 11); a nucleotide sequence encoding a IgG kappa light chain constant region
(SEQ ID NO: 17); polyA sequence (SEQ ID NO: 1134); ITR (SEQ ID NO: 1037)

In some embodiments, the viral genome of an AAV particle described herein comprises a nucleotide sequence comprising the all of the components or a combination of the components as described, e.g., in Tables 18 and 19, or a sequence having at least 70%, 75%, 80%, 85%, 90%, 95%, or 99% sequence identity to any of the aforesaid sequences.

In some embodiments, the present disclosure provides an anti-tau antibody encoded by the nucleotide sequence of SEQ ID NO: 15, or a nucleotide sequence having at least 70%, 75%, 80%, 85%, 90%, 95%, or 99% sequence identity thereto.

In some embodiments, a viral genome, e.g., a viral genome encoding an anti-tau antibody described herein, comprises the nucleotide sequence of SEQ ID NO: 15, or a nucleotide sequence having at least 70%, 75%, 80%, 85%, 90%, 95%, or 99% sequence identity thereto.

AAV Production

The present disclosure provides methods for the generation of parvoviral particles, e.g. AAV particles, by viral genome replication in a viral replication cell.

In accordance with the disclosure, the viral genome comprising a payload region encoding an antibody, an antibody-based composition or fragment thereof, will be incorporated into the AAV particle produced in the viral replication cell. Methods of making AAV particles are well known in the art and are described in e.g., U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353, and WO2001023597; Methods In Molecular Biology, ed. Richard, Humana Press, NJ (1995); O'Reilly et al., Baculovirus Expression Vectors, A Laboratory Manual, Oxford Univ. Press (1994); Samulski et al., *J. Vir.*63:3822-8 (1989); Kajigaya et al., *Proc. Nat'l. Acad. Sci. USA* 88:4646-50 (1991); Ruffing et al., *J. Vir.* 66:6922-30 (1992); Kimbauer et al., *Vir.*, 219:37-44 (1996); Zhao et al., *Vir.*272:382-93 (2000); the contents of each of which are herein incorporated by reference in their entirety. In some embodiments, the AAV particles are made using the methods described in WO2015191508, the contents of which are herein incorporated by reference in their entirety.

Viral replication cells commonly used for production of recombinant AAV viral vectors include but are not limited to 293 cells, COS cells, HeLa cells, KB cells, and other mammalian cell lines as described in U.S. Pat. Nos. 6,156,303, 5,387,484, 5,741,683, 5,691,176, and 5,688,676; U.S. patent publication No. 2002/0081721, and International Patent Publication Nos. WO 00/47757, WO 00/24916, and WO 96/17947, the contents of each of which are herein incorporated by reference in their entireties.

In some embodiments, the AAV particles of the present disclosure may be produced in insect cells (e.g., Sf9 cells).

In some embodiments, the AAV particles of the present disclosure may be produced using triple transfection.

In some embodiments, the AAV particles of the present disclosure may be produced in mammalian cells.

In some embodiments, the AAV particles of the present disclosure may be produced by triple transfection in mammalian cells.

In some embodiments, the AAV particles of the present disclosure may be produced by triple transfection in HEK293 cells.

The present disclosure provides a method for producing an AAV particle comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, 5) harvesting and purifying the viral particle comprising a parvoviral genome.

In some embodiments, the present disclosure provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome.

In some embodiments, the viral construct vector(s) used for AAV production may contain a nucleotide sequence encoding the AAV capsid proteins where the initiation codon of the AAV VP1 capsid protein is a non-ATG, i.e., a suboptimal initiation codon, allowing the expression of a modified ratio of the viral capsid proteins in the production system, to provide improved infectivity of the host cell. In a non-limiting example, a viral construct vector may contain a nucleic acid construct comprising a nucleotide sequence encoding AAV VP1, VP2, and VP3 capsid proteins, wherein the initiation codon for translation of the AAV VP1 capsid protein is CTG, TTG, or GTG, as described in U.S. Pat. No. 8,163,543, the contents of which are herein incorporated by reference in its entirety.

In some embodiments, the viral construct vector(s) used for AAV production may contain a nucleotide sequence encoding the AAV rep proteins where the initiation codon of the AAV rep protein or proteins is a non-ATG. In some embodiments, a single coding sequence is used for the Rep78 and Rep52 proteins, wherein initiation codon for translation of the Rep78 protein is a suboptimal initiation codon, selected from the group consisting of ACG, TTG, CTG and GTG, that effects partial exon skipping upon expression in insect cells, as described in U.S. Pat. No. 8,512,981, the contents of which is herein incorporated by reference in its entirety, for example to promote less abundant expression of Rep78 as compared to Rep52, which may be advantageous in that it promotes high vector yields.

In some embodiments, the viral genome of the AAV particle optionally encodes a selectable marker. The selectable marker may comprise a cell-surface marker, such as any protein expressed on the surface of the cell including, but not limited to receptors, CD markers, lectins, integrins, or truncated versions thereof.

In some embodiments, selectable marker reporter genes are selected from those described in International Application No. WO 96/23810; Heim et al., Current Biology 2:178-182 (1996); Heim et al., Proc. Natl. Acad. Sci. USA (1995); or Heim et al., Science 373:663-664 (1995); WO 96/30540, the contents of each of which are incorporated herein by reference in their entireties).

The AAV viral genomes encoding an anti-tau antibody payload described herein may be useful in the fields of human disease, veterinary applications and a variety of in vivo and in vitro settings. The AAV particles of the present disclosure may be useful in the field of medicine for the treatment, prophylaxis, palliation or amelioration of neurological diseases and/or disorders. In some embodiments, the AAV particles are used for the prevention and/or treatment of a tauopathy.

Various embodiments herein provide a pharmaceutical composition comprising the AAV particles described herein and a pharmaceutically acceptable excipient.

Various embodiments herein provide a method of treating a subject in need thereof comprising administering to the subject a therapeutically effective amount of the pharmaceutical composition described herein.

Certain embodiments of the method provide that the subject is treated by a route of administration of the pharmaceutical composition selected from the group consisting of intravenous, intracerebroventricular, intraparenchymal, intrathecal, subpial and intramuscular, or a combination thereof. Certain embodiments of the method provide that the subject is treated for a tauopathy and/or other neurological disorder. In one aspect of the method, a pathological feature of the tauopathy or other neurological disorder is alleviated and/or the progression of the tauopathy or other neurological disorder is halted, slowed, ameliorated or reversed.

Various embodiments herein describe a method of decreasing the level of soluble tau in the central nervous system of a subject in need thereof comprising administering to said subject an effective amount of the pharmaceutical composition described herein.

Also described herein are compositions, methods, processes, kits and devices for the design, preparation, manufacture and/or formulation of AAV particles. In some embodiments, payloads, such as but not limited to anti-tau antibodies, may be encoded by payload constructs or contained within plasmids or vectors or recombinant adeno-associated viruses (AAVs).

The present disclosure also provides administration and/or delivery methods for vectors and viral particles, e.g., AAV particles, for the treatment or amelioration of neurological disease, such as, but not limited to tauopathy.

III. Formulation and Delivery

Pharmaceutical Compositions

Compounds and AAV particles disclosed herein may be prepared as pharmaceutical compositions. As used herein the term "pharmaceutical composition" refers to compositions including at least one active ingredient and, most often, a pharmaceutically acceptable excipient.

Relative amounts of the active ingredient (e.g. an antibody), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may include between 0.1% and 99% (w/w) of the active ingredient. By way of example, the composition may include between 0.1% and 100%, e.g., between 0.5 and 50%, between 1-30%, between 5-80%, at least 80% (w/w) active ingredient.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, rats, birds, including commercially relevant birds such as poultry, chickens, ducks, geese, and/or turkeys.

In some embodiments, compositions are administered to humans, human patients, or subjects.

Formulations

Compounds and AAV particles of the present disclosure can be formulated using one or more excipients to: (1) increase stability; (2) increase cell permeability; (3) permit the sustained or delayed release (e.g., from a sustained release formulation); and/or (4) alter the biodistribution (e.g., target an antibody to specific tissues or cell types). In addition to traditional excipients such as any and all solvents, dispersion media, diluents, or other liquid vehicles, dispersion or suspension aids, surface active agents, isotonic agents, thickening or emulsifying agents, preservatives, formulations of the present disclosure can include, without limitation, liposomes, lipid nanoparticles, polymers, lipoplexes, core-shell nanoparticles, peptides, proteins, transfected cells (e.g., for transplantation into a subject) and combinations thereof.

Pharmaceutical compositions described herein may be prepared by methods known or hereafter developed in the art of pharmacology. Such preparatory methods may include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition including a predetermined amount of the active ingredient. The amount of the active ingredient is generally equal to the dosage of the active ingredient which would be administered to a subject and/or a convenient fraction of such a dosage such as, for example, one-half or one-third of such a dosage.

In some embodiments, the AAV particles may be formulated in phosphate buffered saline (PBS), in combination with an ethylene oxide/propylene oxide copolymer (also known as Pluronic or poloxamer).

In some embodiments, the AAV particles may be formulated in PBS with 0.001% Pluronic acid (F-68) (poloxamer 188) at a pH of about 7.0.

In some embodiments, the AAV particles may be formulated in PBS with 0.001% Pluronic acid (F-68) (poloxamer 188) at a pH of about 7.3.

In some embodiments, the AAV particles may be formulated in PBS with 0.001% Pluronic acid (F-68) (poloxamer 188) at a pH of about 7.4.

In some embodiments, the AAV particles may be formulated in a solution comprising sodium chloride, sodium phosphate and an ethylene oxide/propylene oxide copolymer.

In some embodiments, the AAV particles may be formulated in a solution comprising sodium chloride, sodium phosphate dibasic, sodium phosphate monobasic and poloxamer 188/Pluronic acid (F-68).

In some embodiments, the AAV particles may be formulated in a solution comprising about 180 mM sodium chloride, about 10 mM sodium phosphate and about 0.001% poloxamer 188. In some embodiments, this formulation may be at a pH of about 7.3. The concentration of sodium chloride in the final solution may be 150 mM-200 mM. As non-limiting examples, the concentration of sodium chloride in the final solution may be 150 mM, 160 mM, 170 mM, 180 mM, 190 mM or 200 mM. The concentration of sodium phosphate in the final solution may be 1 mM-50 mM. As non-limiting examples, the concentration of sodium phosphate in the final solution may be 1 mM, 2 mM, 3 mM, 4 mM, 5 mM, 6 mM, 7 mM, 8 mM, 9 mM, 10 mM, 15 mM, 20 mM, 25 mM, 30 mM, 40 mM, or 50 mM. The concentration of poloxamer 188 (Pluronic acid (F-68)) may be 0.0001%-1%. As non-limiting examples, the concentration of poloxamer 188 (Pluronic acid (F-68)) may be 0.0001%, 0.0005%, 0.001%, 0.005%, 0.01%, 0.05%, 0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

In some embodiments, the AAV particles of the invention may be formulated in a solution comprising about 1.05% sodium chloride, about 0.212% sodium phosphate dibasic, heptahydrate, about 0.025% sodium phosphate monobasic, monohydrate, and 0.001% poloxamer 188, at a pH of about 7.4. As a non-limiting example, the concentration of AAV particle in this formulated solution may be about 0.001%. The concentration of sodium chloride in the final solution may be 0.1-2.0%, with non-limiting examples of 0.1%, 0.25%, 0.5%, 0.75%, 0.95%, 0.96%, 0.97%, 0.98%, 0.99%, 1.00%, 1.01%, 1.02%, 1.03%, 1.04%, 1.05%, 1.06%, 1.07%, 1.08%, 1.09%, 1.10%, 1.25%, 1.5%, 1.75%, or 2%. The concentration of sodium phosphate dibasic in the final solution may be 0.100-0.300% with non-limiting examples including 0.100%, 0.125%, 0.150%, 0.175%, 0.200%, 0.210%, 0.211%, 0.212%, 0.213%, 0.214%, 0.215%, 0.225%, 0.250%, 0.275%, 0.300%. The concentration of sodium phosphate monobasic in the final solution may be 0.010-0.050%, with non-limiting examples of 0.010%, 0.015%, 0.020%, 0.021%, 0.022%, 0.023%, 0.024%, 0.025%, 0.026%, 0.027%, 0.028%, 0.029%, 0.030%, 0.035%, 0.040%, 0.045%, or 0.050%. The concentration of poloxamer 188 (Pluronic acid (F-68)) may be 0.0001%-1%. As non-limiting examples, the concentration of poloxamer 188 (Pluronic acid (F-68)) may be 0.0001%, 0.0005%, 0.001%, 0.005%, 0.01%, 0.05%, 0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

Relative amounts of active ingredient (e.g. antibody), pharmaceutically acceptable excipients, and/or any additional ingredients in pharmaceutical compositions in accordance with the present disclosure may vary, depending upon the identity, size, and/or condition of subjects being treated and further depending upon route of administration. For example, compositions may include between 0.1% and 99% (w/w) of active ingredient. By way of example, compositions may include between 0.1% and 100%, e.g., between 0.5 and 50%, between 1-30%, between 5-80%, or at least 80% (w/w) active ingredient.

According to the present disclosure, compounds may be formulated for CNS delivery. Agents that cross the brain blood barrier may be used. For example, some cell penetrating peptides that can target molecules to the brain blood barrier endothelium may be used for formulation (e.g., Mathupala, *Expert Opin Ther Pat.*, 2009, 19, 137-140; the content of which is incorporated herein by reference in its entirety).

Excipients and Diluents

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by the United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparation are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of conventional excipient media may be contemplated within the scope of the present disclosure, except insofar as any conventional excipient media may be incompatible with certain substances or their derivatives, such as by producing any undesirable biological effects or otherwise interacting in a deleterious manner with any other component(s) of pharmaceutical compositions of the present disclosure.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Inactive Ingredients

In some embodiments, formulations of the present disclosure may include at least one inactive ingredient. As used herein, the term "inactive ingredient" refers to an agent that does not contribute to the activity of a pharmaceutical composition. In some embodiments, all, none or some of the inactive ingredients which may be used in formulations of the present disclosure may be approved by the US Food and Drug Administration (FDA).

Formulations disclosed herein may include cations or anions. Formulations may include $Zn^{2+}$, $Ca^{2+}$, $Cu^{2+}$, $Mn^{2+}$, $Mg^+$, or combinations thereof. As a non-limiting example, formulations may include polymers and complexes with metal cations (See e.g., U.S. Pat. Nos. 6,265,389 and 6,555,525, each of which is herein incorporated by reference in its entirety).

IV. Administration and Dosing

Administration

Compounds and compositions (e.g., AAV particles) of the present disclosure may be administered by any delivery route which results in a therapeutically effective outcome.

In some embodiments, compositions may be administered in a way which allows them to cross the blood-brain barrier, vascular barrier, or other epithelial barrier. Compounds and compositions of the present disclosure may be administered in any suitable form, including, but not limited to, as a liquid solution, as a suspension, or as a solid form suitable for liquid solution or suspension in a liquid solution.

In some embodiments, delivery to a subject may be via a single route administration. In some embodiments, delivery to a subject may be via multi-site route of administration. Administration may include a bolus infusion. Administration may include sustained delivery over a period of minutes, hours, or days. Administration by infusion may include an infusion rate that may be changed depending on the subject, distribution, formulation, or other delivery parameter. Administration may be by more than one route of administration. As non-limiting examples, combination administrations may include intrathecal and intracerebroventricular administration, or intravenous and intraparenchymal administration.

Intravenous Administration

Compounds and compositions of the present disclosure may be administered to a subject by systemic administration. In some embodiments, systemic administration may include intravenous administration. Systemic administration may include intraarterial administration.

Compounds and compositions of the present disclosure may be administered to a subject by intravenous administration. In some embodiments, intravenous administration may be achieved by subcutaneous delivery. In some embodiments, the AAV particle is administered to the subject via focused ultrasound (FUS), e.g., coupled with the intravenous administration of microbubbles (FUS-MB), or MRI-guided FUS coupled with intravenous administration, e.g., as described in Terstappen et al. (Nat Rev Drug Discovery, doi.org/10.1038/s41573-021-00139-y (2021)), Burgess et al. (Expert Rev Neurother. 15(5):477-491 (2015)), and/or Hsu et al. (PLOS One 8(2): 1-8), the contents of which are incorporated herein by reference in its entirety. In some embodiments, the AAV particle is administered to the subject intravenously. Intravenous administration may be achieved by a tail vein injection (e.g., in a mouse model). Intravenous administration may be achieved by retro-orbital injection.

Administration to the CNS

Compounds and compositions of the present disclosure may be administered to a subject by direct injection into the brain. As a non-limiting example, the brain delivery may be by intrahippocampal administration. Administration may be by intraparenchymal administration. In some embodiments, the intraparenchymal administration is to tissue of the central nervous system. Administration may be by intracranial delivery (See, e.g., U.S. Pat. No. 8,119,611; the content of which is incorporated herein by reference in its entirety). Administration may be by injection into the CSF pathway. Non-limiting examples of delivery to the CSF pathway include intrathecal and intracerebroventricular (e.g., intracisternal magna—ICM) administration. Administration to the brain may be by systemic delivery. As a non-limiting example, the systemic delivery may be by intravascular administration. As a non-limiting example, the systemic or intravascular administration may be intravenous. Administration may be by intraocular delivery route. A non-limiting example of intraocular administration includes an intravitreal injection.

Intramuscular Administration

In some embodiments, the AAV particles may be delivered by intramuscular administration. Whilst not wishing to be bound by theory, the multi-nucleated nature of muscle cells provides an advantage to gene transduction subsequent to AAV delivery. Cells of the muscle are capable of expressing recombinant proteins with the appropriate post-translational modifications. The enrichment of muscle tissue with vascular structures allows for transfer to the blood stream and whole-body delivery. Examples of intramuscular administration include systemic (e.g., intravenous), subcutaneous or directly into the muscle. In some embodiments, more than one injection is administered.

In some embodiments, the AAV particles of the present disclosure may be delivered by intramuscular delivery route. (See, e.g., U.S. Pat. No. 6,506,379; the content of which is incorporated herein by reference in its entirety). Non-limiting examples of intramuscular administration include an intravenous injection or a subcutaneous injection.

In some embodiments, the AAV particles of the present disclosure are administered to a subject and transduce muscle of a subject. As a non-limiting example, the AAV particles are administered by intramuscular administration.

In some embodiments, the AAV particles of the present disclosure may be administered to a subject by subcutaneous administration.

In some embodiments, the intramuscular administration is via systemic delivery.

In some embodiments, the intramuscular administration is via intravenous delivery.

In some embodiments, the intramuscular administration is via direct injection to the muscle.

In some embodiments, the muscle is transduced by administration, and this is referred to as intramuscular administration.

In some embodiments, the intramuscular delivery comprises administration at one site.

In some embodiments, the intramuscular delivery comprises administration at more than one site. In some embodiments, the intramuscular delivery comprises administration at two sites. In some embodiments, the intramuscular delivery comprises administration at three sites. In some embodiments, the intramuscular delivery comprises administration at four sites. In some embodiments, the intramuscular delivery comprises administration at more than four sites.

In some embodiments, intramuscular delivery is combined with at least one other method of administration.

In some embodiments, the AAV particles that may be administered to a subject by peripheral injections. Non-limiting examples of peripheral injections include intraperitoneal, intramuscular, intravenous, conjunctival, or joint injection. It was disclosed in the art that the peripheral administration of AAV vectors can be transported to the central nervous system, for example, to the motor neurons (e.g., U.S. Patent Publication Nos. US20100240739 and US20100130594; the content of each of which is incorporated herein by reference in their entirety).

In some embodiments, the AAV particles of the present disclosure may be administered to a subject by intraparenchymal administration. In some embodiments, the intraparenchymal administration is to muscle tissue.

In some embodiments, the AAV particles of the present disclosure are delivered as described in Bright et al 2015 (Neurobiol Aging. 36 (2): 693-709), the contents of which are herein incorporated by reference in their entirety.

In some embodiments, the AAV particles of the present disclosure are administered to the gastrocnemius muscle of a subject. In some embodiments, the AAV particles of the present disclosure are administered to the bicep femorii of the subject. In some embodiments, the AAV particles of the present disclosure are administered to the tibialis anterior muscles. In some embodiments, the AAV particles of the present disclosure are administered to the soleus muscle.

Depot Administration

As described herein, in some embodiments, pharmaceutical compositions, AAV particles of the present disclosure are formulated in depots for extended release. Generally, specific organs or tissues ("target tissues") are targeted for administration.

In some aspects, pharmaceutical compositions, AAV particles of the present disclosure are spatially retained within or proximal to target tissues. Provided are methods of providing pharmaceutical compositions, AAV particles, to target tissues of mammalian subjects by contacting target tissues (which comprise one or more target cells) with pharmaceutical compositions, AAV particles, under conditions such that they are substantially retained in target tissues, meaning that at least 10, 20, 30, 40, 50, 60, 70, 80, 85, 90, 95, 96, 97, 98, 99, 99.9, 99.99 or greater than 99.99% of the composition is retained in the target tissues. Advantageously, retention is determined by measuring the amount of pharmaceutical compositions, AAV particles, that enter one or more target cells. For example, at least 1%, 5%, 10%, 20%, 30%, 40%, 50%, 60%, 70%, 80%, 85%, 90%, 95%, 96%, 97%, 98%, 99%, 99.9%, 99.99%, or greater than 99.99% of pharmaceutical compositions, AAV particles, administered to subjects are present intracellularly at a period of time following administration. For example, intramuscular injection to mammalian subjects may be performed using aqueous compositions comprising pharmaceutical compositions, AAV particles of the present disclosure and one or more transfection reagents, and retention is determined by measuring the amount of pharmaceutical compositions, AAV particles, present in muscle cells.

Certain aspects are directed to methods of providing pharmaceutical compositions, AAV particles of the present disclosure to a target tissues of mammalian subjects, by contacting target tissues (comprising one or more target cells) with pharmaceutical compositions, AAV particles under conditions such that they are substantially retained in such target tissues. Pharmaceutical compositions, AAV particles comprise enough active ingredient such that the effect of interest is produced in at least one target cell. In some embodiments, pharmaceutical compositions, AAV particles generally comprise one or more cell penetration agents, although "naked" formulations (such as without cell penetration agents or other agents) are also contemplated, with or without pharmaceutically acceptable carriers.

Dose and Regimen

The present disclosure provides methods of administering compounds and compositions in accordance with the disclosure to a subject in need thereof. Administration may be in any amount and by any route of administration effective for preventing, treating, managing, or diagnosing diseases, disorders, and/or conditions. The exact amount required may vary from subject to subject, depending on species, age, general condition of the subject, severity of disease, particular composition, mode of administration, mode of activity, and the like. Subjects may be, but are not limited to, humans, mammals, or animals. Compositions may be formulated in unit dosage form for ease of administration and uniformity of dosage. It will be understood, however, that the total daily usage of compositions of the present disclosure may be decided by an attending physician within the scope of sound medical judgment. Specific therapeutically effective, prophylactically effective, or appropriate diagnostic dose levels for any particular individual may vary depending upon a variety of factors including the disorder being treated and severity of the disorder; the activity of specific payloads employed; specific compositions employed; age, body weight, general health, sex, and diet of patients; time of administration, route of administration, and rate of excretion of compounds and compositions employed; duration of treatment; drugs used in combination or coincidental with compounds and compositions employed; and like factors well known in the medical arts.

In some embodiments, compounds and compositions in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, or prophylactic, effect.

In some embodiments, the desired dosage may be delivered using multiple administrations (e.g., two, three, four, or more than four administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event.

Compounds and compositions of the present disclosure may be administered as a "pulse dose" or as a "continuous flow." As used herein, a "pulse dose" is a series of single unit doses of any therapeutic agent administered with a set frequency over a period of time. As used herein, a "continuous flow" is a dose of therapeutic agent administered continuously for a period of time in a single route/single point of contact, i.e., continuous administration event. A total daily dose, an amount given or prescribed in a 24-hour period, may be administered by any of these methods, or as a combination of these methods, or by any other methods suitable for pharmaceutical administration.

In some embodiments, delivery of AAV particles may comprise a total dose between about $1\times10^6$ VG and about $1\times10^{16}$ VG. In some embodiments, delivery may comprise a total dose of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $1.9\times10^{10}$, $2\times10^{10}$, $3\times10^{10}$, $3.73\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $2.5\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG. As a non-limiting example, the total dose is $1\times10^{13}$ VG. As another non-limiting example, the total dose is $2.1\times10^{12}$ VG.

In some embodiments, delivery of AAV particles may comprise a composition concentration between about $1\times10^6$ VG/mL and about $1\times10^{16}$ VG/mL. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/mL. In some embodiments, the delivery comprises a composition concentration of $1\times10^{13}$ VG/mL. In some embodiments, the delivery comprises a composition concentration of $2.1\times10^{12}$ VG/mL.

Combinations

Compounds and compositions of the present disclosure may be used in combination with one or more other therapeutic, prophylactic, research or diagnostic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, research, or diagnostic compositions in combination with agents that may improve their bioavailability, reduce and/or modify their metabolism, inhibit their excretion, and/or modify their distribution within the body.

V. Methods and Uses of the Compositions

In some embodiments, the present disclosure provides methods related to using and evaluating compounds and compositions for therapeutic and diagnostic applications.

Therapeutic Applications

In some embodiments, methods of the present disclosure include methods of treating therapeutic indications using compounds and/or compositions disclosed herein. As used herein, the term "therapeutic indication" refers to any symptom, condition, disorder, or disease that may be alleviated, stabilized, improved, cured, or otherwise addressed by some form of treatment or other therapeutic intervention. In some embodiments, methods of the present disclosure include treating therapeutic indications by administering antibodies disclosed herein.

As used herein the terms "treat," "treatment," and the like, refer to relief from or alleviation of pathological processes. In the context of the present disclosure insofar as it relates to any of the other conditions recited herein below, the terms "treat," "treatment," and the like mean to relieve or alleviate at least one symptom associated with such condition, or to slow or reverse the progression or anticipated progression of such condition.

By "lower" or "reduce" in the context of a disease marker or symptom is meant a significant decrease in such a level, often statistically significant. The decrease may be, for example, at least 10%, at least 20%, at least 30%, at least 40% or more, and is preferably down to a level accepted as within the range of normal for an individual without such a disorder.

By "increase" or "raise" in the context of a disease marker or symptom is meant a significant rise in such level, often statistically significant. The increase may be, for example, at least 10%, at least 20%, at least 30%, at least 40% or more, and is preferably up to a level accepted as within the range of normal for an individual without such disorder.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of a compound or composition described herein, "effective against" a disease or disorder indicates that administration in a clinically appropriate manner results in a beneficial effect for at least a fraction of patients, such as an improvement of symptoms, a cure, a reduction in disease load, reduction in protein aggregation, reduction in neurofibrillary tangles, reduction in neurodegeneration, extension of life, improvement in quality of life, or other effect generally recognized as positive by medical doctors familiar with treating the particular type of disease or disorder.

A treatment or preventive effect is evident when there is a significant improvement, often statistically significant, in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more may be indicative of effective treatment. Efficacy for a given compound or composition may also be judged using an experimental animal model for the given disease as known in the art. When using an experimental animal model, efficacy of treatment is evidenced when a statistically significant modulation in a marker or symptom is observed.

Compounds of the present disclosure and additional therapeutic agents can be administered in combination. Such combinations may be in the same composition, or the additional therapeutic agents can be administered as part of a separate composition or by another method described herein.

In some embodiments, therapeutic indications that may be addressed by methods of the present disclosure include neurological indications. As used herein, a "neurological indication" refers to any therapeutic indication relating to the central nervous system (CNS). Methods of treating neurological indications according to the present disclosure may include administering compounds (e.g., antibodies) and/or compositions described herein. Neurological indications may include neurological diseases and/or disorders involving irregular expression or aggregation of tau. Such indications may include, but are not limited to mild cognitive impairment (MCI), neurodegenerative disease, Alzheimer's disease (AD), frontotemporal dementia and parkinsonism linked to chromosome 17 (FTDP-17), frontotemporal lobar degeneration (FTLD), frontotemporal dementia (FTD), chronic traumatic encephalopathy (CTE), progressive supranuclear palsy (PSP), Down's syndrome, Pick's disease, corticobasal degeneration (CBD), corticobasal syndrome, amyotrophic lateral sclerosis (ALS), a prion disease, Creutzfeldt-Jakob disease (CJD), multiple system atrophy, tangle-only dementia, stroke, and progressive subcortical gliosis.

In some embodiments, an antibody that binds to tau described herein or an AAV particle comprising a payload, e.g., an antibody that binds to tau described herein, can be used to treat a traumatic brain injury (TBI), e.g., as described in Edwards et al. "Traumatic Brain Injury Induces Tau Aggregation and Spreading," *J. Neurotrauma*, 2020, 37(1): 80-92, the contents of which are hereby incorporated by reference in their entirety.

In some embodiments, methods of treating neurological diseases and/or disorders in a subject in need thereof may include one or more of the steps of: (1) deriving, generating, and/or selecting an anti-tau antibody or fragment or composition thereof; and (2) administering the anti-tau antibody or fragment or composition thereof to the subject. Administration to the subject may slow, stop, or reverse disease progression. As a non-limiting example, disease progression may be measured by cognitive tests such as, but not limited to, the Mini-Mental State Exam (MMSE); imaging tests (e.g., positron emission tomography (PET) scan; or PET scan in combination with Braak neuropathological staging and/or serum biomarker staining (e.g., $^{18}$F-flortaucipir, plasma ptau 181, or $^{18}$F-PM-PBB3), or other similar diagnostic tool(s), known to those skilled in the art. As another non-limiting example, disease progression may be measured by change in the pathological features of the brain, CSF or other tissues of the subject, such as, but not limited to a decrease in levels of tau (either soluble or insoluble). In some embodiments, levels of insoluble hyperphosphorylated tau are decreased. In some embodiments, levels of soluble tau are decreased. In some embodiments, both soluble and insoluble tau are decreased. In some embodiments, levels of insoluble hyperphosphorylated tau are increased. In some embodiments, levels of soluble tau are increased. In some embodiments, both insoluble and soluble tau levels are increased. In some embodiments, neurofibrillary tangles are decreased in size, number, density, or combination thereof. In another embodiment, neurofibrillary tangles are increased in size, number, density or combination thereof.

In some embodiments, administration of an anti-tau antibody or a viral genome encoding a anti-tau antibody described herein results in a reduction of tau pathology, e.g., a decrease in a biomarker of tau pathology (e.g., $^{18}$F-flortaucipir, plasma ptau 181, or $^{18}$F-PM-PBB3), e.g., as measured by a PET scan or PET scan in combination with Braak neuropathological staging and/or serum biomarker staining.

Neurodegeneration

Neurodegenerative disease refers to a group of conditions characterized by progressive loss of neuronal structure and function, ultimately leading to neuronal cell death. Neurons are the building blocks of the nervous system(s) and are generally not able to reproduce and/or be replaced, and therefore neuron damage and/or death is especially devastating. Other, non-degenerating diseases that lead to neuronal cell loss, such as stroke, have similarly debilitating outcomes. Targeting molecules that contribute to deteriorating cell structure or function may prove beneficial generally for treatment of neurological indications, including neurodegenerative disease and stroke.

Certain molecules are believed to have inhibitory effects on neurite outgrowth, contributing to the limited ability of the central nervous system to repair damage. Such molecules include, but are not limited to, myelin associated proteins, such as, but not limited to, RGM (Repulsive guidance molecule), NOGO (Neurite outgrowth inhibitor), NOGO receptor, MAG (myelin associated glycoprotein), and MAI (myelin associated inhibitor). In some embodiments, anti-tau antibodies of the present disclosure may be utilized to target the aforementioned antigens (e.g., neurite outgrowth inhibitors).

Many neurodegenerative diseases are associated with aggregation of misfolded proteins, including, but not limited to, alpha synuclein, tau (as in tauopathies), amyloid β, prion proteins, TAR DNA binding protein 43 (TDP-43), and huntingtin (see, e.g. De Genst et al., 2014, Biochim Biophys Acta; 1844(11):1907-1919, and Yu et al., 2013, Neurotherapeutics.; 10(3): 459-472, references therein, all of which are herein incorporated by reference in their entirety). The aggregation results from disease-specific conversion of soluble proteins to an insoluble, highly ordered fibrillary deposit. This conversion is thought to prevent the proper disposal or degradation of misfolded proteins, thereby leading to further aggregation. Conditions associated with alpha synuclein misfolding and aggregation are referred to as "synucleinopathies." In some embodiments, anti-tau antibodies of the present disclosure may be utilized to target misfolded or aggregated proteins.

Alzheimer's Disease

Alzheimer Disease (AD) is a debilitating neurodegenerative disease currently afflicting more than 35 million people worldwide, with that number expected to double in coming decades. Symptomatic treatments have been available for many years but these treatments do not address the underlying pathophysiology. Recent clinical trials using these and other treatments have largely failed and, to date, no known cure has been identified.

The AD brain is characterized by the presence of two forms of pathological aggregates, the extracellular plaques composed of β-amyloid (Aβ) and the intracellular neurofibrillary tangles (NFT) comprised of hyperphosphorylated microtubule associated protein tau. Based on early genetic findings, β-amyloid alterations were thought to initiate disease, with changes in tau considered downstream. Thus, most clinical trials have been Aβ-centric. Although no mutations of the tau gene have been linked to AD, such alterations have been shown to result in a family of dementias known as tauopathies, demonstrating that changes in tau can contribute to neurodegenerative processes. Tau is normally a soluble protein known to associate with microtubules based on the extent of its phosphorylation. Hyperphosphorylation of tau depresses its binding to microtubules and microtubule assembly activity. In tauopathies, the tau becomes hyperphosphorylated, misfolds and aggregates as NFT of paired helical filaments (PHF), twisted ribbons or straight filaments. In AD, NFT pathology, rather than plaque pathology, correlates more closely with neuropathological markers such as neuronal loss, synaptic deficits, severity of disease and cognitive decline. NFT pathology marches through the brain in a stereotyped manner and animal studies suggest a trans-cellular propagation mechanism along neuronal connections.

Several approaches have been proposed for therapeutically interfering with progression of tau pathology and preventing the subsequent molecular and cellular consequences. Given that NFT are composed of a hyperphosphorylated, misfolded and aggregated form of tau, interference at each of these stages has yielded the most avidly pursued set of targets. Introducing agents that limit phosphorylation, block misfolding or prevent aggregation have all generated promising results. Passive and active immunization with late stage anti-phospho-tau antibodies in mouse models have led to dramatic decreases in tau aggregation and improvements in cognitive parameters. It has also been suggested that introduction of anti-tau antibodies can prevent the trans-neuronal spread of tau pathology.

In some embodiments, anti-tau antibodies of the present disclosure may be used according to methods presented herein to treat subjects suffering from AD and other tauopathies. In some cases, methods of the present disclosure may be used to treat subjects suspected of developing AD or other tauopathies.

Frontotemporal Dementia and Parkinsonism Linked to Chromosome 17 (FTDP-17)

Although Alzheimer's disease is, in part, characterized by the presence of tau pathology, no known mutations in the tau gene have been causally linked to the disease. Mutations in the tau gene have been shown to lead to an autosomal dominantly inherited tauopathy known as frontotemporal dementia and parkinsonism linked to chromosome 17 (FTDP-17) and demonstrate that alterations in tau can lead to neurodegenerative changes in the brain. Mutations in the tau gene that lead to FTDP-17 are thought to influence splicing patterns, thereby leading to an elevated proportion of tau with four microtubule binding domains (rather than three). These molecules are considered to be more amyloidogenic, meaning they are more likely to become hyperphosphorylated and more likely to aggregate into NFT (Hutton, M. et al., 1998, Nature 393 (6686): 702-5, the contents of which are herein incorporated by reference in their entirety). Although physically and behaviorally, FTDP-17 patients can appear quite similar to Alzheimer's disease patients, at autopsy FTDP-17 brains lack the prominent Aβ plaque pathology of an AD brain (Gotz, J. et al., 2012, British Journal of Pharmacology 165 (5): 1246-59, the contents of which are herein incorporated by reference in their entirety). Therapeutically targeting the aggregates of tau protein may ameliorate and prevent degenerative changes in the brain and potentially lead to improved cognitive ability.

As of today, there is no treatment to prevent, slow the progression, or cure FTDP-17. Medication may be prescribed to reduce aggressive, agitated or dangerous behavior. There remains a need for therapy affecting the underlying pathophysiology, such as antibody therapies targeting tau protein.

In some embodiments, anti-tau antibodies of the present disclosure may be used to treat subjects suffering from FTDP-17. In some cases, methods of the present disclosure may be used to treat subjects suspected of developing FTDP-17.

Chronic Traumatic Encephalopathy

Unlike the genetically linked tauopathies, chronic traumatic encephalopathy is a degenerative tauopathy linked to repeated head injuries. The disease was first described in boxers whom behaved "punch drunk" and has since been identified primarily in athletes that play American football, ice hockey, wrestling and other contact sports. The brains of those suffering from CTE are characterized by distinctive patterns of brain atrophy accompanied by accumulation of hyperphosphorylated species of aggregated tau in NFT. In CTE, pathological changes in tau are accompanied by a number of other pathobiological processes, such as inflammation (Daneshvar, D. H. et al., 2015 Mol Cell Neurosci 66(Pt B): 81-90, the contents of which are herein incorporated by reference in their entirety). Targeting the tau aggregates may provide reprieve from the progression of the disease and may allow cognitive improvement.

As of today, there is no medical therapy to treat or cure CTE. The condition is only diagnosed after death, due to lack of in vivo techniques to identify CTE specific biomarkers. There remains a need for therapy affecting the underlying pathophysiology, such as antibody therapies targeting tau protein.

In some embodiments, anti-tau antibodies of the present disclosure may be used to treat subjects having or suffering from CTE. In some cases, methods of the present disclosure may be used to treat subjects suspected of developing CTE. In some embodiments, anti-tau antibodies of the present disclosure may be used to treat subjects having a traumatic brain injury (TBI), e.g., CTE.

Prion Diseases

Prion diseases, also known as transmissible spongiform encephalopathies (TSEs), are a group of rare progressive conditions affecting the nervous system. The related conditions are rare and are typically caused by mutations in the PRNP gene which enables production of the prion protein. Gene mutations lead to an abnormally structured prion protein. Alternatively, the abnormal prion may be acquired by exposure from an outside source, e.g. by consumption of beef products containing the abnormal prion protein. Abnormal prions are misfolded, causing the brain tissue to degenerate rapidly. Prion diseases include, but are not limited to, Creutzfeldt-Jakob disease (CJD), Gerstmann-Sträussler-Scheinker syndrome (GSS), fatal insomnia (FFI), variably protease-sensitive prionopathy (VPSPr), and kuru. Prion diseases are rare. Approximately 350 cases of prion diseases are diagnosed in the US annually.

CJD is a degenerative brain disorder characterized by problems with muscular coordination, personality changes including mental impairment, impaired vision, involuntary muscle jerks, weakness and eventually coma. The most common categories of CJD are sporadic, hereditary due to a genetic mutation, and acquired. Sporadic CJD is the most common form affecting people with no known risk factors for the disease. The acquired form of CJD is transmitted by exposure of the brain and nervous system tissue to the prion. As an example, variant CJD (vCDJ) is linked to a bovine spongiform encephalopathy (BSE), also known as a 'mad cow' disease. CJD is fatal and patients typically die within one year of diagnosis.

Prion diseases are associated with an infectious agent consisting of an alternative conformational isoform of the prion protein, PrPSc. PrPSc replication is considered to occur through an induction of the infectious prion in the normal prion protein (PrPC). The replication occurs without a nucleic acid.

As of today, there is no therapy to manage or cure CJD, or other prion diseases. Typically, treatment is aimed at alleviating symptoms and increasing comfort of the patient, e.g. with pain relievers. There remains a need for therapy affecting the underlying pathophysiology.

In some embodiments, anti-tau antibodies of the present disclosure may be used to treat subjects suffering from a prion disease. In some cases, methods of the present disclosure may be used to treat subjects suspected of developing a prion disease.

Diagnostic Applications

In some embodiments, compounds (e.g., antibodies) and compositions of the present disclosure may be used as diagnostics. Anti-tau antibodies may be used to identify, label, or stain cells, tissues, organs, etc. expressing tau proteins. Anti-tau antibodies may be used to identify tau proteins present in tissue sections (e.g., histological tissue sections), including tissue known or suspected of having tau protein aggregates. Such antibodies may in some cases be used to identify subjects with neurological diseases and/or disorders. Tissue sections may be from CNS tissue.

In some embodiments, diagnostic methods of the present disclosure may include the analysis of one or more cells or tissues using immunohistochemical techniques. Such methods may include the use of one or more of any of the anti-tau antibodies described herein. Immunohistochemical methods may include staining tissue sections to determine the presence and/or level of one or more tau proteins or other markers. Tissue sections may be derived from subject CNS tissue (e.g., patient CNS, animal CNS, and CNS from animal models of disease). Tissue sections may come from formalin-fixed or unfixed fresh frozen tissues. In some cases, tissue sections come from formalin fixed paraffin-embedded (FFPE) tissues. Anti-tau antibodies described herein may be used as primary antibodies. Primary antibodies are used to contact tissue sections directly and bind to target epitopes. Primary antibodies may be directly conjugated with a detectable label or may be detected through the use of a detection agent such as a secondary antibody. In some embodiments, primary antibodies or detection agents include an enzyme that can be used to react with a substrate to generate a visible product (e.g., precipitate). Such enzymes may include, but are not limited to horse radish peroxidase, alkaline phosphatase, beta-galactosidase, and catalase.

Anti-tau antibodies described herein may be used according to immunohistochemical methods of the present disclosure to detect tau proteins in tissues or cells. In some cases, these antibodies are used to detect and/or determine the level of tau proteins in tissues. Levels of anti-tau antibodies used in immunohistochemical staining techniques may be varied to increase visible staining or to decrease background levels of staining. In some embodiments, antibody concentrations of from about 0.01 µg/ml to about 50 µg/ml are used. For example, antibody concentrations of from about 0.01 µg/ml to about 1 µg/ml, from about 0.05 µg/ml to about 5 µg/ml, from about 0.1 µg/ml to about 3 µg/ml, from about 1 µg/ml to about 10 µg/ml, from about 2 µg/ml to about 20 µg/ml, from about 3 µg/ml to about 25 µg/ml, from about 4 µg/ml to about 30 µg/ml, or from about 5 µg/ml to about 50 µg/ml may be used.

Levels and/or identities of tau proteins may be determined according to any methods known in the art for identifying proteins and/or quantitating protein levels. In some embodiments, such methods may include, but are not limited to mass spectrometry, array analysis (e.g., antibody array or protein array), Western blotting, flow cytometry, immunoprecipitation, surface plasmon resonance analysis, and ELISA. Tau proteins may in some cases be immunoprecipitated from samples prior to analysis. Such immunoprecipitation may be carried out using anti-tau antibodies disclosed herein. In some embodiments, tau proteins are immunoprecipitated from biological samples using anti-tau antibodies and then identified and/or quantitated using mass spectrometry.

In some embodiments, treatments are informed by diagnostic information generated using anti-tau antibodies. Accordingly, the present disclosure provides methods of treating neurological diseases and/or disorders that include obtaining a sample from a subject, diagnosing one or more neurological diseases and/or disorders using an anti-tau antibody, and administering a treatment selected based on the diagnosis. Such treatments may include treatment with anti-tau antibodies. Anti-tau antibodies administered according to such methods may include any of those described herein.

In some embodiments, the present disclosure provides methods of detecting and/or quantifying tau proteins in samples through the use of capture and detection antibodies. As used herein, a "capture antibody" is an antibody that binds an analyte in a way that it may be isolated or detected. Capture antibodies may be associated with surfaces or other carriers (e.g., beads). Detection antibodies are antibodies that facilitate observation of the presence or absence of an analyte. According to some methods of detecting and/or quantifying tau proteins, both capture antibodies and detection antibodies bind to tau proteins. Capture and detection antibodies may bind to different epitopes or regions of tau proteins to avoid competition for binding. In some embodiments, detection antibodies may be conjugated with a detectable label for direct detection. In some embodiments, binding of detection antibodies may be assessed using a secondary antibody that binds to a constant domain of the detection antibody or to a detectable label of the detection antibody. Capture, detection, and/or secondary antibodies may be derived from different species. This may prevent secondary antibodies from binding to both capture and detection antibodies.

VI. Kits and Devices

Kits

In some embodiments, compounds and composition of the present disclosure may be included in a kit. Such compounds and compositions may include anti-tau antibodies disclosed herein. In a non-limiting example, kits may include reagents for generating anti-tau antibodies, including tau protein antigens. Kits may include additional reagents and/or instructions for use, e.g., for creating or synthesizing anti-tau antibodies. Kits may include one or more buffers. Kits may include additional components, for example, solid supports or substrates for antibody or antigen attachment.

In some embodiments, the present disclosure includes kits for screening, monitoring, and/or diagnosis of a subject that include one or more anti-tau antibodies. Such kits may be used alone or in combination with one or more other methods of screening, monitoring, and/or diagnosis. Kits may include one or more of a buffer, a biological standard, a secondary antibody, a detection reagent, and a composition for sample pre-treatment (e.g., for antigen retrieval, blocking, etc.).

Kit components may be packaged. In some embodiments, kit components are packaged in aqueous media or in lyophilized form. Packaging may include one or more vial, test tube, flask, bottle, syringe or other container into which a component may be placed and/or suitably aliquoted. Where there are multiple kit components (labeling reagent and label may be packaged together), kits may include second, third or other additional containers into which additional components may be separately placed.

When kit components are provided in one and/or more liquid solutions, liquid solutions may be aqueous. Liquid solutions may be provided sterile. Kit components may be provided as dried powder(s). Dried powder components may be provided for reconstitution by kit users, e.g., by addition of suitable solvent. Solvents may also be provided in kits in one or more separate containers. In some embodiments, labeling dyes are provided in dried powder format.

Kits may include instructions for employing kit components as well other reagents not included in the kit. Instructions may include variations that can be implemented.

Devices

Any of the compounds and compositions described herein may be combined with, coated onto, or embedded in, or delivered by a device. Devices may include, but are not limited to, implants, stents, bone replacements, artificial joints, valves, pacemakers, or other implantable therapeutic devices.

VII. Definitions

At various places in the present specification, substituents of compounds of the present disclosure are disclosed in groups or in ranges. It is specifically intended that the present disclosure include each and every individual sub combination of the members of such groups and ranges.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

About: As used herein, the term "about" means+/−10% of the recited value.

AAV Particle: As used herein, an "AAV particle" refers to a particle or a virion comprising an AAV capsid, e.g., an AAV capsid variant, and a polynucleotide, e.g., a viral genome or a vector genome. In some embodiments, the viral genome of the AAV particle comprises at least one payload region and at least one ITR. In some embodiments, an AAV particle of the disclosure is an AAV particle comprising an AAV variant. In some embodiments, the AAV particle is capable of delivering a nucleic acid, e.g., a payload region, encoding a payload to cells, typically, mammalian, e.g., human, cells. In some embodiments, an AAV particle of the present disclosure may be produced recombinantly. In some embodiments, an AAV particle may be derived from any serotype, described herein or known in the art, including combinations of serotypes (e.g., "pseudotyped" AAV) or from various genomes (e.g., single stranded or self-complementary). In some embodiments, the AAV particle may be replication defective and/or targeted. It is to be understood that reference to the AAV particle of the disclosure also includes pharmaceutical compositions thereof, even if not explicitly recited.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Approximately: As used herein, the term "approximately" or "about," as applied to one or more values of interest, refers to a value that is similar to a stated reference value. When referring to a measurable value such as an amount, a temporal duration, and the like, the term is meant to encompass is meant to encompass variations of ±20% or in some instances±10%, or in some instances±5%, or in some instances±1%, or in some instances±0.1

Associated with: As used herein, the terms "associated with," "conjugated," "linked," "attached," and "tethered," when used with respect to two or more entities, means that the entities are physically associated or connected with one another, either directly or via a linker, to form a structure that is sufficiently stable so that the entities remain physically associated, e.g., under working conditions, e.g., under physiological conditions. An "association" need not be through covalent chemical bonding and may include other forms of association or bonding sufficiently stable such that the "associated" entities remain physically associated, e.g., ionic bonding, hydrostatic bonding, hydrophobic bonding, hydrogen bonding, or hybridization-based connectivity.

Capsid: As used herein, the term "capsid" refers to the exterior, e.g., a protein shell, of a virus particle, e.g., an AAV particle, that is substantially (e.g., >50%, >90%, or 100%) protein. In some embodiments, the capsid is an AAV capsid comprising an AAV capsid protein described herein, e.g., a VP1, VP2, and/or VP3 polypeptide. The AAV capsid protein can be a wild-type AAV capsid protein or a variant, e.g., a structural and/or functional variant from a wild-type or a reference capsid protein, referred to herein as an "AAV capsid variant." In some embodiments, the AAV capsid variant described herein has the ability to enclose, e.g., encapsulate, a viral genome and/or is capable of entry into a cell, e.g., a mammalian cell. In some embodiments, the AAV capsid variant described herein may have modified tropism compared to that of a wild-type AAV capsid, e.g., the corresponding wild-type capsid.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of a polynucleotide or polypeptide or may apply to a portion, region or feature thereof.

Encapsulate: As used herein, the term "encapsulate" means to enclose, surround or encase. As an example, a capsid protein, e.g., an AAV capsid variant, often encapsulates a viral genome. In some embodiments, encapsulate within a capsid, e.g., an AAV capsid variant, encompasses 100% coverage by a capsid, as well as less than 100% coverage, e.g., 95% or less. For example, gaps or discontinuities may be present in the capsid so long as the viral genome is retained in the capsid, e.g., prior to entry into a cell.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment of a therapeutic indication as compared to the response obtained without administration of the agent.

Epitope: As used herein, an "epitope" refers to a surface or region on one or more entities that is capable of interacting with an antibody or other binding biomolecule. For example, a protein epitope may contain one or more amino acids and/or post-translational modifications (e.g., phosphorylated residues) which interact with an antibody. In some embodiments, an epitope may be a "conformational epitope," which refers to an epitope involving a specific three-dimensional arrangement of the entity(ies) having or forming the epitope. For example, conformational epitopes of proteins may include combinations of amino acids and/or post-translational modifications from folded, non-linear stretches of amino acid chains.

EvoMap™: As used herein, an EvoMap™ refers to a map of a polypeptide, wherein detailed informatics are presented about the effects of single amino acid mutations within the length of the polypeptide and their influence on the properties and characteristics of that polypeptide.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Fragment: A "fragment," as used herein, refers to a portion. For example, an antibody fragment may comprise a CDR, or a heavy chain variable region, or a scFv, etc. In some embodiments, a fragment is a nucleic acid fragment.

Homology: As used herein, the term "homology" refers to the overall relatedness between polymeric molecules, e.g. between polynucleotide molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H. and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)). In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

Isolated: As used herein, the term "isolated" refers to a substance or entity that is altered or removed from the natural state, e.g., altered or removed from at least some of the components with which it is associated in the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. Such polynucleotides could be part of a vector and/or such polynucleotides or polypeptides could be part of a composition, and still be isolated in that such vector or composition is not part of the environment in which it is found in nature. In some embodiments, an isolated nucleic acid is recombinant or may be incorporated into a vector.

Linker: As used herein "linker" refers to a molecule or group of molecules which connects two molecules. In some embodiments, linkers may be cleavable (e.g., through contact with an enzyme, change in pH, or change in temperature).

MicroRNA (miRNA or miR) binding site: As used herein, a "miR binding site" comprises a nucleic acid sequence (whether RNA or DNA, e.g., differ by "U" of RNA or "T" in DNA) that is capable of binding, or binds, in whole or in part to a microRNA (miR) through complete or partial hybridization. Typically, such binding occurs between the miR and the miR binding site in the reverse complement orientation. In some embodiments, the miR binding site is transcribed from the AAV vector genome encoding the miR binding site.

In some embodiments, a miR binding site may be encoded or transcribed in series. Such a "miR binding site series" or "miRBSs" may include two or more miR binding sites having the same or different nucleic acid sequence.

Modified: As used herein "modified" refers to a changed state or structure of a molecule. Molecules may be modified in many ways including chemically, structurally, and functionally.

Payload: As used herein, "payload" refers to any substance being delivered by an agent. For example, payloads may include therapeutic agents conjugated to antibodies for delivery to a cell, tissue, or region harboring an epitope of the antibody.

Polypeptide: As used herein, "polypeptide" means a polymer of amino acid residues (natural or unnatural) linked together most often by peptide bonds. The term, as used herein, refers to proteins, polypeptides, and peptides of any size, structure, or function. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides and may be associated or linked. The term polypeptide may also apply to amino acid polymers in which one or more amino acid residues are an artificial chemical analogue of a corresponding naturally occurring amino acid.

Polypeptide variant: The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. In some embodiments, a variant comprises a sequence having at least about 50%, at least about 80%, or at least about 90%, identical (homologous) to a native or a reference sequence.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Purified: As used herein, "purify," "purified," "purification" means to make substantially pure or clear from unwanted components, material defilement, admixture or imperfection. "Purified" refers to the state of being pure. "Purification" refers to the process of making pure.

Region: As used herein, the term "region" refers to a zone or general area. In some embodiments, when referring to a protein or protein module, a region may comprise a linear sequence of amino acids along the protein or protein module or may comprise a three-dimensional area, an epitope and/or a cluster of epitopes. In some embodiments, regions comprise terminal regions. As used herein, the term "terminal region" refers to regions located at the ends or termini of a given agent. When referring to proteins, terminal regions may comprise N- and/or C-termini In some embodiments, when referring to a polynucleotide, a region may comprise a linear sequence of nucleic acids along the polynucleotide or may comprise a three-dimensional area, secondary structure, or tertiary structure. In some embodiments, regions comprise terminal regions. As used herein, the term "terminal region" refers to regions located at the ends or termini of a given agent. When referring to polynucleotides, terminal regions may comprise 5' and/or 3' termini.

RNA and DNA: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

Sample: As used herein, the term "sample" refers to a portion or subset of larger entity. A sample from a biological organism or material is referred to herein as a "biological sample" and may include, but is not limited to, tissues, cells, and body fluids (e.g., blood, mucus, lymphatic fluid, synovial fluid, cerebrospinal fluid, saliva, amniotic fluid, amniotic cord blood, urine, vaginal fluid, and semen). Samples may further include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, and organs. Samples may further include a medium, such as a nutrient broth or gel, which may contain cellular components, such as proteins or nucleic acid molecules.

Spacer: As used here, a "spacer" is generally any selected nucleic acid sequence of, e.g., 1, 2, 3, 4, 5, 6, 7, 8, 9, or 10 nucleotides in length, which is located between two or more consecutive miR binding site sequences. Spacers may also be more than 10 nucleotides in length, e.g., 20, 30, 40, or 50 or more than 50 nucleotides.

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, neurodegenerative disease) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity or disfunction of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic Agent: The term "therapeutic agent" refers to any agent that, when administered to a subject, has a therapeutic, diagnostic, and/or prophylactic effect and/or elicits a desired biological and/or pharmacological effect. Therapeutic agents capable of producing a biological effect in living organisms are referred to herein as "drugs."

Therapeutically effective amount: As used herein, the term "therapeutically effective amount" means an amount of an agent (e.g., antibody or other therapeutic agent) to be delivered to a subject suffering from or susceptible to an infection, disease, disorder, and/or condition, that when delivered or administered in that amount is sufficient to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Conservative amino acid substitution: As used herein, a "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Variant: As used herein, the term "variant" refers to a polypeptide or polynucleotide that has an amino acid or a nucleotide sequence that is substantially identical, e.g., having at least 70%, 75%, 80%, 85%, 90%, 95%, or 99% sequence identity to a reference sequence. In some embodiments, the variant is a functional variant.

Functional Variant: As used herein, the term "functional variant" refers to a polypeptide variant or a polynucleotide variant that has at least one activity of the reference sequence.

Vector: As used herein, the term "vector" refers to any molecule or moiety which transports, transduces, or otherwise acts as a carrier of a heterologous molecule. In some embodiments, vectors may be plasmids. Vectors of the present disclosure may be produced recombinantly. The heterologous molecule may be a polynucleotide and/or a polypeptide.

Viral Genome: As used herein, the term "viral genome" refers to the nucleic acid sequence(s) encapsulated in an AAV particle. A viral genome comprises a nucleic acid sequence with at least one payload region encoding a payload and at least one ITR.

EXAMPLES

The antibodies described herein, e.g., as provided in Table 4, were generated and characterized as described in Examples 1-11 in WO 2021/211753, which are hereby incorporated by reference in their entirety.

Example 1. Tau Binding

Variable domain nucleic acid sequences from antibodies obtained from immunizations described in Examples 1 and 2 of WO 2021/211753 (the contents of which are hereby incorporated by reference in its entirety) were used to prepare recombinant mouse IgG antibodies. These candidate antibodies were analyzed for binding to ePHF and specificity for ePHF over wild type tau by direct ELISA.

For direct ePHF and wildtype tau ELISA, plates were first coated with ePHF or wild type tau. Antigen solutions were prepared in PBS and 50 μL were pipetted into each well. Plates were covered and incubated for one hour at 37° C. or overnight at 4° C. Plates were then washed and blocked by addition of 150 μl of blocking buffer to each well and incubated one hour at room temperature. Plates were then washed before addition of serially diluted candidate antibody samples prepared in blocking buffer. Detection of candidate antibody binding was carried out by washing plates and adding a solution of enzyme-labeled secondary antibody in blocking buffer to each well. Secondary antibody binding was detected by addition of substrate and spectrophotometric analysis of resulting reaction product. Half maximal effective concentration (EC50) for antibody binding to ePHF and wild type tau are presented in Table 20.

TABLE 20

| ELISA results | | |
|---|---|---|
| ID# | ePHF EC50 (nM) | Wild type Tau EC50 (nM) |
| V0009 | 0.038 | No binding |
| V0004 | 0.083 | No binding |
| V0024 | 0.125 | No binding |
| V0022 | 0.070 | Not determined |

TABLE 20-continued

ELISA results

| ID# | ePHF EC50 (nM) | Wild type Tau EC50 (nM) |
|---|---|---|
| V0023 | 0.110 | Not determined |
| V0052 | Weak binding | Not determined |

Results of a follow up analysis of antibodies V0022, V0009, V0023, V0024, and V0052 for selectivity for iPHF and ePHF over wild-type tau are shown in Table 27. Overall, the antibodies had a greater than 54-fold selectivity for iPHF over wild-type tau, with V0009, V0022, and V0052 having a greater than 390-fold selectivity for iPHF over wild-type tau. With regard to the selectivity for ePHF over wild-type tau, the anti-tau antibodies V0022, V0009, V0023, and V0024 had a greater than 120-fold selectivity for ePHF over wild-type tau, with V0009 and V0022 having a greater than 200-fold selectivity for ePHF over wild-type tau. Further, these antibodies demonstrated low polyspecificity and good stability in solution at 1 mg/mL.

TABLE 27

Selectivity Results

| Selectivity | Criteria | V0009 | V0022 | V0023 | V0024 | V0052 |
|---|---|---|---|---|---|---|
| iPHF:WT | ≥50 fold | >1450 | >838 | >54.5 | >80 | >396 |
| ePHF:WT | ≥50 fold | >415 | >222 | >140 | >123 | No |

Example 2. Tissue Staining

Variable domain nucleic acid sequences from antibodies obtained from immunizations described above were used to prepare recombinant mouse IgG antibodies and tested for ability to bind pathological tau in human brain tissue sections. Cryo-preserved human brain tissue sections from patients with or without Alzheimer's disease (AD) were mounted on glass slides and washed with PBS. Endogenous peroxidase activity in tissue sections was quenched for 30 minutes at room temperature using a solution of 0.9% hydrogen peroxide and 0.02% Triton-X 100 in 1×PBS. Tissue sections were then washed with PBS and incubated for 1 hour at room temperature with a blocking solution of 10% normal goat serum in PBS with 0.02% Triton-X 100. Candidate antibody solutions were prepared by 1:500 dilution in PBS with protein diluent. Tissue sections were incubated in candidate antibody solutions for 1 hour at room temperature before washing in PBS to remove unbound antibody. Tissue sections were then treated with solutions of biotinylated goat-anti mouse IgG in PBS with protein diluent and incubated for 1 hour at room temperature. Tissue sections were again washed in PBS and treated with a solution of avidin-peroxidase conjugate before incubation for 30 minutes at room temperature. Tissue sections were again washed in PBS prior to treatment with a 3,3' diaminobenzidine tetrahydrochloride (DAB) substrate solution to yield a brown enzymatic precipitate at sites of candidate antibody binding and peroxidase immunocomplex formation. Enzymatic reactions were allowed to proceed for about 1 minute before being halted by rinsing in PBS wash solution. Tissue sections were then mounted for microscopic evaluation of immunostaining (indicating candidate antibody binding). Immunostained tissue sections were ranked based on degree of staining observed. Results are shown in Table 24. In the Table, "−" indicates no staining, and "+," "+/++," "++," "++/+++," and "+++" indicate levels of positive staining from low to high. "+/−" indicates no staining, with the exception of some staining observed in non-disease tissue.

TABLE 24

Tissue staining results

| ID# | Staining level in AD tissue | Staining level in non-AD tissue |
|---|---|---|
| V0024 | +++ | − |
| V0009 | +++ | −/+ |
| V0004 | +++ | −/+ |
| V0022 | +++ | −/+ |
| V0023 | +++ | −/+ |
| V0052 | +/++ | + |

Multiple antibodies yielded positive staining in AD brain tissue sections with little or no positive staining observed in brain tissue sections from non-AD brain tissue.

Similar results were obtained using fixed human brain tissues when assessing antibodies V0004, V0009, V0022, V0023, V0024, and V0052 (Table 28). Similar results were also obtained for these antibodies when comparing brain tissue staining between wild type mice and FTD mutant tau transgenic mice carrying P301S tau mutations.

TABLE 28

Evaluation of binding to tau pathology from patient AD and PSP cases

| Sample (IHC) | V0009 | V0022 | V0023 | V0024 | V0052 |
|---|---|---|---|---|---|
| IHC Fixed - Human AD Brain | Positive | Positive | Positive | Positive | Weak |
| IHC Fixed - Human Control (Ctl) Brain | Negative | Negative | Negative | Negative | Negative |
| IHC Fixed - Human PSP | Positive (weak) | Positive | Positive | Positive | Positive |
| IHC-Fixed - Human Ctl Brain | Negative | Negative | Negative | Negative | Negative |
| IHC Frozen - Human AD Brain | Positive | Positive | Positive | Positive | Positive |
| IHC Frozen - Human PSP | Positive | Positive | Positive | Positive | Positive |
| IHC Frozen - Human Ctl Brain | Negative | Negative | Negative | Negative | weak |

Example 3. iPHF Affinity Analysis

Anti-human tau antibodies were assessed for affinity for iPHF by Octet (ForteBio, Menlo Park, CA) analysis. Recombinant mouse IgG antibodies were prepared with clone-specific variable domain pairs selected from those presented in Table 3 and mouse IgG1 constant domains. Candidate antibodies were immobilized on biosensor tips (ForteBio) in kinetic buffer (ForteBio). Biosensor tips were then washed before introduction of a solution of iPHF in kinetic buffer for analysis of association and dissociation with candidate antibodies. Affinity measurements ($K_D$) were obtained using Data Analysis HT version 11.1 and corrected for background and high-frequency noise. Results are presented in Table 25.

TABLE 25

Affinity analysis results by Octet

| ID# | iPHF $K_D$ (nM) | ID# | IPHF $K_D$ (nM) | ID# | iPHF $K_D$ (nM) |
|---|---|---|---|---|---|
| V009 | 0.2 | V0023 | 4.0 | V0024 | 2.8 |
| V0022 | 0.3 | V0004 | 20.0 | V0052 | 0.6 |

The antibodies shown in Table 25 all demonstrated $K_D$ values less than 150 nM, with antibodies V0009, V0022, V0052, V0024, and V0023 demonstrating $K_D$ values less than 10 nM. Of the antibodies tested, all demonstrated weak or no affinity (greater than 200 nM $K_D$) for wild type tau, except for V00016, which demonstrated nearly equivalent affinity for wild type tau.

Antibodies V0022, V009, V0023, V0024, and V0052 were also assessed for binding to iPHF tau by surface plasmon resonance on a Biacore 8K instrument. Affinity ($K_D$), including $k_{on}$ and $k_{off}$, for each of the anti-tau antibodies tested are provided in Table 28. The data obtained by SPR correlated with what was observed via Octet. These data demonstrated that the antibodies tested bind to immunopurified PHF tau with high affinity and none of the antibodies demonstrated any binding to wild-type tau.

TABLE 28

Affinity analysis results by Biacore/SPR analysis

| ID# | KD (pM) | ka (1/Ms) | kd (1/s) |
|---|---|---|---|
| V0022 | 43.9 | 1.70E+06 | 7.09E−05 |
| V0009 | 296.5 | 2.92E+06 | 7.87E−04 |
| V0023 | 57.8 | 5.22E+05 | 3.00E−05 |
| V0024 | 124.5 | 5.89E+05 | 7.32E−05 |
| V0052 | 4465 (KD1), 2640 (KD2) | 3.0E+07, 6.6E+04 | 1.3E−01, 1.8E−04 |

Example 4. Fine Epitope Mapping of V0022, V0023, and V0024 Anti-Tau Antibodies

As described in Example 9 of WO 2021/211753 (which is hereby incorporated by reference in its entirety), V0022, V0023, and V0024 antibodies were demonstrated to bind close to the tau C-terminus with affinity for peptides corresponding with residues 409-436 of human tau (SEQ ID NO: 920). These antibodies demonstrated the highest affinity (V0022 $K_D$=3.06×10$^{-10}$ M; V0023 $K_D$=2.07×10$^{-10}$ M; V0024 $K_D$-2.25×10$^{-10}$ M) for peptides corresponding with residues 413-430 of human tau (SEQ ID NO: 920). This Example describes the further characterization of the binding specificity of three anti-tau antibodies.

To assess the binding characteristics of V0022, V0023, and V0024, the ability of these antibodies to bind to different phosphorylated species of the Tau409-426 peptide, specifically pS409, pS412, pS413, pT414, pS416, pS422, or a combination thereof (Table 29), was tested by a one point ELISA using a high resolution sub-phospho-peptide library. Briefly, peptides were generated that showed all possible combinations of phosphorylation patterns within known epitopes containing multiple possible phosphorylation sites. One-point ELISA was then used to determine differential binding based on the individual phosphorylation patterns of each peptide. OD values (450 nm) were collected, where a stronger positive signal is shown as a higher OD value, which is indicative of increased binding. A kinetic ELISA was also performed and EC50 values were calculated for each the affinity of each antibody tested to each peptide in Table 29.

TABLE 29

Tau409-426 phospho-peptides

| SEQ ID | Description | Sequence |
|---|---|---|
| 32 | pS409, pS412, pS413, pT414, pS416, pS422 | GSGS(pS)NV(pS)(pS)(pT)G(pS)IDLVD(pS)PQLA |
| 33 | pS422 | GSGSSNVSSTGSIDLVD(pS)PQLA |
| 34 | pS416, pS422 | GSGSSNVSSTG(pS)IDLVD(pS)PQLA |

The V0022, V0023, and V0024 all demonstrated the same binding pattern and were able to bind to all phospho-tau peptides tested, including the peptide that was phosphorylated at pS409, pS412, pS413, pT414, pS416, pS422, the peptide phosphorylated at pS422, and the peptide phosphorylated at pS416 and pS422 (Table 30). This demonstrated that pS422 was necessary and sufficient for binding of the V0022, V0023, and V0024 to phospho-tau. Kinetic ELISA confirmed that V0022, V0023, and V0024 bind pS422 specifically.

TABLE 30

EC50 for V0022, V0023, and V0024 against different phosphorylated tau peptides

| | EC50 (nM) | | |
|---|---|---|---|
| Antibody | pS409, pS412, pS413, pT414, pS416, pS422 | pS422 | pS416, pS422 |
| V0022 | 0.3023 | 0.2876 | 0.2826 |
| V0023 | 0.217 | 0.2337 | 0.2522 |
| V0024 | 0.2223 | 0.2333 | 0.2201 |

Example 5. Engineering Viral Genomes for the Expression of Anti-Tau Antibodies

A viral genomes was designed for AAV delivery of the anti-tau antibody V0022 (Table 4). The nucleotide sequence from 5' ITR to 3' ITR is provided herein in Tables 18 and 19, as SEQ ID NO: 15.

The viral genome construct comprises a nucleotide sequence encoding an antibody that binds to tau. The nucleotide sequence was designed to encode an antibody heavy chain signal sequence (SEQ ID NO: 1 (amino acid) and SEQ ID NO: 1083 (DNA)); a nucleotide sequence encoding a heavy chain variable region (SEQ ID NO: 21 (amino acid) and SEQ ID NO: 7 (DNA); a nucleotide sequence encoding a heavy chain constant region (SEQ ID NO: 16 (amino acid) and SEQ ID NO: 805 (DNA)); a nucleotide sequence encoding a first linker (SEQ ID NO: 1724); a nucleotide sequence encoding a second linker (SEQ ID NO: 1726); a nucleotide sequence encoding a light chain signal sequence (SEQ ID NO: 2 (amino acid) and SEQ ID NO: 1084 (DNA)); a nucleotide sequence encoding a light chain variable region (SEQ ID NO: 93 (amino acid) and SEQ ID NO: 11 (DNA)); and a nucleotide sequence encoding a light chain constant region (SEQ ID NO: 18 (amino acid) and SEQ ID NO: 17 (DNA)). The nucleotide sequence encoding the anti-tau antibody was operably linked to a CMVie enhance (SEQ ID NO: 1050) and a CBA promoter variant (SEQ ID NO: 1042).

The viral genome construct also comprised a 5' ITR of SEQ ID NO: 1035, an intron of SEQ ID NO: 1068, a polyA signal region of SEQ ID NO:1134, and a 3' ITR of SEQ ID NO: 1037.

Example 6. Inhibition of Tau Pathology by Anti-Tau Antibodies in Hippocampal P301S Seeding Model In this Example, the AD-PHF seeded hippocampal P301S model was used for in vivo efficacy studies of anti-tau antibodies and vectorized forms thereof. To establish the hippocampal seeding model, AD brain-derived PHFs was injected into the left hippocampus of 8-weeks-old P301S mice. Efficacy of the V0022, V0009, V0023, V0024, V0052 antibodies alone (passive immunization) and the vectorized V0022 antibody were then investigated.

Briefly, for the passive immunization, the V0022, V009, V0023, V0024, and V0052 antibodies were administered intraperitoneally at 40 mg/kg two times in the week prior to the hippocampal seeding of the PHFs (2 doses), and five additional doses (40 mg/kg per dose) were administered intraperitoneally each week after seeding. For the vectorized administration, AAV particles comprising a VOY101 capsid protein (SEQ ID NO: 803), and a viral genome of SEQ ID NO: 15 (see, e.g., Example 5), which encoded the V0022 antibody under the control of a CMVie enhancer/CBA promoter variant (VOY101_V0022) were administered by intravenous injection two weeks prior to seeding at a dose of either 1e13 vg/kg or 3e13 vg/kg. An IgG or a PBS vehicle was administered as a control. At 6 weeks post-seeding and 8-weeks post the initial dose of either the antibodies alone or the vectorized anti-tau antibody, the brains and hippocampi of each animal were isolated for AT8 ELISA to assess tau pathology.

First, the ability of injected PHFs to induce tau pathology was determined in P301S mice without the injection of anti-tau antibodies. A significant increase of AT8 immunoreactivity (IR) was detected in the PHF injected ipsilateral site but not in vehicle (PBS) injected site. In the tau seed injected mice, tau pathology was detected in the contralateral site to a lesser extent, indicating tau pathology induced by injected PHF can spread across hippocampus. Tau pathology was also detected by IHC staining with AT100 anti-tau antibody. A significant number of CA neurons on the ipsilateral site exhibited tau pathology (AT100 positives).

Table 31 provides the reduction in AT8 IR pathology in the mice following passive administration of the V0009, V0022, V0023, V0024, and V0052 antibodies normalized to the PBS vehicle control. As shown in Table 31, a significant reduction of tau pathology was observed in both the ipsilateral and contralateral hippocampus in mice passively treated with V0022, V0023, and V0024. Additionally, all antibodies investigated demonstrated a significant reduction in tau pathology in the contralateral hippocampus. Comparing the AT8 IR in the ipsilateral hippocampus versus the contralateral hippocampus also demonstrated a robust reduction of tau pathology spreading across the hippocampus in the mice treated by passive immunization of the V0022, V0023, and V0024 anti-tau antibodies.

TABLE 31

Efficacy of anti-tau antibodies administered by passive in vivo compared to PBS vehicle control

| Antibody | Reduction of AT8 IR vs vehicle (PBS) | |
|---|---|---|
| | Ipsilateral Efficacy | Contralateral Efficacy |
| V0009 | None | 43% |
| V0022 | 74% | 71% |
| V0023 | 52% | 55% |
| V0024 | 67% | 72% |
| V0052 | none | 55% |

Table 32 provides the reduction in AT8 IR pathology normalized to an IgG control (efficacy) as well as the viral genome and/or antibody levels in the hippocampus and cerebral spinal fluid (CSF) (biodistribution) in the mice following passive administration (V0022) or vectorized administration (VOY101_V0022) of the V0022 antibody. As shown in Table 32, a dose dependent increase in viral genome or antibody levels was observed in the central nervous system and CSF following vectorized delivery of the V0022 antibody. Additionally, significant reduction in tau pathology was observed in mice treated with the high and low doses of the vectorized V0022 antibody as well as those treated with passive delivery of the V0022 antibody. In fact, passive administration of V0022 resulted in comparable levels of reduction in tau pathology when compared to vectorized delivery at both the high and low dose. These data demonstrate that V0022 administered passively or in a vectorized form (e.g., vectorized in an AAV particle) can significantly reduce tau pathology.

TABLE 32

Efficacy and biodistribution following passive and vectorized administration of the V0022 antibody

| Antibody (Ab) | Dose | Viral genomes per cell | Hippocampus Ab level (ng/g) | CSF Ab levels (ng/mL) | Reduction of AT8 pathology normalized to IgG control |
|---|---|---|---|---|---|
| VOY101_V0022 (vectorized) | 1e13 vg/kg | 8 vg/cell | 2,878 | 358 | 71% |
| | 3e13 vg/kg | 25 vg/cell | 7,310 | 728 | 78% |

TABLE 32-continued

Efficacy and biodistribution following passive and vectorized administration of the V0022 antibody

| Antibody (Ab) | Dose | Viral genomes per cell | Hippocampus Ab level (ng/g) | CSF Ab levels (ng/mL) | Reduction of AT8 pathology normalized to IgG control |
|---|---|---|---|---|---|
| V0022 (passive) | 40 mg/kg | N/A | 887 | 194 | 68.4% |

Example 7. Inhibition of Tau Pathology by the V0022 Antibody in a P301S Intrinsic Model In this Example, the P301S intrinsic model was used for in vivo efficacy studies of the V0022 anti-tau antibody and a vectorized form thereof.

Eight-week-old P301S mice were dosed with AAV particles comprising a VOY101 capsid protein (SEQ ID NO: 803), and a viral genome of SEQ ID NO: 15 (see, e.g., Example 5), which encoded the V0022 antibody under the control of a CMVie enhancer/CBA promoter variant (VOY101_V0022) by intravenous administration or the V0022 antibody by intraperitoneal injection, weekly for 13 weeks at a dose of either 1e13 vg/kg or 3e13 vg/kg for VOY101_V0022 or a dose of 40 mg/kg for the V0022 antibody. Control mice were administered with an IgG control. Tau pathology was not yet developed in these mice at 8 weeks but in untreated mice, continues to progress throughout their lifespan. At 20 weeks of age (e.g., 12 weeks post initial dose of VOY101_V0022 or V0022), mice were sacrificed and the hippocampus and cortex were isolated for biochemical analyses.

Table 33 provides the reduction in AT8 IR pathology normalized to an IgG control (efficacy) as well as the viral genome and/or antibody levels in the hippocampus and CSF (biodistribution) in the mice following passive administration (V0022) or vectorized administration (VOY101_V0022) of the V0022 antibody. As shown in Table 33, a dose dependent increase in viral genome was observed in the central nervous system regions and CSF following vectorized delivery of the V0022 antibody. V0022 antibody expression was observed in the CNS regions as well as the CSF in mice treated by both the vectorized or passive delivery of the V0022 antibody. Additionally, a reduction in tau pathology was observed in mice treated with the high and low doses of the vectorized V0022 antibody as well as those treated with passive delivery of the V0022 antibody. In fact, passive administration of V0022 resulted in comparable levels of reduction in tau pathology when compared to vectorized delivery at both the high and low dose. These data demonstrate that V0022 administered passively or in a vectorized form (e.g., vectorized in an AAV particle) can significantly reduce tau pathology.

TABLE 33

Efficacy and biodistribution in the cortex and hippocampus following passive and vectorized administration of the V0022 antibody

| Antibody and Dose | Viral genomes per cell | | Antibody Levels | | | Reduction of AT8 pathology normalized to IgG control | |
|---|---|---|---|---|---|---|---|
| | Cortex | Hippocampus | Cortex (ng/g) | Hippocampus (ng/g) | CSF (ng/mL) | Cortex | Hippocampus |
| VOY101_V0022 1e13 vg/kg | 10.3 | 4.7 | 2,970 | 3405 | 330 | 42% | 53% |
| VOY101_V0022 3e13 vg/kg | 19.2 | 8.9 | 5,451 | 6277 | 564 | 61% | 66% |
| V0022 40 mg/kg | N/A | N/A | 98 | 628 | 396 | 30% | 40% |

In a second experiment, female 12-week old P301S mice were dosed the V0022 antibody or a vehicle control by intraperitoneal injection weekly for 5 weeks (day 1, 8, 15, 22, and 29) at a dose of 80 mg/kg. At 16-weeks post-initial dose, mice were sacrificed and the cortex, serum, and CSF were isolated for biochemical analyses.

Table 39 provides the pathological tau levels in the cortex and the antibody levels in the CSF and serum. A 66% reduction in in pathological tau signal was observed in the mice that received the V0022 antibody compared to the vehicle control by ELISA which was used to quantify the unbound and bound pathological tau. This demonstrated target engagement by the V0022 antibody.

The tolerability of V0022 was also tested in the P301S mouse following 5 weekly intravenous doses of 30 mg/kg, 80 mg/kg, or 120 mg/kg and all doses were well tolerated. The serum pharmacokinetics (PK) of 80 mg/kg of V0022 in the P301S mouse exhibited a profile expected from a mouse IgG1 antibody, and had a half-life of approximately 12.6 days. Model based PK parameter estimates yielded a clearance rate ($C_L$) of 0.166 mL/day, and central and peripheral volumes of distribution were 0.839 mL and 1.87 mL, respectively.

TABLE 39

Efficacy and biodistribution in the cortex and hippocampus following passive and vectorized administration of the V0022 antibody

| Antibody and Dose | Pathological Tau Levels | | Antibody Levels | |
|---|---|---|---|---|
| | Cortex (ng/mg) All Samples | Cortex (ng/mg) ROUT Identified Outliers Removed | CSF (ng/mL) | Serum (ng/mL) |
| V0022 80 mg/kg | 48 | 29.9 | 818.4 | 1081 |
| Vehicle | 108 | 89.0 | 0 | 0 |

Example 8. Evaluation and Characterization of Humanized V0022 Antibodies

This example describes the humanization of the V0022 antibody and evaluation and characterization of said humanized antibodies. The V0022 antibody specifically targets an epitope in the C-terminus of tau.

A. Generation of Humanized V0022 Antibodies

The HC CDRs (HC CDR1 of SEQ ID NO: 64, HC CDR2 of SEQ ID NO: 1145, and HC CDR3 of SEQ ID NO: 1167) from the murine heavy chain variable region (SEQ ID NO: 21) of V0022, and the LC CDRs (LC CDR1 of SEQ ID NO: 1146, LC CDR2 of SEQ ID NO: 529, and LC CDR3 of SEQ ID NO: 571) of the light chain variable region (SEQ ID NO: 93) of V0022 generated in Example 1 of WO 2021/211753 (the contents of which are hereby incorporated by reference in its entirety), were grafted onto human framework regions. Five different humanized VH sequences and five different humanized VL sequences were generated, and are provided in Tables 4A and 4B, respectively. Each of the five humanized heavy chains comprised a human IgG4 isotype constant region which comprised an S to P mutation at position 228, numbered according to EU numbering. Each of the five humanized light chains comprised a human IgK constant domain (allotype Km3). The humanized V0022 antibody sequences are provided in Tables 4A, 4B, and 4C. The VH/VL and heavy and light chain pairings for the humanized antibodies investigated in this Example are shown in Table 34.

TABLE 34

Humanized V0022 Antibodies

| Antibody | Sequences | Antibody | Sequences |
|---|---|---|---|
| hV0022 control | VH: SEQ ID NO: 21<br>VL: SEQ ID NO: 93<br>HC: SEQ ID NO: 65<br>LC: SEQ ID NO: 66 | Ab3 | VH: SEQ ID NO: 70<br>VL: SEQ ID NO: 72<br>HC: SEQ ID NO: 173<br>LC: SEQ ID NO: 175 |
| Ab2 | VH: SEQ ID NO: 67<br>VL: SEQ ID NO: 72<br>HC: SEQ ID NO: 170<br>LC: SEQ ID NO: 175 | Ab9 | VH: SEQ ID NO: 70<br>VL: SEQ ID NO: 73<br>HC: SEQ ID NO: 173<br>LC: SEQ ID NO: 176 |
| Ab6 | VH: SEQ ID NO: 67<br>VL: SEQ ID NO: 73<br>HC: SEQ ID NO: 170<br>LC: SEQ ID NO: 176 | Ab10 | VH: SEQ ID NO: 70<br>VL: SEQ ID NO: 74<br>HC: SEQ ID NO: 173<br>LC: SEQ ID NO: 177 |
| Ab7 | VH: SEQ ID NO: 68<br>VL: SEQ ID NO: 72<br>HC: SEQ ID NO: 171<br>LC: SEQ ID NO: 175 | Ab11 | VH: SEQ ID NO: 71<br>VL: SEQ ID NO: 72<br>HC: SEQ ID NO: 174<br>LC: SEQ ID NO: 175 |
| Ab8 | VH: SEQ ID NO: 69<br>VL: SEQ ID NO: 72<br>HC: SEQ ID NO: 172<br>LC: SEQ ID NO: 175 | Ab4 | VH: SEQ ID NO: 71<br>VL: SEQ ID NO: 73<br>HC: SEQ ID NO: 174<br>LC: SEQ ID NO: 176 |

TABLE 34-continued

Humanized V0022 Antibodies

| Antibody | Sequences | Antibody | Sequences |
|---|---|---|---|
| Ab1 | VH: SEQ ID NO: 69<br>VL: SEQ ID NO: 73<br>HC: SEQ ID NO: 172<br>LC: SEQ ID NO: 176 | Ab5 | VH: SEQ ID NO: 71<br>VL: SEQ ID NO: 74<br>HC: SEQ ID NO: 174<br>LC: SEQ ID NO: 177 |

B. Affinity, Selectivity, and Immunogenicity of Humanized V0022 Antibodies

Different pairings of the humanized heavy and light chains of the V0022 antibody provided in Tables 4A and 4B, respectively, were analyzed to determine their affinity for immunopurified PHF (iPHF) and a phosphorylated tau peptide of SEQ ID NO: 33 (pTau; phosphorylated at position S422 numbered according to wild-type tau of SEQ ID NO: 920), as well as their selectivity in detecting enriched PHF (ePHF) compared to wild-type Tau. The humanized variants were compared to the murine V0022 antibody control, which comprised a VH of SEQ ID NO: 21, a heavy chain of SEQ ID NO: 65, a VL of SEQ ID NO: 93, and a light chain of SEQ ID NO: 66 (see, e.g., Table 4 above). The phosphorylated tau peptide of SEQ ID NO: 33 comprising a phosphorylated serine at position 422, numbered according to SEQ ID NO: 920, was investigated as this includes the epitope for the humanized V0022 antibodies (see, e.g., Example 4).

Binding of the various humanized antibodies to iPHF or the phosphorylated tau peptide of SEQ ID NO: 33 was assessed by SPR on a Biacore 8K instrument. iPHF or the phosphorylated tau peptide was directly immobilized on the chip. iPHF was directly immobilized on CM5 sensor chip by amine coupling at 199 RU density. For the phosphorylated tau peptide, 1 µg/ml of the biotinylated phosphorylated peptide was captured on Biotin CAP chip via CAPture reagent to achieve 5-10 RU levels. Antibody was then injected using Single Cycle Kinetics (SCK) mode with association and dissociation times of 5 and 10 min, respectively, at a concentration ranging from 0.78 to 2.5 nM. The affinity value, or rate of dissociation ($K_D$), was subsequently calculated. As shown in Table 35, the humanized V0022 antibodies tested all bound to immunopurified PHF tau and the phosphorylated tau peptide with high affinity, as evidenced by the $K_D$ values in the picomolar range.

The ability of the various humanized antibodies to bind ePHF and their specificity for ePHF compared to wild-type tau was also investigated by ELISA. The various humanized antibodies were exposed to a plate coated with either ePHF or wild-type tau. OD readings were taken at 450 nm and plotted against the antibody concentrations tested, and the half maximal effective concentration (EC50) for antibody binding to ePHF or wild type tau was calculated (Table 35). As provided in Table 35, all antibodies showed high affinity for ePHF but no binding to wild-type tau, indicating strong and selective binding to ePHF.

TABLE 35

Affinity and selectivity of humanized V0022 antibodies

| Antibody | Affinity to iPHF (pM) | Affinity to pS422 tau peptide (SEQ ID NO: 33) (pM) | Affinity to ePHF EC50 (nM) | Selectivity: ePHF:WT rec. Tau | Inhibition of ePHF seeding in Biosensor Cells |
|---|---|---|---|---|---|
| V0022 control VH: SEQ ID NO: 21 VL: SEQ ID NO: 93 HC: SEQ ID NO: 8 LC: SEQ ID NO: 12 | 16.5 | | | | 18.2 |
| hV0022 control | 16.2 | | 0.08 | >240 | |
| Ab2 | 29.3 | 38.6 | 0.15 | >133 | 78.1 |
| Ab6 | 39.1 | 39.8 | 0.16 | >124.8 | 17.6 |
| Ab7 | 33.4 | 39.8 | 0.13 | >149.9 | 49.8 |
| Ab8 | 49.6 | 53.3 | 0.17 | >119 | 17.6 |
| Ab1 | 43.4 | 40.8 | 0.085 | >232.9 | 32.2 |
| Ab3 | 32.5 | 45.7 | 0.095 | >210.3 | 58.1 |
| Ab9 | 44 | 76.3 | 0.1 | >198.4 | 49.8 |
| Ab10 | 30.4 | 43.6 | 0.14 | >118.8 | 34.5 |
| Ab11 | 24.9 | 40.3 | 0.16 | >113.8 | 24.1 |
| Ab4 | 35.3 | 36.1 | 0.18 | >122 | 37.9 |
| Ab5 | 24.8 | 29.4 | 0.19 | >128.5 | 43.8 |

These humanized V0022 antibodies also demonstrated low polyspecificity in a baculovirus particles (BVP) ELISA (Table 36), which measures binding to empty BVPs. Predicted aggregation and post-translational modification (PTM) liability were also assessed by in-silico assays and the values are provided for each humanized antibody tested in Table 36.

TABLE 36

Additional characteristics of humanized V0022 antibodies

| Antibody | Polyspecificity | PTM liability | Predicted aggregation |
|---|---|---|---|
| hV0022 control | 3.9 | | Inconclusive |
| Ab2 | 1.8 | 0.505 | Low |
| Ab6 | 1.6 | 0.505 | Inconclusive |
| Ab7 | 6 | 0.505 | Inconclusive |
| Ab8 | 1.6 | 0.505 | Inconclusive |
| Ab1 | 1.7 | 0.505 | Inconclusive |
| Ab3 | 2.2 | 0.505 | Inconclusive |

TABLE 36-continued

Additional characteristics of humanized V0022 antibodies

| Antibody | Polyspecificity | PTM liability | Predicted aggregation |
|---|---|---|---|
| Ab9 | 1.8 | 0.505 | Inconclusive |
| Ab10 | 3.2 | 0.505 | Low |
| Ab11 | 1.6 | 0.505 | Low |
| Ab4 | 1.4 | 0.505 | Low |
| Ab5 | 2.7 | 0.505 | Low |

The humanized antibodies were also assessed for their ability to bind pathological tau in human brain tissue sections isolated from the cortex of patients with or without Alzheimer's disease (AD). Staining was performed as described in Example 2. As provided in Table 37, all antibodies tested demonstrated specific binding to neuronal tau pathology with minimal staining of non-AD cortex tissues. A desirable PTM liability score for the humanized antibodies ranges from 0-1.

TABLE 37

Evaluation of binding to human AD tau pathology of humanized V0022 antibodies

| Antibody | IHC Fixed Human AD Brain | IHC Fixed Human Control Brain | Western Frozen Human AD Brain | Western Frozen Human Control Brain |
|---|---|---|---|---|
| V0022 control VH: SEQ ID NO: 21 VL: SEQ ID NO: 93 HC: SEQ ID NO: 8 LC: SEQ ID NO: 12 | Positive | Negative | Positive | Negative |
| hV0022 control | Positive | Negative | Positive | Negative |
| Ab2 | Positive | Negative | Positive | Negative |
| Ab6 | Positive | Negative | Positive | Negative |
| Ab7 | Positive | Negative | Positive | Negative |
| Ab8 | Positive | Negative | Positive | Negative |
| Ab1 | Positive | Negative | Positive | Negative |
| Ab3 | Positive | Negative | Positive | Negative |
| Ab9 | Positive | Negative | Positive | Negative |
| Ab10 | Positive | Negative | Positive | Negative |
| HC5LC1 | Positive | Negative | Positive | Negative |

TABLE 37-continued

Evaluation of binding to human AD tau pathology of humanized V0022 antibodies

| Antibody | IHC Fixed Human AD Brain | IHC Fixed Human Control Brain | Western Frozen Human AD Brain | Western Frozen Human Control Brain |
|---|---|---|---|---|
| Ab4 | Positive | Negative | Positive | Negative |
| Ab5 | Positive | Negative | Positive | Negative |

The productivity for antibodies Ab1, Ab2, Ab3, Ab4, and Ab5 was also measured as yield from a 2 L stable pool of mammalian cells (Table 40). As shown in Table 40, Ab1, Ab2, and Ab3 led to higher productivity and yield, as compared to Ab4 and Ab5.

TABLE 40

Productivity of humanized V0022 antibodies

| | Ab2 | Ab1 | Ab3 | Ab4 | Ab5 |
|---|---|---|---|---|---|
| Productivity - yield from 2 L stable pool of mammalian cells | 355 mg | 456 mg | 666 mg | 151 mg | 121 mg |

The relative immunogenicity risk of the humanized antibodies, Ab1-Ab5, were assessed by a CD4+ T cell proliferation assay. Samples of the antibodies were incubated with PBMC cells from 50 healthy donors that were representative for the global population based on HLA-DRB1 expression, and cell proliferation was measured by flow cytometry. The stimulation index (SI) was calculated for each antibody as the ratio of the number of proliferating T cells in the sample over the blank (FIG. 1). An SI index of 2.0 or greater was considered a positive response. Ab1 demonstrated a mean SI of less than 2.0, whereas the other antibodies tested (Ab2, Ab3, Ab4, and Ab5) demonstrated SI values closer to 2.0 or greater. The magnitude of the difference between the SI of Ab1 relative to the other humanized antibodies tested was statistically significant (p-value was less than or equal to 0.05). The percentage of responding donors was also calculated (Table 38). Herceptin was used as a control antibody as it has been shown to have a low risk of immunogenicity and less than 10% responders. As shown in Table 38, Ab1 demonstrated the lowest immunogenicity risk, as well as the lowest number of responding donor relative to the other humanized antibodies tested.

TABLE 38

Relative immunogenicity risk of humanized V0022 antibodies

| Antigen | # of Responding donors of 50 total donors | % of Responding donors |
|---|---|---|
| KLH (control) | 50 | 100 |
| Herceptin (control) | 4 | 8 |
| Ab2 | 27 | 54 |
| Ab1 | 12 | 24 |
| Ab3 | 23 | 46 |
| Ab4 | 24 | 48 |
| Ab5 | 25 | 50 |

Antibody Ab1 was administered to P301S mice (intrinsic model) intravenously at a dose of 120 mg/kg on day 1, 8, 15, 22, and 29. Serum was collected on days 6, 13, 20, 27 and 30. Mice administered Ab1 tolerated all 5 doses with no body weight changes and they showed no change in body temperature for up to 60 minutes after receiving the antibody doses. Ab1 antibody levels were assessed in the serum using a pS422 peptide ELISA. The mice showed no decreased serum antibody concentrations over 30 days from the initial dose. Ab1 levels were approximately 500 µg/mL for at least 6-27 days post initial dose and increased to up to about 1000 µg/mL by day 30.

The tolerability and pharmacokinetics of Ab1 was also investigated in non-human primates (NHPs) (cynomolgus macaques, *Macaca fascicularis*). The NHPs were administered a single intravenous dose of the antibody. The NHP was either given a high dose or a mid level dose of the Ab1. Both doses were well tolerated in the NHPs and no adverse effects were observed.

Taken together these data demonstrate that the humanized V0022 antibodies generated are capable of selective binding with strong affinity to pathological tau, e.g., iPHF and ePHF, but not wild-type tau (demonstrated selectivity). These humanized antibodies were also able to bind pathological tau in in brain samples from patients with Alzheimer's disease. Additionally, Ab1 was well tolerated in a mouse model of a tauopathy (e.g., the P301S intrinsic model), demonstrated higher productivity and reduced immunogenicity, blocked paired helical filaments seed-induced tau aggregates in vitro, and selectively stained tau tangles in AD brain samples and the P301S mouse. These data support use of Ab1 in patients with, e.g., mild dementia or mild cognitive impairment due to Alzheimer's disease (AD).

VIII. Equivalents and Scope

The disclosures of the cited sources, for example references, publications, databases, and database entries, cited herein, are incorporated into this application by reference, even if not expressly stated in the citation.

While this invention has been disclosed with reference to specific aspects and embodiments, it is apparent that other aspects, embodiments, and variations of this invention may be devised by others skilled in the art without departing from the true spirit and scope of the invention. The appended claims are intended to be construed to include all such aspects and equivalent variations.

We claim:

1. An antibody that binds to human tau, which comprises a heavy chain variable region (VH) comprising a heavy chain complementarity determining region 1 (HC CDR1) comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a light chain variable region (VL) comprising a light chain complementarity determining region 1 (LC CDR1) comprising the amino acid sequence of SEQ ID NO: 1146, a LC CDR2 comprising the amino acid sequence of SEQ ID NO: 529, and a LC CDR3 comprising the amino acid sequence of SEQ ID NO: 571; and wherein:
   (i) the VH comprises the amino acid V at position 5; S at position 7; A at position 9; V at position 11; K at position 12; S at position 14; A at position 16; K at position 19; V at position 20; R at position 38; Q at position 39; A at position 40; Q at position 43; R at position 67; V at position 68; I at position 71; R at position 72; D at position 73; T at position 74; T at position 76; T at position 84; and L at position 113, numbered according to SEQ ID NO: 21; and
   (ii) the VL comprises the amino acid I at position 2; S at position 7; S at position 12; T at position 14; P at position 15; Q at position 17; P at position 18; Q at position 50; S at position 68; V at position 88; Y at position 92; Q at position 105; and V at position 109, numbered according to SEQ ID NO: 93.

2. The antibody of claim 1, wherein the VH comprises an amino acid sequence at least 95% identical to the amino acid sequence of SEQ ID NO: 69; and the VL comprises an amino acid sequence at least 95% identical to the amino acid sequence of SEQ ID NO: 73.

3. An antibody that binds to human tau comprising a heavy chain variable region (VH) comprising the amino acid sequence of SEQ ID NO: 69; and a light chain variable region (VL) comprising the amino acid sequence of SEQ ID NO: 73.

4. The antibody of claim 3, which is a full length antibody, a bispecific antibody, an Fab, an F(ab')₂, an Fv, or a single chain Fv fragment (scFv).

5. The antibody of claim 3, which comprises a heavy chain constant region selected from IgG1, IgG2, IgG3, or IgG4; and a light chain constant region of kappa or lambda.

6. The antibody of claim 3, which comprises a heavy chain constant region of IgG4 and a light chain constant region of kappa.

7. The antibody of claim 3, which comprises a heavy chain constant region comprising the amino acid sequence of SEQ ID NO: 194, or an amino acid sequence at least 95% identical thereto; and a light chain constant region comprising the amino acid sequence of SEQ ID NO: 200, or an amino acid sequence at least 95% identical thereto.

8. The antibody of claim 1, which:
   (i) binds the C-terminus of a tau protein;
   (ii) binds a phosphorylated residue of a tau protein;
   (iii) binds phosphorylated serine at position 422 (pS422), numbered according to SEQ ID NO: 920;
   (iv) preferentially binds pathological tau compared to wild-type tau;
   (v) reduces or inhibits aggregation of tau; and/or
   (vi) binds an epitope comprising a region formed by a complex of at least two tau proteins.

9. An antibody that binds to human tau, which comprises a heavy chain comprising a HC CDR1 comprising the amino acid sequence of SEQ ID NO: 1144, a HC CDR2 comprising the amino acid sequence of SEQ ID NO: 1145, and a HC CDR3 comprising the amino acid sequence of SEQ ID NO: 410; and a light chain comprising a LC CDR1 comprising the amino acid sequence of SEQ ID NO: 1146, a LC CDR2 comprising the amino acid sequence of SEQ ID NO: 529, and a LC CDR3 comprising the amino acid sequence of SEQ ID NO: 571; and wherein:
   (i) the heavy chain comprises an amino acid sequence at least 95% identical to the amino acid sequence of SEQ ID NO: 172; and the light chain comprises an amino acid sequence at least 95% identical to the amino acid sequence of SEQ ID NO: 176;
   (ii) the heavy chain comprises an amino acid sequence at least 95% identical to the amino acid sequence of SEQ ID NO: 173; and the light chain comprises an amino acid sequence at least 95% identical to the amino acid sequence of SEQ ID NO: 175;
   (iii) the heavy chain comprises an amino acid sequence at least 95% identical to the amino acid sequence of SEQ ID NO: 170; and the light chain comprises an amino acid sequence at least 95% identical to the amino acid sequence of SEQ ID NO: 175;
   (iv) the heavy chain comprises an amino acid sequence at least 95% identical to the amino acid sequence of SEQ ID NO: 174; and the light chain comprises an amino acid sequence at least 95% identical to the amino acid sequence of SEQ ID NO: 176; or
   (v) the heavy chain comprises an amino acid sequence at least 95% identical to the amino acid sequence of SEQ ID NO: 174; and the light chain comprises an amino acid sequence at least 95% identical to the amino acid sequence of SEQ ID NO: 177.

10. The antibody of claim 9, wherein the heavy chain comprises the amino acid sequence of SEQ ID NO: 172; and the light chain comprises the amino acid sequence of SEQ ID NO: 176.

11. The antibody of claim 9, wherein the heavy chain comprises an amino acid sequence at least 95% identical to the amino acid sequence of SEQ ID NO: 172; and the light chain comprises an amino acid sequence at least 95% identical to the amino acid sequence of SEQ ID NO: 176.

12. A nucleic acid encoding the antibody that binds to human tau of claim 1.

13. A pharmaceutical composition comprising the antibody of claim 1, and a pharmaceutically acceptable excipient.

14. A method of delivering an antibody that binds to tau to a subject, comprising administering an effective amount of the antibody of claim 1 to the subject, thereby delivering the antibody that binds to tau to the subject.

15. The method of claim 14, wherein the antibody is administered to the subject intravenously.

16. A method of detecting or determining the level of a tau protein in a sample, comprising contacting the sample with the antibody of claim 3, thereby detecting or determining the level of the tau protein in the sample.

17. A pharmaceutical composition comprising the antibody of claim 3, and a pharmaceutically acceptable excipient.

18. A method of delivering an antibody that binds to tau to a subject, comprising administering an effective amount of the antibody of claim 3 to the subject, thereby delivering the antibody that binds to tau to the subject.

19. A pharmaceutical composition comprising the antibody of claim 10, and a pharmaceutically acceptable excipient.

20. A method of delivering an antibody that binds to tau to a subject, comprising administering an effective amount of the antibody of claim 10 to the subject, thereby delivering the antibody that binds to tau to the subject.

21. The antibody of claim 3, which comprises a human IgG4 constant region, comprising a serine to proline substitution at position 228 according to EU numbering.

22. A nucleic acid encoding an antibody that binds to human tau, wherein the encoded antibody comprises a heavy chain variable region (VH) comprising the amino acid sequence of SEQ ID NO: 69; and a light chain variable region (VL) comprising the amino acid sequence of SEQ ID NO: 73.

23. The nucleic acid of claim 22, wherein the encoded antibody comprises a heavy chain comprising an amino acid sequence at least 95% identical to the amino acid sequence of SEQ ID NO: 172; and a light chain comprising an amino acid sequence at least 95% identical to the amino acid sequence of SEQ ID NO: 176.

24. The nucleic acid of claim 22, wherein the encoded antibody comprises a heavy chain comprising the amino acid sequence of SEQ ID NO: 172; and a light chain comprising the amino acid sequence of SEQ ID NO: 176.

25. The nucleic acid of claim 22, wherein the nucleotide sequence encoding the VH comprises the nucleotide sequence of SEQ ID NO: 158, or a nucleotide sequence at least 95% identical thereto; and the nucleotide sequence encoding the VL comprises the nucleotide sequence of SEQ ID NO: 162, or a nucleotide sequence at least 95% identical thereto.

26. A vector comprising the nucleic acid of claim 22.

27. A host cell comprising the nucleic acid of claim 22.

28. A method of producing an antibody, the method comprising culturing the host cell of claim 27 under conditions suitable for gene expression, thereby producing the antibody.

\* \* \* \* \*

SEQUENCE LISTING

```
Sequence total quantity: 5348
SEQ ID NO: 1             moltype = AA  length = 19
FEATURE                  Location/Qualifiers
source                   1..19
                         mol_type = protein
                         organism = synthetic construct
SEQUENCE: 1
MNFGLSLIFL VLVLKGVQC                                                 19

SEQ ID NO: 2             moltype = AA  length = 19
FEATURE                  Location/Qualifiers
source                   1..19
                         mol_type = protein
                         organism = synthetic construct
SEQUENCE: 2
MKLPVRLLVL MFWIPASSS                                                 19

SEQ ID NO: 3             moltype = AA  length = 6
FEATURE                  Location/Qualifiers
source                   1..6
                         mol_type = protein
                         organism = synthetic construct
SEQUENCE: 3
SGGGGS                                                               6

SEQ ID NO: 4             moltype = AA  length = 113
FEATURE                  Location/Qualifiers
source                   1..113
                         mol_type = protein
                         organism = synthetic construct
SEQUENCE: 4
QVQLQQPGAE LVKPGASVKL SCKASDYTFT NYWMHWVKQR PGRGLEWIGR IDPNSGGTRY     60
NEKFKNKATL TVDKPSSTAY MHLSSLTSED SAVYYCAGDF DVWGTGTTVT VSS            113

SEQ ID NO: 5             moltype =    length =
SEQUENCE: 5
000

SEQ ID NO: 6             moltype =    length =
SEQUENCE: 6
000

SEQ ID NO: 7             moltype = DNA  length = 354
FEATURE                  Location/Qualifiers
source                   1..354
                         mol_type = other DNA
                         organism = synthetic construct
SEQUENCE: 7
caagtgcagc tgcagcagcc tggcaccgag ctggtgaaac ctggatctag cgtgaatctg     60
agctgcaagg ccagcggctt taccttcacc agatactgga tgcactgggt caaggaacgg    120
ccaggccacg gcctggaatg gatcggcaat atcaacccca caacggcgg aacagatttc     180
aacgagaagt tcaagaacaa ggctacactg accgtgcaca aaagctccac caccgtgttc    240
atccagctga gctctctgac aagcgaggac agcgccgtgt actattgtgc cagaggcacc    300
ggcaccggcg ccatggacta ctggggccag ggaacatctg tgacagtgtc cagc          354

SEQ ID NO: 8             moltype = AA  length = 441
FEATURE                  Location/Qualifiers
source                   1..441
                         mol_type = protein
                         organism = synthetic construct
SEQUENCE: 8
QVQLQQPGTE LVKPGSSVNL SCKASGFTFT RYWMHWVKER PGHGLEWIGN INPNNGGTDF     60
NEKFKNKATL TVHKSTTVF IQLSSLTSED SAVYYCARGT GTGAMDYWGQ GTSVTVSSAK     120
TTPPSVYPLA PGSAAQTNSM VTLGCLVKGY FPEPVTVTWN SGSLSSGVHT FPAVLQSDLY    180
TLSSSVTVPS STWPSETVTC NVAHPASSTK VDKKIVPRDC GCKPCICTVP EVSSVFIFPP    240
KPKDVLTITL TPKVTCVVVD ISKDDPEVQF SWFVDDVEVH TAQTQPREEQ FNSTFRSVSE    300
LPIMHQDWLN GKEFKCRVNS AAFPAPIEKT ISKTKGRPKA PQVYTIPPPK EQMAKDKVSL    360
TCMITDFFPE DITVEWQWNG QPAENYKNTQ PIMDTDGSYF VYSKLNVQKS NWEAGNTFTC    420
SVLHEGLHNH HTEKSLSHSP G                                              441

SEQ ID NO: 9             moltype = AA  length = 115
FEATURE                  Location/Qualifiers
source                   1..115
                         mol_type = protein
                         organism = synthetic construct
SEQUENCE: 9
EVQLVESGGA LVQPGGSLSL SCAASGFTFT DYYMSWVRQP PGKALEWLAL IRNKAKGFTT     60
EYSASVKGRF TISRDNSQSI LLFQMNDLRA DDSATYYCVR DINYWGQGTT LTVSS          115
```

```
SEQ ID NO: 10              moltype = DNA  length = 1323
FEATURE                    Location/Qualifiers
source                     1..1323
                           mol_type = other DNA
                           organism = synthetic construct
SEQUENCE: 10
caagtgcagc tgcagcagcc tggcaccgag ctggtgaaac ctggatctag cgtgaatctg    60
agctgcaagg ccagcggctt taccttcacc agatactgga tgcactgggt caaggaacgg   120
ccaggccacg gcctggaatg gatcggcaat atcaaccccca acaacggcgg aacagatttc   180
aacgagaagt tcaagaacaa ggctacactg accgtgcaca aaagctccac caccgtgttc   240
atccagctga gctctctgac aagcgaggac agcgccgtgt actattgtgc cagaggcacc   300
ggcaccggcg ccatggacta ctggggccag ggaacatctg tgacagtgtc cagcgccaaa   360
acgacacccc catcctgtct atccactggcc cctggatctg ctgcccaaac taactccatg   420
gtgaccctgg gatgcctggt caagggctat ttccctgagc cagtgacagt gacctggaac   480
tctggatccc tgtccagcgg tgtgcacacc ttcccagctg tcctgcagtc tgacctctac   540
actctgagca gctcagtgac tgtccctcc agcacctggc ccagtgagac cgtcacctgc   600
aacgttgccc accggccag cagcaccaag gtggacaaga aattgtgcc cagggattgt   660
ggttgtaagc cttgcatatg tacagtccca gaagtatcat ctgtcttcat cttccccca    720
aagcccaagg atgtgctcac cattactctg actcctaagg tcacgtgtgt tgtggtagac   780
atcagcaagg atgatcccga ggtccagttc agctggtttg tagatgatgt ggaggtgcac   840
acagctcaga cgcaaccccg ggaggagcag ttcaacagca ctttccgctc agtcagtgaa   900
cttcccatca tgcaccagga ctggctcaat ggcaaggagt tcaaatgcag ggtcaacagt   960
gcagcttttcc ctgccccat cgagaaaacc atctccaaaa ccaaaggcag accgaaggct  1020
ccacaggtgt acaccattcc acctcccaag gagcagatgg ccaaggataa agtcagtctg  1080
acctgcatga taacagactt cttccctgaa gacattactg tggagtgggt ggaattggg   1140
cagccagcgg agaactacaa gaacactcag cccatcatgg acacagatgg ctcttacttc  1200
gtctacagca agctcaatgt gcagaagagc aactgggagg caggaaatac tttcacctgc  1260
tctgtgttac atgagggcct gcacaaccac catactgaga gagcctctc ccactctcct  1320
ggt                                                                 1323

SEQ ID NO: 11              moltype = DNA  length = 336
FEATURE                    Location/Qualifiers
source                     1..336
                           mol_type = other DNA
                           organism = synthetic construct
SEQUENCE: 11
gatgtggtga tgacacagac ccctctgagc ctgcctgtgt ccctcggcga ccaggccagc    60
atcagctgta gaagcagcca atctctggtg cacaacaatg gcatcaccta cctgtactgg   120
tatctgcaga aacctggcca gagccccaag ctgctgatct accgggtgtc caatcggttc   180
agcggagtgc cagatagatt tggcggatct ggcagcggca ccgacttcac cctgaagatc   240
tctagagtcg aggccgagga cctgggcgtg tacttctgct tccagggcac acacgtgccc   300
agaaccttcg gcggcggaac aaaagctgga atcaag                              336

SEQ ID NO: 12              moltype = AA  length = 219
FEATURE                    Location/Qualifiers
source                     1..219
                           mol_type = protein
                           organism = synthetic construct
SEQUENCE: 12
DVVMTQTPLS LPVSLGDQAS ISCRSSQSLV HNNGITYLYW YLQKPGQSPK LLIYRVSNRF    60
SGVPDRFGGS GSGTDFTLKI SRVEAEDLGV YFCFQGTHVP RTFGGGTKLE IKRADAAPTV   120
SIFPPSSEQL TSGGASVVCF LNNFYPKDIN VKWKIDGSER QNGVLNSWTD QDSKDSTYSM   180
SSTLTLTKDE YERHNSYTCE ATHKTSTSPI VKSFNRNEC                           219

SEQ ID NO: 13              moltype = DNA  length = 657
FEATURE                    Location/Qualifiers
source                     1..657
                           mol_type = other DNA
                           organism = synthetic construct
SEQUENCE: 13
gatgtggtga tgacacagac ccctctgagc ctgcctgtgt ccctcggcga ccaggccagc    60
atcagctgta gaagcagcca atctctggtg cacaacaatg gcatcaccta cctgtactgg   120
tatctgcaga aacctggcca gagccccaag ctgctgatct accgggtgtc caatcggttc   180
agcggagtgc cagatagatt tggcggatct ggcagcggca ccgacttcac cctgaagatc   240
tctagagtcg aggccgagga cctgggcgtg tacttctgct tccagggcac acacgtgccc   300
agaaccttcg gcggcggaac aaaagctgga atcaagcggg ctgatgctgc accaactgta   360
tccatcttcc caccatccag tgagcagtta acatctggag gtgcctcagt cgtgtgcttc   420
ttgaacaact tctaccccaa agacatcaat gtcaagtgga agattgatgg cagtgaacga   480
caaaatggcg tcctgaacag ttggactgat caggacagca agacagcac ctacagcatg   540
agcagcaccc tcacgttgac caaggacgag tatgaacgac ataacagcta cctgtgtgag   600
gccactcaca agacatcaac ttcacccatt gtcaagagct caacaggaa tgagtgt      657

SEQ ID NO: 14              moltype =   length =
SEQUENCE: 14
000

SEQ ID NO: 15              moltype = DNA  length = 3962
FEATURE                    Location/Qualifiers
```

```
source                   1..3962
                         mol_type = other DNA
                         organism = synthetic construct
SEQUENCE: 15
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctaccag ggtaatgggg   180
atcctctaga actatagcta gtcgacattg attattgact agttattaat agtaatcaat   240
tacggggtca ttagttcata gcccatatat ggagttccgc gttacataac ttacggtaaa   300
tggcccgcct ggctgaccgc ccaacgaccc ccgcccattg acgtcaataa tgacgtatgt   360
tcccatagta acgccaatag ggactttcca ttgacgtcaa tgggtggagt atttacggta   420
aactgcccac ttggcagtac atcaagtgta tcatatgcca gtacgcccc ctattgacgt   480
caatgacggt aaatggcccg cctggcatta tgcccagtac atgaccttat gggactttcc   540
tacttggcag tacatctacg tattagtcat cgctattacc atggtcgagg tcgtttctgc   600
ttcactctcc ccatctcccc cccctcccca ccccaatttg tgtatttatt tattttttaa   660
ttattttgtg cagcgatggg ggcggggggg ggggcgcgc gccaggcggg gcggggcggg   720
gcgaggggcg gggcggggcg aggcggagag gtgcggcggc agccaatcag agcggcgcgc   780
tccgaaagtt tccttttatg gcgaggcggc ggcggcggca gcctataaa aagcgaagcg   840
cgcggcgggc gggagcaagc ttcgtttagt gaaccgtcag atcgcctgga gacgccatcc   900
acgctgtttt gacctccata gaagacaccg gaccgatcc agcctccgcg gattcgaatc   960
ccggccggga acgtgcatt ggaacgcgga ttccccgtgc caagagtgac gtaagtaccg  1020
cctatagagt ctataggccc acaaaaaatg ctttcttctt ttaatatact tttttgttta  1080
tcttatttct aatactttcc ctaatctctt tctttcaggg caataatgat acaatgtatc  1140
atgcctcttt gcaccattct aaagaataac agtgataatt tctgggttaa ggcaatagca  1200
atatttctgc atataaatat ttctgcatat aaattgtaac tgatgtaaga ggtttcatat  1260
tgctaatagc agctacaatc cagctaccat tctgctttta ttttatggtt gggataaggc  1320
tggattattc tgagtccaag ctaggccctt ttgctaatca tgttcatacc tcttatcttc  1380
ctcccacagc tcctgggcaa cgtgctggtc tgtgtgctgg cccatcactt ggcaaagaa  1440
ttgggattcg aaccggtgcc gccaccatga acttcgggct cagcttgatt ttccttgtcc  1500
ttgttttaaa aggtgtccag tgtcaagtgc agctgcagca gcctggggcc gagctggtga  1560
aacctggatc tagcgtgaat ctgagctgca aggcagcgg cttttaccttc accagatact  1620
ggatgcactg ggtcaaggaa cggccaggcc acggcctgga atggatcggc aatatcaacc  1680
ccaacaacgg cggaacagat ttcaacgaga agttcaagaa caaggctaca ctgaccgtgc  1740
acaaaagctc caccaccgtg ttcatccagc tgagctctct gacaagcgag gacgcgccg  1800
tgtactattg tgccagaggc accggcaccg cgccatgga ctactgggc cagggaacat  1860
ctgtgacagt gtccagcgcc aaaacgcacc cccatctgt ctatccactg gcccctggat  1920
ctgctgccca aactaactcc atggtgaccc tgggatgcct ggtcaaggc tatttccctg  1980
agccagtgac agtgacctgg aactctggat ccctgtccag cggtgtgcac accttccag   2040
ctgtcctgca gtctgacctc tacactctga gcagctcagt gactgtcccc tccagcacct  2100
ggcccagcga gaccgtcacc tgcaacgttg cccaccccgg cagcagcacc aaggtggaca  2160
agaaaattgt gcccagggat tgtggttgta agccttgcat atgtacagtc cagaagtat   2220
catctgtctt catcttcccc ccaaagccca aggatgtgct caccattact ctgactccta  2280
aggtcacgtg tgttgtggta gacatcagca aggatgatcc cgaggtccag ttcagctgga  2340
ttgtagatga tgtggaggtg cacacagctc agacgcaacc ccgggaggag cagttcaaca  2400
gcactttccg ctcagtcagt gaacttccca tcatgcacca ggactggctc aatggcaagg  2460
agttcaaatg cagggtcaac agtgcagctt ccctgcccc catcgagaaa accatctcca  2520
aaaccaaagg cagaccgaag gctccacagg tgtacaccat tccacctccc aaggagcaga  2580
tggccaagga taaagtcagt ctgacctgca tgataacaga cttcttccct gaagacatta  2640
ctgtggagtg gcagtggaat gggcagccag cggagaacta caagaacact cagcccatca  2700
tggacacaga tggctcttac ttcgtctaca gcaagctcaa tgtgcagaag agcaactggg  2760
aggcaggaaa tacttttacc tgctctgtgt tacatgaggg cctgcacaac caccatactg  2820
agaagagcct ctcccactct cctggtagaa agaggcgaga gggcagagga agtcttctaa  2880
catgcggtga cgtggaggag aatcccggcc ctatgaagtt gcctgttagg ctgttggtgc  2940
tgatgttctg gattcctgct tccagcagtg atgtggtgat gacacagacc cctctgagcc  3000
tgcctgtgtc cctcggcgac caggccagca tcagctgtag aagcagccaa tctctgggac  3060
acaacaatgg catcacctac ctgtactggt atctgcagaa acctggccag agccccaagc  3120
tgctgatcta ccgggtgtcc aatcggttca gcggagtgcc agatagattt ggcggatctg  3180
gcagcggcac cgacttcacc ctgaagatct ctagagtcga ggccgaggac ctgggcgtgt  3240
acttctgctt ccagggcaca cacgtgccca acctccgg cggcggaaca aagctggaaa  3300
tcaagcgggc tgatgctgca ccaactgtat ccatcttccc accatccagt gagcagttaa  3360
catctggagg tgcctcagtc gtgtgcttct tgaacaactt ctaccccaaa gacatcaatg  3420
tcaagtggaa gattgatggc agtgaacgac aaaatggcgt cctgaacagt tggactgatc  3480
aggacagcaa agacagcacc tacagcatga gcagcaccct cacgttgacc aaggacgagt  3540
atgaacgaca taacagctat acctgtgagg ccactcacaa gacatcaact tcacccattg  3600
tcaagagctt caacaggaat gagtgttaac tcgaggacgg ggtgaactac gcctgaggat  3660
ccgatctttt tccctctgcc aaaaattatg gggacatcat gaagcccctt gagcatctga  3720
cttctggcta ataaaggaaa tttattttca ttgcaatagt gtgttggaat ttttgtgtc   3780
tctcactcgg cctaggtaga taagtagcat ggcgggttaa tcattaacta caaggaaccc  3840
ctagtgatgg agttggccac tccctctctg cgcgctcgct cgctcactga ggccgggcga  3900
ccaaaggtcg cccgacgccc gggctttgcc cgggcggcct cagtgagcga gcgagcgcgc  3960
ag                                                                3962

SEQ ID NO: 16     moltype = AA  length = 323
FEATURE           Location/Qualifiers
source            1..323
                  mol_type = protein
                  organism = Mus sp.
SEQUENCE: 16
AKTTPPSVYP LAPGSAAQTN SMVTLGCLVK GYFPEPVTVT WNSGSLSSGV HTFPAVLQSD   60
```

```
LYTLSSSVTV PSSTWPSETV TCNVAHPASS TKVDKKIVPR DCGCKPCICT VPEVSSVFIF    120
PPKPKDVLTI TLTPKVTCVV VDISKDDPEV QFSWFVDDVE VHTAQTQPRE EQFNSTFRSV    180
SELPIMHQDW LNGKEFKCRV NSAAFPAPIE KTISKTKGRP KAPQVYTIPP PKEQMAKDKV    240
SLTCMITDFF PEDITVEWQW NGQPAENYKN TQPIMDTDGS YFVYSKLNVQ KSNWEAGNTF    300
TCSVLHEGLH NHHTEKSLSH SPG                                           323

SEQ ID NO: 17          moltype = DNA   length = 321
FEATURE                Location/Qualifiers
source                 1..321
                       mol_type = genomic DNA
                       organism = Mus sp.
SEQUENCE: 17
cgggctgatg ctgcaccaac tgtatccatc ttcccaccat ccagtgagca gttaacatct    60
ggaggtgcct cagtcgtgtg cttcttgaac aacttctacc ccaaagagac caatgtcaag    120
tggaagattg atggcagtga acgacaaaat ggcgtcctga cagttggac tgatcaggac     180
agcaaagaca gcacctacag catgagcagc accctcacgt tgaccaagga cgagtatgaa    240
cgacataaca gctatacctg tgaggccact cacaagacat caacttcacc cattgtcaag    300
agcttcaaca ggaatgagtg t                                              321

SEQ ID NO: 18          moltype = AA   length = 107
FEATURE                Location/Qualifiers
source                 1..107
                       mol_type = protein
                       organism = Mus sp.
SEQUENCE: 18
RADAAPTVSI FPPSSEQLTS GGASVVCFLN NFYPKDINVK WKIDGSERQN GVLNSWTDQD    60
SKDSTYSMSS TLTLTKDEYE RHNSYTCEAT HKTSTSPIVK SFNRNEC                  107

SEQ ID NO: 19          moltype =    length =
SEQUENCE: 19
000

SEQ ID NO: 20          moltype =    length =
SEQUENCE: 20
000

SEQ ID NO: 21          moltype = AA   length = 118
FEATURE                Location/Qualifiers
source                 1..118
                       mol_type = protein
                       organism = synthetic construct
SEQUENCE: 21
QVQLQQPGTE LVKPGSSVNL SCKASGFTFT RYWMHWVKER PGHGLEWIGN INPNNGGTDF    60
NEKFKNKATL TVHKSSTTVF IQLSSLTSED SAVYYCARGT GTGAMDYWGQ GTSVTVSS     118

SEQ ID NO: 22          moltype = AA   length = 118
FEATURE                Location/Qualifiers
source                 1..118
                       mol_type = protein
                       organism = synthetic construct
SEQUENCE: 22
QVQLQQPGTE LVKPGASVKL SCKASGYTFT IFWMHWVKQR PGHGLEWIGK INPNNGGGDY    60
NEKFKSKATL TVDKSSTTAY LQLSSLTSED SAVYYCARGT GTGAMDYWGQ GTSVTVSS     118

SEQ ID NO: 23          moltype = AA   length = 118
FEATURE                Location/Qualifiers
source                 1..118
                       mol_type = protein
                       organism = synthetic construct
SEQUENCE: 23
QVQLQQPGTE LVKPGASVKL SCKASGYTFT RFWMHWVKQR PGQGLEWIGN INPNNGGTDN    60
NERFKSKATL TVDRSSTAY MQLSSLTSED SAVYYCARGT GTGAMDYWGQ GTSVTVSS      118

SEQ ID NO: 24          moltype =    length =
SEQUENCE: 24
000

SEQ ID NO: 25          moltype =    length =
SEQUENCE: 25
000

SEQ ID NO: 26          moltype =    length =
SEQUENCE: 26
000

SEQ ID NO: 27          moltype =    length =
SEQUENCE: 27
000
```

```
SEQ ID NO: 28            moltype =    length =
SEQUENCE: 28
000

SEQ ID NO: 29            moltype =    length =
SEQUENCE: 29
000

SEQ ID NO: 30            moltype =    length =
SEQUENCE: 30
000

SEQ ID NO: 31            moltype =    length =
SEQUENCE: 31
000

SEQ ID NO: 32            moltype = AA  length = 22
FEATURE                  Location/Qualifiers
source                   1..22
                         mol_type = protein
                         organism = synthetic construct
SITE                     5
                         note = Phosphorylated residue
SITE                     8
                         note = Phosphorylated residue
SITE                     9
                         note = Phosphorylated residue
SITE                     10
                         note = Phosphorylated residue
SITE                     12
                         note = Phosphorylated residue
SITE                     18
                         note = Phosphorylated residue
SEQUENCE: 32
GSGSSNVSST GSIDLVDSPQ LA                                                    22

SEQ ID NO: 33            moltype = AA  length = 22
FEATURE                  Location/Qualifiers
source                   1..22
                         mol_type = protein
                         organism = synthetic construct
SITE                     18
                         note = Phosphorylated residue
SEQUENCE: 33
GSGSSNVSST GSIDLVDSPQ LA                                                    22

SEQ ID NO: 34            moltype = AA  length = 22
FEATURE                  Location/Qualifiers
source                   1..22
                         mol_type = protein
                         organism = synthetic construct
SITE                     12
                         note = Phosphorylated residue
SITE                     18
                         note = Phosphorylated residue
SEQUENCE: 34
GSGSSNVSST GSIDLVDSPQ LA                                                    22

SEQ ID NO: 35            moltype =    length =
SEQUENCE: 35
000

SEQ ID NO: 36            moltype =    length =
SEQUENCE: 36
000

SEQ ID NO: 37            moltype =    length =
SEQUENCE: 37
000

SEQ ID NO: 38            moltype =    length =
SEQUENCE: 38
000

SEQ ID NO: 39            moltype =    length =
SEQUENCE: 39
000

SEQ ID NO: 40            moltype =    length =
```

```
SEQUENCE: 40
000

SEQ ID NO: 41          moltype =   length =
SEQUENCE: 41
000

SEQ ID NO: 42          moltype =   length =
SEQUENCE: 42
000

SEQ ID NO: 43          moltype =   length =
SEQUENCE: 43
000

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype =   length =
SEQUENCE: 47
000

SEQ ID NO: 48          moltype =   length =
SEQUENCE: 48
000

SEQ ID NO: 49          moltype =   length =
SEQUENCE: 49
000

SEQ ID NO: 50          moltype =   length =
SEQUENCE: 50
000

SEQ ID NO: 51          moltype = AA  length = 119
FEATURE                Location/Qualifiers
source                 1..119
                       mol_type = protein
                       organism = synthetic construct
SEQUENCE: 51
QITLKESGPG ILQSSQTLSL TCSFSGFSLS TSAMGVSWIR QPSGEGLEWL AHIYWDDDKR   60
YNPSLKSRLT ISKDTSRNQV FLKITSVDTA DTATYYCARR RRGYGMDYWG QGTSVTVSS   119

SEQ ID NO: 52          moltype =   length =
SEQUENCE: 52
000

SEQ ID NO: 53          moltype =   length =
SEQUENCE: 53
000

SEQ ID NO: 54          moltype =   length =
SEQUENCE: 54
000

SEQ ID NO: 55          moltype =   length =
SEQUENCE: 55
000

SEQ ID NO: 56          moltype =   length =
SEQUENCE: 56
000

SEQ ID NO: 57          moltype =   length =
SEQUENCE: 57
000

SEQ ID NO: 58          moltype =   length =
SEQUENCE: 58
000
```

```
SEQ ID NO: 59          moltype =   length =
SEQUENCE: 59
000

SEQ ID NO: 60          moltype =   length =
SEQUENCE: 60
000

SEQ ID NO: 61          moltype =   length =
SEQUENCE: 61
000

SEQ ID NO: 62          moltype =   length =
SEQUENCE: 62
000

SEQ ID NO: 63          moltype =   length =
SEQUENCE: 63
000

SEQ ID NO: 64          moltype = AA   length = 10
FEATURE                Location/Qualifiers
source                 1..10
                       mol_type = protein
                       organism = synthetic construct
SEQUENCE: 64
GFTFTRYWMH                                                            10

SEQ ID NO: 65          moltype = AA   length = 445
FEATURE                Location/Qualifiers
source                 1..445
                       mol_type = protein
                       organism = synthetic construct
SEQUENCE: 65
QVQLQQPGTE LVKPGSSVNL SCKASGFTFT RYWMHWVKER PGHGLEWIGN INPNNGGTDF      60
NEKFKNKATL TVHKSSTTVF IQLSSLTSED SAVYYCARGT GTGAMDYWGQ GTSVTVSSAS     120
TKGPSVFPLA PCSRSTSEST AALGCLVKDY FPEPVTVSWN SGALTSGVHT FPAVLQSSGL     180
YSLSSVVTVP SSSLGTKTYT CNVDHKPSNT KVDKRVESKY GPPCPPCPAP EFLGGPSVFL     240
FPPKPKDTLM ISRTPEVTCV VVDVSQEDPE VQFNWYVDGV EVHNAKTKPR EEQFNSTYRV     300
VSVLTVLHQD WLNGKEYKCK VSNKGLPSSI EKTISKAKGQ PREPQVYTLP PSQEEMTKNQ     360
VSLTCLVKGF YPSDIAVEWE SNGQPENNYK TTPPVLDSDG SFFLYSRLTV DKSRWQEGNV     420
FSCSVMHEAL HNHYTQKSLS LSLGK                                           445

SEQ ID NO: 66          moltype = AA   length = 219
FEATURE                Location/Qualifiers
source                 1..219
                       mol_type = protein
                       organism = synthetic construct
SEQUENCE: 66
DVVMTQTPLS LPVSLGDQAS ISCRSSQSLV HNNGITYLYW YLQKPGQSPK LLIYRVSNRF      60
SGVPDRFGGS GSGTDFTLKI SRVEAEDLGV YFCFQGTHVP RTFGGGTKLE IKRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 67          moltype = AA   length = 118
FEATURE                Location/Qualifiers
source                 1..118
                       mol_type = protein
                       organism = synthetic construct
SEQUENCE: 67
QVQLVESGAE VKKPGASVKV SCKASGFTFT RYWMHWVKER PGHGLEWMGN INPNNGGTDF      60
NEKFKNRVTI TVHKSASTAY MELSSLRSED TAVYYCARGT GTGAMDYWGQ GTTVTVSS       118

SEQ ID NO: 68          moltype = AA   length = 118
FEATURE                Location/Qualifiers
source                 1..118
                       mol_type = protein
                       organism = synthetic construct
SEQUENCE: 68
QVQLVQSGAE VKKPGASVKV SCKASGFTFT RYWMHWVRER PGHGLEWIGN INPNNGGTDF      60
NEKFKNRVTM TVHKSISTAY MELSSLRSDD SAVYYCARGT GTGAMDYWGQ GTLVTVSS       118

SEQ ID NO: 69          moltype = AA   length = 118
FEATURE                Location/Qualifiers
source                 1..118
                       mol_type = protein
                       organism = synthetic construct
SEQUENCE: 69
```

```
QVQLVQSGAE VKKSGASVKV SCKASGFTFT RYWMHWVRQA PGQGLEWIGN INPNNGGTDF    60
NEKFKNRVTL IRDTSTTTVF IQLTSLTSED SAVYYCARGT GTGAMDYWGQ GTLVTVSS     118

SEQ ID NO: 70            moltype = AA  length = 118
FEATURE                  Location/Qualifiers
source                   1..118
                         mol_type = protein
                         organism = synthetic construct
SEQUENCE: 70
EVQLVQSGAE VKKPGSSVKV SCKASGFTFT RYWMHWVKER PGHGLEWIGN INPNNGGTDF    60
NEKFKNRVTM TVHKSITTAY MELSRLTSDD SAVYYCARGT GTGAMDYWGQ GTLVSVSS     118

SEQ ID NO: 71            moltype = AA  length = 118
FEATURE                  Location/Qualifiers
source                   1..118
                         mol_type = protein
                         organism = synthetic construct
SEQUENCE: 71
QVQLVQSGAE VKKPGASVKV SCKASGFTFT RYWMHWVKER PGQGLEWMGN INPNNGGTDF    60
NEKFKNRVTM TVHKSTSTVF IQLSSLRSED TAVYYCARGT GTGAMDYWGQ GTSVTVSS     118

SEQ ID NO: 72            moltype = AA  length = 112
FEATURE                  Location/Qualifiers
source                   1..112
                         mol_type = protein
                         organism = synthetic construct
SEQUENCE: 72
DVVMTQSPLS LPVTLGQPAS ISCRSSQSLV HNNGITYLYW YQQRPGQSPR LLIYRVSNRF    60
SGVPDRFSGS GSGTDFTLKI SRVEAEDVGV YYCFQGTHVP RTFGQGTKLE IK           112

SEQ ID NO: 73            moltype = AA  length = 112
FEATURE                  Location/Qualifiers
source                   1..112
                         mol_type = protein
                         organism = synthetic construct
SEQUENCE: 73
DIVMTQSPLS LSVTPGQPAS ISCRSSQSLV HNNGITYLYW YLQKPGQSPQ LLIYRVSNRF    60
SGVPDRFSGS GSGTDFTLKI SRVEAEDVGV YYCFQGTHVP RTFGQGTKVE IK           112

SEQ ID NO: 74            moltype = AA  length = 112
FEATURE                  Location/Qualifiers
source                   1..112
                         mol_type = protein
                         organism = synthetic construct
SEQUENCE: 74
DIVMTQTPLS SPVTLGQPAS ISCRSSQSLV HNNGITYLYW YQQRPGQPPR LLIYRVSNRF    60
SGVPDRFSGS GAGTDFTLKI NRVEAEDVGV YFCFQGTHVP RTFGQGTKLE IK           112

SEQ ID NO: 75            moltype = AA  length = 112
FEATURE                  Location/Qualifiers
source                   1..112
                         mol_type = protein
                         organism = synthetic construct
SEQUENCE: 75
DIEMTQSPLS LPVTLGQPAS ISCRSSQSLV HNNGITYLYW YQQRPGQSPR RLIYRVSNRF    60
SGVPDRFSGS GSGTDFTLKI SRVEAEDVGV YFCFQGTHVP RTFGGGTKLE IK           112

SEQ ID NO: 76            moltype = AA  length = 112
FEATURE                  Location/Qualifiers
source                   1..112
                         mol_type = protein
                         organism = synthetic construct
SEQUENCE: 76
EIVLTQSPAT LSLSPGERAT LSCRSSQSLV HNNGITYLYW YLQKPGQAPK LLIYRVSNRF    60
SGIPDRFSGS GPGTDFTLTI SSLEPEDLAV YFCFQGTHVP RTFGGGTKLE IK           112

SEQ ID NO: 77            moltype =    length =
SEQUENCE: 77
000

SEQ ID NO: 78            moltype = AA  length = 107
FEATURE                  Location/Qualifiers
source                   1..107
                         mol_type = protein
                         organism = synthetic construct
SEQUENCE: 78
DIQMTQSPAS LSASVGETVT ITCRASGNIH NYLAWYQQRQ GKSPQLLVYN AKTLPDGVPS    60
RFSGSGSGTQ YSLKINSLQP EDFGSYCCQH FWSTPLTFGA GTKLELK                 107
```

```
SEQ ID NO: 79          moltype =    length =
SEQUENCE: 79
000

SEQ ID NO: 80          moltype =    length =
SEQUENCE: 80
000

SEQ ID NO: 81          moltype =    length =
SEQUENCE: 81
000

SEQ ID NO: 82          moltype =    length =
SEQUENCE: 82
000

SEQ ID NO: 83          moltype = AA   length = 113
FEATURE                Location/Qualifiers
source                 1..113
                       mol_type = protein
                       organism = synthetic construct
SEQUENCE: 83
DIVMSQSPSS LAVSVGEKVT MSCKSSQSLL YSTNQENYLA WYQQKPGQSP KLLIYWASSR    60
ESGVPDRFTG SGSGTDFTLT ISSVKAEDLA VYYCQQYYSY PRTFGGGTKL EIK          113

SEQ ID NO: 84          moltype =    length =
SEQUENCE: 84
000

SEQ ID NO: 85          moltype =    length =
SEQUENCE: 85
000

SEQ ID NO: 86          moltype =    length =
SEQUENCE: 86
000

SEQ ID NO: 87          moltype =    length =
SEQUENCE: 87
000

SEQ ID NO: 88          moltype =    length =
SEQUENCE: 88
000

SEQ ID NO: 89          moltype =    length =
SEQUENCE: 89
000

SEQ ID NO: 90          moltype =    length =
SEQUENCE: 90
000

SEQ ID NO: 91          moltype =    length =
SEQUENCE: 91
000

SEQ ID NO: 92          moltype =    length =
SEQUENCE: 92
000

SEQ ID NO: 93          moltype = AA   length = 112
FEATURE                Location/Qualifiers
source                 1..112
                       mol_type = protein
                       organism = synthetic construct
SEQUENCE: 93
DVVMTQTPLS LPVSLGDQAS ISCRSSQSLV HNNGITYLYW YLQKPGQSPK LLIYRVSNRF    60
SGVPDRFGGS GSGTDFTLKI SRVEAEDLGV YFCFQGTHVP RTFGGGTKLE IK           112

SEQ ID NO: 94          moltype = AA   length = 112
FEATURE                Location/Qualifiers
source                 1..112
                       mol_type = protein
                       organism = synthetic construct
SEQUENCE: 94
DVVMTQTPLS LPVSLGDHAS ISCRSSQSLV HSNGITHLYW YLQRPGQTPK LLIYRVSNRF    60
SGVPDRFSGS GSGTDFTLKI SSVEAEDLGV YFCFQGTHVP RTFGGGTKLE IE           112
```

```
SEQ ID NO: 95           moltype = AA   length = 112
FEATURE                 Location/Qualifiers
source                  1..112
                        mol_type = protein
                        organism = synthetic construct
SEQUENCE: 95
DVVMTQTPLS LPVSLGDQAS ISCRSSQSLV HSNGNTHLYW YLQKPGQSPK LLIYRVSSRF   60
SGVPDRFSGS GSGTDFTLKI SRVEAEDLGV YFCFQGTHVP RTFGGGTKLE IK          112

SEQ ID NO: 96           moltype =    length =
SEQUENCE: 96
000

SEQ ID NO: 97           moltype =    length =
SEQUENCE: 97
000

SEQ ID NO: 98           moltype =    length =
SEQUENCE: 98
000

SEQ ID NO: 99           moltype =    length =
SEQUENCE: 99
000

SEQ ID NO: 100          moltype =    length =
SEQUENCE: 100
000

SEQ ID NO: 101          moltype =    length =
SEQUENCE: 101
000

SEQ ID NO: 102          moltype =    length =
SEQUENCE: 102
000

SEQ ID NO: 103          moltype =    length =
SEQUENCE: 103
000

SEQ ID NO: 104          moltype =    length =
SEQUENCE: 104
000

SEQ ID NO: 105          moltype =    length =
SEQUENCE: 105
000

SEQ ID NO: 106          moltype =    length =
SEQUENCE: 106
000

SEQ ID NO: 107          moltype =    length =
SEQUENCE: 107
000

SEQ ID NO: 108          moltype =    length =
SEQUENCE: 108
000

SEQ ID NO: 109          moltype =    length =
SEQUENCE: 109
000

SEQ ID NO: 110          moltype =    length =
SEQUENCE: 110
000

SEQ ID NO: 111          moltype =    length =
SEQUENCE: 111
000

SEQ ID NO: 112          moltype =    length =
SEQUENCE: 112
000

SEQ ID NO: 113          moltype =    length =
SEQUENCE: 113
```

```
SEQ ID NO: 114           moltype =    length =
SEQUENCE: 114
000

SEQ ID NO: 115           moltype =    length =
SEQUENCE: 115
000

SEQ ID NO: 116           moltype =    length =
SEQUENCE: 116
000

SEQ ID NO: 117           moltype =    length =
SEQUENCE: 117
000

SEQ ID NO: 118           moltype =    length =
SEQUENCE: 118
000

SEQ ID NO: 119           moltype =    length =
SEQUENCE: 119
000

SEQ ID NO: 120           moltype =    length =
SEQUENCE: 120
000

SEQ ID NO: 121           moltype =    length =
SEQUENCE: 121
000

SEQ ID NO: 122           moltype = AA  length = 107
FEATURE                  Location/Qualifiers
source                   1..107
                         mol_type = protein
                         organism = synthetic construct
SEQUENCE: 122
SIVMTQTPKF LLVSAGDRVT ITCKASQSVS NDVAWYQQKP GQSPKLLIYY ASNRCTGVPD   60
RFTGSGYGTD FTFTISTVQA EDLAVYFCQQ DYRSPLTFGA GTKLELK                107

SEQ ID NO: 123           moltype =    length =
SEQUENCE: 123
000

SEQ ID NO: 124           moltype =    length =
SEQUENCE: 124
000

SEQ ID NO: 125           moltype =    length =
SEQUENCE: 125
000

SEQ ID NO: 126           moltype =    length =
SEQUENCE: 126
000

SEQ ID NO: 127           moltype =    length =
SEQUENCE: 127
000

SEQ ID NO: 128           moltype =    length =
SEQUENCE: 128
000

SEQ ID NO: 129           moltype =    length =
SEQUENCE: 129
000

SEQ ID NO: 130           moltype =    length =
SEQUENCE: 130
000

SEQ ID NO: 131           moltype =    length =
SEQUENCE: 131
000
```

-continued

SEQ ID NO: 132          moltype =     length =
SEQUENCE: 132
000

SEQ ID NO: 133          moltype =     length =
SEQUENCE: 133
000

SEQ ID NO: 134          moltype =     length =
SEQUENCE: 134
000

SEQ ID NO: 135          moltype =     length =
SEQUENCE: 135
000

SEQ ID NO: 136          moltype =     length =
SEQUENCE: 136
000

SEQ ID NO: 137          moltype = DNA   length = 2211
FEATURE                 Location/Qualifiers
source                  1..2211
                        mol_type = genomic DNA
                        organism = Adeno-associated virus 9
SEQUENCE: 137
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aagggggagc cggtcaacgc agcagacgcg gcggcccctcg agcacgacaa ggcctacgc   240
cagcagctca aggccggaga caacccgtac ctcaagtaca ccacgccga cgccgagttc   300
caggagcggc tcaaagaaga tacgtctttt gggggcaacc tcgggcgagc agtcttccag   360
gccaaaagga ggcttcttga acctcttggt ctggttgagg aagcggctaa acggctcct   420
ggaagaagaa ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgt cttcaggtgg tggcgcacca gtggcagaca taacgaagg tgccgatgga   660
gtgggtagtt cctcgggaaa ttggcattgc gattcccaat ggctggggga cagagtcatc   720
accaccagca cccgaacctg ggcctgccc acctacaaca atcacctcta caagcaaatc   780
tccaacagca catctggagg atcttcaaat gacaacgcct acttcggcta cagcacccc   840
tgggggtatt ttgactttaa cagattccac tgccacttct caccacgtga ctggcagcga   900
ctcatcaaca acaactgggg attccggcct aagcgactca acttcaagct cttcaacatt   960
caggtcaaag aggttacgga caatgaga gtcaagacca tcgccaataa ccttaccagc  1020
acggtccagg tcttcacgga ctcagactat cagctcccgt acgtgctcgg tcggctcac  1080
gagggctgcc tcccgccgtt cccagcggac gttttcatga tccctcagta cgggtatctg  1140
acgcttaatg atggaagcca ggcgtgggt cgttcgtcct tttactgcct ggaatatttc  1200
ccgtcgcaaa tgctaagaac gggtaacaac ttccagtcaa gctgagagtt gagaacgta  1260
ccttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga aggaccgttt ctttcctttt gtctggatct  1620
ttaattttttg gcaaacaagg aactggaaga gacaacgtgg atgcggacaa agtcatgata  1680
accaacgaag aagaaattaa aactactaac ccggtagcaa ccgagtccta tggacaagtg  1740
gccacaaacc accagagtgc ccaagcacag gcgcagaccg gctgggttca aaaccaagga  1800
atacttcggg gtatggtttg gcaggacaga gatgtgtacc tgcaaggacc catttgggcc  1860
aaaattcctc acacggacgg caactttcac ccttctccgc tgatgggagg gtttggaatg  1920
aagcaccggc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac ccgcccccat tggcaccaga tacctgactc gtaatctgta a           2211

SEQ ID NO: 138          moltype = AA   length = 736
FEATURE                 Location/Qualifiers
source                  1..736
                        mol_type = protein
                        organism = Adeno-associated virus 9
SEQUENCE: 138
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540

```
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 139          moltype =    length =
SEQUENCE: 139
000

SEQ ID NO: 140          moltype =    length =
SEQUENCE: 140
000

SEQ ID NO: 141          moltype =    length =
SEQUENCE: 141
000

SEQ ID NO: 142          moltype =    length =
SEQUENCE: 142
000

SEQ ID NO: 143          moltype =    length =
SEQUENCE: 143
000

SEQ ID NO: 144          moltype =    length =
SEQUENCE: 144
000

SEQ ID NO: 145          moltype =    length =
SEQUENCE: 145
000

SEQ ID NO: 146          moltype =    length =
SEQUENCE: 146
000

SEQ ID NO: 147          moltype =    length =
SEQUENCE: 147
000

SEQ ID NO: 148          moltype =    length =
SEQUENCE: 148
000

SEQ ID NO: 149          moltype =    length =
SEQUENCE: 149
000

SEQ ID NO: 150          moltype = DNA  length = 339
FEATURE                 Location/Qualifiers
source                  1..339
                        mol_type = other DNA
                        organism = synthetic construct
SEQUENCE: 150
caggtccaac tgcagcagcc tggggctgag cttgtgaagc ctggggcttc agtgaagctg   60
tcctgcaagg cttctgacta caccttcacc aactactgga tgcactgggt gaagcagagg  120
cctggacaga gccttgagtg gataggaagg attgatccta atagtggtgg tactaggtac  180
aatgagaagt tcaagaacaa ggccacactg actgttgaca aaccctccag cacagcctac  240
atgcatctca gcagcctgac atctgaggac tctgcggtct attattgtgc aggggacttc  300
gatgtctggg gcacagggac cacggtcacc gtctcctca                        339

SEQ ID NO: 151          moltype =    length =
SEQUENCE: 151
000

SEQ ID NO: 152          moltype =    length =
SEQUENCE: 152
000

SEQ ID NO: 153          moltype =    length =
SEQUENCE: 153
000

SEQ ID NO: 154          moltype =    length =
SEQUENCE: 154
000

SEQ ID NO: 155          moltype = DNA  length = 345
```

```
FEATURE               Location/Qualifiers
source                1..345
                      mol_type = other DNA
                      organism = synthetic construct
SEQUENCE: 155
gaggtgcagc tggtggagtc tggaggagcc ttggtacagc ctgggggttc tctgagtctc    60
tcctgtgcag cttctggatt caccttcact gattactaca tgagctgggt ccgccagcct   120
ccagggaagg cacttgagtg gctggctttg attagaaaca aagctaaagg tttcacaaca   180
gaatacagtg catctgtgaa gggtcggttc accatctcca gagataattc ccaaaagcatc  240
ctccttttc aaatgaatga cctgagagct gacgacagtg ccacttatta ctgtgtaaga   300
gatataaact actggggcca aggcaccact ctcacagtct cctca                   345

SEQ ID NO: 156        moltype = DNA  length = 354
FEATURE               Location/Qualifiers
source                1..354
                      mol_type = other DNA
                      organism = synthetic construct
SEQUENCE: 156
caagtgcagc tggtggagag cggcgccgag gtgaagaagc ctggcgctag cgtgaaggtg    60
agctgcaagg ctagcggctt caccttcaca agatactgga tgcactgggt gaaggagaga   120
cctggccacg gcctggagtg gatgggcaac atcaaccta acaacggcgg caccgacttc   180
aacgagaagt tcaagaacag agtgaccatc accgtgcgtc gaccgcttac                240
atggagctga gcagcctgag aagcgaggac accgccgtgt actactgcgc tagaggcacc   300
ggcaccggcg ccatggacta ctggggccaa ggcaccaccg tgaccgtctc gtcc         354

SEQ ID NO: 157        moltype = DNA  length = 354
FEATURE               Location/Qualifiers
source                1..354
                      mol_type = other DNA
                      organism = synthetic construct
SEQUENCE: 157
caagtgcagc tggtggagag cggcgccgag gtgaagaagc ctggcgctag cgtgaaggtg    60
agctgcaagg ctagcggctt caccttcaca agatactgga tgcactgggt gagagagaga   120
cctggccacg gcctggagtg gatcggcaac atcaaccta acaacggcgg caccgacttc   180
aacgagaagt tcaagaacag agtgaccatg accgtgcaca agagcatcac caccgcctac   240
atggagctga gcagcctgag aagcgacgac agcgccgtgt actactgcgc tagaggcacc   300
ggcaccggcg ccatggacta ctggggccaa ggcaccctgg tgacggtaag ctcc         354

SEQ ID NO: 158        moltype = DNA  length = 354
FEATURE               Location/Qualifiers
source                1..354
                      mol_type = other DNA
                      organism = synthetic construct
SEQUENCE: 158
caagtgcagc tggtgcagag cggcgccgag gtgaagaaga gcggcgctag cgtgaaggtg    60
agctgcaagg ctagcggctt caccttcaca agatactgga tgcactgggt gagacaagcc   120
cctggccaag gcctggagtg gatcggcaac atcaaccta acaacggcgg caccgacttc   180
aacgagaagt tcaagaacag agtgaccctg atcagagaca caagcaccac caccgtgttc   240
attcagctga aagcctgac aagcgaggac agcgccgtgt actactgcgc tagaggcacc   300
ggcaccggcg ccatggacta ctggggccaa ggcaccctgg tgacggtaag ctcc         354

SEQ ID NO: 159        moltype = DNA  length = 354
FEATURE               Location/Qualifiers
source                1..354
                      mol_type = other DNA
                      organism = synthetic construct
SEQUENCE: 159
gaggtgcagc tggtgcagag cggcgccgag gtgaagaagc ctggcagcag cgtgaaggtg    60
agctgcaagg ctagcggctt caccttcaca agatactgga tgcactgggt gaaggagaga   120
cctggccacg gcctggagtg gatcggcaac atcaaccta acaacggcgg caccgacttc   180
aacgagaagt tcaagaacag agtgaccatg accgtgcaca agagcatcac caccgcctac   240
atggagctga gccggttaac ctccgacgac agcgccgtgt actactgcgc tagaggcacc   300
ggcaccggcg ccatggacta ctggggccaa ggcaccctgg tgagcgtgag cagc         354

SEQ ID NO: 160        moltype = DNA  length = 354
FEATURE               Location/Qualifiers
source                1..354
                      mol_type = other DNA
                      organism = synthetic construct
SEQUENCE: 160
caagtgcagc tggtgcagag cggcgccgag gtgaagaagc ctggcgctag cgtgaaggtg    60
agctgcaagg ctagcggctt caccttcaca agatactgga tgcactgggt gaaggagaga   120
cctggccaag gcctggagtg gatgggcaac atcaaccta acaacggcgg caccgacttc   180
aacgagaagt tcaagaacag agtgaccatg accgtgcaca agagcacaag caccgtgttc   240
attcagctga gcagcctgag aagcgaggac accgccgtgt actactgcgc tagaggcacc   300
ggcaccggcg ccatggacta ctggggccaa ggcacaagcg tgacggtaag ctcc         354

SEQ ID NO: 161        moltype = DNA  length = 336
FEATURE               Location/Qualifiers
```

```
source                  1..336
                        mol_type = other DNA
                        organism = synthetic construct
SEQUENCE: 161
gacgtggtga tgacacagag ccctctgagc ctgcctgtga ccctgggaca gcctgctagc    60
atcagctgca gaagctctca gagcctggtg cacaacaacg gcatcaccta cctgtactgg   120
tatcagcaga gacctggaca gagccctaga ctgctgatct acagagtgag caacagattc   180
agcggcgtgc ctgacagatt ctccggctcc ggcagcggca ccgacttcac cctgaagatc   240
agcagagtgg aggccgagga cgtgggcgtg tactactgct ttcaaggcac ccatgtccct   300
agaaccttcg gccaaggcac caagctggag atcaag                             336

SEQ ID NO: 162          moltype = DNA   length = 336
FEATURE                 Location/Qualifiers
source                  1..336
                        mol_type = other DNA
                        organism = synthetic construct
SEQUENCE: 162
gacatcgtga tgacacagag ccctctgagc ctgagcgtga ccctggaca gcctgctagc     60
atcagctgca gaagctctca gagcctggtg cacaacaacg gcatcaccta cctgtactgg   120
tacctgcaga agcctggaca gagccctcag ctgctgatct acagagtgag caacagattc   180
agcggcgtgc ctgacagatt ctccggctcc ggcagcggca ccgacttcac cctgaagatc   240
agcagagtgg aggccgagga cgtgggcgtg tactactgct ttcaaggcac ccatgtccct   300
agaaccttcg gccaaggcac caaggtggag atcaag                             336

SEQ ID NO: 163          moltype = DNA   length = 336
FEATURE                 Location/Qualifiers
source                  1..336
                        mol_type = other DNA
                        organism = synthetic construct
SEQUENCE: 163
gacatcgtga tgacacagac ccctctcagc agcctgtga cccctaggaca gcctgctagc    60
atcagctgca gaagctctca gagcctggtg cacaacaacg gcatcaccta cctgtactgg   120
tatcagcaga gacctggaca gcctcctaga ctgctgatct acagagtgag caacagattc   180
agcggagtac ctgacagatt tagcggttcc ggcgccggca ccgacttcac cctgaagatc   240
agcagagtgg aggccgagga cgtgggcgtg tactactgct ttcaaggcac ccatgtccct   300
agaaccttcg gccaaggcac caagctggag atcaag                             336

SEQ ID NO: 164          moltype = DNA   length = 336
FEATURE                 Location/Qualifiers
source                  1..336
                        mol_type = other DNA
                        organism = synthetic construct
SEQUENCE: 164
gacatcgaga tgacacagag ccctctgagc ctgcctgtga ccctgggaca gcctgctagc    60
atcagctgca gaagctctca gagcctggtg cacaacaacg gcatcaccta cctgtactgg   120
tatcagcaga gacctggaca gagccctaga agactgatct acagagtgag caacagattc   180
agcggcgtgc ctgacagatt ctccggctcc ggcagcggca ccgacttcac cctgaagatc   240
agcagagtgg aggccgagga cgtgggcgtg tacttctgct ttcaaggcac ccatgtccct   300
agaaccttcg gcggcggcac caagctggag atcaag                             336

SEQ ID NO: 165          moltype = DNA   length = 336
FEATURE                 Location/Qualifiers
source                  1..336
                        mol_type = other DNA
                        organism = synthetic construct
SEQUENCE: 165
gagatcgtgc tgacacagag ccctgcgaca ctgagcctga gcctggcgga gagagctacg    60
ctgagctgcc gcagctctca gagcctggtg cacaacaacg gcatcaccta cctgtactgg   120
tacctgcaga agcctggcca agcccctaag ctgctgatct acagagtgag caacagattc   180
agcggcatcc ctgacagatt ctccggctcc ggcccctggca ccgacttcac cctgaccatc   240
agcagcctgg agcctgagga cctggccgtg tacttctgct tccaaggcac ccatgtacct   300
agaaccttcg gcggcggcac caagctggag atcaag                             336

SEQ ID NO: 166          moltype =       length =
SEQUENCE: 166
000

SEQ ID NO: 167          moltype = DNA   length = 354
FEATURE                 Location/Qualifiers
source                  1..354
                        mol_type = other DNA
                        organism = synthetic construct
SEQUENCE: 167
caggtccaac tgcagcagcc tgggactgaa ctggtgaagc ctgggtcttc agtgaacctg    60
tcctgcaagg cttctggctt caccttcacc aggtactgga tgcactgggt gaaggagagg   120
cctggacatg gccttgagtg gattggaaat attaatccta caatggtgg tactgacttc   180
aatgagaagt tcaagaacaa ggccacactg actgtacaca gtcctccac cacagtcttc   240
atccaactca gcagcctgac atctgaggac tctgcggtct attattgtgc aagaggaact   300
gggacgggag ctatggacta ctggggtcaa ggaacctcag tcaccgtctc ctca         354
```

```
SEQ ID NO: 168         moltype = DNA  length = 354
FEATURE                Location/Qualifiers
source                 1..354
                       mol_type = other DNA
                       organism = synthetic construct
SEQUENCE: 168
caggtccaac tgcagcagcc tgggactgaa ctggtgaagc ctggggcttc agtgaagctg    60
tcctgcaagg cttctggcta caccttcacc atcttctgga tgcactgggt gaagcagagg   120
cctggacatg gccttgagtg gattggaaag attaatccta acaatgggag tggtgactac   180
aatgagaaat tcaagagtaa ggccacattg actgtagaca atcctccac cacagcctac    240
ttgcagctca gcagcctgac atctgaggac tctgcggtct attattgtgc aagaggaact   300
gggacgggag ctatggacta ctggggtcaa ggaacctcag tcaccgtctc ctca          354

SEQ ID NO: 169         moltype = DNA  length = 354
FEATURE                Location/Qualifiers
source                 1..354
                       mol_type = other DNA
                       organism = synthetic construct
SEQUENCE: 169
caggtccaac tgcagcagcc tgggactgaa ctggtgaagc ctggggcttc agtgaagctg    60
tcctgcaagg cttctggcta caccttcacc aggttctgga tgcactgggt gaagcagagg   120
cctggacaag gccttgagtg gattggaaat attaatccta acaatggtgg tactgacaat   180
aatgagaggt tcaagagcaa ggccacactg actgtagaca atcctccag cacagcctac    240
atgcagctca gcagcctgac atctgaggac tctgcggtct attattgtgc aagaggaact   300
gggacgggag ctatggacta ctggggtcaa ggaacctcag tcaccgtctc ctca          354

SEQ ID NO: 170         moltype = AA   length = 445
FEATURE                Location/Qualifiers
source                 1..445
                       mol_type = protein
                       organism = synthetic construct
SEQUENCE: 170
QVQLVESGAE VKKPGASVKV SCKASGFTFT RYWMHWVKER PGHGLEWMGN INPNNGGTDF    60
NEKFKNRVTI TVHKSASTAY MELSSLRSED TAVYYCARGT GTGAMDYWGQ GTTVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGK                                         445

SEQ ID NO: 171         moltype = AA   length = 445
FEATURE                Location/Qualifiers
source                 1..445
                       mol_type = protein
                       organism = synthetic construct
SEQUENCE: 171
QVQLVQSGAE VKKPGASVKV SCKASGFTFT RYWMHWVRER PGHGLEWIGN INPNNGGTDF    60
NEKFKNRVTM TVHKSISTAY MELSSLRSDD SAVYYCARGT GTGAMDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGK                                         445

SEQ ID NO: 172         moltype = AA   length = 445
FEATURE                Location/Qualifiers
source                 1..445
                       mol_type = protein
                       organism = synthetic construct
SEQUENCE: 172
QVQLVQSGAE VKKSGASVKV SCKASGFTFT RYWMHWVRQA PGQGLEWIGN INPNNGGTDF    60
NEKFKNRVTL IRDTSTTTVF IQLTSLTSED SAVYYCARGT GTGAMDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFLGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLGK                                         445

SEQ ID NO: 173         moltype = AA   length = 445
FEATURE                Location/Qualifiers
source                 1..445
                       mol_type = protein
                       organism = synthetic construct
SEQUENCE: 173
EVQLVQSGAE VKKPGSSVKV SCKASGFTFT RYWMHWVKER PGHGLEWIGN INPNNGGTDF    60
```

```
NEKFKNRVTM TVHKSITTAY MELSRLTSDD SAVYYCARGT GTGAMDYWGQ GTLVSVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGK                                         445

SEQ ID NO: 174         moltype = AA   length = 445
FEATURE                Location/Qualifiers
source                 1..445
                       mol_type = protein
                       organism = synthetic construct
SEQUENCE: 174
QVQLVQSGAE VKKPGASVKV SCKASGFTFT RYWMHWVKER PGQGLEWMGN INPNNGGTDF     60
NEKFKNRVTM TVHKSTSTVF IQLSSLRSED TAVYYCARGT GTGAMDYWGQ GTSVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFLGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLGK                                         445

SEQ ID NO: 175         moltype = AA   length = 219
FEATURE                Location/Qualifiers
source                 1..219
                       mol_type = protein
                       organism = synthetic construct
SEQUENCE: 175
DVVMTQSPLS LPVTLGQPAS ISCRSSQSLV HNNGITYLYW YQQRPGQSPR LLIYRVSNRF     60
SGVPDRFSGS GSGTDFTLKI SRVEAEDVGV YYCFQGTHVP RTFGQGTKLE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 176         moltype = AA   length = 219
FEATURE                Location/Qualifiers
source                 1..219
                       mol_type = protein
                       organism = synthetic construct
SEQUENCE: 176
DIVMTQSPLS LSVTPGQPAS ISCRSSQSLV HNNGITYLYW YLQKPGQSPQ LLIYRVSNRF     60
SGVPDRFSGS GSGTDFTLKI SRVEAEDVGV YYCFQGTHVP RTFGQGTKVE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 177         moltype = AA   length = 219
FEATURE                Location/Qualifiers
source                 1..219
                       mol_type = protein
                       organism = synthetic construct
SEQUENCE: 177
DIVMTQTPLS SPVTLGQPAS ISCRSSQSLV HNNGITYLYW YQQRPGQPPR LLIYRVSNRF     60
SGVPDRFSGS GAGTDFTLKI NRVEAEDVGV YFCFQGTHVP RTFGQGTKLE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 178         moltype = AA   length = 219
FEATURE                Location/Qualifiers
source                 1..219
                       mol_type = protein
                       organism = synthetic construct
SEQUENCE: 178
DIEMTQSPLS LPVTLGQPAS ISCRSSQSLV HNNGITYLYW YQQRPGQSPR RLIYRVSNRF     60
SGVPDRFSGS GSGTDFTLKI SRVEAEDVGV YFCFQGTHVP RTFGGGTKLE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 179         moltype = AA   length = 219
FEATURE                Location/Qualifiers
source                 1..219
                       mol_type = protein
                       organism = synthetic construct
SEQUENCE: 179
EIVLTQSPAT LSLSPGERAT LSCRSSQSLV HNNGITYLYW YLQKPGQAPK LLIYRVSNRF     60
SGIPDRFSGS GPGTDFTLTI SSLEPEDLAV YFCFQGTHVP RTFGGGTKLE IKRTVAAPSV    120
FIFPPSDEQL KSGTASVVCL LNNFYPREAK VQWKVDNALQ SGNSQESVTE QDSKDSTYSL    180
SSTLTLSKAD YEKHKVYACE VTHQGLSSPV TKSFNRGEC                           219

SEQ ID NO: 180         moltype = DNA   length = 1335
```

```
FEATURE              Location/Qualifiers
source               1..1335
                     mol_type = other DNA
                     organism = synthetic construct
SEQUENCE: 180
caagtgcagc tggtggagag cggcgccgag gtgaagaagc ctggcgctag cgtgaaggtg    60
agctgcaagg ctagcggctt caccttcaca agatactgga tgcactgggt gaaggagaga   120
cctggccacg gcctggagtg gatgggcaac atcaacccta caacggcgg caccgacttc   180
aacgagaagt tcaagaacag agtgaccatc accgtgcaca agagcgcgtc gaccgcttac   240
atggagctga gcagcctgag aagcgaggac accgccgtgt actactgcgc tagaggcacc   300
ggcaccggcg ccatggacta ctggggccaa ggcaccaccg tgaccgtctc gtccgctagc   360
acgaaaggtc caagcgtttt ccctctagcc ccttgcagca gaagcacaag cgagagcacc   420
gccgccctgg gctgccttgt aaaagattac ttccctgagc ctgtgaccgt gagttggaac   480
agcggcgccc tgacaagcgg cgtgcacacc ttccctgccg tgctgcagag cagcggcctg   540
tacagcctga gcagcgtggt gaccgtgcca agcagcagcc tgggcaccaa gacctacacc   600
tgcaacgtga ccacaagcc tagcaacacc aaggtggaca agagagtgga gagcaagtac   660
ggtcctccgt gtccccgtg ccctgcccct gagttcctgg gcggccctc ggtgtttctg   720
tttccaccta agcctaagga caccctgatg atcagcagaa ccctgaggt gacctgcgtg   780
gtggtggacg tgagccaaga ggaccctgag gtgcagttca ctggtacgt ggacggcgtg   840
gaggtgcaca acgccaagac caagcctaga gaggagcagt tcaacagcac ctacagagtg   900
gtgagcgtgc tgaccgtgct gcaccaagac tggctgaacg gcaaggagta caagtgcaag   960
gtgagcaaca agggcctgcc tagttccatt gagaagacca tcagcaaggc caagggacag  1020
cctagagagc tcaagtgta cacctgcct cctagccaag aggagatgac caagaaccaa  1080
gtgagcctga cctgcctggt gaagggattc taccctagcg acatcgccgt ggagtgggag  1140
agcaacggac agcctgagaa caactacaag accaccctc ctgtgctgga cagcgacggc  1200
agcttcttcc tgtacagcag actgaccgtg gacaagagca gatggcaaga gggcaacgtg  1260
ttcagctgca gcgtgatgca cgaggccctg cacaaccact acacagaa gagcctgagc  1320
ctgagcctgg gcaag                                                   1335

SEQ ID NO: 181      moltype = DNA   length = 1335
FEATURE             Location/Qualifiers
source              1..1335
                    mol_type = other DNA
                    organism = synthetic construct
SEQUENCE: 181
caagtgcagc tggtgcagag cggcgccgag gtgaagaagc ctggcgctag cgtgaaggtg    60
agctgcaagg ctagcggctt caccttcaca agatactgga tgcactgggt gagagagaga   120
cctgccacg gcctggagtg gatcggcaac atcaacccta caacggcgg caccgacttc   180
aacgagaagt tcaagaacag agtgaccatg accgtgcaga gcgcatcg accgcctac    240
atggagctga gcagcctgag aagcgacgac agcgccgtgt actactgcgc tagaggcacc   300
ggcaccggcg ccatggacta ctggggccaa ggcaccctgg tgacggtaag ctccgctagc   360
accaagggtc ctagtgtatt tcccctagcc ccttgcagca gaagcacaag cgagagcacc   420
gccgccctgg gctgcttggt gaaggactac ttccctgagc ctgtcacagt gtcctggaat   480
agcggcgccc tgacaagcgg cgtgcacacc ttccctgccg tgctgcagag cagcggcctg   540
tacagcctga gcagcgtggt gaccgtgcct cgtcgagcc tgggcaccaa gacctacacc   600
tgcaacgtga ccacaagcc tagcaacacc aaggtggaca agagagtgga gagcaagtac   660
ggtcctccgt gtccccgtg ccctgccct gagttcctgg gcggcctag cgtgttccta   720
tttccaccta agcctaagga caccctgatg atcagcagaa ccctgaggt gacctgcgtg   780
gtggtggacg tgagccaaga ggaccctgag gtgcagttca ctggtacgt ggacggcgtg   840
gaggtgcaca acgccaagac caagcctaga gaggagcagt tcaacagcac ctacagagtg   900
gtgagcgtgc tgaccgtgct gcaccaagac tggctgaacg gcaaggagta caagtgcaag   960
gtgagcaaca agggcctgcc tagcagtatc gagaagacca tcagcaaggc caagggacag  1020
cctagagagc tcaagtgta cacctgcct cctagccaag aggagatgac caagaaccaa  1080
gtgagcctga cctgcctggt gaaaggtttc taccctagcg acatcgccgt ggagtgggag  1140
agcaacggac agcctgagaa caactacaag accaccctc ctgtgctgga cagcgacggc  1200
agcttcttcc tgtacagcag actgaccgtg gacaagagca gatggcaaga gggcaacgtg  1260
ttcagctgca gcgtgatgca cgaggccctg cacaaccact acacagaa gagcctgagc  1320
ctgagcctgg gcaag                                                   1335

SEQ ID NO: 182      moltype = DNA   length = 1335
FEATURE             Location/Qualifiers
source              1..1335
                    mol_type = other DNA
                    organism = synthetic construct
SEQUENCE: 182
caagtgcagc tggtgcagag cggcgccgag gtgaagaaga cggcgctag cgtgaaggtg    60
agctgcaagg ctagcggctt caccttcaca agatactgga tgcactgggt gagacaagcc   120
cctggccaag gcctggagtg gatcggcaac atcaacccta caacggcgg caccgacttc   180
aacgagaagt tcaagaacag agtgaccctg atcagagaca agaccaccac caccgtgttc   240
attcagctga caagcctgac aagcgaggac agcgccgtgt actactgcgc tagaggcacc   300
ggcaccggcg ccatggacta ctggggccaa ggcaccctgg tgacggtaag ctccgctagc   360
accaagggtc ctagtgtatt tcccctagcc ccttgcagca gaagcacaag cgagagcacc   420
gccgccctgg gctgcttggt gaaggactac ttccctgagc ctgtcacagt gtcctggaat   480
agcggcgccc tgacaagcgg cgtgcacacc ttccctgccg tgctgcagag cagcggcctg   540
tacagcctga gcagcgtggt gaccgtgcct cgtcgagcc tgggcaccaa gacctacacc   600
tgcaacgtga ccacaagcc tagcaacacc aaggtggaca agagagtgga gagcaagtac   660
ggtcctccgt gtccccgtg ccctgccct gagttcctgg gcggcctag cgtgttccta   720
tttccaccta agcctaagga caccctgatg atcagcagaa ccctgaggt gacctgcgtg   780
gtggtggacg tgagccaaga ggaccctgag gtgcagttca ctggtacgt ggacggcgtg   840
```

```
gaggtgcaca acgccaagac caagcctaga gaggagcagt tcaacagcac ctacagagtg    900
gtgagcgtgc tgaccgtgct gcaccaagac tggctgaacg gcaaggagta caagtgcaag    960
gtgagcaaca agggcctgcc tagcagtatc gagaagacca tcagcaaggc caagggacag   1020
cctagagagc tcaagtgtta caccctgcct cctagccaag aggagatgac caagaaccaa   1080
gtgagcctga cctgcctggt aaaaggtttc tacccctagcg acatcgccgt ggagtgggag   1140
agcaacggac agcctgagaa caactacaag accaccctc ctgtgctgga cagcgacggc    1200
agcttcttcc tgtacagcag actgaccgtg gacaagagca gatggcaaga gggcaacgtg   1260
ttcagctgca gcgtgatgca cgaggccctg cacaaccact acacacagaa gagcctgagc   1320
ctgagcctgg gcaag                                                    1335

SEQ ID NO: 183          moltype = DNA   length = 1335
FEATURE                 Location/Qualifiers
source                  1..1335
                        mol_type = other DNA
                        organism = synthetic construct
SEQUENCE: 183
gaggtgcagc tggtgcagag cggcgccgag gtgaagaagc tggcagcag cgtgaaggtg      60
agctgcaagg ctagcggctt caccttcaca agatactgga tgcactggga aggagaga     120
cctggccacg gcctggagtg gatcggcaac atcaaccctc acaacggcgg caccgacttc    180
aacgagaagt tcaagaacag agtgaccatg accgtgcaca agcatcac caccgcctac     240
atggagctga gccggttaac ctccgacgac agcgccgtgt actactgcgc tagaggcacc    300
ggcaccggcg ccatggacta ctggggccaa ggcaccctgg tgagcgtgag cagcgcctag    360
accaagggtc ctagtgtatt tcccctagcc ccttgcagca gaagcacaag cgagagcacc    420
gccgccctgg gctgcttggt gaaggactac ttccctgagc ctgtgaccgt gagctggaac    480
agcggcgccc tgacaagcgg cgtgcacacc ttccctgccg tgctgcagag cagcggcctg    540
tacagcctga gcagcgtggt gaccgtgcct tcgtcgagcc tgggcaccaa gacctacacc    600
tgcaacgtgg accacaagcc tagcaacacc aaggtggaca agagagtgga gagcaagtac    660
ggtcctccgt gtccccgtg ccctgcccct gagttcctgg gcggcctag cgtgttccta    720
tttccaccta agcctaagga cacctgatg atcagcagaa ccctgaggt gacctgcgtg    780
gtgtggacg tgagccaaga ggaccctgag gtgcagttca actggtacgt ggacggcgtg    840
gaggtgcaca acgccaagac caagcctaga gaggagcagt tcaacagcac ctacagagtg    900
gtgagcgtgc tgaccgtgct gcaccaagac tggctgaacg gcaaggagta caagtgcaag    960
gtgagcaaca agggcctgcc tagcagtatc gagaagacca tcagcaaggc caagggacag   1020
cctagagagc tcaagtgtta caccctgcct cctagccaag aggagatgac caagaaccaa   1080
gtgagcctga cctgcctggt aaaaggtttc tacccctagcg acatcgccgt ggagtgggag   1140
agcaacggac agcctgagaa caactacaag accaccctc ctgtgctgga cagcgacggc    1200
agcttcttcc tgtactcccg cctgacggtt gacaagagca gatggcaaga gggcaacgtg   1260
ttcagctgca gcgtgatgca cgaggccctg cacaaccact acacacagaa gagcctgagc   1320
ctgagcctgg gcaag                                                    1335

SEQ ID NO: 184          moltype = DNA   length = 1335
FEATURE                 Location/Qualifiers
source                  1..1335
                        mol_type = other DNA
                        organism = synthetic construct
SEQUENCE: 184
caagtgcagc tggtgcagag cggcgccgag gtgaagaagc tggcgctag cgtgaaggtg      60
agctgcaagg ctagcggctt caccttcaca agatactgga tgcactgggt gaaggagaga    120
cctggccaag gcctggagtg gatgggcaac atcaaccctc acaacggcgg caccgacttc    180
aacgagaagt tcaagaacag agtgaccatg accgtgcaca agagcacaag caccgtgttc    240
attcagctga gcagcctgag aagcgaggac accgccgtgt actactgcgc tagaggcacc    300
ggcaccggcg ccatggacta ctggggccaa ggcacaagcg tgacggtaag ctccgctagc    360
accaagggtc ctagtgtatt tcccctagcc ccttgcagca gaagcacaag cgagagcacc    420
gccgccctgg gctgcttggt gaaggactac ttccctgagc ctgtcacagt gtcctggaat    480
agcggcgccc tgacaagcgg cgtgcacacc ttccctgccg tgctgcagag cagcggcctg    540
tacagcctga gcagcgtggt gaccgtgcct tcgtcgagcc tgggcaccaa gacctacacc    600
tgcaacgtgg accacaagcc tagcaacacc aaggtggaca agagagtgga gagcaagtac    660
ggtcctccgt gtccccgtg ccctgcccct gagttcctgg gcggcctag cgtgttccta    720
tttccaccta agcctaagga cacctgatg atcagcagaa ccctgaggt gacctgcgtg    780
gtggtggacg tgagccaaga ggaccctgag gtgcagttca actggtacgt ggacggcgtg    840
gaggtgcaca acgccaagac caagcctaga gaggagcagt tcaacagcac ctacagagtg    900
gtgagcgtgc tgaccgtgct gcaccaagac tggctgaacg gcaaggagta caagtgcaag    960
gtgagcaaca agggcctgcc tagcagtatc gagaagacca tcagcaaggc caagggacag   1020
cctagagagc tcaagtgtta caccctgcct cctagccaag aggagatgac caagaaccaa   1080
gtgagcctga cctgcctggt aaaaggtttc tacccctagcg acatcgccgt ggagtgggag   1140
agcaacggac agcctgagaa caactacaag accaccctc ctgtgctgga cagcgacggc    1200
agcttcttcc tgtacagcag actgaccgtg gacaagagca gatggcaaga gggcaacgtg   1260
ttcagctgca gcgtgatgca cgaggccctg cacaaccact acacacagaa gagcctgagc   1320
ctgagcctgg gcaag                                                    1335

SEQ ID NO: 185          moltype = DNA   length = 657
FEATURE                 Location/Qualifiers
source                  1..657
                        mol_type = other DNA
                        organism = synthetic construct
SEQUENCE: 185
gacgtggtga tgacacagag ccctctgagc ctgcctgtga ccctgggaca gcctgctagc     60
atcagctgca gctgca gaagctctca gagccggtg cacaacaacg gcatcaccta cctgtactgg    120
tatcagcaga gacctggaca gagccctaga ctgctgatct acagagtgag caacagattc    180
```

-continued

```
agcggcgtgc ctgacagatt ctccggctcc ggcagcggca ccgacttcac cctgaagatc  240
agcagagtgg aggccgagga cgtgggcgtg tactactgct ttcaaggcac ccatgtccct  300
agaaccttcg gccaaggcac caagctggag atcaagagaa ccgtggccgc ccctagcgtg  360
ttcatcttcc ctcctagcga cgagcagctg aagagcggca ccgctagcgt ggtgtgcctg  420
ctgaacaact tctaccctag agaggccaag gtgcagtgga aggtggacaa cgccctgcag  480
agcggcaaca gccaagagag cgtgaccgag caagacagca aggacagcac ctacagcctg  540
agcagcaccc tgaccctgag caaggccgac tacgagaagc acaaggtgta cgcctgcgag  600
gtgacccacc aaggcctgag cagccctgtg accaagagct caacagagg cgagtgc      657

SEQ ID NO: 186         moltype = DNA   length = 657
FEATURE                Location/Qualifiers
source                 1..657
                       mol_type = other DNA
                       organism = synthetic construct
SEQUENCE: 186
gacatcgtga tgacacagag ccctctgagc ctgagcgtga ccctggaca gcctgctagc   60
atcagctgca gaagctctca gagcctggtg cacaacaacg gcatcaccta cctgtactgg  120
tacctgcaga agcctggaca gagccctcag ctgctgatct acagagtgag caacagattc  180
agcggcgtgc ctgacagatt ctccggctcc ggcagcggca ccgacttcac cctgaagatc  240
agcagagtgg aggccgagga cgtgggcgtg tactactgct ttcaaggcac ccatgtccct  300
agaaccttcg gccaaggcac caaggtggag atcaagagaa ccgtggccgc ccctagcgtg  360
ttcatcttcc ctcctagcga cgagcagctg aagagcggca ccgctagcgt ggtgtgcctg  420
ctgaacaact tctaccctag agaggccaag gtgcagtgga aggtggacaa cgccctgcag  480
agcggcaaca gccaagagag cgtgaccgag caagacagca aggacagcac ctacagcctg  540
agcagcaccc tgaccctgag caaggccgac tacgagaagc acaaggtgta cgcctgcgag  600
gtgacccacc aaggcctgag cagccctgtg accaagagct caacagagg cgagtgc      657

SEQ ID NO: 187         moltype = DNA   length = 657
FEATURE                Location/Qualifiers
source                 1..657
                       mol_type = other DNA
                       organism = synthetic construct
SEQUENCE: 187
gacatcgtga tgacacagac ccctctcagc agccctgtga ccctaggaca gcctgctagc   60
atcagctgca gaagctctca gagcctggtg cacaacaacg gcatcaccta cctgtactgg  120
tatcagcaga gacctggaca gcctcctaga ctgctgatct acagagtgag caacagattc  180
agcggagtac ctgacagatt tagcggttcc ggcgccggca ccgacttcac cctgaagatc  240
aacagagtgg aggccgagga cgtgggcgtg tacttctgct ttcaaggcac ccatgtccct  300
agaaccttcg gccaaggcac caagctggag atcaagagaa ccgtggccgc ccctagcgtg  360
ttcatcttcc ctcctagcga cgagcagctg aagagcggca ccgctagcgt ggtgtgcctg  420
ctgaacaact tctaccctag agaggccaag gtgcagtgga aggtggacaa cgccctgcag  480
agcggcaaca gccaagagag cgtgaccgag caagacagca aggacagcac ctacagcctg  540
agcagcaccc tgaccctgag caaggccgac tacgagaagc acaaggtgta cgcctgcgag  600
gtgacccacc aaggcctgtc aagccctgta actaagagct caacagagg cgagtgc      657

SEQ ID NO: 188         moltype = DNA   length = 657
FEATURE                Location/Qualifiers
source                 1..657
                       mol_type = other DNA
                       organism = synthetic construct
SEQUENCE: 188
gacatcgaga tgacacagag ccctctgagc ctgcctgtga ccctgggaca gcctgctagc   60
atcagctgca gaagctctca gagcctggtg cacaacaacg gcatcaccta cctgtactgg  120
tatcagcaga gacctggaca gagccctaga agactgatct acagagtgag caacagattc  180
agcggcgtgc ctgacagatt ctccggctcc ggcagcggca ccgacttcac cctgaagatc  240
agcagagtgg aggccgagga cgtgggcgtg tacttctgct ttcaaggcac ccatgtccct  300
agaaccttcg gcggcggcac caagctggag atcaagagaa ccgtggccgc ccctagcgtg  360
ttcatcttcc ctcctagcga cgagcagctg aagagcggca ccgctagcgt ggtgtgcctg  420
ctgaacaact tctaccctag agaggccaag gtgcagtgga aggtggacaa cgccctgcag  480
agcggcaaca gccaagagag cgtgaccgag caagacagca aggacagcac ctacagcctg  540
agcagcaccc tgaccctgag caaggccgac tacgagaagc acaaggtgta cgcctgcgag  600
gtgacccacc aaggcctgag cagccctgtg accaagagct caacagagg cgagtgc      657

SEQ ID NO: 189         moltype = DNA   length = 657
FEATURE                Location/Qualifiers
source                 1..657
                       mol_type = other DNA
                       organism = synthetic construct
SEQUENCE: 189
gagatcgtgc tgacacagag ccctgcgaca ctgagcctga gcctggcga gagagctacg   60
ctgagctgcc gcagctctca gagcctggtg cacaacaacg gcatcaccta cctgtactgg  120
tacctgcaga agcctggcca agcccctaag ctgctgatct acagagtgag caacagattc  180
agcggcatcc ctgacagatt ctccggctcc ggccctggca ccgacttcac cctgaccatc  240
agcagcctgc agcctgagga cctgccctgt tactctgct tccaaggcac ccatgtacct  300
agaaccttcg gcggcggcac caagctggag atcaagagaa ccgtggccgc ccctagcgtg  360
ttcatcttcc ctcctagcga cgagcagctg aagagcggca ccgctagcgt ggtgtgcctg  420
ctgaacaact tctaccctag agaggccaag gtgcagtgga aggtggacaa cgccctgcag  480
agcggcaaca gccaagagag cgtgaccgag caagacagca aggacagcac ctacagcctg  540
agcagcaccc tgaccctgag caaggccgac tacgagaagc acaaggtgta cgcctgcgag  600
```

```
gtgacccacc aaggcctgag cagccctgtg accaagagct tcaacagagg cgagtgc      657

SEQ ID NO: 190          moltype = DNA   length = 356
FEATURE                 Location/Qualifiers
source                  1..356
                        mol_type = other DNA
                        organism = synthetic construct
SEQUENCE: 190
caagtgcagc tgcagcaacc gggcacagag ctggtgaagc ctggcagcag cgtgaacctg    60
agctgcaagg ctagcggctt caccttcaca agatactgga tgcactgggt gaaggagaga   120
cctggccacg gcctggagtg gatcggcaac atcaaccctta caacggcgg caccgacttc   180
aacgagaagt tcaagaacaa ggccaccctg accgtgcaca agagcagcac caccgtgttc   240
attcagctga gcagcctgac aagcgaggac agcgccgtgt actactgcgc tagaggcacc   300
ggcaccggcg ccatggacta ctggggccaa ggcacaagcg tgaccgtgtc gtcggc       356

SEQ ID NO: 191          moltype = DNA   length = 1335
FEATURE                 Location/Qualifiers
source                  1..1335
                        mol_type = other DNA
                        organism = synthetic construct
SEQUENCE: 191
caagtgcagc tgcagcaacc gggcacagag ctggtgaagc ctggcagcag cgtgaacctg    60
agctgcaagg ctagcggctt caccttcaca agatactgga tgcactgggt gaaggagaga   120
cctggccacg gcctggagtg gatcggcaac atcaaccctta caacggcgg caccgacttc   180
aacgagaagt tcaagaacaa ggccaccctg accgtgcaca agagcagcac caccgtgttc   240
attcagctga gcagcctgac aagcgaggac agcgccgtgt actactgcgc tagaggcacc   300
ggcaccggcg ccatggacta ctggggccaa ggcacaagcg tgaccgtgtc gtcggctagc   360
accaagggtc cttccgtgtt tcctctagcc ccttgcagca gaagcacaag cgagagcacc   420
gccgccctgg gctgcctggt taaagattat ttccctgagc ctgtgaccgt gagctggaat   480
agcggcgccc tgacaagcgg cgtgcacacc ttccctgccg tgctgcagag cagcggcctg   540
tacagcctga gcagcgtggt gaccgtgcct tctagcagca tgggtactaa gacctacacc   600
tgcaacgtgg accacaagcc tagcaacacc aaggtggaca agagagtgga gagcaagtac   660
ggtcctccgt gtccccgtg ccctgcccct gagttcctgg gcggcctag cgttttcttg   720
tttccaccta agcctaagga caccctgatg atcagcagaa ccctgaggt gacctgcgtg   780
gtggtggacg tgagccaaga ggaccctgag gtgcagttca ctggtacgt ggacggcgtg   840
gaggtgcaca acgccaagac caagcctaga gaggagcagt tcaacagcac ctacagagtg   900
gtgagcgtgc tgaccgtgct gcaccaagac tggctgaacg gcaaggagta caagtgcaag   960
gtgagcaaca agggcctgcc tagcagtatt gaaaagacca tcagcaaggc caaggacag  1020
cctagaagc ctcaagtgta cacctgcct cctagccaag aggagatgac caagaaccaa  1080
gtgagcctga cctgcctggt gaaggggttt tacctagcg catcgccgt ggagtgggag  1140
agcaacggac agcctgagaa caactacaag accaccctc tgtgctgga cagcgacggc  1200
agcttcttcc tgtacagcag actgaccgtg gacaagagca gatggcaaga gggcaacgtg  1260
ttcagctgca gcgtgatgca cgaggccctg cacaaccact acacacagaa gagcctgagc  1320
ctgagcctgg gcaag                                                  1335

SEQ ID NO: 192          moltype = DNA   length = 336
FEATURE                 Location/Qualifiers
source                  1..336
                        mol_type = other DNA
                        organism = synthetic construct
SEQUENCE: 192
gacgtggtga tgacacagac ccctctgagc ctgcctgtga gcctgggcga ccaagctagc    60
atcagctgca gaagctctca gagcctggtg cacaacaacg gcatcaccta cctgtactgg   120
tacctgcaga agcctggaca gagccctaag ctgctgatct acagagtgag caacagattc   180
agcggcgtgc ctgacagatt cggcggcagc ggcagcggca ccgacttcac cctgaagatc   240
agcagagtgg aggccgagga cctggcgtg tacttctgct tccaaggcac gcatgtacct   300
agaaccttcg gcggcggcac caagctggag atcaag                             336

SEQ ID NO: 193          moltype = DNA   length = 657
FEATURE                 Location/Qualifiers
source                  1..657
                        mol_type = other DNA
                        organism = synthetic construct
SEQUENCE: 193
gacgtggtga tgacacagac ccctctgagc ctgcctgtga gcctgggcga ccaagctagc    60
atcagctgca gaagctctca gagcctggtg cacaacaacg gcatcaccta cctgtactgg   120
tacctgcaga agcctggaca gagccctaag ctgctgatct acagagtgag caacagattc   180
agcggcgtgc ctgacagatt cggcggcagc ggcagcggca ccgacttcac cctgaagatc   240
agcagagtgg aggccgagga cctggcgtg tacttctgct tccaaggcac gcatgtacct   300
agaaccttcg gcggcggcac caagctggag atcaagaga ccgtggccgc cctagcgtg   360
ttcatcttcc ctcctagcga cgagcagctg aagagcggca ccgctagcgt ggtgtgcctg   420
ctgaacaact ctaccctag agaggccaag gtgcagtgga aggtggacaa cgccctgcag   480
agcggcaaca gccaagagag cgtgaccgag caagacagca aggacagcac ctacagcctg   540
agcagcaccc tgaccctgag caaggccgac tacgagaagc acaaggtgta cgcctgcgag   600
gtgacccacc aaggcctgag cagccctgtg accaagagct tcaacagagg cgagtgc      657

SEQ ID NO: 194          moltype = AA    length = 327
FEATURE                 Location/Qualifiers
source                  1..327
```

```
                        mol_type = protein
                        organism = Homo sapiens
SEQUENCE: 194
ASTKGPSVFP  LAPCSRSTSE  STAALGCLVK  DYFPEPVTVS  WNSGALTSGV  HTFPAVLQSS    60
GLYSLSSVVT  VPSSSLGTKT  YTCNVDHKPS  NTKVDKRVES  KYGPPCPPCP  APEFLGGPSV   120
FLFPPKPKDT  LMISRTPEVT  CVVVDVSQED  PEVQFNWYVD  GVEVHNAKTK  PREEQFNSTY   180
RVVSVLTVLH  QDWLNGKEYK  CKVSNKGLPS  SIEKTISKAK  GQPREPQVYT  LPPSQEEMTK   240
NQVSLTCLVK  GFYPSDIAVE  WESNGQPENN  YKTTPPVLDS  DGSFFLYSRL  TVDKSRWQEG   300
NVFSCSVMHE  ALHNHYTQKS  LSLSLGK                                         327

SEQ ID NO: 195         moltype = DNA  length = 981
FEATURE                Location/Qualifiers
source                 1..981
                       mol_type = genomic DNA
                       organism = Homo sapiens
SEQUENCE: 195
gctagcacca aggggtccttc cgtgtttcct ctagcccctt gcagcagaag cacaagcgag    60
agcaccgccg ccctgggctg cctggttaaa gattatttcc ctgagcctgt gaccgtgagc   120
tggaatagcg gcgccctgac aagcggcgtg cacaccttcc ctgccgtgct gcagagcagc   180
ggcctgtaca gcctgagcag cgtggtgacc gtgccttcta gcagcctggg tactaagacc   240
tacacctgca acgtggacca caagcctagc aacaccaagg tggacaagag agtggagagc   300
aagtacggtc ctccgtgtcc cccgtgccct gcccctgagt tcctgggcgg ccctagcgtt   360
ttcttgtttc cacctaagcc taaggacacc ctgatgatca gcagaacccc tgaggtgacc   420
tgcgtggtgg tggacgtgag ccaagaggac cctgaggtgc agttcaactg gtacgtggac   480
ggcgtggagg tgcacaacgc caagaccaag cctagagagg agcagttcaa cagcacctac   540
agagtggtga gcgtgctgac cgtgctgcac caagactggc tgaacggcaa ggagtacaag   600
tgcaaggtga gcaacaaggg cctgcctagc agtattgaaa agaccatcag caaggccaag   660
ggacagccta gagagcctca agtgtacacc ctgcctccta gccaagagga gatgaccaag   720
aaccaagtga gcctgacctg cctggtgaag gggttttacc ctagcgacat cgccgtggag   780
tgggagagca acggacagcc tgagaacaac tacaagacca cccctcctgt gctggacagc   840
gacggcagct tcttcctgta cagcagactg accgtggaca gagcagatg gcaagagggc   900
aacgtgttca gctgcagcgt gatgcacgag gccctgcaca accactacac acagaagagc   960
ctgagcctga gcctgggcaa g                                              981

SEQ ID NO: 196         moltype = DNA  length = 981
FEATURE                Location/Qualifiers
source                 1..981
                       mol_type = genomic DNA
                       organism = Homo sapiens
SEQUENCE: 196
gctagcacga aggtccaag cgttttccct ctagcccctt gcagcagaag cacaagcgag     60
agcaccgccg ccctgggctg ccttgtaaaa gattacttcc ctgagcctgt gaccgtgagt   120
tggaacagcg gcgccctgac aagcggcgtg cacaccttcc ctgccgtgct gcagagcagc   180
ggcctgtaca gcctgagcag cgtggtgacc gtgccaagca gcagcctggg caccaagacc   240
tacacctgca acgtggacca caagcctagc aacaccaagg tggacaagag agtggagagc   300
aagtacggtc ctccgtgtcc cccgtgccct gcccctgagt tcctgggcgg ccttcggtg    360
tttctgtttc cacctaagcc taaggacacc ctgatgatca gcagaacccc tgaggtgacc   420
tgcgtggtgg tggacgtgag ccaagaggac cctgaggtgc agttcaactg gtacgtggac   480
ggcgtggagg tgcacaacgc caagaccaag cctagagagg agcagttcaa cagcacctac   540
agagtggtga gcgtgctgac cgtgctgcac caagactggc tgaacggcaa ggagtacaag   600
tgcaaggtga gcaacaaggg cctgcctagt tccattgaga agaccatcag caaggccaag   660
ggacagccta gagagcctca agtgtacacc ctgcctccta gccaagagga gatgaccaag   720
aaccaagtga gcctgacctg cctggtgaag ggattctacc ctagcgacat cgccgtggag   780
tgggagagca acggacagcc tgagaacaac tacaagacca cccctcctgt gctggacagc   840
gacggcagct tcttcctgta cagcagactg accgtggaca gagcagatg gcaagagggc   900
aacgtgttca gctgcagcgt gatgcacgag gccctgcaca accactacac acagaagagc   960
ctgagcctga gcctgggcaa g                                              981

SEQ ID NO: 197         moltype = DNA  length = 357
FEATURE                Location/Qualifiers
source                 1..357
                       mol_type = other DNA
                       organism = synthetic construct
SEQUENCE: 197
cagattactc tgaaagagtc tggccctggg atattgcagt cctcccagac cctcagtctg    60
acttgttctt tctctgggtt ttcactgagc acttctgcta tgggtgtgag ttggattcgt   120
cagccttcag gagagggtct ggagtggctg gcacacattt actgggatga tgacaagcgc   180
tataacccat ccctgaagag ccggctcaca atctccaagg ataccccag aaaccaggta   240
ttcctcaaga tcaccagtgt ggacactgca gatactgcca catactactg tgctcgaaga   300
aggaggggt atgtatgga ctactgggt caaggaacct cagtcaccgt ctcctca          357

SEQ ID NO: 198         moltype = DNA  length = 981
FEATURE                Location/Qualifiers
source                 1..981
                       mol_type = genomic DNA
                       organism = Homo sapiens
SEQUENCE: 198
gctagcacca aggtccttag tgtatttccc ctagcccctt gcagcagaag cacaagcgag    60
agcaccgccg ccctgggctg cttggtgaag gactacttcc ctgagcctgt cacagtgtcc   120
```

```
tggaatagcg gcgccctgac aagcggcgtg cacaccttcc ctgccgtgct gcagagcagc  180
ggcctgtaca gcctgagcag cgtggtgacc gtgccttcgt cgagcctggg caccaagacc  240
tacacctgca acgtggacca caagcctagc aacaccaagg tggacaagag agtggagagc  300
aagtacggtc ctccgtgtcc cccgtgccct gcccctgagt tcctgggcgg ccctagcgtg  360
ttcctatttc cacctaagcc taaggacacc ctgatgatca gcagaacccc tgaggtgacc  420
tgcgtggtgg tggacgtgag ccaagaggac cctgaggtgc agttcaactg gtacgtggac  480
ggcgtggagg tgcacaacgc caagaccaag cctagagagg agcagttcaa cagcacctac  540
agagtggtga gcgtgctgac cgtgctgcac caagactggc tgaacggcaa ggagtacaag  600
tgcaaggtga gcaacaaggg cctgcctagc agtatcgaga agaccatcag caaggccaag  660
ggacagccta gagagcctca agtgtacacc ctgcctccta gccaagagga gatgaccaag  720
aaccaagtga gcctgacctg cctggtaaaa ggtttctacc ctagcgacat cgccgtggag  780
tgggagagca acggacagcc tgagaacaac tacaagacca cccctcctgt gctggacagc  840
gacggcagct tcttcctgta cagcagactg accgtggaca gagcagatg gcaagagggc  900
aacgtgttca gctgcagcgt gatgcacgag gccctgcaca accactacac acagaagagc  960
ctgagcctga gcctgggcaa g                                            981

SEQ ID NO: 199            moltype = DNA  length = 981
FEATURE                   Location/Qualifiers
source                    1..981
                          mol_type = genomic DNA
                          organism = Homo sapiens
SEQUENCE: 199
gctagcacca agggtcctag tgtatttccc ctagccccctt gcagcagaag cacaagcgag  60
agcaccgccg ccctgggctg cttggtgaag gactacttcc ctgagcctgt gaccgtgagc  120
tggaacagcg gcgccctgac aagcggcgtg cacaccttcc ctgccgtgct gcagagcagc  180
ggcctgtaca gcctgagcag cgtggtgacc gtgccttcgt cgagcctggg caccaagacc  240
tacacctgca acgtggacca caagcctagc aacaccaagg tggacaagag agtggagagc  300
aagtacggtc ctccgtgtcc cccgtgccct gcccctgagt tcctgggcgg ccctagcgtg  360
ttcctatttc cacctaagcc taaggacacc ctgatgatca gcagaacccc tgaggtgacc  420
tgcgtggtgg tggacgtgag ccaagaggac cctgaggtgc agttcaactg gtacgtggac  480
ggcgtggagg tgcacaacgc caagaccaag cctagagagg agcagttcaa cagcacctac  540
agagtggtga gcgtgctgac cgtgctgcac caagactggc tgaacggcaa ggagtacaag  600
tgcaaggtga gcaacaaggg cctgcctagc agtatcgaga agaccatcag caaggccaag  660
ggacagccta gagagcctca agtgtacacc ctgcctccta gccaagagga gatgaccaag  720
aaccaagtga gcctgacctg cctggtaaaa ggtttctacc ctagcgacat cgccgtggag  780
tgggagagca acggacagcc tgagaacaac tacaagacca cccctcctgt gctggacagc  840
gacggcagct tcttcctgta ctcccgcctg acgttgaca agagcagatg gcaagagggc  900
aacgtgttca gctgcagcgt gatgcacgag gccctgcaca accactacac acagaagagc  960
ctgagcctga gcctgggcaa g                                            981

SEQ ID NO: 200            moltype = AA  length = 107
FEATURE                   Location/Qualifiers
source                    1..107
                          mol_type = protein
                          organism = Homo sapiens
SEQUENCE: 200
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 201            moltype = DNA  length = 321
FEATURE                   Location/Qualifiers
source                    1..321
                          mol_type = genomic DNA
                          organism = Homo sapiens
SEQUENCE: 201
agaaccgtgg ccgcccctag cgtgttcatc ttccctccta gcgacgagca gctgaagagc   60
ggcaccgcta gcgtggtgtg cctgctgaac aacttctacc ctagagaggc caaggtgcag  120
tggaaggtgg acaacgccct gcagagcggc aacagccaag agagcgtgac cgagcaagac  180
agcaaggaca gcacctacag cctgagcagc accctgaccc tgagcaaggc cgactacgag  240
aagcacaagg tgtacgcctg cgaggtgacc caccaaggcc tgagcagccc tgtgaccaag  300
agcttcaaca gaggcgagtg c                                            321

SEQ ID NO: 202            moltype = DNA  length = 321
FEATURE                   Location/Qualifiers
source                    1..321
                          mol_type = genomic DNA
                          organism = Homo sapiens
SEQUENCE: 202
agaaccgtgg ccgcccctag cgtgttcatc ttccctccta gcgacgagca gctgaagagc   60
ggcaccgcta gcgtggtgtg cctgctgaac aacttctacc ctagagaggc caaggtgcag  120
tggaaggtgg acaacgccct gcagagcggc aacagccaag agagcgtgac cgagcaagac  180
agcaaggaca gcacctacag cctgagcagc accctgaccc tgagcaaggc cgactacgag  240
aagcacaagg tgtacgcctg cgaggtgacc caccaaggcc tgtcaagccc tgtaactaag  300
agcttcaaca gaggcgagtg c                                            321

SEQ ID NO: 203            moltype = AA  length = 19
FEATURE                   Location/Qualifiers
source                    1..19
                          mol_type = protein
```

```
                        organism = synthetic construct
SEQUENCE: 203
MGWTLVFLFL LSVTAGVHS                                                    19

SEQ ID NO: 204          moltype = DNA   length = 57
FEATURE                 Location/Qualifiers
source                  1..57
                        mol_type = other DNA
                        organism = synthetic construct
SEQUENCE: 204
atgggctgga ccctggtgtt tctcttcctg ctgagcgtga ccgccggcgt gcacagc          57

SEQ ID NO: 205          moltype = AA    length = 20
FEATURE                 Location/Qualifiers
source                  1..20
                        mol_type = protein
                        organism = synthetic construct
SEQUENCE: 205
MVSSAQFLGL LLLCFQGTRC                                                   20

SEQ ID NO: 206          moltype = DNA   length = 60
FEATURE                 Location/Qualifiers
source                  1..60
                        mol_type = other DNA
                        organism = synthetic construct
SEQUENCE: 206
atggtgagca gcgctcagtt cctgggcctg ctgctgctgt gttttcaagg cacaagatgt       60

SEQ ID NO: 207          moltype = DNA   length = 60
FEATURE                 Location/Qualifiers
source                  1..60
                        mol_type = other DNA
                        organism = synthetic construct
SEQUENCE: 207
atggtgagca gcgctcagtt cctgggcctg ctgctgctgt gcttccaagg cacaagatgc       60

SEQ ID NO: 208          moltype = DNA   length = 60
FEATURE                 Location/Qualifiers
source                  1..60
                        mol_type = other DNA
                        organism = synthetic construct
SEQUENCE: 208
atggtgagca gcgctcagtt cctgggcctg ctgctgctgt gtttccaagg gacaagatgt       60

SEQ ID NO: 209          moltype =       length =
SEQUENCE: 209
000

SEQ ID NO: 210          moltype =       length =
SEQUENCE: 210
000

SEQ ID NO: 211          moltype =       length =
SEQUENCE: 211
000

SEQ ID NO: 212          moltype =       length =
SEQUENCE: 212
000

SEQ ID NO: 213          moltype =       length =
SEQUENCE: 213
000

SEQ ID NO: 214          moltype =       length =
SEQUENCE: 214
000

SEQ ID NO: 215          moltype =       length =
SEQUENCE: 215
000

SEQ ID NO: 216          moltype =       length =
SEQUENCE: 216
000

SEQ ID NO: 217          moltype =       length =
SEQUENCE: 217
000
```

```
SEQ ID NO: 218          moltype =      length =
SEQUENCE: 218
000

SEQ ID NO: 219          moltype =      length =
SEQUENCE: 219
000

SEQ ID NO: 220          moltype =      length =
SEQUENCE: 220
000

SEQ ID NO: 221          moltype =      length =
SEQUENCE: 221
000

SEQ ID NO: 222          moltype =      length =
SEQUENCE: 222
000

SEQ ID NO: 223          moltype =      length =
SEQUENCE: 223
000

SEQ ID NO: 224          moltype = DNA  length = 321
FEATURE                 Location/Qualifiers
source                  1..321
                        mol_type = other DNA
                        organism = synthetic construct
SEQUENCE: 224
gacatccaga tgactcagtc tccagcctcc ctatctgcat ctgtgggaga aactgtcacc   60
atcacatgtc gagcaagtgg gaatattcac aattatttag catggtatca gcagagacag  120
ggaaaatctc ctcagctcct ggtctataat gcaaaaacct taccagatgg tgtgccatca  180
aggttcagtg gcagtggatc aggaacacaa tattctctca agatcaacag cctgcagcct  240
gaagattttg ggagttattg ctgtcaacat ttttggagta ctccgctcac gttcggtgct  300
gggaccaagt tggagctgaa a                                            321

SEQ ID NO: 225          moltype =      length =
SEQUENCE: 225
000

SEQ ID NO: 226          moltype =      length =
SEQUENCE: 226
000

SEQ ID NO: 227          moltype =      length =
SEQUENCE: 227
000

SEQ ID NO: 228          moltype =      length =
SEQUENCE: 228
000

SEQ ID NO: 229          moltype = DNA  length = 339
FEATURE                 Location/Qualifiers
source                  1..339
                        mol_type = other DNA
                        organism = synthetic construct
SEQUENCE: 229
gacattgtga tgtcacagtc tccatcctcc ctagctgtgt cagttggaga gaaggttact   60
atgagctgca agtccagtca gagccttta tatagtacca atcaagagaa ctacttggcc  120
tggtaccagc agaaaccagg gcagtctcct aaactgctga tttactgggc atcctctagg  180
gaatctgggg tccctgatcg ctttacaggc agtggatctg ggacagattt cactctcacc  240
atcagcagtg tgaaggctga agacctggca gtttattact gtcagcaata ttatagctat  300
cctcggacgt tcggtggagg caccaagctg gaaatcaaa                         339

SEQ ID NO: 230          moltype =      length =
SEQUENCE: 230
000

SEQ ID NO: 231          moltype =      length =
SEQUENCE: 231
000

SEQ ID NO: 232          moltype =      length =
SEQUENCE: 232
000
```

| SEQ ID NO: 233 | moltype = length = |
| SEQUENCE: 233 | |
| 000 | |

| SEQ ID NO: 234 | moltype = length = |
| SEQUENCE: 234 | |
| 000 | |

| SEQ ID NO: 235 | moltype = length = |
| SEQUENCE: 235 | |
| 000 | |

| SEQ ID NO: 236 | moltype = length = |
| SEQUENCE: 236 | |
| 000 | |

| SEQ ID NO: 237 | moltype = length = |
| SEQUENCE: 237 | |
| 000 | |

| SEQ ID NO: 238 | moltype = length = |
| SEQUENCE: 238 | |
| 000 | |

| SEQ ID NO: 239 | moltype = length = |
| SEQUENCE: 239 | |
| 000 | |

| SEQ ID NO: 240 | moltype = length = |
| SEQUENCE: 240 | |
| 000 | |

SEQ ID NO: 241     moltype = DNA   length = 336
FEATURE            Location/Qualifiers
source             1..336
                   mol_type = other DNA
                   organism = synthetic construct
SEQUENCE: 241
gatgttgtga tgacccaaac tccactctcc ctgcctgtca gtcttggaga tcaagcttcc    60
atctcttgca gatctagtca gagccttgta cacaacaatg gaatcaccta tttatattgg   120
tacctgcaga agccaggcca gtctccaaag ctcctgatct acagggtttc caaccgattt   180
tctggggtcc cagacaggtt cggtggcagt ggatcaggga cagatttcac actcaagatc   240
agcagagtgg aggctgagga tctgggagtt tatttctgct ttcaaggtac acatgttcct   300
cggacgttcg gtggaggcac caagctggaa atcaaa                              336

SEQ ID NO: 242     moltype = DNA   length = 336
FEATURE            Location/Qualifiers
source             1..336
                   mol_type = other DNA
                   organism = synthetic construct
SEQUENCE: 242
gatgttgtga tgacccaaac tccactctcc ctgcctgtca gtcttggaga tcacgcttcc    60
atctcttgca gatctagtca gagccttgta cacagcaatg gaatcaccca tttatattgg   120
tacctgcaga ggccaggcca gactccaaag ctcctgatct acagggtttc caaccgattt   180
tctggggtcc cagacaggtt cagtggcagt ggatcaggga cagatttcac actcaagatc   240
agcagcgtgg aggctgagga tctgggagtt tatttctgct ttcaaggtac acatgttcct   300
cggacgttcg gtggaggcac caagctggaa atcgaa                              336

SEQ ID NO: 243     moltype = DNA   length = 336
FEATURE            Location/Qualifiers
source             1..336
                   mol_type = other DNA
                   organism = synthetic construct
SEQUENCE: 243
gatgtggtga tgacccaaac tccactctcc ctgcctgtca gtcttggaga tcaggcttcc    60
atctcttgca gatctagtca gagccttgta cacagcaatg gaaacaccca tttatattgg   120
tacctgcaga agccaggcca gtctccaaag ctcctgatct acagggtttc cagccgattt   180
tctggggtcc cagacaggtt cagtggcagt ggatcaggga cagatttcac actcaagatc   240
agcagagtgg aggctgagga tctgggagtt tatttctgct ttcagggtac acatgttcct   300
cggacgttcg gtggaggcac caagctggaa atcaaa                              336

| SEQ ID NO: 244 | moltype = length = |
| SEQUENCE: 244 | |
| 000 | |

| SEQ ID NO: 245 | moltype = length = |
| SEQUENCE: 245 | |
| 000 | |

| | | |
|---|---|---|
| SEQ ID NO: 246 SEQUENCE: 246 | moltype = | length = 000 |
| SEQ ID NO: 247 SEQUENCE: 247 | moltype = | length = 000 |
| SEQ ID NO: 248 SEQUENCE: 248 | moltype = | length = 000 |
| SEQ ID NO: 249 SEQUENCE: 249 | moltype = | length = 000 |
| SEQ ID NO: 250 SEQUENCE: 250 | moltype = | length = 000 |
| SEQ ID NO: 251 SEQUENCE: 251 | moltype = | length = 000 |
| SEQ ID NO: 252 SEQUENCE: 252 | moltype = | length = 000 |
| SEQ ID NO: 253 SEQUENCE: 253 | moltype = | length = 000 |
| SEQ ID NO: 254 SEQUENCE: 254 | moltype = | length = 000 |
| SEQ ID NO: 255 SEQUENCE: 255 | moltype = | length = 000 |
| SEQ ID NO: 256 SEQUENCE: 256 | moltype = | length = 000 |
| SEQ ID NO: 257 SEQUENCE: 257 | moltype = | length = 000 |
| SEQ ID NO: 258 SEQUENCE: 258 | moltype = | length = 000 |
| SEQ ID NO: 259 SEQUENCE: 259 | moltype = | length = 000 |
| SEQ ID NO: 260 SEQUENCE: 260 | moltype = | length = 000 |
| SEQ ID NO: 261 SEQUENCE: 261 | moltype = | length = 000 |
| SEQ ID NO: 262 SEQUENCE: 262 | moltype = | length = 000 |
| SEQ ID NO: 263 SEQUENCE: 263 | moltype = | length = 000 |
| SEQ ID NO: 264 SEQUENCE: 264 | moltype = | length = 000 |
| SEQ ID NO: 265 SEQUENCE: 265 | moltype = | length = 000 |

```
SEQ ID NO: 266          moltype =     length =
SEQUENCE: 266
000

SEQ ID NO: 267          moltype =     length =
SEQUENCE: 267
000

SEQ ID NO: 268          moltype =     length =
SEQUENCE: 268
000

SEQ ID NO: 269          moltype =     length =
SEQUENCE: 269
000

SEQ ID NO: 270          moltype = DNA  length = 321
FEATURE                 Location/Qualifiers
source                  1..321
                        mol_type = other DNA
                        organism = synthetic construct
SEQUENCE: 270
agtattgtga tgacccagac tcccaaattc ctgcttgtat cagcaggaga cagggttacc    60
ataacctgca aggccagtca gagtgtgagt aatgatgtag cttggtacca acagaagcca   120
gggcagtctc ctaaactgct aatatactat gcatccaatc gctgcactgg agtccctgat   180
cgcttcactg gcagtggata tgggacggat ttcactttca ccatcagcac tgtacaggct   240
gaagacctgg cagtttattt ctgtcagcag gattataggt ctccgctcac gttcggtgct   300
gggaccaagc tggagctgaa a                                              321

SEQ ID NO: 271          moltype =     length =
SEQUENCE: 271
000

SEQ ID NO: 272          moltype =     length =
SEQUENCE: 272
000

SEQ ID NO: 273          moltype =     length =
SEQUENCE: 273
000

SEQ ID NO: 274          moltype =     length =
SEQUENCE: 274
000

SEQ ID NO: 275          moltype =     length =
SEQUENCE: 275
000

SEQ ID NO: 276          moltype =     length =
SEQUENCE: 276
000

SEQ ID NO: 277          moltype =     length =
SEQUENCE: 277
000

SEQ ID NO: 278          moltype =     length =
SEQUENCE: 278
000

SEQ ID NO: 279          moltype =     length =
SEQUENCE: 279
000

SEQ ID NO: 280          moltype =     length =
SEQUENCE: 280
000

SEQ ID NO: 281          moltype =     length =
SEQUENCE: 281
000

SEQ ID NO: 282          moltype =     length =
SEQUENCE: 282
000

SEQ ID NO: 283          moltype =     length =
```

```
SEQUENCE: 283
000

SEQ ID NO: 284          moltype =   length =
SEQUENCE: 284
000

SEQ ID NO: 285          moltype =   length =
SEQUENCE: 285
000

SEQ ID NO: 286          moltype =   length =
SEQUENCE: 286
000

SEQ ID NO: 287          moltype =   length =
SEQUENCE: 287
000

SEQ ID NO: 288          moltype =   length =
SEQUENCE: 288
000

SEQ ID NO: 289          moltype =   length =
SEQUENCE: 289
000

SEQ ID NO: 290          moltype =   length =
SEQUENCE: 290
000

SEQ ID NO: 291          moltype =   length =
SEQUENCE: 291
000

SEQ ID NO: 292          moltype =   length =
SEQUENCE: 292
000

SEQ ID NO: 293          moltype =   length =
SEQUENCE: 293
000

SEQ ID NO: 294          moltype =   length =
SEQUENCE: 294
000

SEQ ID NO: 295          moltype =   length =
SEQUENCE: 295
000

SEQ ID NO: 296          moltype =   length =
SEQUENCE: 296
000

SEQ ID NO: 297          moltype =   length =
SEQUENCE: 297
000

SEQ ID NO: 298          moltype =   length =
SEQUENCE: 298
000

SEQ ID NO: 299          moltype = AA  length = 7
FEATURE                 Location/Qualifiers
source                  1..7
                        mol_type = protein
                        organism = synthetic construct
SEQUENCE: 299
DYTFTNY                                                                    7

SEQ ID NO: 300          moltype =   length =
SEQUENCE: 300
000

SEQ ID NO: 301          moltype =   length =
SEQUENCE: 301
000
```

| | | |
|---|---|---|
| SEQ ID NO: 302<br>SEQUENCE: 302<br>000 | moltype =    length = | |
| SEQ ID NO: 303<br>SEQUENCE: 303<br>000 | moltype =    length = | |
| SEQ ID NO: 304<br>FEATURE<br>source<br><br>SEQUENCE: 304<br>GFTFTDY | moltype = AA   length = 7<br>Location/Qualifiers<br>1..7<br>mol_type = protein<br>organism = synthetic construct | <br><br><br><br><br>7 |
| SEQ ID NO: 305<br>SEQUENCE: 305<br>000 | moltype =    length = | |
| SEQ ID NO: 306<br>SEQUENCE: 306<br>000 | moltype =    length = | |
| SEQ ID NO: 307<br>SEQUENCE: 307<br>000 | moltype =    length = | |
| SEQ ID NO: 308<br>SEQUENCE: 308<br>000 | moltype =    length = | |
| SEQ ID NO: 309<br>SEQUENCE: 309<br>000 | moltype =    length = | |
| SEQ ID NO: 310<br>SEQUENCE: 310<br>000 | moltype =    length = | |
| SEQ ID NO: 311<br>SEQUENCE: 311<br>000 | moltype =    length = | |
| SEQ ID NO: 312<br>SEQUENCE: 312<br>000 | moltype =    length = | |
| SEQ ID NO: 313<br>SEQUENCE: 313<br>000 | moltype =    length = | |
| SEQ ID NO: 314<br>FEATURE<br>source<br><br><br>SEQUENCE: 314<br>GFTFTRY | moltype = AA   length = 7<br>Location/Qualifiers<br>1..7<br>mol_type = protein<br>organism = synthetic construct | <br><br><br><br><br>7 |
| SEQ ID NO: 315<br>FEATURE<br>source<br><br><br>SEQUENCE: 315<br>GYTFTIF | moltype = AA   length = 7<br>Location/Qualifiers<br>1..7<br>mol_type = protein<br>organism = synthetic construct | <br><br><br><br><br>7 |
| SEQ ID NO: 316<br>FEATURE<br>source<br><br><br>SEQUENCE: 316<br>GYTFTRF | moltype = AA   length = 7<br>Location/Qualifiers<br>1..7<br>mol_type = protein<br>organism = synthetic construct | <br><br><br><br><br>7 |
| SEQ ID NO: 317<br>SEQUENCE: 317<br>000 | moltype =    length = | |

| | | |
|---|---|---|
| SEQ ID NO: 318<br>SEQUENCE: 318<br>000 | moltype = | length = |
| SEQ ID NO: 319<br>SEQUENCE: 319<br>000 | moltype = | length = |
| SEQ ID NO: 320<br>SEQUENCE: 320<br>000 | moltype = | length = |
| SEQ ID NO: 321<br>SEQUENCE: 321<br>000 | moltype = | length = |
| SEQ ID NO: 322<br>SEQUENCE: 322<br>000 | moltype = | length = |
| SEQ ID NO: 323<br>SEQUENCE: 323<br>000 | moltype = | length = |
| SEQ ID NO: 324<br>SEQUENCE: 324<br>000 | moltype = | length = |
| SEQ ID NO: 325<br>FEATURE<br>source<br>SEQUENCE: 325<br>GFSLSTSAM | moltype = AA   length = 9<br>Location/Qualifiers<br>1..9<br>mol_type = protein<br>organism = synthetic construct | 9 |
| SEQ ID NO: 326<br>SEQUENCE: 326<br>000 | moltype = | length = |
| SEQ ID NO: 327<br>SEQUENCE: 327<br>000 | moltype = | length = |
| SEQ ID NO: 328<br>SEQUENCE: 328<br>000 | moltype = | length = |
| SEQ ID NO: 329<br>SEQUENCE: 329<br>000 | moltype = | length = |
| SEQ ID NO: 330<br>SEQUENCE: 330<br>000 | moltype = | length = |
| SEQ ID NO: 331<br>SEQUENCE: 331<br>000 | moltype = | length = |
| SEQ ID NO: 332<br>SEQUENCE: 332<br>000 | moltype = | length = |
| SEQ ID NO: 333<br>SEQUENCE: 333<br>000 | moltype = | length = |
| SEQ ID NO: 334<br>SEQUENCE: 334<br>000 | moltype = | length = |
| SEQ ID NO: 335<br>SEQUENCE: 335<br>000 | moltype = | length = |
| SEQ ID NO: 336<br>SEQUENCE: 336 | moltype = | length = |

```
000

SEQ ID NO: 337          moltype =    length =
SEQUENCE: 337
000

SEQ ID NO: 338          moltype =    length =
SEQUENCE: 338
000

SEQ ID NO: 339          moltype =    length =
SEQUENCE: 339
000

SEQ ID NO: 340          moltype =    length =
SEQUENCE: 340
000

SEQ ID NO: 341          moltype = AA   length = 6
FEATURE                 Location/Qualifiers
source                  1..6
                        mol_type = protein
                        organism = synthetic construct
SEQUENCE: 341
NPNNGG                                                                    6

SEQ ID NO: 342          moltype =    length =
SEQUENCE: 342
000

SEQ ID NO: 343          moltype = AA   length = 6
FEATURE                 Location/Qualifiers
source                  1..6
                        mol_type = protein
                        organism = synthetic construct
SEQUENCE: 343
DPNSGG                                                                    6

SEQ ID NO: 344          moltype =    length =
SEQUENCE: 344
000

SEQ ID NO: 345          moltype =    length =
SEQUENCE: 345
000

SEQ ID NO: 346          moltype =    length =
SEQUENCE: 346
000

SEQ ID NO: 347          moltype = AA   length = 8
FEATURE                 Location/Qualifiers
source                  1..8
                        mol_type = protein
                        organism = synthetic construct
SEQUENCE: 347
RNKAKGFT                                                                  8

SEQ ID NO: 348          moltype =    length =
SEQUENCE: 348
000

SEQ ID NO: 349          moltype =    length =
SEQUENCE: 349
000

SEQ ID NO: 350          moltype =    length =
SEQUENCE: 350
000

SEQ ID NO: 351          moltype =    length =
SEQUENCE: 351
000

SEQ ID NO: 352          moltype =    length =
SEQUENCE: 352
000

SEQ ID NO: 353          moltype =    length =
```

```
SEQUENCE: 353
000

SEQ ID NO: 354         moltype =   length =
SEQUENCE: 354
000

SEQ ID NO: 355         moltype =   length =
SEQUENCE: 355
000

SEQ ID NO: 356         moltype =   length =
SEQUENCE: 356
000

SEQ ID NO: 357         moltype =   length =
SEQUENCE: 357
000

SEQ ID NO: 358         moltype =   length =
SEQUENCE: 358
000

SEQ ID NO: 359         moltype =   length =
SEQUENCE: 359
000

SEQ ID NO: 360         moltype =   length =
SEQUENCE: 360
000

SEQ ID NO: 361         moltype =   length =
SEQUENCE: 361
000

SEQ ID NO: 362         moltype = AA  length = 5
FEATURE                Location/Qualifiers
source                 1..5
                       mol_type = protein
                       organism = synthetic construct
SEQUENCE: 362
YWDDD                                                                  5

SEQ ID NO: 363         moltype =   length =
SEQUENCE: 363
000

SEQ ID NO: 364         moltype =   length =
SEQUENCE: 364
000

SEQ ID NO: 365         moltype =   length =
SEQUENCE: 365
000

SEQ ID NO: 366         moltype =   length =
SEQUENCE: 366
000

SEQ ID NO: 367         moltype =   length =
SEQUENCE: 367
000

SEQ ID NO: 368         moltype =   length =
SEQUENCE: 368
000

SEQ ID NO: 369         moltype =   length =
SEQUENCE: 369
000

SEQ ID NO: 370         moltype =   length =
SEQUENCE: 370
000

SEQ ID NO: 371         moltype =   length =
SEQUENCE: 371
000
```

| | | |
|---|---|---|
| SEQ ID NO: 372<br>SEQUENCE: 372<br>000 | moltype = | length = |
| SEQ ID NO: 373<br>SEQUENCE: 373<br>000 | moltype = | length = |
| SEQ ID NO: 374<br>SEQUENCE: 374<br>000 | moltype = | length = |
| SEQ ID NO: 375<br>SEQUENCE: 375<br>000 | moltype = | length = |
| SEQ ID NO: 376<br>SEQUENCE: 376<br>000 | moltype = | length = |
| SEQ ID NO: 377<br>SEQUENCE: 377<br>000 | moltype = | length = |
| SEQ ID NO: 378<br>SEQUENCE: 378<br>000 | moltype = | length = |
| SEQ ID NO: 379<br>SEQUENCE: 379<br>000 | moltype = | length = |
| SEQ ID NO: 380<br>SEQUENCE: 380<br>000 | moltype = | length = |
| SEQ ID NO: 381<br>SEQUENCE: 381<br>000 | moltype = | length = |
| SEQ ID NO: 382<br>SEQUENCE: 382<br>000 | moltype = | length = |
| SEQ ID NO: 383<br>SEQUENCE: 383<br>000 | moltype = | length = |
| SEQ ID NO: 384<br>SEQUENCE: 384<br>000 | moltype = | length = |
| SEQ ID NO: 385<br>SEQUENCE: 385<br>000 | moltype = | length = |
| SEQ ID NO: 386<br>SEQUENCE: 386<br>000 | moltype = | length = |
| SEQ ID NO: 387<br>SEQUENCE: 387<br>000 | moltype = | length = |
| SEQ ID NO: 388<br>SEQUENCE: 388<br>000 | moltype = | length = |
| SEQ ID NO: 389<br>SEQUENCE: 389<br>000 | moltype = | length = |
| SEQ ID NO: 390<br>SEQUENCE: 390<br>000 | moltype = | length = |
| SEQ ID NO: 391<br>SEQUENCE: 391<br>000 | moltype = | length = |

| | | |
|---|---|---|
| SEQ ID NO: 392<br>SEQUENCE: 392<br>000 | moltype = length = | |
| SEQ ID NO: 393<br>SEQUENCE: 393<br>000 | moltype = length = | |
| SEQ ID NO: 394<br>SEQUENCE: 394<br>000 | moltype = length = | |
| SEQ ID NO: 395<br>FEATURE<br>source<br>SEQUENCE: 395<br>DFDV | moltype = AA  length = 4<br>Location/Qualifiers<br>1..4<br>mol_type = protein<br>organism = synthetic construct | 4 |
| SEQ ID NO: 396<br>SEQUENCE: 396<br>000 | moltype = length = | |
| SEQ ID NO: 397<br>SEQUENCE: 397<br>000 | moltype = length = | |
| SEQ ID NO: 398<br>SEQUENCE: 398<br>000 | moltype = length = | |
| SEQ ID NO: 399<br>SEQUENCE: 399<br>000 | moltype = length = | |
| SEQ ID NO: 400<br>FEATURE<br>source<br>SEQUENCE: 400<br>DINY | moltype = AA  length = 4<br>Location/Qualifiers<br>1..4<br>mol_type = protein<br>organism = synthetic construct | 4 |
| SEQ ID NO: 401<br>SEQUENCE: 401<br>000 | moltype = length = | |
| SEQ ID NO: 402<br>SEQUENCE: 402<br>000 | moltype = length = | |
| SEQ ID NO: 403<br>SEQUENCE: 403<br>000 | moltype = length = | |
| SEQ ID NO: 404<br>SEQUENCE: 404<br>000 | moltype = length = | |
| SEQ ID NO: 405<br>SEQUENCE: 405<br>000 | moltype = length = | |
| SEQ ID NO: 406<br>SEQUENCE: 406<br>000 | moltype = length = | |
| SEQ ID NO: 407<br>SEQUENCE: 407<br>000 | moltype = length = | |
| SEQ ID NO: 408<br>SEQUENCE: 408<br>000 | moltype = length = | |
| SEQ ID NO: 409<br>SEQUENCE: 409 | moltype = length = | |

```
000

SEQ ID NO: 410          moltype = AA  length = 9
FEATURE                 Location/Qualifiers
source                  1..9
                        mol_type = protein
                        organism = synthetic construct
SEQUENCE: 410
GTGTGAMDY                                                              9

SEQ ID NO: 411          moltype =     length =
SEQUENCE: 411
000

SEQ ID NO: 412          moltype =     length =
SEQUENCE: 412
000

SEQ ID NO: 413          moltype =     length =
SEQUENCE: 413
000

SEQ ID NO: 414          moltype =     length =
SEQUENCE: 414
000

SEQ ID NO: 415          moltype =     length =
SEQUENCE: 415
000

SEQ ID NO: 416          moltype =     length =
SEQUENCE: 416
000

SEQ ID NO: 417          moltype =     length =
SEQUENCE: 417
000

SEQ ID NO: 418          moltype =     length =
SEQUENCE: 418
000

SEQ ID NO: 419          moltype =     length =
SEQUENCE: 419
000

SEQ ID NO: 420          moltype =     length =
SEQUENCE: 420
000

SEQ ID NO: 421          moltype =     length =
SEQUENCE: 421
000

SEQ ID NO: 422          moltype =     length =
SEQUENCE: 422
000

SEQ ID NO: 423          moltype =     length =
SEQUENCE: 423
000

SEQ ID NO: 424          moltype =     length =
SEQUENCE: 424
000

SEQ ID NO: 425          moltype =     length =
SEQUENCE: 425
000

SEQ ID NO: 426          moltype =     length =
SEQUENCE: 426
000

SEQ ID NO: 427          moltype =     length =
SEQUENCE: 427
000

SEQ ID NO: 428          moltype =     length =
```

```
SEQUENCE: 428
000

SEQ ID NO: 429          moltype =     length =
SEQUENCE: 429
000

SEQ ID NO: 430          moltype =     length =
SEQUENCE: 430
000

SEQ ID NO: 431          moltype =     length =
SEQUENCE: 431
000

SEQ ID NO: 432          moltype =     length =
SEQUENCE: 432
000

SEQ ID NO: 433          moltype =     length =
SEQUENCE: 433
000

SEQ ID NO: 434          moltype =     length =
SEQUENCE: 434
000

SEQ ID NO: 435          moltype = AA   length = 9
FEATURE                 Location/Qualifiers
source                  1..9
                        mol_type = protein
                        organism = synthetic construct
SEQUENCE: 435
RRRGYGMDY                                                                 9

SEQ ID NO: 436          moltype =     length =
SEQUENCE: 436
000

SEQ ID NO: 437          moltype =     length =
SEQUENCE: 437
000

SEQ ID NO: 438          moltype =     length =
SEQUENCE: 438
000

SEQ ID NO: 439          moltype =     length =
SEQUENCE: 439
000

SEQ ID NO: 440          moltype =     length =
SEQUENCE: 440
000

SEQ ID NO: 441          moltype =     length =
SEQUENCE: 441
000

SEQ ID NO: 442          moltype =     length =
SEQUENCE: 442
000

SEQ ID NO: 443          moltype =     length =
SEQUENCE: 443
000

SEQ ID NO: 444          moltype =     length =
SEQUENCE: 444
000

SEQ ID NO: 445          moltype =     length =
SEQUENCE: 445
000

SEQ ID NO: 446          moltype =     length =
SEQUENCE: 446
000
```

```
SEQ ID NO: 447           moltype =    length =
SEQUENCE: 447
000

SEQ ID NO: 448           moltype =    length =
SEQUENCE: 448
000

SEQ ID NO: 449           moltype =    length =
SEQUENCE: 449
000

SEQ ID NO: 450           moltype =    length =
SEQUENCE: 450
000

SEQ ID NO: 451           moltype =    length =
SEQUENCE: 451
000

SEQ ID NO: 452           moltype =    length =
SEQUENCE: 452
000

SEQ ID NO: 453           moltype =    length =
SEQUENCE: 453
000

SEQ ID NO: 454           moltype =    length =
SEQUENCE: 454
000

SEQ ID NO: 455           moltype =    length =
SEQUENCE: 455
000

SEQ ID NO: 456           moltype =    length =
SEQUENCE: 456
000

SEQ ID NO: 457           moltype =    length =
SEQUENCE: 457
000

SEQ ID NO: 458           moltype =    length =
SEQUENCE: 458
000

SEQ ID NO: 459           moltype =    length =
SEQUENCE: 459
000

SEQ ID NO: 460           moltype = AA  length = 11
FEATURE                  Location/Qualifiers
source                   1..11
                         mol_type = protein
                         organism = synthetic construct
SEQUENCE: 460
RASGNIHNYL A                                                              11

SEQ ID NO: 461           moltype =    length =
SEQUENCE: 461
000

SEQ ID NO: 462           moltype =    length =
SEQUENCE: 462
000

SEQ ID NO: 463           moltype =    length =
SEQUENCE: 463
000

SEQ ID NO: 464           moltype = AA  length = 17
FEATURE                  Location/Qualifiers
source                   1..17
                         mol_type = protein
                         organism = synthetic construct
SEQUENCE: 464
KSSQSLLYST NQENYLA                                                        17
```

| | | |
|---|---|---|
| SEQ ID NO: 465<br>SEQUENCE: 465<br>000 | moltype = | length = |
| SEQ ID NO: 466<br>SEQUENCE: 466<br>000 | moltype = | length = |
| SEQ ID NO: 467<br>SEQUENCE: 467<br>000 | moltype = | length = |
| SEQ ID NO: 468<br>SEQUENCE: 468<br>000 | moltype = | length = |
| SEQ ID NO: 469<br>SEQUENCE: 469<br>000 | moltype = | length = |
| SEQ ID NO: 470<br>SEQUENCE: 470<br>000 | moltype = | length = |
| SEQ ID NO: 471<br>SEQUENCE: 471<br>000 | moltype = | length = |
| SEQ ID NO: 472<br>SEQUENCE: 472<br>000 | moltype = | length = |
| SEQ ID NO: 473<br>FEATURE<br>source | moltype = AA  length = 11<br>Location/Qualifiers<br>1..11<br>mol_type = protein<br>organism = synthetic construct | |
| SEQUENCE: 473<br>QSLVHNNGIT Y | | 11 |
| SEQ ID NO: 474<br>FEATURE<br>source | moltype = AA  length = 16<br>Location/Qualifiers<br>1..16<br>mol_type = protein<br>organism = synthetic construct | |
| SEQUENCE: 474<br>RSSQSLVHSN GITHLY | | 16 |
| SEQ ID NO: 475<br>FEATURE<br>source | moltype = AA  length = 16<br>Location/Qualifiers<br>1..16<br>mol_type = protein<br>organism = synthetic construct | |
| SEQUENCE: 475<br>RSSQSLVHSN GNTHLY | | 16 |
| SEQ ID NO: 476<br>SEQUENCE: 476<br>000 | moltype = | length = |
| SEQ ID NO: 477<br>SEQUENCE: 477<br>000 | moltype = | length = |
| SEQ ID NO: 478<br>SEQUENCE: 478<br>000 | moltype = | length = |
| SEQ ID NO: 479<br>SEQUENCE: 479<br>000 | moltype = | length = |
| SEQ ID NO: 480<br>SEQUENCE: 480<br>000 | moltype = | length = |
| SEQ ID NO: 481<br>SEQUENCE: 481 | moltype = | length = |

```
SEQ ID NO: 482          moltype =    length =
SEQUENCE: 482
000

SEQ ID NO: 483          moltype =    length =
SEQUENCE: 483
000

SEQ ID NO: 484          moltype =    length =
SEQUENCE: 484
000

SEQ ID NO: 485          moltype =    length =
SEQUENCE: 485
000

SEQ ID NO: 486          moltype =    length =
SEQUENCE: 486
000

SEQ ID NO: 487          moltype =    length =
SEQUENCE: 487
000

SEQ ID NO: 488          moltype =    length =
SEQUENCE: 488
000

SEQ ID NO: 489          moltype =    length =
SEQUENCE: 489
000

SEQ ID NO: 490          moltype =    length =
SEQUENCE: 490
000

SEQ ID NO: 491          moltype =    length =
SEQUENCE: 491
000

SEQ ID NO: 492          moltype =    length =
SEQUENCE: 492
000

SEQ ID NO: 493          moltype =    length =
SEQUENCE: 493
000

SEQ ID NO: 494          moltype =    length =
SEQUENCE: 494
000

SEQ ID NO: 495          moltype = AA  length = 11
FEATURE                 Location/Qualifiers
source                  1..11
                        mol_type = protein
                        organism = synthetic construct
SEQUENCE: 495
KASQSVSNDV A                                                                 11

SEQ ID NO: 496          moltype =    length =
SEQUENCE: 496
000

SEQ ID NO: 497          moltype =    length =
SEQUENCE: 497
000

SEQ ID NO: 498          moltype =    length =
SEQUENCE: 498
000

SEQ ID NO: 499          moltype =    length =
SEQUENCE: 499
000

SEQ ID NO: 500          moltype =    length =
```

| | | |
|---|---|---|
| SEQUENCE: 500 000 | | |
| SEQ ID NO: 501 SEQUENCE: 501 000 | moltype = | length = |
| SEQ ID NO: 502 SEQUENCE: 502 000 | moltype = | length = |
| SEQ ID NO: 503 SEQUENCE: 503 000 | moltype = | length = |
| SEQ ID NO: 504 SEQUENCE: 504 000 | moltype = | length = |
| SEQ ID NO: 505 SEQUENCE: 505 000 | moltype = | length = |
| SEQ ID NO: 506 SEQUENCE: 506 000 | moltype = | length = |
| SEQ ID NO: 507 SEQUENCE: 507 000 | moltype = | length = |
| SEQ ID NO: 508 SEQUENCE: 508 000 | moltype = | length = |
| SEQ ID NO: 509 SEQUENCE: 509 000 | moltype = | length = |
| SEQ ID NO: 510 SEQUENCE: 510 000 | moltype = | length = |
| SEQ ID NO: 511 SEQUENCE: 511 000 | moltype = | length = |
| SEQ ID NO: 512 SEQUENCE: 512 000 | moltype = | length = |
| SEQ ID NO: 513 SEQUENCE: 513 000 | moltype = | length = |
| SEQ ID NO: 514 SEQUENCE: 514 000 | moltype = | length = |
| SEQ ID NO: 515 SEQUENCE: 515 000 | moltype = | length = |
| SEQ ID NO: 516 SEQUENCE: 516 000 | moltype = | length = |
| SEQ ID NO: 517 SEQUENCE: 517 000 | moltype = | length = |
| SEQ ID NO: 518 FEATURE source  SEQUENCE: 518 NAKTLPD | moltype = AA  length = 7 Location/Qualifiers 1..7 mol_type = protein organism = synthetic construct | 7 |

| | | |
|---|---|---|
| SEQ ID NO: 519<br>SEQUENCE: 519<br>000 | moltype =    length = | |
| SEQ ID NO: 520<br>SEQUENCE: 520<br>000 | moltype =    length = | |
| SEQ ID NO: 521<br>SEQUENCE: 521<br>000 | moltype =    length = | |
| SEQ ID NO: 522<br>SEQUENCE: 522<br>000 | moltype =    length = | |
| SEQ ID NO: 523<br>FEATURE<br>source<br><br>SEQUENCE: 523<br>WASSRES | moltype = AA   length = 7<br>Location/Qualifiers<br>1..7<br>mol_type = protein<br>organism = synthetic construct | 7 |
| SEQ ID NO: 524<br>SEQUENCE: 524<br>000 | moltype =    length = | |
| SEQ ID NO: 525<br>SEQUENCE: 525<br>000 | moltype =    length = | |
| SEQ ID NO: 526<br>SEQUENCE: 526<br>000 | moltype =    length = | |
| SEQ ID NO: 527<br>SEQUENCE: 527<br>000 | moltype =    length = | |
| SEQ ID NO: 528<br>SEQUENCE: 528<br>000 | moltype =    length = | |
| SEQ ID NO: 529<br>FEATURE<br>source<br><br>SEQUENCE: 529<br>RVSNRFS | moltype = AA   length = 7<br>Location/Qualifiers<br>1..7<br>mol_type = protein<br>organism = synthetic construct | 7 |
| SEQ ID NO: 530<br>FEATURE<br>source<br><br>SEQUENCE: 530<br>RVSSRFS | moltype = AA   length = 7<br>Location/Qualifiers<br>1..7<br>mol_type = protein<br>organism = synthetic construct | 7 |
| SEQ ID NO: 531<br>SEQUENCE: 531<br>000 | moltype =    length = | |
| SEQ ID NO: 532<br>SEQUENCE: 532<br>000 | moltype =    length = | |
| SEQ ID NO: 533<br>SEQUENCE: 533<br>000 | moltype =    length = | |
| SEQ ID NO: 534<br>SEQUENCE: 534<br>000 | moltype =    length = | |
| SEQ ID NO: 535<br>SEQUENCE: 535<br>000 | moltype =    length = | |

```
SEQ ID NO: 536          moltype =    length =
SEQUENCE: 536
000

SEQ ID NO: 537          moltype =    length =
SEQUENCE: 537
000

SEQ ID NO: 538          moltype =    length =
SEQUENCE: 538
000

SEQ ID NO: 539          moltype =    length =
SEQUENCE: 539
000

SEQ ID NO: 540          moltype = AA  length = 7
FEATURE                 Location/Qualifiers
source                  1..7
                        mol_type = protein
                        organism = synthetic construct
SEQUENCE: 540
YASNRCT                                                                   7

SEQ ID NO: 541          moltype =    length =
SEQUENCE: 541
000

SEQ ID NO: 542          moltype =    length =
SEQUENCE: 542
000

SEQ ID NO: 543          moltype =    length =
SEQUENCE: 543
000

SEQ ID NO: 544          moltype =    length =
SEQUENCE: 544
000

SEQ ID NO: 545          moltype =    length =
SEQUENCE: 545
000

SEQ ID NO: 546          moltype =    length =
SEQUENCE: 546
000

SEQ ID NO: 547          moltype =    length =
SEQUENCE: 547
000

SEQ ID NO: 548          moltype =    length =
SEQUENCE: 548
000

SEQ ID NO: 549          moltype =    length =
SEQUENCE: 549
000

SEQ ID NO: 550          moltype =    length =
SEQUENCE: 550
000

SEQ ID NO: 551          moltype =    length =
SEQUENCE: 551
000

SEQ ID NO: 552          moltype =    length =
SEQUENCE: 552
000

SEQ ID NO: 553          moltype =    length =
SEQUENCE: 553
000

SEQ ID NO: 554          moltype =    length =
SEQUENCE: 554
```

```
SEQ ID NO: 555           moltype =    length =
SEQUENCE: 555
000

SEQ ID NO: 556           moltype =    length =
SEQUENCE: 556
000

SEQ ID NO: 557           moltype = AA  length = 9
FEATURE                  Location/Qualifiers
source                   1..9
                         mol_type = protein
                         organism = synthetic construct
SEQUENCE: 557
QHFWSTPLT                                                                    9

SEQ ID NO: 558           moltype =    length =
SEQUENCE: 558
000

SEQ ID NO: 559           moltype =    length =
SEQUENCE: 559
000

SEQ ID NO: 560           moltype =    length =
SEQUENCE: 560
000

SEQ ID NO: 561           moltype =    length =
SEQUENCE: 561
000

SEQ ID NO: 562           moltype = AA  length = 9
FEATURE                  Location/Qualifiers
source                   1..9
                         mol_type = protein
                         organism = synthetic construct
SEQUENCE: 562
QQYYSYPRT                                                                    9

SEQ ID NO: 563           moltype =    length =
SEQUENCE: 563
000

SEQ ID NO: 564           moltype =    length =
SEQUENCE: 564
000

SEQ ID NO: 565           moltype =    length =
SEQUENCE: 565
000

SEQ ID NO: 566           moltype =    length =
SEQUENCE: 566
000

SEQ ID NO: 567           moltype =    length =
SEQUENCE: 567
000

SEQ ID NO: 568           moltype =    length =
SEQUENCE: 568
000

SEQ ID NO: 569           moltype =    length =
SEQUENCE: 569
000

SEQ ID NO: 570           moltype =    length =
SEQUENCE: 570
000

SEQ ID NO: 571           moltype = AA  length = 9
FEATURE                  Location/Qualifiers
source                   1..9
                         mol_type = protein
                         organism = synthetic construct
```

```
SEQUENCE: 571
FQGTHVPRT                                                              9

SEQ ID NO: 572           moltype =   length =
SEQUENCE: 572
000

SEQ ID NO: 573           moltype =   length =
SEQUENCE: 573
000

SEQ ID NO: 574           moltype =   length =
SEQUENCE: 574
000

SEQ ID NO: 575           moltype =   length =
SEQUENCE: 575
000

SEQ ID NO: 576           moltype =   length =
SEQUENCE: 576
000

SEQ ID NO: 577           moltype =   length =
SEQUENCE: 577
000

SEQ ID NO: 578           moltype =   length =
SEQUENCE: 578
000

SEQ ID NO: 579           moltype =   length =
SEQUENCE: 579
000

SEQ ID NO: 580           moltype =   length =
SEQUENCE: 580
000

SEQ ID NO: 581           moltype =   length =
SEQUENCE: 581
000

SEQ ID NO: 582           moltype =   length =
SEQUENCE: 582
000

SEQ ID NO: 583           moltype =   length =
SEQUENCE: 583
000

SEQ ID NO: 584           moltype =   length =
SEQUENCE: 584
000

SEQ ID NO: 585           moltype =   length =
SEQUENCE: 585
000

SEQ ID NO: 586           moltype =   length =
SEQUENCE: 586
000

SEQ ID NO: 587           moltype = AA  length = 9
FEATURE                  Location/Qualifiers
source                   1..9
                         mol_type = protein
                         organism = synthetic construct
SEQUENCE: 587
QQDYRSPLT                                                              9

SEQ ID NO: 588           moltype =   length =
SEQUENCE: 588
000

SEQ ID NO: 589           moltype =   length =
SEQUENCE: 589
000
```

```
SEQ ID NO: 590           moltype =     length =
SEQUENCE: 590
000

SEQ ID NO: 591           moltype =     length =
SEQUENCE: 591
000

SEQ ID NO: 592           moltype =     length =
SEQUENCE: 592
000

SEQ ID NO: 593           moltype =     length =
SEQUENCE: 593
000

SEQ ID NO: 594           moltype =     length =
SEQUENCE: 594
000

SEQ ID NO: 595           moltype =     length =
SEQUENCE: 595
000

SEQ ID NO: 596           moltype =     length =
SEQUENCE: 596
000

SEQ ID NO: 597           moltype =     length =
SEQUENCE: 597
000

SEQ ID NO: 598           moltype =     length =
SEQUENCE: 598
000

SEQ ID NO: 599           moltype =     length =
SEQUENCE: 599
000

SEQ ID NO: 600           moltype =     length =
SEQUENCE: 600
000

SEQ ID NO: 601           moltype = AA   length = 5
FEATURE                  Location/Qualifiers
source                   1..5
                         mol_type = protein
                         organism = synthetic construct
SEQUENCE: 601
GGGGS                                                                             5

SEQ ID NO: 602           moltype = AA   length = 10
FEATURE                  Location/Qualifiers
source                   1..10
                         mol_type = protein
                         organism = synthetic construct
SEQUENCE: 602
GGGGSGGGGS                                                                       10

SEQ ID NO: 603           moltype = AA   length = 20
FEATURE                  Location/Qualifiers
source                   1..20
                         mol_type = protein
                         organism = synthetic construct
SEQUENCE: 603
GGGGSGGGGS GGGGSGGGGS                                                            20

SEQ ID NO: 604           moltype = AA   length = 25
FEATURE                  Location/Qualifiers
source                   1..25
                         mol_type = protein
                         organism = synthetic construct
SEQUENCE: 604
GGGGSGGGGS GGGGSGGGGS GGGGS                                                      25

SEQ ID NO: 605           moltype = AA   length = 30
FEATURE                  Location/Qualifiers
source                   1..30
```

```
                        mol_type = protein
                        organism = synthetic construct
SEQUENCE: 605
GGGGSGGGGS GGGGSGGGGS GGGGSGGGGS                                    30

SEQ ID NO: 606          moltype =    length =
SEQUENCE: 606
000

SEQ ID NO: 607          moltype = AA   length = 40
FEATURE                 Location/Qualifiers
source                  1..40
                        mol_type = protein
                        organism = synthetic construct
SEQUENCE: 607
GGGGSGGGGS GGGGSGGGGS GGGGSGGGGS GGGGSGGGGS                         40

SEQ ID NO: 608          moltype = AA   length = 5
FEATURE                 Location/Qualifiers
source                  1..5
                        mol_type = protein
                        organism = synthetic construct
SEQUENCE: 608
GGGGS                                                                5

SEQ ID NO: 609          moltype =    length =
SEQUENCE: 609
000

SEQ ID NO: 610          moltype =    length =
SEQUENCE: 610
000

SEQ ID NO: 611          moltype =    length =
SEQUENCE: 611
000

SEQ ID NO: 612          moltype =    length =
SEQUENCE: 612
000

SEQ ID NO: 613          moltype =    length =
SEQUENCE: 613
000

SEQ ID NO: 614          moltype =    length =
SEQUENCE: 614
000

SEQ ID NO: 615          moltype =    length =
SEQUENCE: 615
000

SEQ ID NO: 616          moltype =    length =
SEQUENCE: 616
000

SEQ ID NO: 617          moltype =    length =
SEQUENCE: 617
000

SEQ ID NO: 618          moltype =    length =
SEQUENCE: 618
000

SEQ ID NO: 619          moltype =    length =
SEQUENCE: 619
000

SEQ ID NO: 620          moltype =    length =
SEQUENCE: 620
000

SEQ ID NO: 621          moltype =    length =
SEQUENCE: 621
000

SEQ ID NO: 622          moltype =    length =
SEQUENCE: 622
```

000

SEQ ID NO: 623        moltype =    length =
SEQUENCE: 623
000

SEQ ID NO: 624        moltype =    length =
SEQUENCE: 624
000

SEQ ID NO: 625        moltype =    length =
SEQUENCE: 625
000

SEQ ID NO: 626        moltype =    length =
SEQUENCE: 626
000

SEQ ID NO: 627        moltype =    length =
SEQUENCE: 627
000

SEQ ID NO: 628        moltype =    length =
SEQUENCE: 628
000

SEQ ID NO: 629        moltype =    length =
SEQUENCE: 629
000

SEQ ID NO: 630        moltype =    length =
SEQUENCE: 630
000

SEQ ID NO: 631        moltype =    length =
SEQUENCE: 631
000

SEQ ID NO: 632        moltype =    length =
SEQUENCE: 632
000

SEQ ID NO: 633        moltype =    length =
SEQUENCE: 633
000

SEQ ID NO: 634        moltype =    length =
SEQUENCE: 634
000

SEQ ID NO: 635        moltype =    length =
SEQUENCE: 635
000

SEQ ID NO: 636        moltype =    length =
SEQUENCE: 636
000

SEQ ID NO: 637        moltype =    length =
SEQUENCE: 637
000

SEQ ID NO: 638        moltype =    length =
SEQUENCE: 638
000

SEQ ID NO: 639        moltype =    length =
SEQUENCE: 639
000

SEQ ID NO: 640        moltype =    length =
SEQUENCE: 640
000

SEQ ID NO: 641        moltype =    length =
SEQUENCE: 641
000

SEQ ID NO: 642        moltype =    length =

-continued

| | | |
|---|---|---|
| SEQUENCE: 642 000 | | |
| SEQ ID NO: 643 SEQUENCE: 643 000 | moltype = | length = |
| SEQ ID NO: 644 SEQUENCE: 644 000 | moltype = | length = |
| SEQ ID NO: 645 SEQUENCE: 645 000 | moltype = | length = |
| SEQ ID NO: 646 SEQUENCE: 646 000 | moltype = | length = |
| SEQ ID NO: 647 SEQUENCE: 647 000 | moltype = | length = |
| SEQ ID NO: 648 SEQUENCE: 648 000 | moltype = | length = |
| SEQ ID NO: 649 SEQUENCE: 649 000 | moltype = | length = |
| SEQ ID NO: 650 SEQUENCE: 650 000 | moltype = | length = |
| SEQ ID NO: 651 SEQUENCE: 651 000 | moltype = | length = |
| SEQ ID NO: 652 SEQUENCE: 652 000 | moltype = | length = |
| SEQ ID NO: 653 SEQUENCE: 653 000 | moltype = | length = |
| SEQ ID NO: 654 SEQUENCE: 654 000 | moltype = | length = |
| SEQ ID NO: 655 SEQUENCE: 655 000 | moltype = | length = |
| SEQ ID NO: 656 SEQUENCE: 656 000 | moltype = | length = |
| SEQ ID NO: 657 SEQUENCE: 657 000 | moltype = | length = |
| SEQ ID NO: 658 SEQUENCE: 658 000 | moltype = | length = |
| SEQ ID NO: 659 SEQUENCE: 659 000 | moltype = | length = |
| SEQ ID NO: 660 SEQUENCE: 660 000 | moltype = | length = |
| SEQ ID NO: 661 SEQUENCE: 661 000 | moltype = | length = |

| | | |
|---|---|---|
| SEQ ID NO: 662<br>SEQUENCE: 662 | moltype = | length = 000 |
| SEQ ID NO: 663<br>SEQUENCE: 663 | moltype = | length = 000 |
| SEQ ID NO: 664<br>SEQUENCE: 664 | moltype = | length = 000 |
| SEQ ID NO: 665<br>SEQUENCE: 665 | moltype = | length = 000 |
| SEQ ID NO: 666<br>SEQUENCE: 666 | moltype = | length = 000 |
| SEQ ID NO: 667<br>SEQUENCE: 667 | moltype = | length = 000 |
| SEQ ID NO: 668<br>SEQUENCE: 668 | moltype = | length = 000 |
| SEQ ID NO: 669<br>SEQUENCE: 669 | moltype = | length = 000 |
| SEQ ID NO: 670<br>SEQUENCE: 670 | moltype = | length = 000 |
| SEQ ID NO: 671<br>SEQUENCE: 671 | moltype = | length = 000 |
| SEQ ID NO: 672<br>SEQUENCE: 672 | moltype = | length = 000 |
| SEQ ID NO: 673<br>SEQUENCE: 673 | moltype = | length = 000 |
| SEQ ID NO: 674<br>SEQUENCE: 674 | moltype = | length = 000 |
| SEQ ID NO: 675<br>SEQUENCE: 675 | moltype = | length = 000 |
| SEQ ID NO: 676<br>SEQUENCE: 676 | moltype = | length = 000 |
| SEQ ID NO: 677<br>SEQUENCE: 677 | moltype = | length = 000 |
| SEQ ID NO: 678<br>SEQUENCE: 678 | moltype = | length = 000 |
| SEQ ID NO: 679<br>SEQUENCE: 679 | moltype = | length = 000 |
| SEQ ID NO: 680<br>SEQUENCE: 680 | moltype = | length = 000 |
| SEQ ID NO: 681<br>SEQUENCE: 681 | moltype = | length = 000 |

| | | |
|---|---|---|
| SEQ ID NO: 682
SEQUENCE: 682
000 | moltype = | length = |
| SEQ ID NO: 683
SEQUENCE: 683
000 | moltype = | length = |
| SEQ ID NO: 684
SEQUENCE: 684
000 | moltype = | length = |
| SEQ ID NO: 685
SEQUENCE: 685
000 | moltype = | length = |
| SEQ ID NO: 686
SEQUENCE: 686
000 | moltype = | length = |
| SEQ ID NO: 687
SEQUENCE: 687
000 | moltype = | length = |
| SEQ ID NO: 688
SEQUENCE: 688
000 | moltype = | length = |
| SEQ ID NO: 689
SEQUENCE: 689
000 | moltype = | length = |
| SEQ ID NO: 690
SEQUENCE: 690
000 | moltype = | length = |
| SEQ ID NO: 691
SEQUENCE: 691
000 | moltype = | length = |
| SEQ ID NO: 692
SEQUENCE: 692
000 | moltype = | length = |
| SEQ ID NO: 693
SEQUENCE: 693
000 | moltype = | length = |
| SEQ ID NO: 694
SEQUENCE: 694
000 | moltype = | length = |
| SEQ ID NO: 695
SEQUENCE: 695
000 | moltype = | length = |
| SEQ ID NO: 696
SEQUENCE: 696
000 | moltype = | length = |
| SEQ ID NO: 697
SEQUENCE: 697
000 | moltype = | length = |
| SEQ ID NO: 698
SEQUENCE: 698
000 | moltype = | length = |
| SEQ ID NO: 699
SEQUENCE: 699
000 | moltype = | length = |
| SEQ ID NO: 700
SEQUENCE: 700
000 | moltype = | length = |
| SEQ ID NO: 701
SEQUENCE: 701 | moltype = | length = |

```
000

SEQ ID NO: 702          moltype =    length =
SEQUENCE: 702
000

SEQ ID NO: 703          moltype =    length =
SEQUENCE: 703
000

SEQ ID NO: 704          moltype =    length =
SEQUENCE: 704
000

SEQ ID NO: 705          moltype =    length =
SEQUENCE: 705
000

SEQ ID NO: 706          moltype =    length =
SEQUENCE: 706
000

SEQ ID NO: 707          moltype =    length =
SEQUENCE: 707
000

SEQ ID NO: 708          moltype =    length =
SEQUENCE: 708
000

SEQ ID NO: 709          moltype =    length =
SEQUENCE: 709
000

SEQ ID NO: 710          moltype =    length =
SEQUENCE: 710
000

SEQ ID NO: 711          moltype =    length =
SEQUENCE: 711
000

SEQ ID NO: 712          moltype =    length =
SEQUENCE: 712
000

SEQ ID NO: 713          moltype =    length =
SEQUENCE: 713
000

SEQ ID NO: 714          moltype =    length =
SEQUENCE: 714
000

SEQ ID NO: 715          moltype =    length =
SEQUENCE: 715
000

SEQ ID NO: 716          moltype =    length =
SEQUENCE: 716
000

SEQ ID NO: 717          moltype =    length =
SEQUENCE: 717
000

SEQ ID NO: 718          moltype =    length =
SEQUENCE: 718
000

SEQ ID NO: 719          moltype =    length =
SEQUENCE: 719
000

SEQ ID NO: 720          moltype =    length =
SEQUENCE: 720
000

SEQ ID NO: 721          moltype =    length =
```

SEQUENCE: 721
000

SEQ ID NO: 722       moltype =    length =
SEQUENCE: 722
000

SEQ ID NO: 723       moltype =    length =
SEQUENCE: 723
000

SEQ ID NO: 724       moltype =    length =
SEQUENCE: 724
000

SEQ ID NO: 725       moltype =    length =
SEQUENCE: 725
000

SEQ ID NO: 726       moltype =    length =
SEQUENCE: 726
000

SEQ ID NO: 727       moltype =    length =
SEQUENCE: 727
000

SEQ ID NO: 728       moltype =    length =
SEQUENCE: 728
000

SEQ ID NO: 729       moltype =    length =
SEQUENCE: 729
000

SEQ ID NO: 730       moltype =    length =
SEQUENCE: 730
000

SEQ ID NO: 731       moltype =    length =
SEQUENCE: 731
000

SEQ ID NO: 732       moltype =    length =
SEQUENCE: 732
000

SEQ ID NO: 733       moltype =    length =
SEQUENCE: 733
000

SEQ ID NO: 734       moltype =    length =
SEQUENCE: 734
000

SEQ ID NO: 735       moltype =    length =
SEQUENCE: 735
000

SEQ ID NO: 736       moltype =    length =
SEQUENCE: 736
000

SEQ ID NO: 737       moltype =    length =
SEQUENCE: 737
000

SEQ ID NO: 738       moltype =    length =
SEQUENCE: 738
000

SEQ ID NO: 739       moltype =    length =
SEQUENCE: 739
000

SEQ ID NO: 740       moltype =    length =
SEQUENCE: 740
000

| | | |
|---|---|---|
| SEQ ID NO: 741<br>SEQUENCE: 741<br>000 | moltype = | length = |
| SEQ ID NO: 742<br>SEQUENCE: 742<br>000 | moltype = | length = |
| SEQ ID NO: 743<br>SEQUENCE: 743<br>000 | moltype = | length = |
| SEQ ID NO: 744<br>SEQUENCE: 744<br>000 | moltype = | length = |
| SEQ ID NO: 745<br>SEQUENCE: 745<br>000 | moltype = | length = |
| SEQ ID NO: 746<br>SEQUENCE: 746<br>000 | moltype = | length = |
| SEQ ID NO: 747<br>SEQUENCE: 747<br>000 | moltype = | length = |
| SEQ ID NO: 748<br>SEQUENCE: 748<br>000 | moltype = | length = |
| SEQ ID NO: 749<br>SEQUENCE: 749<br>000 | moltype = | length = |
| SEQ ID NO: 750<br>SEQUENCE: 750<br>000 | moltype = | length = |
| SEQ ID NO: 751<br>SEQUENCE: 751<br>000 | moltype = | length = |
| SEQ ID NO: 752<br>SEQUENCE: 752<br>000 | moltype = | length = |
| SEQ ID NO: 753<br>SEQUENCE: 753<br>000 | moltype = | length = |
| SEQ ID NO: 754<br>SEQUENCE: 754<br>000 | moltype = | length = |
| SEQ ID NO: 755<br>SEQUENCE: 755<br>000 | moltype = | length = |
| SEQ ID NO: 756<br>SEQUENCE: 756<br>000 | moltype = | length = |
| SEQ ID NO: 757<br>SEQUENCE: 757<br>000 | moltype = | length = |
| SEQ ID NO: 758<br>SEQUENCE: 758<br>000 | moltype = | length = |
| SEQ ID NO: 759<br>SEQUENCE: 759<br>000 | moltype = | length = |
| SEQ ID NO: 760<br>SEQUENCE: 760<br>000 | moltype = | length = |

| | | |
|---|---|---|
| SEQ ID NO: 761 SEQUENCE: 761 | moltype = 000 | length = |
| SEQ ID NO: 762 SEQUENCE: 762 | moltype = 000 | length = |
| SEQ ID NO: 763 SEQUENCE: 763 | moltype = 000 | length = |
| SEQ ID NO: 764 SEQUENCE: 764 | moltype = 000 | length = |
| SEQ ID NO: 765 SEQUENCE: 765 | moltype = 000 | length = |
| SEQ ID NO: 766 SEQUENCE: 766 | moltype = 000 | length = |
| SEQ ID NO: 767 SEQUENCE: 767 | moltype = 000 | length = |
| SEQ ID NO: 768 SEQUENCE: 768 | moltype = 000 | length = |
| SEQ ID NO: 769 SEQUENCE: 769 | moltype = 000 | length = |
| SEQ ID NO: 770 SEQUENCE: 770 | moltype = 000 | length = |
| SEQ ID NO: 771 SEQUENCE: 771 | moltype = 000 | length = |
| SEQ ID NO: 772 SEQUENCE: 772 | moltype = 000 | length = |
| SEQ ID NO: 773 SEQUENCE: 773 | moltype = 000 | length = |
| SEQ ID NO: 774 SEQUENCE: 774 | moltype = 000 | length = |
| SEQ ID NO: 775 SEQUENCE: 775 | moltype = 000 | length = |
| SEQ ID NO: 776 SEQUENCE: 776 | moltype = 000 | length = |
| SEQ ID NO: 777 SEQUENCE: 777 | moltype = 000 | length = |
| SEQ ID NO: 778 SEQUENCE: 778 | moltype = 000 | length = |
| SEQ ID NO: 779 SEQUENCE: 779 | moltype = 000 | length = |
| SEQ ID NO: 780 SEQUENCE: 780 | moltype = | length = |

SEQ ID NO: 781      moltype =   length =
SEQUENCE: 781
000

SEQ ID NO: 782      moltype =   length =
SEQUENCE: 782
000

SEQ ID NO: 783      moltype =   length =
SEQUENCE: 783
000

SEQ ID NO: 784      moltype =   length =
SEQUENCE: 784
000

SEQ ID NO: 785      moltype =   length =
SEQUENCE: 785
000

SEQ ID NO: 786      moltype =   length =
SEQUENCE: 786
000

SEQ ID NO: 787      moltype =   length =
SEQUENCE: 787
000

SEQ ID NO: 788      moltype =   length =
SEQUENCE: 788
000

SEQ ID NO: 789      moltype =   length =
SEQUENCE: 789
000

SEQ ID NO: 790      moltype =   length =
SEQUENCE: 790
000

SEQ ID NO: 791      moltype =   length =
SEQUENCE: 791
000

SEQ ID NO: 792      moltype =   length =
SEQUENCE: 792
000

SEQ ID NO: 793      moltype =   length =
SEQUENCE: 793
000

SEQ ID NO: 794      moltype =   length =
SEQUENCE: 794
000

SEQ ID NO: 795      moltype =   length =
SEQUENCE: 795
000

SEQ ID NO: 796      moltype =   length =
SEQUENCE: 796
000

SEQ ID NO: 797      moltype =   length =
SEQUENCE: 797
000

SEQ ID NO: 798      moltype =   length =
SEQUENCE: 798
000

SEQ ID NO: 799      moltype =   length =
SEQUENCE: 799
000

SEQ ID NO: 800      moltype = AA   length = 7

```
FEATURE                 Location/Qualifiers
source                  1..7
                        mol_type = protein
                        organism = synthetic construct
SEQUENCE: 800
NGAVHLY                                                                         7

SEQ ID NO: 801          moltype = AA  length = 7
FEATURE                 Location/Qualifiers
source                  1..7
                        mol_type = protein
                        organism = synthetic construct
SEQUENCE: 801
TLAVVSL                                                                         7

SEQ ID NO: 802          moltype = AA  length = 40
FEATURE                 Location/Qualifiers
source                  1..40
                        mol_type = protein
                        organism = synthetic construct
VARIANT                 1..40
                        note = This sequence may encompass 0-8 GGGGS repeating units
SEQUENCE: 802
GGGGSGGGGS GGGGSGGGGS GGGGSGGGGS GGGGSGGGGS                                     40

SEQ ID NO: 803          moltype = AA  length = 743
FEATURE                 Location/Qualifiers
source                  1..743
                        mol_type = protein
                        organism = unidentified
SEQUENCE: 803
MAADGYLPDW LEDNLSEGIR EWWALKPGAP QPKANQQHQD NARGLVLPGY KYLGPGNGLD               60
KGEPVNAADA AALEHDKAYD QQLKAGDNPY LKYNHADAEF QERLKEDTSF GGNLGRAVFQ              120
AKKRLLEPLG LVEEAAKTAP GKKRPVEQSP QEPDSSAGIG KSGAQPAKKR LNFGQTGDTE              180
SVPDPQPIGE PPAAPSGVGS LTMASGGGAP VADNNEGADG VGSSSGNWHC DSQWLGDRVI              240
TTSTRTWALP TYNNHLYKQI SNSTSGGSSN DNAYFGYSTP WGYFDFNRFH CHFSPRDWQR              300
LINNNWGFRP KRLNFKLFNI QVKEVTDNNG VKTIANNLTS TVQVFTDSDY QLPYVLGSAH              360
EGCLPPFPAD VFMIPQYGYL TLNDGSQAVG RSSFYCLEYF PSQMLRTGNN FQFSYEFENV              420
PFHSSYAHSQ SLDRLMNPLI DQYLYYLSKT INGSGQNQQT LKFSVAGPSN MAVQGRNYIP              480
GPSYRQQRVS TTVTQNNNSE FAWPGASSWA LNGRNSLMNP GPAMASHKEG EDRFFPLSGS              540
LIFGKQGTGR DNVDADKVMI TNEEEIKTTN PVATESYGQV ATNHQSDGTL AVPFKAQAQT              600
GWVQNQGILP GMVWQDRDVY LQGPIWAKIP HTDGNFHPSP LMGGFGMKHP PPQILIKNTP              660
VPADPPTAFN KDKLNSFITQ YSTGQVSVEI EWELQKENSK RWNPEIQYTS NYYKSNNVEF              720
AVNTEGVYSE PRPIGTRYLT RNL                                                     743

SEQ ID NO: 804          moltype = AA  length = 736
FEATURE                 Location/Qualifiers
source                  1..736
                        mol_type = protein
                        organism = Adeno-associated virus 9
SEQUENCE: 804
MAADGYLPDW LEDNLSEGIR EWWALKPGAP QPKANQQHQD NARGLVLPGY KYLGPGNGLD               60
KGEPVNAADA AALEHDKAYD QQLKAGDNPY LKYNHADAEF QERLKEDTSF GGNLGRAVFQ              120
AKKRLLEPLG LVEEAAKTAP GKKRPVEQSP QEPDSSAGIG KSGAQPAKKR LNFGQTGDTE              180
SVPDPQPIGE PPAAPSGVGS LTMASGGGAP VADNNEGADG VGSSSGNWHC DSQWLGDRVI              240
TTSTRTWALP TYNNHLYKQI SNSTSGGSSN DNAYFGYSTP WGYFDFNRFH CHFSPRDWQR              300
LINNNWGFRP KRLNFKLFNI QVKEVTDNNG VKTIANNLTS TVQVFTDSDY QLPYVLGSAH              360
EGCLPPFPAD VFMIPQYGYL TLNDGSQAVG RSSFYCLEYF PSQMLRTGNN FQFSYEFENV              420
PFHSSYAHSQ SLDRLMNPLI DQYLYYLSRT INGSGQNQQT LKFSVAGPSN MAVQGRNYIP              480
GPSYRQQRVS TTVTQNNNSE FAWPGASSWA LNGRNSLMNP GPAMASHKEG EDRFFPLSGS              540
LIFGKQGTGR DNVDADKVMI TNEEEIKTTN PVATESYGQV ATNHQSAQAQ AQTGWVQNQG              600
ILPGMVWQDR DVYLQGPIWA KIPHTDGNFH PSPLMGGFGM KHPPPQILIK NTPVPADPPT              660
AFNKDKLNSF ITQYSTGQVS VEIEWELQKE NSKRWNPEIQ YTSNYYKSNN VEFAVNTEGV              720
YSEPRPIGTR YLTRNL                                                             736

SEQ ID NO: 805          moltype = DNA  length = 969
FEATURE                 Location/Qualifiers
source                  1..969
                        mol_type = genomic DNA
                        organism = Mus sp.
SEQUENCE: 805
gccaaaacga cacccccatc tgtctatcca ctggccctg gatctgctgc ccaaactaac               60
tccatggtga ccctgggatg cctggtcaag ggctatttcc ctgagccagt gacagtgacc             120
tggaactctg gatccctgtc cagcggtgtg cacaccttcc cagctgtcct gcagtctgac             180
ctctacactc tgagcagctc agtgactgtc ccctccagca cctggcccag cgagaccgtc             240
acctgcaacg ttgcccaccc ggccagcagc accaaggtgg acaagaaaat tgtgcccagg             300
gattgtggtt gtaagccttg catatgtaca gtcccagaag tatcatctgt cttcatcttc             360
cccccaaagc caaggatgt gctcaccatt actctgactc ctaaggtcac gtgtgttgtg              420
gtagacatca gcaaggatga tcccgaggtc cagttcagct ggtttgtaga tgatgtggag             480
```

```
gtgcacacag ctcagacgca acccegggag gagcagttca acagcacttt ccgctcagtc  540
agtgaacttc ccatcatgca ccaggactgg ctcaatggca aggagttcaa atgcagggtc  600
aacagtgcag ctttccctgc ccccatcgag aaaaccatct ccaaaaccaa aggcagaccg  660
aaggctccac aggtgtacac cattccacct cccaaggagc agatggccaa ggataaagtc  720
agtctgacct gcatgataac agacttcttc cctgaagaca ttactgtgga gtggcagtgg  780
aatgggcagc cagcggagaa ctacaagaac actcagccca tcatggacac agatggctct  840
tacttcgtct acagcaagct caatgtgcag aagagcaact gggaggcagg aaatactttc  900
acctgctctg tgttacatga gggcctgcac aaccaccata ctgagaagag cctctcccac  960
tctcctggt                                                          969
```

SEQ ID NO: 806        moltype =       length =
SEQUENCE: 806
000

SEQ ID NO: 807        moltype =       length =
SEQUENCE: 807
000

SEQ ID NO: 808        moltype =       length =
SEQUENCE: 808
000

SEQ ID NO: 809        moltype =       length =
SEQUENCE: 809
000

SEQ ID NO: 810        moltype =       length =
SEQUENCE: 810
000

SEQ ID NO: 811        moltype =       length =
SEQUENCE: 811
000

SEQ ID NO: 812        moltype =       length =
SEQUENCE: 812
000

SEQ ID NO: 813        moltype =       length =
SEQUENCE: 813
000

SEQ ID NO: 814        moltype =       length =
SEQUENCE: 814
000

SEQ ID NO: 815        moltype =       length =
SEQUENCE: 815
000

SEQ ID NO: 816        moltype =       length =
SEQUENCE: 816
000

SEQ ID NO: 817        moltype =       length =
SEQUENCE: 817
000

SEQ ID NO: 818        moltype =       length =
SEQUENCE: 818
000

SEQ ID NO: 819        moltype =       length =
SEQUENCE: 819
000

SEQ ID NO: 820        moltype =       length =
SEQUENCE: 820
000

SEQ ID NO: 821        moltype =       length =
SEQUENCE: 821
000

SEQ ID NO: 822        moltype =       length =
SEQUENCE: 822
000

SEQ ID NO: 823        moltype =       length =

| | | |
|---|---|---|
| SEQUENCE: 823 000 | | |
| SEQ ID NO: 824 SEQUENCE: 824 000 | moltype = | length = |
| SEQ ID NO: 825 SEQUENCE: 825 000 | moltype = | length = |
| SEQ ID NO: 826 SEQUENCE: 826 000 | moltype = | length = |
| SEQ ID NO: 827 SEQUENCE: 827 000 | moltype = | length = |
| SEQ ID NO: 828 SEQUENCE: 828 000 | moltype = | length = |
| SEQ ID NO: 829 SEQUENCE: 829 000 | moltype = | length = |
| SEQ ID NO: 830 SEQUENCE: 830 000 | moltype = | length = |
| SEQ ID NO: 831 SEQUENCE: 831 000 | moltype = | length = |
| SEQ ID NO: 832 SEQUENCE: 832 000 | moltype = | length = |
| SEQ ID NO: 833 SEQUENCE: 833 000 | moltype = | length = |
| SEQ ID NO: 834 SEQUENCE: 834 000 | moltype = | length = |
| SEQ ID NO: 835 SEQUENCE: 835 000 | moltype = | length = |
| SEQ ID NO: 836 SEQUENCE: 836 000 | moltype = | length = |
| SEQ ID NO: 837 SEQUENCE: 837 000 | moltype = | length = |
| SEQ ID NO: 838 SEQUENCE: 838 000 | moltype = | length = |
| SEQ ID NO: 839 SEQUENCE: 839 000 | moltype = | length = |
| SEQ ID NO: 840 SEQUENCE: 840 000 | moltype = | length = |
| SEQ ID NO: 841 SEQUENCE: 841 000 | moltype = | length = |
| SEQ ID NO: 842 SEQUENCE: 842 000 | moltype = | length = |

| | | |
|---|---|---|
| SEQ ID NO: 843<br>SEQUENCE: 843<br>000 | moltype = | length = |
| SEQ ID NO: 844<br>SEQUENCE: 844<br>000 | moltype = | length = |
| SEQ ID NO: 845<br>SEQUENCE: 845<br>000 | moltype = | length = |
| SEQ ID NO: 846<br>SEQUENCE: 846<br>000 | moltype = | length = |
| SEQ ID NO: 847<br>SEQUENCE: 847<br>000 | moltype = | length = |
| SEQ ID NO: 848<br>SEQUENCE: 848<br>000 | moltype = | length = |
| SEQ ID NO: 849<br>SEQUENCE: 849<br>000 | moltype = | length = |
| SEQ ID NO: 850<br>SEQUENCE: 850<br>000 | moltype = | length = |
| SEQ ID NO: 851<br>SEQUENCE: 851<br>000 | moltype = | length = |
| SEQ ID NO: 852<br>SEQUENCE: 852<br>000 | moltype = | length = |
| SEQ ID NO: 853<br>SEQUENCE: 853<br>000 | moltype = | length = |
| SEQ ID NO: 854<br>SEQUENCE: 854<br>000 | moltype = | length = |
| SEQ ID NO: 855<br>SEQUENCE: 855<br>000 | moltype = | length = |
| SEQ ID NO: 856<br>SEQUENCE: 856<br>000 | moltype = | length = |
| SEQ ID NO: 857<br>SEQUENCE: 857<br>000 | moltype = | length = |
| SEQ ID NO: 858<br>SEQUENCE: 858<br>000 | moltype = | length = |
| SEQ ID NO: 859<br>SEQUENCE: 859<br>000 | moltype = | length = |
| SEQ ID NO: 860<br>SEQUENCE: 860<br>000 | moltype = | length = |
| SEQ ID NO: 861<br>SEQUENCE: 861<br>000 | moltype = | length = |
| SEQ ID NO: 862<br>SEQUENCE: 862<br>000 | moltype = | length = |

| | | |
|---|---|---|
| SEQ ID NO: 863<br>SEQUENCE: 863<br>000 | moltype = | length = |
| SEQ ID NO: 864<br>SEQUENCE: 864<br>000 | moltype = | length = |
| SEQ ID NO: 865<br>SEQUENCE: 865<br>000 | moltype = | length = |
| SEQ ID NO: 866<br>SEQUENCE: 866<br>000 | moltype = | length = |
| SEQ ID NO: 867<br>SEQUENCE: 867<br>000 | moltype = | length = |
| SEQ ID NO: 868<br>SEQUENCE: 868<br>000 | moltype = | length = |
| SEQ ID NO: 869<br>SEQUENCE: 869<br>000 | moltype = | length = |
| SEQ ID NO: 870<br>SEQUENCE: 870<br>000 | moltype = | length = |
| SEQ ID NO: 871<br>SEQUENCE: 871<br>000 | moltype = | length = |
| SEQ ID NO: 872<br>SEQUENCE: 872<br>000 | moltype = | length = |
| SEQ ID NO: 873<br>SEQUENCE: 873<br>000 | moltype = | length = |
| SEQ ID NO: 874<br>SEQUENCE: 874<br>000 | moltype = | length = |
| SEQ ID NO: 875<br>SEQUENCE: 875<br>000 | moltype = | length = |
| SEQ ID NO: 876<br>SEQUENCE: 876<br>000 | moltype = | length = |
| SEQ ID NO: 877<br>SEQUENCE: 877<br>000 | moltype = | length = |
| SEQ ID NO: 878<br>SEQUENCE: 878<br>000 | moltype = | length = |
| SEQ ID NO: 879<br>SEQUENCE: 879<br>000 | moltype = | length = |
| SEQ ID NO: 880<br>SEQUENCE: 880<br>000 | moltype = | length = |
| SEQ ID NO: 881<br>SEQUENCE: 881<br>000 | moltype = | length = |
| SEQ ID NO: 882<br>SEQUENCE: 882 | moltype = | length = |

000

SEQ ID NO: 883         moltype =    length =
SEQUENCE: 883
000

SEQ ID NO: 884         moltype =    length =
SEQUENCE: 884
000

SEQ ID NO: 885         moltype =    length =
SEQUENCE: 885
000

SEQ ID NO: 886         moltype =    length =
SEQUENCE: 886
000

SEQ ID NO: 887         moltype =    length =
SEQUENCE: 887
000

SEQ ID NO: 888         moltype =    length =
SEQUENCE: 888
000

SEQ ID NO: 889         moltype =    length =
SEQUENCE: 889
000

SEQ ID NO: 890         moltype =    length =
SEQUENCE: 890
000

SEQ ID NO: 891         moltype =    length =
SEQUENCE: 891
000

SEQ ID NO: 892         moltype =    length =
SEQUENCE: 892
000

SEQ ID NO: 893         moltype =    length =
SEQUENCE: 893
000

SEQ ID NO: 894         moltype =    length =
SEQUENCE: 894
000

SEQ ID NO: 895         moltype =    length =
SEQUENCE: 895
000

SEQ ID NO: 896         moltype =    length =
SEQUENCE: 896
000

SEQ ID NO: 897         moltype =    length =
SEQUENCE: 897
000

SEQ ID NO: 898         moltype =    length =
SEQUENCE: 898
000

SEQ ID NO: 899         moltype =    length =
SEQUENCE: 899
000

SEQ ID NO: 900         moltype =    length =
SEQUENCE: 900
000

SEQ ID NO: 901         moltype =    length =
SEQUENCE: 901
000

SEQ ID NO: 902         moltype =    length =

```
SEQUENCE: 902
000

SEQ ID NO: 903          moltype =    length =
SEQUENCE: 903
000

SEQ ID NO: 904          moltype =    length =
SEQUENCE: 904
000

SEQ ID NO: 905          moltype =    length =
SEQUENCE: 905
000

SEQ ID NO: 906          moltype =    length =
SEQUENCE: 906
000

SEQ ID NO: 907          moltype =    length =
SEQUENCE: 907
000

SEQ ID NO: 908          moltype =    length =
SEQUENCE: 908
000

SEQ ID NO: 909          moltype =    length =
SEQUENCE: 909
000

SEQ ID NO: 910          moltype =    length =
SEQUENCE: 910
000

SEQ ID NO: 911          moltype =    length =
SEQUENCE: 911
000

SEQ ID NO: 912          moltype =    length =
SEQUENCE: 912
000

SEQ ID NO: 913          moltype =    length =
SEQUENCE: 913
000

SEQ ID NO: 914          moltype =    length =
SEQUENCE: 914
000

SEQ ID NO: 915          moltype =    length =
SEQUENCE: 915
000

SEQ ID NO: 916          moltype =    length =
SEQUENCE: 916
000

SEQ ID NO: 917          moltype =    length =
SEQUENCE: 917
000

SEQ ID NO: 918          moltype =    length =
SEQUENCE: 918
000

SEQ ID NO: 919          moltype =    length =
SEQUENCE: 919
000

SEQ ID NO: 920          moltype = AA   length = 441
FEATURE                 Location/Qualifiers
source                  1..441
                        mol_type = protein
                        organism = Homo sapiens
SEQUENCE: 920
MAEPRQEFEV MEDHAGTYGL GDRKDQGGYT MHQDQEGDTD AGLKESPLQT PTEDGSEEPG   60
SETSDAKSTP TAEDVTAPLV DEGAPGKQAA AQPHTEIPEG TTAEEAGIGD TPSLEDEAAG  120
```

```
HVTQARMVSK SKDGTGSDDK KAKGADGKTK IATPRGAAPP GQKGQANATR IPAKTPPAPK    180
TPPSSGEPPK SGDRSGYSSP GSPGTPGSRS RTPSLPTPPT REPKKVAVVR TPPKSPSSAK    240
SRLQTAPVPM PDLKNVKSKI GSTENLKHQP GGGKVQIINK KLDLSNVQSK CGSKDNIKHV    300
PGGGSVQIVY KPVDLSKVTS KCGSLGNIHH KPGGGQVEVK SEKLDFKDRV QSKIGSLDNI    360
THVPGGGNKK IETHKLTFRE NAKAKTDHGA EIVYKSPVVS GDTSPRHLSN VSSTGSIDMV    420
DSPQLATLAD EVSASLAKQG L                                             441

SEQ ID NO: 921          moltype = AA  length = 20
FEATURE                 Location/Qualifiers
source                  1..20
                        mol_type = protein
                        organism = synthetic construct
SITE                    8
                        note = Phosphorylated residue
SITE                    13
                        note = Phosphorylated residue
SEQUENCE: 921
TPGSRSRTPS LPTPPTREPK                                               20

SEQ ID NO: 922          moltype = AA  length = 19
FEATURE                 Location/Qualifiers
source                  1..19
                        mol_type = protein
                        organism = synthetic construct
SITE                    9
                        note = Phosphorylated residue
SITE                    11
                        note = Phosphorylated residue
SITE                    14
                        note = Phosphorylated residue
SEQUENCE: 922
GTPGSRSRTP SLPTPPTRE                                                19

SEQ ID NO: 923          moltype = AA  length = 37
FEATURE                 Location/Qualifiers
source                  1..37
                        mol_type = protein
                        organism = synthetic construct
SITE                    18
                        note = Phosphorylated residue
SITE                    26
                        note = Phosphorylated residue
SITE                    31
                        note = Phosphorylated residue
SEQUENCE: 923
RENAKAKTDH GAEIVYKSPV VSGDTSPRHL SNVSSTG                             37

SEQ ID NO: 924          moltype = AA  length = 8
FEATURE                 Location/Qualifiers
source                  1..8
                        mol_type = protein
                        organism = synthetic construct
SEQUENCE: 924
PTREPKKV                                                            8

SEQ ID NO: 925          moltype = AA  length = 7
FEATURE                 Location/Qualifiers
source                  1..7
                        mol_type = protein
                        organism = synthetic construct
SEQUENCE: 925
ARMVSKS                                                             7

SEQ ID NO: 926          moltype = AA  length = 24
FEATURE                 Location/Qualifiers
source                  1..24
                        mol_type = protein
                        organism = synthetic construct
SEQUENCE: 926
SPSSAKSRLQ TAPVPMPDLK NVKS                                          24

SEQ ID NO: 927          moltype =     length =
SEQUENCE: 927
000

SEQ ID NO: 928          moltype =     length =
SEQUENCE: 928
000
```

-continued

| | | |
|---|---|---|
| SEQ ID NO: 929<br>SEQUENCE: 929<br>000 | moltype = | length = |
| SEQ ID NO: 930<br>SEQUENCE: 930<br>000 | moltype = | length = |
| SEQ ID NO: 931<br>SEQUENCE: 931<br>000 | moltype = | length = |
| SEQ ID NO: 932<br>SEQUENCE: 932<br>000 | moltype = | length = |
| SEQ ID NO: 933<br>SEQUENCE: 933<br>000 | moltype = | length = |
| SEQ ID NO: 934<br>SEQUENCE: 934<br>000 | moltype = | length = |
| SEQ ID NO: 935<br>SEQUENCE: 935<br>000 | moltype = | length = |
| SEQ ID NO: 936<br>SEQUENCE: 936<br>000 | moltype = | length = |
| SEQ ID NO: 937<br>SEQUENCE: 937<br>000 | moltype = | length = |
| SEQ ID NO: 938<br>SEQUENCE: 938<br>000 | moltype = | length = |
| SEQ ID NO: 939<br>SEQUENCE: 939<br>000 | moltype = | length = |
| SEQ ID NO: 940<br>SEQUENCE: 940<br>000 | moltype = | length = |
| SEQ ID NO: 941<br>SEQUENCE: 941<br>000 | moltype = | length = |
| SEQ ID NO: 942<br>SEQUENCE: 942<br>000 | moltype = | length = |
| SEQ ID NO: 943<br>SEQUENCE: 943<br>000 | moltype = | length = |
| SEQ ID NO: 944<br>SEQUENCE: 944<br>000 | moltype = | length = |
| SEQ ID NO: 945<br>SEQUENCE: 945<br>000 | moltype = | length = |
| SEQ ID NO: 946<br>SEQUENCE: 946<br>000 | moltype = | length = |
| SEQ ID NO: 947<br>SEQUENCE: 947<br>000 | moltype = | length = |
| SEQ ID NO: 948<br>SEQUENCE: 948<br>000 | moltype = | length = |

| | | |
|---|---|---|
| SEQ ID NO: 949<br>SEQUENCE: 949<br>000 | moltype = | length = |
| SEQ ID NO: 950<br>SEQUENCE: 950<br>000 | moltype = | length = |
| SEQ ID NO: 951<br>SEQUENCE: 951<br>000 | moltype = | length = |
| SEQ ID NO: 952<br>SEQUENCE: 952<br>000 | moltype = | length = |
| SEQ ID NO: 953<br>SEQUENCE: 953<br>000 | moltype = | length = |
| SEQ ID NO: 954<br>SEQUENCE: 954<br>000 | moltype = | length = |
| SEQ ID NO: 955<br>SEQUENCE: 955<br>000 | moltype = | length = |
| SEQ ID NO: 956<br>SEQUENCE: 956<br>000 | moltype = | length = |
| SEQ ID NO: 957<br>SEQUENCE: 957<br>000 | moltype = | length = |
| SEQ ID NO: 958<br>SEQUENCE: 958<br>000 | moltype = | length = |
| SEQ ID NO: 959<br>SEQUENCE: 959<br>000 | moltype = | length = |
| SEQ ID NO: 960<br>SEQUENCE: 960<br>000 | moltype = | length = |
| SEQ ID NO: 961<br>SEQUENCE: 961<br>000 | moltype = | length = |
| SEQ ID NO: 962<br>SEQUENCE: 962<br>000 | moltype = | length = |
| SEQ ID NO: 963<br>SEQUENCE: 963<br>000 | moltype = | length = |
| SEQ ID NO: 964<br>SEQUENCE: 964<br>000 | moltype = | length = |
| SEQ ID NO: 965<br>SEQUENCE: 965<br>000 | moltype = | length = |
| SEQ ID NO: 966<br>SEQUENCE: 966<br>000 | moltype = | length = |
| SEQ ID NO: 967<br>SEQUENCE: 967<br>000 | moltype = | length = |
| SEQ ID NO: 968<br>SEQUENCE: 968 | moltype = | length = |

000

SEQ ID NO: 969      moltype =      length =
SEQUENCE: 969
000

SEQ ID NO: 970      moltype =      length =
SEQUENCE: 970
000

SEQ ID NO: 971      moltype =      length =
SEQUENCE: 971
000

SEQ ID NO: 972      moltype =      length =
SEQUENCE: 972
000

SEQ ID NO: 973      moltype =      length =
SEQUENCE: 973
000

SEQ ID NO: 974      moltype =      length =
SEQUENCE: 974
000

SEQ ID NO: 975      moltype =      length =
SEQUENCE: 975
000

SEQ ID NO: 976      moltype =      length =
SEQUENCE: 976
000

SEQ ID NO: 977      moltype =      length =
SEQUENCE: 977
000

SEQ ID NO: 978      moltype =      length =
SEQUENCE: 978
000

SEQ ID NO: 979      moltype =      length =
SEQUENCE: 979
000

SEQ ID NO: 980      moltype =      length =
SEQUENCE: 980
000

SEQ ID NO: 981      moltype =      length =
SEQUENCE: 981
000

SEQ ID NO: 982      moltype =      length =
SEQUENCE: 982
000

SEQ ID NO: 983      moltype =      length =
SEQUENCE: 983
000

SEQ ID NO: 984      moltype =      length =
SEQUENCE: 984
000

SEQ ID NO: 985      moltype =      length =
SEQUENCE: 985
000

SEQ ID NO: 986      moltype =      length =
SEQUENCE: 986
000

SEQ ID NO: 987      moltype =      length =
SEQUENCE: 987
000

SEQ ID NO: 988      moltype =      length =

| | | |
|---|---|---|
| SEQUENCE: 988 000 | | |
| SEQ ID NO: 989 SEQUENCE: 989 000 | moltype = | length = |
| SEQ ID NO: 990 SEQUENCE: 990 000 | moltype = | length = |
| SEQ ID NO: 991 SEQUENCE: 991 000 | moltype = | length = |
| SEQ ID NO: 992 SEQUENCE: 992 000 | moltype = | length = |
| SEQ ID NO: 993 SEQUENCE: 993 000 | moltype = | length = |
| SEQ ID NO: 994 SEQUENCE: 994 000 | moltype = | length = |
| SEQ ID NO: 995 SEQUENCE: 995 000 | moltype = | length = |
| SEQ ID NO: 996 SEQUENCE: 996 000 | moltype = | length = |
| SEQ ID NO: 997 SEQUENCE: 997 000 | moltype = | length = |
| SEQ ID NO: 998 SEQUENCE: 998 000 | moltype = | length = |
| SEQ ID NO: 999 SEQUENCE: 999 000 | moltype = | length = |
| SEQ ID NO: 1000 SEQUENCE: 1000 000 | moltype = | length = |
| SEQ ID NO: 1001 SEQUENCE: 1001 000 | moltype = | length = |
| SEQ ID NO: 1002 SEQUENCE: 1002 000 | moltype = | length = |
| SEQ ID NO: 1003 SEQUENCE: 1003 000 | moltype = | length = |
| SEQ ID NO: 1004 SEQUENCE: 1004 000 | moltype = | length = |
| SEQ ID NO: 1005 SEQUENCE: 1005 000 | moltype = | length = |
| SEQ ID NO: 1006 SEQUENCE: 1006 000 | moltype = | length = |
| SEQ ID NO: 1007 SEQUENCE: 1007 000 | moltype = | length = |

| | | |
|---|---|---|
| SEQ ID NO: 1008<br>SEQUENCE: 1008 | moltype = | length = 000 |
| SEQ ID NO: 1009<br>SEQUENCE: 1009 | moltype = | length = 000 |
| SEQ ID NO: 1010<br>SEQUENCE: 1010 | moltype = | length = 000 |
| SEQ ID NO: 1011<br>SEQUENCE: 1011 | moltype = | length = 000 |
| SEQ ID NO: 1012<br>SEQUENCE: 1012 | moltype = | length = 000 |
| SEQ ID NO: 1013<br>SEQUENCE: 1013 | moltype = | length = 000 |
| SEQ ID NO: 1014<br>SEQUENCE: 1014 | moltype = | length = 000 |
| SEQ ID NO: 1015<br>SEQUENCE: 1015 | moltype = | length = 000 |
| SEQ ID NO: 1016<br>SEQUENCE: 1016 | moltype = | length = 000 |
| SEQ ID NO: 1017<br>SEQUENCE: 1017 | moltype = | length = 000 |
| SEQ ID NO: 1018<br>SEQUENCE: 1018 | moltype = | length = 000 |
| SEQ ID NO: 1019<br>SEQUENCE: 1019 | moltype = | length = 000 |
| SEQ ID NO: 1020<br>SEQUENCE: 1020 | moltype = | length = 000 |
| SEQ ID NO: 1021<br>SEQUENCE: 1021 | moltype = | length = 000 |
| SEQ ID NO: 1022<br>SEQUENCE: 1022 | moltype = | length = 000 |
| SEQ ID NO: 1023<br>SEQUENCE: 1023 | moltype = | length = 000 |
| SEQ ID NO: 1024<br>SEQUENCE: 1024 | moltype = | length = 000 |
| SEQ ID NO: 1025<br>SEQUENCE: 1025 | moltype = | length = 000 |
| SEQ ID NO: 1026<br>SEQUENCE: 1026 | moltype = | length = 000 |
| SEQ ID NO: 1027<br>SEQUENCE: 1027 | moltype = | length = 000 |

```
SEQ ID NO: 1028         moltype =   length =
SEQUENCE: 1028
000

SEQ ID NO: 1029         moltype = DNA   length = 23
FEATURE                 Location/Qualifiers
source                  1..23
                        mol_type = unassigned DNA
                        organism = unidentified
SEQUENCE: 1029
acaaacacca ttgtcacact cca                                              23

SEQ ID NO: 1030         moltype = DNA   length = 71
FEATURE                 Location/Qualifiers
source                  1..71
                        mol_type = unassigned DNA
                        organism = unidentified
SEQUENCE: 1030
acaaacacca ttgtcacact ccacacaaac accattgtca cactccacac aaacaccatt      60
gtcacactcc a                                                           71

SEQ ID NO: 1031         moltype = DNA   length = 23
FEATURE                 Location/Qualifiers
source                  1..23
                        mol_type = unassigned DNA
                        organism = unidentified
SEQUENCE: 1031
tccataaagt aggaaacact aca                                              23

SEQ ID NO: 1032         moltype = DNA   length = 22
FEATURE                 Location/Qualifiers
source                  1..22
                        mol_type = unassigned DNA
                        organism = unidentified
SEQUENCE: 1032
agtgaattct accagtgcca ta                                               22

SEQ ID NO: 1033         moltype = DNA   length = 24
FEATURE                 Location/Qualifiers
source                  1..24
                        mol_type = unassigned DNA
                        organism = unidentified
SEQUENCE: 1033
agtgtgagtt ctaccattgc caaa                                             24

SEQ ID NO: 1034         moltype = DNA   length = 23
FEATURE                 Location/Qualifiers
source                  1..23
                        mol_type = unassigned DNA
                        organism = unidentified
SEQUENCE: 1034
agcaaaaatg tgctagtgcc aaa                                              23

SEQ ID NO: 1035         moltype = DNA   length = 130
FEATURE                 Location/Qualifiers
source                  1..130
                        mol_type = unassigned DNA
                        organism = unidentified
SEQUENCE: 1035
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
agggggttcct                                                           130

SEQ ID NO: 1036         moltype = DNA   length = 141
FEATURE                 Location/Qualifiers
source                  1..141
                        mol_type = unassigned DNA
                        organism = unidentified
SEQUENCE: 1036
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc t                                               141

SEQ ID NO: 1037         moltype = DNA   length = 130
FEATURE                 Location/Qualifiers
source                  1..130
                        mol_type = unassigned DNA
                        organism = unidentified
```

```
SEQUENCE: 1037
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag                                                          130

SEQ ID NO: 1038         moltype = DNA  length = 141
FEATURE                 Location/Qualifiers
source                  1..141
                        mol_type = unassigned DNA
                        organism = unidentified
SEQUENCE: 1038
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag ctgcctgcag g                                             141

SEQ ID NO: 1039         moltype = DNA  length = 1715
FEATURE                 Location/Qualifiers
source                  1..1715
                        mol_type = other DNA
                        organism = synthetic construct
SEQUENCE: 1039
ctagttatta atagtaatca attacggggt cattagttca tagcccatat atggagttcc    60
gcgttacata acttacggta aatggcccgc ctggctgacc gcccaacgac ccccgcccat   120
tgacgtcaat aatgacgtat gttcccatag taacgccaat agggactttc cattgacgtc   180
aatgggtgga gtatttacgg taaactgccc acttggcagt acatcaagtg tatcatatgc   240
caagtacgcc ccctattgac gtcaatgacg gtaaatggcc cgcctggcat tatgcccagt   300
acatgacctt atgggacttt cctacttggc agtacatcta cgtattagtc atcgctatta   360
ccatggtcga ggtgagcccc acgttctgct tcactctccc catctccccc cctccccac    420
ccccaatttt gtatttattt attttttaat tattttgtgc agcgatgggg gcggggggg    480
ggggggggcg cgcgccaggc ggggcggggc ggggcgaggg gcggggcggg gcgaggcgga   540
gaggtgcggc ggcagccaat cagagcggcg cgctccgaaa gtttcctttt atggcgaggc   600
ggcggcggcg gcggccctat aaaaagcgaa gcgcgcggcg ggcgggagtc gctgcgcgct   660
gccttcgccc cgtgccccgc tccgccgccg cctcgcccg cccgcccgg ctctgactga    720
ccgcgttact cccacaggtg agcgggcggg acggcccttc tcctccgggc tgtaattagc   780
gcttggttta atgacggctt gtttcttttc tgtggctgcg tgaaagcctt gaggggctcc   840
gggagggccc tttgtgcggg gggagcggct cggggggtgc gtgcgtgtgt gtgtgcgtgc   900
ggagcgccgc gtgcggctcc gcgctgcccg gcggctgtga gcgctgcggg cgcggcgcgg   960
ggctttgtgc gctccgcagt gtgcgcgagg ggagcgcggc cggggcggt gccccgcggt   1020
gcgggggggg ctgcgagggg aacaaaggct gcgtgcgtgg tgtgtgcgtg gggggtgag   1080
caggggggtgt gggcgcgtcg gtcgggctgc aaccccccct gcaccccct ccccgagttg   1140
ctgagcacgg cccggcttcg ggtgcgggc tccgtacggg gcgtggcgcg gggctcgccg   1200
tgccgggcgg ggggtggcgg caggtggggg tgccgggcgg ggcggggccg cctcgggccg   1260
ggggaggggctc ggggagggg cgcggcggcc cccggagcgc cggcggctgt cgaggcgcgg   1320
cgagccgcag ccattgcctt ttatggtaat cgtgcgagag ggcgcaggga cttcctttgt   1380
cccaaatctg tgcggagccg aaatctggga ggcgccgccg cacccctct agcgggcgcg   1440
gggcgaagcg gtgcggcgcc ggcaggaagg aaatgggcgg ggagggcctt cgtgcgtcgc   1500
cgcgcgcgcg tcccttctc cctctccagc ctcgggggctg tccgcggggg gacggctgcg   1560
ttcgggggggg acgggcagg gcggggttcg gcttctggcg tgtgaccggc ggctctagag   1620
cctctgctaa ccatgttcat gccttcttct ttttcctaca gctcctgggc aacgtgctgg   1680
ttattgtgct gtctcatcat tttggcaaag aattc                             1715

SEQ ID NO: 1040         moltype = DNA  length = 299
FEATURE                 Location/Qualifiers
source                  1..299
                        mol_type = other DNA
                        organism = synthetic construct
SEQUENCE: 1040
tagcccatat atggagttcc gcgttacata acttacggta aatggcccgc ctggctgacc    60
gcccaacgac ccccgcccat tgacgtcaat aatgacgtat gttcccatag taacgccaat   120
agggactttc cattgacgtc aatgggtgga gtatttacgg taaactgccc acttggcagt   180
acatcaagtg tatcatatgc caagtacgcc ccctattgac gtcaatgacg gtaaatggcc   240
cgcctggcat tatgcccagt acatgacctt atgggacttt cctacttggc agtacatct    299

SEQ ID NO: 1041         moltype = DNA  length = 283
FEATURE                 Location/Qualifiers
source                  1..283
                        mol_type = other DNA
                        organism = synthetic construct
SEQUENCE: 1041
catggtcgag gtgagcccca cgttctgctt cactctcccc atctccccc cctccccacc    60
cccaattttg tatttattta ttttttaatt attttgtgca gcgatggggg cggggggggg   120
ggggggcgc gcgccaggcg gggcggggcg gggcgagggg cggggcgggg cgaggcgag   180
aggtgcggcg gcagccaatc agagcggcgc gctccgaaag tttcctttta tggcgaggcg   240
gcggcggcgg cggccctata aaaagcgaag cgcgcggcg gcg                     283

SEQ ID NO: 1042         moltype = DNA  length = 260
FEATURE                 Location/Qualifiers
source                  1..260
                        mol_type = other DNA
```

```
                        organism = synthetic construct
SEQUENCE: 1042
ccacgttctg cttcactctc cccatctccc cccctcccc accccaatt ttgtatttat    60
ttatttttta attattttgt gcagcgatgg gggcggggg gggggcgcg cgccaggcgg   120
ggcggggcgg ggcgagggc ggggcgggc gaggcggaga ggtgcggcgg cagccaatca   180
gagcggcgcg ctccgaaagt ttccttttat ggcgaggcgg cggcggcggc ggccctataa   240
aaagcgaagc gcgcggcggg                                             260

SEQ ID NO: 1043         moltype = DNA  length = 654
FEATURE                 Location/Qualifiers
source                  1..654
                        mol_type = unassigned DNA
                        organism = unidentified
SEQUENCE: 1043
cgacattgat tattgactag ttattaatag taatcaatta cggggtcatt agttcatagc    60
ccatatatgg agttccgcgt tacataactt acggtaaatg gcccgcctgg ctgaccgccc   120
aacgacccc gcccattgac gtcaataatg acgtatgttc ccatagtaac gccaataggg   180
actttccatt gacgtcaaatg gtggagtat ttacggtaaa ctgcccactt ggcagtacat   240
caagtgtatc atatgccaag tacgcccct attgacgtca atgacggtaa atggcccgc   300
tggcattatg cccagtacat gaccttatgg gactttccta cttggcagta catctacgta   360
ttagtcatcg ctattaccat gtcgaggcca cgttctgctt cactctcccc atctccccc   420
cctccccacc cccaattttg tatttattta tttttaatt attttgtgca gcgatgggg   480
cggggggggg gggcgcgcgc caggcgggc ggggcgggc gaggcgcgg cgggggcgag   540
gcggagaggt gcggcggcag ccaatcagag cggcgcgctc cgaaagtttc cttttatggc   600
gaggcggcgg cggcggcggc cctataaaaa gcgaagcgcg cggcgggcgg gagc       654

SEQ ID NO: 1044         moltype = DNA  length = 699
FEATURE                 Location/Qualifiers
source                  1..699
                        mol_type = unassigned DNA
                        organism = unidentified
SEQUENCE: 1044
gatctaacat atcctggtgt ggagtagcgg acgctgctat gacagaggct cgggggcctg    60
agctggctct gtgagctggg gaggaggcag acagccaggc cttgtctgca agcagacctg   120
gcagcattgg gctggccgcc ccccaggggcc tcctcttcat gcccagtgaa tgactcacct   180
tggcacagac acaatgttcg gggtgggcac agtgcctgct tcccgccgca ccccagcccc   240
cctcaaatgc cttccgagaa gcccattgag caggggcctt gcattgcacc ccagcctgac   300
agcctggcat cttgggataa aagcagcaca gcccctagg ggctgccctt gctgtgtggc   360
gccaccggcg gtggagaaca aggctctatt cagcctgtgc ccaggaaagg ggatcagggg   420
atgcccaggc atggacagtg ggtggcaggg ggggagagga gggctgtctg cttcccagaa   480
gtccaaggac acaaatgggt gaggggagag ctctccccat agctgggctg cggcccaacc   540
ccaccccctc aggctatgcc aggggtgtt gccaggggca cccgggcatc gccagtctag   600
cccactcctt cataaagccc tcgcatccca ggagcgagca gagccagagc aggttggaga   660
ggagacgcat cacctccgct gctcgcgggg atcctctag                        699

SEQ ID NO: 1045         moltype = DNA  length = 557
FEATURE                 Location/Qualifiers
source                  1..557
                        mol_type = unassigned DNA
                        organism = unidentified
SEQUENCE: 1045
tagtatctgc agagggccct gcgtatgagt gcaagtgggt tttaggacca ggatgaggcg    60
gggtggggt gcctacctga cgaccgaccc cgacccactg gacaagcacc caaccccat    120
tccccaaatt gcgcatcccc tatcagagag ggggagggga aacaggatgc ggcgaggcgc   180
gtgcgcactg ccagcttcag caccgcggac agtgcctcg ccccccgcctg ggcgcgcgg   240
ccaccgccgc ctcagcactg aaggcgcgct gacgtcactc gccggtcccc cgcaaactcc   300
ccttccggc cacttggtc gcgtccgcgc cgccgccggc ccagccggac cgcaccacgc   360
gaggcgcgag atagggggc acgggcgcga ccatctgcgc tgcggcgccg gcgactcagc   420
gctgcctcag tctgcggtgg gcagcggagg agtcgtgtcg tgcctgagag cgcagctgtg   480
ctcctgggca ccgcgcagtc cgccccgcg gctcctggcc agaccacccc taggaccccc   540
tgcccaagt cgcagcc                                                 557

SEQ ID NO: 1046         moltype = DNA  length = 382
FEATURE                 Location/Qualifiers
source                  1..382
                        mol_type = other DNA
                        organism = synthetic construct
SEQUENCE: 1046
ctagtcgaca ttgattattg actagttatt aatagtaatc aattacgggg tcattagttc    60
atagcccata tatggagttc cgcgttacat aacttacggt aaatggcccg cctggctgac   120
cgcccaacga ccccgcccca ttgacgtcaa taatgacgta tgttcccata gtaacgccaa   180
tagggacttt ccattgacgt caatgggtgg agtatttacg gtaaactgcc cacttggcag   240
tacatcaagt gtatcatatg ccaagtacgc cccctattga cgtcaatgac ggtaaatggc   300
ccgcctggca ttatgcccag tacatgacct tatgggactt cctacttgg cagtacatct   360
acgtattagt catcgctatt ac                                           382

SEQ ID NO: 1047         moltype = DNA  length = 1736
FEATURE                 Location/Qualifiers
source                  1..1736
```

```
                    mol_type   =  other DNA
                    organism   =  synthetic construct
SEQUENCE: 1047
ctagtcgaca ttgattattg actagttatt aatagtaatc aattacgggg tcattagttc    60
atagcccata tatggagttc cgcgttacat aacttacggt aaatggcccg cctggctgac   120
cgcccaacga cccccgccca ttgacgtcaa taatgacgta tgttcccata gtaacgccaa   180
tagggacttt ccattgacgt caatgggtgg agtatttacg gtaaactgcc cacttggcag   240
tacatcaagt gtatcatatg ccaagtacgc ccctattga cgtcaatgac ggtaaatggc    300
ccgcctggca ttatgcccag tacatgacct tatgggactt tcctacttgg cagtacatct   360
acgtattagt catcgctatt accatggtcg aggtgagccc cacgttctgc ttcactctcc   420
ccatctcccc ccccteccca ccccaatttt tgtatttatt tattttttaa ttattttgtg   480
cagcgatggg gcggggggg ggggggggc gcgcgccagg cggggcgggg cggggcgagg    540
ggcggggcgg ggcgaggcgg agaggtgcgg cggcagccaa tcagagcggc gcgctccgaa   600
agtttccttt tatggcgagg cggcggccgg ggcggcccta taaaaagcga agcgcgcggc   660
gggcgggagt cgctgcgcgc tgccttcgcc ccgtgcccg ctccgccgcc gcctcgcgcc    720
gcccgccccg gctctgactg accgcgttac tcccacaggt gagcgggcgg gacggccctt   780
ctcctccggg ctgtaattag cgcttggttt aatgacggct tgtttctttt ctgtggctgc   840
gtgaaagcct tgagggggctc cgggagggcc ctttgtgcgg gggagcggct cggggggtg   900
cgtgcgtgtg tgtgtgcgtg gggagcgccg cgtgcggctc cgcgctgccc ggcggctgtg   960
agcgctgcgg gcgcggcgcg gggctttgtg cgctccgcag tgtgcgcgag gggagcgcgg  1020
ccggggggcgg tgccccgcgg tgcgggggg gctgcgaggg aacaaaggc tgcgtgcggg   1080
gtgtgtgcgt gggggggtga gcagggggtg tgggcgcgtc ggtcgggctg caaccccccc  1140
tgcacccccc tccccgagtt gctgagcacg gcccggcttc gggtgcgggg ctccgtacgg  1200
ggcgtggcgc ggggctcgcc gtgccggggcg ggggtgggg gcaggtgggg gtgccggggcg 1260
gggcggggcc ggcctcgggcc gggaggggct cggggggaggg gcgcggcggc ccccggagcg  1320
ccggcgggtg tcgaggcgcg gagagccgca gccattgcct tttatggtaa tcgtgcgaga  1380
gggcgcaggg acttccttttg tcccaaatct gtgcggagcc gaaatctggg aggcgccgc   1440
gcaccccctc tagcgggcgc ggggcgaagc ggtgcggcgc cggcaggaag gaaatgggcg  1500
gggagggcct tcgtgcgtcg ccgcgccgcc gtccccttct ccctctccag cctcgggct    1560
gtccgcgggg ggacggctgc cttcgggggg gacggggcag ggcggggttc ggcttctggc  1620
gtgtgaccgg cggctctaga gcctctgcta accatgttca tgccttcttc ttttttcctac  1680
agctcctggg caacgtgctg gttattgtgc tgtctcatca ttttggcaaa gaattc       1736

SEQ ID NO: 1048    moltype =  DNA  length =  365
FEATURE            Location/Qualifiers
source             1..365
                   mol_type   =  unassigned DNA
                   organism   =  unidentified
SEQUENCE: 1048
ctagtcgaca ttgattattg actagttatt aatagtaatc aattacgggg tcattagttc    60
atagcccata tatggagttc cgcgttacat aacttacggt aaatggcccg cctggctgac   120
cgcccaacga cccccgccca ttgacgtcaa taatgacgta tgttcccata gtaacgccaa   180
tagggacttt ccattgacgt caatgggtgg agtatttacg gtaaactgcc cacttggcag   240
tacatcaagt gtatcatatg ccaagtacgc ccctattga cgtcaatgac ggtaaatggc    300
ccgcctggca ttatgcccag tacatgacct tatgggactt tcctacttgg cagtacatct   360
acgta                                                              365

SEQ ID NO: 1049    moltype =  DNA  length =  1714
FEATURE            Location/Qualifiers
source             1..1714
                   mol_type   =  other DNA
                   organism   =  synthetic construct
SEQUENCE: 1049
ctagttatta atagtaatca attacggggt cattagttca tagcccatat atggagttcc    60
gcgttacata acttacggta aatgcccgc ctggctgacc gcccaacgac cccgcccat    120
tgacgtcaat aatgacgtat gttcccatag taacgccaat agggactttc cattgacgtc  180
aatgggtgga gtatttacgg taaactgccc acttggcagt acatcaagtg tatcatatgc  240
caagtacgcc ccctattgac gtcaatgacg gtaaatggcc cgcctggcat tatgcccagt  300
acatgacctt atgggacttt cctacttggc agtacatcta cgtattagtc atcgctatta  360
ccatggtcga ggtgagcccc acgttctgct tcactctccc catctcccc ccctcccac    420
ccccaattt gtatttattt attttttaat tattttgtgc agcgatgggg gcggggggg   480
ggggggggcg cgcgccaggc ggggcgggc ggggcgaggg gcggggcggg gcgaggcgga    540
gaggtgcggc ggcagccaat cagagcggcg cgctccgaaa gttttctttt atggcgaggc  600
ggcggccggg gcggccctat aaaaagcgaa gcgcgcggcg ggcgggagtc gctgcgcgct  660
gccttcgccc cgtgccccgc tccgccgccg cctcgcgccg cccgccccgg ctctgactga  720
ccgcgttact cccacaggtg agcgggcggg acgcccttc tcctccgggc tgtaattagc   780
gcttggttta atgacggctt gtttcttttc tgtggctgcg tgaaagcctt gagggggctcc  840
gggagggccc tttgtgcggg gggagcggct cggggggtgt gtgcgtgtgt gtgtgcgtgg   900
ggagcgccgc gtgcggctcc gcgctgcccg gcggctgtga gcgctgcgcg cgccgcgccg    960
ggctttgtgc gctccgcagt gtgcgcgagg ggagcgcggc cggggcggt gccccgcggt   1020
gcgggggg ctgcgagggg aacaaaggct gcgtgcgggg tgtgtgcgtg gggggtgag    1080
cagggggtgt gggcgcgtcg gtcgggctgc aaccccccct gcacccccct cccgagttg   1140
ctgagcacgg cccggcttcg ggtgcgggc tccgtacggg gcgtggcgcg ggctcgccg    1200
tgccggggcg ggggtgggcg gcaggtgggg gtgccggggcg gggcggggcc ggcctcgggcc  1260
gggaggggct cggggaggg gcgcggcggc ccccggagcg ccggcggtgt cgaggcgcgg   1320
cgagccgcag ccattgcctt ttatggtaat cgtgcgagag gcgcaggga cttccttttgt   1380
cccaaatctg tgcggagccg aaatctggga ggcgccgcg cacccctct agcgggcgcg   1440
gggcgaagcg gtgcggcgcc ggcaggaagg aaatgggcgg ggagggcctt cgtgcgtcgc  1500
cgcgccgcc tcccctcttc cctctccagc ctcgggctg tccgcggggg gacggctgcc   1560
```

```
ttcgggggg  acgggcagg  gcggggttcg  gcttctggcg  tgtgaccggc  ggctctagag  1620
cctctgctaa  ccatgttcat  gccttcttct  ttttcctaca  gctcctgggc  aacgtgctgg  1680
ttattgtgct  gtctcatcat  tttggcaaag  aatt                                1714

SEQ ID NO: 1050          moltype = DNA  length = 380
FEATURE                  Location/Qualifiers
source                   1..380
                         mol_type = other DNA
                         organism = synthetic construct
SEQUENCE: 1050
gacattgatt  attgactagt  tattaatagt  aatcaattac  ggggtcatta  gttcatagcc   60
catatatgga  gttccgcgtt  acataactta  cggtaaatgg  cccgcctggc  tgaccgccca  120
acgaccccg   cccattgacg  tcaataatga  cgtatgttcc  catagtaacg  ccaataggga  180
ctttccattg  acgtcaatgg  gtggagtatt  tacggtaaac  tgcccacttg  gcagtacatc  240
aagtgtatca  tatgccaagt  acgccccta   ttgacgtcaa  tgacggtaaa  tggcccgcct  300
ggcattatgc  ccagtacatg  accttatggg  acttcctac   ttggcagtac  atctacgtat  360
tagtcatcgc  tattaccatg                                                  380

SEQ ID NO: 1051          moltype = DNA  length = 134
FEATURE                  Location/Qualifiers
source                   1..134
                         mol_type = other DNA
                         organism = synthetic construct
SEQUENCE: 1051
tcagatcgcc  tggagacgcc  atccacgctg  ttttgacctc  catagaagac  accgggaccg   60
atccagcctc  cgcggattcg  aatcccggcc  gggaacggtg  cattggaacg  cggattcccc  120
gtgccaagag  tgac                                                        134

SEQ ID NO: 1052          moltype = DNA  length = 102
FEATURE                  Location/Qualifiers
source                   1..102
                         mol_type = other DNA
                         organism = synthetic construct
SEQUENCE: 1052
ttgacctcca  tagaagacac  cgggaccgat  ccagcctccg  cggattcgaa  tcccggccgg   60
gaacggtgca  ttggaacgcg  gattccccgt  gccaagagtg  ac                      102

SEQ ID NO: 1053          moltype = DNA  length = 59
FEATURE                  Location/Qualifiers
source                   1..59
                         mol_type = other DNA
                         organism = synthetic construct
SEQUENCE: 1053
attcgaatcc  cggccgggaa  cggtgcattg  gaacgcggat  tccccgtgcc  aagagtgac    59

SEQ ID NO: 1054          moltype = DNA  length = 53
FEATURE                  Location/Qualifiers
source                   1..53
                         mol_type = genomic DNA
                         organism = Homo sapiens
SEQUENCE: 1054
ctcctgggca  acgtgctggt  ctgtgtgctg  gcccatcact  ttggcaaaga  att           53

SEQ ID NO: 1055          moltype = DNA  length = 54
FEATURE                  Location/Qualifiers
source                   1..54
                         mol_type = unassigned DNA
                         organism = unidentified
SEQUENCE: 1055
ctcctgggca  acgtgctggt  tattgtgctg  tctcatcatt  ttggcaaaga  attc          54

SEQ ID NO: 1056          moltype = DNA  length = 32
FEATURE                  Location/Qualifiers
source                   1..32
                         mol_type = other DNA
                         organism = synthetic construct
SEQUENCE: 1056
gtaagtaccg  cctatagagt  ctataggccc  ac                                   32

SEQ ID NO: 1057          moltype = DNA  length = 15
FEATURE                  Location/Qualifiers
source                   1..15
                         mol_type = other DNA
                         organism = synthetic construct
SEQUENCE: 1057
gtaagtaccg  cctat                                                        15

SEQ ID NO: 1058          moltype = DNA  length = 347
FEATURE                  Location/Qualifiers
```

```
source                   1..347
                         mol_type = other DNA
                         organism = synthetic construct
SEQUENCE: 1058
aaaaaatgct tcttcttttt aatatacttt tttgtttatc ttatttctaa tactttccct    60
aatctctttc tttcagggca ataatgatac aatgtatcat gcctctttgc accattctaa   120
agaataacag tgataatttc tgggttaagg caatagcaat atttctgcat ataaatattt   180
ctgcatataa attgtaactg atgtaagagg tttcatattg ctaatagcag ctacaatcca   240
gctaccattc tgctttatt ttatggttgg gataaggctg gattattctg agtccaagct   300
aggccctttt gctaatcatg ttcataccctc ttatcttcct cccacag               347

SEQ ID NO: 1059          moltype = DNA    length = 168
FEATURE                  Location/Qualifiers
source                   1..168
                         mol_type = other DNA
                         organism = synthetic construct
SEQUENCE: 1059
tctgcatata aattgtaact gatgtaagag gtttcatatt gctaatagca gctacaatcc    60
agctaccatt ctgctttat tttatggttg ggataaggct ggattattct gagtccaagc   120
taggcccttt tgctaatcat gttcatacct cttatcttcc tcccacag                168

SEQ ID NO: 1060          moltype = DNA    length = 73
FEATURE                  Location/Qualifiers
source                   1..73
                         mol_type = other DNA
                         organism = synthetic construct
SEQUENCE: 1060
aaaaaatgct tcttcttttt aatatacttt tcttttgcta atcatgttca tacctcttat    60
cttcctccca cag                                                       73

SEQ ID NO: 1061          moltype = DNA    length = 73
FEATURE                  Location/Qualifiers
source                   1..73
                         mol_type = other DNA
                         organism = synthetic construct
SEQUENCE: 1061
aggctggatt attctgagtc caagctaggc ccttttgcta atcatgttca tacctcttat    60
cttcctccca cag                                                       73

SEQ ID NO: 1062          moltype = DNA    length = 73
FEATURE                  Location/Qualifiers
source                   1..73
                         mol_type = other DNA
                         organism = synthetic construct
SEQUENCE: 1062
aaaaaatgct tcttcttttt caagctaggc ccttttgcta atcatgttca tacctcttat    60
cttcctccca cag                                                       73

SEQ ID NO: 1063          moltype = DNA    length = 53
FEATURE                  Location/Qualifiers
source                   1..53
                         mol_type = other DNA
                         organism = synthetic construct
SEQUENCE: 1063
caagctaggc ccttttgcta atcatgttca tacctcttat cttcctccca cag           53

SEQ ID NO: 1064          moltype = DNA    length = 172
FEATURE                  Location/Qualifiers
source                   1..172
                         mol_type = genomic DNA
                         organism = Simian virus 40
SEQUENCE: 1064
gaactgaaaa accagaaagt taactggtaa gtttagtctt tttgtctttt atttcaggtc    60
ccggatccgg tggtggtgca aatcaaagaa ctgctcctca gtggatgttg cctttacttc   120
taggcctgta cggaagtgtt acttctgctc taaaagctgc ggaattgtac cc            172

SEQ ID NO: 1065          moltype = DNA    length = 1074
FEATURE                  Location/Qualifiers
source                   1..1074
                         mol_type = unassigned DNA
                         organism = unidentified
SEQUENCE: 1065
ggagtcgctg cgcgctgcct tcgccccgtg cccgctccg ccgccgcctc gcgccgcccg    60
ccccgctct gactgaccgc gttactccca caggtgagcg ggcgggacgg cccttctcct   120
ccgggctgta attagcgctt ggtttaatga cggcttgttt cttttctgtg gctgcgtgaa   180
agccttgagg ggctccggga gggccctttt gcggggggga gcggctcggg gggtgcgtgc   240
gtgtgtgtgt gcgtggggag cgccgcgtgc ggctccgcgc tgcccggcgg ctgtgagcgc   300
tgcgggcgcg gcgcggggct ttgtgcgctc cgcagtgtgc gcgaggggag gcggccgggg   360
ggcggtgccc cgcggtgcgg gggggctgc gaggggaaca aaggctgcgt gcggggtgtg   420
```

```
tgcgtggggg ggtgagcagg gggtgtgggc gcgtcggtcg ggctgcaacc ccccctgcac    480
cccctcccc gagttgctga gcacggcccg gcttcgggtg cggggctccg tacgggggcgt   540
ggcgcgggc tcgccgtgcc gggcggggg tggcggcagg tgggggtgcc gggcggggcg    600
gggccgcctc gggccgggga gggctcgggg gaggggcgcg gcggccccg gagcgccggc   660
ggctgtcgag gcgcggcgag ccgcagccat tgccttttat ggtaatcgtg cgagagggcg   720
cagggacttc cttttgtccca aatctgtgcg gagccgaaat ctgggaggcg ccgccgcacc   780
ccctctagcg ggcgcgggc gaagcggtgc ggcgccggca ggaaggaaat gggcggggag   840
ggccttcgtg cgtcgccgcg ccgccgtccc cttctccctc tccagcctcg gggctgtccg   900
cggggggacg gctgccttcg ggggggacgg ggcagggcgg ggttcggctt ctggcgtgtg   960
accggcggct ctagagcctc tgctaaccat gttcatgcct tctctttttt cctacagctc  1020
ctgggcaacg tgctggttat tgtgctgtct catcattttg gcaaagaatt cgag        1074

SEQ ID NO: 1066         moltype = DNA   length = 41
FEATURE                 Location/Qualifiers
source                  1..41
                        mol_type = unassigned DNA
                        organism = unidentified
SEQUENCE: 1066
cctctgctaa ccatgttcat gccttcttct ttttcctaca g                       41

SEQ ID NO: 1067         moltype = DNA   length = 566
FEATURE                 Location/Qualifiers
source                  1..566
                        mol_type = other DNA
                        organism = synthetic construct
SEQUENCE: 1067
tcagatcgcc tggagacgcc atccacgctg ttttgacctc catagaagac accgggaccg    60
atccagcctc cgcggattcg aatcccggcc gggaacggtg cattggaacg cggattcccc   120
gtgccaagag tgacgtaagt accgcctata gagtctatag gcccacaaaa aatgctttct   180
tcttttaata tactttttg tttatcttat ttctaatact ttccctaatc tctttctttc   240
agggcaataa tgatacaatg tatcatgcct ctttgcacca ttctaaagaa taacagtgat   300
aatttctggg ttaaggcaat agcaatattt ctgcatataa atatttctgc atataaattg   360
taactgatgt aagaggtttc atattgctaa tagcagctac aatccagcta ccattctgct   420
tttattttat ggttgggata aggctggatt attctgagtc caagctaggc ccttttgcta   480
atcatgttca tacctcttat cttcctccca cagctcctgg caacgtgct ggtctgtgtg   540
ctggcccatc actttggcaa agaatt                                        566

SEQ ID NO: 1068         moltype = DNA   length = 491
FEATURE                 Location/Qualifiers
source                  1..491
                        mol_type = other DNA
                        organism = synthetic construct
SEQUENCE: 1068
attcgaatcc cggccgggaa cggtgcattg gaacgcggat tccccgtgcc aagagtgacg    60
taagtaccgc ctatagagtc tataggccca caaaaaatgc tttcttcttt taatatactt   120
ttttgtttat cttatttcta atactttccc taatctcttt ctttcagggc aataatgata   180
caatgtatca tgcctctttg caccattcta agaataacag tgataattct ctgggttaag   240
gcaatagcaa tatttctgca tataaattgt aactgatgta agag                    300
gtttcatatt gctaatagca gctacaatcc agctaccatt ctgcttttat tttatggttg   360
ggataaggct ggattattct gagtccaagc taggcccttt tgctaatcat gttcatacct   420
cttatcttcc tcccacagct cctgggcaac gtgctggtct gtgtgctggc ccatcacttt   480
ggcaaagaat t                                                        491

SEQ ID NO: 1069         moltype = DNA   length = 387
FEATURE                 Location/Qualifiers
source                  1..387
                        mol_type = other DNA
                        organism = synthetic construct
SEQUENCE: 1069
tcagatcgcc tggagacgcc atccacgctg ttttgacctc catagaagac accgggaccg    60
atccagcctc cgcggattcg aatcccggcc gggaacggtg cattggaacg cggattcccc   120
gtgccaagag tgacgtaagt accgcctata gagtctatag gcccactctg catataaatt   180
gtaactgatg taagaggttt catattgcta atagcagcta caatccagct accattctgc   240
ttttatttta tggttgggat aaggctggat tattctgagt ccaagctagg ccttttgct   300
aatcatgttc atacctctta tcttcctccc acagctcctg gcaacgtgc tggtctgtgt   360
gctggcccat cactttggca aagaatt                                       387

SEQ ID NO: 1070         moltype = DNA   length = 292
FEATURE                 Location/Qualifiers
source                  1..292
                        mol_type = other DNA
                        organism = synthetic construct
SEQUENCE: 1070
tcagatcgcc tggagacgcc atccacgctg ttttgacctc catagaagac accgggaccg    60
atccaggtaa gtaccgccta tagagtctat aggcccacaa aaaatgcttt cttcttttaa   120
tatactttt tgtttatctt atttctaata ctttccctaa tctctttcgc tggattattc   180
tgagtccaag ctaggccctt ttgctaatca tgttcatacc tcttatcttc ctcccacagc   240
tcctgggcaa cgtgctggtc tgtgtgctgg cccatcactt tggcaaagaa tt           292
```

```
SEQ ID NO: 1071         moltype = DNA   length = 84
FEATURE                 Location/Qualifiers
source                  1..84
                        mol_type = other DNA
                        organism = synthetic construct
SEQUENCE: 1071
atggcgacgg gttcaagaac ttccctactt cttgcatttg gcctgctttg tttgccgtgg    60
ttacaggagg gctcggcagc tgcc                                          84

SEQ ID NO: 1072         moltype = DNA   length = 93
FEATURE                 Location/Qualifiers
source                  1..93
                        mol_type = other DNA
                        organism = synthetic construct
SEQUENCE: 1072
gccgccacca tggcgacggg ttcaagaact ccctacttc ttgcatttgg cctgctttgt    60
ttgccgtggt tacaggaggg ctcggcagct gcc                                93

SEQ ID NO: 1073         moltype = DNA   length = 96
FEATURE                 Location/Qualifiers
source                  1..96
                        mol_type = other DNA
                        organism = synthetic construct
SEQUENCE: 1073
gccgccacca tggggtgca cgaatgtcct gcctggctgt ggcttctcct gtccctgctg     60
tcgctccctc tgggcctccc agtcctgggc gctgcc                             96

SEQ ID NO: 1074         moltype = DNA   length = 66
FEATURE                 Location/Qualifiers
source                  1..66
                        mol_type = other DNA
                        organism = synthetic construct
SEQUENCE: 1074
gccgccacca tgggagtcaa agttctgttt gccctgatct gcatcgctgt ggccgaggcc    60
gctgcc                                                              66

SEQ ID NO: 1075         moltype = DNA   length = 72
FEATURE                 Location/Qualifiers
source                  1..72
                        mol_type = other DNA
                        organism = synthetic construct
SEQUENCE: 1075
gccgccacca tgaaacacct gtggttcttc ctcctgctgg tggcagctcc cagatgggtc    60
ctgtccgctg cc                                                       72

SEQ ID NO: 1076         moltype = DNA   length = 93
FEATURE                 Location/Qualifiers
source                  1..93
                        mol_type = other DNA
                        organism = synthetic construct
SEQUENCE: 1076
gccgccacca tggacctcct gcacaagaac atgaaacacc tgtggttctt cctcctcctg    60
gtggcagctc ccagatgggt gctgtccgct gcc                                93

SEQ ID NO: 1077         moltype = DNA   length = 69
FEATURE                 Location/Qualifiers
source                  1..69
                        mol_type = other DNA
                        organism = synthetic construct
SEQUENCE: 1077
gccgccacca tggctttcct ctggctcctc tcctgctggg ccctcctggg taccaccttc    60
ggcgctgcc                                                           69

SEQ ID NO: 1078         moltype = DNA   length = 81
FEATURE                 Location/Qualifiers
source                  1..81
                        mol_type = other DNA
                        organism = synthetic construct
SEQUENCE: 1078
gccgccacca tgccccccaa gaagtgcctg ctgctgctgc tgaccctgct gctgctgatc    60
tccaccacct tcggcgctgc c                                             81

SEQ ID NO: 1079         moltype = DNA   length = 12
FEATURE                 Location/Qualifiers
source                  1..12
                        mol_type = other DNA
                        organism = synthetic construct
SEQUENCE: 1079
gccgccacca tg                                                       12
```

```
SEQ ID NO: 1080        moltype = DNA  length = 81
FEATURE                Location/Qualifiers
source                 1..81
                       mol_type = other DNA
                       organism = synthetic construct
SEQUENCE: 1080
gccgccacca tggacatgag ggtccctgct cagctcctgg ggctcctgct gctctggctc    60
tcaggtgcca gatgtgctgc c                                              81

SEQ ID NO: 1081        moltype = DNA  length = 66
FEATURE                Location/Qualifiers
source                 1..66
                       mol_type = other DNA
                       organism = synthetic construct
SEQUENCE: 1081
gccgccacca tggaaatcaa ggtgctgttt gccctcatct gtattgctgt tgctgaggca    60
gctgcc                                                               66

SEQ ID NO: 1082        moltype = DNA  length = 78
FEATURE                Location/Qualifiers
source                 1..78
                       mol_type = other DNA
                       organism = synthetic construct
SEQUENCE: 1082
gccgccacca tggagacaga cacactcctg ctatgggtac tgctgctctg ggttccaggt    60
tccactggtg acgctgcc                                                  78

SEQ ID NO: 1083        moltype = DNA  length = 57
FEATURE                Location/Qualifiers
source                 1..57
                       mol_type = other DNA
                       organism = synthetic construct
SEQUENCE: 1083
atgaacttcg ggctcagctt gattttcctt gtccttgttt taaaaggtgt ccagtgt       57

SEQ ID NO: 1084        moltype = DNA  length = 57
FEATURE                Location/Qualifiers
source                 1..57
                       mol_type = other DNA
                       organism = synthetic construct
SEQUENCE: 1084
atgggatgga gctggatctt tctctttctc ctgtcaggaa ctacaggtgt cctctct       57

SEQ ID NO: 1085        moltype = DNA  length = 57
FEATURE                Location/Qualifiers
source                 1..57
                       mol_type = other DNA
                       organism = synthetic construct
SEQUENCE: 1085
atgaagttgc ctgttaggct gttggtgctg atgttctgga ttcctgcttc cagcagt       57

SEQ ID NO: 1086        moltype = DNA  length = 411
FEATURE                Location/Qualifiers
source                 1..411
                       mol_type = other DNA
                       organism = synthetic construct
SEQUENCE: 1086
atgaacttcg ggctcagctt gattttcctt gtccttgttt taaaaggtgt ccagtgtgag    60
gtgaagctgg tggagagcgg cggcgacctg gtgaagcctg gcggcagcct gaagctgagc   120
tgcgccgcca gcggcttcac cttcagcagc tacgccatga gctgggtgag acagaaccct   180
gagaagagac tggagtgggt ggccagcatc agcaagggcg gcaacaccta ctaccctaac   240
agcgtgaagg gcagattcac catcagcaga gacaacgcca gaaacatcct gtacctgcag   300
atgagcagcc tgagaagcga ggacaccgcc ctgtactact gcgccagagg ctggggcgac   360
tacggctggt tcgcctactg gggccaggtg accctggtga ccgtgagcgc c            411

SEQ ID NO: 1087        moltype =      length =
SEQUENCE: 1087
000

SEQ ID NO: 1088        moltype =      length =
SEQUENCE: 1088
000

SEQ ID NO: 1089        moltype = DNA  length = 11
FEATURE                Location/Qualifiers
source                 1..11
                       mol_type = other DNA
                       organism = synthetic construct
```

-continued

SEQUENCE: 1089
gaggagccac c                                                               11

SEQ ID NO: 1090        moltype =    length =
SEQUENCE: 1090
000

SEQ ID NO: 1091        moltype =    length =
SEQUENCE: 1091
000

SEQ ID NO: 1092        moltype =    length =
SEQUENCE: 1092
000

SEQ ID NO: 1093        moltype =    length =
SEQUENCE: 1093
000

SEQ ID NO: 1094        moltype =    length =
SEQUENCE: 1094
000

SEQ ID NO: 1095        moltype =    length =
SEQUENCE: 1095
000

SEQ ID NO: 1096        moltype =    length =
SEQUENCE: 1096
000

SEQ ID NO: 1097        moltype =    length =
SEQUENCE: 1097
000

SEQ ID NO: 1098        moltype =    length =
SEQUENCE: 1098
000

SEQ ID NO: 1099        moltype =    length =
SEQUENCE: 1099
000

SEQ ID NO: 1100        moltype =    length =
SEQUENCE: 1100
000

SEQ ID NO: 1101        moltype =    length =
SEQUENCE: 1101
000

SEQ ID NO: 1102        moltype =    length =
SEQUENCE: 1102
000

SEQ ID NO: 1103        moltype =    length =
SEQUENCE: 1103
000

SEQ ID NO: 1104        moltype =    length =
SEQUENCE: 1104
000

SEQ ID NO: 1105        moltype =    length =
SEQUENCE: 1105
000

SEQ ID NO: 1106        moltype =    length =
SEQUENCE: 1106
000

SEQ ID NO: 1107        moltype =    length =
SEQUENCE: 1107
000

SEQ ID NO: 1108        moltype =    length =
SEQUENCE: 1108
000

| | | |
|---|---|---|
| SEQ ID NO: 1109<br>SEQUENCE: 1109<br>000 | moltype = | length = |
| SEQ ID NO: 1110<br>SEQUENCE: 1110<br>000 | moltype = | length = |
| SEQ ID NO: 1111<br>SEQUENCE: 1111<br>000 | moltype = | length = |
| SEQ ID NO: 1112<br>SEQUENCE: 1112<br>000 | moltype = | length = |
| SEQ ID NO: 1113<br>SEQUENCE: 1113<br>000 | moltype = | length = |
| SEQ ID NO: 1114<br>SEQUENCE: 1114<br>000 | moltype = | length = |
| SEQ ID NO: 1115<br>SEQUENCE: 1115<br>000 | moltype = | length = |
| SEQ ID NO: 1116<br>SEQUENCE: 1116<br>000 | moltype = | length = |
| SEQ ID NO: 1117<br>SEQUENCE: 1117<br>000 | moltype = | length = |
| SEQ ID NO: 1118<br>SEQUENCE: 1118<br>000 | moltype = | length = |
| SEQ ID NO: 1119<br>SEQUENCE: 1119<br>000 | moltype = | length = |
| SEQ ID NO: 1120<br>SEQUENCE: 1120<br>000 | moltype = | length = |
| SEQ ID NO: 1121<br>SEQUENCE: 1121<br>000 | moltype = | length = |
| SEQ ID NO: 1122<br>SEQUENCE: 1122<br>000 | moltype = | length = |
| SEQ ID NO: 1123<br>SEQUENCE: 1123<br>000 | moltype = | length = |
| SEQ ID NO: 1124<br>SEQUENCE: 1124<br>000 | moltype = | length = |
| SEQ ID NO: 1125<br>SEQUENCE: 1125<br>000 | moltype = | length = |
| SEQ ID NO: 1126<br>SEQUENCE: 1126<br>000 | moltype = | length = |
| SEQ ID NO: 1127<br>SEQUENCE: 1127<br>000 | moltype = | length = |
| SEQ ID NO: 1128<br>SEQUENCE: 1128<br>000 | moltype = | length = |

SEQ ID NO: 1129          moltype =      length =
SEQUENCE: 1129
000

SEQ ID NO: 1130          moltype =      length =
SEQUENCE: 1130
000

SEQ ID NO: 1131          moltype =      length =
SEQUENCE: 1131
000

SEQ ID NO: 1132          moltype =      length =
SEQUENCE: 1132
000

SEQ ID NO: 1133          moltype =      length =
SEQUENCE: 1133
000

SEQ ID NO: 1134          moltype = DNA   length = 127
FEATURE                  Location/Qualifiers
source                   1..127
                         mol_type = other DNA
                         organism = synthetic construct
SEQUENCE: 1134
gatctttttc cctctgccaa aaattatggg gacatcatga agcccttga gcatctgact    60
tctggctaat aaaggaaatt tatttcatt gcaatagtgt gttggaattt tttgtgtctc   120
tcactcg                                                            127

SEQ ID NO: 1135          moltype = DNA   length = 477
FEATURE                  Location/Qualifiers
source                   1..477
                         mol_type = other DNA
                         organism = synthetic construct
SEQUENCE: 1135
gggtggcatc cctgtgaccc ctccccagtg cctctcctgg ccctggaagt tgccactcca    60
gtgcccacca gccttgtcct aataaaatta agttgcatca ttttgtctga ctaggtgtcc   120
ttctataata ttatggggtg aggggggtg gtatggagca aggggcaagt tgggaagaca   180
acctgtaggg cctgcggggt ctattgggaa ccaagctgga gtgcagtggc acaatcttgg   240
ctcactgcaa tctccgcctc ctgggttcaa gcgattctcc tgcctcagcc tcccgagttg   300
tgggattcc aggcatgcat gaccaggctc agctaatttt tgttttttg gtagagacgg    360
ggtttcacca tattggccag gctggtctcc aactccaat ctcaggtgat ctacccacct    420
tggcctccca aattgctggg attacaggcg tgaaccactg ctcccttccc tgtcctt      477

SEQ ID NO: 1136          moltype = DNA   length = 552
FEATURE                  Location/Qualifiers
source                   1..552
                         mol_type = other DNA
                         organism = synthetic construct
SEQUENCE: 1136
gaattcactc ctcaggtgca ggctgccatat cagaaggtgg tggctggtgt ggccaatgcc    60
ctggctcaca ataccactg agatcttttt ccctctgcca aaattatgg ggacatcatg    120
aagccccttg agcatctgac ttctggctaa taaaggaaatt ttattttcat tgcaatagtg   180
tgttggaatt ttttgtgtct ctcactcgga aggacatatg ggagggcaaa tcattttaaaa   240
catcagaatg agtatttggt ttagagtttg gcaacatatg cccatatgct ggctgccatg   300
aacaaaggtt ggctataaag aggtcatcag tatatgaaac agcccctgc tgtccattcc    360
ttattccata gaaaagcctt gacttgaggt tagatttttt ttatatttg ttttgtgtta    420
tttttttctt taacatccct aaaattttcc ttacatgttt tactagccag atttttcctc    480
ctctcctgac tactcccagt catagctgtc cctcttctct tatggagatc cctcgacctg   540
cagcccaagc tt                                                       552

SEQ ID NO: 1137          moltype =      length =
SEQUENCE: 1137
000

SEQ ID NO: 1138          moltype =      length =
SEQUENCE: 1138
000

SEQ ID NO: 1139          moltype =      length =
SEQUENCE: 1139
000

SEQ ID NO: 1140          moltype = AA    length = 5
FEATURE                  Location/Qualifiers
source                   1..5
                         mol_type = protein -continued

```
                        organism = synthetic construct
SEQUENCE: 1140
NYWMH                                                              5

SEQ ID NO: 1141         moltype = AA   length = 17
FEATURE                 Location/Qualifiers
source                  1..17
                        mol_type = protein
                        organism = synthetic construct
SEQUENCE: 1141
RIDPNSGGTR YNEKFKN                                                17

SEQ ID NO: 1142         moltype = AA   length = 5
FEATURE                 Location/Qualifiers
source                  1..5
                        mol_type = protein
                        organism = synthetic construct
SEQUENCE: 1142
DYYMS                                                              5

SEQ ID NO: 1143         moltype = AA   length = 19
FEATURE                 Location/Qualifiers
source                  1..19
                        mol_type = protein
                        organism = synthetic construct
SEQUENCE: 1143
LIRNKAKGFT TEYSASVKG                                              19

SEQ ID NO: 1144         moltype = AA   length = 5
FEATURE                 Location/Qualifiers
source                  1..5
                        mol_type = protein
                        organism = synthetic construct
SEQUENCE: 1144
RYWMH                                                              5

SEQ ID NO: 1145         moltype = AA   length = 17
FEATURE                 Location/Qualifiers
source                  1..17
                        mol_type = protein
                        organism = synthetic construct
SEQUENCE: 1145
NINPNNGGTD FNEKFKN                                                17

SEQ ID NO: 1146         moltype = AA   length = 16
FEATURE                 Location/Qualifiers
source                  1..16
                        mol_type = protein
                        organism = synthetic construct
SEQUENCE: 1146
RSSQSLVHNN GITYLY                                                 16

SEQ ID NO: 1147         moltype = AA   length = 5
FEATURE                 Location/Qualifiers
source                  1..5
                        mol_type = protein
                        organism = synthetic construct
SEQUENCE: 1147
IFWMH                                                              5

SEQ ID NO: 1148         moltype = AA   length = 17
FEATURE                 Location/Qualifiers
source                  1..17
                        mol_type = protein
                        organism = synthetic construct
SEQUENCE: 1148
KINPNNGGGD YNEKFKS                                                17

SEQ ID NO: 1149         moltype = AA   length = 5
FEATURE                 Location/Qualifiers
source                  1..5
                        mol_type = protein
                        organism = synthetic construct
SEQUENCE: 1149
RFWMH                                                              5

SEQ ID NO: 1150         moltype = AA   length = 17
FEATURE                 Location/Qualifiers
source                  1..17
```

```
                              -continued
                          mol_type = protein
                          organism = synthetic construct
SEQUENCE: 1150
NINPNNGGTD NNERFKS                                              17

SEQ ID NO: 1151           moltype = AA  length = 7
FEATURE                   Location/Qualifiers
source                    1..7
                          mol_type = protein
                          organism = synthetic construct
SEQUENCE: 1151
TLAVPFK                                                          7

SEQ ID NO: 1152           moltype = AA  length = 7
FEATURE                   Location/Qualifiers
source                    1..7
                          mol_type = protein
                          organism = synthetic construct
SEQUENCE: 1152
TSAMGVS                                                          7

SEQ ID NO: 1153           moltype = AA  length = 16
FEATURE                   Location/Qualifiers
source                    1..16
                          mol_type = protein
                          organism = synthetic construct
SEQUENCE: 1153
HIYWDDDKRY NPSLKS                                               16

SEQ ID NO: 1154           moltype = AA  length = 16
FEATURE                   Location/Qualifiers
source                    1..16
                          mol_type = protein
                          organism = synthetic construct
SEQUENCE: 1154
RSSQSLVHNN GITYLY                                               16

SEQ ID NO: 1155           moltype = AA  length = 8
FEATURE                   Location/Qualifiers
source                    1..8
                          mol_type = protein
                          organism = synthetic construct
SEQUENCE: 1155
DYTFTNYW                                                         8

SEQ ID NO: 1156           moltype = AA  length = 8
FEATURE                   Location/Qualifiers
source                    1..8
                          mol_type = protein
                          organism = synthetic construct
SEQUENCE: 1156
IDPNSGGT                                                         8

SEQ ID NO: 1157           moltype = AA  length = 6
FEATURE                   Location/Qualifiers
source                    1..6
                          mol_type = protein
                          organism = synthetic construct
SEQUENCE: 1157
AGDFDV                                                           6

SEQ ID NO: 1158           moltype = AA  length = 6
FEATURE                   Location/Qualifiers
source                    1..6
                          mol_type = protein
                          organism = synthetic construct
SEQUENCE: 1158
GNIHNY                                                           6

SEQ ID NO: 1159           moltype =     length =
SEQUENCE: 1159
000

SEQ ID NO: 1160           moltype = AA  length = 8
FEATURE                   Location/Qualifiers
source                    1..8
                          mol_type = protein
                          organism = synthetic construct
SEQUENCE: 1160
```

```
GFTFTDYY                                                                               8

SEQ ID NO: 1161        moltype = AA   length = 10
FEATURE                Location/Qualifiers
source                 1..10
                       mol_type = protein
                       organism = synthetic construct
SEQUENCE: 1161
IRNKAKGFTT                                                                            10

SEQ ID NO: 1162        moltype = AA   length = 6
FEATURE                Location/Qualifiers
source                 1..6
                       mol_type = protein
                       organism = synthetic construct
SEQUENCE: 1162
VRDINY                                                                                 6

SEQ ID NO: 1163        moltype = AA   length = 12
FEATURE                Location/Qualifiers
source                 1..12
                       mol_type = protein
                       organism = synthetic construct
SEQUENCE: 1163
QSLLYSTNQE NY                                                                         12

SEQ ID NO: 1164        moltype =     length =
SEQUENCE: 1164
000

SEQ ID NO: 1165        moltype = AA   length = 8
FEATURE                Location/Qualifiers
source                 1..8
                       mol_type = protein
                       organism = synthetic construct
SEQUENCE: 1165
GFTFTRYW                                                                               8

SEQ ID NO: 1166        moltype = AA   length = 8
FEATURE                Location/Qualifiers
source                 1..8
                       mol_type = protein
                       organism = synthetic construct
SEQUENCE: 1166
INPNNGGT                                                                               8

SEQ ID NO: 1167        moltype = AA   length = 11
FEATURE                Location/Qualifiers
source                 1..11
                       mol_type = protein
                       organism = synthetic construct
SEQUENCE: 1167
ARGTGTGAMD Y                                                                          11

SEQ ID NO: 1168        moltype = AA   length = 8
FEATURE                Location/Qualifiers
source                 1..8
                       mol_type = protein
                       organism = synthetic construct
SEQUENCE: 1168
GYTFTIFW                                                                               8

SEQ ID NO: 1169        moltype = AA   length = 8
FEATURE                Location/Qualifiers
source                 1..8
                       mol_type = protein
                       organism = synthetic construct
SEQUENCE: 1169
INPNNGGG                                                                               8

SEQ ID NO: 1170        moltype = AA   length = 11
FEATURE                Location/Qualifiers
source                 1..11
                       mol_type = protein
                       organism = synthetic construct
SEQUENCE: 1170
QSLVHSNGIT H                                                                          11

SEQ ID NO: 1171        moltype = AA   length = 8
```

```
FEATURE                 Location/Qualifiers
source                  1..8
                        mol_type = protein
                        organism = synthetic construct
SEQUENCE: 1171
GYTFTRFW                                                                    8

SEQ ID NO: 1172         moltype = AA  length = 11
FEATURE                 Location/Qualifiers
source                  1..11
                        mol_type = protein
                        organism = synthetic construct
SEQUENCE: 1172
QSLVHSNGNT H                                                               11

SEQ ID NO: 1173         moltype = AA  length = 10
FEATURE                 Location/Qualifiers
source                  1..10
                        mol_type = protein
                        organism = synthetic construct
SEQUENCE: 1173
GFSLSTSAMG                                                                 10

SEQ ID NO: 1174         moltype = AA  length = 7
FEATURE                 Location/Qualifiers
source                  1..7
                        mol_type = protein
                        organism = synthetic construct
SEQUENCE: 1174
IYWDDDK                                                                     7

SEQ ID NO: 1175         moltype = AA  length = 11
FEATURE                 Location/Qualifiers
source                  1..11
                        mol_type = protein
                        organism = synthetic construct
SEQUENCE: 1175
ARRRGYGMD Y                                                                11

SEQ ID NO: 1176         moltype = AA  length = 6
FEATURE                 Location/Qualifiers
source                  1..6
                        mol_type = protein
                        organism = synthetic construct
SEQUENCE: 1176
QSVSND                                                                      6

SEQ ID NO: 1177         moltype =   length =
SEQUENCE: 1177
000

SEQ ID NO: 1178         moltype =   length =
SEQUENCE: 1178
000

SEQ ID NO: 1179         moltype =   length =
SEQUENCE: 1179
000

SEQ ID NO: 1180         moltype = AA  length = 7
FEATURE                 Location/Qualifiers
source                  1..7
                        mol_type = protein
                        organism = synthetic construct
VARIANT                 2
                        note = F or Y
VARIANT                 6
                        note = R or I
VARIANT                 7
                        note = Y or F
SEQUENCE: 1180
GXTFTXX                                                                     7

SEQ ID NO: 1181         moltype = AA  length = 16
FEATURE                 Location/Qualifiers
source                  1..16
                        mol_type = protein
                        organism = synthetic construct
VARIANT                 9
```

```
                         note = N or S
VARIANT                  12
                         note = I or N
VARIANT                  14
                         note = Y or H
SEQUENCE: 1181
RSSQSLVHXN GXTXLY                                                        16

SEQ ID NO: 1182          moltype = AA  length = 7
FEATURE                  Location/Qualifiers
source                   1..7
                         mol_type = protein
                         organism = synthetic construct
VARIANT                  4
                         note = N or S
SEQUENCE: 1182
RVSXRFS                                                                   7

SEQ ID NO: 1183          moltype =  length =
SEQUENCE: 1183
000

SEQ ID NO: 1184          moltype = AA  length = 17
FEATURE                  Location/Qualifiers
source                   1..17
                         mol_type = protein
                         organism = synthetic construct
VARIANT                  1
                         note = N or K
VARIANT                  9
                         note = T or G
VARIANT                  11
                         note = F, Y or N
VARIANT                  14
                         note = K or R
VARIANT                  17
                         note = N or S
SEQUENCE: 1184
XINPNNGGXD XNEXFKX                                                       17

SEQ ID NO: 1185          moltype = AA  length = 16
FEATURE                  Location/Qualifiers
source                   1..16
                         mol_type = protein
                         organism = synthetic construct
VARIANT                  9
                         note = N or S
VARIANT                  12
                         note = I or N
VARIANT                  14
                         note = Y or H
SEQUENCE: 1185
RSSQSLVHXN GXTXLY                                                        16

SEQ ID NO: 1186          moltype = AA  length = 8
FEATURE                  Location/Qualifiers
source                   1..8
                         mol_type = protein
                         organism = synthetic construct
VARIANT                  2
                         note = F or Y
VARIANT                  6
                         note = R or I
VARIANT                  7
                         note = Y or F
SEQUENCE: 1186
GXTFTXXW                                                                  8

SEQ ID NO: 1187          moltype = AA  length = 8
FEATURE                  Location/Qualifiers
source                   1..8
                         mol_type = protein
                         organism = synthetic construct
VARIANT                  8
                         note = T or G
SEQUENCE: 1187
INPNNGGX                                                                  8

SEQ ID NO: 1188          moltype = AA  length = 11
```

```
FEATURE                 Location/Qualifiers
source                  1..11
                        mol_type = protein
                        organism = synthetic construct
VARIANT                 6
                        note = N or S
VARIANT                 9
                        note = I or N
VARIANT                 11
                        note = Y or H
SEQUENCE: 1188
QSLVHXNGXT X                                                            11

SEQ ID NO: 1189         moltype = AA   length = 324
FEATURE                 Location/Qualifiers
source                  1..324
                        mol_type = protein
                        organism = Mus sp.
SEQUENCE: 1189
AKTTPPSVYP LAPGSAAQTN SMVTLGCLVK GYFPEPVTVT WNSGSLSSGV HTFPAVLQSD        60
LYTLSSSVTV PSSPRPSETV TCNVAHPASS TKVDKKIVPR DCGCKPCICT VPEVSSVFIF       120
PPKPKDVLTI TLTPKVTCVV VDISKDDPEV QFSWFVDDVE VHTAQTQPRE EQFNSTFRSV       180
SELPIMHQDW LNGKEFKCRV NSAAFPAPIE KTISKTKGRP KAPQVYTIPP PKEQMAKDKV       240
SLTCMITDFF PEDITVEWQW NGQPAENYKN TQPIMNTNGS YFVYSKLNVQ KSNWEAGNTF       300
TCSVLHEGLH NHHTEKSLSH SPGK                                             324

SEQ ID NO: 1190         moltype = AA   length = 393
FEATURE                 Location/Qualifiers
source                  1..393
                        mol_type = protein
                        organism = Mus sp.
SEQUENCE: 1190
AKTTPPSVYP LAPGSAAQTN SMVTLGCLVK GYFPEPVTVT WNSGSLSSGV HTFPAVLQSD        60
LYTLSSSVTV PSSPRPSETV TCNVAHPASS TKVDKKIVPR DCGCKPCICT VPEVSSVFIF       120
PPKPKDVLTI TLTPKVTCVV VDISKDDPEV QFSWFVDDVE VHTAQTQPRE EQFNSTFRSV       180
SELPIMHQDW LNGKEFKCRV NSAAFPAPIE KTISKTKGRP KAPQVYTIPP PKEQMAKDKV       240
SLTCMITDFF PEDITVEWQW NGQPAENYKN TQPIMNTNGS YFVYSKLNVQ KSNWEAGNTF       300
TCSVLHEGLH NHHTEKSLSH SPGLQLDETC AEAQDGELDG LWTTITIFIS LFLLSVCYSA       360
AVTLFKVKWI FSSVVELKQT LVPEYKNMIG QAP                                   393

SEQ ID NO: 1191         moltype = AA   length = 330
FEATURE                 Location/Qualifiers
source                  1..330
                        mol_type = protein
                        organism = Mus sp.
SEQUENCE: 1191
AKTTAPSVYP LAPVCGDTTG SSVTLGCLVK GYFPEPVTLT WNSGSLSSGV HTFPAVLQSD        60
LYTLSSSVTV TSSTWPSQSI TCNVAHPASS TKVDKKIEPR GPTIKPCPPC KCPAPNLLGG       120
PSVFIFPPKI KDVLMISLSP IVTCVVVDVS EDDPDVQISW FVNNVEVHTA QTQTHREDYN       180
STLRVVSALP IQHQDWMSGK EFKCKVNNKD LPAPIERTIS KPKGSVRAPQ VYVLPPPEEE       240
MTKKQVTLTC MVTDFMPEDI YVEWTNNGKT ELNYKNTEPV LDSDGSYFMY SKLRVEKKNW       300
VERNSYSCSV VHEGLHNHHT TKSFSRTPGK                                       330

SEQ ID NO: 1192         moltype = DNA   length = 990
FEATURE                 Location/Qualifiers
source                  1..990
                        mol_type = genomic DNA
                        organism = Mus sp.
SEQUENCE: 1192
gctaaaacaa cagccccatc ggtctatcca ctggcccctg tgtgtggaga tacaactggc        60
tcctcggtga ctctaggatg cctggtcaag ggttatttcc ctgagccagt gaccttgacc       120
tggaactctg gatccctgtc cagtggtgtg cacaccttcc cagctgtcct gcagtctgac       180
ctctacaccc tcagcagctc agtgactgta acctcgagca cctggcccag ccagtccatc       240
acctgcaatg tggcccaccc ggcaagcagc accaaggtgg acaagaaaat tgagcccaga       300
gggcccacaa tcaagccctg tcctccatgc aaatgcccag cacctaacct cttggggtgga      360
ccatccgtct tcatcttccc tccaaagatc aaggatgtac tcatgatctc cctgagccca       420
atagtcacat gtgtggtggt ggatgtgagc gaggatgacc cagatgtcca gatcagctgg       480
tttgtgaaca acgtggaagt acacacagct cagacacaga cccatagaga ggattacaac       540
agtactctcc gggtggtcag tgccctcccc atccagcacc aggactggat gagtggcaag       600
gagttcaaat gcaaggtcaa caacaaagac ctcccagcgc ccatcgagag aaccatctca       660
aaacccaaag ggtcagtaag agctccacag gtatatgtct tgcctccacc agaagaagag       720
atgactaaga acaggtcac tctgacctgc atggtcacag acttcatgcc tgaagacatt       780
tacgtggagt ggaccaacaa cgggaaaaca gagctaaact acaagaacac tgaaccagtc       840
ctggactctg atggttctta cttcatgtac agcaagctga gagtggaaaa gaagaactgg       900
gtggaaagaa atagctactc ctgttcagtg gtccacgagg gtctgcacaa tcaccacacg       960
actaagagct tctccccgga ctccgggtaaa                                      990

SEQ ID NO: 1193         moltype = AA   length = 335
FEATURE                 Location/Qualifiers
```

```
source                      1..335
                            mol_type = protein
                            organism = Mus sp.
SEQUENCE: 1193
AKTTAPSVYP LVPVCGGTTG SSVTLGCLVK GYFPEPVTLT WNSGSLSSGV HTFPALLQSG    60
LYTLSSSVTV TSNTWPSQTI TCNVAHPASS TKVDKKIEPR VPITQNPCPP HQRVPPCAAP   120
DLLGGPSVFI FPPKIKDVLM ISLSPMVTCV VVDVSEDDPD VQISWFVNNV EVHTAQTQTH   180
REDYNSTLRV VSALPIQHQD WMSGKEFKCK VNNRALPSPI EKTISKPRGP VRAPQVYVLP   240
PPAEEMTKKE FSLTCMITGF LPAEIAVDWT SNGRTEQNYK NTATVLDSDG SYFMYSKLRV   300
QKSTWERGSL FACSVVHEVL HNHLTTKTIS RSLGK                              335

SEQ ID NO: 1194             moltype = AA  length = 404
FEATURE                     Location/Qualifiers
source                      1..404
                            mol_type = protein
                            organism = Mus sp.
SEQUENCE: 1194
KTTPPSVYPL APGCGDTTGS SVTLGCLVKG YFPESVTVTW NSGSLSSSVH TFPALLQSGL    60
YTMSSSVTVP SSTWPSQTVT CSVAHPASST TVDKKLEPSG PISTINPCPP CKECHKCPAP   120
NLEGGPSVFI FPPNIKDVLM ISLTPKVTCV VVDVSEDDPD VQISWFVNNV EVHTAQTQTH   180
REDYNSTIRV VSTLPIQHQD WMSGKEFKCK VNNKDLPSPI ERTISKIKGL VRAPQVYILP   240
PPAEQLSRKD VSLTCLVVGF NPGDISVEWT SNGHTEENYK DTAPVLDSDG SYFIYSKLNM   300
KTSKWEKTDS FSCNVRHEGL KNYYLKKTIS RSPGLDLDDI CAEAKDGELD GLWTTITIFI   360
SLFLLSVCYS ASVTLFKVKW IFSSVVELKQ KISPDYRNMI GQGA                    404

SEQ ID NO: 1195             moltype = AA  length = 403
FEATURE                     Location/Qualifiers
source                      1..403
                            mol_type = protein
                            organism = Mus sp.
SEQUENCE: 1195
KTTAPSVYPL APVCGGTTGS SVTLGCLVKG YFPEPVTLTW NSGSLSSGVH TFPALLQSGL    60
YTLSSSVTVT SNTWPSQTIT CNVAHPASST KVDKKIEPRV PITQNPCPPL KECPPCAAPD   120
LLGGPSVFIF PPKIKDVLMI SLSPMVTCVV VDVSEDDPDV QISWFVNNVE VHTAQTQTHR   180
EDYNSTLRVV SALPIQHQDW MSGKEFKCKV NNRALPSPIE KTISKPRGPV RAPQVYVLPP   240
PAEEMTKKEF SLTCMITGFL PAEIAVDWTS NGRTEQNYKN TATVLDSDGS YFMYSKLRVQ   300
KSTWERGSLF ACSVVHEGLH NHLTTKTISR SLGLDLDDVC TEAQDGELDG LWTTITIFIS   360
LFLLSVCYSA SVTLFKVKWI FSSVVELKQK ISPDYRNMIG QGA                     403

SEQ ID NO: 1196             moltype = AA  length = 398
FEATURE                     Location/Qualifiers
source                      1..398
                            mol_type = protein
                            organism = Mus sp.
SEQUENCE: 1196
TTTAPSVYPL VPGCSDTSGS SVTLGCLVKG YFPEPVTVKW NYGALSSGVR TVSSVLQSGF    60
YSLSSSVTVT SSTWPSQTVI CNVAHPASKT ELIKRIEPRI PKPSTPPGSS CPPGNILGGP   120
SVFIFPPKPK DALMISLTPK VTCVVVDVSE DDPDVHVSWF VDNKEVHTAW TQPREAQYNS   180
TFRVVSALPI QHQDWMRGKE FKCKVNNKAL PAPIERTISK PKGRAQTPQV YTIPPPREQM   240
SKKKVSLTCL VTNFFSEAIS VEWERNGELE QDYKNTPPIL DSDGTYFLYS KLTVDTDSWL   300
QGEIFTCSVV HEALHNHHTQ KNLSRSPELE LNETCAEAQD GELDGLWTTI TIFISLFLLS   360
VCYSASVTLF KVKWIFSSVV QVKQTAIPDY RNMIGQGA                           398

SEQ ID NO: 1197             moltype = AA  length = 106
FEATURE                     Location/Qualifiers
source                      1..106
                            mol_type = protein
                            organism = Mus sp.
SEQUENCE: 1197
ADAAPTVSIF PPSSEQLTSG GASVVCFLNN FYPKDINVKW KIDGSERQNG VLNSWTDQDS    60
KDSTYSMSST LTLTKDEYER HNSYTCEATH KTSTSPIVKS FNRNEC                  106

SEQ ID NO: 1198             moltype = DNA  length = 318
FEATURE                     Location/Qualifiers
source                      1..318
                            mol_type = genomic DNA
                            organism = Mus sp.
SEQUENCE: 1198
gcagatgctg caccaactgt atccatcttc ccaccatcca gtgagcagtt aacatctgga    60
ggtgcctcag tcgtgtgctt cttgaacaac ttctacccca agacatcaa tgtcaagtgg   120
aagattgatg gcagtgaacg acaaaatggc gtcctgaaca gttggactga tcaggacagc   180
aaagacagcc cctacagcat gagcagcacc ctcacgttga ccaaggacga gtatgaacga   240
cataacagct atacctgtga ggccactcac aagacatcaa cttcacccat tgtcaagagc   300
ttcaacagga atgagtgt                                                 318

SEQ ID NO: 1199             moltype = AA  length = 105
FEATURE                     Location/Qualifiers
source                      1..105
                            mol_type = protein
```

```
                        organism = Mus sp.
SEQUENCE: 1199
QPKSSPSVTL FPPSSEELET NKATLVCTIT DFYPGVVTVD WKVDGTPVTQ GMETTQPSKQ    60
SNNKYMASSY LTLTARAWER HSSYSCQVTH EGHTVEKSLS RADCS                  105

SEQ ID NO: 1200         moltype = AA   length = 104
FEATURE                 Location/Qualifiers
source                  1..104
                        mol_type = protein
                        organism = Mus sp.
SEQUENCE: 1200
QPKSTPTLTV FPPSSEELKE NKATLVCLIS NFSPSGVTVA WKANGTPITQ GVDTSNPTKE    60
GNKFMASSFL HLTSDQWRSH NSFTCQVTHE GDTVEKSLSP AECL                   104

SEQ ID NO: 1201         moltype = AA   length = 104
FEATURE                 Location/Qualifiers
source                  1..104
                        mol_type = protein
                        organism = Mus sp.
SEQUENCE: 1201
QPKSTPTLTM FPPSPEELQE NKATLVCLIS NFSPSGVTVA WKANGTPITQ GVDTSNPTKE    60
DNKYMASSFL HLTSDQWRSH NSFTCQVTHE GDTVEKSLSP AECL                   104

SEQ ID NO: 1202         moltype = AA   length = 329
FEATURE                 Location/Qualifiers
source                  1..329
                        mol_type = protein
                        organism = Homo sapiens
SEQUENCE: 1202
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 1203         moltype = DNA   length = 987
FEATURE                 Location/Qualifiers
source                  1..987
                        mol_type = genomic DNA
                        organism = Homo sapiens
SEQUENCE: 1203
gccagcacaa aagggcccag tgtgttcccg ctcgcaccaa gcagcaaatc aacgtcaggc    60
ggcacagccg cgtttggttg ccttgtaaaa gactacttcc cagaaccagt tacggtgtca   120
tggaacagtg gtgcactcac gagcggcgtt catacctccc cgccgtactc acagagttca   180
ggtctttact cactttccag cgtggtcaca gtaccgtcaa gctctcttgg aacacagaca   240
tatatctgta acgtaaatca taagcctagc aataccaaag tcgataaacg agtggaaccc   300
aagagttgtg ataaaaccca cacctgtccc ccttgcccgg caccggaact gctgggtggt   360
ccatcagtat tcttgtttcc gcctaagcca aaggacacac tgatgatatc agaactcca    420
gaggttacgt gcgtagtcgt ggacgtcagt catgaagacc ccgaagttaa gttcaactgg   480
tacgtggatg gtgtggaagt acataatgcg aagacgaaac ccaggaagaa acaatataac   540
tcaacttata gggtagtcag cgtcttgact gtacttcacc aagattggtt gaatggcaaa   600
gagtacaaat gcaaggtaag caacaaagca ttgcctgcgc caatcgaaaa gactatctca   660
aaagcaaagg gccagccacg cgaaccacaa gtgtatacat tgccgcccag tcggaagaa    720
atgacgaaaa atcaagtcag tctcacatgc ctcgtgaaag gattttatcc ctctgacata   780
gctgtggagt gggaaagtaa tggccaaccc gaaaataatt acaaaacgac gcctcccgtt   840
ttggactcag atgggagttt ttttccttac agtaagctga cggttgacaa agcaggtgg    900
caacaaggga acgtcttttc ttgtagtgtg atgcatgagg cgctccacaa tcattacact   960
caaaaatcct tgagcctgtc tccaggc                                     987

SEQ ID NO: 1204         moltype = AA   length = 326
FEATURE                 Location/Qualifiers
source                  1..326
                        mol_type = protein
                        organism = Homo sapiens
SEQUENCE: 1204
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDISVEW ESNGQPENNY KTTPPMLDSD GSFFLYSKLT VDKSRWQQGN   300
VFSCSVMHEA LHNHYTQKSL SLSPGK                                       326

SEQ ID NO: 1205         moltype = AA   length = 377
FEATURE                 Location/Qualifiers
source                  1..377
                        mol_type = protein
                        organism = Homo sapiens
SEQUENCE: 1205
```

```
ASTKGPSVFP LAPCSRSTSG GTAALGCLVK DYFPEPVTVS WNSGALTSGV HTFPAVLQSS    60
GLYSLSSVVT VPSSSLGTQT YTCNVNHKPS NTKVDKRVEL KTPLGDTTHT CPRCPEPKSC   120
DTPPPCPRCP EPKSCDTPPP CPRCPEPKSC DTPPPCPRCP APELLGGPSV FLFPPKPKDT   180
LMISRTPEVT CVVVDVSHED PEVQFKWYVD GVEVHNAKTK PREEQYNSTF RVVSVLTVLH   240
QDWLNGKEYK CKVSNKALPA PIEKTISKTK GQPREPQVYT LPPSREEMTK NQVSLTCLVK   300
GFYPSDIAVE WESSGQPENN YNTTPPMLDS DGSFFLYSKL TVDKSRWQQG NIFSCSVMHE   360
ALHNRFTQKS LSLSPGK                                                  377

SEQ ID NO: 1206         moltype = AA  length = 327
FEATURE                 Location/Qualifiers
source                  1..327
                        mol_type = protein
                        organism = Homo sapiens
SEQUENCE: 1206
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 1207         moltype = AA  length = 106
FEATURE                 Location/Qualifiers
source                  1..106
                        mol_type = protein
                        organism = Homo sapiens
SEQUENCE: 1207
GQPKANPTVT LFPPSSEELQ ANKATLVCLI SDFYPGAVTV AWKADGSPVK AGVETTKPSK    60
QSNNKYAASS YLSLTPEQWK SHRSYSCQVT HEGSTVEKTV APTECS                 106

SEQ ID NO: 1208         moltype = AA  length = 106
FEATURE                 Location/Qualifiers
source                  1..106
                        mol_type = protein
                        organism = Homo sapiens
SEQUENCE: 1208
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                 106

SEQ ID NO: 1209         moltype = AA  length = 106
FEATURE                 Location/Qualifiers
source                  1..106
                        mol_type = protein
                        organism = Homo sapiens
SEQUENCE: 1209
GQPKAAPSVT LFPPSSEELQ ANKATLVCLI SDFYPGAVTV AWKADSSPVK AGVETTTPSK    60
QSNNKYAASS YLSLTPEQWK SHKSYSCQVT HEGSTVEKTV APTECS                 106

SEQ ID NO: 1210         moltype = AA  length = 106
FEATURE                 Location/Qualifiers
source                  1..106
                        mol_type = protein
                        organism = Homo sapiens
SEQUENCE: 1210
GQPKAAPSVT LFPPSSEELQ ANKATLVCLI SDFYPGAVKV AWKADGSPVN TGVETTTPSK    60
QSNNKYAASS YLSLTPEQWK SHRSYSCQVT HEGSTVEKTV APAECS                 106

SEQ ID NO: 1211         moltype = AA  length = 106
FEATURE                 Location/Qualifiers
source                  1..106
                        mol_type = protein
                        organism = Homo sapiens
SEQUENCE: 1211
GQPKAAPSVT LFPPSSEELQ ANKATLVCLV SDFNPGAVTV AWKADGSPVK VGVETTKPSK    60
QSNNKYAASS YLSLTPEQWK SHRSYSCRVT HEGSTVEKTV APAECS                 106

SEQ ID NO: 1212         moltype = AA  length = 106
FEATURE                 Location/Qualifiers
source                  1..106
                        mol_type = protein
                        organism = Homo sapiens
SEQUENCE: 1212
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 1213         moltype = DNA  length = 318
FEATURE                 Location/Qualifiers
source                  1..318
                        mol_type = genomic DNA
``` organism = Homo sapiens
SEQUENCE: 1213
actgtcgcag caccttctgt cttcatcttt ccgccaagcg atgaacagtt gaaatctgga    60
acagcgtccg tggtgtgcct gctcaacaac ttctatcctc gggaagcgaa ggtgcaatgg   120
aaggtagata atgctcttca gagtggcaat tcccaagagt cagttacgga gcaagatagc   180
aaggacagca cgtattccct gtctagtacg ttgactcttt ccaaggctga ctatgaaaag   240
cacaaggtgt atgcctgtga agtaacccac caaggtctct caagtcctgt aactaagagc   300
tttaatcgag gagaatgc                                                 318

SEQ ID NO: 1214         moltype =    length =
SEQUENCE: 1214
000

SEQ ID NO: 1215         moltype =    length =
SEQUENCE: 1215
000

SEQ ID NO: 1216         moltype =    length =
SEQUENCE: 1216
000

SEQ ID NO: 1217         moltype =    length =
SEQUENCE: 1217
000

SEQ ID NO: 1218         moltype =    length =
SEQUENCE: 1218
000

SEQ ID NO: 1219         moltype =    length =
SEQUENCE: 1219
000

SEQ ID NO: 1220         moltype =    length =
SEQUENCE: 1220
000

SEQ ID NO: 1221         moltype =    length =
SEQUENCE: 1221
000

SEQ ID NO: 1222         moltype =    length =
SEQUENCE: 1222
000

SEQ ID NO: 1223         moltype =    length =
SEQUENCE: 1223
000

SEQ ID NO: 1224         moltype =    length =
SEQUENCE: 1224
000

SEQ ID NO: 1225         moltype =    length =
SEQUENCE: 1225
000

SEQ ID NO: 1226         moltype =    length =
SEQUENCE: 1226
000

SEQ ID NO: 1227         moltype =    length =
SEQUENCE: 1227
000

SEQ ID NO: 1228         moltype =    length =
SEQUENCE: 1228
000

SEQ ID NO: 1229         moltype =    length =
SEQUENCE: 1229
000

SEQ ID NO: 1230         moltype =    length =
SEQUENCE: 1230
000

SEQ ID NO: 1231         moltype =    length =
SEQUENCE: 1231

000

SEQ ID NO: 1232         moltype =    length =
SEQUENCE: 1232
000

SEQ ID NO: 1233         moltype =    length =
SEQUENCE: 1233
000

SEQ ID NO: 1234         moltype =    length =
SEQUENCE: 1234
000

SEQ ID NO: 1235         moltype =    length =
SEQUENCE: 1235
000

SEQ ID NO: 1236         moltype =    length =
SEQUENCE: 1236
000

SEQ ID NO: 1237         moltype =    length =
SEQUENCE: 1237
000

SEQ ID NO: 1238         moltype =    length =
SEQUENCE: 1238
000

SEQ ID NO: 1239         moltype =    length =
SEQUENCE: 1239
000

SEQ ID NO: 1240         moltype =    length =
SEQUENCE: 1240
000

SEQ ID NO: 1241         moltype =    length =
SEQUENCE: 1241
000

SEQ ID NO: 1242         moltype =    length =
SEQUENCE: 1242
000

SEQ ID NO: 1243         moltype =    length =
SEQUENCE: 1243
000

SEQ ID NO: 1244         moltype =    length =
SEQUENCE: 1244
000

SEQ ID NO: 1245         moltype =    length =
SEQUENCE: 1245
000

SEQ ID NO: 1246         moltype =    length =
SEQUENCE: 1246
000

SEQ ID NO: 1247         moltype =    length =
SEQUENCE: 1247
000

SEQ ID NO: 1248         moltype =    length =
SEQUENCE: 1248
000

SEQ ID NO: 1249         moltype =    length =
SEQUENCE: 1249
000

SEQ ID NO: 1250         moltype =    length =
SEQUENCE: 1250
000

SEQ ID NO: 1251         moltype =    length =

| | | |
|---|---|---|
| SEQUENCE: 1251 000 | | |
| SEQ ID NO: 1252 SEQUENCE: 1252 000 | moltype = | length = |
| SEQ ID NO: 1253 SEQUENCE: 1253 000 | moltype = | length = |
| SEQ ID NO: 1254 SEQUENCE: 1254 000 | moltype = | length = |
| SEQ ID NO: 1255 SEQUENCE: 1255 000 | moltype = | length = |
| SEQ ID NO: 1256 SEQUENCE: 1256 000 | moltype = | length = |
| SEQ ID NO: 1257 SEQUENCE: 1257 000 | moltype = | length = |
| SEQ ID NO: 1258 SEQUENCE: 1258 000 | moltype = | length = |
| SEQ ID NO: 1259 SEQUENCE: 1259 000 | moltype = | length = |
| SEQ ID NO: 1260 SEQUENCE: 1260 000 | moltype = | length = |
| SEQ ID NO: 1261 SEQUENCE: 1261 000 | moltype = | length = |
| SEQ ID NO: 1262 FEATURE source | moltype = AA  length = 7 Location/Qualifiers 1..7 mol_type = protein organism = synthetic construct | |
| SEQUENCE: 1262 TLAVPFK | | 7 |
| SEQ ID NO: 1263 SEQUENCE: 1263 000 | moltype = | length = |
| SEQ ID NO: 1264 SEQUENCE: 1264 000 | moltype = | length = |
| SEQ ID NO: 1265 SEQUENCE: 1265 000 | moltype = | length = |
| SEQ ID NO: 1266 SEQUENCE: 1266 000 | moltype = | length = |
| SEQ ID NO: 1267 SEQUENCE: 1267 000 | moltype = | length = |
| SEQ ID NO: 1268 SEQUENCE: 1268 000 | moltype = | length = |
| SEQ ID NO: 1269 SEQUENCE: 1269 000 | moltype = | length = |

| | | |
|---|---|---|
| SEQ ID NO: 1270<br>SEQUENCE: 1270<br>000 | moltype = | length = |
| SEQ ID NO: 1271<br>SEQUENCE: 1271<br>000 | moltype = | length = |
| SEQ ID NO: 1272<br>SEQUENCE: 1272<br>000 | moltype = | length = |
| SEQ ID NO: 1273<br>SEQUENCE: 1273<br>000 | moltype = | length = |
| SEQ ID NO: 1274<br>SEQUENCE: 1274<br>000 | moltype = | length = |
| SEQ ID NO: 1275<br>SEQUENCE: 1275<br>000 | moltype = | length = |
| SEQ ID NO: 1276<br>SEQUENCE: 1276<br>000 | moltype = | length = |
| SEQ ID NO: 1277<br>SEQUENCE: 1277<br>000 | moltype = | length = |
| SEQ ID NO: 1278<br>SEQUENCE: 1278<br>000 | moltype = | length = |
| SEQ ID NO: 1279<br>SEQUENCE: 1279<br>000 | moltype = | length = |
| SEQ ID NO: 1280<br>SEQUENCE: 1280<br>000 | moltype = | length = |
| SEQ ID NO: 1281<br>SEQUENCE: 1281<br>000 | moltype = | length = |
| SEQ ID NO: 1282<br>SEQUENCE: 1282<br>000 | moltype = | length = |
| SEQ ID NO: 1283<br>SEQUENCE: 1283<br>000 | moltype = | length = |
| SEQ ID NO: 1284<br>SEQUENCE: 1284<br>000 | moltype = | length = |
| SEQ ID NO: 1285<br>SEQUENCE: 1285<br>000 | moltype = | length = |
| SEQ ID NO: 1286<br>SEQUENCE: 1286<br>000 | moltype = | length = |
| SEQ ID NO: 1287<br>SEQUENCE: 1287<br>000 | moltype = | length = |
| SEQ ID NO: 1288<br>SEQUENCE: 1288<br>000 | moltype = | length = |
| SEQ ID NO: 1289<br>SEQUENCE: 1289<br>000 | moltype = | length = |

| | | |
|---|---|---|
| SEQ ID NO: 1290 SEQUENCE: 1290 | moltype = | length = 000 |
| SEQ ID NO: 1291 SEQUENCE: 1291 | moltype = | length = 000 |
| SEQ ID NO: 1292 SEQUENCE: 1292 | moltype = | length = 000 |
| SEQ ID NO: 1293 SEQUENCE: 1293 | moltype = | length = 000 |
| SEQ ID NO: 1294 SEQUENCE: 1294 | moltype = | length = 000 |
| SEQ ID NO: 1295 SEQUENCE: 1295 | moltype = | length = 000 |
| SEQ ID NO: 1296 SEQUENCE: 1296 | moltype = | length = 000 |
| SEQ ID NO: 1297 SEQUENCE: 1297 | moltype = | length = 000 |
| SEQ ID NO: 1298 SEQUENCE: 1298 | moltype = | length = 000 |
| SEQ ID NO: 1299 SEQUENCE: 1299 | moltype = | length = 000 |
| SEQ ID NO: 1300 SEQUENCE: 1300 | moltype = | length = 000 |
| SEQ ID NO: 1301 SEQUENCE: 1301 | moltype = | length = 000 |
| SEQ ID NO: 1302 SEQUENCE: 1302 | moltype = | length = 000 |
| SEQ ID NO: 1303 SEQUENCE: 1303 | moltype = | length = 000 |
| SEQ ID NO: 1304 SEQUENCE: 1304 | moltype = | length = 000 |
| SEQ ID NO: 1305 SEQUENCE: 1305 | moltype = | length = 000 |
| SEQ ID NO: 1306 SEQUENCE: 1306 | moltype = | length = 000 |
| SEQ ID NO: 1307 SEQUENCE: 1307 | moltype = | length = 000 |
| SEQ ID NO: 1308 SEQUENCE: 1308 | moltype = | length = 000 |
| SEQ ID NO: 1309 SEQUENCE: 1309 | moltype = | length = |

000

SEQ ID NO: 1310          moltype =     length =
SEQUENCE: 1310
000

SEQ ID NO: 1311          moltype =     length =
SEQUENCE: 1311
000

SEQ ID NO: 1312          moltype =     length =
SEQUENCE: 1312
000

SEQ ID NO: 1313          moltype =     length =
SEQUENCE: 1313
000

SEQ ID NO: 1314          moltype =     length =
SEQUENCE: 1314
000

SEQ ID NO: 1315          moltype =     length =
SEQUENCE: 1315
000

SEQ ID NO: 1316          moltype =     length =
SEQUENCE: 1316
000

SEQ ID NO: 1317          moltype =     length =
SEQUENCE: 1317
000

SEQ ID NO: 1318          moltype =     length =
SEQUENCE: 1318
000

SEQ ID NO: 1319          moltype =     length =
SEQUENCE: 1319
000

SEQ ID NO: 1320          moltype =     length =
SEQUENCE: 1320
000

SEQ ID NO: 1321          moltype =     length =
SEQUENCE: 1321
000

SEQ ID NO: 1322          moltype =     length =
SEQUENCE: 1322
000

SEQ ID NO: 1323          moltype =     length =
SEQUENCE: 1323
000

SEQ ID NO: 1324          moltype =     length =
SEQUENCE: 1324
000

SEQ ID NO: 1325          moltype =     length =
SEQUENCE: 1325
000

SEQ ID NO: 1326          moltype =     length =
SEQUENCE: 1326
000

SEQ ID NO: 1327          moltype =     length =
SEQUENCE: 1327
000

SEQ ID NO: 1328          moltype =     length =
SEQUENCE: 1328
000

SEQ ID NO: 1329          moltype =     length =

-continued

SEQUENCE: 1329
000

SEQ ID NO: 1330    moltype =    length =
SEQUENCE: 1330
000

SEQ ID NO: 1331    moltype =    length =
SEQUENCE: 1331
000

SEQ ID NO: 1332    moltype =    length =
SEQUENCE: 1332
000

SEQ ID NO: 1333    moltype =    length =
SEQUENCE: 1333
000

SEQ ID NO: 1334    moltype =    length =
SEQUENCE: 1334
000

SEQ ID NO: 1335    moltype =    length =
SEQUENCE: 1335
000

SEQ ID NO: 1336    moltype =    length =
SEQUENCE: 1336
000

SEQ ID NO: 1337    moltype =    length =
SEQUENCE: 1337
000

SEQ ID NO: 1338    moltype =    length =
SEQUENCE: 1338
000

SEQ ID NO: 1339    moltype =    length =
SEQUENCE: 1339
000

SEQ ID NO: 1340    moltype =    length =
SEQUENCE: 1340
000

SEQ ID NO: 1341    moltype =    length =
SEQUENCE: 1341
000

SEQ ID NO: 1342    moltype =    length =
SEQUENCE: 1342
000

SEQ ID NO: 1343    moltype =    length =
SEQUENCE: 1343
000

SEQ ID NO: 1344    moltype =    length =
SEQUENCE: 1344
000

SEQ ID NO: 1345    moltype =    length =
SEQUENCE: 1345
000

SEQ ID NO: 1346    moltype =    length =
SEQUENCE: 1346
000

SEQ ID NO: 1347    moltype =    length =
SEQUENCE: 1347
000

SEQ ID NO: 1348    moltype =    length =
SEQUENCE: 1348
000

| | | |
|---|---|---|
| SEQ ID NO: 1349<br>SEQUENCE: 1349<br>000 | moltype = | length = |
| SEQ ID NO: 1350<br>SEQUENCE: 1350<br>000 | moltype = | length = |
| SEQ ID NO: 1351<br>SEQUENCE: 1351<br>000 | moltype = | length = |
| SEQ ID NO: 1352<br>SEQUENCE: 1352<br>000 | moltype = | length = |
| SEQ ID NO: 1353<br>SEQUENCE: 1353<br>000 | moltype = | length = |
| SEQ ID NO: 1354<br>SEQUENCE: 1354<br>000 | moltype = | length = |
| SEQ ID NO: 1355<br>SEQUENCE: 1355<br>000 | moltype = | length = |
| SEQ ID NO: 1356<br>SEQUENCE: 1356<br>000 | moltype = | length = |
| SEQ ID NO: 1357<br>SEQUENCE: 1357<br>000 | moltype = | length = |
| SEQ ID NO: 1358<br>SEQUENCE: 1358<br>000 | moltype = | length = |
| SEQ ID NO: 1359<br>SEQUENCE: 1359<br>000 | moltype = | length = |
| SEQ ID NO: 1360<br>SEQUENCE: 1360<br>000 | moltype = | length = |
| SEQ ID NO: 1361<br>SEQUENCE: 1361<br>000 | moltype = | length = |
| SEQ ID NO: 1362<br>SEQUENCE: 1362<br>000 | moltype = | length = |
| SEQ ID NO: 1363<br>SEQUENCE: 1363<br>000 | moltype = | length = |
| SEQ ID NO: 1364<br>SEQUENCE: 1364<br>000 | moltype = | length = |
| SEQ ID NO: 1365<br>SEQUENCE: 1365<br>000 | moltype = | length = |
| SEQ ID NO: 1366<br>SEQUENCE: 1366<br>000 | moltype = | length = |
| SEQ ID NO: 1367<br>SEQUENCE: 1367<br>000 | moltype = | length = |
| SEQ ID NO: 1368<br>SEQUENCE: 1368<br>000 | moltype = | length = |

| | | |
|---|---|---|
| SEQ ID NO: 1369 SEQUENCE: 1369 | moltype = 000 | length = |
| SEQ ID NO: 1370 SEQUENCE: 1370 | moltype = 000 | length = |
| SEQ ID NO: 1371 SEQUENCE: 1371 | moltype = 000 | length = |
| SEQ ID NO: 1372 SEQUENCE: 1372 | moltype = 000 | length = |
| SEQ ID NO: 1373 SEQUENCE: 1373 | moltype = 000 | length = |
| SEQ ID NO: 1374 SEQUENCE: 1374 | moltype = 000 | length = |
| SEQ ID NO: 1375 SEQUENCE: 1375 | moltype = 000 | length = |
| SEQ ID NO: 1376 SEQUENCE: 1376 | moltype = 000 | length = |
| SEQ ID NO: 1377 SEQUENCE: 1377 | moltype = 000 | length = |
| SEQ ID NO: 1378 SEQUENCE: 1378 | moltype = 000 | length = |
| SEQ ID NO: 1379 SEQUENCE: 1379 | moltype = 000 | length = |
| SEQ ID NO: 1380 SEQUENCE: 1380 | moltype = 000 | length = |
| SEQ ID NO: 1381 SEQUENCE: 1381 | moltype = 000 | length = |
| SEQ ID NO: 1382 SEQUENCE: 1382 | moltype = 000 | length = |
| SEQ ID NO: 1383 SEQUENCE: 1383 | moltype = 000 | length = |
| SEQ ID NO: 1384 SEQUENCE: 1384 | moltype = 000 | length = |
| SEQ ID NO: 1385 SEQUENCE: 1385 | moltype = 000 | length = |
| SEQ ID NO: 1386 SEQUENCE: 1386 | moltype = 000 | length = |
| SEQ ID NO: 1387 SEQUENCE: 1387 | moltype = 000 | length = |
| SEQ ID NO: 1388 SEQUENCE: 1388 | moltype = | length = |

```
000

SEQ ID NO: 1389           moltype =    length =
SEQUENCE: 1389
000

SEQ ID NO: 1390           moltype =    length =
SEQUENCE: 1390
000

SEQ ID NO: 1391           moltype =    length =
SEQUENCE: 1391
000

SEQ ID NO: 1392           moltype =    length =
SEQUENCE: 1392
000

SEQ ID NO: 1393           moltype =    length =
SEQUENCE: 1393
000

SEQ ID NO: 1394           moltype =    length =
SEQUENCE: 1394
000

SEQ ID NO: 1395           moltype =    length =
SEQUENCE: 1395
000

SEQ ID NO: 1396           moltype =    length =
SEQUENCE: 1396
000

SEQ ID NO: 1397           moltype =    length =
SEQUENCE: 1397
000

SEQ ID NO: 1398           moltype =    length =
SEQUENCE: 1398
000

SEQ ID NO: 1399           moltype =    length =
SEQUENCE: 1399
000

SEQ ID NO: 1400           moltype =    length =
SEQUENCE: 1400
000

SEQ ID NO: 1401           moltype =    length =
SEQUENCE: 1401
000

SEQ ID NO: 1402           moltype =    length =
SEQUENCE: 1402
000

SEQ ID NO: 1403           moltype =    length =
SEQUENCE: 1403
000

SEQ ID NO: 1404           moltype =    length =
SEQUENCE: 1404
000

SEQ ID NO: 1405           moltype =    length =
SEQUENCE: 1405
000

SEQ ID NO: 1406           moltype =    length =
SEQUENCE: 1406
000

SEQ ID NO: 1407           moltype =    length =
SEQUENCE: 1407
000

SEQ ID NO: 1408           moltype =    length =
```

| | | |
|---|---|---|
| SEQUENCE: 1408 000 | | |
| SEQ ID NO: 1409 SEQUENCE: 1409 000 | moltype = | length = |
| SEQ ID NO: 1410 SEQUENCE: 1410 000 | moltype = | length = |
| SEQ ID NO: 1411 SEQUENCE: 1411 000 | moltype = | length = |
| SEQ ID NO: 1412 SEQUENCE: 1412 000 | moltype = | length = |
| SEQ ID NO: 1413 SEQUENCE: 1413 000 | moltype = | length = |
| SEQ ID NO: 1414 SEQUENCE: 1414 000 | moltype = | length = |
| SEQ ID NO: 1415 SEQUENCE: 1415 000 | moltype = | length = |
| SEQ ID NO: 1416 SEQUENCE: 1416 000 | moltype = | length = |
| SEQ ID NO: 1417 SEQUENCE: 1417 000 | moltype = | length = |
| SEQ ID NO: 1418 SEQUENCE: 1418 000 | moltype = | length = |
| SEQ ID NO: 1419 SEQUENCE: 1419 000 | moltype = | length = |
| SEQ ID NO: 1420 SEQUENCE: 1420 000 | moltype = | length = |
| SEQ ID NO: 1421 SEQUENCE: 1421 000 | moltype = | length = |
| SEQ ID NO: 1422 SEQUENCE: 1422 000 | moltype = | length = |
| SEQ ID NO: 1423 SEQUENCE: 1423 000 | moltype = | length = |
| SEQ ID NO: 1424 SEQUENCE: 1424 000 | moltype = | length = |
| SEQ ID NO: 1425 SEQUENCE: 1425 000 | moltype = | length = |
| SEQ ID NO: 1426 SEQUENCE: 1426 000 | moltype = | length = |
| SEQ ID NO: 1427 SEQUENCE: 1427 000 | moltype = | length = |

| | | |
|---|---|---|
| SEQ ID NO: 1428<br>SEQUENCE: 1428<br>000 | moltype = | length = |
| SEQ ID NO: 1429<br>SEQUENCE: 1429<br>000 | moltype = | length = |
| SEQ ID NO: 1430<br>SEQUENCE: 1430<br>000 | moltype = | length = |
| SEQ ID NO: 1431<br>SEQUENCE: 1431<br>000 | moltype = | length = |
| SEQ ID NO: 1432<br>SEQUENCE: 1432<br>000 | moltype = | length = |
| SEQ ID NO: 1433<br>SEQUENCE: 1433<br>000 | moltype = | length = |
| SEQ ID NO: 1434<br>SEQUENCE: 1434<br>000 | moltype = | length = |
| SEQ ID NO: 1435<br>SEQUENCE: 1435<br>000 | moltype = | length = |
| SEQ ID NO: 1436<br>SEQUENCE: 1436<br>000 | moltype = | length = |
| SEQ ID NO: 1437<br>SEQUENCE: 1437<br>000 | moltype = | length = |
| SEQ ID NO: 1438<br>SEQUENCE: 1438<br>000 | moltype = | length = |
| SEQ ID NO: 1439<br>SEQUENCE: 1439<br>000 | moltype = | length = |
| SEQ ID NO: 1440<br>SEQUENCE: 1440<br>000 | moltype = | length = |
| SEQ ID NO: 1441<br>SEQUENCE: 1441<br>000 | moltype = | length = |
| SEQ ID NO: 1442<br>SEQUENCE: 1442<br>000 | moltype = | length = |
| SEQ ID NO: 1443<br>SEQUENCE: 1443<br>000 | moltype = | length = |
| SEQ ID NO: 1444<br>SEQUENCE: 1444<br>000 | moltype = | length = |
| SEQ ID NO: 1445<br>SEQUENCE: 1445<br>000 | moltype = | length = |
| SEQ ID NO: 1446<br>SEQUENCE: 1446<br>000 | moltype = | length = |
| SEQ ID NO: 1447<br>SEQUENCE: 1447<br>000 | moltype = | length = |

SEQ ID NO: 1448        moltype =      length =
SEQUENCE: 1448
000

SEQ ID NO: 1449        moltype =      length =
SEQUENCE: 1449
000

SEQ ID NO: 1450        moltype =      length =
SEQUENCE: 1450
000

SEQ ID NO: 1451        moltype =      length =
SEQUENCE: 1451
000

SEQ ID NO: 1452        moltype =      length =
SEQUENCE: 1452
000

SEQ ID NO: 1453        moltype =      length =
SEQUENCE: 1453
000

SEQ ID NO: 1454        moltype =      length =
SEQUENCE: 1454
000

SEQ ID NO: 1455        moltype =      length =
SEQUENCE: 1455
000

SEQ ID NO: 1456        moltype =      length =
SEQUENCE: 1456
000

SEQ ID NO: 1457        moltype =      length =
SEQUENCE: 1457
000

SEQ ID NO: 1458        moltype =      length =
SEQUENCE: 1458
000

SEQ ID NO: 1459        moltype =      length =
SEQUENCE: 1459
000

SEQ ID NO: 1460        moltype =      length =
SEQUENCE: 1460
000

SEQ ID NO: 1461        moltype =      length =
SEQUENCE: 1461
000

SEQ ID NO: 1462        moltype =      length =
SEQUENCE: 1462
000

SEQ ID NO: 1463        moltype =      length =
SEQUENCE: 1463
000

SEQ ID NO: 1464        moltype =      length =
SEQUENCE: 1464
000

SEQ ID NO: 1465        moltype =      length =
SEQUENCE: 1465
000

SEQ ID NO: 1466        moltype =      length =
SEQUENCE: 1466
000

SEQ ID NO: 1467        moltype =      length =
SEQUENCE: 1467

-continued

000

SEQ ID NO: 1468  moltype =  length =
SEQUENCE: 1468
000

SEQ ID NO: 1469  moltype =  length =
SEQUENCE: 1469
000

SEQ ID NO: 1470  moltype =  length =
SEQUENCE: 1470
000

SEQ ID NO: 1471  moltype =  length =
SEQUENCE: 1471
000

SEQ ID NO: 1472  moltype =  length =
SEQUENCE: 1472
000

SEQ ID NO: 1473  moltype =  length =
SEQUENCE: 1473
000

SEQ ID NO: 1474  moltype =  length =
SEQUENCE: 1474
000

SEQ ID NO: 1475  moltype =  length =
SEQUENCE: 1475
000

SEQ ID NO: 1476  moltype =  length =
SEQUENCE: 1476
000

SEQ ID NO: 1477  moltype =  length =
SEQUENCE: 1477
000

SEQ ID NO: 1478  moltype =  length =
SEQUENCE: 1478
000

SEQ ID NO: 1479  moltype =  length =
SEQUENCE: 1479
000

SEQ ID NO: 1480  moltype =  length =
SEQUENCE: 1480
000

SEQ ID NO: 1481  moltype =  length =
SEQUENCE: 1481
000

SEQ ID NO: 1482  moltype =  length =
SEQUENCE: 1482
000

SEQ ID NO: 1483  moltype =  length =
SEQUENCE: 1483
000

SEQ ID NO: 1484  moltype =  length =
SEQUENCE: 1484
000

SEQ ID NO: 1485  moltype =  length =
SEQUENCE: 1485
000

SEQ ID NO: 1486  moltype =  length =
SEQUENCE: 1486
000

SEQ ID NO: 1487  moltype =  length =

-continued

```
SEQUENCE: 1487
000

SEQ ID NO: 1488          moltype =    length =
SEQUENCE: 1488
000

SEQ ID NO: 1489          moltype =    length =
SEQUENCE: 1489
000

SEQ ID NO: 1490          moltype =    length =
SEQUENCE: 1490
000

SEQ ID NO: 1491          moltype =    length =
SEQUENCE: 1491
000

SEQ ID NO: 1492          moltype =    length =
SEQUENCE: 1492
000

SEQ ID NO: 1493          moltype =    length =
SEQUENCE: 1493
000

SEQ ID NO: 1494          moltype =    length =
SEQUENCE: 1494
000

SEQ ID NO: 1495          moltype =    length =
SEQUENCE: 1495
000

SEQ ID NO: 1496          moltype =    length =
SEQUENCE: 1496
000

SEQ ID NO: 1497          moltype =    length =
SEQUENCE: 1497
000

SEQ ID NO: 1498          moltype =    length =
SEQUENCE: 1498
000

SEQ ID NO: 1499          moltype =    length =
SEQUENCE: 1499
000

SEQ ID NO: 1500          moltype =    length =
SEQUENCE: 1500
000

SEQ ID NO: 1501          moltype =    length =
SEQUENCE: 1501
000

SEQ ID NO: 1502          moltype =    length =
SEQUENCE: 1502
000

SEQ ID NO: 1503          moltype =    length =
SEQUENCE: 1503
000

SEQ ID NO: 1504          moltype =    length =
SEQUENCE: 1504
000

SEQ ID NO: 1505          moltype =    length =
SEQUENCE: 1505
000

SEQ ID NO: 1506          moltype =    length =
SEQUENCE: 1506
000
```

| | | |
|---|---|---|
| SEQ ID NO: 1507 SEQUENCE: 1507 | moltype = | length = 000 |
| SEQ ID NO: 1508 SEQUENCE: 1508 | moltype = | length = 000 |
| SEQ ID NO: 1509 SEQUENCE: 1509 | moltype = | length = 000 |
| SEQ ID NO: 1510 SEQUENCE: 1510 | moltype = | length = 000 |
| SEQ ID NO: 1511 SEQUENCE: 1511 | moltype = | length = 000 |
| SEQ ID NO: 1512 SEQUENCE: 1512 | moltype = | length = 000 |
| SEQ ID NO: 1513 SEQUENCE: 1513 | moltype = | length = 000 |
| SEQ ID NO: 1514 SEQUENCE: 1514 | moltype = | length = 000 |
| SEQ ID NO: 1515 SEQUENCE: 1515 | moltype = | length = 000 |
| SEQ ID NO: 1516 SEQUENCE: 1516 | moltype = | length = 000 |
| SEQ ID NO: 1517 SEQUENCE: 1517 | moltype = | length = 000 |
| SEQ ID NO: 1518 SEQUENCE: 1518 | moltype = | length = 000 |
| SEQ ID NO: 1519 SEQUENCE: 1519 | moltype = | length = 000 |
| SEQ ID NO: 1520 SEQUENCE: 1520 | moltype = | length = 000 |
| SEQ ID NO: 1521 SEQUENCE: 1521 | moltype = | length = 000 |
| SEQ ID NO: 1522 SEQUENCE: 1522 | moltype = | length = 000 |
| SEQ ID NO: 1523 SEQUENCE: 1523 | moltype = | length = 000 |
| SEQ ID NO: 1524 SEQUENCE: 1524 | moltype = | length = 000 |
| SEQ ID NO: 1525 SEQUENCE: 1525 | moltype = | length = 000 |
| SEQ ID NO: 1526 SEQUENCE: 1526 | moltype = | length = 000 |

```
SEQ ID NO: 1527         moltype =    length =
SEQUENCE: 1527
000

SEQ ID NO: 1528         moltype =    length =
SEQUENCE: 1528
000

SEQ ID NO: 1529         moltype =    length =
SEQUENCE: 1529
000

SEQ ID NO: 1530         moltype =    length =
SEQUENCE: 1530
000

SEQ ID NO: 1531         moltype =    length =
SEQUENCE: 1531
000

SEQ ID NO: 1532         moltype =    length =
SEQUENCE: 1532
000

SEQ ID NO: 1533         moltype =    length =
SEQUENCE: 1533
000

SEQ ID NO: 1534         moltype =    length =
SEQUENCE: 1534
000

SEQ ID NO: 1535         moltype =    length =
SEQUENCE: 1535
000

SEQ ID NO: 1536         moltype =    length =
SEQUENCE: 1536
000

SEQ ID NO: 1537         moltype =    length =
SEQUENCE: 1537
000

SEQ ID NO: 1538         moltype =    length =
SEQUENCE: 1538
000

SEQ ID NO: 1539         moltype =    length =
SEQUENCE: 1539
000

SEQ ID NO: 1540         moltype =    length =
SEQUENCE: 1540
000

SEQ ID NO: 1541         moltype =    length =
SEQUENCE: 1541
000

SEQ ID NO: 1542         moltype =    length =
SEQUENCE: 1542
000

SEQ ID NO: 1543         moltype =    length =
SEQUENCE: 1543
000

SEQ ID NO: 1544         moltype =    length =
SEQUENCE: 1544
000

SEQ ID NO: 1545         moltype =    length =
SEQUENCE: 1545
000

SEQ ID NO: 1546         moltype =    length =
SEQUENCE: 1546
```

000

SEQ ID NO: 1547 moltype = length =
SEQUENCE: 1547
000

SEQ ID NO: 1548 moltype = length =
SEQUENCE: 1548
000

SEQ ID NO: 1549 moltype = length =
SEQUENCE: 1549
000

SEQ ID NO: 1550 moltype = length =
SEQUENCE: 1550
000

SEQ ID NO: 1551 moltype = length =
SEQUENCE: 1551
000

SEQ ID NO: 1552 moltype = length =
SEQUENCE: 1552
000

SEQ ID NO: 1553 moltype = length =
SEQUENCE: 1553
000

SEQ ID NO: 1554 moltype = length =
SEQUENCE: 1554
000

SEQ ID NO: 1555 moltype = length =
SEQUENCE: 1555
000

SEQ ID NO: 1556 moltype = length =
SEQUENCE: 1556
000

SEQ ID NO: 1557 moltype = length =
SEQUENCE: 1557
000

SEQ ID NO: 1558 moltype = length =
SEQUENCE: 1558
000

SEQ ID NO: 1559 moltype = length =
SEQUENCE: 1559
000

SEQ ID NO: 1560 moltype = length =
SEQUENCE: 1560
000

SEQ ID NO: 1561 moltype = length =
SEQUENCE: 1561
000

SEQ ID NO: 1562 moltype = length =
SEQUENCE: 1562
000

SEQ ID NO: 1563 moltype = length =
SEQUENCE: 1563
000

SEQ ID NO: 1564 moltype = length =
SEQUENCE: 1564
000

SEQ ID NO: 1565 moltype = length =
SEQUENCE: 1565
000

SEQ ID NO: 1566 moltype = length =

```
SEQUENCE: 1566
000

SEQ ID NO: 1567         moltype =     length =
SEQUENCE: 1567
000

SEQ ID NO: 1568         moltype =     length =
SEQUENCE: 1568
000

SEQ ID NO: 1569         moltype =     length =
SEQUENCE: 1569
000

SEQ ID NO: 1570         moltype =     length =
SEQUENCE: 1570
000

SEQ ID NO: 1571         moltype =     length =
SEQUENCE: 1571
000

SEQ ID NO: 1572         moltype =     length =
SEQUENCE: 1572
000

SEQ ID NO: 1573         moltype =     length =
SEQUENCE: 1573
000

SEQ ID NO: 1574         moltype =     length =
SEQUENCE: 1574
000

SEQ ID NO: 1575         moltype =     length =
SEQUENCE: 1575
000

SEQ ID NO: 1576         moltype =     length =
SEQUENCE: 1576
000

SEQ ID NO: 1577         moltype =     length =
SEQUENCE: 1577
000

SEQ ID NO: 1578         moltype =     length =
SEQUENCE: 1578
000

SEQ ID NO: 1579         moltype =     length =
SEQUENCE: 1579
000

SEQ ID NO: 1580         moltype =     length =
SEQUENCE: 1580
000

SEQ ID NO: 1581         moltype =     length =
SEQUENCE: 1581
000

SEQ ID NO: 1582         moltype =     length =
SEQUENCE: 1582
000

SEQ ID NO: 1583         moltype =     length =
SEQUENCE: 1583
000

SEQ ID NO: 1584         moltype =     length =
SEQUENCE: 1584
000

SEQ ID NO: 1585         moltype =     length =
SEQUENCE: 1585
000
```

| | | |
|---|---|---|
| SEQ ID NO: 1586
SEQUENCE: 1586
000 | moltype = | length = |
| SEQ ID NO: 1587
SEQUENCE: 1587
000 | moltype = | length = |
| SEQ ID NO: 1588
SEQUENCE: 1588
000 | moltype = | length = |
| SEQ ID NO: 1589
SEQUENCE: 1589
000 | moltype = | length = |
| SEQ ID NO: 1590
SEQUENCE: 1590
000 | moltype = | length = |
| SEQ ID NO: 1591
SEQUENCE: 1591
000 | moltype = | length = |
| SEQ ID NO: 1592
SEQUENCE: 1592
000 | moltype = | length = |
| SEQ ID NO: 1593
SEQUENCE: 1593
000 | moltype = | length = |
| SEQ ID NO: 1594
SEQUENCE: 1594
000 | moltype = | length = |
| SEQ ID NO: 1595
SEQUENCE: 1595
000 | moltype = | length = |
| SEQ ID NO: 1596
SEQUENCE: 1596
000 | moltype = | length = |
| SEQ ID NO: 1597
SEQUENCE: 1597
000 | moltype = | length = |
| SEQ ID NO: 1598
SEQUENCE: 1598
000 | moltype = | length = |
| SEQ ID NO: 1599
SEQUENCE: 1599
000 | moltype = | length = |
| SEQ ID NO: 1600
SEQUENCE: 1600
000 | moltype = | length = |
| SEQ ID NO: 1601
SEQUENCE: 1601
000 | moltype = | length = |
| SEQ ID NO: 1602
SEQUENCE: 1602
000 | moltype = | length = |
| SEQ ID NO: 1603
SEQUENCE: 1603
000 | moltype = | length = |
| SEQ ID NO: 1604
SEQUENCE: 1604
000 | moltype = | length = |
| SEQ ID NO: 1605
SEQUENCE: 1605
000 | moltype = | length = |

| | | |
|---|---|---|
| SEQ ID NO: 1606 SEQUENCE: 1606 000 | moltype = | length = |
| SEQ ID NO: 1607 SEQUENCE: 1607 000 | moltype = | length = |
| SEQ ID NO: 1608 SEQUENCE: 1608 000 | moltype = | length = |
| SEQ ID NO: 1609 SEQUENCE: 1609 000 | moltype = | length = |
| SEQ ID NO: 1610 SEQUENCE: 1610 000 | moltype = | length = |
| SEQ ID NO: 1611 SEQUENCE: 1611 000 | moltype = | length = |
| SEQ ID NO: 1612 SEQUENCE: 1612 000 | moltype = | length = |
| SEQ ID NO: 1613 SEQUENCE: 1613 000 | moltype = | length = |
| SEQ ID NO: 1614 SEQUENCE: 1614 000 | moltype = | length = |
| SEQ ID NO: 1615 SEQUENCE: 1615 000 | moltype = | length = |
| SEQ ID NO: 1616 SEQUENCE: 1616 000 | moltype = | length = |
| SEQ ID NO: 1617 SEQUENCE: 1617 000 | moltype = | length = |
| SEQ ID NO: 1618 SEQUENCE: 1618 000 | moltype = | length = |
| SEQ ID NO: 1619 SEQUENCE: 1619 000 | moltype = | length = |
| SEQ ID NO: 1620 SEQUENCE: 1620 000 | moltype = | length = |
| SEQ ID NO: 1621 SEQUENCE: 1621 000 | moltype = | length = |
| SEQ ID NO: 1622 SEQUENCE: 1622 000 | moltype = | length = |
| SEQ ID NO: 1623 SEQUENCE: 1623 000 | moltype = | length = |
| SEQ ID NO: 1624 SEQUENCE: 1624 000 | moltype = | length = |
| SEQ ID NO: 1625 SEQUENCE: 1625 | moltype = | length = |

000

SEQ ID NO: 1626         moltype =    length =
SEQUENCE: 1626
000

SEQ ID NO: 1627         moltype =    length =
SEQUENCE: 1627
000

SEQ ID NO: 1628         moltype =    length =
SEQUENCE: 1628
000

SEQ ID NO: 1629         moltype =    length =
SEQUENCE: 1629
000

SEQ ID NO: 1630         moltype =    length =
SEQUENCE: 1630
000

SEQ ID NO: 1631         moltype =    length =
SEQUENCE: 1631
000

SEQ ID NO: 1632         moltype =    length =
SEQUENCE: 1632
000

SEQ ID NO: 1633         moltype =    length =
SEQUENCE: 1633
000

SEQ ID NO: 1634         moltype =    length =
SEQUENCE: 1634
000

SEQ ID NO: 1635         moltype =    length =
SEQUENCE: 1635
000

SEQ ID NO: 1636         moltype =    length =
SEQUENCE: 1636
000

SEQ ID NO: 1637         moltype =    length =
SEQUENCE: 1637
000

SEQ ID NO: 1638         moltype =    length =
SEQUENCE: 1638
000

SEQ ID NO: 1639         moltype =    length =
SEQUENCE: 1639
000

SEQ ID NO: 1640         moltype =    length =
SEQUENCE: 1640
000

SEQ ID NO: 1641         moltype =    length =
SEQUENCE: 1641
000

SEQ ID NO: 1642         moltype =    length =
SEQUENCE: 1642
000

SEQ ID NO: 1643         moltype =    length =
SEQUENCE: 1643
000

SEQ ID NO: 1644         moltype =    length =
SEQUENCE: 1644
000

SEQ ID NO: 1645         moltype =    length =

-continued

| | | |
|---|---|---|
| SEQUENCE: 1645 000 | | |
| SEQ ID NO: 1646 SEQUENCE: 1646 000 | moltype = | length = |
| SEQ ID NO: 1647 SEQUENCE: 1647 000 | moltype = | length = |
| SEQ ID NO: 1648 SEQUENCE: 1648 000 | moltype = | length = |
| SEQ ID NO: 1649 SEQUENCE: 1649 000 | moltype = | length = |
| SEQ ID NO: 1650 SEQUENCE: 1650 000 | moltype = | length = |
| SEQ ID NO: 1651 SEQUENCE: 1651 000 | moltype = | length = |
| SEQ ID NO: 1652 SEQUENCE: 1652 000 | moltype = | length = |
| SEQ ID NO: 1653 SEQUENCE: 1653 000 | moltype = | length = |
| SEQ ID NO: 1654 SEQUENCE: 1654 000 | moltype = | length = |
| SEQ ID NO: 1655 SEQUENCE: 1655 000 | moltype = | length = |
| SEQ ID NO: 1656 SEQUENCE: 1656 000 | moltype = | length = |
| SEQ ID NO: 1657 SEQUENCE: 1657 000 | moltype = | length = |
| SEQ ID NO: 1658 SEQUENCE: 1658 000 | moltype = | length = |
| SEQ ID NO: 1659 SEQUENCE: 1659 000 | moltype = | length = |
| SEQ ID NO: 1660 SEQUENCE: 1660 000 | moltype = | length = |
| SEQ ID NO: 1661 SEQUENCE: 1661 000 | moltype = | length = |
| SEQ ID NO: 1662 SEQUENCE: 1662 000 | moltype = | length = |
| SEQ ID NO: 1663 SEQUENCE: 1663 000 | moltype = | length = |
| SEQ ID NO: 1664 SEQUENCE: 1664 000 | moltype = | length = |

| | | |
|---|---|---|
| SEQ ID NO: 1665<br>SEQUENCE: 1665<br>000 | moltype = | length = |
| SEQ ID NO: 1666<br>SEQUENCE: 1666<br>000 | moltype = | length = |
| SEQ ID NO: 1667<br>SEQUENCE: 1667<br>000 | moltype = | length = |
| SEQ ID NO: 1668<br>SEQUENCE: 1668<br>000 | moltype = | length = |
| SEQ ID NO: 1669<br>SEQUENCE: 1669<br>000 | moltype = | length = |
| SEQ ID NO: 1670<br>SEQUENCE: 1670<br>000 | moltype = | length = |
| SEQ ID NO: 1671<br>SEQUENCE: 1671<br>000 | moltype = | length = |
| SEQ ID NO: 1672<br>SEQUENCE: 1672<br>000 | moltype = | length = |
| SEQ ID NO: 1673<br>SEQUENCE: 1673<br>000 | moltype = | length = |
| SEQ ID NO: 1674<br>SEQUENCE: 1674<br>000 | moltype = | length = |
| SEQ ID NO: 1675<br>SEQUENCE: 1675<br>000 | moltype = | length = |
| SEQ ID NO: 1676<br>SEQUENCE: 1676<br>000 | moltype = | length = |
| SEQ ID NO: 1677<br>SEQUENCE: 1677<br>000 | moltype = | length = |
| SEQ ID NO: 1678<br>SEQUENCE: 1678<br>000 | moltype = | length = |
| SEQ ID NO: 1679<br>SEQUENCE: 1679<br>000 | moltype = | length = |
| SEQ ID NO: 1680<br>SEQUENCE: 1680<br>000 | moltype = | length = |
| SEQ ID NO: 1681<br>SEQUENCE: 1681<br>000 | moltype = | length = |
| SEQ ID NO: 1682<br>SEQUENCE: 1682<br>000 | moltype = | length = |
| SEQ ID NO: 1683<br>SEQUENCE: 1683<br>000 | moltype = | length = |
| SEQ ID NO: 1684<br>SEQUENCE: 1684<br>000 | moltype = | length = |

| | | |
|---|---|---|
| SEQ ID NO: 1685 SEQUENCE: 1685 000 | moltype = | length = |
| SEQ ID NO: 1686 SEQUENCE: 1686 000 | moltype = | length = |
| SEQ ID NO: 1687 SEQUENCE: 1687 000 | moltype = | length = |
| SEQ ID NO: 1688 SEQUENCE: 1688 000 | moltype = | length = |
| SEQ ID NO: 1689 SEQUENCE: 1689 000 | moltype = | length = |
| SEQ ID NO: 1690 SEQUENCE: 1690 000 | moltype = | length = |
| SEQ ID NO: 1691 SEQUENCE: 1691 000 | moltype = | length = |
| SEQ ID NO: 1692 SEQUENCE: 1692 000 | moltype = | length = |
| SEQ ID NO: 1693 SEQUENCE: 1693 000 | moltype = | length = |
| SEQ ID NO: 1694 SEQUENCE: 1694 000 | moltype = | length = |
| SEQ ID NO: 1695 SEQUENCE: 1695 000 | moltype = | length = |
| SEQ ID NO: 1696 SEQUENCE: 1696 000 | moltype = | length = |
| SEQ ID NO: 1697 SEQUENCE: 1697 000 | moltype = | length = |
| SEQ ID NO: 1698 SEQUENCE: 1698 000 | moltype = | length = |
| SEQ ID NO: 1699 SEQUENCE: 1699 000 | moltype = | length = |
| SEQ ID NO: 1700 SEQUENCE: 1700 000 | moltype = | length = |
| SEQ ID NO: 1701 SEQUENCE: 1701 000 | moltype = | length = |
| SEQ ID NO: 1702 SEQUENCE: 1702 000 | moltype = | length = |
| SEQ ID NO: 1703 SEQUENCE: 1703 000 | moltype = | length = |
| SEQ ID NO: 1704 SEQUENCE: 1704 | moltype = | length = |

| | | |
|---|---|---|
| SEQ ID NO: 1705 SEQUENCE: 1705 000 | moltype = | length = |
| SEQ ID NO: 1706 SEQUENCE: 1706 000 | moltype = | length = |
| SEQ ID NO: 1707 SEQUENCE: 1707 000 | moltype = | length = |
| SEQ ID NO: 1708 SEQUENCE: 1708 000 | moltype = | length = |
| SEQ ID NO: 1709 SEQUENCE: 1709 000 | moltype = | length = |
| SEQ ID NO: 1710 SEQUENCE: 1710 000 | moltype = | length = |
| SEQ ID NO: 1711 SEQUENCE: 1711 000 | moltype = | length = |
| SEQ ID NO: 1712 SEQUENCE: 1712 000 | moltype = | length = |
| SEQ ID NO: 1713 SEQUENCE: 1713 000 | moltype = | length = |
| SEQ ID NO: 1714 SEQUENCE: 1714 000 | moltype = | length = |
| SEQ ID NO: 1715 SEQUENCE: 1715 000 | moltype = | length = |
| SEQ ID NO: 1716 SEQUENCE: 1716 000 | moltype = | length = |
| SEQ ID NO: 1717 SEQUENCE: 1717 000 | moltype = | length = |
| SEQ ID NO: 1718 SEQUENCE: 1718 000 | moltype = | length = |
| SEQ ID NO: 1719 SEQUENCE: 1719 000 | moltype = | length = |
| SEQ ID NO: 1720 SEQUENCE: 1720 000 | moltype = | length = |
| SEQ ID NO: 1721 SEQUENCE: 1721 000 | moltype = | length = |
| SEQ ID NO: 1722 SEQUENCE: 1722 000 | moltype = | length = |
| SEQ ID NO: 1723 SEQUENCE: 1723 000 | moltype = | length = |
| SEQ ID NO: 1724 | moltype = DNA | length = 12 |

```
FEATURE                 Location/Qualifiers
source                  1..12
                        mol_type = other DNA
                        organism = synthetic construct
SEQUENCE: 1724
agaaagaggc ga                                                           12

SEQ ID NO: 1725         moltype = DNA   length = 12
FEATURE                 Location/Qualifiers
source                  1..12
                        mol_type = other DNA
                        organism = synthetic construct
SEQUENCE: 1725
cgggccaagc gg                                                           12

SEQ ID NO: 1726         moltype = DNA   length = 54
FEATURE                 Location/Qualifiers
source                  1..54
                        mol_type = other DNA
                        organism = synthetic construct
SEQUENCE: 1726
gagggcagag gaagtcttct aacatgcggt gacgtggagg agaatcccgg ccct             54

SEQ ID NO: 1727         moltype = DNA   length = 75
FEATURE                 Location/Qualifiers
source                  1..75
                        mol_type = other DNA
                        organism = synthetic construct
SEQUENCE: 1727
ggaagcggag tgaaacagac tttgaatttt gaccttctca agttggcggg agacgtggag       60
tccaaccctg gacct                                                        75

SEQ ID NO: 1728         moltype = DNA   length = 66
FEATURE                 Location/Qualifiers
source                  1..66
                        mol_type = other DNA
                        organism = synthetic construct
SEQUENCE: 1728
ggaagcggag ctactaactt cagcctgctg aagcaggctg agacgtgga ggagaaccct        60
ggacct                                                                  66

SEQ ID NO: 1729         moltype = DNA   length = 18
FEATURE                 Location/Qualifiers
source                  1..18
                        mol_type = other DNA
                        organism = synthetic construct
SEQUENCE: 1729
tccggaggcg gcggcagc                                                     18

SEQ ID NO: 1730         moltype = DNA   length = 45
FEATURE                 Location/Qualifiers
source                  1..45
                        mol_type = other DNA
                        organism = synthetic construct
SEQUENCE: 1730
ggtggtggtg gtagcggcgg cggcggctct ggtggtggtg gatcc                       45

SEQ ID NO: 1731         moltype = DNA   length = 75
FEATURE                 Location/Qualifiers
source                  1..75
                        mol_type = other DNA
                        organism = synthetic construct
SEQUENCE: 1731
ggcggaggtg gctccggagg cggaggcagc ggcggaggtg ggtctggcgg aggcgggtgc       60
ggcggaggtg gctcc                                                        75

SEQ ID NO: 1732         moltype = DNA   length = 609
FEATURE                 Location/Qualifiers
source                  1..609
                        mol_type = other DNA
                        organism = synthetic construct
SEQUENCE: 1732
aattccgccc ctctcccccc ccccctctc cctccccccc ccctaacgtt actggccgaa        60
gccgcttgga ataaggccgg tgtgcgtttg tctatatgtt attttccacc atattgccgt      120
cttttggcaa tgtgagggcc cggaaacctg gccctgtctt cttgacgagc attcctaggg     180
gtctttcccc tctcgccaaa ggaatgcaag gtctgttgaa tgtcgtgaag gaagcagttc     240
ctctggaagc ttcttgaaga caaacaacgt ctgtagcgac cctttgcagg cagcggaacc     300
ccccacctgg cgacaggtgc ctctgcggcc aaaagccacg tgtataagat acacctgcaa     360
aggcggcaca accccagtgc cacgttgtga gttggatagt tgtggaaaga gtcaaatggc     420
```

```
tctcctcaag cgtattcaac aaggggctga aggatgccca gaaggtaccc cattgtatgg   480
gatctgatct ggggcctcgg tgcacatgct ttacatgtgt ttagtcgagg ttaaaaaaac   540
gtctaggccc cccgaaccac ggggacgtgg ttttcctttg aaaaacacga tgataatatg   600
gccacaacc                                                           609

SEQ ID NO: 1733         moltype = DNA   length = 623
FEATURE                 Location/Qualifiers
source                  1..623
                        mol_type = other DNA
                        organism = synthetic construct
SEQUENCE: 1733
taacgaattc cgcccctctc cccccccccc ctctccctcc cccccccta acgttactgg   60
ccgaagccgc ttggaataag gccggtgtgc gtttgtctat atgttatttt ccaccatatt   120
gccgtctttt ggcaatgtga gggcccggaa acctggccct gtcttcttga cgagcattcc   180
tagggggtctt tccctctcg ccaaaggaat gcaaggtctg ttgaatgtcg tgaaggaagc   240
agttcctctg gaagcttctt gaagacaaac aacgtctgta gcgacccttt gcaggcagcg   300
gaaccccca cctggcgaca ggtgcctctg cggccaaaag ccacgtgtat aagatacacc   360
tgcaaaggcg gcacaacccc agtgccacgt tgtgagttgg atagttgtgg aaagagtcaa   420
atggctctcc tcaagcgtat tcaacaaggg gctgaaggat gcccagaagg taccccattg   480
tatgggatct gatctggggc ctcggtgcac atgctttaca tgtgtttagt cgaggttaaa   540
aaaacgtcta ggcccccga accacgggga cgtggttttc ctttgaaaaa cacgatgata   600
atatggccac aaccgccgcc acc                                           623

SEQ ID NO: 1734         moltype = DNA   length = 54
FEATURE                 Location/Qualifiers
source                  1..54
                        mol_type = other DNA
                        organism = synthetic construct
SEQUENCE: 1734
gtggagagga agtgctgcgt ggagtgccca ccatgccctg cccctcctgt ggcc          54

SEQ ID NO: 1735         moltype = DNA   length = 108
FEATURE                 Location/Qualifiers
source                  1..108
                        mol_type = other DNA
                        organism = synthetic construct
SEQUENCE: 1735
gagctcaaaa ccccacttgg tgacacaact cacacatgcc cacggtgccc agagcccaaa   60
tcttgtgaca cacctccccc gtgcccacgg tgcccagcac ctgaactc                108

SEQ ID NO: 1736         moltype = DNA   length = 153
FEATURE                 Location/Qualifiers
source                  1..153
                        mol_type = other DNA
                        organism = synthetic construct
SEQUENCE: 1736
gagctcaaaa ccccacttgg tgacacaact cacacatgcc cacggtgccc agagcccaaa   60
tcttgtgaca cacctccccc gtgcccacgg tgcccagagc ccaaatcttg tgacacacct   120
ccccatgcc cacggtgccc agcacctgaa ctc                                 153

SEQ ID NO: 1737         moltype = DNA   length = 198
FEATURE                 Location/Qualifiers
source                  1..198
                        mol_type = other DNA
                        organism = synthetic construct
SEQUENCE: 1737
gagctcaaaa ccccacttgg tgacacaact cacacatgcc cacggtgccc agagcccaaa   60
tcttgtgaca cacctccccc gtgcccacgg tgcccagagc ccaaatcttg tgacacacct   120
ccccatgcc cacggtgccc agagcccaaa tcttgtgaca cacctccccc gtgcccaagg   180
tgcccagcac ctgaactc                                                 198

SEQ ID NO: 1738         moltype = DNA   length = 45
FEATURE                 Location/Qualifiers
source                  1..45
                        mol_type = other DNA
                        organism = synthetic construct
SEQUENCE: 1738
gtgcccaggg attgtggttg taagccttgc atatgtacag tccca                    45

SEQ ID NO: 1739         moltype = DNA   length = 18
FEATURE                 Location/Qualifiers
source                  1..18
                        mol_type = other DNA
                        organism = synthetic construct
SEQUENCE: 1739
gtgcccaggg attgtggt                                                  18

SEQ ID NO: 1740         moltype =    length =
SEQUENCE: 1740
```

000

SEQ ID NO: 1741         moltype =    length =
SEQUENCE: 1741
000

SEQ ID NO: 1742         moltype =    length =
SEQUENCE: 1742
000

SEQ ID NO: 1743         moltype =    length =
SEQUENCE: 1743
000

SEQ ID NO: 1744         moltype =    length =
SEQUENCE: 1744
000

SEQ ID NO: 1745         moltype =    length =
SEQUENCE: 1745
000

SEQ ID NO: 1746         moltype =    length =
SEQUENCE: 1746
000

SEQ ID NO: 1747         moltype =    length =
SEQUENCE: 1747
000

SEQ ID NO: 1748         moltype =    length =
SEQUENCE: 1748
000

SEQ ID NO: 1749         moltype =    length =
SEQUENCE: 1749
000

SEQ ID NO: 1750         moltype =    length =
SEQUENCE: 1750
000

SEQ ID NO: 1751         moltype =    length =
SEQUENCE: 1751
000

SEQ ID NO: 1752         moltype =    length =
SEQUENCE: 1752
000

SEQ ID NO: 1753         moltype =    length =
SEQUENCE: 1753
000

SEQ ID NO: 1754         moltype =    length =
SEQUENCE: 1754
000

SEQ ID NO: 1755         moltype =    length =
SEQUENCE: 1755
000

SEQ ID NO: 1756         moltype =    length =
SEQUENCE: 1756
000

SEQ ID NO: 1757         moltype =    length =
SEQUENCE: 1757
000

SEQ ID NO: 1758         moltype =    length =
SEQUENCE: 1758
000

SEQ ID NO: 1759         moltype =    length =
SEQUENCE: 1759
000

SEQ ID NO: 1760         moltype =    length =

| | | |
|---|---|---|
| SEQUENCE: 1760 000 | | |
| SEQ ID NO: 1761 SEQUENCE: 1761 000 | moltype = | length = |
| SEQ ID NO: 1762 SEQUENCE: 1762 000 | moltype = | length = |
| SEQ ID NO: 1763 SEQUENCE: 1763 000 | moltype = | length = |
| SEQ ID NO: 1764 SEQUENCE: 1764 000 | moltype = | length = |
| SEQ ID NO: 1765 SEQUENCE: 1765 000 | moltype = | length = |
| SEQ ID NO: 1766 SEQUENCE: 1766 000 | moltype = | length = |
| SEQ ID NO: 1767 SEQUENCE: 1767 000 | moltype = | length = |
| SEQ ID NO: 1768 SEQUENCE: 1768 000 | moltype = | length = |
| SEQ ID NO: 1769 SEQUENCE: 1769 000 | moltype = | length = |
| SEQ ID NO: 1770 SEQUENCE: 1770 000 | moltype = | length = |
| SEQ ID NO: 1771 SEQUENCE: 1771 000 | moltype = | length = |
| SEQ ID NO: 1772 SEQUENCE: 1772 000 | moltype = | length = |
| SEQ ID NO: 1773 SEQUENCE: 1773 000 | moltype = | length = |
| SEQ ID NO: 1774 SEQUENCE: 1774 000 | moltype = | length = |
| SEQ ID NO: 1775 SEQUENCE: 1775 000 | moltype = | length = |
| SEQ ID NO: 1776 SEQUENCE: 1776 000 | moltype = | length = |
| SEQ ID NO: 1777 SEQUENCE: 1777 000 | moltype = | length = |
| SEQ ID NO: 1778 SEQUENCE: 1778 000 | moltype = | length = |
| SEQ ID NO: 1779 SEQUENCE: 1779 000 | moltype = | length = |

| | | |
|---|---|---|
| SEQ ID NO: 1780<br>SEQUENCE: 1780<br>000 | moltype = | length = |
| SEQ ID NO: 1781<br>SEQUENCE: 1781<br>000 | moltype = | length = |
| SEQ ID NO: 1782<br>SEQUENCE: 1782<br>000 | moltype = | length = |
| SEQ ID NO: 1783<br>SEQUENCE: 1783<br>000 | moltype = | length = |
| SEQ ID NO: 1784<br>SEQUENCE: 1784<br>000 | moltype = | length = |
| SEQ ID NO: 1785<br>SEQUENCE: 1785<br>000 | moltype = | length = |
| SEQ ID NO: 1786<br>SEQUENCE: 1786<br>000 | moltype = | length = |
| SEQ ID NO: 1787<br>SEQUENCE: 1787<br>000 | moltype = | length = |
| SEQ ID NO: 1788<br>SEQUENCE: 1788<br>000 | moltype = | length = |
| SEQ ID NO: 1789<br>SEQUENCE: 1789<br>000 | moltype = | length = |
| SEQ ID NO: 1790<br>SEQUENCE: 1790<br>000 | moltype = | length = |
| SEQ ID NO: 1791<br>SEQUENCE: 1791<br>000 | moltype = | length = |
| SEQ ID NO: 1792<br>SEQUENCE: 1792<br>000 | moltype = | length = |
| SEQ ID NO: 1793<br>SEQUENCE: 1793<br>000 | moltype = | length = |
| SEQ ID NO: 1794<br>SEQUENCE: 1794<br>000 | moltype = | length = |
| SEQ ID NO: 1795<br>SEQUENCE: 1795<br>000 | moltype = | length = |
| SEQ ID NO: 1796<br>SEQUENCE: 1796<br>000 | moltype = | length = |
| SEQ ID NO: 1797<br>SEQUENCE: 1797<br>000 | moltype = | length = |
| SEQ ID NO: 1798<br>SEQUENCE: 1798<br>000 | moltype = | length = |
| SEQ ID NO: 1799<br>SEQUENCE: 1799<br>000 | moltype = | length = |

| | | |
|---|---|---|
| SEQ ID NO: 1800<br>SEQUENCE: 1800<br>000 | moltype = | length = |
| SEQ ID NO: 1801<br>SEQUENCE: 1801<br>000 | moltype = | length = |
| SEQ ID NO: 1802<br>SEQUENCE: 1802<br>000 | moltype = | length = |
| SEQ ID NO: 1803<br>SEQUENCE: 1803<br>000 | moltype = | length = |
| SEQ ID NO: 1804<br>SEQUENCE: 1804<br>000 | moltype = | length = |
| SEQ ID NO: 1805<br>SEQUENCE: 1805<br>000 | moltype = | length = |
| SEQ ID NO: 1806<br>SEQUENCE: 1806<br>000 | moltype = | length = |
| SEQ ID NO: 1807<br>SEQUENCE: 1807<br>000 | moltype = | length = |
| SEQ ID NO: 1808<br>SEQUENCE: 1808<br>000 | moltype = | length = |
| SEQ ID NO: 1809<br>SEQUENCE: 1809<br>000 | moltype = | length = |
| SEQ ID NO: 1810<br>SEQUENCE: 1810<br>000 | moltype = | length = |
| SEQ ID NO: 1811<br>SEQUENCE: 1811<br>000 | moltype = | length = |
| SEQ ID NO: 1812<br>SEQUENCE: 1812<br>000 | moltype = | length = |
| SEQ ID NO: 1813<br>SEQUENCE: 1813<br>000 | moltype = | length = |
| SEQ ID NO: 1814<br>SEQUENCE: 1814<br>000 | moltype = | length = |
| SEQ ID NO: 1815<br>SEQUENCE: 1815<br>000 | moltype = | length = |
| SEQ ID NO: 1816<br>SEQUENCE: 1816<br>000 | moltype = | length = |
| SEQ ID NO: 1817<br>SEQUENCE: 1817<br>000 | moltype = | length = |
| SEQ ID NO: 1818<br>SEQUENCE: 1818<br>000 | moltype = | length = |
| SEQ ID NO: 1819<br>SEQUENCE: 1819 | moltype = | length = |

000

SEQ ID NO: 1820          moltype =     length =
SEQUENCE: 1820
000

SEQ ID NO: 1821          moltype =     length =
SEQUENCE: 1821
000

SEQ ID NO: 1822          moltype =     length =
SEQUENCE: 1822
000

SEQ ID NO: 1823          moltype =     length =
SEQUENCE: 1823
000

SEQ ID NO: 1824          moltype =     length =
SEQUENCE: 1824
000

SEQ ID NO: 1825          moltype =     length =
SEQUENCE: 1825
000

SEQ ID NO: 1826          moltype =     length =
SEQUENCE: 1826
000

SEQ ID NO: 1827          moltype =     length =
SEQUENCE: 1827
000

SEQ ID NO: 1828          moltype =     length =
SEQUENCE: 1828
000

SEQ ID NO: 1829          moltype =     length =
SEQUENCE: 1829
000

SEQ ID NO: 1830          moltype =     length =
SEQUENCE: 1830
000

SEQ ID NO: 1831          moltype =     length =
SEQUENCE: 1831
000

SEQ ID NO: 1832          moltype =     length =
SEQUENCE: 1832
000

SEQ ID NO: 1833          moltype =     length =
SEQUENCE: 1833
000

SEQ ID NO: 1834          moltype =     length =
SEQUENCE: 1834
000

SEQ ID NO: 1835          moltype =     length =
SEQUENCE: 1835
000

SEQ ID NO: 1836          moltype =     length =
SEQUENCE: 1836
000

SEQ ID NO: 1837          moltype =     length =
SEQUENCE: 1837
000

SEQ ID NO: 1838          moltype =     length =
SEQUENCE: 1838
000

SEQ ID NO: 1839          moltype =     length =

```
SEQUENCE: 1839
000

SEQ ID NO: 1840        moltype =     length =
SEQUENCE: 1840
000

SEQ ID NO: 1841        moltype =     length =
SEQUENCE: 1841
000

SEQ ID NO: 1842        moltype =     length =
SEQUENCE: 1842
000

SEQ ID NO: 1843        moltype =     length =
SEQUENCE: 1843
000

SEQ ID NO: 1844        moltype =     length =
SEQUENCE: 1844
000

SEQ ID NO: 1845        moltype =     length =
SEQUENCE: 1845
000

SEQ ID NO: 1846        moltype =     length =
SEQUENCE: 1846
000

SEQ ID NO: 1847        moltype =     length =
SEQUENCE: 1847
000

SEQ ID NO: 1848        moltype =     length =
SEQUENCE: 1848
000

SEQ ID NO: 1849        moltype =     length =
SEQUENCE: 1849
000

SEQ ID NO: 1850        moltype =     length =
SEQUENCE: 1850
000

SEQ ID NO: 1851        moltype =     length =
SEQUENCE: 1851
000

SEQ ID NO: 1852        moltype =     length =
SEQUENCE: 1852
000

SEQ ID NO: 1853        moltype =     length =
SEQUENCE: 1853
000

SEQ ID NO: 1854        moltype =     length =
SEQUENCE: 1854
000

SEQ ID NO: 1855        moltype =     length =
SEQUENCE: 1855
000

SEQ ID NO: 1856        moltype =     length =
SEQUENCE: 1856
000

SEQ ID NO: 1857        moltype =     length =
SEQUENCE: 1857
000

SEQ ID NO: 1858        moltype =     length =
SEQUENCE: 1858
000
```

| | | |
|---|---|---|
| SEQ ID NO: 1859 SEQUENCE: 1859 | moltype = | length = 000 |
| SEQ ID NO: 1860 SEQUENCE: 1860 | moltype = | length = 000 |
| SEQ ID NO: 1861 SEQUENCE: 1861 | moltype = | length = 000 |
| SEQ ID NO: 1862 SEQUENCE: 1862 | moltype = | length = 000 |
| SEQ ID NO: 1863 SEQUENCE: 1863 | moltype = | length = 000 |
| SEQ ID NO: 1864 SEQUENCE: 1864 | moltype = | length = 000 |
| SEQ ID NO: 1865 SEQUENCE: 1865 | moltype = | length = 000 |
| SEQ ID NO: 1866 SEQUENCE: 1866 | moltype = | length = 000 |
| SEQ ID NO: 1867 SEQUENCE: 1867 | moltype = | length = 000 |
| SEQ ID NO: 1868 SEQUENCE: 1868 | moltype = | length = 000 |
| SEQ ID NO: 1869 SEQUENCE: 1869 | moltype = | length = 000 |
| SEQ ID NO: 1870 SEQUENCE: 1870 | moltype = | length = 000 |
| SEQ ID NO: 1871 SEQUENCE: 1871 | moltype = | length = 000 |
| SEQ ID NO: 1872 SEQUENCE: 1872 | moltype = | length = 000 |
| SEQ ID NO: 1873 SEQUENCE: 1873 | moltype = | length = 000 |
| SEQ ID NO: 1874 SEQUENCE: 1874 | moltype = | length = 000 |
| SEQ ID NO: 1875 SEQUENCE: 1875 | moltype = | length = 000 |
| SEQ ID NO: 1876 SEQUENCE: 1876 | moltype = | length = 000 |
| SEQ ID NO: 1877 SEQUENCE: 1877 | moltype = | length = 000 |
| SEQ ID NO: 1878 SEQUENCE: 1878 | moltype = | length = 000 |

| | | |
|---|---|---|
| SEQ ID NO: 1879 SEQUENCE: 1879 000 | moltype = | length = |
| SEQ ID NO: 1880 SEQUENCE: 1880 000 | moltype = | length = |
| SEQ ID NO: 1881 SEQUENCE: 1881 000 | moltype = | length = |
| SEQ ID NO: 1882 SEQUENCE: 1882 000 | moltype = | length = |
| SEQ ID NO: 1883 SEQUENCE: 1883 000 | moltype = | length = |
| SEQ ID NO: 1884 SEQUENCE: 1884 000 | moltype = | length = |
| SEQ ID NO: 1885 SEQUENCE: 1885 000 | moltype = | length = |
| SEQ ID NO: 1886 SEQUENCE: 1886 000 | moltype = | length = |
| SEQ ID NO: 1887 SEQUENCE: 1887 000 | moltype = | length = |
| SEQ ID NO: 1888 SEQUENCE: 1888 000 | moltype = | length = |
| SEQ ID NO: 1889 SEQUENCE: 1889 000 | moltype = | length = |
| SEQ ID NO: 1890 SEQUENCE: 1890 000 | moltype = | length = |
| SEQ ID NO: 1891 SEQUENCE: 1891 000 | moltype = | length = |
| SEQ ID NO: 1892 SEQUENCE: 1892 000 | moltype = | length = |
| SEQ ID NO: 1893 SEQUENCE: 1893 000 | moltype = | length = |
| SEQ ID NO: 1894 SEQUENCE: 1894 000 | moltype = | length = |
| SEQ ID NO: 1895 SEQUENCE: 1895 000 | moltype = | length = |
| SEQ ID NO: 1896 SEQUENCE: 1896 000 | moltype = | length = |
| SEQ ID NO: 1897 SEQUENCE: 1897 000 | moltype = | length = |
| SEQ ID NO: 1898 SEQUENCE: 1898 | moltype = | length = |

000

SEQ ID NO: 1899        moltype =     length =
SEQUENCE: 1899
000

SEQ ID NO: 1900        moltype =     length =
SEQUENCE: 1900
000

SEQ ID NO: 1901        moltype =     length =
SEQUENCE: 1901
000

SEQ ID NO: 1902        moltype =     length =
SEQUENCE: 1902
000

SEQ ID NO: 1903        moltype =     length =
SEQUENCE: 1903
000

SEQ ID NO: 1904        moltype =     length =
SEQUENCE: 1904
000

SEQ ID NO: 1905        moltype =     length =
SEQUENCE: 1905
000

SEQ ID NO: 1906        moltype =     length =
SEQUENCE: 1906
000

SEQ ID NO: 1907        moltype =     length =
SEQUENCE: 1907
000

SEQ ID NO: 1908        moltype =     length =
SEQUENCE: 1908
000

SEQ ID NO: 1909        moltype =     length =
SEQUENCE: 1909
000

SEQ ID NO: 1910        moltype =     length =
SEQUENCE: 1910
000

SEQ ID NO: 1911        moltype =     length =
SEQUENCE: 1911
000

SEQ ID NO: 1912        moltype =     length =
SEQUENCE: 1912
000

SEQ ID NO: 1913        moltype =     length =
SEQUENCE: 1913
000

SEQ ID NO: 1914        moltype =     length =
SEQUENCE: 1914
000

SEQ ID NO: 1915        moltype =     length =
SEQUENCE: 1915
000

SEQ ID NO: 1916        moltype =     length =
SEQUENCE: 1916
000

SEQ ID NO: 1917        moltype =     length =
SEQUENCE: 1917
000

SEQ ID NO: 1918        moltype =     length =

-continued

```
SEQUENCE: 1918
000

SEQ ID NO: 1919          moltype =   length =
SEQUENCE: 1919
000

SEQ ID NO: 1920          moltype =   length =
SEQUENCE: 1920
000

SEQ ID NO: 1921          moltype =   length =
SEQUENCE: 1921
000

SEQ ID NO: 1922          moltype =   length =
SEQUENCE: 1922
000

SEQ ID NO: 1923          moltype =   length =
SEQUENCE: 1923
000

SEQ ID NO: 1924          moltype =   length =
SEQUENCE: 1924
000

SEQ ID NO: 1925          moltype =   length =
SEQUENCE: 1925
000

SEQ ID NO: 1926          moltype =   length =
SEQUENCE: 1926
000

SEQ ID NO: 1927          moltype =   length =
SEQUENCE: 1927
000

SEQ ID NO: 1928          moltype =   length =
SEQUENCE: 1928
000

SEQ ID NO: 1929          moltype =   length =
SEQUENCE: 1929
000

SEQ ID NO: 1930          moltype =   length =
SEQUENCE: 1930
000

SEQ ID NO: 1931          moltype =   length =
SEQUENCE: 1931
000

SEQ ID NO: 1932          moltype =   length =
SEQUENCE: 1932
000

SEQ ID NO: 1933          moltype =   length =
SEQUENCE: 1933
000

SEQ ID NO: 1934          moltype =   length =
SEQUENCE: 1934
000

SEQ ID NO: 1935          moltype =   length =
SEQUENCE: 1935
000

SEQ ID NO: 1936          moltype =   length =
SEQUENCE: 1936
000

SEQ ID NO: 1937          moltype =   length =
SEQUENCE: 1937
000
```

| | | |
|---|---|---|
| SEQ ID NO: 1938 SEQUENCE: 1938 000 | moltype = | length = |
| SEQ ID NO: 1939 SEQUENCE: 1939 000 | moltype = | length = |
| SEQ ID NO: 1940 SEQUENCE: 1940 000 | moltype = | length = |
| SEQ ID NO: 1941 SEQUENCE: 1941 000 | moltype = | length = |
| SEQ ID NO: 1942 SEQUENCE: 1942 000 | moltype = | length = |
| SEQ ID NO: 1943 SEQUENCE: 1943 000 | moltype = | length = |
| SEQ ID NO: 1944 SEQUENCE: 1944 000 | moltype = | length = |
| SEQ ID NO: 1945 SEQUENCE: 1945 000 | moltype = | length = |
| SEQ ID NO: 1946 SEQUENCE: 1946 000 | moltype = | length = |
| SEQ ID NO: 1947 SEQUENCE: 1947 000 | moltype = | length = |
| SEQ ID NO: 1948 SEQUENCE: 1948 000 | moltype = | length = |
| SEQ ID NO: 1949 SEQUENCE: 1949 000 | moltype = | length = |
| SEQ ID NO: 1950 SEQUENCE: 1950 000 | moltype = | length = |
| SEQ ID NO: 1951 SEQUENCE: 1951 000 | moltype = | length = |
| SEQ ID NO: 1952 SEQUENCE: 1952 000 | moltype = | length = |
| SEQ ID NO: 1953 SEQUENCE: 1953 000 | moltype = | length = |
| SEQ ID NO: 1954 SEQUENCE: 1954 000 | moltype = | length = |
| SEQ ID NO: 1955 SEQUENCE: 1955 000 | moltype = | length = |
| SEQ ID NO: 1956 SEQUENCE: 1956 000 | moltype = | length = |
| SEQ ID NO: 1957 SEQUENCE: 1957 000 | moltype = | length = |

SEQ ID NO: 1958		moltype =	length =
SEQUENCE: 1958
000

SEQ ID NO: 1959		moltype =	length =
SEQUENCE: 1959
000

SEQ ID NO: 1960		moltype =	length =
SEQUENCE: 1960
000

SEQ ID NO: 1961		moltype =	length =
SEQUENCE: 1961
000

SEQ ID NO: 1962		moltype =	length =
SEQUENCE: 1962
000

SEQ ID NO: 1963		moltype =	length =
SEQUENCE: 1963
000

SEQ ID NO: 1964		moltype =	length =
SEQUENCE: 1964
000

SEQ ID NO: 1965		moltype =	length =
SEQUENCE: 1965
000

SEQ ID NO: 1966		moltype =	length =
SEQUENCE: 1966
000

SEQ ID NO: 1967		moltype =	length =
SEQUENCE: 1967
000

SEQ ID NO: 1968		moltype =	length =
SEQUENCE: 1968
000

SEQ ID NO: 1969		moltype =	length =
SEQUENCE: 1969
000

SEQ ID NO: 1970		moltype =	length =
SEQUENCE: 1970
000

SEQ ID NO: 1971		moltype =	length =
SEQUENCE: 1971
000

SEQ ID NO: 1972		moltype =	length =
SEQUENCE: 1972
000

SEQ ID NO: 1973		moltype =	length =
SEQUENCE: 1973
000

SEQ ID NO: 1974		moltype =	length =
SEQUENCE: 1974
000

SEQ ID NO: 1975		moltype =	length =
SEQUENCE: 1975
000

SEQ ID NO: 1976		moltype =	length =
SEQUENCE: 1976
000

SEQ ID NO: 1977		moltype =	length =
SEQUENCE: 1977

-continued

000

SEQ ID NO: 1978          moltype =    length =
SEQUENCE: 1978
000

SEQ ID NO: 1979          moltype =    length =
SEQUENCE: 1979
000

SEQ ID NO: 1980          moltype =    length =
SEQUENCE: 1980
000

SEQ ID NO: 1981          moltype =    length =
SEQUENCE: 1981
000

SEQ ID NO: 1982          moltype =    length =
SEQUENCE: 1982
000

SEQ ID NO: 1983          moltype =    length =
SEQUENCE: 1983
000

SEQ ID NO: 1984          moltype =    length =
SEQUENCE: 1984
000

SEQ ID NO: 1985          moltype =    length =
SEQUENCE: 1985
000

SEQ ID NO: 1986          moltype =    length =
SEQUENCE: 1986
000

SEQ ID NO: 1987          moltype =    length =
SEQUENCE: 1987
000

SEQ ID NO: 1988          moltype =    length =
SEQUENCE: 1988
000

SEQ ID NO: 1989          moltype =    length =
SEQUENCE: 1989
000

SEQ ID NO: 1990          moltype =    length =
SEQUENCE: 1990
000

SEQ ID NO: 1991          moltype =    length =
SEQUENCE: 1991
000

SEQ ID NO: 1992          moltype =    length =
SEQUENCE: 1992
000

SEQ ID NO: 1993          moltype =    length =
SEQUENCE: 1993
000

SEQ ID NO: 1994          moltype =    length =
SEQUENCE: 1994
000

SEQ ID NO: 1995          moltype =    length =
SEQUENCE: 1995
000

SEQ ID NO: 1996          moltype =    length =
SEQUENCE: 1996
000

SEQ ID NO: 1997          moltype =    length =

-continued

| | | |
|---|---|---|
| SEQ ID NO: 1997 SEQUENCE: 1997 000 | moltype = | length = |
| SEQ ID NO: 1998 SEQUENCE: 1998 000 | moltype = | length = |
| SEQ ID NO: 1999 SEQUENCE: 1999 000 | moltype = | length = |
| SEQ ID NO: 2000 SEQUENCE: 2000 000 | moltype = | length = |
| SEQ ID NO: 2001 SEQUENCE: 2001 000 | moltype = | length = |
| SEQ ID NO: 2002 SEQUENCE: 2002 000 | moltype = | length = |
| SEQ ID NO: 2003 SEQUENCE: 2003 000 | moltype = | length = |
| SEQ ID NO: 2004 SEQUENCE: 2004 000 | moltype = | length = |
| SEQ ID NO: 2005 SEQUENCE: 2005 000 | moltype = | length = |
| SEQ ID NO: 2006 SEQUENCE: 2006 000 | moltype = | length = |
| SEQ ID NO: 2007 SEQUENCE: 2007 000 | moltype = | length = |
| SEQ ID NO: 2008 SEQUENCE: 2008 000 | moltype = | length = |
| SEQ ID NO: 2009 SEQUENCE: 2009 000 | moltype = | length = |
| SEQ ID NO: 2010 SEQUENCE: 2010 000 | moltype = | length = |
| SEQ ID NO: 2011 SEQUENCE: 2011 000 | moltype = | length = |
| SEQ ID NO: 2012 SEQUENCE: 2012 000 | moltype = | length = |
| SEQ ID NO: 2013 SEQUENCE: 2013 000 | moltype = | length = |
| SEQ ID NO: 2014 SEQUENCE: 2014 000 | moltype = | length = |
| SEQ ID NO: 2015 SEQUENCE: 2015 000 | moltype = | length = |
| SEQ ID NO: 2016 SEQUENCE: 2016 000 | moltype = | length = |

| | | |
|---|---|---|
| SEQ ID NO: 2017 SEQUENCE: 2017 000 | moltype = | length = |
| SEQ ID NO: 2018 SEQUENCE: 2018 000 | moltype = | length = |
| SEQ ID NO: 2019 SEQUENCE: 2019 000 | moltype = | length = |
| SEQ ID NO: 2020 SEQUENCE: 2020 000 | moltype = | length = |
| SEQ ID NO: 2021 SEQUENCE: 2021 000 | moltype = | length = |
| SEQ ID NO: 2022 SEQUENCE: 2022 000 | moltype = | length = |
| SEQ ID NO: 2023 SEQUENCE: 2023 000 | moltype = | length = |
| SEQ ID NO: 2024 SEQUENCE: 2024 000 | moltype = | length = |
| SEQ ID NO: 2025 SEQUENCE: 2025 000 | moltype = | length = |
| SEQ ID NO: 2026 SEQUENCE: 2026 000 | moltype = | length = |
| SEQ ID NO: 2027 SEQUENCE: 2027 000 | moltype = | length = |
| SEQ ID NO: 2028 SEQUENCE: 2028 000 | moltype = | length = |
| SEQ ID NO: 2029 SEQUENCE: 2029 000 | moltype = | length = |
| SEQ ID NO: 2030 SEQUENCE: 2030 000 | moltype = | length = |
| SEQ ID NO: 2031 SEQUENCE: 2031 000 | moltype = | length = |
| SEQ ID NO: 2032 SEQUENCE: 2032 000 | moltype = | length = |
| SEQ ID NO: 2033 SEQUENCE: 2033 000 | moltype = | length = |
| SEQ ID NO: 2034 SEQUENCE: 2034 000 | moltype = | length = |
| SEQ ID NO: 2035 SEQUENCE: 2035 000 | moltype = | length = |
| SEQ ID NO: 2036 SEQUENCE: 2036 000 | moltype = | length = |

| | | |
|---|---|---|
| SEQ ID NO: 2037<br>SEQUENCE: 2037<br>000 | moltype = | length = |
| SEQ ID NO: 2038<br>SEQUENCE: 2038<br>000 | moltype = | length = |
| SEQ ID NO: 2039<br>SEQUENCE: 2039<br>000 | moltype = | length = |
| SEQ ID NO: 2040<br>SEQUENCE: 2040<br>000 | moltype = | length = |
| SEQ ID NO: 2041<br>SEQUENCE: 2041<br>000 | moltype = | length = |
| SEQ ID NO: 2042<br>SEQUENCE: 2042<br>000 | moltype = | length = |
| SEQ ID NO: 2043<br>SEQUENCE: 2043<br>000 | moltype = | length = |
| SEQ ID NO: 2044<br>SEQUENCE: 2044<br>000 | moltype = | length = |
| SEQ ID NO: 2045<br>SEQUENCE: 2045<br>000 | moltype = | length = |
| SEQ ID NO: 2046<br>SEQUENCE: 2046<br>000 | moltype = | length = |
| SEQ ID NO: 2047<br>SEQUENCE: 2047<br>000 | moltype = | length = |
| SEQ ID NO: 2048<br>SEQUENCE: 2048<br>000 | moltype = | length = |
| SEQ ID NO: 2049<br>SEQUENCE: 2049<br>000 | moltype = | length = |
| SEQ ID NO: 2050<br>SEQUENCE: 2050<br>000 | moltype = | length = |
| SEQ ID NO: 2051<br>SEQUENCE: 2051<br>000 | moltype = | length = |
| SEQ ID NO: 2052<br>SEQUENCE: 2052<br>000 | moltype = | length = |
| SEQ ID NO: 2053<br>SEQUENCE: 2053<br>000 | moltype = | length = |
| SEQ ID NO: 2054<br>SEQUENCE: 2054<br>000 | moltype = | length = |
| SEQ ID NO: 2055<br>SEQUENCE: 2055<br>000 | moltype = | length = |
| SEQ ID NO: 2056<br>SEQUENCE: 2056 | moltype = | length = |

000

SEQ ID NO: 2057 moltype = length =
SEQUENCE: 2057
000

SEQ ID NO: 2058 moltype = length =
SEQUENCE: 2058
000

SEQ ID NO: 2059 moltype = length =
SEQUENCE: 2059
000

SEQ ID NO: 2060 moltype = length =
SEQUENCE: 2060
000

SEQ ID NO: 2061 moltype = length =
SEQUENCE: 2061
000

SEQ ID NO: 2062 moltype = length =
SEQUENCE: 2062
000

SEQ ID NO: 2063 moltype = length =
SEQUENCE: 2063
000

SEQ ID NO: 2064 moltype = length =
SEQUENCE: 2064
000

SEQ ID NO: 2065 moltype = length =
SEQUENCE: 2065
000

SEQ ID NO: 2066 moltype = length =
SEQUENCE: 2066
000

SEQ ID NO: 2067 moltype = length =
SEQUENCE: 2067
000

SEQ ID NO: 2068 moltype = length =
SEQUENCE: 2068
000

SEQ ID NO: 2069 moltype = length =
SEQUENCE: 2069
000

SEQ ID NO: 2070 moltype = length =
SEQUENCE: 2070
000

SEQ ID NO: 2071 moltype = length =
SEQUENCE: 2071
000

SEQ ID NO: 2072 moltype = length =
SEQUENCE: 2072
000

SEQ ID NO: 2073 moltype = length =
SEQUENCE: 2073
000

SEQ ID NO: 2074 moltype = length =
SEQUENCE: 2074
000

SEQ ID NO: 2075 moltype = length =
SEQUENCE: 2075
000

SEQ ID NO: 2076 moltype = length =

| | | |
|---|---|---|
| SEQ ID NO: 2077<br>SEQUENCE: 2077<br>000 | moltype = | length = |
| SEQ ID NO: 2078<br>SEQUENCE: 2078<br>000 | moltype = | length = |
| SEQ ID NO: 2079<br>SEQUENCE: 2079<br>000 | moltype = | length = |
| SEQ ID NO: 2080<br>SEQUENCE: 2080<br>000 | moltype = | length = |
| SEQ ID NO: 2081<br>SEQUENCE: 2081<br>000 | moltype = | length = |
| SEQ ID NO: 2082<br>SEQUENCE: 2082<br>000 | moltype = | length = |
| SEQ ID NO: 2083<br>SEQUENCE: 2083<br>000 | moltype = | length = |
| SEQ ID NO: 2084<br>SEQUENCE: 2084<br>000 | moltype = | length = |
| SEQ ID NO: 2085<br>SEQUENCE: 2085<br>000 | moltype = | length = |
| SEQ ID NO: 2086<br>SEQUENCE: 2086<br>000 | moltype = | length = |
| SEQ ID NO: 2087<br>SEQUENCE: 2087<br>000 | moltype = | length = |
| SEQ ID NO: 2088<br>SEQUENCE: 2088<br>000 | moltype = | length = |
| SEQ ID NO: 2089<br>SEQUENCE: 2089<br>000 | moltype = | length = |
| SEQ ID NO: 2090<br>SEQUENCE: 2090<br>000 | moltype = | length = |
| SEQ ID NO: 2091<br>SEQUENCE: 2091<br>000 | moltype = | length = |
| SEQ ID NO: 2092<br>SEQUENCE: 2092<br>000 | moltype = | length = |
| SEQ ID NO: 2093<br>SEQUENCE: 2093<br>000 | moltype = | length = |
| SEQ ID NO: 2094<br>SEQUENCE: 2094<br>000 | moltype = | length = |
| SEQ ID NO: 2095<br>SEQUENCE: 2095<br>000 | moltype = | length = |

-continued

| SEQ ID NO: 2096 | moltype = | length = |
|---|---|---|
| SEQUENCE: 2096 | | |
| 000 | | |

| SEQ ID NO: 2097 | moltype = | length = |
|---|---|---|
| SEQUENCE: 2097 | | |
| 000 | | |

| SEQ ID NO: 2098 | moltype = | length = |
|---|---|---|
| SEQUENCE: 2098 | | |
| 000 | | |

| SEQ ID NO: 2099 | moltype = | length = |
|---|---|---|
| SEQUENCE: 2099 | | |
| 000 | | |

| SEQ ID NO: 2100 | moltype = | length = |
|---|---|---|
| SEQUENCE: 2100 | | |
| 000 | | |

| SEQ ID NO: 2101 | moltype = | length = |
|---|---|---|
| SEQUENCE: 2101 | | |
| 000 | | |

| SEQ ID NO: 2102 | moltype = | length = |
|---|---|---|
| SEQUENCE: 2102 | | |
| 000 | | |

| SEQ ID NO: 2103 | moltype = | length = |
|---|---|---|
| SEQUENCE: 2103 | | |
| 000 | | |

| SEQ ID NO: 2104 | moltype = | length = |
|---|---|---|
| SEQUENCE: 2104 | | |
| 000 | | |

| SEQ ID NO: 2105 | moltype = | length = |
|---|---|---|
| SEQUENCE: 2105 | | |
| 000 | | |

| SEQ ID NO: 2106 | moltype = | length = |
|---|---|---|
| SEQUENCE: 2106 | | |
| 000 | | |

| SEQ ID NO: 2107 | moltype = | length = |
|---|---|---|
| SEQUENCE: 2107 | | |
| 000 | | |

| SEQ ID NO: 2108 | moltype = | length = |
|---|---|---|
| SEQUENCE: 2108 | | |
| 000 | | |

| SEQ ID NO: 2109 | moltype = | length = |
|---|---|---|
| SEQUENCE: 2109 | | |
| 000 | | |

| SEQ ID NO: 2110 | moltype = | length = |
|---|---|---|
| SEQUENCE: 2110 | | |
| 000 | | |

| SEQ ID NO: 2111 | moltype = | length = |
|---|---|---|
| SEQUENCE: 2111 | | |
| 000 | | |

| SEQ ID NO: 2112 | moltype = | length = |
|---|---|---|
| SEQUENCE: 2112 | | |
| 000 | | |

| SEQ ID NO: 2113 | moltype = | length = |
|---|---|---|
| SEQUENCE: 2113 | | |
| 000 | | |

| SEQ ID NO: 2114 | moltype = | length = |
|---|---|---|
| SEQUENCE: 2114 | | |
| 000 | | |

| SEQ ID NO: 2115 | moltype = | length = |
|---|---|---|
| SEQUENCE: 2115 | | |
| 000 | | |

SEQ ID NO: 2116         moltype =          length =
SEQUENCE: 2116
000

SEQ ID NO: 2117         moltype =          length =
SEQUENCE: 2117
000

SEQ ID NO: 2118         moltype =          length =
SEQUENCE: 2118
000

SEQ ID NO: 2119         moltype =          length =
SEQUENCE: 2119
000

SEQ ID NO: 2120         moltype =          length =
SEQUENCE: 2120
000

SEQ ID NO: 2121         moltype =          length =
SEQUENCE: 2121
000

SEQ ID NO: 2122         moltype =          length =
SEQUENCE: 2122
000

SEQ ID NO: 2123         moltype =          length =
SEQUENCE: 2123
000

SEQ ID NO: 2124         moltype =          length =
SEQUENCE: 2124
000

SEQ ID NO: 2125         moltype =          length =
SEQUENCE: 2125
000

SEQ ID NO: 2126         moltype =          length =
SEQUENCE: 2126
000

SEQ ID NO: 2127         moltype =          length =
SEQUENCE: 2127
000

SEQ ID NO: 2128         moltype =          length =
SEQUENCE: 2128
000

SEQ ID NO: 2129         moltype =          length =
SEQUENCE: 2129
000

SEQ ID NO: 2130         moltype =          length =
SEQUENCE: 2130
000

SEQ ID NO: 2131         moltype =          length =
SEQUENCE: 2131
000

SEQ ID NO: 2132         moltype =          length =
SEQUENCE: 2132
000

SEQ ID NO: 2133         moltype =          length =
SEQUENCE: 2133
000

SEQ ID NO: 2134         moltype =          length =
SEQUENCE: 2134
000

SEQ ID NO: 2135         moltype =          length =
SEQUENCE: 2135

000

SEQ ID NO: 2136          moltype =      length =
SEQUENCE: 2136
000

SEQ ID NO: 2137          moltype =      length =
SEQUENCE: 2137
000

SEQ ID NO: 2138          moltype =      length =
SEQUENCE: 2138
000

SEQ ID NO: 2139          moltype =      length =
SEQUENCE: 2139
000

SEQ ID NO: 2140          moltype =      length =
SEQUENCE: 2140
000

SEQ ID NO: 2141          moltype =      length =
SEQUENCE: 2141
000

SEQ ID NO: 2142          moltype =      length =
SEQUENCE: 2142
000

SEQ ID NO: 2143          moltype =      length =
SEQUENCE: 2143
000

SEQ ID NO: 2144          moltype =      length =
SEQUENCE: 2144
000

SEQ ID NO: 2145          moltype =      length =
SEQUENCE: 2145
000

SEQ ID NO: 2146          moltype =      length =
SEQUENCE: 2146
000

SEQ ID NO: 2147          moltype =      length =
SEQUENCE: 2147
000

SEQ ID NO: 2148          moltype =      length =
SEQUENCE: 2148
000

SEQ ID NO: 2149          moltype =      length =
SEQUENCE: 2149
000

SEQ ID NO: 2150          moltype =      length =
SEQUENCE: 2150
000

SEQ ID NO: 2151          moltype =      length =
SEQUENCE: 2151
000

SEQ ID NO: 2152          moltype =      length =
SEQUENCE: 2152
000

SEQ ID NO: 2153          moltype =      length =
SEQUENCE: 2153
000

SEQ ID NO: 2154          moltype =      length =
SEQUENCE: 2154
000

SEQ ID NO: 2155          moltype =      length =

| | | |
|---|---|---|
| SEQUENCE: 2155 000 | | |
| SEQ ID NO: 2156 SEQUENCE: 2156 000 | moltype = | length = |
| SEQ ID NO: 2157 SEQUENCE: 2157 000 | moltype = | length = |
| SEQ ID NO: 2158 SEQUENCE: 2158 000 | moltype = | length = |
| SEQ ID NO: 2159 SEQUENCE: 2159 000 | moltype = | length = |
| SEQ ID NO: 2160 SEQUENCE: 2160 000 | moltype = | length = |
| SEQ ID NO: 2161 SEQUENCE: 2161 000 | moltype = | length = |
| SEQ ID NO: 2162 SEQUENCE: 2162 000 | moltype = | length = |
| SEQ ID NO: 2163 SEQUENCE: 2163 000 | moltype = | length = |
| SEQ ID NO: 2164 SEQUENCE: 2164 000 | moltype = | length = |
| SEQ ID NO: 2165 SEQUENCE: 2165 000 | moltype = | length = |
| SEQ ID NO: 2166 SEQUENCE: 2166 000 | moltype = | length = |
| SEQ ID NO: 2167 SEQUENCE: 2167 000 | moltype = | length = |
| SEQ ID NO: 2168 SEQUENCE: 2168 000 | moltype = | length = |
| SEQ ID NO: 2169 SEQUENCE: 2169 000 | moltype = | length = |
| SEQ ID NO: 2170 SEQUENCE: 2170 000 | moltype = | length = |
| SEQ ID NO: 2171 SEQUENCE: 2171 000 | moltype = | length = |
| SEQ ID NO: 2172 SEQUENCE: 2172 000 | moltype = | length = |
| SEQ ID NO: 2173 SEQUENCE: 2173 000 | moltype = | length = |
| SEQ ID NO: 2174 SEQUENCE: 2174 000 | moltype = | length = |

| | | |
|---|---|---|
| SEQ ID NO: 2175<br>SEQUENCE: 2175<br>000 | moltype = | length = |
| SEQ ID NO: 2176<br>SEQUENCE: 2176<br>000 | moltype = | length = |
| SEQ ID NO: 2177<br>SEQUENCE: 2177<br>000 | moltype = | length = |
| SEQ ID NO: 2178<br>SEQUENCE: 2178<br>000 | moltype = | length = |
| SEQ ID NO: 2179<br>SEQUENCE: 2179<br>000 | moltype = | length = |
| SEQ ID NO: 2180<br>SEQUENCE: 2180<br>000 | moltype = | length = |
| SEQ ID NO: 2181<br>SEQUENCE: 2181<br>000 | moltype = | length = |
| SEQ ID NO: 2182<br>SEQUENCE: 2182<br>000 | moltype = | length = |
| SEQ ID NO: 2183<br>SEQUENCE: 2183<br>000 | moltype = | length = |
| SEQ ID NO: 2184<br>SEQUENCE: 2184<br>000 | moltype = | length = |
| SEQ ID NO: 2185<br>SEQUENCE: 2185<br>000 | moltype = | length = |
| SEQ ID NO: 2186<br>SEQUENCE: 2186<br>000 | moltype = | length = |
| SEQ ID NO: 2187<br>SEQUENCE: 2187<br>000 | moltype = | length = |
| SEQ ID NO: 2188<br>SEQUENCE: 2188<br>000 | moltype = | length = |
| SEQ ID NO: 2189<br>SEQUENCE: 2189<br>000 | moltype = | length = |
| SEQ ID NO: 2190<br>SEQUENCE: 2190<br>000 | moltype = | length = |
| SEQ ID NO: 2191<br>SEQUENCE: 2191<br>000 | moltype = | length = |
| SEQ ID NO: 2192<br>SEQUENCE: 2192<br>000 | moltype = | length = |
| SEQ ID NO: 2193<br>SEQUENCE: 2193<br>000 | moltype = | length = |
| SEQ ID NO: 2194<br>SEQUENCE: 2194<br>000 | moltype = | length = |

SEQ ID NO: 2195        moltype =     length =
SEQUENCE: 2195
000

SEQ ID NO: 2196        moltype =     length =
SEQUENCE: 2196
000

SEQ ID NO: 2197        moltype =     length =
SEQUENCE: 2197
000

SEQ ID NO: 2198        moltype =     length =
SEQUENCE: 2198
000

SEQ ID NO: 2199        moltype =     length =
SEQUENCE: 2199
000

SEQ ID NO: 2200        moltype =     length =
SEQUENCE: 2200
000

SEQ ID NO: 2201        moltype =     length =
SEQUENCE: 2201
000

SEQ ID NO: 2202        moltype =     length =
SEQUENCE: 2202
000

SEQ ID NO: 2203        moltype =     length =
SEQUENCE: 2203
000

SEQ ID NO: 2204        moltype =     length =
SEQUENCE: 2204
000

SEQ ID NO: 2205        moltype =     length =
SEQUENCE: 2205
000

SEQ ID NO: 2206        moltype =     length =
SEQUENCE: 2206
000

SEQ ID NO: 2207        moltype =     length =
SEQUENCE: 2207
000

SEQ ID NO: 2208        moltype =     length =
SEQUENCE: 2208
000

SEQ ID NO: 2209        moltype =     length =
SEQUENCE: 2209
000

SEQ ID NO: 2210        moltype =     length =
SEQUENCE: 2210
000

SEQ ID NO: 2211        moltype =     length =
SEQUENCE: 2211
000

SEQ ID NO: 2212        moltype =     length =
SEQUENCE: 2212
000

SEQ ID NO: 2213        moltype =     length =
SEQUENCE: 2213
000

SEQ ID NO: 2214        moltype =     length =
SEQUENCE: 2214

000

SEQ ID NO: 2215    moltype =    length =
SEQUENCE: 2215
000

SEQ ID NO: 2216    moltype =    length =
SEQUENCE: 2216
000

SEQ ID NO: 2217    moltype =    length =
SEQUENCE: 2217
000

SEQ ID NO: 2218    moltype =    length =
SEQUENCE: 2218
000

SEQ ID NO: 2219    moltype =    length =
SEQUENCE: 2219
000

SEQ ID NO: 2220    moltype =    length =
SEQUENCE: 2220
000

SEQ ID NO: 2221    moltype =    length =
SEQUENCE: 2221
000

SEQ ID NO: 2222    moltype =    length =
SEQUENCE: 2222
000

SEQ ID NO: 2223    moltype =    length =
SEQUENCE: 2223
000

SEQ ID NO: 2224    moltype =    length =
SEQUENCE: 2224
000

SEQ ID NO: 2225    moltype =    length =
SEQUENCE: 2225
000

SEQ ID NO: 2226    moltype =    length =
SEQUENCE: 2226
000

SEQ ID NO: 2227    moltype =    length =
SEQUENCE: 2227
000

SEQ ID NO: 2228    moltype =    length =
SEQUENCE: 2228
000

SEQ ID NO: 2229    moltype =    length =
SEQUENCE: 2229
000

SEQ ID NO: 2230    moltype =    length =
SEQUENCE: 2230
000

SEQ ID NO: 2231    moltype =    length =
SEQUENCE: 2231
000

SEQ ID NO: 2232    moltype =    length =
SEQUENCE: 2232
000

SEQ ID NO: 2233    moltype =    length =
SEQUENCE: 2233
000

SEQ ID NO: 2234    moltype =    length =

```
SEQUENCE: 2234
000

SEQ ID NO: 2235        moltype =    length =
SEQUENCE: 2235
000

SEQ ID NO: 2236        moltype =    length =
SEQUENCE: 2236
000

SEQ ID NO: 2237        moltype =    length =
SEQUENCE: 2237
000

SEQ ID NO: 2238        moltype =    length =
SEQUENCE: 2238
000

SEQ ID NO: 2239        moltype =    length =
SEQUENCE: 2239
000

SEQ ID NO: 2240        moltype =    length =
SEQUENCE: 2240
000

SEQ ID NO: 2241        moltype =    length =
SEQUENCE: 2241
000

SEQ ID NO: 2242        moltype =    length =
SEQUENCE: 2242
000

SEQ ID NO: 2243        moltype =    length =
SEQUENCE: 2243
000

SEQ ID NO: 2244        moltype = DNA  length = 198
FEATURE                Location/Qualifiers
source                 1..198
                       mol_type = other DNA
                       organism = synthetic construct
SEQUENCE: 2244
gagctcaaaa ccccacttgg tgacacaact cacacatgcc cacggtgccc agagcccaaa    60
tcttgtgaca cacctccccc gtgcccacgg tgcccagagc ccaaatcttg tgacacaact   120
cacacatgcc cacggtgccc agagcccaaa tcttgtgaca cacctccccc gtgcccaagg   180
tgcccagcac ctgaactc                                                 198

SEQ ID NO: 2245        moltype = DNA  length = 15
FEATURE                Location/Qualifiers
source                 1..15
                       mol_type = other DNA
                       organism = synthetic construct
SEQUENCE: 2245
ggtggtggtg gatcc                                                    15

SEQ ID NO: 2246        moltype = DNA  length = 30
FEATURE                Location/Qualifiers
source                 1..30
                       mol_type = other DNA
                       organism = synthetic construct
SEQUENCE: 2246
ggtggtggtg gatccggtgg tggtggatcc                                    30

SEQ ID NO: 2247        moltype = DNA  length = 45
FEATURE                Location/Qualifiers
source                 1..45
                       mol_type = other DNA
                       organism = synthetic construct
SEQUENCE: 2247
ggtggtggtg gatccggtgg tggtggatcc ggtggtggtg gatcc                   45

SEQ ID NO: 2248        moltype = DNA  length = 60
FEATURE                Location/Qualifiers
source                 1..60
                       mol_type = other DNA
                       organism = synthetic construct
```

```
SEQUENCE: 2248
ggtggtggtg gatccggtgg tggtggatcc ggtggtggtg gatccggtgg tggtggatcc   60

SEQ ID NO: 2249         moltype = DNA  length = 75
FEATURE                 Location/Qualifiers
source                  1..75
                        mol_type = other DNA
                        organism = synthetic construct
SEQUENCE: 2249
ggtggtggtg gtagcggcgg cggcggctct ggtggtggtg gatccggtgg tggtggatcc   60
ggtggtggtg gatcc                                                    75

SEQ ID NO: 2250         moltype = DNA  length = 75
FEATURE                 Location/Qualifiers
source                  1..75
                        mol_type = other DNA
                        organism = synthetic construct
SEQUENCE: 2250
ggtggtggtg gatccggtgg tggtggatcc ggtggtggtg gatccggtgg tggtggatcc   60
ggtggtggtg gatcc                                                    75

SEQ ID NO: 2251         moltype = DNA  length = 90
FEATURE                 Location/Qualifiers
source                  1..90
                        mol_type = other DNA
                        organism = synthetic construct
SEQUENCE: 2251
ggtggtggtg gtagcggcgg cggcggctct ggtggtggtg gatccggtgg tggtggatcc   60
ggtggtggtg gatccggtgg tggtggatcc                                    90

SEQ ID NO: 2252         moltype = DNA  length = 120
FEATURE                 Location/Qualifiers
source                  1..120
                        mol_type = other DNA
                        organism = synthetic construct
SEQUENCE: 2252
ggtggtggtg gtagcggcgg cggcggctct ggtggtggtg gatccggtgg tggtggatcc   60
ggtggtggtg gatccggtgg tggtggatcc ggtggtggtg gatccggtgg tggtggatcc  120

SEQ ID NO: 2253         moltype = DNA  length = 120
FEATURE                 Location/Qualifiers
source                  1..120
                        mol_type = other DNA
                        organism = synthetic construct
SEQUENCE: 2253
ggtggtggtg gatccggtgg tggtggatcc ggtggtggtg gatccggtgg tggtggatcc   60
ggtggtggtg gatccggtgg tggtggatcc ggtggtggtg gatccggtgg tggtggatcc  120

SEQ ID NO: 2254         moltype = DNA  length = 60
FEATURE                 Location/Qualifiers
source                  1..60
                        mol_type = other DNA
                        organism = synthetic construct
SEQUENCE: 2254
ggtggtggtg gtagcggcgg cggcggctct ggtggtggtg gatccggtgg tggtggatcc   60

SEQ ID NO: 2255         moltype =     length =
SEQUENCE: 2255
000

SEQ ID NO: 2256         moltype =     length =
SEQUENCE: 2256
000

SEQ ID NO: 2257         moltype =     length =
SEQUENCE: 2257
000

SEQ ID NO: 2258         moltype =     length =
SEQUENCE: 2258
000

SEQ ID NO: 2259         moltype = DNA  length = 90
FEATURE                 Location/Qualifiers
source                  1..90
                        mol_type = other DNA
                        organism = synthetic construct
SEQUENCE: 2259
ggtggtggtg gatccggtgg tggtggatcc ggtggtggtg gatccggtgg tggtggatcc   60
```
ggtggtggtg gatccggtgg tggtggatcc                                            90

SEQ ID NO: 2260       moltype =    length =
SEQUENCE: 2260
000

SEQ ID NO: 2261       moltype =    length =
SEQUENCE: 2261
000

SEQ ID NO: 2262       moltype =    length =
SEQUENCE: 2262
000

SEQ ID NO: 2263       moltype =    length =
SEQUENCE: 2263
000

SEQ ID NO: 2264       moltype =    length =
SEQUENCE: 2264
000

SEQ ID NO: 2265       moltype =    length =
SEQUENCE: 2265
000

SEQ ID NO: 2266       moltype =    length =
SEQUENCE: 2266
000

SEQ ID NO: 2267       moltype =    length =
SEQUENCE: 2267
000

SEQ ID NO: 2268       moltype =    length =
SEQUENCE: 2268
000

SEQ ID NO: 2269       moltype =    length =
SEQUENCE: 2269
000

SEQ ID NO: 2270       moltype =    length =
SEQUENCE: 2270
000

SEQ ID NO: 2271       moltype =    length =
SEQUENCE: 2271
000

SEQ ID NO: 2272       moltype =    length =
SEQUENCE: 2272
000

SEQ ID NO: 2273       moltype =    length =
SEQUENCE: 2273
000

SEQ ID NO: 2274       moltype =    length =
SEQUENCE: 2274
000

SEQ ID NO: 2275       moltype =    length =
SEQUENCE: 2275
000

SEQ ID NO: 2276       moltype =    length =
SEQUENCE: 2276
000

SEQ ID NO: 2277       moltype =    length =
SEQUENCE: 2277
000

SEQ ID NO: 2278       moltype =    length =
SEQUENCE: 2278
000

SEQ ID NO: 2279       moltype =    length =

| | | |
|---|---|---|
| SEQUENCE: 2279 000 | | |
| SEQ ID NO: 2280 SEQUENCE: 2280 000 | moltype = | length = |
| SEQ ID NO: 2281 SEQUENCE: 2281 000 | moltype = | length = |
| SEQ ID NO: 2282 SEQUENCE: 2282 000 | moltype = | length = |
| SEQ ID NO: 2283 SEQUENCE: 2283 000 | moltype = | length = |
| SEQ ID NO: 2284 SEQUENCE: 2284 000 | moltype = | length = |
| SEQ ID NO: 2285 SEQUENCE: 2285 000 | moltype = | length = |
| SEQ ID NO: 2286 SEQUENCE: 2286 000 | moltype = | length = |
| SEQ ID NO: 2287 SEQUENCE: 2287 000 | moltype = | length = |
| SEQ ID NO: 2288 SEQUENCE: 2288 000 | moltype = | length = |
| SEQ ID NO: 2289 SEQUENCE: 2289 000 | moltype = | length = |
| SEQ ID NO: 2290 SEQUENCE: 2290 000 | moltype = | length = |
| SEQ ID NO: 2291 SEQUENCE: 2291 000 | moltype = | length = |
| SEQ ID NO: 2292 SEQUENCE: 2292 000 | moltype = | length = |
| SEQ ID NO: 2293 SEQUENCE: 2293 000 | moltype = | length = |
| SEQ ID NO: 2294 SEQUENCE: 2294 000 | moltype = | length = |
| SEQ ID NO: 2295 SEQUENCE: 2295 000 | moltype = | length = |
| SEQ ID NO: 2296 SEQUENCE: 2296 000 | moltype = | length = |
| SEQ ID NO: 2297 SEQUENCE: 2297 000 | moltype = | length = |
| SEQ ID NO: 2298 SEQUENCE: 2298 000 | moltype = | length = |

| | | |
|---|---|---|
| SEQ ID NO: 2299<br>SEQUENCE: 2299<br>000 | moltype = | length = |
| SEQ ID NO: 2300<br>SEQUENCE: 2300<br>000 | moltype = | length = |
| SEQ ID NO: 2301<br>SEQUENCE: 2301<br>000 | moltype = | length = |
| SEQ ID NO: 2302<br>SEQUENCE: 2302<br>000 | moltype = | length = |
| SEQ ID NO: 2303<br>SEQUENCE: 2303<br>000 | moltype = | length = |
| SEQ ID NO: 2304<br>SEQUENCE: 2304<br>000 | moltype = | length = |
| SEQ ID NO: 2305<br>SEQUENCE: 2305<br>000 | moltype = | length = |
| SEQ ID NO: 2306<br>SEQUENCE: 2306<br>000 | moltype = | length = |
| SEQ ID NO: 2307<br>SEQUENCE: 2307<br>000 | moltype = | length = |
| SEQ ID NO: 2308<br>SEQUENCE: 2308<br>000 | moltype = | length = |
| SEQ ID NO: 2309<br>SEQUENCE: 2309<br>000 | moltype = | length = |
| SEQ ID NO: 2310<br>SEQUENCE: 2310<br>000 | moltype = | length = |
| SEQ ID NO: 2311<br>SEQUENCE: 2311<br>000 | moltype = | length = |
| SEQ ID NO: 2312<br>SEQUENCE: 2312<br>000 | moltype = | length = |
| SEQ ID NO: 2313<br>SEQUENCE: 2313<br>000 | moltype = | length = |
| SEQ ID NO: 2314<br>SEQUENCE: 2314<br>000 | moltype = | length = |
| SEQ ID NO: 2315<br>SEQUENCE: 2315<br>000 | moltype = | length = |
| SEQ ID NO: 2316<br>SEQUENCE: 2316<br>000 | moltype = | length = |
| SEQ ID NO: 2317<br>SEQUENCE: 2317<br>000 | moltype = | length = |
| SEQ ID NO: 2318<br>SEQUENCE: 2318<br>000 | moltype = | length = |

| | | |
|---|---|---|
| SEQ ID NO: 2319 SEQUENCE: 2319 000 | moltype = | length = |
| SEQ ID NO: 2320 SEQUENCE: 2320 000 | moltype = | length = |
| SEQ ID NO: 2321 SEQUENCE: 2321 000 | moltype = | length = |
| SEQ ID NO: 2322 SEQUENCE: 2322 000 | moltype = | length = |
| SEQ ID NO: 2323 SEQUENCE: 2323 000 | moltype = | length = |
| SEQ ID NO: 2324 SEQUENCE: 2324 000 | moltype = | length = |
| SEQ ID NO: 2325 SEQUENCE: 2325 000 | moltype = | length = |
| SEQ ID NO: 2326 SEQUENCE: 2326 000 | moltype = | length = |
| SEQ ID NO: 2327 SEQUENCE: 2327 000 | moltype = | length = |
| SEQ ID NO: 2328 SEQUENCE: 2328 000 | moltype = | length = |
| SEQ ID NO: 2329 SEQUENCE: 2329 000 | moltype = | length = |
| SEQ ID NO: 2330 SEQUENCE: 2330 000 | moltype = | length = |
| SEQ ID NO: 2331 SEQUENCE: 2331 000 | moltype = | length = |
| SEQ ID NO: 2332 SEQUENCE: 2332 000 | moltype = | length = |
| SEQ ID NO: 2333 SEQUENCE: 2333 000 | moltype = | length = |
| SEQ ID NO: 2334 SEQUENCE: 2334 000 | moltype = | length = |
| SEQ ID NO: 2335 SEQUENCE: 2335 000 | moltype = | length = |
| SEQ ID NO: 2336 SEQUENCE: 2336 000 | moltype = | length = |
| SEQ ID NO: 2337 SEQUENCE: 2337 000 | moltype = | length = |
| SEQ ID NO: 2338 SEQUENCE: 2338 | moltype = | length = |

000

SEQ ID NO: 2339        moltype =     length =
SEQUENCE: 2339
000

SEQ ID NO: 2340        moltype =     length =
SEQUENCE: 2340
000

SEQ ID NO: 2341        moltype =     length =
SEQUENCE: 2341
000

SEQ ID NO: 2342        moltype =     length =
SEQUENCE: 2342
000

SEQ ID NO: 2343        moltype =     length =
SEQUENCE: 2343
000

SEQ ID NO: 2344        moltype =     length =
SEQUENCE: 2344
000

SEQ ID NO: 2345        moltype =     length =
SEQUENCE: 2345
000

SEQ ID NO: 2346        moltype =     length =
SEQUENCE: 2346
000

SEQ ID NO: 2347        moltype =     length =
SEQUENCE: 2347
000

SEQ ID NO: 2348        moltype =     length =
SEQUENCE: 2348
000

SEQ ID NO: 2349        moltype =     length =
SEQUENCE: 2349
000

SEQ ID NO: 2350        moltype =     length =
SEQUENCE: 2350
000

SEQ ID NO: 2351        moltype =     length =
SEQUENCE: 2351
000

SEQ ID NO: 2352        moltype =     length =
SEQUENCE: 2352
000

SEQ ID NO: 2353        moltype =     length =
SEQUENCE: 2353
000

SEQ ID NO: 2354        moltype =     length =
SEQUENCE: 2354
000

SEQ ID NO: 2355        moltype =     length =
SEQUENCE: 2355
000

SEQ ID NO: 2356        moltype =     length =
SEQUENCE: 2356
000

SEQ ID NO: 2357        moltype =     length =
SEQUENCE: 2357
000

SEQ ID NO: 2358        moltype =     length =

| | | |
|---|---|---|
| SEQUENCE: 2358 000 | | |
| SEQ ID NO: 2359 SEQUENCE: 2359 000 | moltype = | length = |
| SEQ ID NO: 2360 SEQUENCE: 2360 000 | moltype = | length = |
| SEQ ID NO: 2361 SEQUENCE: 2361 000 | moltype = | length = |
| SEQ ID NO: 2362 SEQUENCE: 2362 000 | moltype = | length = |
| SEQ ID NO: 2363 SEQUENCE: 2363 000 | moltype = | length = |
| SEQ ID NO: 2364 SEQUENCE: 2364 000 | moltype = | length = |
| SEQ ID NO: 2365 SEQUENCE: 2365 000 | moltype = | length = |
| SEQ ID NO: 2366 SEQUENCE: 2366 000 | moltype = | length = |
| SEQ ID NO: 2367 SEQUENCE: 2367 000 | moltype = | length = |
| SEQ ID NO: 2368 SEQUENCE: 2368 000 | moltype = | length = |
| SEQ ID NO: 2369 SEQUENCE: 2369 000 | moltype = | length = |
| SEQ ID NO: 2370 SEQUENCE: 2370 000 | moltype = | length = |
| SEQ ID NO: 2371 SEQUENCE: 2371 000 | moltype = | length = |
| SEQ ID NO: 2372 SEQUENCE: 2372 000 | moltype = | length = |
| SEQ ID NO: 2373 SEQUENCE: 2373 000 | moltype = | length = |
| SEQ ID NO: 2374 SEQUENCE: 2374 000 | moltype = | length = |
| SEQ ID NO: 2375 SEQUENCE: 2375 000 | moltype = | length = |
| SEQ ID NO: 2376 SEQUENCE: 2376 000 | moltype = | length = |
| SEQ ID NO: 2377 SEQUENCE: 2377 000 | moltype = | length = |

| | | |
|---|---|---|
| SEQ ID NO: 2378<br>SEQUENCE: 2378 | moltype = | length = 000 |
| SEQ ID NO: 2379<br>SEQUENCE: 2379 | moltype = | length = 000 |
| SEQ ID NO: 2380<br>SEQUENCE: 2380 | moltype = | length = 000 |
| SEQ ID NO: 2381<br>SEQUENCE: 2381 | moltype = | length = 000 |
| SEQ ID NO: 2382<br>SEQUENCE: 2382 | moltype = | length = 000 |
| SEQ ID NO: 2383<br>SEQUENCE: 2383 | moltype = | length = 000 |
| SEQ ID NO: 2384<br>SEQUENCE: 2384 | moltype = | length = 000 |
| SEQ ID NO: 2385<br>SEQUENCE: 2385 | moltype = | length = 000 |
| SEQ ID NO: 2386<br>SEQUENCE: 2386 | moltype = | length = 000 |
| SEQ ID NO: 2387<br>SEQUENCE: 2387 | moltype = | length = 000 |
| SEQ ID NO: 2388<br>SEQUENCE: 2388 | moltype = | length = 000 |
| SEQ ID NO: 2389<br>SEQUENCE: 2389 | moltype = | length = 000 |
| SEQ ID NO: 2390<br>SEQUENCE: 2390 | moltype = | length = 000 |
| SEQ ID NO: 2391<br>SEQUENCE: 2391 | moltype = | length = 000 |
| SEQ ID NO: 2392<br>SEQUENCE: 2392 | moltype = | length = 000 |
| SEQ ID NO: 2393<br>SEQUENCE: 2393 | moltype = | length = 000 |
| SEQ ID NO: 2394<br>SEQUENCE: 2394 | moltype = | length = 000 |
| SEQ ID NO: 2395<br>SEQUENCE: 2395 | moltype = | length = 000 |
| SEQ ID NO: 2396<br>SEQUENCE: 2396 | moltype = | length = 000 |
| SEQ ID NO: 2397<br>SEQUENCE: 2397 | moltype = | length = 000 |

| | | |
|---|---|---|
| SEQ ID NO: 2398<br>SEQUENCE: 2398<br>000 | moltype = | length = |
| SEQ ID NO: 2399<br>SEQUENCE: 2399<br>000 | moltype = | length = |
| SEQ ID NO: 2400<br>SEQUENCE: 2400<br>000 | moltype = | length = |
| SEQ ID NO: 2401<br>SEQUENCE: 2401<br>000 | moltype = | length = |
| SEQ ID NO: 2402<br>SEQUENCE: 2402<br>000 | moltype = | length = |
| SEQ ID NO: 2403<br>SEQUENCE: 2403<br>000 | moltype = | length = |
| SEQ ID NO: 2404<br>SEQUENCE: 2404<br>000 | moltype = | length = |
| SEQ ID NO: 2405<br>SEQUENCE: 2405<br>000 | moltype = | length = |
| SEQ ID NO: 2406<br>SEQUENCE: 2406<br>000 | moltype = | length = |
| SEQ ID NO: 2407<br>SEQUENCE: 2407<br>000 | moltype = | length = |
| SEQ ID NO: 2408<br>SEQUENCE: 2408<br>000 | moltype = | length = |
| SEQ ID NO: 2409<br>SEQUENCE: 2409<br>000 | moltype = | length = |
| SEQ ID NO: 2410<br>SEQUENCE: 2410<br>000 | moltype = | length = |
| SEQ ID NO: 2411<br>SEQUENCE: 2411<br>000 | moltype = | length = |
| SEQ ID NO: 2412<br>SEQUENCE: 2412<br>000 | moltype = | length = |
| SEQ ID NO: 2413<br>SEQUENCE: 2413<br>000 | moltype = | length = |
| SEQ ID NO: 2414<br>SEQUENCE: 2414<br>000 | moltype = | length = |
| SEQ ID NO: 2415<br>SEQUENCE: 2415<br>000 | moltype = | length = |
| SEQ ID NO: 2416<br>SEQUENCE: 2416<br>000 | moltype = | length = |
| SEQ ID NO: 2417<br>SEQUENCE: 2417 | moltype = | length = |

-continued

000

SEQ ID NO: 2418    moltype =    length =
SEQUENCE: 2418
000

SEQ ID NO: 2419    moltype =    length =
SEQUENCE: 2419
000

SEQ ID NO: 2420    moltype =    length =
SEQUENCE: 2420
000

SEQ ID NO: 2421    moltype =    length =
SEQUENCE: 2421
000

SEQ ID NO: 2422    moltype =    length =
SEQUENCE: 2422
000

SEQ ID NO: 2423    moltype =    length =
SEQUENCE: 2423
000

SEQ ID NO: 2424    moltype =    length =
SEQUENCE: 2424
000

SEQ ID NO: 2425    moltype =    length =
SEQUENCE: 2425
000

SEQ ID NO: 2426    moltype =    length =
SEQUENCE: 2426
000

SEQ ID NO: 2427    moltype =    length =
SEQUENCE: 2427
000

SEQ ID NO: 2428    moltype =    length =
SEQUENCE: 2428
000

SEQ ID NO: 2429    moltype =    length =
SEQUENCE: 2429
000

SEQ ID NO: 2430    moltype =    length =
SEQUENCE: 2430
000

SEQ ID NO: 2431    moltype =    length =
SEQUENCE: 2431
000

SEQ ID NO: 2432    moltype =    length =
SEQUENCE: 2432
000

SEQ ID NO: 2433    moltype =    length =
SEQUENCE: 2433
000

SEQ ID NO: 2434    moltype =    length =
SEQUENCE: 2434
000

SEQ ID NO: 2435    moltype =    length =
SEQUENCE: 2435
000

SEQ ID NO: 2436    moltype =    length =
SEQUENCE: 2436
000

SEQ ID NO: 2437    moltype =    length =

-continued

SEQUENCE: 2437
000

SEQ ID NO: 2438      moltype =    length =
SEQUENCE: 2438
000

SEQ ID NO: 2439      moltype =    length =
SEQUENCE: 2439
000

SEQ ID NO: 2440      moltype =    length =
SEQUENCE: 2440
000

SEQ ID NO: 2441      moltype =    length =
SEQUENCE: 2441
000

SEQ ID NO: 2442      moltype =    length =
SEQUENCE: 2442
000

SEQ ID NO: 2443      moltype =    length =
SEQUENCE: 2443
000

SEQ ID NO: 2444      moltype =    length =
SEQUENCE: 2444
000

SEQ ID NO: 2445      moltype =    length =
SEQUENCE: 2445
000

SEQ ID NO: 2446      moltype =    length =
SEQUENCE: 2446
000

SEQ ID NO: 2447      moltype =    length =
SEQUENCE: 2447
000

SEQ ID NO: 2448      moltype =    length =
SEQUENCE: 2448
000

SEQ ID NO: 2449      moltype =    length =
SEQUENCE: 2449
000

SEQ ID NO: 2450      moltype =    length =
SEQUENCE: 2450
000

SEQ ID NO: 2451      moltype =    length =
SEQUENCE: 2451
000

SEQ ID NO: 2452      moltype =    length =
SEQUENCE: 2452
000

SEQ ID NO: 2453      moltype =    length =
SEQUENCE: 2453
000

SEQ ID NO: 2454      moltype =    length =
SEQUENCE: 2454
000

SEQ ID NO: 2455      moltype =    length =
SEQUENCE: 2455
000

SEQ ID NO: 2456      moltype =    length =
SEQUENCE: 2456
000

| | | |
|---|---|---|
| SEQ ID NO: 2457<br>SEQUENCE: 2457<br>000 | moltype = | length = |
| SEQ ID NO: 2458<br>SEQUENCE: 2458<br>000 | moltype = | length = |
| SEQ ID NO: 2459<br>SEQUENCE: 2459<br>000 | moltype = | length = |
| SEQ ID NO: 2460<br>SEQUENCE: 2460<br>000 | moltype = | length = |
| SEQ ID NO: 2461<br>SEQUENCE: 2461<br>000 | moltype = | length = |
| SEQ ID NO: 2462<br>SEQUENCE: 2462<br>000 | moltype = | length = |
| SEQ ID NO: 2463<br>SEQUENCE: 2463<br>000 | moltype = | length = |
| SEQ ID NO: 2464<br>SEQUENCE: 2464<br>000 | moltype = | length = |
| SEQ ID NO: 2465<br>SEQUENCE: 2465<br>000 | moltype = | length = |
| SEQ ID NO: 2466<br>SEQUENCE: 2466<br>000 | moltype = | length = |
| SEQ ID NO: 2467<br>SEQUENCE: 2467<br>000 | moltype = | length = |
| SEQ ID NO: 2468<br>SEQUENCE: 2468<br>000 | moltype = | length = |
| SEQ ID NO: 2469<br>SEQUENCE: 2469<br>000 | moltype = | length = |
| SEQ ID NO: 2470<br>SEQUENCE: 2470<br>000 | moltype = | length = |
| SEQ ID NO: 2471<br>SEQUENCE: 2471<br>000 | moltype = | length = |
| SEQ ID NO: 2472<br>SEQUENCE: 2472<br>000 | moltype = | length = |
| SEQ ID NO: 2473<br>SEQUENCE: 2473<br>000 | moltype = | length = |
| SEQ ID NO: 2474<br>SEQUENCE: 2474<br>000 | moltype = | length = |
| SEQ ID NO: 2475<br>SEQUENCE: 2475<br>000 | moltype = | length = |
| SEQ ID NO: 2476<br>SEQUENCE: 2476<br>000 | moltype = | length = |

SEQ ID NO: 2477    moltype =    length =
SEQUENCE: 2477
000

SEQ ID NO: 2478    moltype =    length =
SEQUENCE: 2478
000

SEQ ID NO: 2479    moltype =    length =
SEQUENCE: 2479
000

SEQ ID NO: 2480    moltype =    length =
SEQUENCE: 2480
000

SEQ ID NO: 2481    moltype =    length =
SEQUENCE: 2481
000

SEQ ID NO: 2482    moltype =    length =
SEQUENCE: 2482
000

SEQ ID NO: 2483    moltype =    length =
SEQUENCE: 2483
000

SEQ ID NO: 2484    moltype =    length =
SEQUENCE: 2484
000

SEQ ID NO: 2485    moltype =    length =
SEQUENCE: 2485
000

SEQ ID NO: 2486    moltype =    length =
SEQUENCE: 2486
000

SEQ ID NO: 2487    moltype =    length =
SEQUENCE: 2487
000

SEQ ID NO: 2488    moltype =    length =
SEQUENCE: 2488
000

SEQ ID NO: 2489    moltype =    length =
SEQUENCE: 2489
000

SEQ ID NO: 2490    moltype =    length =
SEQUENCE: 2490
000

SEQ ID NO: 2491    moltype =    length =
SEQUENCE: 2491
000

SEQ ID NO: 2492    moltype =    length =
SEQUENCE: 2492
000

SEQ ID NO: 2493    moltype =    length =
SEQUENCE: 2493
000

SEQ ID NO: 2494    moltype =    length =
SEQUENCE: 2494
000

SEQ ID NO: 2495    moltype =    length =
SEQUENCE: 2495
000

SEQ ID NO: 2496    moltype =    length =
SEQUENCE: 2496

000

SEQ ID NO: 2497         moltype =    length =
SEQUENCE: 2497
000

SEQ ID NO: 2498         moltype =    length =
SEQUENCE: 2498
000

SEQ ID NO: 2499         moltype =    length =
SEQUENCE: 2499
000

SEQ ID NO: 2500         moltype =    length =
SEQUENCE: 2500
000

SEQ ID NO: 2501         moltype =    length =
SEQUENCE: 2501
000

SEQ ID NO: 2502         moltype =    length =
SEQUENCE: 2502
000

SEQ ID NO: 2503         moltype =    length =
SEQUENCE: 2503
000

SEQ ID NO: 2504         moltype =    length =
SEQUENCE: 2504
000

SEQ ID NO: 2505         moltype =    length =
SEQUENCE: 2505
000

SEQ ID NO: 2506         moltype =    length =
SEQUENCE: 2506
000

SEQ ID NO: 2507         moltype =    length =
SEQUENCE: 2507
000

SEQ ID NO: 2508         moltype =    length =
SEQUENCE: 2508
000

SEQ ID NO: 2509         moltype =    length =
SEQUENCE: 2509
000

SEQ ID NO: 2510         moltype =    length =
SEQUENCE: 2510
000

SEQ ID NO: 2511         moltype =    length =
SEQUENCE: 2511
000

SEQ ID NO: 2512         moltype =    length =
SEQUENCE: 2512
000

SEQ ID NO: 2513         moltype =    length =
SEQUENCE: 2513
000

SEQ ID NO: 2514         moltype =    length =
SEQUENCE: 2514
000

SEQ ID NO: 2515         moltype =    length =
SEQUENCE: 2515
000

SEQ ID NO: 2516         moltype =    length =

-continued

| | | |
|---|---|---|
| SEQ ID NO: 2516 SEQUENCE: 2516 000 | | |
| SEQ ID NO: 2517 SEQUENCE: 2517 000 | moltype = | length = |
| SEQ ID NO: 2518 SEQUENCE: 2518 000 | moltype = | length = |
| SEQ ID NO: 2519 SEQUENCE: 2519 000 | moltype = | length = |
| SEQ ID NO: 2520 SEQUENCE: 2520 000 | moltype = | length = |
| SEQ ID NO: 2521 SEQUENCE: 2521 000 | moltype = | length = |
| SEQ ID NO: 2522 SEQUENCE: 2522 000 | moltype = | length = |
| SEQ ID NO: 2523 SEQUENCE: 2523 000 | moltype = | length = |
| SEQ ID NO: 2524 SEQUENCE: 2524 000 | moltype = | length = |
| SEQ ID NO: 2525 SEQUENCE: 2525 000 | moltype = | length = |
| SEQ ID NO: 2526 SEQUENCE: 2526 000 | moltype = | length = |
| SEQ ID NO: 2527 SEQUENCE: 2527 000 | moltype = | length = |
| SEQ ID NO: 2528 SEQUENCE: 2528 000 | moltype = | length = |
| SEQ ID NO: 2529 SEQUENCE: 2529 000 | moltype = | length = |
| SEQ ID NO: 2530 SEQUENCE: 2530 000 | moltype = | length = |
| SEQ ID NO: 2531 SEQUENCE: 2531 000 | moltype = | length = |
| SEQ ID NO: 2532 SEQUENCE: 2532 000 | moltype = | length = |
| SEQ ID NO: 2533 SEQUENCE: 2533 000 | moltype = | length = |
| SEQ ID NO: 2534 SEQUENCE: 2534 000 | moltype = | length = |
| SEQ ID NO: 2535 SEQUENCE: 2535 000 | moltype = | length = |

| | | |
|---|---|---|
| SEQ ID NO: 2536 SEQUENCE: 2536 | moltype = | length = 000 |
| SEQ ID NO: 2537 SEQUENCE: 2537 | moltype = | length = 000 |
| SEQ ID NO: 2538 SEQUENCE: 2538 | moltype = | length = 000 |
| SEQ ID NO: 2539 SEQUENCE: 2539 | moltype = | length = 000 |
| SEQ ID NO: 2540 SEQUENCE: 2540 | moltype = | length = 000 |
| SEQ ID NO: 2541 SEQUENCE: 2541 | moltype = | length = 000 |
| SEQ ID NO: 2542 SEQUENCE: 2542 | moltype = | length = 000 |
| SEQ ID NO: 2543 SEQUENCE: 2543 | moltype = | length = 000 |
| SEQ ID NO: 2544 SEQUENCE: 2544 | moltype = | length = 000 |
| SEQ ID NO: 2545 SEQUENCE: 2545 | moltype = | length = 000 |
| SEQ ID NO: 2546 SEQUENCE: 2546 | moltype = | length = 000 |
| SEQ ID NO: 2547 SEQUENCE: 2547 | moltype = | length = 000 |
| SEQ ID NO: 2548 SEQUENCE: 2548 | moltype = | length = 000 |
| SEQ ID NO: 2549 SEQUENCE: 2549 | moltype = | length = 000 |
| SEQ ID NO: 2550 SEQUENCE: 2550 | moltype = | length = 000 |
| SEQ ID NO: 2551 SEQUENCE: 2551 | moltype = | length = 000 |
| SEQ ID NO: 2552 SEQUENCE: 2552 | moltype = | length = 000 |
| SEQ ID NO: 2553 SEQUENCE: 2553 | moltype = | length = 000 |
| SEQ ID NO: 2554 SEQUENCE: 2554 | moltype = | length = 000 |
| SEQ ID NO: 2555 SEQUENCE: 2555 | moltype = | length = 000 |

```
SEQ ID NO: 2556       moltype =      length =
SEQUENCE: 2556
000

SEQ ID NO: 2557       moltype =      length =
SEQUENCE: 2557
000

SEQ ID NO: 2558       moltype =      length =
SEQUENCE: 2558
000

SEQ ID NO: 2559       moltype =      length =
SEQUENCE: 2559
000

SEQ ID NO: 2560       moltype =      length =
SEQUENCE: 2560
000

SEQ ID NO: 2561       moltype =      length =
SEQUENCE: 2561
000

SEQ ID NO: 2562       moltype =      length =
SEQUENCE: 2562
000

SEQ ID NO: 2563       moltype =      length =
SEQUENCE: 2563
000

SEQ ID NO: 2564       moltype =      length =
SEQUENCE: 2564
000

SEQ ID NO: 2565       moltype =      length =
SEQUENCE: 2565
000

SEQ ID NO: 2566       moltype =      length =
SEQUENCE: 2566
000

SEQ ID NO: 2567       moltype =      length =
SEQUENCE: 2567
000

SEQ ID NO: 2568       moltype =      length =
SEQUENCE: 2568
000

SEQ ID NO: 2569       moltype =      length =
SEQUENCE: 2569
000

SEQ ID NO: 2570       moltype =      length =
SEQUENCE: 2570
000

SEQ ID NO: 2571       moltype =      length =
SEQUENCE: 2571
000

SEQ ID NO: 2572       moltype =      length =
SEQUENCE: 2572
000

SEQ ID NO: 2573       moltype =      length =
SEQUENCE: 2573
000

SEQ ID NO: 2574       moltype =      length =
SEQUENCE: 2574
000

SEQ ID NO: 2575       moltype =      length =
SEQUENCE: 2575
```

-continued

SEQ ID NO: 2576     moltype =     length =
SEQUENCE: 2576
000

SEQ ID NO: 2577     moltype =     length =
SEQUENCE: 2577
000

SEQ ID NO: 2578     moltype =     length =
SEQUENCE: 2578
000

SEQ ID NO: 2579     moltype =     length =
SEQUENCE: 2579
000

SEQ ID NO: 2580     moltype =     length =
SEQUENCE: 2580
000

SEQ ID NO: 2581     moltype =     length =
SEQUENCE: 2581
000

SEQ ID NO: 2582     moltype =     length =
SEQUENCE: 2582
000

SEQ ID NO: 2583     moltype =     length =
SEQUENCE: 2583
000

SEQ ID NO: 2584     moltype =     length =
SEQUENCE: 2584
000

SEQ ID NO: 2585     moltype =     length =
SEQUENCE: 2585
000

SEQ ID NO: 2586     moltype =     length =
SEQUENCE: 2586
000

SEQ ID NO: 2587     moltype =     length =
SEQUENCE: 2587
000

SEQ ID NO: 2588     moltype =     length =
SEQUENCE: 2588
000

SEQ ID NO: 2589     moltype =     length =
SEQUENCE: 2589
000

SEQ ID NO: 2590     moltype =     length =
SEQUENCE: 2590
000

SEQ ID NO: 2591     moltype =     length =
SEQUENCE: 2591
000

SEQ ID NO: 2592     moltype =     length =
SEQUENCE: 2592
000

SEQ ID NO: 2593     moltype =     length =
SEQUENCE: 2593
000

SEQ ID NO: 2594     moltype =     length =
SEQUENCE: 2594
000

SEQ ID NO: 2595     moltype =     length =

| SEQ ID NO: 2595 SEQUENCE: 2595 000 | moltype = | length = |
|---|---|---|
| SEQ ID NO: 2596 SEQUENCE: 2596 000 | moltype = | length = |
| SEQ ID NO: 2597 SEQUENCE: 2597 000 | moltype = | length = |
| SEQ ID NO: 2598 SEQUENCE: 2598 000 | moltype = | length = |
| SEQ ID NO: 2599 SEQUENCE: 2599 000 | moltype = | length = |
| SEQ ID NO: 2600 SEQUENCE: 2600 000 | moltype = | length = |
| SEQ ID NO: 2601 SEQUENCE: 2601 000 | moltype = | length = |
| SEQ ID NO: 2602 SEQUENCE: 2602 000 | moltype = | length = |
| SEQ ID NO: 2603 SEQUENCE: 2603 000 | moltype = | length = |
| SEQ ID NO: 2604 SEQUENCE: 2604 000 | moltype = | length = |
| SEQ ID NO: 2605 SEQUENCE: 2605 000 | moltype = | length = |
| SEQ ID NO: 2606 SEQUENCE: 2606 000 | moltype = | length = |
| SEQ ID NO: 2607 SEQUENCE: 2607 000 | moltype = | length = |
| SEQ ID NO: 2608 SEQUENCE: 2608 000 | moltype = | length = |
| SEQ ID NO: 2609 SEQUENCE: 2609 000 | moltype = | length = |
| SEQ ID NO: 2610 SEQUENCE: 2610 000 | moltype = | length = |
| SEQ ID NO: 2611 SEQUENCE: 2611 000 | moltype = | length = |
| SEQ ID NO: 2612 SEQUENCE: 2612 000 | moltype = | length = |
| SEQ ID NO: 2613 SEQUENCE: 2613 000 | moltype = | length = |
| SEQ ID NO: 2614 SEQUENCE: 2614 000 | moltype = | length = |

| | | |
|---|---|---|
| SEQ ID NO: 2615<br>SEQUENCE: 2615<br>000 | moltype = | length = |
| SEQ ID NO: 2616<br>SEQUENCE: 2616<br>000 | moltype = | length = |
| SEQ ID NO: 2617<br>SEQUENCE: 2617<br>000 | moltype = | length = |
| SEQ ID NO: 2618<br>SEQUENCE: 2618<br>000 | moltype = | length = |
| SEQ ID NO: 2619<br>SEQUENCE: 2619<br>000 | moltype = | length = |
| SEQ ID NO: 2620<br>SEQUENCE: 2620<br>000 | moltype = | length = |
| SEQ ID NO: 2621<br>SEQUENCE: 2621<br>000 | moltype = | length = |
| SEQ ID NO: 2622<br>SEQUENCE: 2622<br>000 | moltype = | length = |
| SEQ ID NO: 2623<br>SEQUENCE: 2623<br>000 | moltype = | length = |
| SEQ ID NO: 2624<br>SEQUENCE: 2624<br>000 | moltype = | length = |
| SEQ ID NO: 2625<br>SEQUENCE: 2625<br>000 | moltype = | length = |
| SEQ ID NO: 2626<br>SEQUENCE: 2626<br>000 | moltype = | length = |
| SEQ ID NO: 2627<br>SEQUENCE: 2627<br>000 | moltype = | length = |
| SEQ ID NO: 2628<br>SEQUENCE: 2628<br>000 | moltype = | length = |
| SEQ ID NO: 2629<br>SEQUENCE: 2629<br>000 | moltype = | length = |
| SEQ ID NO: 2630<br>SEQUENCE: 2630<br>000 | moltype = | length = |
| SEQ ID NO: 2631<br>SEQUENCE: 2631<br>000 | moltype = | length = |
| SEQ ID NO: 2632<br>SEQUENCE: 2632<br>000 | moltype = | length = |
| SEQ ID NO: 2633<br>SEQUENCE: 2633<br>000 | moltype = | length = |
| SEQ ID NO: 2634<br>SEQUENCE: 2634<br>000 | moltype = | length = |

SEQ ID NO: 2635          moltype =     length =
SEQUENCE: 2635
000

SEQ ID NO: 2636          moltype =     length =
SEQUENCE: 2636
000

SEQ ID NO: 2637          moltype =     length =
SEQUENCE: 2637
000

SEQ ID NO: 2638          moltype =     length =
SEQUENCE: 2638
000

SEQ ID NO: 2639          moltype =     length =
SEQUENCE: 2639
000

SEQ ID NO: 2640          moltype =     length =
SEQUENCE: 2640
000

SEQ ID NO: 2641          moltype =     length =
SEQUENCE: 2641
000

SEQ ID NO: 2642          moltype =     length =
SEQUENCE: 2642
000

SEQ ID NO: 2643          moltype =     length =
SEQUENCE: 2643
000

SEQ ID NO: 2644          moltype =     length =
SEQUENCE: 2644
000

SEQ ID NO: 2645          moltype =     length =
SEQUENCE: 2645
000

SEQ ID NO: 2646          moltype =     length =
SEQUENCE: 2646
000

SEQ ID NO: 2647          moltype =     length =
SEQUENCE: 2647
000

SEQ ID NO: 2648          moltype =     length =
SEQUENCE: 2648
000

SEQ ID NO: 2649          moltype =     length =
SEQUENCE: 2649
000

SEQ ID NO: 2650          moltype =     length =
SEQUENCE: 2650
000

SEQ ID NO: 2651          moltype =     length =
SEQUENCE: 2651
000

SEQ ID NO: 2652          moltype =     length =
SEQUENCE: 2652
000

SEQ ID NO: 2653          moltype =     length =
SEQUENCE: 2653
000

SEQ ID NO: 2654          moltype =     length =
SEQUENCE: 2654

000

SEQ ID NO: 2655        moltype =     length =
SEQUENCE: 2655
000

SEQ ID NO: 2656        moltype =     length =
SEQUENCE: 2656
000

SEQ ID NO: 2657        moltype =     length =
SEQUENCE: 2657
000

SEQ ID NO: 2658        moltype =     length =
SEQUENCE: 2658
000

SEQ ID NO: 2659        moltype =     length =
SEQUENCE: 2659
000

SEQ ID NO: 2660        moltype =     length =
SEQUENCE: 2660
000

SEQ ID NO: 2661        moltype =     length =
SEQUENCE: 2661
000

SEQ ID NO: 2662        moltype =     length =
SEQUENCE: 2662
000

SEQ ID NO: 2663        moltype =     length =
SEQUENCE: 2663
000

SEQ ID NO: 2664        moltype =     length =
SEQUENCE: 2664
000

SEQ ID NO: 2665        moltype =     length =
SEQUENCE: 2665
000

SEQ ID NO: 2666        moltype =     length =
SEQUENCE: 2666
000

SEQ ID NO: 2667        moltype =     length =
SEQUENCE: 2667
000

SEQ ID NO: 2668        moltype =     length =
SEQUENCE: 2668
000

SEQ ID NO: 2669        moltype =     length =
SEQUENCE: 2669
000

SEQ ID NO: 2670        moltype =     length =
SEQUENCE: 2670
000

SEQ ID NO: 2671        moltype =     length =
SEQUENCE: 2671
000

SEQ ID NO: 2672        moltype =     length =
SEQUENCE: 2672
000

SEQ ID NO: 2673        moltype =     length =
SEQUENCE: 2673
000

SEQ ID NO: 2674        moltype =     length =

SEQUENCE: 2674
000

SEQ ID NO: 2675         moltype =    length =
SEQUENCE: 2675
000

SEQ ID NO: 2676         moltype =    length =
SEQUENCE: 2676
000

SEQ ID NO: 2677         moltype =    length =
SEQUENCE: 2677
000

SEQ ID NO: 2678         moltype =    length =
SEQUENCE: 2678
000

SEQ ID NO: 2679         moltype =    length =
SEQUENCE: 2679
000

SEQ ID NO: 2680         moltype =    length =
SEQUENCE: 2680
000

SEQ ID NO: 2681         moltype =    length =
SEQUENCE: 2681
000

SEQ ID NO: 2682         moltype =    length =
SEQUENCE: 2682
000

SEQ ID NO: 2683         moltype =    length =
SEQUENCE: 2683
000

SEQ ID NO: 2684         moltype =    length =
SEQUENCE: 2684
000

SEQ ID NO: 2685         moltype =    length =
SEQUENCE: 2685
000

SEQ ID NO: 2686         moltype =    length =
SEQUENCE: 2686
000

SEQ ID NO: 2687         moltype =    length =
SEQUENCE: 2687
000

SEQ ID NO: 2688         moltype =    length =
SEQUENCE: 2688
000

SEQ ID NO: 2689         moltype =    length =
SEQUENCE: 2689
000

SEQ ID NO: 2690         moltype =    length =
SEQUENCE: 2690
000

SEQ ID NO: 2691         moltype =    length =
SEQUENCE: 2691
000

SEQ ID NO: 2692         moltype =    length =
SEQUENCE: 2692
000

SEQ ID NO: 2693         moltype =    length =
SEQUENCE: 2693
000

| | | |
|---|---|---|
| SEQ ID NO: 2694<br>SEQUENCE: 2694<br>000 | moltype = | length = |
| SEQ ID NO: 2695<br>SEQUENCE: 2695<br>000 | moltype = | length = |
| SEQ ID NO: 2696<br>SEQUENCE: 2696<br>000 | moltype = | length = |
| SEQ ID NO: 2697<br>SEQUENCE: 2697<br>000 | moltype = | length = |
| SEQ ID NO: 2698<br>SEQUENCE: 2698<br>000 | moltype = | length = |
| SEQ ID NO: 2699<br>SEQUENCE: 2699<br>000 | moltype = | length = |
| SEQ ID NO: 2700<br>SEQUENCE: 2700<br>000 | moltype = | length = |
| SEQ ID NO: 2701<br>SEQUENCE: 2701<br>000 | moltype = | length = |
| SEQ ID NO: 2702<br>SEQUENCE: 2702<br>000 | moltype = | length = |
| SEQ ID NO: 2703<br>SEQUENCE: 2703<br>000 | moltype = | length = |
| SEQ ID NO: 2704<br>SEQUENCE: 2704<br>000 | moltype = | length = |
| SEQ ID NO: 2705<br>SEQUENCE: 2705<br>000 | moltype = | length = |
| SEQ ID NO: 2706<br>SEQUENCE: 2706<br>000 | moltype = | length = |
| SEQ ID NO: 2707<br>SEQUENCE: 2707<br>000 | moltype = | length = |
| SEQ ID NO: 2708<br>SEQUENCE: 2708<br>000 | moltype = | length = |
| SEQ ID NO: 2709<br>SEQUENCE: 2709<br>000 | moltype = | length = |
| SEQ ID NO: 2710<br>SEQUENCE: 2710<br>000 | moltype = | length = |
| SEQ ID NO: 2711<br>SEQUENCE: 2711<br>000 | moltype = | length = |
| SEQ ID NO: 2712<br>SEQUENCE: 2712<br>000 | moltype = | length = |
| SEQ ID NO: 2713<br>SEQUENCE: 2713<br>000 | moltype = | length = |

| | | |
|---|---|---|
| SEQ ID NO: 2714<br>SEQUENCE: 2714<br>000 | moltype = | length = |
| SEQ ID NO: 2715<br>SEQUENCE: 2715<br>000 | moltype = | length = |
| SEQ ID NO: 2716<br>SEQUENCE: 2716<br>000 | moltype = | length = |
| SEQ ID NO: 2717<br>SEQUENCE: 2717<br>000 | moltype = | length = |
| SEQ ID NO: 2718<br>SEQUENCE: 2718<br>000 | moltype = | length = |
| SEQ ID NO: 2719<br>SEQUENCE: 2719<br>000 | moltype = | length = |
| SEQ ID NO: 2720<br>SEQUENCE: 2720<br>000 | moltype = | length = |
| SEQ ID NO: 2721<br>SEQUENCE: 2721<br>000 | moltype = | length = |
| SEQ ID NO: 2722<br>SEQUENCE: 2722<br>000 | moltype = | length = |
| SEQ ID NO: 2723<br>SEQUENCE: 2723<br>000 | moltype = | length = |
| SEQ ID NO: 2724<br>SEQUENCE: 2724<br>000 | moltype = | length = |
| SEQ ID NO: 2725<br>SEQUENCE: 2725<br>000 | moltype = | length = |
| SEQ ID NO: 2726<br>SEQUENCE: 2726<br>000 | moltype = | length = |
| SEQ ID NO: 2727<br>SEQUENCE: 2727<br>000 | moltype = | length = |
| SEQ ID NO: 2728<br>SEQUENCE: 2728<br>000 | moltype = | length = |
| SEQ ID NO: 2729<br>SEQUENCE: 2729<br>000 | moltype = | length = |
| SEQ ID NO: 2730<br>SEQUENCE: 2730<br>000 | moltype = | length = |
| SEQ ID NO: 2731<br>SEQUENCE: 2731<br>000 | moltype = | length = |
| SEQ ID NO: 2732<br>SEQUENCE: 2732<br>000 | moltype = | length = |
| SEQ ID NO: 2733<br>SEQUENCE: 2733 | moltype = | length = |

-continued

000

SEQ ID NO: 2734    moltype =    length =
SEQUENCE: 2734
000

SEQ ID NO: 2735    moltype =    length =
SEQUENCE: 2735
000

SEQ ID NO: 2736    moltype =    length =
SEQUENCE: 2736
000

SEQ ID NO: 2737    moltype =    length =
SEQUENCE: 2737
000

SEQ ID NO: 2738    moltype =    length =
SEQUENCE: 2738
000

SEQ ID NO: 2739    moltype =    length =
SEQUENCE: 2739
000

SEQ ID NO: 2740    moltype =    length =
SEQUENCE: 2740
000

SEQ ID NO: 2741    moltype =    length =
SEQUENCE: 2741
000

SEQ ID NO: 2742    moltype =    length =
SEQUENCE: 2742
000

SEQ ID NO: 2743    moltype =    length =
SEQUENCE: 2743
000

SEQ ID NO: 2744    moltype =    length =
SEQUENCE: 2744
000

SEQ ID NO: 2745    moltype =    length =
SEQUENCE: 2745
000

SEQ ID NO: 2746    moltype =    length =
SEQUENCE: 2746
000

SEQ ID NO: 2747    moltype =    length =
SEQUENCE: 2747
000

SEQ ID NO: 2748    moltype =    length =
SEQUENCE: 2748
000

SEQ ID NO: 2749    moltype =    length =
SEQUENCE: 2749
000

SEQ ID NO: 2750    moltype =    length =
SEQUENCE: 2750
000

SEQ ID NO: 2751    moltype =    length =
SEQUENCE: 2751
000

SEQ ID NO: 2752    moltype =    length =
SEQUENCE: 2752
000

SEQ ID NO: 2753    moltype =    length =

```
SEQUENCE: 2753
000

SEQ ID NO: 2754        moltype =    length =
SEQUENCE: 2754
000

SEQ ID NO: 2755        moltype =    length =
SEQUENCE: 2755
000

SEQ ID NO: 2756        moltype =    length =
SEQUENCE: 2756
000

SEQ ID NO: 2757        moltype =    length =
SEQUENCE: 2757
000

SEQ ID NO: 2758        moltype =    length =
SEQUENCE: 2758
000

SEQ ID NO: 2759        moltype =    length =
SEQUENCE: 2759
000

SEQ ID NO: 2760        moltype =    length =
SEQUENCE: 2760
000

SEQ ID NO: 2761        moltype =    length =
SEQUENCE: 2761
000

SEQ ID NO: 2762        moltype =    length =
SEQUENCE: 2762
000

SEQ ID NO: 2763        moltype =    length =
SEQUENCE: 2763
000

SEQ ID NO: 2764        moltype =    length =
SEQUENCE: 2764
000

SEQ ID NO: 2765        moltype =    length =
SEQUENCE: 2765
000

SEQ ID NO: 2766        moltype =    length =
SEQUENCE: 2766
000

SEQ ID NO: 2767        moltype =    length =
SEQUENCE: 2767
000

SEQ ID NO: 2768        moltype =    length =
SEQUENCE: 2768
000

SEQ ID NO: 2769        moltype =    length =
SEQUENCE: 2769
000

SEQ ID NO: 2770        moltype =    length =
SEQUENCE: 2770
000

SEQ ID NO: 2771        moltype =    length =
SEQUENCE: 2771
000

SEQ ID NO: 2772        moltype =    length =
SEQUENCE: 2772
000
```

-continued

SEQ ID NO: 2773          moltype =          length =
SEQUENCE: 2773
000

SEQ ID NO: 2774          moltype =          length =
SEQUENCE: 2774
000

SEQ ID NO: 2775          moltype =          length =
SEQUENCE: 2775
000

SEQ ID NO: 2776          moltype =          length =
SEQUENCE: 2776
000

SEQ ID NO: 2777          moltype =          length =
SEQUENCE: 2777
000

SEQ ID NO: 2778          moltype =          length =
SEQUENCE: 2778
000

SEQ ID NO: 2779          moltype =          length =
SEQUENCE: 2779
000

SEQ ID NO: 2780          moltype =          length =
SEQUENCE: 2780
000

SEQ ID NO: 2781          moltype =          length =
SEQUENCE: 2781
000

SEQ ID NO: 2782          moltype =          length =
SEQUENCE: 2782
000

SEQ ID NO: 2783          moltype =          length =
SEQUENCE: 2783
000

SEQ ID NO: 2784          moltype =          length =
SEQUENCE: 2784
000

SEQ ID NO: 2785          moltype =          length =
SEQUENCE: 2785
000

SEQ ID NO: 2786          moltype =          length =
SEQUENCE: 2786
000

SEQ ID NO: 2787          moltype =          length =
SEQUENCE: 2787
000

SEQ ID NO: 2788          moltype =          length =
SEQUENCE: 2788
000

SEQ ID NO: 2789          moltype =          length =
SEQUENCE: 2789
000

SEQ ID NO: 2790          moltype =          length =
SEQUENCE: 2790
000

SEQ ID NO: 2791          moltype =          length =
SEQUENCE: 2791
000

SEQ ID NO: 2792          moltype =          length =
SEQUENCE: 2792
000

| | | |
|---|---|---|
| SEQ ID NO: 2793 SEQUENCE: 2793 000 | moltype = | length = |
| SEQ ID NO: 2794 SEQUENCE: 2794 000 | moltype = | length = |
| SEQ ID NO: 2795 SEQUENCE: 2795 000 | moltype = | length = |
| SEQ ID NO: 2796 SEQUENCE: 2796 000 | moltype = | length = |
| SEQ ID NO: 2797 SEQUENCE: 2797 000 | moltype = | length = |
| SEQ ID NO: 2798 SEQUENCE: 2798 000 | moltype = | length = |
| SEQ ID NO: 2799 SEQUENCE: 2799 000 | moltype = | length = |
| SEQ ID NO: 2800 SEQUENCE: 2800 000 | moltype = | length = |
| SEQ ID NO: 2801 SEQUENCE: 2801 000 | moltype = | length = |
| SEQ ID NO: 2802 SEQUENCE: 2802 000 | moltype = | length = |
| SEQ ID NO: 2803 SEQUENCE: 2803 000 | moltype = | length = |
| SEQ ID NO: 2804 SEQUENCE: 2804 000 | moltype = | length = |
| SEQ ID NO: 2805 SEQUENCE: 2805 000 | moltype = | length = |
| SEQ ID NO: 2806 SEQUENCE: 2806 000 | moltype = | length = |
| SEQ ID NO: 2807 SEQUENCE: 2807 000 | moltype = | length = |
| SEQ ID NO: 2808 SEQUENCE: 2808 000 | moltype = | length = |
| SEQ ID NO: 2809 SEQUENCE: 2809 000 | moltype = | length = |
| SEQ ID NO: 2810 SEQUENCE: 2810 000 | moltype = | length = |
| SEQ ID NO: 2811 SEQUENCE: 2811 000 | moltype = | length = |
| SEQ ID NO: 2812 SEQUENCE: 2812 | moltype = | length = |

000

SEQ ID NO: 2813      moltype =     length =
SEQUENCE: 2813
000

SEQ ID NO: 2814      moltype =     length =
SEQUENCE: 2814
000

SEQ ID NO: 2815      moltype =     length =
SEQUENCE: 2815
000

SEQ ID NO: 2816      moltype =     length =
SEQUENCE: 2816
000

SEQ ID NO: 2817      moltype =     length =
SEQUENCE: 2817
000

SEQ ID NO: 2818      moltype =     length =
SEQUENCE: 2818
000

SEQ ID NO: 2819      moltype =     length =
SEQUENCE: 2819
000

SEQ ID NO: 2820      moltype =     length =
SEQUENCE: 2820
000

SEQ ID NO: 2821      moltype =     length =
SEQUENCE: 2821
000

SEQ ID NO: 2822      moltype =     length =
SEQUENCE: 2822
000

SEQ ID NO: 2823      moltype =     length =
SEQUENCE: 2823
000

SEQ ID NO: 2824      moltype =     length =
SEQUENCE: 2824
000

SEQ ID NO: 2825      moltype =     length =
SEQUENCE: 2825
000

SEQ ID NO: 2826      moltype =     length =
SEQUENCE: 2826
000

SEQ ID NO: 2827      moltype =     length =
SEQUENCE: 2827
000

SEQ ID NO: 2828      moltype =     length =
SEQUENCE: 2828
000

SEQ ID NO: 2829      moltype =     length =
SEQUENCE: 2829
000

SEQ ID NO: 2830      moltype =     length =
SEQUENCE: 2830
000

SEQ ID NO: 2831      moltype =     length =
SEQUENCE: 2831
000

SEQ ID NO: 2832      moltype =     length =

```
SEQUENCE: 2832
000

SEQ ID NO: 2833        moltype =    length =
SEQUENCE: 2833
000

SEQ ID NO: 2834        moltype =    length =
SEQUENCE: 2834
000

SEQ ID NO: 2835        moltype =    length =
SEQUENCE: 2835
000

SEQ ID NO: 2836        moltype =    length =
SEQUENCE: 2836
000

SEQ ID NO: 2837        moltype =    length =
SEQUENCE: 2837
000

SEQ ID NO: 2838        moltype =    length =
SEQUENCE: 2838
000

SEQ ID NO: 2839        moltype =    length =
SEQUENCE: 2839
000

SEQ ID NO: 2840        moltype =    length =
SEQUENCE: 2840
000

SEQ ID NO: 2841        moltype =    length =
SEQUENCE: 2841
000

SEQ ID NO: 2842        moltype =    length =
SEQUENCE: 2842
000

SEQ ID NO: 2843        moltype =    length =
SEQUENCE: 2843
000

SEQ ID NO: 2844        moltype =    length =
SEQUENCE: 2844
000

SEQ ID NO: 2845        moltype =    length =
SEQUENCE: 2845
000

SEQ ID NO: 2846        moltype =    length =
SEQUENCE: 2846
000

SEQ ID NO: 2847        moltype =    length =
SEQUENCE: 2847
000

SEQ ID NO: 2848        moltype =    length =
SEQUENCE: 2848
000

SEQ ID NO: 2849        moltype =    length =
SEQUENCE: 2849
000

SEQ ID NO: 2850        moltype =    length =
SEQUENCE: 2850
000

SEQ ID NO: 2851        moltype =    length =
SEQUENCE: 2851
000
```

| | | |
|---|---|---|
| SEQ ID NO: 2852 SEQUENCE: 2852 | moltype = | length = 000 |
| SEQ ID NO: 2853 SEQUENCE: 2853 | moltype = | length = 000 |
| SEQ ID NO: 2854 SEQUENCE: 2854 | moltype = | length = 000 |
| SEQ ID NO: 2855 SEQUENCE: 2855 | moltype = | length = 000 |
| SEQ ID NO: 2856 SEQUENCE: 2856 | moltype = | length = 000 |
| SEQ ID NO: 2857 SEQUENCE: 2857 | moltype = | length = 000 |
| SEQ ID NO: 2858 SEQUENCE: 2858 | moltype = | length = 000 |
| SEQ ID NO: 2859 SEQUENCE: 2859 | moltype = | length = 000 |
| SEQ ID NO: 2860 SEQUENCE: 2860 | moltype = | length = 000 |
| SEQ ID NO: 2861 SEQUENCE: 2861 | moltype = | length = 000 |
| SEQ ID NO: 2862 SEQUENCE: 2862 | moltype = | length = 000 |
| SEQ ID NO: 2863 SEQUENCE: 2863 | moltype = | length = 000 |
| SEQ ID NO: 2864 SEQUENCE: 2864 | moltype = | length = 000 |
| SEQ ID NO: 2865 SEQUENCE: 2865 | moltype = | length = 000 |
| SEQ ID NO: 2866 SEQUENCE: 2866 | moltype = | length = 000 |
| SEQ ID NO: 2867 SEQUENCE: 2867 | moltype = | length = 000 |
| SEQ ID NO: 2868 SEQUENCE: 2868 | moltype = | length = 000 |
| SEQ ID NO: 2869 SEQUENCE: 2869 | moltype = | length = 000 |
| SEQ ID NO: 2870 SEQUENCE: 2870 | moltype = | length = 000 |
| SEQ ID NO: 2871 SEQUENCE: 2871 | moltype = | length = 000 |

SEQ ID NO: 2872     moltype =     length =
SEQUENCE: 2872
000

SEQ ID NO: 2873     moltype =     length =
SEQUENCE: 2873
000

SEQ ID NO: 2874     moltype =     length =
SEQUENCE: 2874
000

SEQ ID NO: 2875     moltype =     length =
SEQUENCE: 2875
000

SEQ ID NO: 2876     moltype =     length =
SEQUENCE: 2876
000

SEQ ID NO: 2877     moltype =     length =
SEQUENCE: 2877
000

SEQ ID NO: 2878     moltype =     length =
SEQUENCE: 2878
000

SEQ ID NO: 2879     moltype =     length =
SEQUENCE: 2879
000

SEQ ID NO: 2880     moltype =     length =
SEQUENCE: 2880
000

SEQ ID NO: 2881     moltype =     length =
SEQUENCE: 2881
000

SEQ ID NO: 2882     moltype =     length =
SEQUENCE: 2882
000

SEQ ID NO: 2883     moltype =     length =
SEQUENCE: 2883
000

SEQ ID NO: 2884     moltype =     length =
SEQUENCE: 2884
000

SEQ ID NO: 2885     moltype =     length =
SEQUENCE: 2885
000

SEQ ID NO: 2886     moltype =     length =
SEQUENCE: 2886
000

SEQ ID NO: 2887     moltype =     length =
SEQUENCE: 2887
000

SEQ ID NO: 2888     moltype =     length =
SEQUENCE: 2888
000

SEQ ID NO: 2889     moltype =     length =
SEQUENCE: 2889
000

SEQ ID NO: 2890     moltype =     length =
SEQUENCE: 2890
000

SEQ ID NO: 2891     moltype =     length =
SEQUENCE: 2891

000

SEQ ID NO: 2892        moltype =     length =
SEQUENCE: 2892
000

SEQ ID NO: 2893        moltype =     length =
SEQUENCE: 2893
000

SEQ ID NO: 2894        moltype =     length =
SEQUENCE: 2894
000

SEQ ID NO: 2895        moltype =     length =
SEQUENCE: 2895
000

SEQ ID NO: 2896        moltype =     length =
SEQUENCE: 2896
000

SEQ ID NO: 2897        moltype =     length =
SEQUENCE: 2897
000

SEQ ID NO: 2898        moltype =     length =
SEQUENCE: 2898
000

SEQ ID NO: 2899        moltype =     length =
SEQUENCE: 2899
000

SEQ ID NO: 2900        moltype =     length =
SEQUENCE: 2900
000

SEQ ID NO: 2901        moltype =     length =
SEQUENCE: 2901
000

SEQ ID NO: 2902        moltype =     length =
SEQUENCE: 2902
000

SEQ ID NO: 2903        moltype =     length =
SEQUENCE: 2903
000

SEQ ID NO: 2904        moltype =     length =
SEQUENCE: 2904
000

SEQ ID NO: 2905        moltype =     length =
SEQUENCE: 2905
000

SEQ ID NO: 2906        moltype =     length =
SEQUENCE: 2906
000

SEQ ID NO: 2907        moltype =     length =
SEQUENCE: 2907
000

SEQ ID NO: 2908        moltype =     length =
SEQUENCE: 2908
000

SEQ ID NO: 2909        moltype =     length =
SEQUENCE: 2909
000

SEQ ID NO: 2910        moltype =     length =
SEQUENCE: 2910
000

SEQ ID NO: 2911        moltype =     length =

```
SEQUENCE: 2911
000

SEQ ID NO: 2912          moltype =    length =
SEQUENCE: 2912
000

SEQ ID NO: 2913          moltype =    length =
SEQUENCE: 2913
000

SEQ ID NO: 2914          moltype =    length =
SEQUENCE: 2914
000

SEQ ID NO: 2915          moltype =    length =
SEQUENCE: 2915
000

SEQ ID NO: 2916          moltype =    length =
SEQUENCE: 2916
000

SEQ ID NO: 2917          moltype =    length =
SEQUENCE: 2917
000

SEQ ID NO: 2918          moltype =    length =
SEQUENCE: 2918
000

SEQ ID NO: 2919          moltype =    length =
SEQUENCE: 2919
000

SEQ ID NO: 2920          moltype =    length =
SEQUENCE: 2920
000

SEQ ID NO: 2921          moltype =    length =
SEQUENCE: 2921
000

SEQ ID NO: 2922          moltype =    length =
SEQUENCE: 2922
000

SEQ ID NO: 2923          moltype =    length =
SEQUENCE: 2923
000

SEQ ID NO: 2924          moltype =    length =
SEQUENCE: 2924
000

SEQ ID NO: 2925          moltype =    length =
SEQUENCE: 2925
000

SEQ ID NO: 2926          moltype =    length =
SEQUENCE: 2926
000

SEQ ID NO: 2927          moltype =    length =
SEQUENCE: 2927
000

SEQ ID NO: 2928          moltype =    length =
SEQUENCE: 2928
000

SEQ ID NO: 2929          moltype =    length =
SEQUENCE: 2929
000

SEQ ID NO: 2930          moltype =    length =
SEQUENCE: 2930
000
```

-continued

SEQ ID NO: 2931　　moltype =　length =
SEQUENCE: 2931
000

SEQ ID NO: 2932　　moltype =　length =
SEQUENCE: 2932
000

SEQ ID NO: 2933　　moltype =　length =
SEQUENCE: 2933
000

SEQ ID NO: 2934　　moltype =　length =
SEQUENCE: 2934
000

SEQ ID NO: 2935　　moltype =　length =
SEQUENCE: 2935
000

SEQ ID NO: 2936　　moltype =　length =
SEQUENCE: 2936
000

SEQ ID NO: 2937　　moltype =　length =
SEQUENCE: 2937
000

SEQ ID NO: 2938　　moltype =　length =
SEQUENCE: 2938
000

SEQ ID NO: 2939　　moltype =　length =
SEQUENCE: 2939
000

SEQ ID NO: 2940　　moltype =　length =
SEQUENCE: 2940
000

SEQ ID NO: 2941　　moltype =　length =
SEQUENCE: 2941
000

SEQ ID NO: 2942　　moltype =　length =
SEQUENCE: 2942
000

SEQ ID NO: 2943　　moltype =　length =
SEQUENCE: 2943
000

SEQ ID NO: 2944　　moltype =　length =
SEQUENCE: 2944
000

SEQ ID NO: 2945　　moltype =　length =
SEQUENCE: 2945
000

SEQ ID NO: 2946　　moltype =　length =
SEQUENCE: 2946
000

SEQ ID NO: 2947　　moltype =　length =
SEQUENCE: 2947
000

SEQ ID NO: 2948　　moltype =　length =
SEQUENCE: 2948
000

SEQ ID NO: 2949　　moltype =　length =
SEQUENCE: 2949
000

SEQ ID NO: 2950　　moltype =　length =
SEQUENCE: 2950
000

| | | |
|---|---|---|
| SEQ ID NO: 2951 SEQUENCE: 2951 000 | moltype = | length = |
| SEQ ID NO: 2952 SEQUENCE: 2952 000 | moltype = | length = |
| SEQ ID NO: 2953 SEQUENCE: 2953 000 | moltype = | length = |
| SEQ ID NO: 2954 SEQUENCE: 2954 000 | moltype = | length = |
| SEQ ID NO: 2955 SEQUENCE: 2955 000 | moltype = | length = |
| SEQ ID NO: 2956 SEQUENCE: 2956 000 | moltype = | length = |
| SEQ ID NO: 2957 SEQUENCE: 2957 000 | moltype = | length = |
| SEQ ID NO: 2958 SEQUENCE: 2958 000 | moltype = | length = |
| SEQ ID NO: 2959 SEQUENCE: 2959 000 | moltype = | length = |
| SEQ ID NO: 2960 SEQUENCE: 2960 000 | moltype = | length = |
| SEQ ID NO: 2961 SEQUENCE: 2961 000 | moltype = | length = |
| SEQ ID NO: 2962 SEQUENCE: 2962 000 | moltype = | length = |
| SEQ ID NO: 2963 SEQUENCE: 2963 000 | moltype = | length = |
| SEQ ID NO: 2964 SEQUENCE: 2964 000 | moltype = | length = |
| SEQ ID NO: 2965 SEQUENCE: 2965 000 | moltype = | length = |
| SEQ ID NO: 2966 SEQUENCE: 2966 000 | moltype = | length = |
| SEQ ID NO: 2967 SEQUENCE: 2967 000 | moltype = | length = |
| SEQ ID NO: 2968 SEQUENCE: 2968 000 | moltype = | length = |
| SEQ ID NO: 2969 SEQUENCE: 2969 000 | moltype = | length = |
| SEQ ID NO: 2970 SEQUENCE: 2970 | moltype = | length = |

000

SEQ ID NO: 2971        moltype =      length =
SEQUENCE: 2971
000

SEQ ID NO: 2972        moltype =      length =
SEQUENCE: 2972
000

SEQ ID NO: 2973        moltype =      length =
SEQUENCE: 2973
000

SEQ ID NO: 2974        moltype =      length =
SEQUENCE: 2974
000

SEQ ID NO: 2975        moltype =      length =
SEQUENCE: 2975
000

SEQ ID NO: 2976        moltype =      length =
SEQUENCE: 2976
000

SEQ ID NO: 2977        moltype =      length =
SEQUENCE: 2977
000

SEQ ID NO: 2978        moltype =      length =
SEQUENCE: 2978
000

SEQ ID NO: 2979        moltype =      length =
SEQUENCE: 2979
000

SEQ ID NO: 2980        moltype =      length =
SEQUENCE: 2980
000

SEQ ID NO: 2981        moltype =      length =
SEQUENCE: 2981
000

SEQ ID NO: 2982        moltype =      length =
SEQUENCE: 2982
000

SEQ ID NO: 2983        moltype =      length =
SEQUENCE: 2983
000

SEQ ID NO: 2984        moltype =      length =
SEQUENCE: 2984
000

SEQ ID NO: 2985        moltype =      length =
SEQUENCE: 2985
000

SEQ ID NO: 2986        moltype =      length =
SEQUENCE: 2986
000

SEQ ID NO: 2987        moltype =      length =
SEQUENCE: 2987
000

SEQ ID NO: 2988        moltype =      length =
SEQUENCE: 2988
000

SEQ ID NO: 2989        moltype =      length =
SEQUENCE: 2989
000

SEQ ID NO: 2990        moltype =      length =

```
SEQUENCE: 2990
000

SEQ ID NO: 2991          moltype =    length =
SEQUENCE: 2991
000

SEQ ID NO: 2992          moltype =    length =
SEQUENCE: 2992
000

SEQ ID NO: 2993          moltype =    length =
SEQUENCE: 2993
000

SEQ ID NO: 2994          moltype =    length =
SEQUENCE: 2994
000

SEQ ID NO: 2995          moltype =    length =
SEQUENCE: 2995
000

SEQ ID NO: 2996          moltype =    length =
SEQUENCE: 2996
000

SEQ ID NO: 2997          moltype =    length =
SEQUENCE: 2997
000

SEQ ID NO: 2998          moltype =    length =
SEQUENCE: 2998
000

SEQ ID NO: 2999          moltype =    length =
SEQUENCE: 2999
000

SEQ ID NO: 3000          moltype =    length =
SEQUENCE: 3000
000

SEQ ID NO: 3001          moltype =    length =
SEQUENCE: 3001
000

SEQ ID NO: 3002          moltype =    length =
SEQUENCE: 3002
000

SEQ ID NO: 3003          moltype =    length =
SEQUENCE: 3003
000

SEQ ID NO: 3004          moltype =    length =
SEQUENCE: 3004
000

SEQ ID NO: 3005          moltype =    length =
SEQUENCE: 3005
000

SEQ ID NO: 3006          moltype =    length =
SEQUENCE: 3006
000

SEQ ID NO: 3007          moltype =    length =
SEQUENCE: 3007
000

SEQ ID NO: 3008          moltype =    length =
SEQUENCE: 3008
000

SEQ ID NO: 3009          moltype =    length =
SEQUENCE: 3009
000
```

| | | |
|---|---|---|
| SEQ ID NO: 3010<br>SEQUENCE: 3010<br>000 | moltype = | length = |
| SEQ ID NO: 3011<br>SEQUENCE: 3011<br>000 | moltype = | length = |
| SEQ ID NO: 3012<br>SEQUENCE: 3012<br>000 | moltype = | length = |
| SEQ ID NO: 3013<br>SEQUENCE: 3013<br>000 | moltype = | length = |
| SEQ ID NO: 3014<br>SEQUENCE: 3014<br>000 | moltype = | length = |
| SEQ ID NO: 3015<br>SEQUENCE: 3015<br>000 | moltype = | length = |
| SEQ ID NO: 3016<br>SEQUENCE: 3016<br>000 | moltype = | length = |
| SEQ ID NO: 3017<br>SEQUENCE: 3017<br>000 | moltype = | length = |
| SEQ ID NO: 3018<br>SEQUENCE: 3018<br>000 | moltype = | length = |
| SEQ ID NO: 3019<br>SEQUENCE: 3019<br>000 | moltype = | length = |
| SEQ ID NO: 3020<br>SEQUENCE: 3020<br>000 | moltype = | length = |
| SEQ ID NO: 3021<br>SEQUENCE: 3021<br>000 | moltype = | length = |
| SEQ ID NO: 3022<br>SEQUENCE: 3022<br>000 | moltype = | length = |
| SEQ ID NO: 3023<br>SEQUENCE: 3023<br>000 | moltype = | length = |
| SEQ ID NO: 3024<br>SEQUENCE: 3024<br>000 | moltype = | length = |
| SEQ ID NO: 3025<br>SEQUENCE: 3025<br>000 | moltype = | length = |
| SEQ ID NO: 3026<br>SEQUENCE: 3026<br>000 | moltype = | length = |
| SEQ ID NO: 3027<br>SEQUENCE: 3027<br>000 | moltype = | length = |
| SEQ ID NO: 3028<br>SEQUENCE: 3028<br>000 | moltype = | length = |
| SEQ ID NO: 3029<br>SEQUENCE: 3029<br>000 | moltype = | length = |

| | | |
|---|---|---|
| SEQ ID NO: 3030 SEQUENCE: 3030 | moltype = | length = 000 |
| SEQ ID NO: 3031 SEQUENCE: 3031 | moltype = | length = 000 |
| SEQ ID NO: 3032 SEQUENCE: 3032 | moltype = | length = 000 |
| SEQ ID NO: 3033 SEQUENCE: 3033 | moltype = | length = 000 |
| SEQ ID NO: 3034 SEQUENCE: 3034 | moltype = | length = 000 |
| SEQ ID NO: 3035 SEQUENCE: 3035 | moltype = | length = 000 |
| SEQ ID NO: 3036 SEQUENCE: 3036 | moltype = | length = 000 |
| SEQ ID NO: 3037 SEQUENCE: 3037 | moltype = | length = 000 |
| SEQ ID NO: 3038 SEQUENCE: 3038 | moltype = | length = 000 |
| SEQ ID NO: 3039 SEQUENCE: 3039 | moltype = | length = 000 |
| SEQ ID NO: 3040 SEQUENCE: 3040 | moltype = | length = 000 |
| SEQ ID NO: 3041 SEQUENCE: 3041 | moltype = | length = 000 |
| SEQ ID NO: 3042 SEQUENCE: 3042 | moltype = | length = 000 |
| SEQ ID NO: 3043 SEQUENCE: 3043 | moltype = | length = 000 |
| SEQ ID NO: 3044 SEQUENCE: 3044 | moltype = | length = 000 |
| SEQ ID NO: 3045 SEQUENCE: 3045 | moltype = | length = 000 |
| SEQ ID NO: 3046 SEQUENCE: 3046 | moltype = | length = 000 |
| SEQ ID NO: 3047 SEQUENCE: 3047 | moltype = | length = 000 |
| SEQ ID NO: 3048 SEQUENCE: 3048 | moltype = | length = 000 |
| SEQ ID NO: 3049 SEQUENCE: 3049 | moltype = | length = |

-continued

000

SEQ ID NO: 3050          moltype =     length =
SEQUENCE: 3050
000

SEQ ID NO: 3051          moltype =     length =
SEQUENCE: 3051
000

SEQ ID NO: 3052          moltype =     length =
SEQUENCE: 3052
000

SEQ ID NO: 3053          moltype =     length =
SEQUENCE: 3053
000

SEQ ID NO: 3054          moltype =     length =
SEQUENCE: 3054
000

SEQ ID NO: 3055          moltype =     length =
SEQUENCE: 3055
000

SEQ ID NO: 3056          moltype =     length =
SEQUENCE: 3056
000

SEQ ID NO: 3057          moltype =     length =
SEQUENCE: 3057
000

SEQ ID NO: 3058          moltype =     length =
SEQUENCE: 3058
000

SEQ ID NO: 3059          moltype =     length =
SEQUENCE: 3059
000

SEQ ID NO: 3060          moltype =     length =
SEQUENCE: 3060
000

SEQ ID NO: 3061          moltype =     length =
SEQUENCE: 3061
000

SEQ ID NO: 3062          moltype =     length =
SEQUENCE: 3062
000

SEQ ID NO: 3063          moltype =     length =
SEQUENCE: 3063
000

SEQ ID NO: 3064          moltype =     length =
SEQUENCE: 3064
000

SEQ ID NO: 3065          moltype =     length =
SEQUENCE: 3065
000

SEQ ID NO: 3066          moltype =     length =
SEQUENCE: 3066
000

SEQ ID NO: 3067          moltype =     length =
SEQUENCE: 3067
000

SEQ ID NO: 3068          moltype =     length =
SEQUENCE: 3068
000

SEQ ID NO: 3069          moltype =     length =

-continued

SEQUENCE: 3069
000

SEQ ID NO: 3070        moltype =     length =
SEQUENCE: 3070
000

SEQ ID NO: 3071        moltype =     length =
SEQUENCE: 3071
000

SEQ ID NO: 3072        moltype =     length =
SEQUENCE: 3072
000

SEQ ID NO: 3073        moltype =     length =
SEQUENCE: 3073
000

SEQ ID NO: 3074        moltype =     length =
SEQUENCE: 3074
000

SEQ ID NO: 3075        moltype =     length =
SEQUENCE: 3075
000

SEQ ID NO: 3076        moltype =     length =
SEQUENCE: 3076
000

SEQ ID NO: 3077        moltype =     length =
SEQUENCE: 3077
000

SEQ ID NO: 3078        moltype =     length =
SEQUENCE: 3078
000

SEQ ID NO: 3079        moltype =     length =
SEQUENCE: 3079
000

SEQ ID NO: 3080        moltype =     length =
SEQUENCE: 3080
000

SEQ ID NO: 3081        moltype =     length =
SEQUENCE: 3081
000

SEQ ID NO: 3082        moltype =     length =
SEQUENCE: 3082
000

SEQ ID NO: 3083        moltype =     length =
SEQUENCE: 3083
000

SEQ ID NO: 3084        moltype =     length =
SEQUENCE: 3084
000

SEQ ID NO: 3085        moltype =     length =
SEQUENCE: 3085
000

SEQ ID NO: 3086        moltype =     length =
SEQUENCE: 3086
000

SEQ ID NO: 3087        moltype =     length =
SEQUENCE: 3087
000

SEQ ID NO: 3088        moltype =     length =
SEQUENCE: 3088
000

| | | |
|---|---|---|
| SEQ ID NO: 3089<br>SEQUENCE: 3089<br>000 | moltype = | length = |
| SEQ ID NO: 3090<br>SEQUENCE: 3090<br>000 | moltype = | length = |
| SEQ ID NO: 3091<br>SEQUENCE: 3091<br>000 | moltype = | length = |
| SEQ ID NO: 3092<br>SEQUENCE: 3092<br>000 | moltype = | length = |
| SEQ ID NO: 3093<br>SEQUENCE: 3093<br>000 | moltype = | length = |
| SEQ ID NO: 3094<br>SEQUENCE: 3094<br>000 | moltype = | length = |
| SEQ ID NO: 3095<br>SEQUENCE: 3095<br>000 | moltype = | length = |
| SEQ ID NO: 3096<br>SEQUENCE: 3096<br>000 | moltype = | length = |
| SEQ ID NO: 3097<br>SEQUENCE: 3097<br>000 | moltype = | length = |
| SEQ ID NO: 3098<br>SEQUENCE: 3098<br>000 | moltype = | length = |
| SEQ ID NO: 3099<br>SEQUENCE: 3099<br>000 | moltype = | length = |
| SEQ ID NO: 3100<br>SEQUENCE: 3100<br>000 | moltype = | length = |
| SEQ ID NO: 3101<br>SEQUENCE: 3101<br>000 | moltype = | length = |
| SEQ ID NO: 3102<br>SEQUENCE: 3102<br>000 | moltype = | length = |
| SEQ ID NO: 3103<br>SEQUENCE: 3103<br>000 | moltype = | length = |
| SEQ ID NO: 3104<br>SEQUENCE: 3104<br>000 | moltype = | length = |
| SEQ ID NO: 3105<br>SEQUENCE: 3105<br>000 | moltype = | length = |
| SEQ ID NO: 3106<br>SEQUENCE: 3106<br>000 | moltype = | length = |
| SEQ ID NO: 3107<br>SEQUENCE: 3107<br>000 | moltype = | length = |
| SEQ ID NO: 3108<br>SEQUENCE: 3108<br>000 | moltype = | length = |

| | | |
|---|---|---|
| SEQ ID NO: 3109<br>SEQUENCE: 3109<br>000 | moltype = | length = |
| SEQ ID NO: 3110<br>SEQUENCE: 3110<br>000 | moltype = | length = |
| SEQ ID NO: 3111<br>SEQUENCE: 3111<br>000 | moltype = | length = |
| SEQ ID NO: 3112<br>SEQUENCE: 3112<br>000 | moltype = | length = |
| SEQ ID NO: 3113<br>SEQUENCE: 3113<br>000 | moltype = | length = |
| SEQ ID NO: 3114<br>SEQUENCE: 3114<br>000 | moltype = | length = |
| SEQ ID NO: 3115<br>SEQUENCE: 3115<br>000 | moltype = | length = |
| SEQ ID NO: 3116<br>SEQUENCE: 3116<br>000 | moltype = | length = |
| SEQ ID NO: 3117<br>SEQUENCE: 3117<br>000 | moltype = | length = |
| SEQ ID NO: 3118<br>SEQUENCE: 3118<br>000 | moltype = | length = |
| SEQ ID NO: 3119<br>SEQUENCE: 3119<br>000 | moltype = | length = |
| SEQ ID NO: 3120<br>SEQUENCE: 3120<br>000 | moltype = | length = |
| SEQ ID NO: 3121<br>SEQUENCE: 3121<br>000 | moltype = | length = |
| SEQ ID NO: 3122<br>SEQUENCE: 3122<br>000 | moltype = | length = |
| SEQ ID NO: 3123<br>SEQUENCE: 3123<br>000 | moltype = | length = |
| SEQ ID NO: 3124<br>SEQUENCE: 3124<br>000 | moltype = | length = |
| SEQ ID NO: 3125<br>SEQUENCE: 3125<br>000 | moltype = | length = |
| SEQ ID NO: 3126<br>SEQUENCE: 3126<br>000 | moltype = | length = |
| SEQ ID NO: 3127<br>SEQUENCE: 3127<br>000 | moltype = | length = |
| SEQ ID NO: 3128<br>SEQUENCE: 3128 | moltype = | length = |

000

SEQ ID NO: 3129       moltype =    length =
SEQUENCE: 3129
000

SEQ ID NO: 3130       moltype =    length =
SEQUENCE: 3130
000

SEQ ID NO: 3131       moltype =    length =
SEQUENCE: 3131
000

SEQ ID NO: 3132       moltype =    length =
SEQUENCE: 3132
000

SEQ ID NO: 3133       moltype =    length =
SEQUENCE: 3133
000

SEQ ID NO: 3134       moltype =    length =
SEQUENCE: 3134
000

SEQ ID NO: 3135       moltype =    length =
SEQUENCE: 3135
000

SEQ ID NO: 3136       moltype =    length =
SEQUENCE: 3136
000

SEQ ID NO: 3137       moltype =    length =
SEQUENCE: 3137
000

SEQ ID NO: 3138       moltype =    length =
SEQUENCE: 3138
000

SEQ ID NO: 3139       moltype =    length =
SEQUENCE: 3139
000

SEQ ID NO: 3140       moltype =    length =
SEQUENCE: 3140
000

SEQ ID NO: 3141       moltype =    length =
SEQUENCE: 3141
000

SEQ ID NO: 3142       moltype =    length =
SEQUENCE: 3142
000

SEQ ID NO: 3143       moltype =    length =
SEQUENCE: 3143
000

SEQ ID NO: 3144       moltype =    length =
SEQUENCE: 3144
000

SEQ ID NO: 3145       moltype =    length =
SEQUENCE: 3145
000

SEQ ID NO: 3146       moltype =    length =
SEQUENCE: 3146
000

SEQ ID NO: 3147       moltype =    length =
SEQUENCE: 3147
000

SEQ ID NO: 3148       moltype =    length =

```
SEQUENCE: 3148
000

SEQ ID NO: 3149          moltype =      length =
SEQUENCE: 3149
000

SEQ ID NO: 3150          moltype =      length =
SEQUENCE: 3150
000

SEQ ID NO: 3151          moltype =      length =
SEQUENCE: 3151
000

SEQ ID NO: 3152          moltype =      length =
SEQUENCE: 3152
000

SEQ ID NO: 3153          moltype =      length =
SEQUENCE: 3153
000

SEQ ID NO: 3154          moltype =      length =
SEQUENCE: 3154
000

SEQ ID NO: 3155          moltype =      length =
SEQUENCE: 3155
000

SEQ ID NO: 3156          moltype =      length =
SEQUENCE: 3156
000

SEQ ID NO: 3157          moltype =      length =
SEQUENCE: 3157
000

SEQ ID NO: 3158          moltype =      length =
SEQUENCE: 3158
000

SEQ ID NO: 3159          moltype =      length =
SEQUENCE: 3159
000

SEQ ID NO: 3160          moltype =      length =
SEQUENCE: 3160
000

SEQ ID NO: 3161          moltype =      length =
SEQUENCE: 3161
000

SEQ ID NO: 3162          moltype =      length =
SEQUENCE: 3162
000

SEQ ID NO: 3163          moltype =      length =
SEQUENCE: 3163
000

SEQ ID NO: 3164          moltype =      length =
SEQUENCE: 3164
000

SEQ ID NO: 3165          moltype =      length =
SEQUENCE: 3165
000

SEQ ID NO: 3166          moltype =      length =
SEQUENCE: 3166
000

SEQ ID NO: 3167          moltype =      length =
SEQUENCE: 3167
000
```

| | | |
|---|---|---|
| SEQ ID NO: 3168<br>SEQUENCE: 3168<br>000 | moltype = | length = |
| SEQ ID NO: 3169<br>SEQUENCE: 3169<br>000 | moltype = | length = |
| SEQ ID NO: 3170<br>SEQUENCE: 3170<br>000 | moltype = | length = |
| SEQ ID NO: 3171<br>SEQUENCE: 3171<br>000 | moltype = | length = |
| SEQ ID NO: 3172<br>SEQUENCE: 3172<br>000 | moltype = | length = |
| SEQ ID NO: 3173<br>SEQUENCE: 3173<br>000 | moltype = | length = |
| SEQ ID NO: 3174<br>SEQUENCE: 3174<br>000 | moltype = | length = |
| SEQ ID NO: 3175<br>SEQUENCE: 3175<br>000 | moltype = | length = |
| SEQ ID NO: 3176<br>SEQUENCE: 3176<br>000 | moltype = | length = |
| SEQ ID NO: 3177<br>SEQUENCE: 3177<br>000 | moltype = | length = |
| SEQ ID NO: 3178<br>SEQUENCE: 3178<br>000 | moltype = | length = |
| SEQ ID NO: 3179<br>SEQUENCE: 3179<br>000 | moltype = | length = |
| SEQ ID NO: 3180<br>SEQUENCE: 3180<br>000 | moltype = | length = |
| SEQ ID NO: 3181<br>SEQUENCE: 3181<br>000 | moltype = | length = |
| SEQ ID NO: 3182<br>SEQUENCE: 3182<br>000 | moltype = | length = |
| SEQ ID NO: 3183<br>SEQUENCE: 3183<br>000 | moltype = | length = |
| SEQ ID NO: 3184<br>SEQUENCE: 3184<br>000 | moltype = | length = |
| SEQ ID NO: 3185<br>SEQUENCE: 3185<br>000 | moltype = | length = |
| SEQ ID NO: 3186<br>SEQUENCE: 3186<br>000 | moltype = | length = |
| SEQ ID NO: 3187<br>SEQUENCE: 3187<br>000 | moltype = | length = |

| | | |
|---|---|---|
| SEQ ID NO: 3188<br>SEQUENCE: 3188<br>000 | moltype = | length = |
| SEQ ID NO: 3189<br>SEQUENCE: 3189<br>000 | moltype = | length = |
| SEQ ID NO: 3190<br>SEQUENCE: 3190<br>000 | moltype = | length = |
| SEQ ID NO: 3191<br>SEQUENCE: 3191<br>000 | moltype = | length = |
| SEQ ID NO: 3192<br>SEQUENCE: 3192<br>000 | moltype = | length = |
| SEQ ID NO: 3193<br>SEQUENCE: 3193<br>000 | moltype = | length = |
| SEQ ID NO: 3194<br>SEQUENCE: 3194<br>000 | moltype = | length = |
| SEQ ID NO: 3195<br>SEQUENCE: 3195<br>000 | moltype = | length = |
| SEQ ID NO: 3196<br>SEQUENCE: 3196<br>000 | moltype = | length = |
| SEQ ID NO: 3197<br>SEQUENCE: 3197<br>000 | moltype = | length = |
| SEQ ID NO: 3198<br>SEQUENCE: 3198<br>000 | moltype = | length = |
| SEQ ID NO: 3199<br>SEQUENCE: 3199<br>000 | moltype = | length = |
| SEQ ID NO: 3200<br>SEQUENCE: 3200<br>000 | moltype = | length = |
| SEQ ID NO: 3201<br>SEQUENCE: 3201<br>000 | moltype = | length = |
| SEQ ID NO: 3202<br>SEQUENCE: 3202<br>000 | moltype = | length = |
| SEQ ID NO: 3203<br>SEQUENCE: 3203<br>000 | moltype = | length = |
| SEQ ID NO: 3204<br>SEQUENCE: 3204<br>000 | moltype = | length = |
| SEQ ID NO: 3205<br>SEQUENCE: 3205<br>000 | moltype = | length = |
| SEQ ID NO: 3206<br>SEQUENCE: 3206<br>000 | moltype = | length = |
| SEQ ID NO: 3207<br>SEQUENCE: 3207 | moltype = | length = |

000

SEQ ID NO: 3208          moltype =     length =
SEQUENCE: 3208
000

SEQ ID NO: 3209          moltype =     length =
SEQUENCE: 3209
000

SEQ ID NO: 3210          moltype =     length =
SEQUENCE: 3210
000

SEQ ID NO: 3211          moltype =     length =
SEQUENCE: 3211
000

SEQ ID NO: 3212          moltype =     length =
SEQUENCE: 3212
000

SEQ ID NO: 3213          moltype =     length =
SEQUENCE: 3213
000

SEQ ID NO: 3214          moltype =     length =
SEQUENCE: 3214
000

SEQ ID NO: 3215          moltype =     length =
SEQUENCE: 3215
000

SEQ ID NO: 3216          moltype =     length =
SEQUENCE: 3216
000

SEQ ID NO: 3217          moltype =     length =
SEQUENCE: 3217
000

SEQ ID NO: 3218          moltype =     length =
SEQUENCE: 3218
000

SEQ ID NO: 3219          moltype =     length =
SEQUENCE: 3219
000

SEQ ID NO: 3220          moltype =     length =
SEQUENCE: 3220
000

SEQ ID NO: 3221          moltype =     length =
SEQUENCE: 3221
000

SEQ ID NO: 3222          moltype =     length =
SEQUENCE: 3222
000

SEQ ID NO: 3223          moltype =     length =
SEQUENCE: 3223
000

SEQ ID NO: 3224          moltype =     length =
SEQUENCE: 3224
000

SEQ ID NO: 3225          moltype =     length =
SEQUENCE: 3225
000

SEQ ID NO: 3226          moltype =     length =
SEQUENCE: 3226
000

SEQ ID NO: 3227          moltype =     length =

-continued

```
SEQUENCE: 3227
000

SEQ ID NO: 3228          moltype =     length =
SEQUENCE: 3228
000

SEQ ID NO: 3229          moltype =     length =
SEQUENCE: 3229
000

SEQ ID NO: 3230          moltype =     length =
SEQUENCE: 3230
000

SEQ ID NO: 3231          moltype =     length =
SEQUENCE: 3231
000

SEQ ID NO: 3232          moltype =     length =
SEQUENCE: 3232
000

SEQ ID NO: 3233          moltype =     length =
SEQUENCE: 3233
000

SEQ ID NO: 3234          moltype =     length =
SEQUENCE: 3234
000

SEQ ID NO: 3235          moltype =     length =
SEQUENCE: 3235
000

SEQ ID NO: 3236          moltype =     length =
SEQUENCE: 3236
000

SEQ ID NO: 3237          moltype =     length =
SEQUENCE: 3237
000

SEQ ID NO: 3238          moltype =     length =
SEQUENCE: 3238
000

SEQ ID NO: 3239          moltype =     length =
SEQUENCE: 3239
000

SEQ ID NO: 3240          moltype =     length =
SEQUENCE: 3240
000

SEQ ID NO: 3241          moltype =     length =
SEQUENCE: 3241
000

SEQ ID NO: 3242          moltype =     length =
SEQUENCE: 3242
000

SEQ ID NO: 3243          moltype =     length =
SEQUENCE: 3243
000

SEQ ID NO: 3244          moltype =     length =
SEQUENCE: 3244
000

SEQ ID NO: 3245          moltype =     length =
SEQUENCE: 3245
000

SEQ ID NO: 3246          moltype =     length =
SEQUENCE: 3246
000
```

-continued

SEQ ID NO: 3247        moltype =      length =
SEQUENCE: 3247
000

SEQ ID NO: 3248        moltype =      length =
SEQUENCE: 3248
000

SEQ ID NO: 3249        moltype =      length =
SEQUENCE: 3249
000

SEQ ID NO: 3250        moltype =      length =
SEQUENCE: 3250
000

SEQ ID NO: 3251        moltype =      length =
SEQUENCE: 3251
000

SEQ ID NO: 3252        moltype =      length =
SEQUENCE: 3252
000

SEQ ID NO: 3253        moltype =      length =
SEQUENCE: 3253
000

SEQ ID NO: 3254        moltype =      length =
SEQUENCE: 3254
000

SEQ ID NO: 3255        moltype =      length =
SEQUENCE: 3255
000

SEQ ID NO: 3256        moltype =      length =
SEQUENCE: 3256
000

SEQ ID NO: 3257        moltype =      length =
SEQUENCE: 3257
000

SEQ ID NO: 3258        moltype =      length =
SEQUENCE: 3258
000

SEQ ID NO: 3259        moltype =      length =
SEQUENCE: 3259
000

SEQ ID NO: 3260        moltype =      length =
SEQUENCE: 3260
000

SEQ ID NO: 3261        moltype =      length =
SEQUENCE: 3261
000

SEQ ID NO: 3262        moltype =      length =
SEQUENCE: 3262
000

SEQ ID NO: 3263        moltype =      length =
SEQUENCE: 3263
000

SEQ ID NO: 3264        moltype =      length =
SEQUENCE: 3264
000

SEQ ID NO: 3265        moltype =      length =
SEQUENCE: 3265
000

SEQ ID NO: 3266        moltype =      length =
SEQUENCE: 3266
000

SEQ ID NO: 3267        moltype =    length =
SEQUENCE: 3267
000

SEQ ID NO: 3268        moltype =    length =
SEQUENCE: 3268
000

SEQ ID NO: 3269        moltype =    length =
SEQUENCE: 3269
000

SEQ ID NO: 3270        moltype =    length =
SEQUENCE: 3270
000

SEQ ID NO: 3271        moltype =    length =
SEQUENCE: 3271
000

SEQ ID NO: 3272        moltype =    length =
SEQUENCE: 3272
000

SEQ ID NO: 3273        moltype =    length =
SEQUENCE: 3273
000

SEQ ID NO: 3274        moltype =    length =
SEQUENCE: 3274
000

SEQ ID NO: 3275        moltype =    length =
SEQUENCE: 3275
000

SEQ ID NO: 3276        moltype =    length =
SEQUENCE: 3276
000

SEQ ID NO: 3277        moltype =    length =
SEQUENCE: 3277
000

SEQ ID NO: 3278        moltype =    length =
SEQUENCE: 3278
000

SEQ ID NO: 3279        moltype =    length =
SEQUENCE: 3279
000

SEQ ID NO: 3280        moltype =    length =
SEQUENCE: 3280
000

SEQ ID NO: 3281        moltype =    length =
SEQUENCE: 3281
000

SEQ ID NO: 3282        moltype =    length =
SEQUENCE: 3282
000

SEQ ID NO: 3283        moltype =    length =
SEQUENCE: 3283
000

SEQ ID NO: 3284        moltype =    length =
SEQUENCE: 3284
000

SEQ ID NO: 3285        moltype =    length =
SEQUENCE: 3285
000

SEQ ID NO: 3286        moltype =    length =
SEQUENCE: 3286

000

SEQ ID NO: 3287    moltype =    length =
SEQUENCE: 3287
000

SEQ ID NO: 3288    moltype =    length =
SEQUENCE: 3288
000

SEQ ID NO: 3289    moltype =    length =
SEQUENCE: 3289
000

SEQ ID NO: 3290    moltype =    length =
SEQUENCE: 3290
000

SEQ ID NO: 3291    moltype =    length =
SEQUENCE: 3291
000

SEQ ID NO: 3292    moltype =    length =
SEQUENCE: 3292
000

SEQ ID NO: 3293    moltype =    length =
SEQUENCE: 3293
000

SEQ ID NO: 3294    moltype =    length =
SEQUENCE: 3294
000

SEQ ID NO: 3295    moltype =    length =
SEQUENCE: 3295
000

SEQ ID NO: 3296    moltype =    length =
SEQUENCE: 3296
000

SEQ ID NO: 3297    moltype =    length =
SEQUENCE: 3297
000

SEQ ID NO: 3298    moltype =    length =
SEQUENCE: 3298
000

SEQ ID NO: 3299    moltype =    length =
SEQUENCE: 3299
000

SEQ ID NO: 3300    moltype =    length =
SEQUENCE: 3300
000

SEQ ID NO: 3301    moltype =    length =
SEQUENCE: 3301
000

SEQ ID NO: 3302    moltype =    length =
SEQUENCE: 3302
000

SEQ ID NO: 3303    moltype =    length =
SEQUENCE: 3303
000

SEQ ID NO: 3304    moltype =    length =
SEQUENCE: 3304
000

SEQ ID NO: 3305    moltype =    length =
SEQUENCE: 3305
000

SEQ ID NO: 3306    moltype =    length =

-continued

| | | |
|---|---|---|
| SEQ ID NO: 3306 SEQUENCE: 3306 000 | | |
| SEQ ID NO: 3307 SEQUENCE: 3307 000 | moltype = | length = |
| SEQ ID NO: 3308 SEQUENCE: 3308 000 | moltype = | length = |
| SEQ ID NO: 3309 SEQUENCE: 3309 000 | moltype = | length = |
| SEQ ID NO: 3310 SEQUENCE: 3310 000 | moltype = | length = |
| SEQ ID NO: 3311 SEQUENCE: 3311 000 | moltype = | length = |
| SEQ ID NO: 3312 SEQUENCE: 3312 000 | moltype = | length = |
| SEQ ID NO: 3313 SEQUENCE: 3313 000 | moltype = | length = |
| SEQ ID NO: 3314 SEQUENCE: 3314 000 | moltype = | length = |
| SEQ ID NO: 3315 SEQUENCE: 3315 000 | moltype = | length = |
| SEQ ID NO: 3316 SEQUENCE: 3316 000 | moltype = | length = |
| SEQ ID NO: 3317 SEQUENCE: 3317 000 | moltype = | length = |
| SEQ ID NO: 3318 SEQUENCE: 3318 000 | moltype = | length = |
| SEQ ID NO: 3319 SEQUENCE: 3319 000 | moltype = | length = |
| SEQ ID NO: 3320 SEQUENCE: 3320 000 | moltype = | length = |
| SEQ ID NO: 3321 SEQUENCE: 3321 000 | moltype = | length = |
| SEQ ID NO: 3322 SEQUENCE: 3322 000 | moltype = | length = |
| SEQ ID NO: 3323 SEQUENCE: 3323 000 | moltype = | length = |
| SEQ ID NO: 3324 SEQUENCE: 3324 000 | moltype = | length = |
| SEQ ID NO: 3325 SEQUENCE: 3325 000 | moltype = | length = |

| | | |
|---|---|---|
| SEQ ID NO: 3326<br>SEQUENCE: 3326<br>000 | moltype = | length = |
| SEQ ID NO: 3327<br>SEQUENCE: 3327<br>000 | moltype = | length = |
| SEQ ID NO: 3328<br>SEQUENCE: 3328<br>000 | moltype = | length = |
| SEQ ID NO: 3329<br>SEQUENCE: 3329<br>000 | moltype = | length = |
| SEQ ID NO: 3330<br>SEQUENCE: 3330<br>000 | moltype = | length = |
| SEQ ID NO: 3331<br>SEQUENCE: 3331<br>000 | moltype = | length = |
| SEQ ID NO: 3332<br>SEQUENCE: 3332<br>000 | moltype = | length = |
| SEQ ID NO: 3333<br>SEQUENCE: 3333<br>000 | moltype = | length = |
| SEQ ID NO: 3334<br>SEQUENCE: 3334<br>000 | moltype = | length = |
| SEQ ID NO: 3335<br>SEQUENCE: 3335<br>000 | moltype = | length = |
| SEQ ID NO: 3336<br>SEQUENCE: 3336<br>000 | moltype = | length = |
| SEQ ID NO: 3337<br>SEQUENCE: 3337<br>000 | moltype = | length = |
| SEQ ID NO: 3338<br>SEQUENCE: 3338<br>000 | moltype = | length = |
| SEQ ID NO: 3339<br>SEQUENCE: 3339<br>000 | moltype = | length = |
| SEQ ID NO: 3340<br>SEQUENCE: 3340<br>000 | moltype = | length = |
| SEQ ID NO: 3341<br>SEQUENCE: 3341<br>000 | moltype = | length = |
| SEQ ID NO: 3342<br>SEQUENCE: 3342<br>000 | moltype = | length = |
| SEQ ID NO: 3343<br>SEQUENCE: 3343<br>000 | moltype = | length = |
| SEQ ID NO: 3344<br>SEQUENCE: 3344<br>000 | moltype = | length = |
| SEQ ID NO: 3345<br>SEQUENCE: 3345<br>000 | moltype = | length = |

```
SEQ ID NO: 3346        moltype =     length =
SEQUENCE: 3346
000

SEQ ID NO: 3347        moltype =     length =
SEQUENCE: 3347
000

SEQ ID NO: 3348        moltype =     length =
SEQUENCE: 3348
000

SEQ ID NO: 3349        moltype =     length =
SEQUENCE: 3349
000

SEQ ID NO: 3350        moltype =     length =
SEQUENCE: 3350
000

SEQ ID NO: 3351        moltype =     length =
SEQUENCE: 3351
000

SEQ ID NO: 3352        moltype =     length =
SEQUENCE: 3352
000

SEQ ID NO: 3353        moltype =     length =
SEQUENCE: 3353
000

SEQ ID NO: 3354        moltype =     length =
SEQUENCE: 3354
000

SEQ ID NO: 3355        moltype =     length =
SEQUENCE: 3355
000

SEQ ID NO: 3356        moltype =     length =
SEQUENCE: 3356
000

SEQ ID NO: 3357        moltype =     length =
SEQUENCE: 3357
000

SEQ ID NO: 3358        moltype =     length =
SEQUENCE: 3358
000

SEQ ID NO: 3359        moltype =     length =
SEQUENCE: 3359
000

SEQ ID NO: 3360        moltype =     length =
SEQUENCE: 3360
000

SEQ ID NO: 3361        moltype =     length =
SEQUENCE: 3361
000

SEQ ID NO: 3362        moltype =     length =
SEQUENCE: 3362
000

SEQ ID NO: 3363        moltype =     length =
SEQUENCE: 3363
000

SEQ ID NO: 3364        moltype =     length =
SEQUENCE: 3364
000

SEQ ID NO: 3365        moltype =     length =
SEQUENCE: 3365
```

000

SEQ ID NO: 3366          moltype =          length =
SEQUENCE: 3366
000

SEQ ID NO: 3367          moltype =          length =
SEQUENCE: 3367
000

SEQ ID NO: 3368          moltype =          length =
SEQUENCE: 3368
000

SEQ ID NO: 3369          moltype =          length =
SEQUENCE: 3369
000

SEQ ID NO: 3370          moltype =          length =
SEQUENCE: 3370
000

SEQ ID NO: 3371          moltype =          length =
SEQUENCE: 3371
000

SEQ ID NO: 3372          moltype =          length =
SEQUENCE: 3372
000

SEQ ID NO: 3373          moltype =          length =
SEQUENCE: 3373
000

SEQ ID NO: 3374          moltype =          length =
SEQUENCE: 3374
000

SEQ ID NO: 3375          moltype =          length =
SEQUENCE: 3375
000

SEQ ID NO: 3376          moltype =          length =
SEQUENCE: 3376
000

SEQ ID NO: 3377          moltype =          length =
SEQUENCE: 3377
000

SEQ ID NO: 3378          moltype =          length =
SEQUENCE: 3378
000

SEQ ID NO: 3379          moltype =          length =
SEQUENCE: 3379
000

SEQ ID NO: 3380          moltype =          length =
SEQUENCE: 3380
000

SEQ ID NO: 3381          moltype =          length =
SEQUENCE: 3381
000

SEQ ID NO: 3382          moltype =          length =
SEQUENCE: 3382
000

SEQ ID NO: 3383          moltype =          length =
SEQUENCE: 3383
000

SEQ ID NO: 3384          moltype =          length =
SEQUENCE: 3384
000

SEQ ID NO: 3385          moltype =          length =

| | | |
|---|---|---|
| SEQUENCE: 3385 000 | | |
| SEQ ID NO: 3386 SEQUENCE: 3386 000 | moltype = | length = |
| SEQ ID NO: 3387 SEQUENCE: 3387 000 | moltype = | length = |
| SEQ ID NO: 3388 SEQUENCE: 3388 000 | moltype = | length = |
| SEQ ID NO: 3389 SEQUENCE: 3389 000 | moltype = | length = |
| SEQ ID NO: 3390 SEQUENCE: 3390 000 | moltype = | length = |
| SEQ ID NO: 3391 SEQUENCE: 3391 000 | moltype = | length = |
| SEQ ID NO: 3392 SEQUENCE: 3392 000 | moltype = | length = |
| SEQ ID NO: 3393 SEQUENCE: 3393 000 | moltype = | length = |
| SEQ ID NO: 3394 SEQUENCE: 3394 000 | moltype = | length = |
| SEQ ID NO: 3395 SEQUENCE: 3395 000 | moltype = | length = |
| SEQ ID NO: 3396 SEQUENCE: 3396 000 | moltype = | length = |
| SEQ ID NO: 3397 SEQUENCE: 3397 000 | moltype = | length = |
| SEQ ID NO: 3398 SEQUENCE: 3398 000 | moltype = | length = |
| SEQ ID NO: 3399 SEQUENCE: 3399 000 | moltype = | length = |
| SEQ ID NO: 3400 SEQUENCE: 3400 000 | moltype = | length = |
| SEQ ID NO: 3401 SEQUENCE: 3401 000 | moltype = | length = |
| SEQ ID NO: 3402 SEQUENCE: 3402 000 | moltype = | length = |
| SEQ ID NO: 3403 SEQUENCE: 3403 000 | moltype = | length = |
| SEQ ID NO: 3404 SEQUENCE: 3404 000 | moltype = | length = |

| | | |
|---|---|---|
| SEQ ID NO: 3405<br>SEQUENCE: 3405<br>000 | moltype = | length = |
| SEQ ID NO: 3406<br>SEQUENCE: 3406<br>000 | moltype = | length = |
| SEQ ID NO: 3407<br>SEQUENCE: 3407<br>000 | moltype = | length = |
| SEQ ID NO: 3408<br>SEQUENCE: 3408<br>000 | moltype = | length = |
| SEQ ID NO: 3409<br>SEQUENCE: 3409<br>000 | moltype = | length = |
| SEQ ID NO: 3410<br>SEQUENCE: 3410<br>000 | moltype = | length = |
| SEQ ID NO: 3411<br>SEQUENCE: 3411<br>000 | moltype = | length = |
| SEQ ID NO: 3412<br>SEQUENCE: 3412<br>000 | moltype = | length = |
| SEQ ID NO: 3413<br>SEQUENCE: 3413<br>000 | moltype = | length = |
| SEQ ID NO: 3414<br>SEQUENCE: 3414<br>000 | moltype = | length = |
| SEQ ID NO: 3415<br>SEQUENCE: 3415<br>000 | moltype = | length = |
| SEQ ID NO: 3416<br>SEQUENCE: 3416<br>000 | moltype = | length = |
| SEQ ID NO: 3417<br>SEQUENCE: 3417<br>000 | moltype = | length = |
| SEQ ID NO: 3418<br>SEQUENCE: 3418<br>000 | moltype = | length = |
| SEQ ID NO: 3419<br>SEQUENCE: 3419<br>000 | moltype = | length = |
| SEQ ID NO: 3420<br>SEQUENCE: 3420<br>000 | moltype = | length = |
| SEQ ID NO: 3421<br>SEQUENCE: 3421<br>000 | moltype = | length = |
| SEQ ID NO: 3422<br>SEQUENCE: 3422<br>000 | moltype = | length = |
| SEQ ID NO: 3423<br>SEQUENCE: 3423<br>000 | moltype = | length = |
| SEQ ID NO: 3424<br>SEQUENCE: 3424<br>000 | moltype = | length = |

| | | |
|---|---|---|
| SEQ ID NO: 3425<br>SEQUENCE: 3425<br>000 | moltype = | length = |
| SEQ ID NO: 3426<br>SEQUENCE: 3426<br>000 | moltype = | length = |
| SEQ ID NO: 3427<br>SEQUENCE: 3427<br>000 | moltype = | length = |
| SEQ ID NO: 3428<br>SEQUENCE: 3428<br>000 | moltype = | length = |
| SEQ ID NO: 3429<br>SEQUENCE: 3429<br>000 | moltype = | length = |
| SEQ ID NO: 3430<br>SEQUENCE: 3430<br>000 | moltype = | length = |
| SEQ ID NO: 3431<br>SEQUENCE: 3431<br>000 | moltype = | length = |
| SEQ ID NO: 3432<br>SEQUENCE: 3432<br>000 | moltype = | length = |
| SEQ ID NO: 3433<br>SEQUENCE: 3433<br>000 | moltype = | length = |
| SEQ ID NO: 3434<br>SEQUENCE: 3434<br>000 | moltype = | length = |
| SEQ ID NO: 3435<br>SEQUENCE: 3435<br>000 | moltype = | length = |
| SEQ ID NO: 3436<br>SEQUENCE: 3436<br>000 | moltype = | length = |
| SEQ ID NO: 3437<br>SEQUENCE: 3437<br>000 | moltype = | length = |
| SEQ ID NO: 3438<br>SEQUENCE: 3438<br>000 | moltype = | length = |
| SEQ ID NO: 3439<br>SEQUENCE: 3439<br>000 | moltype = | length = |
| SEQ ID NO: 3440<br>SEQUENCE: 3440<br>000 | moltype = | length = |
| SEQ ID NO: 3441<br>SEQUENCE: 3441<br>000 | moltype = | length = |
| SEQ ID NO: 3442<br>SEQUENCE: 3442<br>000 | moltype = | length = |
| SEQ ID NO: 3443<br>SEQUENCE: 3443<br>000 | moltype = | length = |
| SEQ ID NO: 3444<br>SEQUENCE: 3444 | moltype = | length = |

000

SEQ ID NO: 3445         moltype =     length =
SEQUENCE: 3445
000

SEQ ID NO: 3446         moltype =     length =
SEQUENCE: 3446
000

SEQ ID NO: 3447         moltype =     length =
SEQUENCE: 3447
000

SEQ ID NO: 3448         moltype =     length =
SEQUENCE: 3448
000

SEQ ID NO: 3449         moltype =     length =
SEQUENCE: 3449
000

SEQ ID NO: 3450         moltype =     length =
SEQUENCE: 3450
000

SEQ ID NO: 3451         moltype =     length =
SEQUENCE: 3451
000

SEQ ID NO: 3452         moltype =     length =
SEQUENCE: 3452
000

SEQ ID NO: 3453         moltype =     length =
SEQUENCE: 3453
000

SEQ ID NO: 3454         moltype =     length =
SEQUENCE: 3454
000

SEQ ID NO: 3455         moltype =     length =
SEQUENCE: 3455
000

SEQ ID NO: 3456         moltype =     length =
SEQUENCE: 3456
000

SEQ ID NO: 3457         moltype =     length =
SEQUENCE: 3457
000

SEQ ID NO: 3458         moltype =     length =
SEQUENCE: 3458
000

SEQ ID NO: 3459         moltype =     length =
SEQUENCE: 3459
000

SEQ ID NO: 3460         moltype =     length =
SEQUENCE: 3460
000

SEQ ID NO: 3461         moltype =     length =
SEQUENCE: 3461
000

SEQ ID NO: 3462         moltype =     length =
SEQUENCE: 3462
000

SEQ ID NO: 3463         moltype =     length =
SEQUENCE: 3463
000

SEQ ID NO: 3464         moltype =     length =

-continued

| | | |
|---|---|---|
| SEQ ID NO: 3465 SEQUENCE: 3465 000 | moltype = | length = |
| SEQ ID NO: 3466 SEQUENCE: 3466 000 | moltype = | length = |
| SEQ ID NO: 3467 SEQUENCE: 3467 000 | moltype = | length = |
| SEQ ID NO: 3468 SEQUENCE: 3468 000 | moltype = | length = |
| SEQ ID NO: 3469 SEQUENCE: 3469 000 | moltype = | length = |
| SEQ ID NO: 3470 SEQUENCE: 3470 000 | moltype = | length = |
| SEQ ID NO: 3471 SEQUENCE: 3471 000 | moltype = | length = |
| SEQ ID NO: 3472 SEQUENCE: 3472 000 | moltype = | length = |
| SEQ ID NO: 3473 SEQUENCE: 3473 000 | moltype = | length = |
| SEQ ID NO: 3474 SEQUENCE: 3474 000 | moltype = | length = |
| SEQ ID NO: 3475 SEQUENCE: 3475 000 | moltype = | length = |
| SEQ ID NO: 3476 SEQUENCE: 3476 000 | moltype = | length = |
| SEQ ID NO: 3477 SEQUENCE: 3477 000 | moltype = | length = |
| SEQ ID NO: 3478 SEQUENCE: 3478 000 | moltype = | length = |
| SEQ ID NO: 3479 SEQUENCE: 3479 000 | moltype = | length = |
| SEQ ID NO: 3480 SEQUENCE: 3480 000 | moltype = | length = |
| SEQ ID NO: 3481 SEQUENCE: 3481 000 | moltype = | length = |
| SEQ ID NO: 3482 SEQUENCE: 3482 000 | moltype = | length = |
| SEQ ID NO: 3483 SEQUENCE: 3483 000 | moltype = | length = |

| | | |
|---|---|---|
| SEQ ID NO: 3484<br>SEQUENCE: 3484<br>000 | moltype = | length = |
| SEQ ID NO: 3485<br>SEQUENCE: 3485<br>000 | moltype = | length = |
| SEQ ID NO: 3486<br>SEQUENCE: 3486<br>000 | moltype = | length = |
| SEQ ID NO: 3487<br>SEQUENCE: 3487<br>000 | moltype = | length = |
| SEQ ID NO: 3488<br>SEQUENCE: 3488<br>000 | moltype = | length = |
| SEQ ID NO: 3489<br>SEQUENCE: 3489<br>000 | moltype = | length = |
| SEQ ID NO: 3490<br>SEQUENCE: 3490<br>000 | moltype = | length = |
| SEQ ID NO: 3491<br>SEQUENCE: 3491<br>000 | moltype = | length = |
| SEQ ID NO: 3492<br>SEQUENCE: 3492<br>000 | moltype = | length = |
| SEQ ID NO: 3493<br>SEQUENCE: 3493<br>000 | moltype = | length = |
| SEQ ID NO: 3494<br>SEQUENCE: 3494<br>000 | moltype = | length = |
| SEQ ID NO: 3495<br>SEQUENCE: 3495<br>000 | moltype = | length = |
| SEQ ID NO: 3496<br>SEQUENCE: 3496<br>000 | moltype = | length = |
| SEQ ID NO: 3497<br>SEQUENCE: 3497<br>000 | moltype = | length = |
| SEQ ID NO: 3498<br>SEQUENCE: 3498<br>000 | moltype = | length = |
| SEQ ID NO: 3499<br>SEQUENCE: 3499<br>000 | moltype = | length = |
| SEQ ID NO: 3500<br>SEQUENCE: 3500<br>000 | moltype = | length = |
| SEQ ID NO: 3501<br>SEQUENCE: 3501<br>000 | moltype = | length = |
| SEQ ID NO: 3502<br>SEQUENCE: 3502<br>000 | moltype = | length = |
| SEQ ID NO: 3503<br>SEQUENCE: 3503<br>000 | moltype = | length = |

| | | |
|---|---|---|
| SEQ ID NO: 3504<br>SEQUENCE: 3504<br>000 | moltype = | length = |
| SEQ ID NO: 3505<br>SEQUENCE: 3505<br>000 | moltype = | length = |
| SEQ ID NO: 3506<br>SEQUENCE: 3506<br>000 | moltype = | length = |
| SEQ ID NO: 3507<br>SEQUENCE: 3507<br>000 | moltype = | length = |
| SEQ ID NO: 3508<br>SEQUENCE: 3508<br>000 | moltype = | length = |
| SEQ ID NO: 3509<br>SEQUENCE: 3509<br>000 | moltype = | length = |
| SEQ ID NO: 3510<br>SEQUENCE: 3510<br>000 | moltype = | length = |
| SEQ ID NO: 3511<br>SEQUENCE: 3511<br>000 | moltype = | length = |
| SEQ ID NO: 3512<br>SEQUENCE: 3512<br>000 | moltype = | length = |
| SEQ ID NO: 3513<br>SEQUENCE: 3513<br>000 | moltype = | length = |
| SEQ ID NO: 3514<br>SEQUENCE: 3514<br>000 | moltype = | length = |
| SEQ ID NO: 3515<br>SEQUENCE: 3515<br>000 | moltype = | length = |
| SEQ ID NO: 3516<br>SEQUENCE: 3516<br>000 | moltype = | length = |
| SEQ ID NO: 3517<br>SEQUENCE: 3517<br>000 | moltype = | length = |
| SEQ ID NO: 3518<br>SEQUENCE: 3518<br>000 | moltype = | length = |
| SEQ ID NO: 3519<br>SEQUENCE: 3519<br>000 | moltype = | length = |
| SEQ ID NO: 3520<br>SEQUENCE: 3520<br>000 | moltype = | length = |
| SEQ ID NO: 3521<br>SEQUENCE: 3521<br>000 | moltype = | length = |
| SEQ ID NO: 3522<br>SEQUENCE: 3522<br>000 | moltype = | length = |
| SEQ ID NO: 3523<br>SEQUENCE: 3523 | moltype = | length = |

000

SEQ ID NO: 3524         moltype =      length =
SEQUENCE: 3524
000

SEQ ID NO: 3525         moltype =      length =
SEQUENCE: 3525
000

SEQ ID NO: 3526         moltype =      length =
SEQUENCE: 3526
000

SEQ ID NO: 3527         moltype =      length =
SEQUENCE: 3527
000

SEQ ID NO: 3528         moltype =      length =
SEQUENCE: 3528
000

SEQ ID NO: 3529         moltype =      length =
SEQUENCE: 3529
000

SEQ ID NO: 3530         moltype =      length =
SEQUENCE: 3530
000

SEQ ID NO: 3531         moltype =      length =
SEQUENCE: 3531
000

SEQ ID NO: 3532         moltype =      length =
SEQUENCE: 3532
000

SEQ ID NO: 3533         moltype =      length =
SEQUENCE: 3533
000

SEQ ID NO: 3534         moltype =      length =
SEQUENCE: 3534
000

SEQ ID NO: 3535         moltype =      length =
SEQUENCE: 3535
000

SEQ ID NO: 3536         moltype =      length =
SEQUENCE: 3536
000

SEQ ID NO: 3537         moltype =      length =
SEQUENCE: 3537
000

SEQ ID NO: 3538         moltype =      length =
SEQUENCE: 3538
000

SEQ ID NO: 3539         moltype =      length =
SEQUENCE: 3539
000

SEQ ID NO: 3540         moltype =      length =
SEQUENCE: 3540
000

SEQ ID NO: 3541         moltype =      length =
SEQUENCE: 3541
000

SEQ ID NO: 3542         moltype =      length =
SEQUENCE: 3542
000

SEQ ID NO: 3543         moltype =      length =

```
SEQUENCE: 3543
000

SEQ ID NO: 3544          moltype =      length =
SEQUENCE: 3544
000

SEQ ID NO: 3545          moltype =      length =
SEQUENCE: 3545
000

SEQ ID NO: 3546          moltype =      length =
SEQUENCE: 3546
000

SEQ ID NO: 3547          moltype =      length =
SEQUENCE: 3547
000

SEQ ID NO: 3548          moltype =      length =
SEQUENCE: 3548
000

SEQ ID NO: 3549          moltype =      length =
SEQUENCE: 3549
000

SEQ ID NO: 3550          moltype =      length =
SEQUENCE: 3550
000

SEQ ID NO: 3551          moltype =      length =
SEQUENCE: 3551
000

SEQ ID NO: 3552          moltype =      length =
SEQUENCE: 3552
000

SEQ ID NO: 3553          moltype =      length =
SEQUENCE: 3553
000

SEQ ID NO: 3554          moltype =      length =
SEQUENCE: 3554
000

SEQ ID NO: 3555          moltype =      length =
SEQUENCE: 3555
000

SEQ ID NO: 3556          moltype =      length =
SEQUENCE: 3556
000

SEQ ID NO: 3557          moltype =      length =
SEQUENCE: 3557
000

SEQ ID NO: 3558          moltype =      length =
SEQUENCE: 3558
000

SEQ ID NO: 3559          moltype =      length =
SEQUENCE: 3559
000

SEQ ID NO: 3560          moltype =      length =
SEQUENCE: 3560
000

SEQ ID NO: 3561          moltype =      length =
SEQUENCE: 3561
000

SEQ ID NO: 3562          moltype =      length =
SEQUENCE: 3562
000
```

| | | |
|---|---|---|
| SEQ ID NO: 3563<br>SEQUENCE: 3563<br>000 | moltype = | length = |
| SEQ ID NO: 3564<br>SEQUENCE: 3564<br>000 | moltype = | length = |
| SEQ ID NO: 3565<br>SEQUENCE: 3565<br>000 | moltype = | length = |
| SEQ ID NO: 3566<br>SEQUENCE: 3566<br>000 | moltype = | length = |
| SEQ ID NO: 3567<br>SEQUENCE: 3567<br>000 | moltype = | length = |
| SEQ ID NO: 3568<br>SEQUENCE: 3568<br>000 | moltype = | length = |
| SEQ ID NO: 3569<br>SEQUENCE: 3569<br>000 | moltype = | length = |
| SEQ ID NO: 3570<br>SEQUENCE: 3570<br>000 | moltype = | length = |
| SEQ ID NO: 3571<br>SEQUENCE: 3571<br>000 | moltype = | length = |
| SEQ ID NO: 3572<br>SEQUENCE: 3572<br>000 | moltype = | length = |
| SEQ ID NO: 3573<br>SEQUENCE: 3573<br>000 | moltype = | length = |
| SEQ ID NO: 3574<br>SEQUENCE: 3574<br>000 | moltype = | length = |
| SEQ ID NO: 3575<br>SEQUENCE: 3575<br>000 | moltype = | length = |
| SEQ ID NO: 3576<br>SEQUENCE: 3576<br>000 | moltype = | length = |
| SEQ ID NO: 3577<br>SEQUENCE: 3577<br>000 | moltype = | length = |
| SEQ ID NO: 3578<br>SEQUENCE: 3578<br>000 | moltype = | length = |
| SEQ ID NO: 3579<br>SEQUENCE: 3579<br>000 | moltype = | length = |
| SEQ ID NO: 3580<br>SEQUENCE: 3580<br>000 | moltype = | length = |
| SEQ ID NO: 3581<br>SEQUENCE: 3581<br>000 | moltype = | length = |
| SEQ ID NO: 3582<br>SEQUENCE: 3582<br>000 | moltype = | length = |

SEQ ID NO: 3583      moltype =    length =
SEQUENCE: 3583
000

SEQ ID NO: 3584      moltype =    length =
SEQUENCE: 3584
000

SEQ ID NO: 3585      moltype =    length =
SEQUENCE: 3585
000

SEQ ID NO: 3586      moltype =    length =
SEQUENCE: 3586
000

SEQ ID NO: 3587      moltype =    length =
SEQUENCE: 3587
000

SEQ ID NO: 3588      moltype =    length =
SEQUENCE: 3588
000

SEQ ID NO: 3589      moltype =    length =
SEQUENCE: 3589
000

SEQ ID NO: 3590      moltype =    length =
SEQUENCE: 3590
000

SEQ ID NO: 3591      moltype =    length =
SEQUENCE: 3591
000

SEQ ID NO: 3592      moltype =    length =
SEQUENCE: 3592
000

SEQ ID NO: 3593      moltype =    length =
SEQUENCE: 3593
000

SEQ ID NO: 3594      moltype =    length =
SEQUENCE: 3594
000

SEQ ID NO: 3595      moltype =    length =
SEQUENCE: 3595
000

SEQ ID NO: 3596      moltype =    length =
SEQUENCE: 3596
000

SEQ ID NO: 3597      moltype =    length =
SEQUENCE: 3597
000

SEQ ID NO: 3598      moltype =    length =
SEQUENCE: 3598
000

SEQ ID NO: 3599      moltype =    length =
SEQUENCE: 3599
000

SEQ ID NO: 3600      moltype =    length =
SEQUENCE: 3600
000

SEQ ID NO: 3601      moltype =    length =
SEQUENCE: 3601
000

SEQ ID NO: 3602      moltype =    length =
SEQUENCE: 3602

000

SEQ ID NO: 3603        moltype =     length =
SEQUENCE: 3603
000

SEQ ID NO: 3604        moltype =     length =
SEQUENCE: 3604
000

SEQ ID NO: 3605        moltype =     length =
SEQUENCE: 3605
000

SEQ ID NO: 3606        moltype =     length =
SEQUENCE: 3606
000

SEQ ID NO: 3607        moltype =     length =
SEQUENCE: 3607
000

SEQ ID NO: 3608        moltype =     length =
SEQUENCE: 3608
000

SEQ ID NO: 3609        moltype =     length =
SEQUENCE: 3609
000

SEQ ID NO: 3610        moltype =     length =
SEQUENCE: 3610
000

SEQ ID NO: 3611        moltype =     length =
SEQUENCE: 3611
000

SEQ ID NO: 3612        moltype =     length =
SEQUENCE: 3612
000

SEQ ID NO: 3613        moltype =     length =
SEQUENCE: 3613
000

SEQ ID NO: 3614        moltype =     length =
SEQUENCE: 3614
000

SEQ ID NO: 3615        moltype =     length =
SEQUENCE: 3615
000

SEQ ID NO: 3616        moltype =     length =
SEQUENCE: 3616
000

SEQ ID NO: 3617        moltype =     length =
SEQUENCE: 3617
000

SEQ ID NO: 3618        moltype =     length =
SEQUENCE: 3618
000

SEQ ID NO: 3619        moltype =     length =
SEQUENCE: 3619
000

SEQ ID NO: 3620        moltype =     length =
SEQUENCE: 3620
000

SEQ ID NO: 3621        moltype =     length =
SEQUENCE: 3621
000

SEQ ID NO: 3622        moltype =     length =

```
SEQUENCE: 3622
000

SEQ ID NO: 3623         moltype = DNA  length = 2232
FEATURE                 Location/Qualifiers
source                  1..2232
                        mol_type = other DNA
                        organism = synthetic construct
SEQUENCE: 3623
atggctgccg atggttatct tccagattgg ctcgaggaca accttagtga aggaattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aaggggagc cggtcaacgc agcagacgcg gcggccctcg agccgacaa ggcctacgac    240
cagcagctca aggccggaga caacccgtac ctcaagtaca accagccga cgccgagttc   300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcggaaa ttggcattgc gattcccaat ggctggggga cagagtcatc   720
accaccagca cccgaacctg gccctgccc acctacaaca atcacctcta caagcaaatc   780
tccaacagca catctggagg atcttcaaat gacaacgcct acttcggcta cagcacccc   840
tggggtatt ttgacttcaa cagattccac tgccacttct caccacgtga ctggcagcga   900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tcccactcat 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatgac gtaatagctt gatgaatcct 1560
ggacctgcta tggccagcca caagaagga gaggaccgtt tctttccttt gtctggatct 1620
ttaatttttg caaacaagg aactggaaga gacaacgtgg atgcggacaa agtcatgata 1680
accaacgaag aagaattaa aactactaac ccggtagcaa cggagtccta tggacaagtg 1740
gccacaaacc accagagtcc gcttaatggt gccgtccatc tttatgctca agcgcagacc 1800
ggctgggttc aaaaccaagg aatacttccg ggtatggttt ggcaggacag agatgtgtac 1860
ctgcaaggac ccatttgggc caaaattcct cacacggacg gcaactttca cccttctccg 1920
ctgatggag ggtttggaat gaagcacccg cctcctcaga tcctcatcaa aaacacacct 1980
gtacctgccg atcctccaac ggccttcaac aaggacaagc tgaactcttt catcacccag 2040
tattctactg gccaagtcag cgtggagatc gagtgggagc tgcagaagga aaacagcaag 2100
cggtggaacc cggagatcca gtacacttcc aactattaca gtctaataa tgttgaattt 2160
gctgttaata ctgaaggtgt atatagtgaa ccccgccca ttggcaccag ataccctgact 2220
cgtaatctgt aa                                                     2232

SEQ ID NO: 3624         moltype = DNA  length = 2232
FEATURE                 Location/Qualifiers
source                  1..2232
                        mol_type = other DNA
                        organism = synthetic construct
SEQUENCE: 3624
atggctgccg atggttatct tccagattgg ctcgaggaca accttagtga aggaattcgc   60
gagtggtggg ctttgaaacc tggagcccct caacccaagg caaatcaaca acatcaagac  120
aacgctcgag gtcttgtgct tccgggttac aaataccttg acccggcaa cggactcgac   180
aaggggagc cggtcaacgc agcagacgcg gcggccctcg agcacgacaa ggcctacgac   240
cagcagctca aggccggaga caacccgtac ctcaagtaca accagccga cgccgagttc   300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcggaaa ttggcattgc gattcccaat ggctggggga cagagtcatc   720
accaccagca cccgaacctg gccctgccc acctacaaca atcacctcta caagcaaatc   780
tccaacagca catctggagg atcttcaaat gacaacgcct acttcggcta cagcacccc   840
tggggtatt ttgacttcaa cagattccac tgccacttct caccacgtga ctggcagcga   900
ctcatcaaca acaactgggg attccggcct aagcgactca acttcaagct cttcaacatt  960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tcccactcat 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
```

```
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata    1680
accaacgaag aagaaattaa aactactaac ccggtagcaa cggagtccta tggacaagtg   1740
gccacaaacc accagagtgc acaggctcgt gattctccga agggttggca ggcgcagacc   1800
ggctgggttc aaaaccaagg aatacttccg ggtatggttt ggcaggacag agatgtgtac   1860
ctgcaaggac ccatttgggc caaaattcct cacacggacg gcaactttca cccttctccg   1920
ctgatgggag ggtttggaat gaagcacccg cctcctcaga tcctcatcaa aaacacacct   1980
gtacctgccg atcctccaac ggccttcaac aaggacaagc tgaactcttt catcacccag   2040
tattctactg gccaagtcag cgtggagatc gagtgggagc tgcagaagga aaacagcaag   2100
cggtggaacc cggagatcca gtacacttcc aactattaca agtctaataa tgttgaattt   2160
gctgttaata ctgaaggtgt atatagtgaa ccccgcccca ttggcaccag ataccctgact   2220
cgtaatctgt aa                                                       2232

SEQ ID NO: 3625        moltype = DNA  length = 2232
FEATURE                Location/Qualifiers
source                 1..2232
                       mol_type = other DNA
                       organism = synthetic construct
SEQUENCE: 3625
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggccctcg agcacgacaa ggcctacgac    240
cagcagctca aggccggaga caacccgtac ctcaagtaca ccacgccga cgccgagttc    300
caggagcggc tcaaagaaga tacgtctttt ggggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtgcagaca ataacgaagg tgccgatgga    660
gtgggtagtt cctcgggaaa ttggcattgc gattcccaat ggctggggga cagagtcatc   720
accaccagca cccgaacctg ggccctgccc acctacaaca tcacctcta caagcaaatc    780
tccaacagca catctggagg atcttcaaat gacaacgcct acttcggcta cagcaccccc   840
tggggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagccggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacgctt ctggacaaga tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttg gcaaacaagg aactggaaga gacaacgtgg atgcggacaa agtcatgata    1680
accaacgaag aagaaattaa aactactaac ccggtagcaa cggagtccta tggacaagtg   1740
gccacaaacc accagagtgc acaggctcgt gattctccga agggttggca ggcgcagacc   1800
ggctgggttc aaaaccaagg aatacttccg ggtatggttt ggcaggacag agatgtgtac   1860
ctgcaaggac ccatttgggc caaaattcct cacacggacg gcaactttca cccttctccg   1920
ctgatgggag ggtttggaat gaagcacccg cctcctcaga tcctcatcaa aaacacacct   1980
gtacctgccg atcctccaac ggccttcaac aaggacaagc tgaactcttt catcacccag   2040
tattctactg gccaagtcag cgtggagatc gagtgggagc tgcagaagga aaacagcaag   2100
cgctggaacc cggagatcca gtacacttcc aactattaca agtctaataa tgttgaattt   2160
gctgttaata ctgaaggtgt atatagtgaa ccccgcccca ttggcaccag ataccctgact   2220
cgtaatctgt aa                                                       2232

SEQ ID NO: 3626        moltype = DNA  length = 2232
FEATURE                Location/Qualifiers
source                 1..2232
                       mol_type = other DNA
                       organism = synthetic construct
SEQUENCE: 3626
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg gacccggcaa cggactcgac   180
aaggggagc cggtcaacgc agcagacgcg gcggccctcg agcacgacaa ggcctacgac    240
cagcagctca aggccggaga caacccgtac ctcaagtaca ccacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtgcagaca ataacgaagg tgccgatgga    660
gtgggtagtt cctcgggaaa ttggcattgc gattcccaat ggctggggga cagagtcatc   720
accaccagca cccgaacctg ggccctgccc acctacaaca tcacctcta caagcaaatc    780
tccaacagca catctggagg atcttcaaat gacaacgcct acttcggcta cagcaccccc   840
```

```
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc acaggcttat tctacggatg tgaggatgca ggcgcagacc   1800
ggctgggttc aaaaccaagg aatacttccg ggtatggttt ggcaggacag agatgtgtac   1860
ctgcaaggac ccatttgggc caaaattcct cacacggacg gcaactttca cccttctccg   1920
ctgatgggag ggtttggaat gaagcacccg cctcctcaga tcctcatcaa aaacacacct   1980
gtacctgccg atcctccaac ggccttcaac aaggacaagc tgaactcttt catcacccag   2040
tattctactg gccaagtcag cgtggagatc gagtgggagc tgcagaagga aaacagcaag   2100
cggtggaacc cggagatcca gtacacttcc aactattaca agtctaataa tgttgaattt   2160
gctgttaata ctgaaggtgt atatagtgaa ccccgcccca ttggcaccag ataccctgact   2220
cgtaatctgt aa                                                       2232

SEQ ID NO: 3627        moltype = DNA   length = 2232
FEATURE                Location/Qualifiers
source                 1..2232
                       mol_type = other DNA
                       organism = synthetic construct
SEQUENCE: 3627
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccgggttac aaataccttg acccggcaa cggactcgac    180
aaggggggagc cggtcaacgc agcagccgcg ggcgccctgc agcacgacaa ggcctacgac    240
cagcagctca aggccggaga caacccgtac ctcaagtaca ccacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc ggtgattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgc ttcaggtgg tggcgcacca gtggcagaca taacgaagg tgccgatgga    660
gtgggtagtt cctcgggaaa ttggcattgc gattcccaat ggctggggga cagagtccag    720
accaccagca cccgaacctg ggcctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc acagattgtt atgaattcgt tgaaggctca ggcgcagacc   1800
ggctgggttc aaaaccaagg aatacttccg ggtatggttt ggcaggacag agatgtgtac   1860
ctgcaaggac ccatttgggc caaaattcct cacacggacg gcaactttca cccttctccg   1920
ctgatgggag ggtttggaat gaagcacccg cctcctcaga tcctcatcaa aaacacacct   1980
gtacctgccg atcctccaac ggccttcaac aaggacaagc tgaactcttt catcacccag   2040
tattctactg gccaagtcag cgtggagatc gagtgggagc tgcagaagga aaacagcaag   2100
cggtggaacc cggagatcca gtacacttcc aactattaca agtctaataa tgttgaattt   2160
gctgttaata ctgaaggtgt atatagtgaa ccccgcccca ttggcaccag ataccctgact   2220
cgtaatctgt aa                                                       2232

SEQ ID NO: 3628        moltype = DNA   length = 2232
FEATURE                Location/Qualifiers
source                 1..2232
                       mol_type = other DNA
                       organism = synthetic construct
SEQUENCE: 3628
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccgggttac aaataccttg acccggcaa cggactcgac    180
```

```
aaggggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcgggaaa ttggcattgc gattccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaagga gaggaccgtt tctttccttt gtctggatct   1620
ttaattttg gcaaacaagg aactggaaga gacaacgtgg atgcgacaa agtcatgata   1680
accaacgaag aagaaattaa aactactaac ccggtagcaa cggagtccta tggacaagtg   1740
gccacaaacc accagagtgc acaggctcgg gagagtcctc gtgggctgca ggcgcagacc   1800
ggctgggttc aaaaccaagg aatacttccg ggtatggttt ggcaggacag agatgtgtac   1860
ctgcaaggac ccatttgggc caaaattcct cacacggacg gcaactttca cccttctccg   1920
ctgatgggag ggtttggaat gaagcacccg cctcctcaga tcctcatcaa aaacacacct   1980
gtacctgccg atcctccaac ggccttcaac aaggacaagc tgaactcttt catcacccag   2040
tattctactg gccaagtcag cgtggagatc gagtgggagc tgcagaagga aaacagcaag   2100
cggtggaacc cggagatcca gtacacttcc aactattaca agtctaataa tgttgaattt   2160
gctgttaata ctgaaggtgt atatagtgaa ccccgcccca ttggcaccag atacctgact   2220
cgtaatctgt aa                                                        2232
```

| SEQ ID NO: 3629<br>FEATURE<br>source | moltype = DNA length = 2232<br>Location/Qualifiers<br>1..2232<br>mol_type = other DNA<br>organism = synthetic construct |

SEQUENCE: 3629
```
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag tcttgtgct tccggggttac aaataccttg acccggcaa cggactcgac   180
aagggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtggcagaca taacgaagg tgccgatgga   660
gtgggtagtt cctcgggaaa ttggcattgc gattccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggaccgtt tctttccttt gtctggatct  1620
ttaattttg gcaaacaagg aactggaaga gacaacgtgg atgcgacaa agtcatgata  1680
accaacgaag aagaaattaa aactactaac ccggtagcaa cggagtccta tggacaagtg  1740
gccacaaacc accagagtgc acaggctagt tttaatgata ctagggctca ggcgcagacc  1800
ggctgggttc aaaaccaagg aatacttccg ggtatggttt ggcaggacag agatgtgtac  1860
ctgcaaggac ccatttgggc caaaattcct cacacggacg gcaactttca cccttctccg  1920
ctgatgggag ggtttggaat gaagcacccg cctcctcaga tcctcatcaa aaacacacct  1980
gtacctgccg atcctccaac ggccttcaac aaggacaagc tgaactcttt catcacccag  2040
tattctactg gccaagtcag cgtggagatc gagtgggagc tgcagaagga aaacagcaag  2100
cggtggaacc cggagatcca gtacacttcc aactattaca agtctaataa tgttgaattt  2160
gctgttaata ctgaaggtgt atatagtgaa ccccgcccca ttggcaccag atacctgact  2220
```

```
cgtaatctgt aa                                                            2232

SEQ ID NO: 3630          moltype = DNA   length = 2232
FEATURE                  Location/Qualifiers
source                   1..2232
                         mol_type = other DNA
                         organism = synthetic construct
SEQUENCE: 3630
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcgggaaa ttggcattgc gattccaat ggctggggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct   1560
ggacctgcta tggccagcca caaagaagga gggaccgttt tctttcctt gtctggatct  1620
ttaattttg gcaaacaagg aactggaaga gacaacgtgg atgcggacaa agtcatgata  1680
accaacgaag aagaaattaa aactactaac cggtagcaa cggagtccta tggacaagtg  1740
gccacaaacc accagagtgg tggtacgttg gccgtcgtgt cgcttgctca ggcgcagacc  1800
ggctgggttc aaaaccaagg aatacttcg ggtatggttt gacaggacgg agatgtgtac  1860
ctgcaaggac ccatttgggc caaaattcct cacacggacg gcaactttca cccttctccg  1920
ctgatgggag ggtttggaat gaagcaccg cctcctcaga tcctcatcaa aaacacacct  1980
gtacctgccg atcctccaac ggccttcaac aaggacaagc tgaactcttt catcacccag  2040
tattctactg gccaagtcag cgtggagatc gagtgggagc tgcagaagga aaacagcaag  2100
cggtggaacc cggagatcca gtacacttcc aactattaca agtctaataa tgttgaattt  2160
gctgttaata ctgaaggtgt atatagtgaa ccccgcccca ttggcaccag atacctgact  2220
cgtaatctgt aa                                                        2232

SEQ ID NO: 3631          moltype = DNA   length = 2232
FEATURE                  Location/Qualifiers
source                   1..2232
                         mol_type = other DNA
                         organism = synthetic construct
SEQUENCE: 3631
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg acccggcaa cggactcgac    180
aaggggggagc cggtcaacgc agcagacgcg gcggccctcg agcacgacaa ggcctacgac   240
cagcagctca aggccggaga caacccgtac ctcaagtaca accacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcgggaaa ttggcattgc gattccaat ggctggggga cagagtcatc    720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactggggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctgagcttc ttcttgggct ctcaatggac gtaatagctt gatgaatcct  1560
```

```
ggacctgcta tggccagcca caaagaagga gaggaccgtt tctttccttt gtctggatct    1620
ttaattttg  gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc acaggcttat gggttgccga agggtcctca ggcgcagacc    1800
ggctgggttc aaaaccaagg aatacttccg ggtatggttt gcaggacag  agatgtgtac    1860
ctgcaaggac ccatttgggc caaaattcct cacacggacg gcaactttca cccttctccg    1920
ctgatgggag gtttggaat  gaagcacccg cctcctcaga tcctcatcaa aaacacacct    1980
gtacctgccg atcctccaac ggccttcaac aaggacaagc tgaactcttt catcacccag    2040
tattctactg gccaagtcag cgtggagatc gagtgggagc tgcagaagga aaacagcaag    2100
cggtggaacc cggagatcca gtacacttcc aactattaca agtctaataa tgttgaattt    2160
gctgttaata ctgaaggtgt atatagtgaa ccccgcccca ttggcaccag atacctgact    2220
cgtaatctgt aa                                                       2232

SEQ ID NO: 3632         moltype = DNA  length = 2232
FEATURE                 Location/Qualifiers
source                  1..2232
                        mol_type = other DNA
                        organism = synthetic construct
SEQUENCE: 3632
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccggttac  aaataccttg gacccggcaa cggactcgac    180
aaggggagc  cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt ggggcaacc  tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcggtg  cacagcccgc taaaagaga  ctcaatttcg gtcagactgg cgacacagag    540
tcagtcccag accctcaacc aatcggagaa cctcccgcag cccctcagg  tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggcctgcc   acctacaaca tcacctcta  caagcaaatc    780
tccaacagca catctggagg atcttcaaat gacaacgcct acttcggcta cagcaccccc    840
tgggggtatt ttgacttcaa cagattccac tgccactcct caccacgtga ctggcagcga    900
ctcatcaaca acaactgggg attccggcct aagcgactca acttcaagct cttcaacatt    960
caggtcaaag aggttacgga caacaatgga gtcaagacca cgccaataa  ccttaccagc   1020
acggtccagg tcttcacgga ctcagactat cagctcccgt acgtgctcgg tcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatattc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgctc agggaagaaa ctacatacct   1440
ggacccagct accgacaaca acgtgtctca accactgtga ctcaaaacaa caacagcgaa   1500
tttgcttggc ctgagcttc  ttctgggct  tcaatggac  gtaatagctt gatgaatcct   1560
ggacctgcta tggccagcca caagaagga  gaggaccgtt tctttccttt gtctggatct   1620
ttaattttg  gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc acaggcttcg actgggacgc ttcggcttca ggcgcagacc   1800
ggctgggttc aaaaccaagg aatacttccg ggtatggttt gcaggacag  agatgtgtac   1860
ctgcaaggac ccatttgggc caaaattcct cacacggacg gcaactttca cccttctccg   1920
ctgatgggag gtttggaat  gaagcacccg cctcctcaga tcctcatcaa aaacacacct   1980
gtacctgccg atcctccaac ggccttcaac aaggacaagc tgaactcttt catcacccag   2040
tattctactg gccaagtcag cgtggagatc gagtgggagc tgcagaagga aaacagcaag   2100
cggtggaacc cggagatcca gtacacttcc aactattaca agtctaataa tgttgaattt   2160
gctgttaata ctgaaggtgt atatagtgaa ccccgcccca ttggcaccag atacctgact   2220
cgtaatctgt aa                                                      2232

SEQ ID NO: 3633         moltype = DNA  length = 2232
FEATURE                 Location/Qualifiers
source                  1..2232
                        mol_type = other DNA
                        organism = synthetic construct
SEQUENCE: 3633
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccggttac  aaataccttg gacccggcaa cggactcgac    180
aaggggagc  cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt ggggcaacc  tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcggtg  cacagcccgc taaaagaga  ctcaatttcg gtcagactgg cgacacagag    540
tcagtcccag accctcaacc aatcggagaa cctcccgcag cccctcagg  tgtgggatct    600
cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggcctgcc   acctacaaca tcacctcta  caagcaaatc    780
tccaacagca catctggagg atcttcaaat gacaacgcct acttcggcta cagcaccccc    840
tgggggtatt ttgacttcaa cagattccac tgccactcct caccacgtga ctggcagcga    900
```

```
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc gcaggcgtat tcgacggatg agaggatgca ggcgcagacc   1800
ggctgggttc aaaaccaagg aatacttccg ggtatggttt ggcaggacag agatgtgtac   1860
ctgcaaggac ccatttgggc caaaattcct cacacgacg gcaactttca cccttctccg    1920
ctgatgggag ggtttggaat gaagcacccg cctcctcaga tcctcatcaa aaacacacct   1980
gtacctgccg atcctccaac ggccttcaac aaggacaagc tgaactcttt catcacccag   2040
tattctactg gccaagtcag cgtggagatc gagtgggagc tgcagaagga aaacagcaag   2100
cggtggaacc cggagatcca gtacacttcc aactattaca agtctaataa tgttgaattt   2160
gctgttaata ctgaaggtgt atatagtgaa cccccgcccca ttggcaccag ataccctgact   2220
cgtaatctgt aa                                                       2232

SEQ ID NO: 3634        moltype = DNA  length = 2232
FEATURE                Location/Qualifiers
source                 1..2232
                       mol_type = other DNA
                       organism = synthetic construct
SEQUENCE: 3634
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccggggtac aaataccttg acccggcaa cggactcgac    180
aaggggggagc cggtcaacgc agcagacgcg gcggccctcg agcacgacaa ggcctacgac    240
cagcagctca aggccggaga caacccgtac ctcaagtaca accaccgcga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacagagag    540
tcagtcccag accctcaacc aatcggagaa cctcccgcag cccctcagg tgtgggatct    600
cttacaatgg cttcaggtgg tggcgcacca gtggcagaca ataacgaagg tgccgatgga    660
gtgggtagtt cctcggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tggggggtatt ttgacttcaa cagattccac tgccactct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caaagaagga gaggaccgtt tctttccttt gtctggatct   1620
ttaattttttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc gcaggcgtat tcgacggatg agaggaagca ggcgcagacc   1800
ggctgggttc aaaaccaagg aatacttccg ggtatggttt ggcaggacag agatgtgtac   1860
ctgcaaggac ccatttgggc caaaattcct cacacgacg gcaactttca cccttctccg    1920
ctgatgggag ggtttggaat gaagcacccg cctcctcaga tcctcatcaa aaacacacct   1980
gtacctgccg atcctccaac ggccttcaac aaggacaagc tgaactcttt catcacccag   2040
tattctactg gccaagtcag cgtggagatc gagtgggagc tgcagaagga aaacagcaag   2100
cggtggaacc cggagatcca gtacacttcc aactattaca agtctaataa tgttgaattt   2160
gctgttaata ctgaaggtgt atatagtgaa cccccgcccca ttggcaccag ataccctgact   2220
cgtaatctgt aa                                                       2232

SEQ ID NO: 3635        moltype = DNA  length = 2232
FEATURE                Location/Qualifiers
source                 1..2232
                       mol_type = other DNA
                       organism = synthetic construct
SEQUENCE: 3635
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccggggtac aaataccttg acccggcaa cggactcgac    180
aaggggggagc cggtcaacgc agcagacgcg gcggccctcg agcacgacaa ggcctacgac    240
```

-continued

```
cagcagctca aggccggaga caacccgtac ctcaagtaca accacgccga cgccgagttc 300
caggagcggc tcaaagaaga tacgtctttt gggggcaacc tcgggcgagc agtcttccag 360
gccaaaaaga ggcttcttga acctcttggt ctggttgagg aagcggctaa gacggctcct 420
ggaaagaaga ggcctgtaga gcagtctcct caggaaccgg actcctccgc gggtattggc 480
aaatcgggtg cacagcccgc taaaaagaga ctcaatttcg gtcagactgg cgacacagag 540
tcagtcccag accctcaacc aatcggagaa cctcccgcag ccccctcagg tgtgggatct 600
cttacaatgg cttcaggtgg tggcgcacca gtggcagaca ataacgaagg tgccgatgga 660
gtgggtagtt cctcgggaaa ttggcattgc gattcccaat ggctggggga cagagtcatc 720
accaccagca cccgaacctg ggcccctgcc acctacaaca atcacctcta caagcaaatc 780
tccaacagca catctggagg atcttcaaat gacaacgcct acttcggcta cagcaccccc 840
tggggggtatt ttgacttcaa cagattccac tgccacttct caccacgtga ctggcagcga 900
ctcatcaaca caactgggg attccggcct aagcgactca acttcaagct cttcaacatt 960
caggtcaaag aggttacgga caacaatgga gtcaagacca tcgccaataa ccttaccagc 1020
acggtccagg tcttcacgga ctcagactat cagctcccgt acgtgctcgg gtcggctcac 1080
gagggctgcc tcccgccgtt cccagcggac gttttcatga ttcctcagta cgggtatctg 1140
acgcttaatg atggaagcca ggccgtgggt cgttcgtcct tttactgcct ggaatatttc 1200
ccgtcgcaaa tgctaagaac gggtaacaac ttccagttca gctacgagtt tgagaacgta 1260
cctttccata gcagctacgc tcacagccaa agcctggacc gactaatgaa tccactcatc 1320
gaccaatact tgtactatct ctcaaagact attaacggtt ctggacagaa tcaacaaacg 1380
ctaaaattca gtgtggccgg acccagcaac atggctgtcc agggaagaaa ctacatacct 1440
ggacccagct accgacaaca acgtgtctca accactgtga ctcaaaacaa caacagcgaa 1500
tttgcttggc ctggagcttc ttcttgggct ctcaatggac gtaatagtct gatgaatcct 1560
ggacctgcta tggccagcca caagaagga gaggaccgtt tctttccttt gtctggatct 1620
ttaattttg gcaaacaagg aactggaaga gacaacgtgg atgcggacaa agtcatgata 1680
accaacgaag aagaaattaa aactactaac ccggtagcaa cggagtccta tggacaagtg 1740
gccacaaacc accagagtgc acaggcttat gtttcgtctg ttaaagatgc ggcgcagacc 1800
ggctgggttc aaaaccaagg aatacttccg ggtatggttt ggcaggacag agatgtgtac 1860
ctgcaaggac ccatttgggc caaaattcct cacacggacg gcaactttca cccttctccg 1920
ctgatggagg ggtttggaat gaagcacccg cctcctcaga tcctcatcaa aaacacacct 1980
gtacctgccg atcctccaac ggccttcaac aaggacaagc tgaactcttt catcacccag 2040
tattctactg gccaagtcag cgtggagatc gagtgggagc tgcagaagga aaacagcaag 2100
cggtggaacc cggagatcca gtacacttcc aactattaca gtctaataa tgttgaattt 2160
gctgttaata ctgaaggtgt atatagtgaa ccccgcccca ttggcaccag atacctgact 2220
cgtaatctgt aa                                                      2232

SEQ ID NO: 3636       moltype = AA  length = 743
FEATURE               Location/Qualifiers
source                1..743
                      mol_type = protein
                      organism = synthetic construct
SEQUENCE: 3636
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSPLNG AVHLYAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 3637       moltype = AA  length = 743
FEATURE               Location/Qualifiers
source                1..743
                      mol_type = protein
                      organism = synthetic construct
SEQUENCE: 3637
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAR DSPKGWQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 3638       moltype = AA  length = 743
FEATURE               Location/Qualifiers
source                1..743
                      mol_type = protein
```

```
                        organism = synthetic construct
SEQUENCE: 3638
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGGAPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAY STDVRMQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 3639          moltype = AA  length = 743
FEATURE                  Location/Qualifiers
source                   1..743
                         mol_type = protein
                         organism = synthetic construct
SEQUENCE: 3639
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQIV MNSLKAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 3640          moltype = AA  length = 743
FEATURE                  Location/Qualifiers
source                   1..743
                         mol_type = protein
                         organism = synthetic construct
SEQUENCE: 3640
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAR ESPRGLQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 3641          moltype = AA  length = 743
FEATURE                  Location/Qualifiers
source                   1..743
                         mol_type = protein
                         organism = synthetic construct
SEQUENCE: 3641
MAADGYLPDW LEDNLSEGIR EWWALKPGAP QPKANQQHQD NARGLVLPGY KYLGPGNGLD   60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAS FNDTRAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 3642          moltype = AA  length = 743
FEATURE                  Location/Qualifiers
source                   1..743
```

```
                            mol_type = protein
                            organism = synthetic construct
SEQUENCE: 3642
MAADGYLPDW  LEDNLSEGIR  EWWALKPGAP  QPKANQQHQD  NARGLVLPGY  KYLGPGNGLD   60
KGEPVNAADA  AALEHDKAYD  QQLKAGDNPY  LKYNHADAEF  QERLKEDTSF  GGNLGRAVFQ  120
AKKRLLEPLG  LVEEAAKTAP  GKKRPVEQSP  QEPDSSAGIG  KSGAQPAKKR  LNFGQTGDTE  180
SVPDPQPIGE  PPAAPSGVGS  LTMASGGGAP  VADNNEGADG  VGSSSGNWHC  DSQWLGDRVI  240
TTSTRTWALP  TYNNHLYKQI  SNSTSGGSSN  DNAYFGYSTP  WGYFDFNRFH  CHFSPRDWQR  300
LINNNWGFRP  KRLNFKLFNI  QVKEVTDNNG  VKTIANNLTS  TVQVFTDSDY  QLPYVLGSAH  360
EGCLPPFPAD  VFMIPQYGYL  TLNDGSQAVG  RSSFYCLEYF  PSQMLRTGNN  FQFSYEFENV  420
PFHSSYAHSQ  SLDRLMNPLI  DQYLYYLSKT  INGSGQNQQT  LKFSVAGPSN  MAVQGRNYIP  480
GPSYRQQRVS  TTVTQNNNSE  FAWPGASSWA  LNGRNSLMNP  GPAMASHKEG  EDRFFPLSGS  540
LIFGKQGTGR  DNVDADKVMI  TNEEEIKTTN  PVATESYGQV  ATNHQSGGTL  AVVSLAQAQT  600
GWVQNQGILP  GMVWQDRDVY  LQGPIWAKIP  HTDGNFHPSP  LMGGFGMKHP  PPQILIKNTP  660
VPADPPTAFN  KDKLNSFITQ  YSTGQVSVEI  EWELQKENSK  RWNPEIQYTS  NYYKSNNVEF  720
AVNTEGVYSE  PRPIGTRYLT  RNL                                             743

SEQ ID NO: 3643             moltype = AA    length = 743
FEATURE                     Location/Qualifiers
source                      1..743
                            mol_type = protein
                            organism = synthetic construct
SEQUENCE: 3643
MAADGYLPDW  LEDNLSEGIR  EWWALKPGAP  QPKANQQHQD  NARGLVLPGY  KYLGPGNGLD   60
KGEPVNAADA  AALEHDKAYD  QQLKAGDNPY  LKYNHADAEF  QERLKEDTSF  GGNLGRAVFQ  120
AKKRLLEPLG  LVEEAAKTAP  GKKRPVEQSP  QEPDSSAGIG  KSGAQPAKKR  LNFGQTGDTE  180
SVPDPQPIGE  PPAAPSGVGS  LTMASGGGAP  VADNNEGADG  VGSSSGNWHC  DSQWLGDRVI  240
TTSTRTWALP  TYNNHLYKQI  SNSTSGGSSN  DNAYFGYSTP  WGYFDFNRFH  CHFSPRDWQR  300
LINNNWGFRP  KRLNFKLFNI  QVKEVTDNNG  VKTIANNLTS  TVQVFTDSDY  QLPYVLGSAH  360
EGCLPPFPAD  VFMIPQYGYL  TLNDGSQAVG  RSSFYCLEYF  PSQMLRTGNN  FQFSYEFENV  420
PFHSSYAHSQ  SLDRLMNPLI  DQYLYYLSKT  INGSGQNQQT  LKFSVAGPSN  MAVQGRNYIP  480
GPSYRQQRVS  TTVTQNNNSE  FAWPGASSWA  LNGRNSLMNP  GPAMASHKEG  EDRFFPLSGS  540
LIFGKQGTGR  DNVDADKVMI  TNEEEIKTTN  PVATESYGQV  ATNHQSAQAY  GLPKGPQAQT  600
GWVQNQGILP  GMVWQDRDVY  LQGPIWAKIP  HTDGNFHPSP  LMGGFGMKHP  PPQILIKNTP  660
VPADPPTAFN  KDKLNSFITQ  YSTGQVSVEI  EWELQKENSK  RWNPEIQYTS  NYYKSNNVEF  720
AVNTEGVYSE  PRPIGTRYLT  RNL                                             743

SEQ ID NO: 3644             moltype = AA    length = 743
FEATURE                     Location/Qualifiers
source                      1..743
                            mol_type = protein
                            organism = synthetic construct
SEQUENCE: 3644
MAADGYLPDW  LEDNLSEGIR  EWWALKPGAP  QPKANQQHQD  NARGLVLPGY  KYLGPGNGLD   60
KGEPVNAADA  AALEHDKAYD  QQLKAGDNPY  LKYNHADAEF  QERLKEDTSF  GGNLGRAVFQ  120
AKKRLLEPLG  LVEEAAKTAP  GKKRPVEQSP  QEPDSSAGIG  KSGAQPAKKR  LNFGQTGDTE  180
SVPDPQPIGE  PPAAPSGVGS  LTMASGGGAP  VADNNEGADG  VGSSSGNWHC  DSQWLGDRVI  240
TTSTRTWALP  TYNNHLYKQI  SNSTSGGSSN  DNAYFGYSTP  WGYFDFNRFH  CHFSPRDWQR  300
LINNNWGFRP  KRLNFKLFNI  QVKEVTDNNG  VKTIANNLTS  TVQVFTDSDY  QLPYVLGSAH  360
EGCLPPFPAD  VFMIPQYGYL  TLNDGSQAVG  RSSFYCLEYF  PSQMLRTGNN  FQFSYEFENV  420
PFHSSYAHSQ  SLDRLMNPLI  DQYLYYLSKT  INGSGQNQQT  LKFSVAGPSN  MAVQGRNYIP  480
GPSYRQQRVS  TTVTQNNNSE  FAWPGASSWA  LNGRNSLMNP  GPAMASHKEG  EDRFFPLSGS  540
LIFGKQGTGR  DNVDADKVMI  TNEEEIKTTN  PVATESYGQV  ATNHQSAQAS  TGTLRLQAQT  600
GWVQNQGILP  GMVWQDRDVY  LQGPIWAKIP  HTDGNFHPSP  LMGGFGMKHP  PPQILIKNTP  660
VPADPPTAFN  KDKLNSFITQ  YSTGQVSVEI  EWELQKENSK  RWNPEIQYTS  NYYKSNNVEF  720
AVNTEGVYSE  PRPIGTRYLT  RNL                                             743

SEQ ID NO: 3645             moltype = AA    length = 743
FEATURE                     Location/Qualifiers
source                      1..743
                            mol_type = protein
                            organism = synthetic construct
SEQUENCE: 3645
MAADGYLPDW  LEDNLSEGIR  EWWALKPGAP  QPKANQQHQD  NARGLVLPGY  KYLGPGNGLD   60
KGEPVNAADA  AALEHDKAYD  QQLKAGDNPY  LKYNHADAEF  QERLKEDTSF  GGNLGRAVFQ  120
AKKRLLEPLG  LVEEAAKTAP  GKKRPVEQSP  QEPDSSAGIG  KSGAQPAKKR  LNFGQTGDTE  180
SVPDPQPIGE  PPAAPSGVGS  LTMASGGGAP  VADNNEGADG  VGSSSGNWHC  DSQWLGDRVI  240
TTSTRTWALP  TYNNHLYKQI  SNSTSGGSSN  DNAYFGYSTP  WGYFDFNRFH  CHFSPRDWQR  300
LINNNWGFRP  KRLNFKLFNI  QVKEVTDNNG  VKTIANNLTS  TVQVFTDSDY  QLPYVLGSAH  360
EGCLPPFPAD  VFMIPQYGYL  TLNDGSQAVG  RSSFYCLEYF  PSQMLRTGNN  FQFSYEFENV  420
PFHSSYAHSQ  SLDRLMNPLI  DQYLYYLSKT  INGSGQNQQT  LKFSVAGPSN  MAVQGRNYIP  480
GPSYRQQRVS  TTVTQNNNSE  FAWPGASSWA  LNGRNSLMNP  GPAMASHKEG  EDRFFPLSGS  540
LIFGKQGTGR  DNVDADKVMI  TNEEEIKTTN  PVATESYGQV  ATNHQSAQAY  STDERMQAQT  600
GWVQNQGILP  GMVWQDRDVY  LQGPIWAKIP  HTDGNFHPSP  LMGGFGMKHP  PPQILIKNTP  660
VPADPPTAFN  KDKLNSFITQ  YSTGQVSVEI  EWELQKENSK  RWNPEIQYTS  NYYKSNNVEF  720
AVNTEGVYSE  PRPIGTRYLT  RNL                                             743

SEQ ID NO: 3646             moltype = AA    length = 743
FEATURE                     Location/Qualifiers
```

```
source                  1..743
                        mol_type = protein
                        organism = synthetic construct
SEQUENCE: 3646
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAY STDERKQAQT   600
GWVQNQGILP GMVWQDRDVY LQGPIWAKIP HTDGNFHPSP LMGGFGMKHP PPQILIKNTP   660
VPADPPTAFN KDKLNSFITQ YSTGQVSVEI EWELQKENSK RWNPEIQYTS NYYKSNNVEF   720
AVNTEGVYSE PRPIGTRYLT RNL                                          743

SEQ ID NO: 3647         moltype = AA    length = 743
FEATURE                 Location/Qualifiers
source                  1..743
                        mol_type = protein
                        organism = synthetic construct
SEQUENCE: 3647
MAADGYLPDW LEDNLSEGIR EWWALKPGAP QPKANQQHQD NARGLVLPGY KYLGPGNGLD    60
KGEPVNAADA AALEHDKAYD QQLKAGDNPY LKYNHADAEF QERLKEDTSF GGNLGRAVFQ   120
AKKRLLEPLG LVEEAAKTAP GKKRPVEQSP QEPDSSAGIG KSGAQPAKKR LNFGQTGDTE   180
SVPDPQPIGE PPAAPSGVGS LTMASGGGAP VADNNEGADG VGSSSGNWHC DSQWLGDRVI   240
TTSTRTWALP TYNNHLYKQI SNSTSGGSSN DNAYFGYSTP WGYFDFNRFH CHFSPRDWQR   300
LINNNWGFRP KRLNFKLFNI QVKEVTDNNG VKTIANNLTS TVQVFTDSDY QLPYVLGSAH   360
EGCLPPFPAD VFMIPQYGYL TLNDGSQAVG RSSFYCLEYF PSQMLRTGNN FQFSYEFENV   420
PFHSSYAHSQ SLDRLMNPLI DQYLYYLSKT INGSGQNQQT LKFSVAGPSN MAVQGRNYIP   480
GPSYRQQRVS TTVTQNNNSE FAWPGASSWA LNGRNSLMNP GPAMASHKEG EDRFFPLSGS   540
LIFGKQGTGR DNVDADKVMI TNEEEIKTTN PVATESYGQV ATNHQSAQAY VSSVKMQAQT   600
GWVQNQGILP GMVWQDRDVY LQGPIWAKIP HTDGNFHPSP LMGGFGMKHP PPQILIKNTP   660
VPADPPTAFN KDKLNSFITQ YSTGQVSVEI EWELQKENSK RWNPEIQYTS NYYKSNNVEF   720
AVNTEGVYSE PRPIGTRYLT RNL                                          743

SEQ ID NO: 3648         moltype = AA    length = 9
FEATURE                 Location/Qualifiers
source                  1..9
                        mol_type = protein
                        organism = synthetic construct
SEQUENCE: 3648
PLNGAVHLY                                                            9

SEQ ID NO: 3649         moltype = AA    length = 7
FEATURE                 Location/Qualifiers
source                  1..7
                        mol_type = protein
                        organism = synthetic construct
SEQUENCE: 3649
RDSPKGW                                                              7

SEQ ID NO: 3650         moltype = AA    length = 7
FEATURE                 Location/Qualifiers
source                  1..7
                        mol_type = protein
                        organism = synthetic construct
SEQUENCE: 3650
YSTDVRM                                                              7

SEQ ID NO: 3651         moltype = AA    length = 7
FEATURE                 Location/Qualifiers
source                  1..7
                        mol_type = protein
                        organism = synthetic construct
SEQUENCE: 3651
IVMNSLK                                                              7

SEQ ID NO: 3652         moltype = AA    length = 7
FEATURE                 Location/Qualifiers
source                  1..7
                        mol_type = protein
                        organism = synthetic construct
SEQUENCE: 3652
RESPRGL                                                              7

SEQ ID NO: 3653         moltype = AA    length = 7
```

```
FEATURE                 Location/Qualifiers
source                  1..7
                        mol_type = protein
                        organism = synthetic construct
SEQUENCE: 3653
SFNDTRA                                                                         7

SEQ ID NO: 3654         moltype = AA  length = 9
FEATURE                 Location/Qualifiers
source                  1..9
                        mol_type = protein
                        organism = synthetic construct
SEQUENCE: 3654
GGTLAVVSL                                                                       9

SEQ ID NO: 3655         moltype = AA  length = 7
FEATURE                 Location/Qualifiers
source                  1..7
                        mol_type = protein
                        organism = synthetic construct
SEQUENCE: 3655
YGLPKGP                                                                         7

SEQ ID NO: 3656         moltype = AA  length = 7
FEATURE                 Location/Qualifiers
source                  1..7
                        mol_type = protein
                        organism = synthetic construct
SEQUENCE: 3656
STGTLRL                                                                         7

SEQ ID NO: 3657         moltype = AA  length = 7
FEATURE                 Location/Qualifiers
source                  1..7
                        mol_type = protein
                        organism = synthetic construct
SEQUENCE: 3657
YSTDERM                                                                         7

SEQ ID NO: 3658         moltype = AA  length = 7
FEATURE                 Location/Qualifiers
source                  1..7
                        mol_type = protein
                        organism = synthetic construct
SEQUENCE: 3658
YSTDERK                                                                         7

SEQ ID NO: 3659         moltype = AA  length = 7
FEATURE                 Location/Qualifiers
source                  1..7
                        mol_type = protein
                        organism = synthetic construct
SEQUENCE: 3659
YVSSVKM                                                                         7

SEQ ID NO: 3660         moltype = DNA  length = 27
FEATURE                 Location/Qualifiers
source                  1..27
                        mol_type = other DNA
                        organism = synthetic construct
SEQUENCE: 3660
ccgcttaatg gtgccgtcca tctttat                                                  27

SEQ ID NO: 3661         moltype = DNA  length = 23
FEATURE                 Location/Qualifiers
source                  1..23
                        mol_type = other DNA
                        organism = synthetic construct
SEQUENCE: 3661
cgtgattctc cgaagggttg gca                                                      23

SEQ ID NO: 3662         moltype = DNA  length = 23
FEATURE                 Location/Qualifiers
source                  1..23
                        mol_type = other DNA
                        organism = synthetic construct
SEQUENCE: 3662
tattctacgg atgtgaggat gca                                                      23
```

| | | |
|---|---|---|
| SEQ ID NO: 3663<br>FEATURE<br>source | moltype = DNA   length = 23<br>Location/Qualifiers<br>1..23<br>mol_type = other DNA<br>organism = synthetic construct | |
| SEQUENCE: 3663<br>attgttatga attcgttgaa ggc | | 23 |
| SEQ ID NO: 3664<br>FEATURE<br>source | moltype = DNA   length = 23<br>Location/Qualifiers<br>1..23<br>mol_type = other DNA<br>organism = synthetic construct | |
| SEQUENCE: 3664<br>cgggagagtc ctcgtgggct gca | | 23 |
| SEQ ID NO: 3665<br>FEATURE<br>source | moltype = DNA   length = 23<br>Location/Qualifiers<br>1..23<br>mol_type = other DNA<br>organism = synthetic construct | |
| SEQUENCE: 3665<br>agttttaatg atactagggc tca | | 23 |
| SEQ ID NO: 3666<br>FEATURE<br>source | moltype = DNA   length = 27<br>Location/Qualifiers<br>1..27<br>mol_type = other DNA<br>organism = synthetic construct | |
| SEQUENCE: 3666<br>ggtggtacgt tggccgtcgt gtcgctt | | 27 |
| SEQ ID NO: 3667<br>FEATURE<br>source | moltype = DNA   length = 21<br>Location/Qualifiers<br>1..21<br>mol_type = other DNA<br>organism = synthetic construct | |
| SEQUENCE: 3667<br>tatgggttgc cgaagggtcc t | | 21 |
| SEQ ID NO: 3668<br>FEATURE<br>source | moltype = DNA   length = 21<br>Location/Qualifiers<br>1..21<br>mol_type = other DNA<br>organism = synthetic construct | |
| SEQUENCE: 3668<br>tcgactggga cgcttcggct t | | 21 |
| SEQ ID NO: 3669<br>FEATURE<br>source | moltype = DNA   length = 21<br>Location/Qualifiers<br>1..21<br>mol_type = other DNA<br>organism = synthetic construct | |
| SEQUENCE: 3669<br>tattcgacgg atgagaggat g | | 21 |
| SEQ ID NO: 3670<br>FEATURE<br>source | moltype = DNA   length = 21<br>Location/Qualifiers<br>1..21<br>mol_type = other DNA<br>organism = synthetic construct | |
| SEQUENCE: 3670<br>tattcgacgg atgagaggaa g | | 21 |
| SEQ ID NO: 3671<br>FEATURE<br>source | moltype = DNA   length = 21<br>Location/Qualifiers<br>1..21<br>mol_type = other DNA<br>organism = synthetic construct | |
| SEQUENCE: 3671<br>tatgtttcgt ctgttaagat g | | 21 |
| SEQ ID NO: 3672<br>SEQUENCE: 3672<br>000 | moltype =    length = | |
| SEQ ID NO: 3673<br>SEQUENCE: 3673<br>000 | moltype =    length = | |

SEQ ID NO: 3674        moltype =     length =
SEQUENCE: 3674
000

SEQ ID NO: 3675        moltype =     length =
SEQUENCE: 3675
000

SEQ ID NO: 3676        moltype =     length =
SEQUENCE: 3676
000

SEQ ID NO: 3677        moltype =     length =
SEQUENCE: 3677
000

SEQ ID NO: 3678        moltype =     length =
SEQUENCE: 3678
000

SEQ ID NO: 3679        moltype =     length =
SEQUENCE: 3679
000

SEQ ID NO: 3680        moltype =     length =
SEQUENCE: 3680
000

SEQ ID NO: 3681        moltype =     length =
SEQUENCE: 3681
000

SEQ ID NO: 3682        moltype =     length =
SEQUENCE: 3682
000

SEQ ID NO: 3683        moltype =     length =
SEQUENCE: 3683
000

SEQ ID NO: 3684        moltype =     length =
SEQUENCE: 3684
000

SEQ ID NO: 3685        moltype =     length =
SEQUENCE: 3685
000

SEQ ID NO: 3686        moltype =     length =
SEQUENCE: 3686
000

SEQ ID NO: 3687        moltype =     length =
SEQUENCE: 3687
000

SEQ ID NO: 3688        moltype =     length =
SEQUENCE: 3688
000

SEQ ID NO: 3689        moltype =     length =
SEQUENCE: 3689
000

SEQ ID NO: 3690        moltype =     length =
SEQUENCE: 3690
000

SEQ ID NO: 3691        moltype =     length =
SEQUENCE: 3691
000

SEQ ID NO: 3692        moltype =     length =
SEQUENCE: 3692
000

SEQ ID NO: 3693        moltype =     length =
SEQUENCE: 3693

000

SEQ ID NO: 3694    moltype =    length =
SEQUENCE: 3694
000

SEQ ID NO: 3695    moltype =    length =
SEQUENCE: 3695
000

SEQ ID NO: 3696    moltype =    length =
SEQUENCE: 3696
000

SEQ ID NO: 3697    moltype =    length =
SEQUENCE: 3697
000

SEQ ID NO: 3698    moltype =    length =
SEQUENCE: 3698
000

SEQ ID NO: 3699    moltype =    length =
SEQUENCE: 3699
000

SEQ ID NO: 3700    moltype =    length =
SEQUENCE: 3700
000

SEQ ID NO: 3701    moltype =    length =
SEQUENCE: 3701
000

SEQ ID NO: 3702    moltype =    length =
SEQUENCE: 3702
000

SEQ ID NO: 3703    moltype =    length =
SEQUENCE: 3703
000

SEQ ID NO: 3704    moltype =    length =
SEQUENCE: 3704
000

SEQ ID NO: 3705    moltype =    length =
SEQUENCE: 3705
000

SEQ ID NO: 3706    moltype =    length =
SEQUENCE: 3706
000

SEQ ID NO: 3707    moltype =    length =
SEQUENCE: 3707
000

SEQ ID NO: 3708    moltype =    length =
SEQUENCE: 3708
000

SEQ ID NO: 3709    moltype =    length =
SEQUENCE: 3709
000

SEQ ID NO: 3710    moltype =    length =
SEQUENCE: 3710
000

SEQ ID NO: 3711    moltype =    length =
SEQUENCE: 3711
000

SEQ ID NO: 3712    moltype =    length =
SEQUENCE: 3712
000

SEQ ID NO: 3713    moltype =    length =

-continued

SEQUENCE: 3713
000

SEQ ID NO: 3714         moltype =   length =
SEQUENCE: 3714
000

SEQ ID NO: 3715         moltype =   length =
SEQUENCE: 3715
000

SEQ ID NO: 3716         moltype =   length =
SEQUENCE: 3716
000

SEQ ID NO: 3717         moltype =   length =
SEQUENCE: 3717
000

SEQ ID NO: 3718         moltype =   length =
SEQUENCE: 3718
000

SEQ ID NO: 3719         moltype =   length =
SEQUENCE: 3719
000

SEQ ID NO: 3720         moltype =   length =
SEQUENCE: 3720
000

SEQ ID NO: 3721         moltype =   length =
SEQUENCE: 3721
000

SEQ ID NO: 3722         moltype =   length =
SEQUENCE: 3722
000

SEQ ID NO: 3723         moltype =   length =
SEQUENCE: 3723
000

SEQ ID NO: 3724         moltype =   length =
SEQUENCE: 3724
000

SEQ ID NO: 3725         moltype =   length =
SEQUENCE: 3725
000

SEQ ID NO: 3726         moltype =   length =
SEQUENCE: 3726
000

SEQ ID NO: 3727         moltype =   length =
SEQUENCE: 3727
000

SEQ ID NO: 3728         moltype =   length =
SEQUENCE: 3728
000

SEQ ID NO: 3729         moltype =   length =
SEQUENCE: 3729
000

SEQ ID NO: 3730         moltype =   length =
SEQUENCE: 3730
000

SEQ ID NO: 3731         moltype =   length =
SEQUENCE: 3731
000

SEQ ID NO: 3732         moltype =   length =
SEQUENCE: 3732
000

-continued

| | | |
|---|---|---|
| SEQ ID NO: 3733<br>SEQUENCE: 3733<br>000 | moltype = | length = |
| SEQ ID NO: 3734<br>SEQUENCE: 3734<br>000 | moltype = | length = |
| SEQ ID NO: 3735<br>SEQUENCE: 3735<br>000 | moltype = | length = |
| SEQ ID NO: 3736<br>SEQUENCE: 3736<br>000 | moltype = | length = |
| SEQ ID NO: 3737<br>SEQUENCE: 3737<br>000 | moltype = | length = |
| SEQ ID NO: 3738<br>SEQUENCE: 3738<br>000 | moltype = | length = |
| SEQ ID NO: 3739<br>SEQUENCE: 3739<br>000 | moltype = | length = |
| SEQ ID NO: 3740<br>SEQUENCE: 3740<br>000 | moltype = | length = |
| SEQ ID NO: 3741<br>SEQUENCE: 3741<br>000 | moltype = | length = |
| SEQ ID NO: 3742<br>SEQUENCE: 3742<br>000 | moltype = | length = |
| SEQ ID NO: 3743<br>SEQUENCE: 3743<br>000 | moltype = | length = |
| SEQ ID NO: 3744<br>SEQUENCE: 3744<br>000 | moltype = | length = |
| SEQ ID NO: 3745<br>SEQUENCE: 3745<br>000 | moltype = | length = |
| SEQ ID NO: 3746<br>SEQUENCE: 3746<br>000 | moltype = | length = |
| SEQ ID NO: 3747<br>SEQUENCE: 3747<br>000 | moltype = | length = |
| SEQ ID NO: 3748<br>SEQUENCE: 3748<br>000 | moltype = | length = |
| SEQ ID NO: 3749<br>SEQUENCE: 3749<br>000 | moltype = | length = |
| SEQ ID NO: 3750<br>SEQUENCE: 3750<br>000 | moltype = | length = |
| SEQ ID NO: 3751<br>SEQUENCE: 3751<br>000 | moltype = | length = |
| SEQ ID NO: 3752<br>SEQUENCE: 3752<br>000 | moltype = | length = |

| | | |
|---|---|---|
| SEQ ID NO: 3753<br>SEQUENCE: 3753<br>000 | moltype = | length = |
| SEQ ID NO: 3754<br>SEQUENCE: 3754<br>000 | moltype = | length = |
| SEQ ID NO: 3755<br>SEQUENCE: 3755<br>000 | moltype = | length = |
| SEQ ID NO: 3756<br>SEQUENCE: 3756<br>000 | moltype = | length = |
| SEQ ID NO: 3757<br>SEQUENCE: 3757<br>000 | moltype = | length = |
| SEQ ID NO: 3758<br>SEQUENCE: 3758<br>000 | moltype = | length = |
| SEQ ID NO: 3759<br>SEQUENCE: 3759<br>000 | moltype = | length = |
| SEQ ID NO: 3760<br>SEQUENCE: 3760<br>000 | moltype = | length = |
| SEQ ID NO: 3761<br>SEQUENCE: 3761<br>000 | moltype = | length = |
| SEQ ID NO: 3762<br>SEQUENCE: 3762<br>000 | moltype = | length = |
| SEQ ID NO: 3763<br>SEQUENCE: 3763<br>000 | moltype = | length = |
| SEQ ID NO: 3764<br>SEQUENCE: 3764<br>000 | moltype = | length = |
| SEQ ID NO: 3765<br>SEQUENCE: 3765<br>000 | moltype = | length = |
| SEQ ID NO: 3766<br>SEQUENCE: 3766<br>000 | moltype = | length = |
| SEQ ID NO: 3767<br>SEQUENCE: 3767<br>000 | moltype = | length = |
| SEQ ID NO: 3768<br>SEQUENCE: 3768<br>000 | moltype = | length = |
| SEQ ID NO: 3769<br>SEQUENCE: 3769<br>000 | moltype = | length = |
| SEQ ID NO: 3770<br>SEQUENCE: 3770<br>000 | moltype = | length = |
| SEQ ID NO: 3771<br>SEQUENCE: 3771<br>000 | moltype = | length = |
| SEQ ID NO: 3772<br>SEQUENCE: 3772 | moltype = | length = |

-continued

000

SEQ ID NO: 3773  moltype =  length =
SEQUENCE: 3773
000

SEQ ID NO: 3774  moltype =  length =
SEQUENCE: 3774
000

SEQ ID NO: 3775  moltype =  length =
SEQUENCE: 3775
000

SEQ ID NO: 3776  moltype =  length =
SEQUENCE: 3776
000

SEQ ID NO: 3777  moltype =  length =
SEQUENCE: 3777
000

SEQ ID NO: 3778  moltype =  length =
SEQUENCE: 3778
000

SEQ ID NO: 3779  moltype =  length =
SEQUENCE: 3779
000

SEQ ID NO: 3780  moltype =  length =
SEQUENCE: 3780
000

SEQ ID NO: 3781  moltype =  length =
SEQUENCE: 3781
000

SEQ ID NO: 3782  moltype =  length =
SEQUENCE: 3782
000

SEQ ID NO: 3783  moltype =  length =
SEQUENCE: 3783
000

SEQ ID NO: 3784  moltype =  length =
SEQUENCE: 3784
000

SEQ ID NO: 3785  moltype =  length =
SEQUENCE: 3785
000

SEQ ID NO: 3786  moltype =  length =
SEQUENCE: 3786
000

SEQ ID NO: 3787  moltype =  length =
SEQUENCE: 3787
000

SEQ ID NO: 3788  moltype =  length =
SEQUENCE: 3788
000

SEQ ID NO: 3789  moltype =  length =
SEQUENCE: 3789
000

SEQ ID NO: 3790  moltype =  length =
SEQUENCE: 3790
000

SEQ ID NO: 3791  moltype =  length =
SEQUENCE: 3791
000

SEQ ID NO: 3792  moltype =  length =

| | | |
|---|---|---|
| SEQUENCE: 3792 000 | | |
| SEQ ID NO: 3793 SEQUENCE: 3793 000 | moltype = | length = |
| SEQ ID NO: 3794 SEQUENCE: 3794 000 | moltype = | length = |
| SEQ ID NO: 3795 SEQUENCE: 3795 000 | moltype = | length = |
| SEQ ID NO: 3796 SEQUENCE: 3796 000 | moltype = | length = |
| SEQ ID NO: 3797 SEQUENCE: 3797 000 | moltype = | length = |
| SEQ ID NO: 3798 SEQUENCE: 3798 000 | moltype = | length = |
| SEQ ID NO: 3799 SEQUENCE: 3799 000 | moltype = | length = |
| SEQ ID NO: 3800 SEQUENCE: 3800 000 | moltype = | length = |
| SEQ ID NO: 3801 SEQUENCE: 3801 000 | moltype = | length = |
| SEQ ID NO: 3802 SEQUENCE: 3802 000 | moltype = | length = |
| SEQ ID NO: 3803 SEQUENCE: 3803 000 | moltype = | length = |
| SEQ ID NO: 3804 SEQUENCE: 3804 000 | moltype = | length = |
| SEQ ID NO: 3805 SEQUENCE: 3805 000 | moltype = | length = |
| SEQ ID NO: 3806 SEQUENCE: 3806 000 | moltype = | length = |
| SEQ ID NO: 3807 SEQUENCE: 3807 000 | moltype = | length = |
| SEQ ID NO: 3808 SEQUENCE: 3808 000 | moltype = | length = |
| SEQ ID NO: 3809 SEQUENCE: 3809 000 | moltype = | length = |
| SEQ ID NO: 3810 SEQUENCE: 3810 000 | moltype = | length = |
| SEQ ID NO: 3811 SEQUENCE: 3811 000 | moltype = | length = |

| | | |
|---|---|---|
| SEQ ID NO: 3812 SEQUENCE: 3812 | moltype = | length = 000 |
| SEQ ID NO: 3813 SEQUENCE: 3813 | moltype = | length = 000 |
| SEQ ID NO: 3814 SEQUENCE: 3814 | moltype = | length = 000 |
| SEQ ID NO: 3815 SEQUENCE: 3815 | moltype = | length = 000 |
| SEQ ID NO: 3816 SEQUENCE: 3816 | moltype = | length = 000 |
| SEQ ID NO: 3817 SEQUENCE: 3817 | moltype = | length = 000 |
| SEQ ID NO: 3818 SEQUENCE: 3818 | moltype = | length = 000 |
| SEQ ID NO: 3819 SEQUENCE: 3819 | moltype = | length = 000 |
| SEQ ID NO: 3820 SEQUENCE: 3820 | moltype = | length = 000 |
| SEQ ID NO: 3821 SEQUENCE: 3821 | moltype = | length = 000 |
| SEQ ID NO: 3822 SEQUENCE: 3822 | moltype = | length = 000 |
| SEQ ID NO: 3823 SEQUENCE: 3823 | moltype = | length = 000 |
| SEQ ID NO: 3824 SEQUENCE: 3824 | moltype = | length = 000 |
| SEQ ID NO: 3825 SEQUENCE: 3825 | moltype = | length = 000 |
| SEQ ID NO: 3826 SEQUENCE: 3826 | moltype = | length = 000 |
| SEQ ID NO: 3827 SEQUENCE: 3827 | moltype = | length = 000 |
| SEQ ID NO: 3828 SEQUENCE: 3828 | moltype = | length = 000 |
| SEQ ID NO: 3829 SEQUENCE: 3829 | moltype = | length = 000 |
| SEQ ID NO: 3830 SEQUENCE: 3830 | moltype = | length = 000 |
| SEQ ID NO: 3831 SEQUENCE: 3831 | moltype = | length = 000 |

-continued

SEQ ID NO: 3832            moltype =     length =
SEQUENCE: 3832
000

SEQ ID NO: 3833            moltype =     length =
SEQUENCE: 3833
000

SEQ ID NO: 3834            moltype =     length =
SEQUENCE: 3834
000

SEQ ID NO: 3835            moltype =     length =
SEQUENCE: 3835
000

SEQ ID NO: 3836            moltype =     length =
SEQUENCE: 3836
000

SEQ ID NO: 3837            moltype =     length =
SEQUENCE: 3837
000

SEQ ID NO: 3838            moltype =     length =
SEQUENCE: 3838
000

SEQ ID NO: 3839            moltype =     length =
SEQUENCE: 3839
000

SEQ ID NO: 3840            moltype =     length =
SEQUENCE: 3840
000

SEQ ID NO: 3841            moltype =     length =
SEQUENCE: 3841
000

SEQ ID NO: 3842            moltype =     length =
SEQUENCE: 3842
000

SEQ ID NO: 3843            moltype =     length =
SEQUENCE: 3843
000

SEQ ID NO: 3844            moltype =     length =
SEQUENCE: 3844
000

SEQ ID NO: 3845            moltype =     length =
SEQUENCE: 3845
000

SEQ ID NO: 3846            moltype =     length =
SEQUENCE: 3846
000

SEQ ID NO: 3847            moltype =     length =
SEQUENCE: 3847
000

SEQ ID NO: 3848            moltype =     length =
SEQUENCE: 3848
000

SEQ ID NO: 3849            moltype =     length =
SEQUENCE: 3849
000

SEQ ID NO: 3850            moltype =     length =
SEQUENCE: 3850
000

SEQ ID NO: 3851            moltype =     length =
SEQUENCE: 3851

000

SEQ ID NO: 3852          moltype =    length =
SEQUENCE: 3852
000

SEQ ID NO: 3853          moltype =    length =
SEQUENCE: 3853
000

SEQ ID NO: 3854          moltype =    length =
SEQUENCE: 3854
000

SEQ ID NO: 3855          moltype =    length =
SEQUENCE: 3855
000

SEQ ID NO: 3856          moltype =    length =
SEQUENCE: 3856
000

SEQ ID NO: 3857          moltype =    length =
SEQUENCE: 3857
000

SEQ ID NO: 3858          moltype =    length =
SEQUENCE: 3858
000

SEQ ID NO: 3859          moltype =    length =
SEQUENCE: 3859
000

SEQ ID NO: 3860          moltype =    length =
SEQUENCE: 3860
000

SEQ ID NO: 3861          moltype =    length =
SEQUENCE: 3861
000

SEQ ID NO: 3862          moltype =    length =
SEQUENCE: 3862
000

SEQ ID NO: 3863          moltype =    length =
SEQUENCE: 3863
000

SEQ ID NO: 3864          moltype =    length =
SEQUENCE: 3864
000

SEQ ID NO: 3865          moltype =    length =
SEQUENCE: 3865
000

SEQ ID NO: 3866          moltype =    length =
SEQUENCE: 3866
000

SEQ ID NO: 3867          moltype =    length =
SEQUENCE: 3867
000

SEQ ID NO: 3868          moltype =    length =
SEQUENCE: 3868
000

SEQ ID NO: 3869          moltype =    length =
SEQUENCE: 3869
000

SEQ ID NO: 3870          moltype =    length =
SEQUENCE: 3870
000

SEQ ID NO: 3871          moltype =    length =

| | | |
|---|---|---|
| SEQUENCE: 3871 000 | | |
| SEQ ID NO: 3872 SEQUENCE: 3872 000 | moltype = | length = |
| SEQ ID NO: 3873 SEQUENCE: 3873 000 | moltype = | length = |
| SEQ ID NO: 3874 SEQUENCE: 3874 000 | moltype = | length = |
| SEQ ID NO: 3875 SEQUENCE: 3875 000 | moltype = | length = |
| SEQ ID NO: 3876 SEQUENCE: 3876 000 | moltype = | length = |
| SEQ ID NO: 3877 SEQUENCE: 3877 000 | moltype = | length = |
| SEQ ID NO: 3878 SEQUENCE: 3878 000 | moltype = | length = |
| SEQ ID NO: 3879 SEQUENCE: 3879 000 | moltype = | length = |
| SEQ ID NO: 3880 SEQUENCE: 3880 000 | moltype = | length = |
| SEQ ID NO: 3881 SEQUENCE: 3881 000 | moltype = | length = |
| SEQ ID NO: 3882 SEQUENCE: 3882 000 | moltype = | length = |
| SEQ ID NO: 3883 SEQUENCE: 3883 000 | moltype = | length = |
| SEQ ID NO: 3884 SEQUENCE: 3884 000 | moltype = | length = |
| SEQ ID NO: 3885 SEQUENCE: 3885 000 | moltype = | length = |
| SEQ ID NO: 3886 SEQUENCE: 3886 000 | moltype = | length = |
| SEQ ID NO: 3887 SEQUENCE: 3887 000 | moltype = | length = |
| SEQ ID NO: 3888 SEQUENCE: 3888 000 | moltype = | length = |
| SEQ ID NO: 3889 SEQUENCE: 3889 000 | moltype = | length = |
| SEQ ID NO: 3890 SEQUENCE: 3890 000 | moltype = | length = |

| | | |
|---|---|---|
| SEQ ID NO: 3891 SEQUENCE: 3891 | moltype = | length = 000 |
| SEQ ID NO: 3892 SEQUENCE: 3892 | moltype = | length = 000 |
| SEQ ID NO: 3893 SEQUENCE: 3893 | moltype = | length = 000 |
| SEQ ID NO: 3894 SEQUENCE: 3894 | moltype = | length = 000 |
| SEQ ID NO: 3895 SEQUENCE: 3895 | moltype = | length = 000 |
| SEQ ID NO: 3896 SEQUENCE: 3896 | moltype = | length = 000 |
| SEQ ID NO: 3897 SEQUENCE: 3897 | moltype = | length = 000 |
| SEQ ID NO: 3898 SEQUENCE: 3898 | moltype = | length = 000 |
| SEQ ID NO: 3899 SEQUENCE: 3899 | moltype = | length = 000 |
| SEQ ID NO: 3900 SEQUENCE: 3900 | moltype = | length = 000 |
| SEQ ID NO: 3901 SEQUENCE: 3901 | moltype = | length = 000 |
| SEQ ID NO: 3902 SEQUENCE: 3902 | moltype = | length = 000 |
| SEQ ID NO: 3903 SEQUENCE: 3903 | moltype = | length = 000 |
| SEQ ID NO: 3904 SEQUENCE: 3904 | moltype = | length = 000 |
| SEQ ID NO: 3905 SEQUENCE: 3905 | moltype = | length = 000 |
| SEQ ID NO: 3906 SEQUENCE: 3906 | moltype = | length = 000 |
| SEQ ID NO: 3907 SEQUENCE: 3907 | moltype = | length = 000 |
| SEQ ID NO: 3908 SEQUENCE: 3908 | moltype = | length = 000 |
| SEQ ID NO: 3909 SEQUENCE: 3909 | moltype = | length = 000 |
| SEQ ID NO: 3910 SEQUENCE: 3910 | moltype = | length = 000 |

| | | |
|---|---|---|
| SEQ ID NO: 3911 SEQUENCE: 3911 000 | moltype = | length = |
| SEQ ID NO: 3912 SEQUENCE: 3912 000 | moltype = | length = |
| SEQ ID NO: 3913 SEQUENCE: 3913 000 | moltype = | length = |
| SEQ ID NO: 3914 SEQUENCE: 3914 000 | moltype = | length = |
| SEQ ID NO: 3915 SEQUENCE: 3915 000 | moltype = | length = |
| SEQ ID NO: 3916 SEQUENCE: 3916 000 | moltype = | length = |
| SEQ ID NO: 3917 SEQUENCE: 3917 000 | moltype = | length = |
| SEQ ID NO: 3918 SEQUENCE: 3918 000 | moltype = | length = |
| SEQ ID NO: 3919 SEQUENCE: 3919 000 | moltype = | length = |
| SEQ ID NO: 3920 SEQUENCE: 3920 000 | moltype = | length = |
| SEQ ID NO: 3921 SEQUENCE: 3921 000 | moltype = | length = |
| SEQ ID NO: 3922 SEQUENCE: 3922 000 | moltype = | length = |
| SEQ ID NO: 3923 SEQUENCE: 3923 000 | moltype = | length = |
| SEQ ID NO: 3924 SEQUENCE: 3924 000 | moltype = | length = |
| SEQ ID NO: 3925 SEQUENCE: 3925 000 | moltype = | length = |
| SEQ ID NO: 3926 SEQUENCE: 3926 000 | moltype = | length = |
| SEQ ID NO: 3927 SEQUENCE: 3927 000 | moltype = | length = |
| SEQ ID NO: 3928 SEQUENCE: 3928 000 | moltype = | length = |
| SEQ ID NO: 3929 SEQUENCE: 3929 000 | moltype = | length = |
| SEQ ID NO: 3930 SEQUENCE: 3930 | moltype = | length = |

000

SEQ ID NO: 3931         moltype =      length =
SEQUENCE: 3931
000

SEQ ID NO: 3932         moltype =      length =
SEQUENCE: 3932
000

SEQ ID NO: 3933         moltype =      length =
SEQUENCE: 3933
000

SEQ ID NO: 3934         moltype =      length =
SEQUENCE: 3934
000

SEQ ID NO: 3935         moltype =      length =
SEQUENCE: 3935
000

SEQ ID NO: 3936         moltype =      length =
SEQUENCE: 3936
000

SEQ ID NO: 3937         moltype =      length =
SEQUENCE: 3937
000

SEQ ID NO: 3938         moltype =      length =
SEQUENCE: 3938
000

SEQ ID NO: 3939         moltype =      length =
SEQUENCE: 3939
000

SEQ ID NO: 3940         moltype =      length =
SEQUENCE: 3940
000

SEQ ID NO: 3941         moltype =      length =
SEQUENCE: 3941
000

SEQ ID NO: 3942         moltype =      length =
SEQUENCE: 3942
000

SEQ ID NO: 3943         moltype =      length =
SEQUENCE: 3943
000

SEQ ID NO: 3944         moltype =      length =
SEQUENCE: 3944
000

SEQ ID NO: 3945         moltype =      length =
SEQUENCE: 3945
000

SEQ ID NO: 3946         moltype =      length =
SEQUENCE: 3946
000

SEQ ID NO: 3947         moltype =      length =
SEQUENCE: 3947
000

SEQ ID NO: 3948         moltype =      length =
SEQUENCE: 3948
000

SEQ ID NO: 3949         moltype =      length =
SEQUENCE: 3949
000

SEQ ID NO: 3950         moltype =      length =

| | | | |
|---|---|---|---|
| SEQUENCE: 3950 000 | | | |
| SEQ ID NO: 3951 SEQUENCE: 3951 000 | moltype = | length = | |
| SEQ ID NO: 3952 SEQUENCE: 3952 000 | moltype = | length = | |
| SEQ ID NO: 3953 SEQUENCE: 3953 000 | moltype = | length = | |
| SEQ ID NO: 3954 SEQUENCE: 3954 000 | moltype = | length = | |
| SEQ ID NO: 3955 SEQUENCE: 3955 000 | moltype = | length = | |
| SEQ ID NO: 3956 SEQUENCE: 3956 000 | moltype = | length = | |
| SEQ ID NO: 3957 SEQUENCE: 3957 000 | moltype = | length = | |
| SEQ ID NO: 3958 SEQUENCE: 3958 000 | moltype = | length = | |
| SEQ ID NO: 3959 SEQUENCE: 3959 000 | moltype = | length = | |
| SEQ ID NO: 3960 SEQUENCE: 3960 000 | moltype = | length = | |
| SEQ ID NO: 3961 SEQUENCE: 3961 000 | moltype = | length = | |
| SEQ ID NO: 3962 SEQUENCE: 3962 000 | moltype = | length = | |
| SEQ ID NO: 3963 SEQUENCE: 3963 000 | moltype = | length = | |
| SEQ ID NO: 3964 SEQUENCE: 3964 000 | moltype = | length = | |
| SEQ ID NO: 3965 SEQUENCE: 3965 000 | moltype = | length = | |
| SEQ ID NO: 3966 SEQUENCE: 3966 000 | moltype = | length = | |
| SEQ ID NO: 3967 SEQUENCE: 3967 000 | moltype = | length = | |
| SEQ ID NO: 3968 SEQUENCE: 3968 000 | moltype = | length = | |
| SEQ ID NO: 3969 SEQUENCE: 3969 000 | moltype = | length = | |

| | | |
|---|---|---|
| SEQ ID NO: 3970 SEQUENCE: 3970 | moltype = | length = 000 |
| SEQ ID NO: 3971 SEQUENCE: 3971 | moltype = | length = 000 |
| SEQ ID NO: 3972 SEQUENCE: 3972 | moltype = | length = 000 |
| SEQ ID NO: 3973 SEQUENCE: 3973 | moltype = | length = 000 |
| SEQ ID NO: 3974 SEQUENCE: 3974 | moltype = | length = 000 |
| SEQ ID NO: 3975 SEQUENCE: 3975 | moltype = | length = 000 |
| SEQ ID NO: 3976 SEQUENCE: 3976 | moltype = | length = 000 |
| SEQ ID NO: 3977 SEQUENCE: 3977 | moltype = | length = 000 |
| SEQ ID NO: 3978 SEQUENCE: 3978 | moltype = | length = 000 |
| SEQ ID NO: 3979 SEQUENCE: 3979 | moltype = | length = 000 |
| SEQ ID NO: 3980 SEQUENCE: 3980 | moltype = | length = 000 |
| SEQ ID NO: 3981 SEQUENCE: 3981 | moltype = | length = 000 |
| SEQ ID NO: 3982 SEQUENCE: 3982 | moltype = | length = 000 |
| SEQ ID NO: 3983 SEQUENCE: 3983 | moltype = | length = 000 |
| SEQ ID NO: 3984 SEQUENCE: 3984 | moltype = | length = 000 |
| SEQ ID NO: 3985 SEQUENCE: 3985 | moltype = | length = 000 |
| SEQ ID NO: 3986 SEQUENCE: 3986 | moltype = | length = 000 |
| SEQ ID NO: 3987 SEQUENCE: 3987 | moltype = | length = 000 |
| SEQ ID NO: 3988 SEQUENCE: 3988 | moltype = | length = 000 |
| SEQ ID NO: 3989 SEQUENCE: 3989 | moltype = | length = 000 |

| | | |
|---|---|---|
| SEQ ID NO: 3990 SEQUENCE: 3990 | moltype = | length = 000 |
| SEQ ID NO: 3991 SEQUENCE: 3991 | moltype = | length = 000 |
| SEQ ID NO: 3992 SEQUENCE: 3992 | moltype = | length = 000 |
| SEQ ID NO: 3993 SEQUENCE: 3993 | moltype = | length = 000 |
| SEQ ID NO: 3994 SEQUENCE: 3994 | moltype = | length = 000 |
| SEQ ID NO: 3995 SEQUENCE: 3995 | moltype = | length = 000 |
| SEQ ID NO: 3996 SEQUENCE: 3996 | moltype = | length = 000 |
| SEQ ID NO: 3997 SEQUENCE: 3997 | moltype = | length = 000 |
| SEQ ID NO: 3998 SEQUENCE: 3998 | moltype = | length = 000 |
| SEQ ID NO: 3999 SEQUENCE: 3999 | moltype = | length = 000 |
| SEQ ID NO: 4000 SEQUENCE: 4000 | moltype = | length = 000 |
| SEQ ID NO: 4001 SEQUENCE: 4001 | moltype = | length = 000 |
| SEQ ID NO: 4002 SEQUENCE: 4002 | moltype = | length = 000 |
| SEQ ID NO: 4003 SEQUENCE: 4003 | moltype = | length = 000 |
| SEQ ID NO: 4004 SEQUENCE: 4004 | moltype = | length = 000 |
| SEQ ID NO: 4005 SEQUENCE: 4005 | moltype = | length = 000 |
| SEQ ID NO: 4006 SEQUENCE: 4006 | moltype = | length = 000 |
| SEQ ID NO: 4007 SEQUENCE: 4007 | moltype = | length = 000 |
| SEQ ID NO: 4008 SEQUENCE: 4008 | moltype = | length = 000 |
| SEQ ID NO: 4009 SEQUENCE: 4009 | moltype = | length = |

000

SEQ ID NO: 4010        moltype =    length =
SEQUENCE: 4010
000

SEQ ID NO: 4011        moltype =    length =
SEQUENCE: 4011
000

SEQ ID NO: 4012        moltype =    length =
SEQUENCE: 4012
000

SEQ ID NO: 4013        moltype =    length =
SEQUENCE: 4013
000

SEQ ID NO: 4014        moltype =    length =
SEQUENCE: 4014
000

SEQ ID NO: 4015        moltype =    length =
SEQUENCE: 4015
000

SEQ ID NO: 4016        moltype =    length =
SEQUENCE: 4016
000

SEQ ID NO: 4017        moltype =    length =
SEQUENCE: 4017
000

SEQ ID NO: 4018        moltype =    length =
SEQUENCE: 4018
000

SEQ ID NO: 4019        moltype =    length =
SEQUENCE: 4019
000

SEQ ID NO: 4020        moltype =    length =
SEQUENCE: 4020
000

SEQ ID NO: 4021        moltype =    length =
SEQUENCE: 4021
000

SEQ ID NO: 4022        moltype =    length =
SEQUENCE: 4022
000

SEQ ID NO: 4023        moltype =    length =
SEQUENCE: 4023
000

SEQ ID NO: 4024        moltype =    length =
SEQUENCE: 4024
000

SEQ ID NO: 4025        moltype =    length =
SEQUENCE: 4025
000

SEQ ID NO: 4026        moltype =    length =
SEQUENCE: 4026
000

SEQ ID NO: 4027        moltype =    length =
SEQUENCE: 4027
000

SEQ ID NO: 4028        moltype =    length =
SEQUENCE: 4028
000

SEQ ID NO: 4029        moltype =    length =

| | | |
|---|---|---|
| SEQUENCE: 4029 000 | | |
| SEQ ID NO: 4030 SEQUENCE: 4030 000 | moltype = | length = |
| SEQ ID NO: 4031 SEQUENCE: 4031 000 | moltype = | length = |
| SEQ ID NO: 4032 SEQUENCE: 4032 000 | moltype = | length = |
| SEQ ID NO: 4033 SEQUENCE: 4033 000 | moltype = | length = |
| SEQ ID NO: 4034 SEQUENCE: 4034 000 | moltype = | length = |
| SEQ ID NO: 4035 SEQUENCE: 4035 000 | moltype = | length = |
| SEQ ID NO: 4036 SEQUENCE: 4036 000 | moltype = | length = |
| SEQ ID NO: 4037 SEQUENCE: 4037 000 | moltype = | length = |
| SEQ ID NO: 4038 SEQUENCE: 4038 000 | moltype = | length = |
| SEQ ID NO: 4039 SEQUENCE: 4039 000 | moltype = | length = |
| SEQ ID NO: 4040 SEQUENCE: 4040 000 | moltype = | length = |
| SEQ ID NO: 4041 SEQUENCE: 4041 000 | moltype = | length = |
| SEQ ID NO: 4042 SEQUENCE: 4042 000 | moltype = | length = |
| SEQ ID NO: 4043 SEQUENCE: 4043 000 | moltype = | length = |
| SEQ ID NO: 4044 SEQUENCE: 4044 000 | moltype = | length = |
| SEQ ID NO: 4045 SEQUENCE: 4045 000 | moltype = | length = |
| SEQ ID NO: 4046 SEQUENCE: 4046 000 | moltype = | length = |
| SEQ ID NO: 4047 SEQUENCE: 4047 000 | moltype = | length = |
| SEQ ID NO: 4048 SEQUENCE: 4048 000 | moltype = | length = |

| | | |
|---|---|---|
| SEQ ID NO: 4049<br>SEQUENCE: 4049<br>000 | moltype = | length = |
| SEQ ID NO: 4050<br>SEQUENCE: 4050<br>000 | moltype = | length = |
| SEQ ID NO: 4051<br>SEQUENCE: 4051<br>000 | moltype = | length = |
| SEQ ID NO: 4052<br>SEQUENCE: 4052<br>000 | moltype = | length = |
| SEQ ID NO: 4053<br>SEQUENCE: 4053<br>000 | moltype = | length = |
| SEQ ID NO: 4054<br>SEQUENCE: 4054<br>000 | moltype = | length = |
| SEQ ID NO: 4055<br>SEQUENCE: 4055<br>000 | moltype = | length = |
| SEQ ID NO: 4056<br>SEQUENCE: 4056<br>000 | moltype = | length = |
| SEQ ID NO: 4057<br>SEQUENCE: 4057<br>000 | moltype = | length = |
| SEQ ID NO: 4058<br>SEQUENCE: 4058<br>000 | moltype = | length = |
| SEQ ID NO: 4059<br>SEQUENCE: 4059<br>000 | moltype = | length = |
| SEQ ID NO: 4060<br>SEQUENCE: 4060<br>000 | moltype = | length = |
| SEQ ID NO: 4061<br>SEQUENCE: 4061<br>000 | moltype = | length = |
| SEQ ID NO: 4062<br>SEQUENCE: 4062<br>000 | moltype = | length = |
| SEQ ID NO: 4063<br>SEQUENCE: 4063<br>000 | moltype = | length = |
| SEQ ID NO: 4064<br>SEQUENCE: 4064<br>000 | moltype = | length = |
| SEQ ID NO: 4065<br>SEQUENCE: 4065<br>000 | moltype = | length = |
| SEQ ID NO: 4066<br>SEQUENCE: 4066<br>000 | moltype = | length = |
| SEQ ID NO: 4067<br>SEQUENCE: 4067<br>000 | moltype = | length = |
| SEQ ID NO: 4068<br>SEQUENCE: 4068<br>000 | moltype = | length = |

| | | |
|---|---|---|
| SEQ ID NO: 4069 SEQUENCE: 4069 000 | moltype = | length = |
| SEQ ID NO: 4070 SEQUENCE: 4070 000 | moltype = | length = |
| SEQ ID NO: 4071 SEQUENCE: 4071 000 | moltype = | length = |
| SEQ ID NO: 4072 SEQUENCE: 4072 000 | moltype = | length = |
| SEQ ID NO: 4073 SEQUENCE: 4073 000 | moltype = | length = |
| SEQ ID NO: 4074 SEQUENCE: 4074 000 | moltype = | length = |
| SEQ ID NO: 4075 SEQUENCE: 4075 000 | moltype = | length = |
| SEQ ID NO: 4076 SEQUENCE: 4076 000 | moltype = | length = |
| SEQ ID NO: 4077 SEQUENCE: 4077 000 | moltype = | length = |
| SEQ ID NO: 4078 SEQUENCE: 4078 000 | moltype = | length = |
| SEQ ID NO: 4079 SEQUENCE: 4079 000 | moltype = | length = |
| SEQ ID NO: 4080 SEQUENCE: 4080 000 | moltype = | length = |
| SEQ ID NO: 4081 SEQUENCE: 4081 000 | moltype = | length = |
| SEQ ID NO: 4082 SEQUENCE: 4082 000 | moltype = | length = |
| SEQ ID NO: 4083 SEQUENCE: 4083 000 | moltype = | length = |
| SEQ ID NO: 4084 SEQUENCE: 4084 000 | moltype = | length = |
| SEQ ID NO: 4085 SEQUENCE: 4085 000 | moltype = | length = |
| SEQ ID NO: 4086 SEQUENCE: 4086 000 | moltype = | length = |
| SEQ ID NO: 4087 SEQUENCE: 4087 000 | moltype = | length = |
| SEQ ID NO: 4088 SEQUENCE: 4088 | moltype = | length = |

-continued

000

SEQ ID NO: 4089          moltype =     length =
SEQUENCE: 4089
000

SEQ ID NO: 4090          moltype =     length =
SEQUENCE: 4090
000

SEQ ID NO: 4091          moltype =     length =
SEQUENCE: 4091
000

SEQ ID NO: 4092          moltype =     length =
SEQUENCE: 4092
000

SEQ ID NO: 4093          moltype =     length =
SEQUENCE: 4093
000

SEQ ID NO: 4094          moltype =     length =
SEQUENCE: 4094
000

SEQ ID NO: 4095          moltype =     length =
SEQUENCE: 4095
000

SEQ ID NO: 4096          moltype =     length =
SEQUENCE: 4096
000

SEQ ID NO: 4097          moltype =     length =
SEQUENCE: 4097
000

SEQ ID NO: 4098          moltype =     length =
SEQUENCE: 4098
000

SEQ ID NO: 4099          moltype =     length =
SEQUENCE: 4099
000

SEQ ID NO: 4100          moltype =     length =
SEQUENCE: 4100
000

SEQ ID NO: 4101          moltype =     length =
SEQUENCE: 4101
000

SEQ ID NO: 4102          moltype =     length =
SEQUENCE: 4102
000

SEQ ID NO: 4103          moltype =     length =
SEQUENCE: 4103
000

SEQ ID NO: 4104          moltype =     length =
SEQUENCE: 4104
000

SEQ ID NO: 4105          moltype =     length =
SEQUENCE: 4105
000

SEQ ID NO: 4106          moltype =     length =
SEQUENCE: 4106
000

SEQ ID NO: 4107          moltype =     length =
SEQUENCE: 4107
000

SEQ ID NO: 4108          moltype =     length =

| | | |
|---|---|---|
| SEQUENCE: 4108 000 | | |
| SEQ ID NO: 4109 SEQUENCE: 4109 000 | moltype = | length = |
| SEQ ID NO: 4110 SEQUENCE: 4110 000 | moltype = | length = |
| SEQ ID NO: 4111 SEQUENCE: 4111 000 | moltype = | length = |
| SEQ ID NO: 4112 SEQUENCE: 4112 000 | moltype = | length = |
| SEQ ID NO: 4113 SEQUENCE: 4113 000 | moltype = | length = |
| SEQ ID NO: 4114 SEQUENCE: 4114 000 | moltype = | length = |
| SEQ ID NO: 4115 SEQUENCE: 4115 000 | moltype = | length = |
| SEQ ID NO: 4116 SEQUENCE: 4116 000 | moltype = | length = |
| SEQ ID NO: 4117 SEQUENCE: 4117 000 | moltype = | length = |
| SEQ ID NO: 4118 SEQUENCE: 4118 000 | moltype = | length = |
| SEQ ID NO: 4119 SEQUENCE: 4119 000 | moltype = | length = |
| SEQ ID NO: 4120 SEQUENCE: 4120 000 | moltype = | length = |
| SEQ ID NO: 4121 SEQUENCE: 4121 000 | moltype = | length = |
| SEQ ID NO: 4122 SEQUENCE: 4122 000 | moltype = | length = |
| SEQ ID NO: 4123 SEQUENCE: 4123 000 | moltype = | length = |
| SEQ ID NO: 4124 SEQUENCE: 4124 000 | moltype = | length = |
| SEQ ID NO: 4125 SEQUENCE: 4125 000 | moltype = | length = |
| SEQ ID NO: 4126 SEQUENCE: 4126 000 | moltype = | length = |
| SEQ ID NO: 4127 SEQUENCE: 4127 000 | moltype = | length = |

| | | |
|---|---|---|
| SEQ ID NO: 4128 SEQUENCE: 4128 | moltype = | length = 000 |
| SEQ ID NO: 4129 SEQUENCE: 4129 | moltype = | length = 000 |
| SEQ ID NO: 4130 SEQUENCE: 4130 | moltype = | length = 000 |
| SEQ ID NO: 4131 SEQUENCE: 4131 | moltype = | length = 000 |
| SEQ ID NO: 4132 SEQUENCE: 4132 | moltype = | length = 000 |
| SEQ ID NO: 4133 SEQUENCE: 4133 | moltype = | length = 000 |
| SEQ ID NO: 4134 SEQUENCE: 4134 | moltype = | length = 000 |
| SEQ ID NO: 4135 SEQUENCE: 4135 | moltype = | length = 000 |
| SEQ ID NO: 4136 SEQUENCE: 4136 | moltype = | length = 000 |
| SEQ ID NO: 4137 SEQUENCE: 4137 | moltype = | length = 000 |
| SEQ ID NO: 4138 SEQUENCE: 4138 | moltype = | length = 000 |
| SEQ ID NO: 4139 SEQUENCE: 4139 | moltype = | length = 000 |
| SEQ ID NO: 4140 SEQUENCE: 4140 | moltype = | length = 000 |
| SEQ ID NO: 4141 SEQUENCE: 4141 | moltype = | length = 000 |
| SEQ ID NO: 4142 SEQUENCE: 4142 | moltype = | length = 000 |
| SEQ ID NO: 4143 SEQUENCE: 4143 | moltype = | length = 000 |
| SEQ ID NO: 4144 SEQUENCE: 4144 | moltype = | length = 000 |
| SEQ ID NO: 4145 SEQUENCE: 4145 | moltype = | length = 000 |
| SEQ ID NO: 4146 SEQUENCE: 4146 | moltype = | length = 000 |
| SEQ ID NO: 4147 SEQUENCE: 4147 | moltype = | length = 000 |

| | | |
|---|---|---|
| SEQ ID NO: 4148 SEQUENCE: 4148 000 | moltype = | length = |
| SEQ ID NO: 4149 SEQUENCE: 4149 000 | moltype = | length = |
| SEQ ID NO: 4150 SEQUENCE: 4150 000 | moltype = | length = |
| SEQ ID NO: 4151 SEQUENCE: 4151 000 | moltype = | length = |
| SEQ ID NO: 4152 SEQUENCE: 4152 000 | moltype = | length = |
| SEQ ID NO: 4153 SEQUENCE: 4153 000 | moltype = | length = |
| SEQ ID NO: 4154 SEQUENCE: 4154 000 | moltype = | length = |
| SEQ ID NO: 4155 SEQUENCE: 4155 000 | moltype = | length = |
| SEQ ID NO: 4156 SEQUENCE: 4156 000 | moltype = | length = |
| SEQ ID NO: 4157 SEQUENCE: 4157 000 | moltype = | length = |
| SEQ ID NO: 4158 SEQUENCE: 4158 000 | moltype = | length = |
| SEQ ID NO: 4159 SEQUENCE: 4159 000 | moltype = | length = |
| SEQ ID NO: 4160 SEQUENCE: 4160 000 | moltype = | length = |
| SEQ ID NO: 4161 SEQUENCE: 4161 000 | moltype = | length = |
| SEQ ID NO: 4162 SEQUENCE: 4162 000 | moltype = | length = |
| SEQ ID NO: 4163 SEQUENCE: 4163 000 | moltype = | length = |
| SEQ ID NO: 4164 SEQUENCE: 4164 000 | moltype = | length = |
| SEQ ID NO: 4165 SEQUENCE: 4165 000 | moltype = | length = |
| SEQ ID NO: 4166 SEQUENCE: 4166 000 | moltype = | length = |
| SEQ ID NO: 4167 SEQUENCE: 4167 | moltype = | length = |

000

SEQ ID NO: 4168          moltype =      length =
SEQUENCE: 4168
000

SEQ ID NO: 4169          moltype =      length =
SEQUENCE: 4169
000

SEQ ID NO: 4170          moltype =      length =
SEQUENCE: 4170
000

SEQ ID NO: 4171          moltype =      length =
SEQUENCE: 4171
000

SEQ ID NO: 4172          moltype =      length =
SEQUENCE: 4172
000

SEQ ID NO: 4173          moltype =      length =
SEQUENCE: 4173
000

SEQ ID NO: 4174          moltype =      length =
SEQUENCE: 4174
000

SEQ ID NO: 4175          moltype =      length =
SEQUENCE: 4175
000

SEQ ID NO: 4176          moltype =      length =
SEQUENCE: 4176
000

SEQ ID NO: 4177          moltype =      length =
SEQUENCE: 4177
000

SEQ ID NO: 4178          moltype =      length =
SEQUENCE: 4178
000

SEQ ID NO: 4179          moltype =      length =
SEQUENCE: 4179
000

SEQ ID NO: 4180          moltype =      length =
SEQUENCE: 4180
000

SEQ ID NO: 4181          moltype =      length =
SEQUENCE: 4181
000

SEQ ID NO: 4182          moltype =      length =
SEQUENCE: 4182
000

SEQ ID NO: 4183          moltype =      length =
SEQUENCE: 4183
000

SEQ ID NO: 4184          moltype =      length =
SEQUENCE: 4184
000

SEQ ID NO: 4185          moltype =      length =
SEQUENCE: 4185
000

SEQ ID NO: 4186          moltype =      length =
SEQUENCE: 4186
000

SEQ ID NO: 4187          moltype =      length =

-continued

| | | |
|---|---|---|
| SEQUENCE: 4187 000 | | |
| SEQ ID NO: 4188 SEQUENCE: 4188 000 | moltype = | length = |
| SEQ ID NO: 4189 SEQUENCE: 4189 000 | moltype = | length = |
| SEQ ID NO: 4190 SEQUENCE: 4190 000 | moltype = | length = |
| SEQ ID NO: 4191 SEQUENCE: 4191 000 | moltype = | length = |
| SEQ ID NO: 4192 SEQUENCE: 4192 000 | moltype = | length = |
| SEQ ID NO: 4193 SEQUENCE: 4193 000 | moltype = | length = |
| SEQ ID NO: 4194 SEQUENCE: 4194 000 | moltype = | length = |
| SEQ ID NO: 4195 SEQUENCE: 4195 000 | moltype = | length = |
| SEQ ID NO: 4196 SEQUENCE: 4196 000 | moltype = | length = |
| SEQ ID NO: 4197 SEQUENCE: 4197 000 | moltype = | length = |
| SEQ ID NO: 4198 SEQUENCE: 4198 000 | moltype = | length = |
| SEQ ID NO: 4199 SEQUENCE: 4199 000 | moltype = | length = |
| SEQ ID NO: 4200 SEQUENCE: 4200 000 | moltype = | length = |
| SEQ ID NO: 4201 SEQUENCE: 4201 000 | moltype = | length = |
| SEQ ID NO: 4202 SEQUENCE: 4202 000 | moltype = | length = |
| SEQ ID NO: 4203 SEQUENCE: 4203 000 | moltype = | length = |
| SEQ ID NO: 4204 SEQUENCE: 4204 000 | moltype = | length = |
| SEQ ID NO: 4205 SEQUENCE: 4205 000 | moltype = | length = |
| SEQ ID NO: 4206 SEQUENCE: 4206 000 | moltype = | length = |

| | | |
|---|---|---|
| SEQ ID NO: 4207<br>SEQUENCE: 4207 | moltype = | length = 000 |
| SEQ ID NO: 4208<br>SEQUENCE: 4208 | moltype = | length = 000 |
| SEQ ID NO: 4209<br>SEQUENCE: 4209 | moltype = | length = 000 |
| SEQ ID NO: 4210<br>SEQUENCE: 4210 | moltype = | length = 000 |
| SEQ ID NO: 4211<br>SEQUENCE: 4211 | moltype = | length = 000 |
| SEQ ID NO: 4212<br>SEQUENCE: 4212 | moltype = | length = 000 |
| SEQ ID NO: 4213<br>SEQUENCE: 4213 | moltype = | length = 000 |
| SEQ ID NO: 4214<br>SEQUENCE: 4214 | moltype = | length = 000 |
| SEQ ID NO: 4215<br>SEQUENCE: 4215 | moltype = | length = 000 |
| SEQ ID NO: 4216<br>SEQUENCE: 4216 | moltype = | length = 000 |
| SEQ ID NO: 4217<br>SEQUENCE: 4217 | moltype = | length = 000 |
| SEQ ID NO: 4218<br>SEQUENCE: 4218 | moltype = | length = 000 |
| SEQ ID NO: 4219<br>SEQUENCE: 4219 | moltype = | length = 000 |
| SEQ ID NO: 4220<br>SEQUENCE: 4220 | moltype = | length = 000 |
| SEQ ID NO: 4221<br>SEQUENCE: 4221 | moltype = | length = 000 |
| SEQ ID NO: 4222<br>SEQUENCE: 4222 | moltype = | length = 000 |
| SEQ ID NO: 4223<br>SEQUENCE: 4223 | moltype = | length = 000 |
| SEQ ID NO: 4224<br>SEQUENCE: 4224 | moltype = | length = 000 |
| SEQ ID NO: 4225<br>SEQUENCE: 4225 | moltype = | length = 000 |
| SEQ ID NO: 4226<br>SEQUENCE: 4226 | moltype = | length = 000 |

| | | |
|---|---|---|
| SEQ ID NO: 4227<br>SEQUENCE: 4227<br>000 | moltype = | length = |
| SEQ ID NO: 4228<br>SEQUENCE: 4228<br>000 | moltype = | length = |
| SEQ ID NO: 4229<br>SEQUENCE: 4229<br>000 | moltype = | length = |
| SEQ ID NO: 4230<br>SEQUENCE: 4230<br>000 | moltype = | length = |
| SEQ ID NO: 4231<br>SEQUENCE: 4231<br>000 | moltype = | length = |
| SEQ ID NO: 4232<br>SEQUENCE: 4232<br>000 | moltype = | length = |
| SEQ ID NO: 4233<br>SEQUENCE: 4233<br>000 | moltype = | length = |
| SEQ ID NO: 4234<br>SEQUENCE: 4234<br>000 | moltype = | length = |
| SEQ ID NO: 4235<br>SEQUENCE: 4235<br>000 | moltype = | length = |
| SEQ ID NO: 4236<br>SEQUENCE: 4236<br>000 | moltype = | length = |
| SEQ ID NO: 4237<br>SEQUENCE: 4237<br>000 | moltype = | length = |
| SEQ ID NO: 4238<br>SEQUENCE: 4238<br>000 | moltype = | length = |
| SEQ ID NO: 4239<br>SEQUENCE: 4239<br>000 | moltype = | length = |
| SEQ ID NO: 4240<br>SEQUENCE: 4240<br>000 | moltype = | length = |
| SEQ ID NO: 4241<br>SEQUENCE: 4241<br>000 | moltype = | length = |
| SEQ ID NO: 4242<br>SEQUENCE: 4242<br>000 | moltype = | length = |
| SEQ ID NO: 4243<br>SEQUENCE: 4243<br>000 | moltype = | length = |
| SEQ ID NO: 4244<br>SEQUENCE: 4244<br>000 | moltype = | length = |
| SEQ ID NO: 4245<br>SEQUENCE: 4245<br>000 | moltype = | length = |
| SEQ ID NO: 4246<br>SEQUENCE: 4246 | moltype = | length = |

000

SEQ ID NO: 4247        moltype =     length =
SEQUENCE: 4247
000

SEQ ID NO: 4248        moltype =     length =
SEQUENCE: 4248
000

SEQ ID NO: 4249        moltype =     length =
SEQUENCE: 4249
000

SEQ ID NO: 4250        moltype =     length =
SEQUENCE: 4250
000

SEQ ID NO: 4251        moltype =     length =
SEQUENCE: 4251
000

SEQ ID NO: 4252        moltype =     length =
SEQUENCE: 4252
000

SEQ ID NO: 4253        moltype =     length =
SEQUENCE: 4253
000

SEQ ID NO: 4254        moltype =     length =
SEQUENCE: 4254
000

SEQ ID NO: 4255        moltype =     length =
SEQUENCE: 4255
000

SEQ ID NO: 4256        moltype =     length =
SEQUENCE: 4256
000

SEQ ID NO: 4257        moltype =     length =
SEQUENCE: 4257
000

SEQ ID NO: 4258        moltype =     length =
SEQUENCE: 4258
000

SEQ ID NO: 4259        moltype =     length =
SEQUENCE: 4259
000

SEQ ID NO: 4260        moltype =     length =
SEQUENCE: 4260
000

SEQ ID NO: 4261        moltype =     length =
SEQUENCE: 4261
000

SEQ ID NO: 4262        moltype =     length =
SEQUENCE: 4262
000

SEQ ID NO: 4263        moltype =     length =
SEQUENCE: 4263
000

SEQ ID NO: 4264        moltype =     length =
SEQUENCE: 4264
000

SEQ ID NO: 4265        moltype =     length =
SEQUENCE: 4265
000

SEQ ID NO: 4266        moltype =     length =

-continued

SEQUENCE: 4266
000

SEQ ID NO: 4267          moltype =    length =
SEQUENCE: 4267
000

SEQ ID NO: 4268          moltype =    length =
SEQUENCE: 4268
000

SEQ ID NO: 4269          moltype =    length =
SEQUENCE: 4269
000

SEQ ID NO: 4270          moltype =    length =
SEQUENCE: 4270
000

SEQ ID NO: 4271          moltype =    length =
SEQUENCE: 4271
000

SEQ ID NO: 4272          moltype =    length =
SEQUENCE: 4272
000

SEQ ID NO: 4273          moltype =    length =
SEQUENCE: 4273
000

SEQ ID NO: 4274          moltype =    length =
SEQUENCE: 4274
000

SEQ ID NO: 4275          moltype =    length =
SEQUENCE: 4275
000

SEQ ID NO: 4276          moltype =    length =
SEQUENCE: 4276
000

SEQ ID NO: 4277          moltype =    length =
SEQUENCE: 4277
000

SEQ ID NO: 4278          moltype =    length =
SEQUENCE: 4278
000

SEQ ID NO: 4279          moltype =    length =
SEQUENCE: 4279
000

SEQ ID NO: 4280          moltype =    length =
SEQUENCE: 4280
000

SEQ ID NO: 4281          moltype =    length =
SEQUENCE: 4281
000

SEQ ID NO: 4282          moltype =    length =
SEQUENCE: 4282
000

SEQ ID NO: 4283          moltype =    length =
SEQUENCE: 4283
000

SEQ ID NO: 4284          moltype =    length =
SEQUENCE: 4284
000

SEQ ID NO: 4285          moltype =    length =
SEQUENCE: 4285
000

| | | |
|---|---|---|
| SEQ ID NO: 4286 SEQUENCE: 4286 | moltype = | length = 000 |
| SEQ ID NO: 4287 SEQUENCE: 4287 | moltype = | length = 000 |
| SEQ ID NO: 4288 SEQUENCE: 4288 | moltype = | length = 000 |
| SEQ ID NO: 4289 SEQUENCE: 4289 | moltype = | length = 000 |
| SEQ ID NO: 4290 SEQUENCE: 4290 | moltype = | length = 000 |
| SEQ ID NO: 4291 SEQUENCE: 4291 | moltype = | length = 000 |
| SEQ ID NO: 4292 SEQUENCE: 4292 | moltype = | length = 000 |
| SEQ ID NO: 4293 SEQUENCE: 4293 | moltype = | length = 000 |
| SEQ ID NO: 4294 SEQUENCE: 4294 | moltype = | length = 000 |
| SEQ ID NO: 4295 SEQUENCE: 4295 | moltype = | length = 000 |
| SEQ ID NO: 4296 SEQUENCE: 4296 | moltype = | length = 000 |
| SEQ ID NO: 4297 SEQUENCE: 4297 | moltype = | length = 000 |
| SEQ ID NO: 4298 SEQUENCE: 4298 | moltype = | length = 000 |
| SEQ ID NO: 4299 SEQUENCE: 4299 | moltype = | length = 000 |
| SEQ ID NO: 4300 SEQUENCE: 4300 | moltype = | length = 000 |
| SEQ ID NO: 4301 SEQUENCE: 4301 | moltype = | length = 000 |
| SEQ ID NO: 4302 SEQUENCE: 4302 | moltype = | length = 000 |
| SEQ ID NO: 4303 SEQUENCE: 4303 | moltype = | length = 000 |
| SEQ ID NO: 4304 SEQUENCE: 4304 | moltype = | length = 000 |
| SEQ ID NO: 4305 SEQUENCE: 4305 | moltype = | length = 000 |

| SEQ ID NO: 4306 | moltype = | length = |
|---|---|---|
| SEQUENCE: 4306 000 | | |

| SEQ ID NO: 4307 | moltype = | length = |
|---|---|---|
| SEQUENCE: 4307 000 | | |

| SEQ ID NO: 4308 | moltype = | length = |
|---|---|---|
| SEQUENCE: 4308 000 | | |

| SEQ ID NO: 4309 | moltype = | length = |
|---|---|---|
| SEQUENCE: 4309 000 | | |

| SEQ ID NO: 4310 | moltype = | length = |
|---|---|---|
| SEQUENCE: 4310 000 | | |

| SEQ ID NO: 4311 | moltype = | length = |
|---|---|---|
| SEQUENCE: 4311 000 | | |

| SEQ ID NO: 4312 | moltype = | length = |
|---|---|---|
| SEQUENCE: 4312 000 | | |

| SEQ ID NO: 4313 | moltype = | length = |
|---|---|---|
| SEQUENCE: 4313 000 | | |

| SEQ ID NO: 4314 | moltype = | length = |
|---|---|---|
| SEQUENCE: 4314 000 | | |

| SEQ ID NO: 4315 | moltype = | length = |
|---|---|---|
| SEQUENCE: 4315 000 | | |

| SEQ ID NO: 4316 | moltype = | length = |
|---|---|---|
| SEQUENCE: 4316 000 | | |

| SEQ ID NO: 4317 | moltype = | length = |
|---|---|---|
| SEQUENCE: 4317 000 | | |

| SEQ ID NO: 4318 | moltype = | length = |
|---|---|---|
| SEQUENCE: 4318 000 | | |

| SEQ ID NO: 4319 | moltype = | length = |
|---|---|---|
| SEQUENCE: 4319 000 | | |

| SEQ ID NO: 4320 | moltype = | length = |
|---|---|---|
| SEQUENCE: 4320 000 | | |

| SEQ ID NO: 4321 | moltype = | length = |
|---|---|---|
| SEQUENCE: 4321 000 | | |

| SEQ ID NO: 4322 | moltype = | length = |
|---|---|---|
| SEQUENCE: 4322 000 | | |

| SEQ ID NO: 4323 | moltype = | length = |
|---|---|---|
| SEQUENCE: 4323 000 | | |

| SEQ ID NO: 4324 | moltype = | length = |
|---|---|---|
| SEQUENCE: 4324 000 | | |

| SEQ ID NO: 4325 | moltype = | length = |
|---|---|---|
| SEQUENCE: 4325 | | |

-continued

000

SEQ ID NO: 4326         moltype =     length =
SEQUENCE: 4326
000

SEQ ID NO: 4327         moltype =     length =
SEQUENCE: 4327
000

SEQ ID NO: 4328         moltype =     length =
SEQUENCE: 4328
000

SEQ ID NO: 4329         moltype =     length =
SEQUENCE: 4329
000

SEQ ID NO: 4330         moltype =     length =
SEQUENCE: 4330
000

SEQ ID NO: 4331         moltype =     length =
SEQUENCE: 4331
000

SEQ ID NO: 4332         moltype =     length =
SEQUENCE: 4332
000

SEQ ID NO: 4333         moltype =     length =
SEQUENCE: 4333
000

SEQ ID NO: 4334         moltype =     length =
SEQUENCE: 4334
000

SEQ ID NO: 4335         moltype =     length =
SEQUENCE: 4335
000

SEQ ID NO: 4336         moltype =     length =
SEQUENCE: 4336
000

SEQ ID NO: 4337         moltype =     length =
SEQUENCE: 4337
000

SEQ ID NO: 4338         moltype =     length =
SEQUENCE: 4338
000

SEQ ID NO: 4339         moltype =     length =
SEQUENCE: 4339
000

SEQ ID NO: 4340         moltype =     length =
SEQUENCE: 4340
000

SEQ ID NO: 4341         moltype =     length =
SEQUENCE: 4341
000

SEQ ID NO: 4342         moltype =     length =
SEQUENCE: 4342
000

SEQ ID NO: 4343         moltype =     length =
SEQUENCE: 4343
000

SEQ ID NO: 4344         moltype =     length =
SEQUENCE: 4344
000

SEQ ID NO: 4345         moltype =     length =

| | | |
|---|---|---|
| SEQUENCE: 4345 000 | | |
| SEQ ID NO: 4346 SEQUENCE: 4346 000 | moltype = | length = |
| SEQ ID NO: 4347 SEQUENCE: 4347 000 | moltype = | length = |
| SEQ ID NO: 4348 SEQUENCE: 4348 000 | moltype = | length = |
| SEQ ID NO: 4349 SEQUENCE: 4349 000 | moltype = | length = |
| SEQ ID NO: 4350 SEQUENCE: 4350 000 | moltype = | length = |
| SEQ ID NO: 4351 SEQUENCE: 4351 000 | moltype = | length = |
| SEQ ID NO: 4352 SEQUENCE: 4352 000 | moltype = | length = |
| SEQ ID NO: 4353 SEQUENCE: 4353 000 | moltype = | length = |
| SEQ ID NO: 4354 SEQUENCE: 4354 000 | moltype = | length = |
| SEQ ID NO: 4355 SEQUENCE: 4355 000 | moltype = | length = |
| SEQ ID NO: 4356 SEQUENCE: 4356 000 | moltype = | length = |
| SEQ ID NO: 4357 SEQUENCE: 4357 000 | moltype = | length = |
| SEQ ID NO: 4358 SEQUENCE: 4358 000 | moltype = | length = |
| SEQ ID NO: 4359 SEQUENCE: 4359 000 | moltype = | length = |
| SEQ ID NO: 4360 SEQUENCE: 4360 000 | moltype = | length = |
| SEQ ID NO: 4361 SEQUENCE: 4361 000 | moltype = | length = |
| SEQ ID NO: 4362 SEQUENCE: 4362 000 | moltype = | length = |
| SEQ ID NO: 4363 SEQUENCE: 4363 000 | moltype = | length = |
| SEQ ID NO: 4364 SEQUENCE: 4364 000 | moltype = | length = |

| | | |
|---|---|---|
| SEQ ID NO: 4365<br>SEQUENCE: 4365<br>000 | moltype = | length = |
| SEQ ID NO: 4366<br>SEQUENCE: 4366<br>000 | moltype = | length = |
| SEQ ID NO: 4367<br>SEQUENCE: 4367<br>000 | moltype = | length = |
| SEQ ID NO: 4368<br>SEQUENCE: 4368<br>000 | moltype = | length = |
| SEQ ID NO: 4369<br>SEQUENCE: 4369<br>000 | moltype = | length = |
| SEQ ID NO: 4370<br>SEQUENCE: 4370<br>000 | moltype = | length = |
| SEQ ID NO: 4371<br>SEQUENCE: 4371<br>000 | moltype = | length = |
| SEQ ID NO: 4372<br>SEQUENCE: 4372<br>000 | moltype = | length = |
| SEQ ID NO: 4373<br>SEQUENCE: 4373<br>000 | moltype = | length = |
| SEQ ID NO: 4374<br>SEQUENCE: 4374<br>000 | moltype = | length = |
| SEQ ID NO: 4375<br>SEQUENCE: 4375<br>000 | moltype = | length = |
| SEQ ID NO: 4376<br>SEQUENCE: 4376<br>000 | moltype = | length = |
| SEQ ID NO: 4377<br>SEQUENCE: 4377<br>000 | moltype = | length = |
| SEQ ID NO: 4378<br>SEQUENCE: 4378<br>000 | moltype = | length = |
| SEQ ID NO: 4379<br>SEQUENCE: 4379<br>000 | moltype = | length = |
| SEQ ID NO: 4380<br>SEQUENCE: 4380<br>000 | moltype = | length = |
| SEQ ID NO: 4381<br>SEQUENCE: 4381<br>000 | moltype = | length = |
| SEQ ID NO: 4382<br>SEQUENCE: 4382<br>000 | moltype = | length = |
| SEQ ID NO: 4383<br>SEQUENCE: 4383<br>000 | moltype = | length = |
| SEQ ID NO: 4384<br>SEQUENCE: 4384<br>000 | moltype = | length = |

| | | |
|---|---|---|
| SEQ ID NO: 4385 SEQUENCE: 4385 000 | moltype = | length = |
| SEQ ID NO: 4386 SEQUENCE: 4386 000 | moltype = | length = |
| SEQ ID NO: 4387 SEQUENCE: 4387 000 | moltype = | length = |
| SEQ ID NO: 4388 SEQUENCE: 4388 000 | moltype = | length = |
| SEQ ID NO: 4389 SEQUENCE: 4389 000 | moltype = | length = |
| SEQ ID NO: 4390 SEQUENCE: 4390 000 | moltype = | length = |
| SEQ ID NO: 4391 SEQUENCE: 4391 000 | moltype = | length = |
| SEQ ID NO: 4392 SEQUENCE: 4392 000 | moltype = | length = |
| SEQ ID NO: 4393 SEQUENCE: 4393 000 | moltype = | length = |
| SEQ ID NO: 4394 SEQUENCE: 4394 000 | moltype = | length = |
| SEQ ID NO: 4395 SEQUENCE: 4395 000 | moltype = | length = |
| SEQ ID NO: 4396 SEQUENCE: 4396 000 | moltype = | length = |
| SEQ ID NO: 4397 SEQUENCE: 4397 000 | moltype = | length = |
| SEQ ID NO: 4398 SEQUENCE: 4398 000 | moltype = | length = |
| SEQ ID NO: 4399 SEQUENCE: 4399 000 | moltype = | length = |
| SEQ ID NO: 4400 SEQUENCE: 4400 000 | moltype = | length = |
| SEQ ID NO: 4401 SEQUENCE: 4401 000 | moltype = | length = |
| SEQ ID NO: 4402 SEQUENCE: 4402 000 | moltype = | length = |
| SEQ ID NO: 4403 SEQUENCE: 4403 000 | moltype = | length = |
| SEQ ID NO: 4404 SEQUENCE: 4404 | moltype = | length = |

```
SEQ ID NO: 4405           moltype =    length =
SEQUENCE: 4405
000

SEQ ID NO: 4406           moltype =    length =
SEQUENCE: 4406
000

SEQ ID NO: 4407           moltype =    length =
SEQUENCE: 4407
000

SEQ ID NO: 4408           moltype =    length =
SEQUENCE: 4408
000

SEQ ID NO: 4409           moltype =    length =
SEQUENCE: 4409
000

SEQ ID NO: 4410           moltype =    length =
SEQUENCE: 4410
000

SEQ ID NO: 4411           moltype =    length =
SEQUENCE: 4411
000

SEQ ID NO: 4412           moltype =    length =
SEQUENCE: 4412
000

SEQ ID NO: 4413           moltype =    length =
SEQUENCE: 4413
000

SEQ ID NO: 4414           moltype =    length =
SEQUENCE: 4414
000

SEQ ID NO: 4415           moltype =    length =
SEQUENCE: 4415
000

SEQ ID NO: 4416           moltype =    length =
SEQUENCE: 4416
000

SEQ ID NO: 4417           moltype =    length =
SEQUENCE: 4417
000

SEQ ID NO: 4418           moltype =    length =
SEQUENCE: 4418
000

SEQ ID NO: 4419           moltype =    length =
SEQUENCE: 4419
000

SEQ ID NO: 4420           moltype =    length =
SEQUENCE: 4420
000

SEQ ID NO: 4421           moltype =    length =
SEQUENCE: 4421
000

SEQ ID NO: 4422           moltype =    length =
SEQUENCE: 4422
000

SEQ ID NO: 4423           moltype =    length =
SEQUENCE: 4423
000

SEQ ID NO: 4424           moltype =    length =
```

```
SEQUENCE: 4424
000

SEQ ID NO: 4425          moltype =     length =
SEQUENCE: 4425
000

SEQ ID NO: 4426          moltype =     length =
SEQUENCE: 4426
000

SEQ ID NO: 4427          moltype =     length =
SEQUENCE: 4427
000

SEQ ID NO: 4428          moltype =     length =
SEQUENCE: 4428
000

SEQ ID NO: 4429          moltype =     length =
SEQUENCE: 4429
000

SEQ ID NO: 4430          moltype =     length =
SEQUENCE: 4430
000

SEQ ID NO: 4431          moltype =     length =
SEQUENCE: 4431
000

SEQ ID NO: 4432          moltype =     length =
SEQUENCE: 4432
000

SEQ ID NO: 4433          moltype =     length =
SEQUENCE: 4433
000

SEQ ID NO: 4434          moltype =     length =
SEQUENCE: 4434
000

SEQ ID NO: 4435          moltype =     length =
SEQUENCE: 4435
000

SEQ ID NO: 4436          moltype =     length =
SEQUENCE: 4436
000

SEQ ID NO: 4437          moltype =     length =
SEQUENCE: 4437
000

SEQ ID NO: 4438          moltype =     length =
SEQUENCE: 4438
000

SEQ ID NO: 4439          moltype =     length =
SEQUENCE: 4439
000

SEQ ID NO: 4440          moltype =     length =
SEQUENCE: 4440
000

SEQ ID NO: 4441          moltype =     length =
SEQUENCE: 4441
000

SEQ ID NO: 4442          moltype =     length =
SEQUENCE: 4442
000

SEQ ID NO: 4443          moltype =     length =
SEQUENCE: 4443
000
```

| | | |
|---|---|---|
| SEQ ID NO: 4444<br>SEQUENCE: 4444<br>000 | moltype = | length = |
| SEQ ID NO: 4445<br>SEQUENCE: 4445<br>000 | moltype = | length = |
| SEQ ID NO: 4446<br>SEQUENCE: 4446<br>000 | moltype = | length = |
| SEQ ID NO: 4447<br>SEQUENCE: 4447<br>000 | moltype = | length = |
| SEQ ID NO: 4448<br>SEQUENCE: 4448<br>000 | moltype = | length = |
| SEQ ID NO: 4449<br>SEQUENCE: 4449<br>000 | moltype = | length = |
| SEQ ID NO: 4450<br>SEQUENCE: 4450<br>000 | moltype = | length = |
| SEQ ID NO: 4451<br>SEQUENCE: 4451<br>000 | moltype = | length = |
| SEQ ID NO: 4452<br>SEQUENCE: 4452<br>000 | moltype = | length = |
| SEQ ID NO: 4453<br>SEQUENCE: 4453<br>000 | moltype = | length = |
| SEQ ID NO: 4454<br>SEQUENCE: 4454<br>000 | moltype = | length = |
| SEQ ID NO: 4455<br>SEQUENCE: 4455<br>000 | moltype = | length = |
| SEQ ID NO: 4456<br>SEQUENCE: 4456<br>000 | moltype = | length = |
| SEQ ID NO: 4457<br>SEQUENCE: 4457<br>000 | moltype = | length = |
| SEQ ID NO: 4458<br>SEQUENCE: 4458<br>000 | moltype = | length = |
| SEQ ID NO: 4459<br>SEQUENCE: 4459<br>000 | moltype = | length = |
| SEQ ID NO: 4460<br>SEQUENCE: 4460<br>000 | moltype = | length = |
| SEQ ID NO: 4461<br>SEQUENCE: 4461<br>000 | moltype = | length = |
| SEQ ID NO: 4462<br>SEQUENCE: 4462<br>000 | moltype = | length = |
| SEQ ID NO: 4463<br>SEQUENCE: 4463<br>000 | moltype = | length = |

-continued

SEQ ID NO: 4464    moltype =    length =
SEQUENCE: 4464
000

SEQ ID NO: 4465    moltype =    length =
SEQUENCE: 4465
000

SEQ ID NO: 4466    moltype =    length =
SEQUENCE: 4466
000

SEQ ID NO: 4467    moltype =    length =
SEQUENCE: 4467
000

SEQ ID NO: 4468    moltype =    length =
SEQUENCE: 4468
000

SEQ ID NO: 4469    moltype =    length =
SEQUENCE: 4469
000

SEQ ID NO: 4470    moltype =    length =
SEQUENCE: 4470
000

SEQ ID NO: 4471    moltype =    length =
SEQUENCE: 4471
000

SEQ ID NO: 4472    moltype =    length =
SEQUENCE: 4472
000

SEQ ID NO: 4473    moltype =    length =
SEQUENCE: 4473
000

SEQ ID NO: 4474    moltype =    length =
SEQUENCE: 4474
000

SEQ ID NO: 4475    moltype =    length =
SEQUENCE: 4475
000

SEQ ID NO: 4476    moltype =    length =
SEQUENCE: 4476
000

SEQ ID NO: 4477    moltype =    length =
SEQUENCE: 4477
000

SEQ ID NO: 4478    moltype =    length =
SEQUENCE: 4478
000

SEQ ID NO: 4479    moltype =    length =
SEQUENCE: 4479
000

SEQ ID NO: 4480    moltype =    length =
SEQUENCE: 4480
000

SEQ ID NO: 4481    moltype =    length =
SEQUENCE: 4481
000

SEQ ID NO: 4482    moltype =    length =
SEQUENCE: 4482
000

SEQ ID NO: 4483    moltype =    length =
SEQUENCE: 4483

-continued

000

SEQ ID NO: 4484          moltype =    length =
SEQUENCE: 4484
000

SEQ ID NO: 4485          moltype =    length =
SEQUENCE: 4485
000

SEQ ID NO: 4486          moltype =    length =
SEQUENCE: 4486
000

SEQ ID NO: 4487          moltype =    length =
SEQUENCE: 4487
000

SEQ ID NO: 4488          moltype =    length =
SEQUENCE: 4488
000

SEQ ID NO: 4489          moltype =    length =
SEQUENCE: 4489
000

SEQ ID NO: 4490          moltype =    length =
SEQUENCE: 4490
000

SEQ ID NO: 4491          moltype =    length =
SEQUENCE: 4491
000

SEQ ID NO: 4492          moltype =    length =
SEQUENCE: 4492
000

SEQ ID NO: 4493          moltype =    length =
SEQUENCE: 4493
000

SEQ ID NO: 4494          moltype =    length =
SEQUENCE: 4494
000

SEQ ID NO: 4495          moltype =    length =
SEQUENCE: 4495
000

SEQ ID NO: 4496          moltype =    length =
SEQUENCE: 4496
000

SEQ ID NO: 4497          moltype =    length =
SEQUENCE: 4497
000

SEQ ID NO: 4498          moltype =    length =
SEQUENCE: 4498
000

SEQ ID NO: 4499          moltype =    length =
SEQUENCE: 4499
000

SEQ ID NO: 4500          moltype =    length =
SEQUENCE: 4500
000

SEQ ID NO: 4501          moltype =    length =
SEQUENCE: 4501
000

SEQ ID NO: 4502          moltype =    length =
SEQUENCE: 4502
000

SEQ ID NO: 4503          moltype =    length =

| | | |
|---|---|---|
| SEQUENCE: 4503 000 | | |
| SEQ ID NO: 4504 SEQUENCE: 4504 000 | moltype = | length = |
| SEQ ID NO: 4505 SEQUENCE: 4505 000 | moltype = | length = |
| SEQ ID NO: 4506 SEQUENCE: 4506 000 | moltype = | length = |
| SEQ ID NO: 4507 SEQUENCE: 4507 000 | moltype = | length = |
| SEQ ID NO: 4508 SEQUENCE: 4508 000 | moltype = | length = |
| SEQ ID NO: 4509 SEQUENCE: 4509 000 | moltype = | length = |
| SEQ ID NO: 4510 SEQUENCE: 4510 000 | moltype = | length = |
| SEQ ID NO: 4511 SEQUENCE: 4511 000 | moltype = | length = |
| SEQ ID NO: 4512 SEQUENCE: 4512 000 | moltype = | length = |
| SEQ ID NO: 4513 SEQUENCE: 4513 000 | moltype = | length = |
| SEQ ID NO: 4514 SEQUENCE: 4514 000 | moltype = | length = |
| SEQ ID NO: 4515 SEQUENCE: 4515 000 | moltype = | length = |
| SEQ ID NO: 4516 SEQUENCE: 4516 000 | moltype = | length = |
| SEQ ID NO: 4517 SEQUENCE: 4517 000 | moltype = | length = |
| SEQ ID NO: 4518 SEQUENCE: 4518 000 | moltype = | length = |
| SEQ ID NO: 4519 SEQUENCE: 4519 000 | moltype = | length = |
| SEQ ID NO: 4520 SEQUENCE: 4520 000 | moltype = | length = |
| SEQ ID NO: 4521 SEQUENCE: 4521 000 | moltype = | length = |
| SEQ ID NO: 4522 SEQUENCE: 4522 000 | moltype = | length = |

| | | |
|---|---|---|
| SEQ ID NO: 4523<br>SEQUENCE: 4523<br>000 | moltype = | length = |
| SEQ ID NO: 4524<br>SEQUENCE: 4524<br>000 | moltype = | length = |
| SEQ ID NO: 4525<br>SEQUENCE: 4525<br>000 | moltype = | length = |
| SEQ ID NO: 4526<br>SEQUENCE: 4526<br>000 | moltype = | length = |
| SEQ ID NO: 4527<br>SEQUENCE: 4527<br>000 | moltype = | length = |
| SEQ ID NO: 4528<br>SEQUENCE: 4528<br>000 | moltype = | length = |
| SEQ ID NO: 4529<br>SEQUENCE: 4529<br>000 | moltype = | length = |
| SEQ ID NO: 4530<br>SEQUENCE: 4530<br>000 | moltype = | length = |
| SEQ ID NO: 4531<br>SEQUENCE: 4531<br>000 | moltype = | length = |
| SEQ ID NO: 4532<br>SEQUENCE: 4532<br>000 | moltype = | length = |
| SEQ ID NO: 4533<br>SEQUENCE: 4533<br>000 | moltype = | length = |
| SEQ ID NO: 4534<br>SEQUENCE: 4534<br>000 | moltype = | length = |
| SEQ ID NO: 4535<br>SEQUENCE: 4535<br>000 | moltype = | length = |
| SEQ ID NO: 4536<br>SEQUENCE: 4536<br>000 | moltype = | length = |
| SEQ ID NO: 4537<br>SEQUENCE: 4537<br>000 | moltype = | length = |
| SEQ ID NO: 4538<br>SEQUENCE: 4538<br>000 | moltype = | length = |
| SEQ ID NO: 4539<br>SEQUENCE: 4539<br>000 | moltype = | length = |
| SEQ ID NO: 4540<br>SEQUENCE: 4540<br>000 | moltype = | length = |
| SEQ ID NO: 4541<br>SEQUENCE: 4541<br>000 | moltype = | length = |
| SEQ ID NO: 4542<br>SEQUENCE: 4542<br>000 | moltype = | length = |

```
SEQ ID NO: 4543         moltype =    length =
SEQUENCE: 4543
000

SEQ ID NO: 4544         moltype =    length =
SEQUENCE: 4544
000

SEQ ID NO: 4545         moltype = AA  length = 4
FEATURE                 Location/Qualifiers
source                  1..4
                        mol_type = protein
                        organism = unidentified
SEQUENCE: 4545
KDEL                                                                      4

SEQ ID NO: 4546         moltype =    length =
SEQUENCE: 4546
000

SEQ ID NO: 4547         moltype =    length =
SEQUENCE: 4547
000

SEQ ID NO: 4548         moltype =    length =
SEQUENCE: 4548
000

SEQ ID NO: 4549         moltype =    length =
SEQUENCE: 4549
000

SEQ ID NO: 4550         moltype =    length =
SEQUENCE: 4550
000

SEQ ID NO: 4551         moltype =    length =
SEQUENCE: 4551
000

SEQ ID NO: 4552         moltype =    length =
SEQUENCE: 4552
000

SEQ ID NO: 4553         moltype =    length =
SEQUENCE: 4553
000

SEQ ID NO: 4554         moltype =    length =
SEQUENCE: 4554
000

SEQ ID NO: 4555         moltype =    length =
SEQUENCE: 4555
000

SEQ ID NO: 4556         moltype =    length =
SEQUENCE: 4556
000

SEQ ID NO: 4557         moltype =    length =
SEQUENCE: 4557
000

SEQ ID NO: 4558         moltype =    length =
SEQUENCE: 4558
000

SEQ ID NO: 4559         moltype =    length =
SEQUENCE: 4559
000

SEQ ID NO: 4560         moltype =    length =
SEQUENCE: 4560
000

SEQ ID NO: 4561         moltype =    length =
SEQUENCE: 4561
```

000

SEQ ID NO: 4562        moltype =    length =
SEQUENCE: 4562
000

SEQ ID NO: 4563        moltype =    length =
SEQUENCE: 4563
000

SEQ ID NO: 4564        moltype =    length =
SEQUENCE: 4564
000

SEQ ID NO: 4565        moltype =    length =
SEQUENCE: 4565
000

SEQ ID NO: 4566        moltype =    length =
SEQUENCE: 4566
000

SEQ ID NO: 4567        moltype =    length =
SEQUENCE: 4567
000

SEQ ID NO: 4568        moltype =    length =
SEQUENCE: 4568
000

SEQ ID NO: 4569        moltype =    length =
SEQUENCE: 4569
000

SEQ ID NO: 4570        moltype =    length =
SEQUENCE: 4570
000

SEQ ID NO: 4571        moltype =    length =
SEQUENCE: 4571
000

SEQ ID NO: 4572        moltype =    length =
SEQUENCE: 4572
000

SEQ ID NO: 4573        moltype =    length =
SEQUENCE: 4573
000

SEQ ID NO: 4574        moltype =    length =
SEQUENCE: 4574
000

SEQ ID NO: 4575        moltype =    length =
SEQUENCE: 4575
000

SEQ ID NO: 4576        moltype =    length =
SEQUENCE: 4576
000

SEQ ID NO: 4577        moltype =    length =
SEQUENCE: 4577
000

SEQ ID NO: 4578        moltype =    length =
SEQUENCE: 4578
000

SEQ ID NO: 4579        moltype =    length =
SEQUENCE: 4579
000

SEQ ID NO: 4580        moltype =    length =
SEQUENCE: 4580
000

SEQ ID NO: 4581        moltype =    length =

```
SEQUENCE: 4581
000

SEQ ID NO: 4582          moltype =     length =
SEQUENCE: 4582
000

SEQ ID NO: 4583          moltype =     length =
SEQUENCE: 4583
000

SEQ ID NO: 4584          moltype =     length =
SEQUENCE: 4584
000

SEQ ID NO: 4585          moltype =     length =
SEQUENCE: 4585
000

SEQ ID NO: 4586          moltype =     length =
SEQUENCE: 4586
000

SEQ ID NO: 4587          moltype =     length =
SEQUENCE: 4587
000

SEQ ID NO: 4588          moltype =     length =
SEQUENCE: 4588
000

SEQ ID NO: 4589          moltype =     length =
SEQUENCE: 4589
000

SEQ ID NO: 4590          moltype =     length =
SEQUENCE: 4590
000

SEQ ID NO: 4591          moltype =     length =
SEQUENCE: 4591
000

SEQ ID NO: 4592          moltype =     length =
SEQUENCE: 4592
000

SEQ ID NO: 4593          moltype =     length =
SEQUENCE: 4593
000

SEQ ID NO: 4594          moltype =     length =
SEQUENCE: 4594
000

SEQ ID NO: 4595          moltype =     length =
SEQUENCE: 4595
000

SEQ ID NO: 4596          moltype =     length =
SEQUENCE: 4596
000

SEQ ID NO: 4597          moltype =     length =
SEQUENCE: 4597
000

SEQ ID NO: 4598          moltype =     length =
SEQUENCE: 4598
000

SEQ ID NO: 4599          moltype =     length =
SEQUENCE: 4599
000

SEQ ID NO: 4600          moltype =     length =
SEQUENCE: 4600
000
```

| | | |
|---|---|---|
| SEQ ID NO: 4601 SEQUENCE: 4601 | moltype = | length = 000 |
| SEQ ID NO: 4602 SEQUENCE: 4602 | moltype = | length = 000 |
| SEQ ID NO: 4603 SEQUENCE: 4603 | moltype = | length = 000 |
| SEQ ID NO: 4604 SEQUENCE: 4604 | moltype = | length = 000 |
| SEQ ID NO: 4605 SEQUENCE: 4605 | moltype = | length = 000 |
| SEQ ID NO: 4606 SEQUENCE: 4606 | moltype = | length = 000 |
| SEQ ID NO: 4607 SEQUENCE: 4607 | moltype = | length = 000 |
| SEQ ID NO: 4608 SEQUENCE: 4608 | moltype = | length = 000 |
| SEQ ID NO: 4609 SEQUENCE: 4609 | moltype = | length = 000 |
| SEQ ID NO: 4610 SEQUENCE: 4610 | moltype = | length = 000 |
| SEQ ID NO: 4611 SEQUENCE: 4611 | moltype = | length = 000 |
| SEQ ID NO: 4612 SEQUENCE: 4612 | moltype = | length = 000 |
| SEQ ID NO: 4613 SEQUENCE: 4613 | moltype = | length = 000 |
| SEQ ID NO: 4614 SEQUENCE: 4614 | moltype = | length = 000 |
| SEQ ID NO: 4615 SEQUENCE: 4615 | moltype = | length = 000 |
| SEQ ID NO: 4616 SEQUENCE: 4616 | moltype = | length = 000 |
| SEQ ID NO: 4617 SEQUENCE: 4617 | moltype = | length = 000 |
| SEQ ID NO: 4618 SEQUENCE: 4618 | moltype = | length = 000 |
| SEQ ID NO: 4619 SEQUENCE: 4619 | moltype = | length = 000 |
| SEQ ID NO: 4620 SEQUENCE: 4620 | moltype = | length = 000 |

SEQ ID NO: 4621    moltype =    length =
SEQUENCE: 4621
000

SEQ ID NO: 4622    moltype =    length =
SEQUENCE: 4622
000

SEQ ID NO: 4623    moltype =    length =
SEQUENCE: 4623
000

SEQ ID NO: 4624    moltype =    length =
SEQUENCE: 4624
000

SEQ ID NO: 4625    moltype =    length =
SEQUENCE: 4625
000

SEQ ID NO: 4626    moltype =    length =
SEQUENCE: 4626
000

SEQ ID NO: 4627    moltype =    length =
SEQUENCE: 4627
000

SEQ ID NO: 4628    moltype =    length =
SEQUENCE: 4628
000

SEQ ID NO: 4629    moltype =    length =
SEQUENCE: 4629
000

SEQ ID NO: 4630    moltype =    length =
SEQUENCE: 4630
000

SEQ ID NO: 4631    moltype =    length =
SEQUENCE: 4631
000

SEQ ID NO: 4632    moltype =    length =
SEQUENCE: 4632
000

SEQ ID NO: 4633    moltype =    length =
SEQUENCE: 4633
000

SEQ ID NO: 4634    moltype =    length =
SEQUENCE: 4634
000

SEQ ID NO: 4635    moltype =    length =
SEQUENCE: 4635
000

SEQ ID NO: 4636    moltype =    length =
SEQUENCE: 4636
000

SEQ ID NO: 4637    moltype =    length =
SEQUENCE: 4637
000

SEQ ID NO: 4638    moltype =    length =
SEQUENCE: 4638
000

SEQ ID NO: 4639    moltype =    length =
SEQUENCE: 4639
000

SEQ ID NO: 4640    moltype =    length =
SEQUENCE: 4640

000

SEQ ID NO: 4641            moltype =        length =
SEQUENCE: 4641
000

SEQ ID NO: 4642            moltype =        length =
SEQUENCE: 4642
000

SEQ ID NO: 4643            moltype =        length =
SEQUENCE: 4643
000

SEQ ID NO: 4644            moltype =        length =
SEQUENCE: 4644
000

SEQ ID NO: 4645            moltype =        length =
SEQUENCE: 4645
000

SEQ ID NO: 4646            moltype =        length =
SEQUENCE: 4646
000

SEQ ID NO: 4647            moltype =        length =
SEQUENCE: 4647
000

SEQ ID NO: 4648            moltype =        length =
SEQUENCE: 4648
000

SEQ ID NO: 4649            moltype =        length =
SEQUENCE: 4649
000

SEQ ID NO: 4650            moltype =        length =
SEQUENCE: 4650
000

SEQ ID NO: 4651            moltype =        length =
SEQUENCE: 4651
000

SEQ ID NO: 4652            moltype =        length =
SEQUENCE: 4652
000

SEQ ID NO: 4653            moltype =        length =
SEQUENCE: 4653
000

SEQ ID NO: 4654            moltype =        length =
SEQUENCE: 4654
000

SEQ ID NO: 4655            moltype =        length =
SEQUENCE: 4655
000

SEQ ID NO: 4656            moltype =        length =
SEQUENCE: 4656
000

SEQ ID NO: 4657            moltype =        length =
SEQUENCE: 4657
000

SEQ ID NO: 4658            moltype =        length =
SEQUENCE: 4658
000

SEQ ID NO: 4659            moltype =        length =
SEQUENCE: 4659
000

SEQ ID NO: 4660            moltype =        length =

```
SEQUENCE: 4660
000

SEQ ID NO: 4661            moltype =    length =
SEQUENCE: 4661
000

SEQ ID NO: 4662            moltype =    length =
SEQUENCE: 4662
000

SEQ ID NO: 4663            moltype =    length =
SEQUENCE: 4663
000

SEQ ID NO: 4664            moltype =    length =
SEQUENCE: 4664
000

SEQ ID NO: 4665            moltype =    length =
SEQUENCE: 4665
000

SEQ ID NO: 4666            moltype =    length =
SEQUENCE: 4666
000

SEQ ID NO: 4667            moltype =    length =
SEQUENCE: 4667
000

SEQ ID NO: 4668            moltype =    length =
SEQUENCE: 4668
000

SEQ ID NO: 4669            moltype =    length =
SEQUENCE: 4669
000

SEQ ID NO: 4670            moltype =    length =
SEQUENCE: 4670
000

SEQ ID NO: 4671            moltype =    length =
SEQUENCE: 4671
000

SEQ ID NO: 4672            moltype =    length =
SEQUENCE: 4672
000

SEQ ID NO: 4673            moltype =    length =
SEQUENCE: 4673
000

SEQ ID NO: 4674            moltype =    length =
SEQUENCE: 4674
000

SEQ ID NO: 4675            moltype =    length =
SEQUENCE: 4675
000

SEQ ID NO: 4676            moltype =    length =
SEQUENCE: 4676
000

SEQ ID NO: 4677            moltype =    length =
SEQUENCE: 4677
000

SEQ ID NO: 4678            moltype =    length =
SEQUENCE: 4678
000

SEQ ID NO: 4679            moltype = DNA   length = 22
FEATURE                    Location/Qualifiers
source                     1..22
                           mol_type = unassigned DNA
```

```
                        organism = unidentified
SEQUENCE: 4679
atacatactt ctttacattc ca                                              22

SEQ ID NO: 4680         moltype =    length =
SEQUENCE: 4680
000

SEQ ID NO: 4681         moltype =    length =
SEQUENCE: 4681
000

SEQ ID NO: 4682         moltype =    length =
SEQUENCE: 4682
000

SEQ ID NO: 4683         moltype =    length =
SEQUENCE: 4683
000

SEQ ID NO: 4684         moltype =    length =
SEQUENCE: 4684
000

SEQ ID NO: 4685         moltype =    length =
SEQUENCE: 4685
000

SEQ ID NO: 4686         moltype =    length =
SEQUENCE: 4686
000

SEQ ID NO: 4687         moltype =    length =
SEQUENCE: 4687
000

SEQ ID NO: 4688         moltype =    length =
SEQUENCE: 4688
000

SEQ ID NO: 4689         moltype =    length =
SEQUENCE: 4689
000

SEQ ID NO: 4690         moltype =    length =
SEQUENCE: 4690
000

SEQ ID NO: 4691         moltype =    length =
SEQUENCE: 4691
000

SEQ ID NO: 4692         moltype =    length =
SEQUENCE: 4692
000

SEQ ID NO: 4693         moltype =    length =
SEQUENCE: 4693
000

SEQ ID NO: 4694         moltype =    length =
SEQUENCE: 4694
000

SEQ ID NO: 4695         moltype =    length =
SEQUENCE: 4695
000

SEQ ID NO: 4696         moltype =    length =
SEQUENCE: 4696
000

SEQ ID NO: 4697         moltype =    length =
SEQUENCE: 4697
000

SEQ ID NO: 4698         moltype =    length =
SEQUENCE: 4698
000
```

| | | |
|---|---|---|
| SEQ ID NO: 4699 SEQUENCE: 4699 | moltype = | length = 000 |
| SEQ ID NO: 4700 SEQUENCE: 4700 | moltype = | length = 000 |
| SEQ ID NO: 4701 SEQUENCE: 4701 | moltype = | length = 000 |
| SEQ ID NO: 4702 SEQUENCE: 4702 | moltype = | length = 000 |
| SEQ ID NO: 4703 SEQUENCE: 4703 | moltype = | length = 000 |
| SEQ ID NO: 4704 SEQUENCE: 4704 | moltype = | length = 000 |
| SEQ ID NO: 4705 SEQUENCE: 4705 | moltype = | length = 000 |
| SEQ ID NO: 4706 SEQUENCE: 4706 | moltype = | length = 000 |
| SEQ ID NO: 4707 SEQUENCE: 4707 | moltype = | length = 000 |
| SEQ ID NO: 4708 SEQUENCE: 4708 | moltype = | length = 000 |
| SEQ ID NO: 4709 SEQUENCE: 4709 | moltype = | length = 000 |
| SEQ ID NO: 4710 SEQUENCE: 4710 | moltype = | length = 000 |
| SEQ ID NO: 4711 SEQUENCE: 4711 | moltype = | length = 000 |
| SEQ ID NO: 4712 SEQUENCE: 4712 | moltype = | length = 000 |
| SEQ ID NO: 4713 SEQUENCE: 4713 | moltype = | length = 000 |
| SEQ ID NO: 4714 SEQUENCE: 4714 | moltype = | length = 000 |
| SEQ ID NO: 4715 SEQUENCE: 4715 | moltype = | length = 000 |
| SEQ ID NO: 4716 SEQUENCE: 4716 | moltype = | length = 000 |
| SEQ ID NO: 4717 SEQUENCE: 4717 | moltype = | length = 000 |
| SEQ ID NO: 4718 SEQUENCE: 4718 | moltype = | length = |

000

SEQ ID NO: 4719     moltype =    length =
SEQUENCE: 4719
000

SEQ ID NO: 4720     moltype =    length =
SEQUENCE: 4720
000

SEQ ID NO: 4721     moltype =    length =
SEQUENCE: 4721
000

SEQ ID NO: 4722     moltype =    length =
SEQUENCE: 4722
000

SEQ ID NO: 4723     moltype =    length =
SEQUENCE: 4723
000

SEQ ID NO: 4724     moltype =    length =
SEQUENCE: 4724
000

SEQ ID NO: 4725     moltype =    length =
SEQUENCE: 4725
000

SEQ ID NO: 4726     moltype =    length =
SEQUENCE: 4726
000

SEQ ID NO: 4727     moltype =    length =
SEQUENCE: 4727
000

SEQ ID NO: 4728     moltype =    length =
SEQUENCE: 4728
000

SEQ ID NO: 4729     moltype =    length =
SEQUENCE: 4729
000

SEQ ID NO: 4730     moltype =    length =
SEQUENCE: 4730
000

SEQ ID NO: 4731     moltype =    length =
SEQUENCE: 4731
000

SEQ ID NO: 4732     moltype =    length =
SEQUENCE: 4732
000

SEQ ID NO: 4733     moltype =    length =
SEQUENCE: 4733
000

SEQ ID NO: 4734     moltype =    length =
SEQUENCE: 4734
000

SEQ ID NO: 4735     moltype =    length =
SEQUENCE: 4735
000

SEQ ID NO: 4736     moltype =    length =
SEQUENCE: 4736
000

SEQ ID NO: 4737     moltype =    length =
SEQUENCE: 4737
000

SEQ ID NO: 4738     moltype =    length =

-continued

```
SEQUENCE: 4738
000

SEQ ID NO: 4739              moltype =     length =
SEQUENCE: 4739
000

SEQ ID NO: 4740              moltype =     length =
SEQUENCE: 4740
000

SEQ ID NO: 4741              moltype =     length =
SEQUENCE: 4741
000

SEQ ID NO: 4742              moltype =     length =
SEQUENCE: 4742
000

SEQ ID NO: 4743              moltype =     length =
SEQUENCE: 4743
000

SEQ ID NO: 4744              moltype =     length =
SEQUENCE: 4744
000

SEQ ID NO: 4745              moltype =     length =
SEQUENCE: 4745
000

SEQ ID NO: 4746              moltype =     length =
SEQUENCE: 4746
000

SEQ ID NO: 4747              moltype =     length =
SEQUENCE: 4747
000

SEQ ID NO: 4748              moltype =     length =
SEQUENCE: 4748
000

SEQ ID NO: 4749              moltype =     length =
SEQUENCE: 4749
000

SEQ ID NO: 4750              moltype =     length =
SEQUENCE: 4750
000

SEQ ID NO: 4751              moltype =     length =
SEQUENCE: 4751
000

SEQ ID NO: 4752              moltype =     length =
SEQUENCE: 4752
000

SEQ ID NO: 4753              moltype =     length =
SEQUENCE: 4753
000

SEQ ID NO: 4754              moltype =     length =
SEQUENCE: 4754
000

SEQ ID NO: 4755              moltype =     length =
SEQUENCE: 4755
000

SEQ ID NO: 4756              moltype =     length =
SEQUENCE: 4756
000

SEQ ID NO: 4757              moltype =     length =
SEQUENCE: 4757
000
```

| | | |
|---|---|---|
| SEQ ID NO: 4758 SEQUENCE: 4758 | moltype = | length = 000 |
| SEQ ID NO: 4759 SEQUENCE: 4759 | moltype = | length = 000 |
| SEQ ID NO: 4760 SEQUENCE: 4760 | moltype = | length = 000 |
| SEQ ID NO: 4761 SEQUENCE: 4761 | moltype = | length = 000 |
| SEQ ID NO: 4762 SEQUENCE: 4762 | moltype = | length = 000 |
| SEQ ID NO: 4763 SEQUENCE: 4763 | moltype = | length = 000 |
| SEQ ID NO: 4764 SEQUENCE: 4764 | moltype = | length = 000 |
| SEQ ID NO: 4765 SEQUENCE: 4765 | moltype = | length = 000 |
| SEQ ID NO: 4766 SEQUENCE: 4766 | moltype = | length = 000 |
| SEQ ID NO: 4767 SEQUENCE: 4767 | moltype = | length = 000 |
| SEQ ID NO: 4768 SEQUENCE: 4768 | moltype = | length = 000 |
| SEQ ID NO: 4769 SEQUENCE: 4769 | moltype = | length = 000 |
| SEQ ID NO: 4770 SEQUENCE: 4770 | moltype = | length = 000 |
| SEQ ID NO: 4771 SEQUENCE: 4771 | moltype = | length = 000 |
| SEQ ID NO: 4772 SEQUENCE: 4772 | moltype = | length = 000 |
| SEQ ID NO: 4773 SEQUENCE: 4773 | moltype = | length = 000 |
| SEQ ID NO: 4774 SEQUENCE: 4774 | moltype = | length = 000 |
| SEQ ID NO: 4775 SEQUENCE: 4775 | moltype = | length = 000 |
| SEQ ID NO: 4776 SEQUENCE: 4776 | moltype = | length = 000 |
| SEQ ID NO: 4777 SEQUENCE: 4777 | moltype = | length = 000 |

SEQ ID NO: 4778    moltype =    length =
SEQUENCE: 4778
000

SEQ ID NO: 4779    moltype =    length =
SEQUENCE: 4779
000

SEQ ID NO: 4780    moltype =    length =
SEQUENCE: 4780
000

SEQ ID NO: 4781    moltype =    length =
SEQUENCE: 4781
000

SEQ ID NO: 4782    moltype =    length =
SEQUENCE: 4782
000

SEQ ID NO: 4783    moltype =    length =
SEQUENCE: 4783
000

SEQ ID NO: 4784    moltype =    length =
SEQUENCE: 4784
000

SEQ ID NO: 4785    moltype =    length =
SEQUENCE: 4785
000

SEQ ID NO: 4786    moltype =    length =
SEQUENCE: 4786
000

SEQ ID NO: 4787    moltype =    length =
SEQUENCE: 4787
000

SEQ ID NO: 4788    moltype =    length =
SEQUENCE: 4788
000

SEQ ID NO: 4789    moltype =    length =
SEQUENCE: 4789
000

SEQ ID NO: 4790    moltype =    length =
SEQUENCE: 4790
000

SEQ ID NO: 4791    moltype =    length =
SEQUENCE: 4791
000

SEQ ID NO: 4792    moltype =    length =
SEQUENCE: 4792
000

SEQ ID NO: 4793    moltype =    length =
SEQUENCE: 4793
000

SEQ ID NO: 4794    moltype =    length =
SEQUENCE: 4794
000

SEQ ID NO: 4795    moltype =    length =
SEQUENCE: 4795
000

SEQ ID NO: 4796    moltype =    length =
SEQUENCE: 4796
000

SEQ ID NO: 4797    moltype =    length =
SEQUENCE: 4797

000

SEQ ID NO: 4798          moltype =      length =
SEQUENCE: 4798
000

SEQ ID NO: 4799          moltype =      length =
SEQUENCE: 4799
000

SEQ ID NO: 4800          moltype =      length =
SEQUENCE: 4800
000

SEQ ID NO: 4801          moltype =      length =
SEQUENCE: 4801
000

SEQ ID NO: 4802          moltype =      length =
SEQUENCE: 4802
000

SEQ ID NO: 4803          moltype =      length =
SEQUENCE: 4803
000

SEQ ID NO: 4804          moltype =      length =
SEQUENCE: 4804
000

SEQ ID NO: 4805          moltype =      length =
SEQUENCE: 4805
000

SEQ ID NO: 4806          moltype =      length =
SEQUENCE: 4806
000

SEQ ID NO: 4807          moltype =      length =
SEQUENCE: 4807
000

SEQ ID NO: 4808          moltype =      length =
SEQUENCE: 4808
000

SEQ ID NO: 4809          moltype =      length =
SEQUENCE: 4809
000

SEQ ID NO: 4810          moltype =      length =
SEQUENCE: 4810
000

SEQ ID NO: 4811          moltype =      length =
SEQUENCE: 4811
000

SEQ ID NO: 4812          moltype =      length =
SEQUENCE: 4812
000

SEQ ID NO: 4813          moltype =      length =
SEQUENCE: 4813
000

SEQ ID NO: 4814          moltype =      length =
SEQUENCE: 4814
000

SEQ ID NO: 4815          moltype =      length =
SEQUENCE: 4815
000

SEQ ID NO: 4816          moltype =      length =
SEQUENCE: 4816
000

SEQ ID NO: 4817          moltype =      length =

-continued

SEQUENCE: 4817
000

SEQ ID NO: 4818          moltype =     length =
SEQUENCE: 4818
000

SEQ ID NO: 4819          moltype =     length =
SEQUENCE: 4819
000

SEQ ID NO: 4820          moltype =     length =
SEQUENCE: 4820
000

SEQ ID NO: 4821          moltype =     length =
SEQUENCE: 4821
000

SEQ ID NO: 4822          moltype =     length =
SEQUENCE: 4822
000

SEQ ID NO: 4823          moltype =     length =
SEQUENCE: 4823
000

SEQ ID NO: 4824          moltype =     length =
SEQUENCE: 4824
000

SEQ ID NO: 4825          moltype =     length =
SEQUENCE: 4825
000

SEQ ID NO: 4826          moltype =     length =
SEQUENCE: 4826
000

SEQ ID NO: 4827          moltype =     length =
SEQUENCE: 4827
000

SEQ ID NO: 4828          moltype =     length =
SEQUENCE: 4828
000

SEQ ID NO: 4829          moltype =     length =
SEQUENCE: 4829
000

SEQ ID NO: 4830          moltype =     length =
SEQUENCE: 4830
000

SEQ ID NO: 4831          moltype =     length =
SEQUENCE: 4831
000

SEQ ID NO: 4832          moltype =     length =
SEQUENCE: 4832
000

SEQ ID NO: 4833          moltype =     length =
SEQUENCE: 4833
000

SEQ ID NO: 4834          moltype =     length =
SEQUENCE: 4834
000

SEQ ID NO: 4835          moltype =     length =
SEQUENCE: 4835
000

SEQ ID NO: 4836          moltype =     length =
SEQUENCE: 4836
000

| | | |
|---|---|---|
| SEQ ID NO: 4837<br>SEQUENCE: 4837<br>000 | moltype = | length = |
| SEQ ID NO: 4838<br>SEQUENCE: 4838<br>000 | moltype = | length = |
| SEQ ID NO: 4839<br>SEQUENCE: 4839<br>000 | moltype = | length = |
| SEQ ID NO: 4840<br>SEQUENCE: 4840<br>000 | moltype = | length = |
| SEQ ID NO: 4841<br>SEQUENCE: 4841<br>000 | moltype = | length = |
| SEQ ID NO: 4842<br>SEQUENCE: 4842<br>000 | moltype = | length = |
| SEQ ID NO: 4843<br>SEQUENCE: 4843<br>000 | moltype = | length = |
| SEQ ID NO: 4844<br>SEQUENCE: 4844<br>000 | moltype = | length = |
| SEQ ID NO: 4845<br>SEQUENCE: 4845<br>000 | moltype = | length = |
| SEQ ID NO: 4846<br>SEQUENCE: 4846<br>000 | moltype = | length = |
| SEQ ID NO: 4847<br>SEQUENCE: 4847<br>000 | moltype = | length = |
| SEQ ID NO: 4848<br>SEQUENCE: 4848<br>000 | moltype = | length = |
| SEQ ID NO: 4849<br>SEQUENCE: 4849<br>000 | moltype = | length = |
| SEQ ID NO: 4850<br>SEQUENCE: 4850<br>000 | moltype = | length = |
| SEQ ID NO: 4851<br>SEQUENCE: 4851<br>000 | moltype = | length = |
| SEQ ID NO: 4852<br>SEQUENCE: 4852<br>000 | moltype = | length = |
| SEQ ID NO: 4853<br>SEQUENCE: 4853<br>000 | moltype = | length = |
| SEQ ID NO: 4854<br>SEQUENCE: 4854<br>000 | moltype = | length = |
| SEQ ID NO: 4855<br>SEQUENCE: 4855<br>000 | moltype = | length = |
| SEQ ID NO: 4856<br>SEQUENCE: 4856<br>000 | moltype = | length = |

| | | |
|---|---|---|
| SEQ ID NO: 4857<br>SEQUENCE: 4857<br>000 | moltype = | length = |
| SEQ ID NO: 4858<br>SEQUENCE: 4858<br>000 | moltype = | length = |
| SEQ ID NO: 4859<br>SEQUENCE: 4859<br>000 | moltype = | length = |
| SEQ ID NO: 4860<br>SEQUENCE: 4860<br>000 | moltype = | length = |
| SEQ ID NO: 4861<br>SEQUENCE: 4861<br>000 | moltype = | length = |
| SEQ ID NO: 4862<br>SEQUENCE: 4862<br>000 | moltype = | length = |
| SEQ ID NO: 4863<br>SEQUENCE: 4863<br>000 | moltype = | length = |
| SEQ ID NO: 4864<br>SEQUENCE: 4864<br>000 | moltype = | length = |
| SEQ ID NO: 4865<br>SEQUENCE: 4865<br>000 | moltype = | length = |
| SEQ ID NO: 4866<br>SEQUENCE: 4866<br>000 | moltype = | length = |
| SEQ ID NO: 4867<br>SEQUENCE: 4867<br>000 | moltype = | length = |
| SEQ ID NO: 4868<br>SEQUENCE: 4868<br>000 | moltype = | length = |
| SEQ ID NO: 4869<br>SEQUENCE: 4869<br>000 | moltype = | length = |
| SEQ ID NO: 4870<br>SEQUENCE: 4870<br>000 | moltype = | length = |
| SEQ ID NO: 4871<br>SEQUENCE: 4871<br>000 | moltype = | length = |
| SEQ ID NO: 4872<br>SEQUENCE: 4872<br>000 | moltype = | length = |
| SEQ ID NO: 4873<br>SEQUENCE: 4873<br>000 | moltype = | length = |
| SEQ ID NO: 4874<br>SEQUENCE: 4874<br>000 | moltype = | length = |
| SEQ ID NO: 4875<br>SEQUENCE: 4875<br>000 | moltype = | length = |
| SEQ ID NO: 4876<br>SEQUENCE: 4876 | moltype = | length = |

-continued

000

SEQ ID NO: 4877      moltype =     length =
SEQUENCE: 4877
000

SEQ ID NO: 4878      moltype =     length =
SEQUENCE: 4878
000

SEQ ID NO: 4879      moltype =     length =
SEQUENCE: 4879
000

SEQ ID NO: 4880      moltype =     length =
SEQUENCE: 4880
000

SEQ ID NO: 4881      moltype =     length =
SEQUENCE: 4881
000

SEQ ID NO: 4882      moltype =     length =
SEQUENCE: 4882
000

SEQ ID NO: 4883      moltype =     length =
SEQUENCE: 4883
000

SEQ ID NO: 4884      moltype =     length =
SEQUENCE: 4884
000

SEQ ID NO: 4885      moltype =     length =
SEQUENCE: 4885
000

SEQ ID NO: 4886      moltype =     length =
SEQUENCE: 4886
000

SEQ ID NO: 4887      moltype =     length =
SEQUENCE: 4887
000

SEQ ID NO: 4888      moltype =     length =
SEQUENCE: 4888
000

SEQ ID NO: 4889      moltype =     length =
SEQUENCE: 4889
000

SEQ ID NO: 4890      moltype =     length =
SEQUENCE: 4890
000

SEQ ID NO: 4891      moltype =     length =
SEQUENCE: 4891
000

SEQ ID NO: 4892      moltype =     length =
SEQUENCE: 4892
000

SEQ ID NO: 4893      moltype =     length =
SEQUENCE: 4893
000

SEQ ID NO: 4894      moltype =     length =
SEQUENCE: 4894
000

SEQ ID NO: 4895      moltype =     length =
SEQUENCE: 4895
000

SEQ ID NO: 4896      moltype =     length =

SEQUENCE: 4896
000

SEQ ID NO: 4897        moltype =    length =
SEQUENCE: 4897
000

SEQ ID NO: 4898        moltype =    length =
SEQUENCE: 4898
000

SEQ ID NO: 4899        moltype =    length =
SEQUENCE: 4899
000

SEQ ID NO: 4900        moltype =    length =
SEQUENCE: 4900
000

SEQ ID NO: 4901        moltype =    length =
SEQUENCE: 4901
000

SEQ ID NO: 4902        moltype =    length =
SEQUENCE: 4902
000

SEQ ID NO: 4903        moltype =    length =
SEQUENCE: 4903
000

SEQ ID NO: 4904        moltype =    length =
SEQUENCE: 4904
000

SEQ ID NO: 4905        moltype =    length =
SEQUENCE: 4905
000

SEQ ID NO: 4906        moltype =    length =
SEQUENCE: 4906
000

SEQ ID NO: 4907        moltype =    length =
SEQUENCE: 4907
000

SEQ ID NO: 4908        moltype =    length =
SEQUENCE: 4908
000

SEQ ID NO: 4909        moltype =    length =
SEQUENCE: 4909
000

SEQ ID NO: 4910        moltype =    length =
SEQUENCE: 4910
000

SEQ ID NO: 4911        moltype =    length =
SEQUENCE: 4911
000

SEQ ID NO: 4912        moltype =    length =
SEQUENCE: 4912
000

SEQ ID NO: 4913        moltype =    length =
SEQUENCE: 4913
000

SEQ ID NO: 4914        moltype =    length =
SEQUENCE: 4914
000

SEQ ID NO: 4915        moltype =    length =
SEQUENCE: 4915
000

| | | |
|---|---|---|
| SEQ ID NO: 4916<br>SEQUENCE: 4916 | moltype = | length = 000 |
| SEQ ID NO: 4917<br>SEQUENCE: 4917 | moltype = | length = 000 |
| SEQ ID NO: 4918<br>SEQUENCE: 4918 | moltype = | length = 000 |
| SEQ ID NO: 4919<br>SEQUENCE: 4919 | moltype = | length = 000 |
| SEQ ID NO: 4920<br>SEQUENCE: 4920 | moltype = | length = 000 |
| SEQ ID NO: 4921<br>SEQUENCE: 4921 | moltype = | length = 000 |
| SEQ ID NO: 4922<br>SEQUENCE: 4922 | moltype = | length = 000 |
| SEQ ID NO: 4923<br>SEQUENCE: 4923 | moltype = | length = 000 |
| SEQ ID NO: 4924<br>SEQUENCE: 4924 | moltype = | length = 000 |
| SEQ ID NO: 4925<br>SEQUENCE: 4925 | moltype = | length = 000 |
| SEQ ID NO: 4926<br>SEQUENCE: 4926 | moltype = | length = 000 |
| SEQ ID NO: 4927<br>SEQUENCE: 4927 | moltype = | length = 000 |
| SEQ ID NO: 4928<br>SEQUENCE: 4928 | moltype = | length = 000 |
| SEQ ID NO: 4929<br>SEQUENCE: 4929 | moltype = | length = 000 |
| SEQ ID NO: 4930<br>SEQUENCE: 4930 | moltype = | length = 000 |
| SEQ ID NO: 4931<br>SEQUENCE: 4931 | moltype = | length = 000 |
| SEQ ID NO: 4932<br>SEQUENCE: 4932 | moltype = | length = 000 |
| SEQ ID NO: 4933<br>SEQUENCE: 4933 | moltype = | length = 000 |
| SEQ ID NO: 4934<br>SEQUENCE: 4934 | moltype = | length = 000 |
| SEQ ID NO: 4935<br>SEQUENCE: 4935 | moltype = | length = 000 |

SEQ ID NO: 4936    moltype =    length =
SEQUENCE: 4936
000

SEQ ID NO: 4937    moltype =    length =
SEQUENCE: 4937
000

SEQ ID NO: 4938    moltype =    length =
SEQUENCE: 4938
000

SEQ ID NO: 4939    moltype =    length =
SEQUENCE: 4939
000

SEQ ID NO: 4940    moltype =    length =
SEQUENCE: 4940
000

SEQ ID NO: 4941    moltype =    length =
SEQUENCE: 4941
000

SEQ ID NO: 4942    moltype =    length =
SEQUENCE: 4942
000

SEQ ID NO: 4943    moltype =    length =
SEQUENCE: 4943
000

SEQ ID NO: 4944    moltype =    length =
SEQUENCE: 4944
000

SEQ ID NO: 4945    moltype =    length =
SEQUENCE: 4945
000

SEQ ID NO: 4946    moltype =    length =
SEQUENCE: 4946
000

SEQ ID NO: 4947    moltype =    length =
SEQUENCE: 4947
000

SEQ ID NO: 4948    moltype =    length =
SEQUENCE: 4948
000

SEQ ID NO: 4949    moltype =    length =
SEQUENCE: 4949
000

SEQ ID NO: 4950    moltype =    length =
SEQUENCE: 4950
000

SEQ ID NO: 4951    moltype =    length =
SEQUENCE: 4951
000

SEQ ID NO: 4952    moltype =    length =
SEQUENCE: 4952
000

SEQ ID NO: 4953    moltype =    length =
SEQUENCE: 4953
000

SEQ ID NO: 4954    moltype =    length =
SEQUENCE: 4954
000

SEQ ID NO: 4955    moltype =    length =
SEQUENCE: 4955

000

SEQ ID NO: 4956        moltype =     length =
SEQUENCE: 4956
000

SEQ ID NO: 4957        moltype =     length =
SEQUENCE: 4957
000

SEQ ID NO: 4958        moltype =     length =
SEQUENCE: 4958
000

SEQ ID NO: 4959        moltype =     length =
SEQUENCE: 4959
000

SEQ ID NO: 4960        moltype =     length =
SEQUENCE: 4960
000

SEQ ID NO: 4961        moltype =     length =
SEQUENCE: 4961
000

SEQ ID NO: 4962        moltype =     length =
SEQUENCE: 4962
000

SEQ ID NO: 4963        moltype =     length =
SEQUENCE: 4963
000

SEQ ID NO: 4964        moltype =     length =
SEQUENCE: 4964
000

SEQ ID NO: 4965        moltype =     length =
SEQUENCE: 4965
000

SEQ ID NO: 4966        moltype =     length =
SEQUENCE: 4966
000

SEQ ID NO: 4967        moltype =     length =
SEQUENCE: 4967
000

SEQ ID NO: 4968        moltype =     length =
SEQUENCE: 4968
000

SEQ ID NO: 4969        moltype =     length =
SEQUENCE: 4969
000

SEQ ID NO: 4970        moltype =     length =
SEQUENCE: 4970
000

SEQ ID NO: 4971        moltype =     length =
SEQUENCE: 4971
000

SEQ ID NO: 4972        moltype =     length =
SEQUENCE: 4972
000

SEQ ID NO: 4973        moltype =     length =
SEQUENCE: 4973
000

SEQ ID NO: 4974        moltype =     length =
SEQUENCE: 4974
000

SEQ ID NO: 4975        moltype =     length =

-continued

| | | |
|---|---|---|
| SEQUENCE: 4975 000 | | |
| SEQ ID NO: 4976 SEQUENCE: 4976 000 | moltype = | length = |
| SEQ ID NO: 4977 SEQUENCE: 4977 000 | moltype = | length = |
| SEQ ID NO: 4978 SEQUENCE: 4978 000 | moltype = | length = |
| SEQ ID NO: 4979 SEQUENCE: 4979 000 | moltype = | length = |
| SEQ ID NO: 4980 SEQUENCE: 4980 000 | moltype = | length = |
| SEQ ID NO: 4981 SEQUENCE: 4981 000 | moltype = | length = |
| SEQ ID NO: 4982 SEQUENCE: 4982 000 | moltype = | length = |
| SEQ ID NO: 4983 SEQUENCE: 4983 000 | moltype = | length = |
| SEQ ID NO: 4984 SEQUENCE: 4984 000 | moltype = | length = |
| SEQ ID NO: 4985 SEQUENCE: 4985 000 | moltype = | length = |
| SEQ ID NO: 4986 SEQUENCE: 4986 000 | moltype = | length = |
| SEQ ID NO: 4987 SEQUENCE: 4987 000 | moltype = | length = |
| SEQ ID NO: 4988 SEQUENCE: 4988 000 | moltype = | length = |
| SEQ ID NO: 4989 SEQUENCE: 4989 000 | moltype = | length = |
| SEQ ID NO: 4990 SEQUENCE: 4990 000 | moltype = | length = |
| SEQ ID NO: 4991 SEQUENCE: 4991 000 | moltype = | length = |
| SEQ ID NO: 4992 SEQUENCE: 4992 000 | moltype = | length = |
| SEQ ID NO: 4993 SEQUENCE: 4993 000 | moltype = | length = |
| SEQ ID NO: 4994 SEQUENCE: 4994 000 | moltype = | length = |

| | | |
|---|---|---|
| SEQ ID NO: 4995<br>SEQUENCE: 4995<br>000 | moltype = | length = |
| SEQ ID NO: 4996<br>SEQUENCE: 4996<br>000 | moltype = | length = |
| SEQ ID NO: 4997<br>SEQUENCE: 4997<br>000 | moltype = | length = |
| SEQ ID NO: 4998<br>SEQUENCE: 4998<br>000 | moltype = | length = |
| SEQ ID NO: 4999<br>SEQUENCE: 4999<br>000 | moltype = | length = |
| SEQ ID NO: 5000<br>SEQUENCE: 5000<br>000 | moltype = | length = |
| SEQ ID NO: 5001<br>SEQUENCE: 5001<br>000 | moltype = | length = |
| SEQ ID NO: 5002<br>SEQUENCE: 5002<br>000 | moltype = | length = |
| SEQ ID NO: 5003<br>SEQUENCE: 5003<br>000 | moltype = | length = |
| SEQ ID NO: 5004<br>SEQUENCE: 5004<br>000 | moltype = | length = |
| SEQ ID NO: 5005<br>SEQUENCE: 5005<br>000 | moltype = | length = |
| SEQ ID NO: 5006<br>SEQUENCE: 5006<br>000 | moltype = | length = |
| SEQ ID NO: 5007<br>SEQUENCE: 5007<br>000 | moltype = | length = |
| SEQ ID NO: 5008<br>SEQUENCE: 5008<br>000 | moltype = | length = |
| SEQ ID NO: 5009<br>SEQUENCE: 5009<br>000 | moltype = | length = |
| SEQ ID NO: 5010<br>SEQUENCE: 5010<br>000 | moltype = | length = |
| SEQ ID NO: 5011<br>SEQUENCE: 5011<br>000 | moltype = | length = |
| SEQ ID NO: 5012<br>SEQUENCE: 5012<br>000 | moltype = | length = |
| SEQ ID NO: 5013<br>SEQUENCE: 5013<br>000 | moltype = | length = |
| SEQ ID NO: 5014<br>SEQUENCE: 5014<br>000 | moltype = | length = |

SEQ ID NO: 5015        moltype =    length =
SEQUENCE: 5015
000

SEQ ID NO: 5016        moltype =    length =
SEQUENCE: 5016
000

SEQ ID NO: 5017        moltype =    length =
SEQUENCE: 5017
000

SEQ ID NO: 5018        moltype =    length =
SEQUENCE: 5018
000

SEQ ID NO: 5019        moltype =    length =
SEQUENCE: 5019
000

SEQ ID NO: 5020        moltype =    length =
SEQUENCE: 5020
000

SEQ ID NO: 5021        moltype =    length =
SEQUENCE: 5021
000

SEQ ID NO: 5022        moltype =    length =
SEQUENCE: 5022
000

SEQ ID NO: 5023        moltype =    length =
SEQUENCE: 5023
000

SEQ ID NO: 5024        moltype =    length =
SEQUENCE: 5024
000

SEQ ID NO: 5025        moltype =    length =
SEQUENCE: 5025
000

SEQ ID NO: 5026        moltype =    length =
SEQUENCE: 5026
000

SEQ ID NO: 5027        moltype =    length =
SEQUENCE: 5027
000

SEQ ID NO: 5028        moltype =    length =
SEQUENCE: 5028
000

SEQ ID NO: 5029        moltype =    length =
SEQUENCE: 5029
000

SEQ ID NO: 5030        moltype =    length =
SEQUENCE: 5030
000

SEQ ID NO: 5031        moltype =    length =
SEQUENCE: 5031
000

SEQ ID NO: 5032        moltype =    length =
SEQUENCE: 5032
000

SEQ ID NO: 5033        moltype =    length =
SEQUENCE: 5033
000

SEQ ID NO: 5034        moltype =    length =
SEQUENCE: 5034

000

SEQ ID NO: 5035          moltype =     length =
SEQUENCE: 5035
000

SEQ ID NO: 5036          moltype =     length =
SEQUENCE: 5036
000

SEQ ID NO: 5037          moltype =     length =
SEQUENCE: 5037
000

SEQ ID NO: 5038          moltype =     length =
SEQUENCE: 5038
000

SEQ ID NO: 5039          moltype =     length =
SEQUENCE: 5039
000

SEQ ID NO: 5040          moltype =     length =
SEQUENCE: 5040
000

SEQ ID NO: 5041          moltype =     length =
SEQUENCE: 5041
000

SEQ ID NO: 5042          moltype =     length =
SEQUENCE: 5042
000

SEQ ID NO: 5043          moltype =     length =
SEQUENCE: 5043
000

SEQ ID NO: 5044          moltype =     length =
SEQUENCE: 5044
000

SEQ ID NO: 5045          moltype =     length =
SEQUENCE: 5045
000

SEQ ID NO: 5046          moltype =     length =
SEQUENCE: 5046
000

SEQ ID NO: 5047          moltype =     length =
SEQUENCE: 5047
000

SEQ ID NO: 5048          moltype =     length =
SEQUENCE: 5048
000

SEQ ID NO: 5049          moltype =     length =
SEQUENCE: 5049
000

SEQ ID NO: 5050          moltype =     length =
SEQUENCE: 5050
000

SEQ ID NO: 5051          moltype =     length =
SEQUENCE: 5051
000

SEQ ID NO: 5052          moltype =     length =
SEQUENCE: 5052
000

SEQ ID NO: 5053          moltype =     length =
SEQUENCE: 5053
000

SEQ ID NO: 5054          moltype =     length =

| | | |
|---|---|---|
| SEQUENCE: 5054 000 | | |
| SEQ ID NO: 5055 SEQUENCE: 5055 000 | moltype = | length = |
| SEQ ID NO: 5056 SEQUENCE: 5056 000 | moltype = | length = |
| SEQ ID NO: 5057 SEQUENCE: 5057 000 | moltype = | length = |
| SEQ ID NO: 5058 SEQUENCE: 5058 000 | moltype = | length = |
| SEQ ID NO: 5059 SEQUENCE: 5059 000 | moltype = | length = |
| SEQ ID NO: 5060 SEQUENCE: 5060 000 | moltype = | length = |
| SEQ ID NO: 5061 SEQUENCE: 5061 000 | moltype = | length = |
| SEQ ID NO: 5062 SEQUENCE: 5062 000 | moltype = | length = |
| SEQ ID NO: 5063 SEQUENCE: 5063 000 | moltype = | length = |
| SEQ ID NO: 5064 SEQUENCE: 5064 000 | moltype = | length = |
| SEQ ID NO: 5065 SEQUENCE: 5065 000 | moltype = | length = |
| SEQ ID NO: 5066 SEQUENCE: 5066 000 | moltype = | length = |
| SEQ ID NO: 5067 SEQUENCE: 5067 000 | moltype = | length = |
| SEQ ID NO: 5068 SEQUENCE: 5068 000 | moltype = | length = |
| SEQ ID NO: 5069 SEQUENCE: 5069 000 | moltype = | length = |
| SEQ ID NO: 5070 SEQUENCE: 5070 000 | moltype = | length = |
| SEQ ID NO: 5071 SEQUENCE: 5071 000 | moltype = | length = |
| SEQ ID NO: 5072 SEQUENCE: 5072 000 | moltype = | length = |
| SEQ ID NO: 5073 SEQUENCE: 5073 000 | moltype = | length = |

| | | |
|---|---|---|
| SEQ ID NO: 5074 SEQUENCE: 5074 | moltype = | length = 000 |
| SEQ ID NO: 5075 SEQUENCE: 5075 | moltype = | length = 000 |
| SEQ ID NO: 5076 SEQUENCE: 5076 | moltype = | length = 000 |
| SEQ ID NO: 5077 SEQUENCE: 5077 | moltype = | length = 000 |
| SEQ ID NO: 5078 SEQUENCE: 5078 | moltype = | length = 000 |
| SEQ ID NO: 5079 SEQUENCE: 5079 | moltype = | length = 000 |
| SEQ ID NO: 5080 SEQUENCE: 5080 | moltype = | length = 000 |
| SEQ ID NO: 5081 SEQUENCE: 5081 | moltype = | length = 000 |
| SEQ ID NO: 5082 SEQUENCE: 5082 | moltype = | length = 000 |
| SEQ ID NO: 5083 SEQUENCE: 5083 | moltype = | length = 000 |
| SEQ ID NO: 5084 SEQUENCE: 5084 | moltype = | length = 000 |
| SEQ ID NO: 5085 SEQUENCE: 5085 | moltype = | length = 000 |
| SEQ ID NO: 5086 SEQUENCE: 5086 | moltype = | length = 000 |
| SEQ ID NO: 5087 SEQUENCE: 5087 | moltype = | length = 000 |
| SEQ ID NO: 5088 SEQUENCE: 5088 | moltype = | length = 000 |
| SEQ ID NO: 5089 SEQUENCE: 5089 | moltype = | length = 000 |
| SEQ ID NO: 5090 SEQUENCE: 5090 | moltype = | length = 000 |
| SEQ ID NO: 5091 SEQUENCE: 5091 | moltype = | length = 000 |
| SEQ ID NO: 5092 SEQUENCE: 5092 | moltype = | length = 000 |
| SEQ ID NO: 5093 SEQUENCE: 5093 | moltype = | length = 000 |

| SEQ ID NO: 5094 | moltype = | length = |
|---|---|---|
| SEQUENCE: 5094 | | |
| 000 | | |

| SEQ ID NO: 5095 | moltype = | length = |
|---|---|---|
| SEQUENCE: 5095 | | |
| 000 | | |

| SEQ ID NO: 5096 | moltype = | length = |
|---|---|---|
| SEQUENCE: 5096 | | |
| 000 | | |

| SEQ ID NO: 5097 | moltype = | length = |
|---|---|---|
| SEQUENCE: 5097 | | |
| 000 | | |

| SEQ ID NO: 5098 | moltype = | length = |
|---|---|---|
| SEQUENCE: 5098 | | |
| 000 | | |

| SEQ ID NO: 5099 | moltype = | length = |
|---|---|---|
| SEQUENCE: 5099 | | |
| 000 | | |

| SEQ ID NO: 5100 | moltype = | length = |
|---|---|---|
| SEQUENCE: 5100 | | |
| 000 | | |

| SEQ ID NO: 5101 | moltype = | length = |
|---|---|---|
| SEQUENCE: 5101 | | |
| 000 | | |

| SEQ ID NO: 5102 | moltype = | length = |
|---|---|---|
| SEQUENCE: 5102 | | |
| 000 | | |

| SEQ ID NO: 5103 | moltype = | length = |
|---|---|---|
| SEQUENCE: 5103 | | |
| 000 | | |

| SEQ ID NO: 5104 | moltype = | length = |
|---|---|---|
| SEQUENCE: 5104 | | |
| 000 | | |

| SEQ ID NO: 5105 | moltype = | length = |
|---|---|---|
| SEQUENCE: 5105 | | |
| 000 | | |

| SEQ ID NO: 5106 | moltype = | length = |
|---|---|---|
| SEQUENCE: 5106 | | |
| 000 | | |

| SEQ ID NO: 5107 | moltype = | length = |
|---|---|---|
| SEQUENCE: 5107 | | |
| 000 | | |

| SEQ ID NO: 5108 | moltype = | length = |
|---|---|---|
| SEQUENCE: 5108 | | |
| 000 | | |

| SEQ ID NO: 5109 | moltype = | length = |
|---|---|---|
| SEQUENCE: 5109 | | |
| 000 | | |

| SEQ ID NO: 5110 | moltype = | length = |
|---|---|---|
| SEQUENCE: 5110 | | |
| 000 | | |

| SEQ ID NO: 5111 | moltype = | length = |
|---|---|---|
| SEQUENCE: 5111 | | |
| 000 | | |

| SEQ ID NO: 5112 | moltype = | length = |
|---|---|---|
| SEQUENCE: 5112 | | |
| 000 | | |

| SEQ ID NO: 5113 | moltype = | length = |
|---|---|---|
| SEQUENCE: 5113 | | |

000

SEQ ID NO: 5114          moltype =     length =
SEQUENCE: 5114
000

SEQ ID NO: 5115          moltype =     length =
SEQUENCE: 5115
000

SEQ ID NO: 5116          moltype =     length =
SEQUENCE: 5116
000

SEQ ID NO: 5117          moltype =     length =
SEQUENCE: 5117
000

SEQ ID NO: 5118          moltype =     length =
SEQUENCE: 5118
000

SEQ ID NO: 5119          moltype =     length =
SEQUENCE: 5119
000

SEQ ID NO: 5120          moltype =     length =
SEQUENCE: 5120
000

SEQ ID NO: 5121          moltype =     length =
SEQUENCE: 5121
000

SEQ ID NO: 5122          moltype =     length =
SEQUENCE: 5122
000

SEQ ID NO: 5123          moltype =     length =
SEQUENCE: 5123
000

SEQ ID NO: 5124          moltype =     length =
SEQUENCE: 5124
000

SEQ ID NO: 5125          moltype =     length =
SEQUENCE: 5125
000

SEQ ID NO: 5126          moltype =     length =
SEQUENCE: 5126
000

SEQ ID NO: 5127          moltype =     length =
SEQUENCE: 5127
000

SEQ ID NO: 5128          moltype =     length =
SEQUENCE: 5128
000

SEQ ID NO: 5129          moltype =     length =
SEQUENCE: 5129
000

SEQ ID NO: 5130          moltype =     length =
SEQUENCE: 5130
000

SEQ ID NO: 5131          moltype =     length =
SEQUENCE: 5131
000

SEQ ID NO: 5132          moltype =     length =
SEQUENCE: 5132
000

SEQ ID NO: 5133          moltype =     length =

```
SEQUENCE: 5133
000

SEQ ID NO: 5134          moltype =     length =
SEQUENCE: 5134
000

SEQ ID NO: 5135          moltype =     length =
SEQUENCE: 5135
000

SEQ ID NO: 5136          moltype =     length =
SEQUENCE: 5136
000

SEQ ID NO: 5137          moltype =     length =
SEQUENCE: 5137
000

SEQ ID NO: 5138          moltype =     length =
SEQUENCE: 5138
000

SEQ ID NO: 5139          moltype =     length =
SEQUENCE: 5139
000

SEQ ID NO: 5140          moltype =     length =
SEQUENCE: 5140
000

SEQ ID NO: 5141          moltype =     length =
SEQUENCE: 5141
000

SEQ ID NO: 5142          moltype =     length =
SEQUENCE: 5142
000

SEQ ID NO: 5143          moltype =     length =
SEQUENCE: 5143
000

SEQ ID NO: 5144          moltype =     length =
SEQUENCE: 5144
000

SEQ ID NO: 5145          moltype =     length =
SEQUENCE: 5145
000

SEQ ID NO: 5146          moltype =     length =
SEQUENCE: 5146
000

SEQ ID NO: 5147          moltype =     length =
SEQUENCE: 5147
000

SEQ ID NO: 5148          moltype =     length =
SEQUENCE: 5148
000

SEQ ID NO: 5149          moltype =     length =
SEQUENCE: 5149
000

SEQ ID NO: 5150          moltype =     length =
SEQUENCE: 5150
000

SEQ ID NO: 5151          moltype =     length =
SEQUENCE: 5151
000

SEQ ID NO: 5152          moltype =     length =
SEQUENCE: 5152
000
```

| | | |
|---|---|---|
| SEQ ID NO: 5153<br>SEQUENCE: 5153<br>000 | moltype = | length = |
| SEQ ID NO: 5154<br>SEQUENCE: 5154<br>000 | moltype = | length = |
| SEQ ID NO: 5155<br>SEQUENCE: 5155<br>000 | moltype = | length = |
| SEQ ID NO: 5156<br>SEQUENCE: 5156<br>000 | moltype = | length = |
| SEQ ID NO: 5157<br>SEQUENCE: 5157<br>000 | moltype = | length = |
| SEQ ID NO: 5158<br>SEQUENCE: 5158<br>000 | moltype = | length = |
| SEQ ID NO: 5159<br>SEQUENCE: 5159<br>000 | moltype = | length = |
| SEQ ID NO: 5160<br>SEQUENCE: 5160<br>000 | moltype = | length = |
| SEQ ID NO: 5161<br>FEATURE<br>source<br><br>SEQUENCE: 5161<br>ggaggaggag gaagt | moltype = DNA   length = 15<br>Location/Qualifiers<br>1..15<br>mol_type = other DNA<br>organism = synthetic construct | 15 |
| SEQ ID NO: 5162<br>FEATURE<br>source<br><br>SEQUENCE: 5162<br>ggaggtggag gttct | moltype = DNA   length = 15<br>Location/Qualifiers<br>1..15<br>mol_type = other DNA<br>organism = synthetic construct | 15 |
| SEQ ID NO: 5163<br>SEQUENCE: 5163<br>000 | moltype = | length = |
| SEQ ID NO: 5164<br>SEQUENCE: 5164<br>000 | moltype = | length = |
| SEQ ID NO: 5165<br>SEQUENCE: 5165<br>000 | moltype = | length = |
| SEQ ID NO: 5166<br>SEQUENCE: 5166<br>000 | moltype = | length = |
| SEQ ID NO: 5167<br>SEQUENCE: 5167<br>000 | moltype = | length = |
| SEQ ID NO: 5168<br>SEQUENCE: 5168<br>000 | moltype = | length = |
| SEQ ID NO: 5169<br>SEQUENCE: 5169<br>000 | moltype = | length = |
| SEQ ID NO: 5170<br>SEQUENCE: 5170<br>000 | moltype = | length = |

| | | |
|---|---|---|
| SEQ ID NO: 5171 SEQUENCE: 5171 000 | moltype = | length = |
| SEQ ID NO: 5172 SEQUENCE: 5172 000 | moltype = | length = |
| SEQ ID NO: 5173 SEQUENCE: 5173 000 | moltype = | length = |
| SEQ ID NO: 5174 SEQUENCE: 5174 000 | moltype = | length = |
| SEQ ID NO: 5175 SEQUENCE: 5175 000 | moltype = | length = |
| SEQ ID NO: 5176 SEQUENCE: 5176 000 | moltype = | length = |
| SEQ ID NO: 5177 SEQUENCE: 5177 000 | moltype = | length = |
| SEQ ID NO: 5178 SEQUENCE: 5178 000 | moltype = | length = |
| SEQ ID NO: 5179 SEQUENCE: 5179 000 | moltype = | length = |
| SEQ ID NO: 5180 SEQUENCE: 5180 000 | moltype = | length = |
| SEQ ID NO: 5181 SEQUENCE: 5181 000 | moltype = | length = |
| SEQ ID NO: 5182 SEQUENCE: 5182 000 | moltype = | length = |
| SEQ ID NO: 5183 SEQUENCE: 5183 000 | moltype = | length = |
| SEQ ID NO: 5184 SEQUENCE: 5184 000 | moltype = | length = |
| SEQ ID NO: 5185 SEQUENCE: 5185 000 | moltype = | length = |
| SEQ ID NO: 5186 SEQUENCE: 5186 000 | moltype = | length = |
| SEQ ID NO: 5187 SEQUENCE: 5187 000 | moltype = | length = |
| SEQ ID NO: 5188 SEQUENCE: 5188 000 | moltype = | length = |
| SEQ ID NO: 5189 SEQUENCE: 5189 000 | moltype = | length = |
| SEQ ID NO: 5190 SEQUENCE: 5190 | moltype = | length = |

000

SEQ ID NO: 5191      moltype =     length =
SEQUENCE: 5191
000

SEQ ID NO: 5192      moltype =     length =
SEQUENCE: 5192
000

SEQ ID NO: 5193      moltype =     length =
SEQUENCE: 5193
000

SEQ ID NO: 5194      moltype =     length =
SEQUENCE: 5194
000

SEQ ID NO: 5195      moltype =     length =
SEQUENCE: 5195
000

SEQ ID NO: 5196      moltype =     length =
SEQUENCE: 5196
000

SEQ ID NO: 5197      moltype =     length =
SEQUENCE: 5197
000

SEQ ID NO: 5198      moltype =     length =
SEQUENCE: 5198
000

SEQ ID NO: 5199      moltype =     length =
SEQUENCE: 5199
000

SEQ ID NO: 5200      moltype =     length =
SEQUENCE: 5200
000

SEQ ID NO: 5201      moltype =     length =
SEQUENCE: 5201
000

SEQ ID NO: 5202      moltype =     length =
SEQUENCE: 5202
000

SEQ ID NO: 5203      moltype =     length =
SEQUENCE: 5203
000

SEQ ID NO: 5204      moltype =     length =
SEQUENCE: 5204
000

SEQ ID NO: 5205      moltype =     length =
SEQUENCE: 5205
000

SEQ ID NO: 5206      moltype =     length =
SEQUENCE: 5206
000

SEQ ID NO: 5207      moltype =     length =
SEQUENCE: 5207
000

SEQ ID NO: 5208      moltype =     length =
SEQUENCE: 5208
000

SEQ ID NO: 5209      moltype =     length =
SEQUENCE: 5209
000

SEQ ID NO: 5210      moltype =     length =

```
SEQUENCE: 5210
000

SEQ ID NO: 5211          moltype =    length =
SEQUENCE: 5211
000

SEQ ID NO: 5212          moltype =    length =
SEQUENCE: 5212
000

SEQ ID NO: 5213          moltype =    length =
SEQUENCE: 5213
000

SEQ ID NO: 5214          moltype =    length =
SEQUENCE: 5214
000

SEQ ID NO: 5215          moltype =    length =
SEQUENCE: 5215
000

SEQ ID NO: 5216          moltype =    length =
SEQUENCE: 5216
000

SEQ ID NO: 5217          moltype =    length =
SEQUENCE: 5217
000

SEQ ID NO: 5218          moltype =    length =
SEQUENCE: 5218
000

SEQ ID NO: 5219          moltype =    length =
SEQUENCE: 5219
000

SEQ ID NO: 5220          moltype =    length =
SEQUENCE: 5220
000

SEQ ID NO: 5221          moltype =    length =
SEQUENCE: 5221
000

SEQ ID NO: 5222          moltype =    length =
SEQUENCE: 5222
000

SEQ ID NO: 5223          moltype =    length =
SEQUENCE: 5223
000

SEQ ID NO: 5224          moltype =    length =
SEQUENCE: 5224
000

SEQ ID NO: 5225          moltype =    length =
SEQUENCE: 5225
000

SEQ ID NO: 5226          moltype =    length =
SEQUENCE: 5226
000

SEQ ID NO: 5227          moltype =    length =
SEQUENCE: 5227
000

SEQ ID NO: 5228          moltype =    length =
SEQUENCE: 5228
000

SEQ ID NO: 5229          moltype =    length =
SEQUENCE: 5229
000
```

| | | |
|---|---|---|
| SEQ ID NO: 5230 SEQUENCE: 5230 | moltype = | length = 000 |
| SEQ ID NO: 5231 SEQUENCE: 5231 | moltype = | length = 000 |
| SEQ ID NO: 5232 SEQUENCE: 5232 | moltype = | length = 000 |
| SEQ ID NO: 5233 SEQUENCE: 5233 | moltype = | length = 000 |
| SEQ ID NO: 5234 SEQUENCE: 5234 | moltype = | length = 000 |
| SEQ ID NO: 5235 SEQUENCE: 5235 | moltype = | length = 000 |
| SEQ ID NO: 5236 SEQUENCE: 5236 | moltype = | length = 000 |
| SEQ ID NO: 5237 SEQUENCE: 5237 | moltype = | length = 000 |
| SEQ ID NO: 5238 SEQUENCE: 5238 | moltype = | length = 000 |
| SEQ ID NO: 5239 SEQUENCE: 5239 | moltype = | length = 000 |
| SEQ ID NO: 5240 SEQUENCE: 5240 | moltype = | length = 000 |
| SEQ ID NO: 5241 SEQUENCE: 5241 | moltype = | length = 000 |
| SEQ ID NO: 5242 SEQUENCE: 5242 | moltype = | length = 000 |
| SEQ ID NO: 5243 SEQUENCE: 5243 | moltype = | length = 000 |
| SEQ ID NO: 5244 SEQUENCE: 5244 | moltype = | length = 000 |
| SEQ ID NO: 5245 SEQUENCE: 5245 | moltype = | length = 000 |
| SEQ ID NO: 5246 SEQUENCE: 5246 | moltype = | length = 000 |
| SEQ ID NO: 5247 SEQUENCE: 5247 | moltype = | length = 000 |
| SEQ ID NO: 5248 SEQUENCE: 5248 | moltype = | length = 000 |
| SEQ ID NO: 5249 SEQUENCE: 5249 | moltype = | length = 000 |

| | | |
|---|---|---|
| SEQ ID NO: 5250 SEQUENCE: 5250 | moltype = | length = 000 |
| SEQ ID NO: 5251 SEQUENCE: 5251 | moltype = | length = 000 |
| SEQ ID NO: 5252 SEQUENCE: 5252 | moltype = | length = 000 |
| SEQ ID NO: 5253 SEQUENCE: 5253 | moltype = | length = 000 |
| SEQ ID NO: 5254 SEQUENCE: 5254 | moltype = | length = 000 |
| SEQ ID NO: 5255 SEQUENCE: 5255 | moltype = | length = 000 |
| SEQ ID NO: 5256 SEQUENCE: 5256 | moltype = | length = 000 |
| SEQ ID NO: 5257 SEQUENCE: 5257 | moltype = | length = 000 |
| SEQ ID NO: 5258 SEQUENCE: 5258 | moltype = | length = 000 |
| SEQ ID NO: 5259 SEQUENCE: 5259 | moltype = | length = 000 |
| SEQ ID NO: 5260 SEQUENCE: 5260 | moltype = | length = 000 |
| SEQ ID NO: 5261 SEQUENCE: 5261 | moltype = | length = 000 |
| SEQ ID NO: 5262 SEQUENCE: 5262 | moltype = | length = 000 |
| SEQ ID NO: 5263 SEQUENCE: 5263 | moltype = | length = 000 |
| SEQ ID NO: 5264 SEQUENCE: 5264 | moltype = | length = 000 |
| SEQ ID NO: 5265 SEQUENCE: 5265 | moltype = | length = 000 |
| SEQ ID NO: 5266 SEQUENCE: 5266 | moltype = | length = 000 |
| SEQ ID NO: 5267 SEQUENCE: 5267 | moltype = | length = 000 |
| SEQ ID NO: 5268 SEQUENCE: 5268 | moltype = | length = 000 |
| SEQ ID NO: 5269 SEQUENCE: 5269 | moltype = | length = |

000

SEQ ID NO: 5270      moltype =    length =
SEQUENCE: 5270
000

SEQ ID NO: 5271      moltype =    length =
SEQUENCE: 5271
000

SEQ ID NO: 5272      moltype =    length =
SEQUENCE: 5272
000

SEQ ID NO: 5273      moltype =    length =
SEQUENCE: 5273
000

SEQ ID NO: 5274      moltype =    length =
SEQUENCE: 5274
000

SEQ ID NO: 5275      moltype =    length =
SEQUENCE: 5275
000

SEQ ID NO: 5276      moltype =    length =
SEQUENCE: 5276
000

SEQ ID NO: 5277      moltype =    length =
SEQUENCE: 5277
000

SEQ ID NO: 5278      moltype =    length =
SEQUENCE: 5278
000

SEQ ID NO: 5279      moltype =    length =
SEQUENCE: 5279
000

SEQ ID NO: 5280      moltype =    length =
SEQUENCE: 5280
000

SEQ ID NO: 5281      moltype =    length =
SEQUENCE: 5281
000

SEQ ID NO: 5282      moltype =    length =
SEQUENCE: 5282
000

SEQ ID NO: 5283      moltype =    length =
SEQUENCE: 5283
000

SEQ ID NO: 5284      moltype =    length =
SEQUENCE: 5284
000

SEQ ID NO: 5285      moltype =    length =
SEQUENCE: 5285
000

SEQ ID NO: 5286      moltype =    length =
SEQUENCE: 5286
000

SEQ ID NO: 5287      moltype =    length =
SEQUENCE: 5287
000

SEQ ID NO: 5288      moltype =    length =
SEQUENCE: 5288
000

SEQ ID NO: 5289      moltype =    length =

-continued

```
SEQUENCE: 5289
000

SEQ ID NO: 5290           moltype =    length =
SEQUENCE: 5290
000

SEQ ID NO: 5291           moltype =    length =
SEQUENCE: 5291
000

SEQ ID NO: 5292           moltype =    length =
SEQUENCE: 5292
000

SEQ ID NO: 5293           moltype =    length =
SEQUENCE: 5293
000

SEQ ID NO: 5294           moltype =    length =
SEQUENCE: 5294
000

SEQ ID NO: 5295           moltype =    length =
SEQUENCE: 5295
000

SEQ ID NO: 5296           moltype =    length =
SEQUENCE: 5296
000

SEQ ID NO: 5297           moltype =    length =
SEQUENCE: 5297
000

SEQ ID NO: 5298           moltype =    length =
SEQUENCE: 5298
000

SEQ ID NO: 5299           moltype =    length =
SEQUENCE: 5299
000

SEQ ID NO: 5300           moltype =    length =
SEQUENCE: 5300
000

SEQ ID NO: 5301           moltype =    length =
SEQUENCE: 5301
000

SEQ ID NO: 5302           moltype =    length =
SEQUENCE: 5302
000

SEQ ID NO: 5303           moltype =    length =
SEQUENCE: 5303
000

SEQ ID NO: 5304           moltype =    length =
SEQUENCE: 5304
000

SEQ ID NO: 5305           moltype =    length =
SEQUENCE: 5305
000

SEQ ID NO: 5306           moltype =    length =
SEQUENCE: 5306
000

SEQ ID NO: 5307           moltype =    length =
SEQUENCE: 5307
000

SEQ ID NO: 5308           moltype =    length =
SEQUENCE: 5308
000
```

| | | |
|---|---|---|
| SEQ ID NO: 5309<br>SEQUENCE: 5309<br>000 | moltype = | length = |
| SEQ ID NO: 5310<br>SEQUENCE: 5310<br>000 | moltype = | length = |
| SEQ ID NO: 5311<br>SEQUENCE: 5311<br>000 | moltype = | length = |
| SEQ ID NO: 5312<br>SEQUENCE: 5312<br>000 | moltype = | length = |
| SEQ ID NO: 5313<br>SEQUENCE: 5313<br>000 | moltype = | length = |
| SEQ ID NO: 5314<br>SEQUENCE: 5314<br>000 | moltype = | length = |
| SEQ ID NO: 5315<br>SEQUENCE: 5315<br>000 | moltype = | length = |
| SEQ ID NO: 5316<br>SEQUENCE: 5316<br>000 | moltype = | length = |
| SEQ ID NO: 5317<br>SEQUENCE: 5317<br>000 | moltype = | length = |
| SEQ ID NO: 5318<br>SEQUENCE: 5318<br>000 | moltype = | length = |
| SEQ ID NO: 5319<br>SEQUENCE: 5319<br>000 | moltype = | length = |
| SEQ ID NO: 5320<br>SEQUENCE: 5320<br>000 | moltype = | length = |
| SEQ ID NO: 5321<br>SEQUENCE: 5321<br>000 | moltype = | length = |
| SEQ ID NO: 5322<br>SEQUENCE: 5322<br>000 | moltype = | length = |
| SEQ ID NO: 5323<br>SEQUENCE: 5323<br>000 | moltype = | length = |
| SEQ ID NO: 5324<br>SEQUENCE: 5324<br>000 | moltype = | length = |
| SEQ ID NO: 5325<br>SEQUENCE: 5325<br>000 | moltype = | length = |
| SEQ ID NO: 5326<br>SEQUENCE: 5326<br>000 | moltype = | length = |
| SEQ ID NO: 5327<br>SEQUENCE: 5327<br>000 | moltype = | length = |
| SEQ ID NO: 5328<br>SEQUENCE: 5328<br>000 | moltype = | length = |

SEQ ID NO: 5329      moltype =     length =
SEQUENCE: 5329
000

SEQ ID NO: 5330      moltype =     length =
SEQUENCE: 5330
000

SEQ ID NO: 5331      moltype =     length =
SEQUENCE: 5331
000

SEQ ID NO: 5332      moltype =     length =
SEQUENCE: 5332
000

SEQ ID NO: 5333      moltype =     length =
SEQUENCE: 5333
000

SEQ ID NO: 5334      moltype =     length =
SEQUENCE: 5334
000

SEQ ID NO: 5335      moltype =     length =
SEQUENCE: 5335
000

SEQ ID NO: 5336      moltype =     length =
SEQUENCE: 5336
000

SEQ ID NO: 5337      moltype =     length =
SEQUENCE: 5337
000

SEQ ID NO: 5338      moltype =     length =
SEQUENCE: 5338
000

SEQ ID NO: 5339      moltype =     length =
SEQUENCE: 5339
000

SEQ ID NO: 5340      moltype =     length =
SEQUENCE: 5340
000

SEQ ID NO: 5341      moltype =     length =
SEQUENCE: 5341
000

SEQ ID NO: 5342      moltype =     length =
SEQUENCE: 5342
000

SEQ ID NO: 5343      moltype =     length =
SEQUENCE: 5343
000

SEQ ID NO: 5344      moltype =     length =
SEQUENCE: 5344
000

SEQ ID NO: 5345      moltype =     length =
SEQUENCE: 5345
000

SEQ ID NO: 5346      moltype =     length =
SEQUENCE: 5346
000

SEQ ID NO: 5347      moltype = DNA   length = 45
FEATURE              Location/Qualifiers
source               1..45
                     mol_type = other DNA
                     organism = synthetic construct
SEQUENCE: 5347

```
ggtggtggtg gatccggagg aggaggaagt ggaggtggag gttct                       45

SEQ ID NO: 5348         moltype = AA  length = 15
FEATURE                 Location/Qualifiers
source                  1..15
                        mol_type = protein
                        organism = synthetic construct
SEQUENCE: 5348
GGGGSGGGGS GGGGS                                                        15
```